US010256419B2

(12) United States Patent
Brooks et al.

(10) Patent No.: US 10,256,419 B2
(45) Date of Patent: *Apr. 9, 2019

(54) ORGANIC ELECTROLUMINESCENT MATERIALS AND DEVICES

(71) Applicant: Universal Display Corporation, Ewing, NJ (US)

(72) Inventors: Jason Brooks, Philadelphia, PA (US); Geza Szigethy, Ewing, NJ (US); Glenn Morello, Pittsburgh, PA (US); Jun Deng, Murrysville, PA (US); Peter I. Djurovich, Long Beach, CA (US); Hsiao-Fan Chen, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 428 days.

This patent is subject to a terminal disclaimer.

(21) Appl. No.: 14/933,684

(22) Filed: Nov. 5, 2015

(65) Prior Publication Data

US 2016/0072082 A1 Mar. 10, 2016

Related U.S. Application Data

(63) Continuation-in-part of application No. PCT/US2015/029269, filed on May 5, 2015.

(60) Provisional application No. 62/082,970, filed on Nov. 21, 2014, provisional application No. 61/990,239, filed on May 8, 2014.

(51) Int. Cl.
| | | |
|---|---|---|
| *H01L 51/54* | (2006.01) | |
| *C09K 11/06* | (2006.01) | |
| *H01L 51/00* | (2006.01) | |
| *C07F 15/00* | (2006.01) | |
| *C07D 471/16* | (2006.01) | |
| *C07D 498/16* | (2006.01) | |
| *C07D 513/16* | (2006.01) | |
| *C09K 11/02* | (2006.01) | |
| *H01L 27/32* | (2006.01) | |
| *C07F 7/18* | (2006.01) | |
| *H01L 51/50* | (2006.01) | |
| *H01L 51/52* | (2006.01) | |

(52) U.S. Cl.
CPC ........ *H01L 51/0085* (2013.01); *C07D 471/16* (2013.01); *C07D 498/16* (2013.01); *C07D 513/16* (2013.01); *C07F 7/1804* (2013.01); *C07F 15/0033* (2013.01); *C07F 15/0086* (2013.01); *C09K 11/025* (2013.01); *C09K 11/06* (2013.01); *H01L 27/32* (2013.01); *H01L 51/005* (2013.01); *H01L 51/0072* (2013.01); *H01L 51/0073* (2013.01); *H01L 51/0074* (2013.01); *H01L 51/0087* (2013.01); *C09K 2211/1007* (2013.01); *C09K 2211/1011* (2013.01); *C09K 2211/1022* (2013.01); *C09K 2211/1044* (2013.01); *C09K 2211/1088* (2013.01); *C09K 2211/185* (2013.01); *H01L 51/5012* (2013.01); *H01L 51/5016* (2013.01); *H01L 51/5206* (2013.01); *H01L 51/5221* (2013.01)

(58) Field of Classification Search
CPC ... C09K 11/06; C09K 11/025; C09K 2211/00; C09K 2211/10; C09K 2211/1007; C09K 2211/1011; C09K 2211/1022; C09K 2211/1044; C09K 2211/1088; C09K 2211/185; C07D 471/16; C07D 498/16; C07D 513/16; C07F 7/00; C07F 7/1852; C07F 15/00; C07F 15/0033; C07F 15/0086; H01L 27/32; H01L 51/0032; H01L 51/005; H01L 51/0071; H01L 51/0072; H01L 51/0073; H01L 51/0074; H01L 51/0085; H01L 51/0087; H01L 51/0086; H01L 51/50; H01L 51/5012; H01L 51/5016; H01L 51/5206; H01L 51/5221
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Extended European Search Report dated Aug. 31, 2016 for corresponding European Application No. 16001000.5.

(Continued)

*Primary Examiner* — Andrew K Bohaty
(74) *Attorney, Agent, or Firm* — Duane Morris LLP

(57) ABSTRACT

Imidazophenanthridine ligands and metal complexes are provided. The compounds exhibit improved stability through a linking substitution that links a nitrogen bonded carbon of an imidizole ring to a carbon on the adjacent fused aryl ring. The compounds may be used in organic light emitting devices, particularly as emissive dopants, providing devices with improved efficiency, stability, and manufacturing. In particular, the compounds provided herein may be used in blue devices having high efficiency.

19 Claims, 8 Drawing Sheets

(56) References Cited

U.S. PATENT DOCUMENTS

| | | |
|---|---|---|
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2004/0247933 A1 | 12/2004 | Thoms |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0082284 A1 | 4/2007 | Stoessel et al. |
| 2007/0190359 A1* | 8/2007 | Knowles ............ C07F 15/0033 428/690 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0223276 A1 | 9/2012 | Parham et al. |
| 2012/0223634 A1* | 9/2012 | Xia .................. C09K 11/06 313/504 |
| 2012/0292607 A1 | 11/2012 | Watanabe et al. |
| 2013/0168656 A1 | 7/2013 | Tsai et al. |
| 2014/0014930 A1 | 1/2014 | Hirose et al. |
| 2014/0110642 A1 | 4/2014 | Stoessel et al. |
| 2014/0364605 A1 | 12/2014 | Li et al. |
| 2015/0194616 A1 | 7/2015 | Li et al. |
| 2015/0207086 A1 | 7/2015 | Li et al. |
| 2016/0072082 A1 | 3/2016 | Brooks et al. |
| 2017/0162802 A1 | 6/2017 | Weaver et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2012-004529 | 1/2012 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2008/156879 | 12/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2015/171627 | 11/2015 |

OTHER PUBLICATIONS

International Search Report and Written Opinion dated Jul. 24, 2015 for corresponding PCT Application No. PCT/US15/29269.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

(56) References Cited

OTHER PUBLICATIONS

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhigiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4'4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

International Preliminary Report on Patentability issued in connection with International patent application No. PCT/US15/29269, dated Nov. 8, 2016, 10 pages.

Notice of Reasons for Rejection dated Jul. 3, 2018 for corresponding Japanese Patent Application No. 2016-567017.

(56) References Cited

OTHER PUBLICATIONS

Li, G.uijie et al. "Modifying Emission Spectral Bandwidth of Phosphorescent Platinum(II) Complexes Through Synthetic Control" Inorg. Chem. 2017, 56, pp. 8244-8256.

Fleetham, Tyler et al., "Efficient "Pure" Blue OLEDs Employing Tetradentate Pt Complexes with a Narrow Spectral Bandwidth" Adv. Mater. 2014, 26, pp. 7116-7121.

Zhu, Zhi-Qiang et al., "Efficient Cyclometalated Platinum(II) Complex with Superior Operational Stability" Adv. Mater. 2017, 29, 1605002, pp. 1-5.

Fleetham, Tyler B. et al. "Tetradentate Pt(II) Complexes with 6-Membered Chelate Rings: A New Route for Stable and Efficient Blue Organic Light Emitting Diodes" Chem. Mater. 2016, 28, pp. 3276-3282.

Fleetham, Tyler et al. "Efficient and stable single-doped white OLEDs using a palladium-based phosphorescent excimer†" Chem. Sci., 2017, 8, pp. 7983-7990.

\* cited by examiner

ORGANIC ELECTROLUMINESCENT MATERIALS AND DEVICES

CROSS-REFERENCE TO RELATED APPLICATIONS

This application is a continuation-in-part of PCT application Serial No. PCT/US15/29269, filed on May 5, 2015, which claims priority to U.S. Provisional Application Ser. No. 61/990,239, filed on May 8, 2014, and to U.S. Provisional Application Ser. No. 62/082,970, filed on Nov. 21, 2014, the entire contents of which are incorporated herein by reference.

FIELD OF THE INVENTION

The present invention generally relates to novel compounds, compositions comprising the same, and applications of the compounds and compositions, including organic electroluminescent devices comprising the compounds and/or compositions.

JOINT RESEARCH AGREEMENT

The claimed inventions were made by, on behalf of, and/or in connection with one or more of the following parties to a joint university corporation research agreement: University of Southern California, and the Universal Display Corporation. The agreement was in effect on and before the date the claimed inventions were made, and the claimed inventions were made as a result of activities undertaken within the scope of the agreement.

BACKGROUND OF THE INVENTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238; 6,310,360; 6,830,828 and 6,835,469; U.S. Patent Application Publication No. 2002-0182441; and WO 2002/074015.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays, emission from a white backlight is filtered using absorption filters to produce red, green and blue emission. The same technique can also be used with OLEDs. The white OLED can be either a single EML device or a stacked structure. Color may be measured using CIE coordinates, which are well known to the art.

One example of a green emissive molecule is tris(2-phenylpyridine) iridium, denoted Ir(ppy)$_3$, which has the following structure:

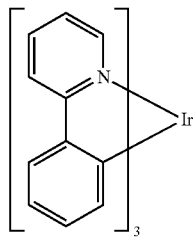

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an aspect of the present disclosure, a compound having a structure $(L_A)_n ML_m$ according to the following Formula 1 is disclosed:

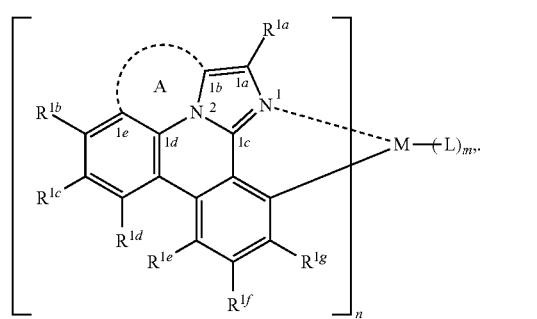

Formula 1

In Formula 1, M is a metal having an atomic weight greater than 40, n has a value of at least 1 and m+n is the maximum number of ligands that may be attached to the metal M; wherein A is a linking group having two to three linking atoms, wherein the linking atoms are each independently selected from the group consisting of C, Si, O, S, N, B or combinations thereof; wherein the linking atoms form at least one single bond between two linking atoms; wherein $R^{1a}$-$R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

According to another aspect of the present disclosure, an organic light emitting device is disclosed. The OLED comprises an anode; a cathode; and an organic layer disposed between the anode and the cathode, wherein the organic layer comprises the compound having the structure according to Formula 1.

According to another aspect of the present disclosure, a formulation comprising the compound having the structure according to Formula 1 is also disclosed.

According to another aspect of the present disclosure, a compound having a structure according to Formula (1a) shown below is disclosed.

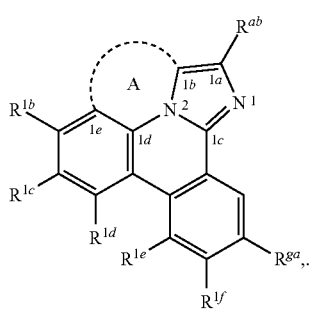

Formula (1a)

In Formula (1a), A is a linking group having two to three linking atoms, wherein the linking atoms are each independently selected from the group consisting of C, Si, O, S, N, B or combinations thereof;

wherein $R^{ab}$, $R^{ga}$ and $R^{1b}$ to $R^{1f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof; wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof; and wherein any one of the ring atoms to which $R^{ab}$, $R^{ga}$, and $R^{1b}$ to $R^{1f}$ are attached may be replaced with a nitrogen atom, wherein when the ring atom is replaced with a nitrogen atom the corresponding R group is not present.

According to another aspect of the present disclosure, the compound of Formula (1a) can be a compound having a structure represented by structural formulas, Formula (2a) and Formula (2b) tethered together as defined below:

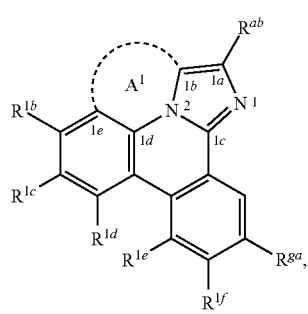

Formula (2a)

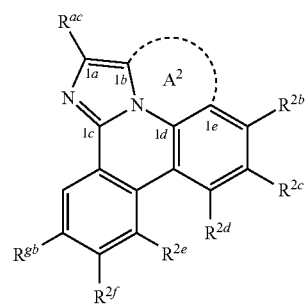

Formula (2b)

wherein $A^1$ and $A^2$ are each a first linking group having two to three linking atoms, wherein the linking atoms are each independently selected from the group consisting of C, Si, O, S, N, B and combinations thereof, and wherein $R^{ac}$, $R^{gb}$, and $R^{2b}$ to $R^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof; wherein the compound is tethered together via at least one second linking group formed between $R^{ab}$ and $R^{ac}$ and/or $R^{ga}$ and $R^{gb}$, wherein at least one second linking group has one to three linking atoms and each linking atom is independently selected from the group consisting of B, N, P, O, S, Se, C, Si, Ge and combinations thereof; and any one of the ring atoms to which $R^{1b}$ to $R^{1f}$ and $R^{2b}$ to $R^{2f}$ are attached may be replaced with a nitrogen atom, wherein when the ring atom is replaced with a nitrogen atom the corresponding R group is not present.

According to another aspect of the present disclosure, the compound of Formula (1a) can be a compound having a structure represented by Formula (3a) shown below:

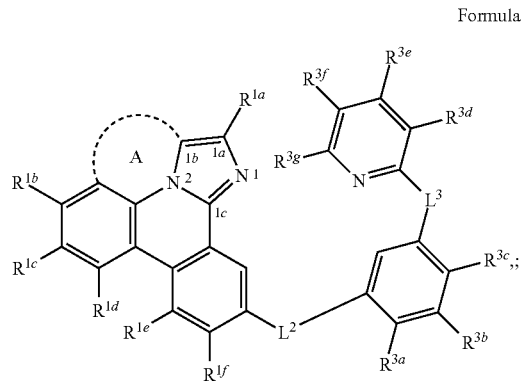

Formula (3a)

wherein $L^2$ and $L^3$ are each independently selected from the group consisting of a single bond, $BR^1$, $NR^1$, $PR^1$, O, S, Se, C=O, S=O, $SO_2$, $CR^1R^2$, $SiR^1R^2$, and $GeR^1R^2$;

wherein $R^{3a}$ to $R^{3f}$, are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein each $R^1$ and $R^2$ is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any two adjacent $R^{1f}$, $R^{3a}$, $R^{3c}$, $R^{3d}$, $R^1$ and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings;

and wherein $L^3$ and $R^{3c}$, $L^3$ and $R^{3d}$, or $L^3$ and both $R^{3c}$ and $R^{3d}$ are optionally joined to form one or more rings.

BRIEF DESCRIPTION OF THE DRAWINGS

The foregoing summary, as well as the following detailed description of exemplary embodiments of the compounds, compositions and devices in accordance with the present invention, will be better understood when read in conjunction with the appended drawings of exemplary embodiments. It should be understood, however, that the invention is not limited to the precise arrangements and instrumentalities shown.

In the drawings.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Imidazophenanthridines are useful ligands that can provide 460 nm emission when ligated to both platinum and iridium metals. Phosphorescent imidazophenanthridine complexes can provide deep blue emission with tunable photoluminescent quantum yield ranging from nearly zero to unity. Unfortunately, the device lifetime is limited for both iridium and platinum based blue-emitting complexes. We provide a strategy herein to improve the stability of the imidazophenanthridine ligand by addressing a bond on the ligand that is shown by computational theory, mass spec fragmentation analysis, and photooxidative studies to be a weak bond due to polycyclic ring strain and electronic structure.

Figure 1:
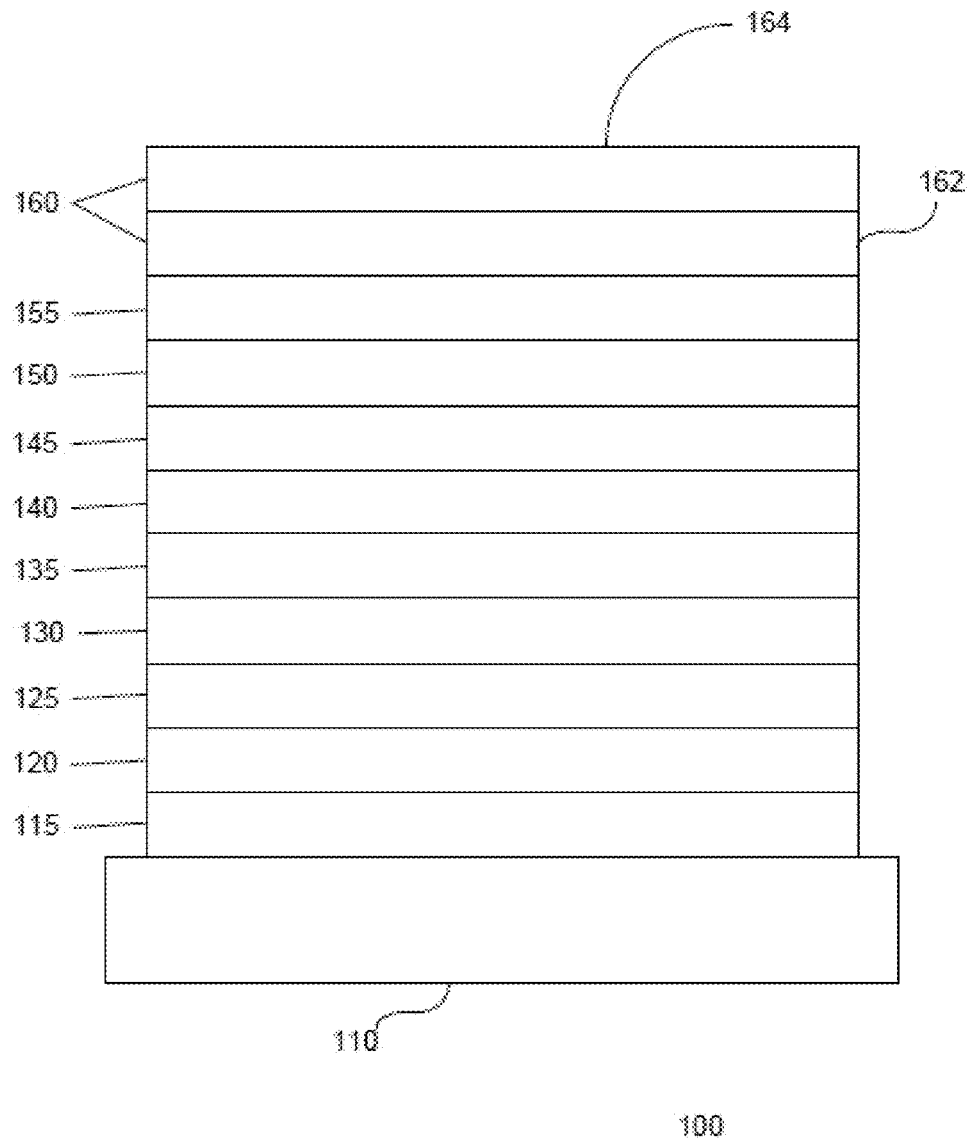
FIG. 1 shows an exemplary organic light emitting device 100.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S.

Patent Application Publication No. 2004/0174116, which is incorporated by reference in its entirety. A description of protective layers may be found in U.S. Patent Application Publication No. 2004/0174116, which is incorporated by reference in its entirety.

Figure 2:
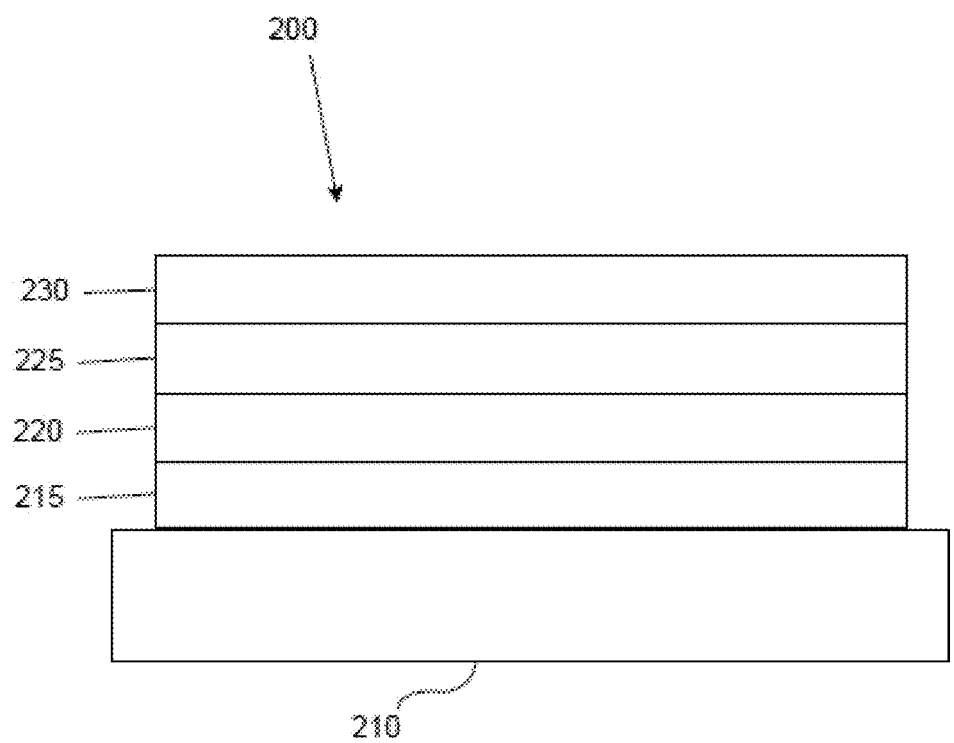
FIG. 2 illustrates an exemplary organic light emitting device 200 according to the present disclosure.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247, 190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable devices, laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein means a straight or branched chain saturated acyclic hydrocarbon radical, which may optionally be substituted with any suitable substituent.

Accordingly, an alkyl radical in accordance with the present invention can comprise any combination of primary, secondary, tertiary and quaternary carbon atoms. Exemplary alkyl radicals include, but are not limited to, $C_1$-$C_{20}$-alkyl, $C_1$-$C_{18}$-alkyl, $C_1$-$C_{16}$-alkyl, $C_1$-$C_{14}$-alkyl, $C_1$-$C_{12}$-alkyl, $C_1$-$C_{10}$-alkyl, $C_1$-$C_8$-alkyl, $C_1$-$C_6$-alkyl, $C_1$-$C_4$-alkyl, $C_1$-$C_3$-alkyl, and $C_2$-alkyl. Specific examples include methyl, ethyl, 1-propyl, 2-propyl, 2-methyl-1-propyl, 1-butyl, 2-butyl, t-butyl, n-octyl, n-decyl, and n-hexadecyl.

As used herein, the term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

As used herein, the term "alkenyl" means acyclic branched or unbranched hydrocarbon radical having one or more carbon-carbon double bonds. Exemplary alkenyl radicals include, but are not limited to, $C_1$-$C_{20}$-alkenyl radical, $C_2$-$C_{18}$-alkenyl radical, $C_2$-$C_{16}$-alkenyl radical, $C_2$-$C_{14}$-alkenyl radical, $C_2$-$C_{12}$-alkenyl radical, $C_2$-$C_{10}$-alkenyl radical, $C_2$-$C_8$-alkenyl radical, $C_2$-$C_6$-alkenyl radical, $C_2$-$C_4$-alkenyl radical, $C_2$-$C_3$-alkenyl radical, and $C_2$-alkenyl radical. Specific examples include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

As used herein, the term "alkylene" means an optionally substituted saturated straight or branched chain hydrocarbon radical. Exemplary alkylene radicals include, but are not limited to, $C_1$-$C_{20}$-alkylene, $C_2$-$C_{18}$-alkylene, $C_2$-$C_{16}$-alkylene, $C_2$-$C_{14}$-alkylene, $C_2$-$C_{12}$-alkylene, $C_2$-$C_{10}$-alkylene, $C_2$-$C_8$-alkylene, $C_2$-$C_6$-alkylene, $C_2$-$C_4$-alkylene, $C_2$-$C_3$-alkylene, and $C_2$-alkylene. Specific examples of alkylene include, but are not limited to, methylene, dimethylene, and trimethylene.

As used herein, the term "alkynyl" means an acyclic branched or unbranched hydrocarbon having at least one carbon-carbon triple bond. Exemplary alkylene radicals include, but are not limited to, $C_1$-$C_{20}$-alkynyl radical, $C_2$-$C_{18}$-alkynyl radical, $C_2$-$C_{16}$-alkynyl radical, $C_2$-$C_{14}$-alkynyl radical, $C_2$-$C_{12}$-alkynyl radical, $C_2$-$C_{10}$-alkynyl radical, $C_2$-$C_8$-alkynyl radical, $C_2$-$C_6$-alkynyl radical, $C_2$-$C_4$-alkynyl radical, $C_2$-$C_3$-alkynyl radical, and $C_2$-alkynyl radical. Specific examples of alkynyl include, but are not limited to, propargyl, and 3-pentynyl, acetylenyl, propynyl, 1-butynyl, 2-butynyl, 1-pentynyl, 2-pentynyl, and 3-methyl-1-butynyl.

As used herein, the term "aralkyl" means one or more aryl radicals as defined herein attached through an alkyl bridge (e.g., -alkyl-(aryl)$_j$, wherein j is 1, 2 or 3). Specific examples of aralkyl include, but are not limited to, benzyl (—CH$_2$-phenyl, i.e., Bn), diphenyl methyl (—CH$_2$-(phenyl)$_2$) and trityl (—C-(phenyl)$_3$). Additionally, the aralkyl group may be optionally substituted.

Unless stated otherwise, as used herein, the term "heterocycle" and variants of the term, including "heterocyclic group" and "heterocyclyl," means an optionally substituted monocyclic or polycyclic ring system having as ring members atoms of at least two different elements and wherein the monocyclic or polycyclic ring system is either saturated, unsaturated or aromatic. In some embodiments, heterocyle comprises carbon atoms and at least one heteroatom. In some embodiments, heterocyle comprises carbon atoms and at least one heteroatom selected from nitrogen, oxygen, silicon, selenium, and sulfur, and wherein the nitrogen, oxygen, silicon, selenium, and sulfur heteroatoms may be optionally oxidized, and the nitrogen heteroatom may be optionally quaternized. Examples of heterocycle include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

As used herein, the term "aryl" means an optionally substituted monocyclic or polycyclic aromatic hydrocarbon. Specific examples of aryl include, but are not limited to, phenyl, phenyl, 4-methylphenyl, 2,6-dimethylphenyl, naphthyl, anthracenyl, and phenanthrenyl. The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

As used herein, the term "heteroaryl" means an optionally substituted monocyclic or polycyclic aromatic hydrocarbon having at least one heteroatom and at least one carbon atom. In some embodiments, the at least one heteroatom is selected from nitrogen, oxygen, silicon, selenium, and sulfur. Specific examples of heteroaryl include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

According to an aspect of the present disclosure, a compound having a structure $(L_A)_n ML_m$ according to Formula 1 shown below is disclosed.

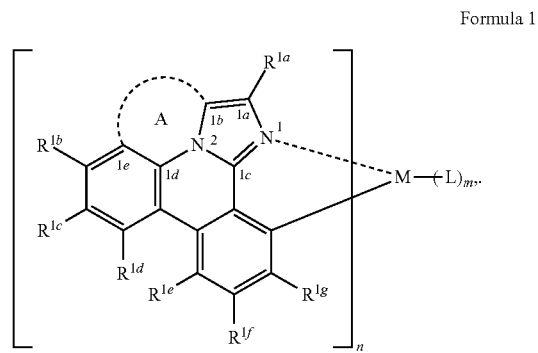

Formula 1

In Formula I, M is a metal having an atomic weight greater than 40, n has a value of at least 1 and m+n is the maximum number of ligands that may be attached to the metal;

wherein A is a linking group having two to three linking atoms, wherein the linking atoms are each independently selected from the group consisting of C, Si, O, S, N, B or combinations thereof;

wherein the linking atoms form at least one single bond between two linking atoms;

wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

In some embodiments of the compound of Formula 1, one of the ring atoms to which $R^{1b}$ to $R^{1g}$ are attached is a nitrogen atom. In some embodiments, the ring atom to which $R^{1e}$ is attached a nitrogen atom.

In one embodiment, the compound has a triplet excited state and wherein the linking group A stabilizes the bond between $N^2$ and $C^{1b}$ from cleavage when the compound is in the triplet excited state.

In one embodiment, the compound has a peak emissive wavelength less than 500 nm. In another embodiment, the compound has a peak emissive wavelength less than 480 nm. In yet another embodiment, the compound has a peak emissive wavelength ranging from 400 nm to 500 nm.

In some embodiments of the compound of Formula 1, the linking group A is a saturated group.

In one embodiment of the compound of Formula 1, the linking group A is independently selected from the group consisting of —CR¹R²—CR³R⁴—, —CR¹R²—CR³R⁴—CR⁵R⁶—, —CR¹R²—NR³—, —CR¹=CR²—CR³R⁴—, —O—SiR¹R²—, —CR¹R²—S—, —CR¹R²—O—, and —C—SiR¹R²—, wherein the substituents R¹ to R⁶ can be same or different, and are independently selected from the group consisting of hydrogen, deuterium, alkyl, cycloalkyl, aryl, heteroaryl, and combinations thereof; wherein any adjacent R¹ to R⁶ are optionally connected to form a saturated five membered ring or a saturated six membered ring. Any adjacent substituents refers to any two of substituents that are possible to form the ring. The two adjacent substituents can be on the same atom, or on different atoms. The linking group A can be selected from the group consisting of:

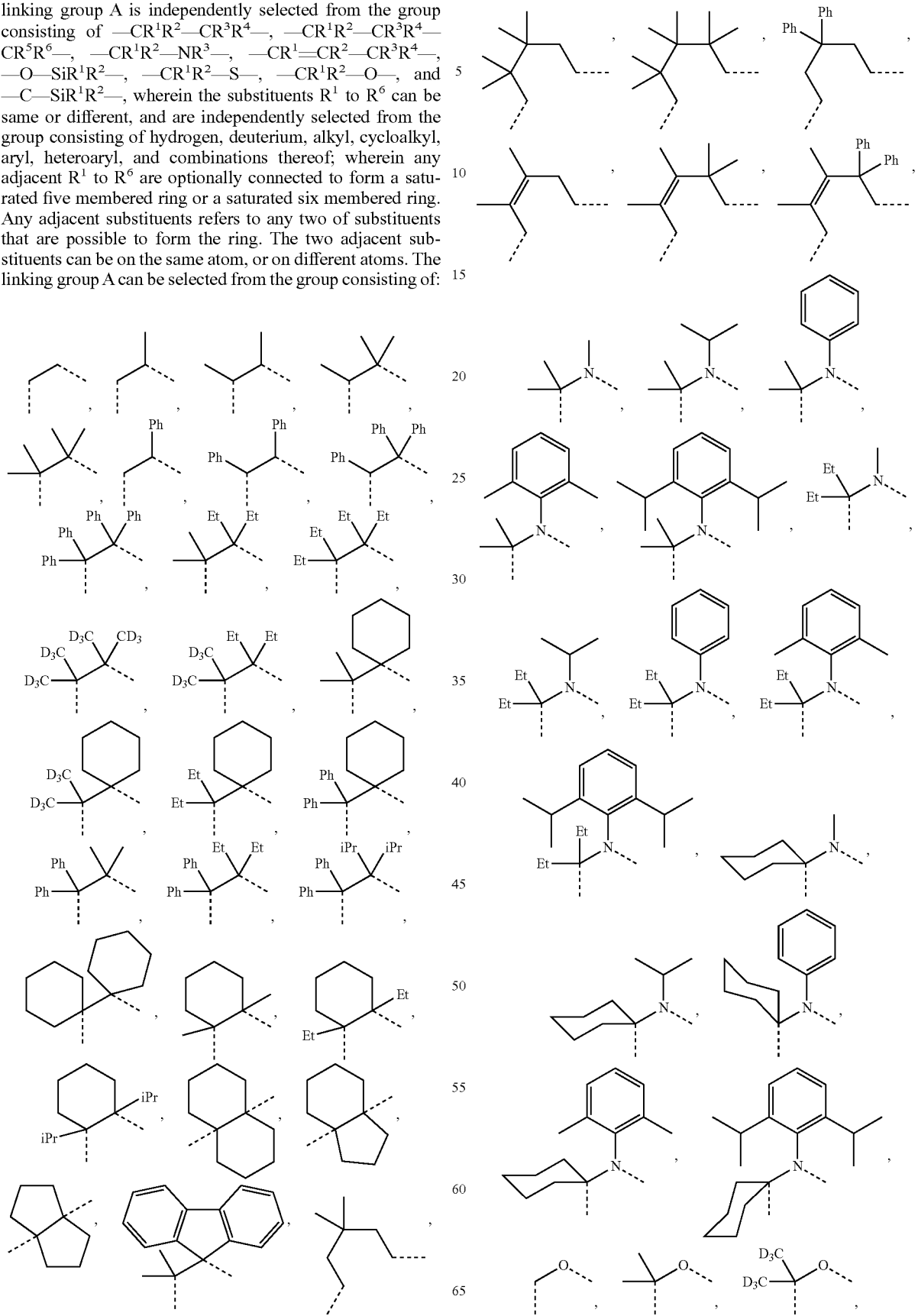

-continued

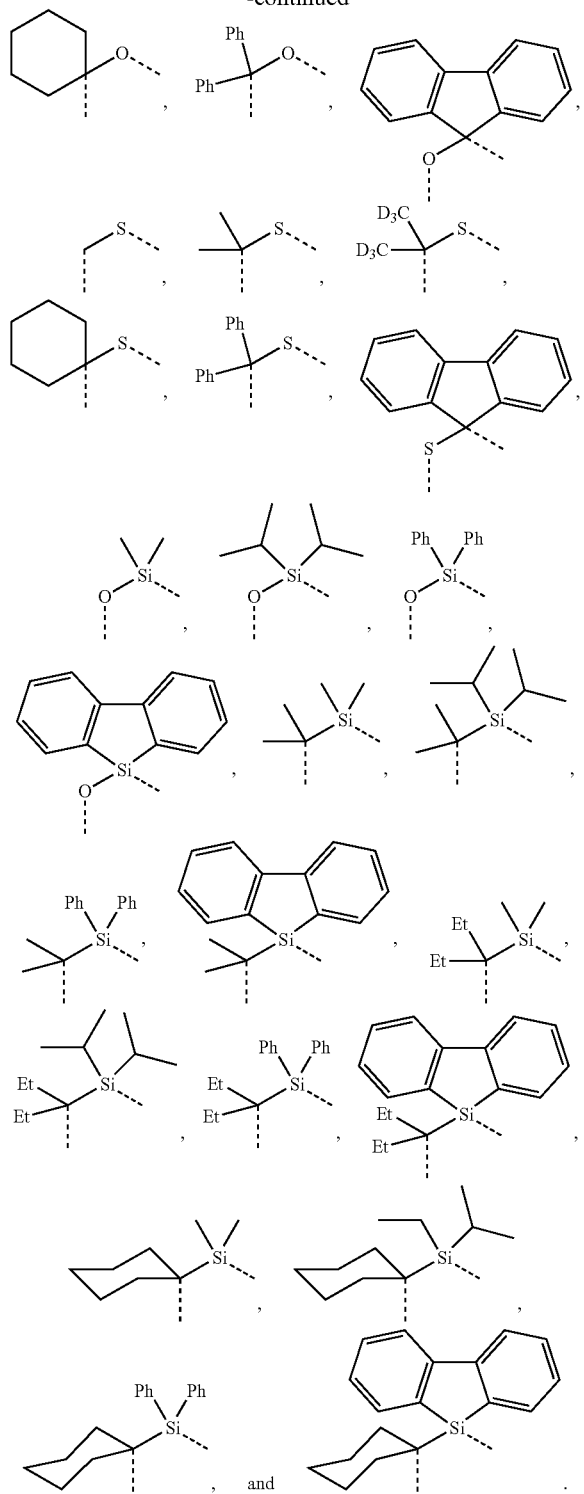

and

In some embodiments where the linking group A is independently selected from the group consisting of —CR$^1$R$^2$—CR$^3$R$^4$—, —CR$^1$R$^2$—CR$^3$R$^4$—CR$^5$R$^6$—, —CR$^1$R$^2$—NR$^3$—, —CR$^1$=CR$^2$—CR$^3$R$^4$—, —O—SiR$^1$R$^2$—, —CR$^1$R$^2$—S—, —CR$^1$R$^2$—O—, and —C—SiR$^1$R$^2$—, wherein the substituents R$^1$ to R$^6$ can be same or different, and are independently selected from the group consisting of hydrogen, deuterium, alkyl, cycloalkyl, aryl, heteroaryl, and combinations thereof; at least one adjacent R$^1$ to R$^6$ are connected to form a saturated five membered ring or a saturated six membered ring. In some embodiments, at least two adjacent R$^1$ to R$^6$, if present, are connected to form a saturated five membered ring or a saturated six membered ring. In some embodiments, each R$^1$ to R$^6$ are independently selected from the group consisting of alkyl, cycloalkyl, aryl, heteroaryl, partially or fully deuterated variants thereof, and combinations thereof; wherein any adjacent R$^1$ to R$^6$ are optionally connected to form a saturated five membered ring or a saturated six membered ring.

In some embodiments where the linking group A is independently selected from the group consisting of —CR$^1$R$^2$—CR$^3$R$^4$—, —CR$^1$R$^2$—CR$^3$R$^4$—CR$^5$R$^6$—, —CR$^1$R$^2$—NR$^3$—, —CR$^1$=CR$^2$—CR$^3$R$^4$—, —O—SiR$^1$R$^2$—, —CR$^1$R$^2$—S—, —CR$^1$R$^2$—O—, and —C—SiR$^1$R$^2$—, wherein the substituents R$^1$ to R$^6$ can be same or different, and are independently selected from the group consisting of hydrogen, deuterium, alkyl, cycloalkyl, aryl, heteroaryl, and combinations thereof; each R$^1$ to R$^6$ are independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, partially or fully deuterated variants thereof and combinations thereof. In some embodiments, each R$^1$ to R$^6$ are independently selected from the group consisting of alkyl, partially or fully deuterated variants thereof, and combinations thereof; wherein any adjacent R$^1$ to R$^6$ are optionally connected to form a saturated five membered ring or a saturated six membered ring.

In some embodiments of the compound of Formula 1, at least one of R$^{1a}$ to R$^{1g}$ is selected from the group consisting of alkyl, cycloalkyl, aryl, heteroaryl, partially or fully deuterated variants thereof, and combinations thereof. In other embodiments, at least one of R$^{1b}$, R$^{1d}$ and R$^{1e}$ is selected from the group consisting of alkyl, cycloalkyl, aryl, heteroaryl, partially or fully deuterated variants thereof, and combinations thereof. In other embodiments, R$^{1d}$ is selected from the group consisting of alkyl, cycloalkyl, aryl, heteroaryl, partially or fully deuterated variants thereof, and combinations thereof. In other embodiments, R$^{1a}$ is selected from the group consisting of alkyl, cycloalkyl, aryl, heteroaryl, partially or fully deuterated variants thereof, and combinations thereof.

In some embodiments of the compound of Formula 1, the metal M is selected from the group consisting of Re, Ru, Os, Rh, Ir, Pd, Pt, and Au. In some embodiments, the metal M is selected from the group consisting of Ir and Pt.

In some embodiments of the compound of Formula 1, the ligand $L_A$ is selected from the group consisting of:

| $L_A$ | Linker A | R$^{1a}$ | R$^{1b}$ | R$^{1c}$ | R$^{1d}$ | R$^{1e}$ | R$^{1f}$ | R$^{1g}$ |
|---|---|---|---|---|---|---|---|---|
| $L_A$1 | | H | H | H | H | H | H | H |
| $L_A$2 | | Me | H | H | H | H | H | H |
| $L_A$3 | | H | Me | H | H | H | H | H |
| $L_A$4 | | H | H | Me | H | H | H | H |
| $L_A$5 | | H | H | H | Me | H | H | H |
| $L_A$6 | | H | H | H | H | Me | H | H |
| $L_A$7 | | CD$_3$ | H | H | H | H | H | H |
| $L_A$8 | | H | CD$_3$ | H | H | H | H | H |
| $L_A$9 | | H | H | CD$_3$ | H | H | H | H |
| $L_A$10 | | H | H | H | CD$_3$ | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A11$ | | H | H | H | H | CD$_3$ | H | H |
| $L_A12$ | | $^i$Pr | H | H | H | H | H | H |
| $L_A13$ | | H | $^i$Pr | H | H | H | H | H |
| $L_A14$ | | H | H | $^i$Pr | H | H | H | H |
| $L_A15$ | | H | H | H | $^i$Pr | H | H | H |
| $L_A16$ | | H | H | H | H | $^i$Pr | H | H |
| $L_A17$ | | Ph | H | H | H | H | H | H |
| $L_A18$ | | H | Ph | H | H | H | H | H |
| $L_A19$ | | H | H | Ph | H | H | H | H |
| $L_A20$ | | H | H | H | Ph | H | H | H |
| $L_A21$ | | H | H | H | H | Ph | H | H |
| $L_A22$ | | Me | Me | H | H | H | H | H |
| $L_A23$ | | Me | H | Me | H | H | H | H |
| $L_A24$ | | M | H | H | Me | H | H | H |
| $L_A25$ | | Me | H | H | H | Me | H | H |
| $L_A26$ | | Me | CD$_3$ | H | H | H | H | H |
| $L_A27$ | | Me | H | CD$_3$ | H | H | H | H |
| $L_A28$ | | Me | H | H | CD$_3$ | H | H | H |
| $L_A29$ | | Me | H | H | H | CD$_3$ | H | H |
| $L_A30$ | | Me | $^i$Pr | H | H | H | H | H |
| $L_A31$ | | Me | H | $^i$Pr | H | H | H | H |
| $L_A32$ | | Me | H | H | $^i$Pr | H | H | H |
| $L_A33$ | | Me | H | H | H | $^i$Pr | H | H |
| $L_A34$ | | Me | Ph | H | H | H | H | H |
| $L_A35$ | | Me | H | Ph | H | H | H | H |
| $L_A36$ | | Me | H | H | Ph | H | H | H |
| $L_A37$ | | Me | H | H | H | Ph | H | H |
| $L_A38$ | | CD$_3$ | Me | H | H | H | H | H |
| $L_A39$ | | CD$_3$ | H | Me | H | H | H | H |
| $L_A40$ | | CD$_3$ | H | H | Me | H | H | H |
| $L_A41$ | | CD$_3$ | H | H | H | Me | H | H |
| $L_A42$ | | CD$_3$ | CD$_3$ | H | H | H | H | H |
| $L_A43$ | | CD$_3$ | H | CD$_3$ | H | H | H | H |
| $L_A44$ | | CD$_3$ | H | H | CD$_3$ | H | H | H |
| $L_A45$ | | CD$_3$ | H | H | H | CD$_3$ | H | H |
| $L_A46$ | | CD$_3$ | $^i$Pr | H | H | H | H | H |
| $L_A47$ | | CD$_3$ | H | $^i$Pr | H | H | H | H |
| $L_A48$ | | CD$_3$ | H | H | $^i$Pr | H | H | H |
| $L_A49$ | | CD$_3$ | H | H | H | $^i$Pr | H | H |
| $L_A50$ | | CD$_3$ | Ph | H | H | H | H | H |
| $L_A51$ | | CD$_3$ | H | Ph | H | H | H | H |
| $L_A52$ | (branched linker, C$^{1b}$···C$^{1e}$) | CD$_3$ | H | H | Ph | H | H | H |
| $L_A53$ | | CD$_3$ | H | H | H | Ph | H | H |
| $L_A54$ | | $^i$Pr | Me | H | H | H | H | H |
| $L_A55$ | | $^i$Pr | H | Me | H | H | H | H |
| $L_A56$ | | $^i$Pr | H | H | Me | H | H | H |
| $L_A57$ | | $^i$Pr | H | H | H | Me | H | H |
| $L_A58$ | | $^i$Pr | CD$_3$ | H | H | H | H | H |
| $L_A59$ | | $^i$Pr | H | CD$_3$ | H | H | H | H |
| $L_A60$ | | $^i$Pr | H | H | CD$_3$ | H | H | H |
| $L_A61$ | | $^i$Pr | H | H | H | CD$_3$ | H | H |
| $L_A62$ | | $^i$Pr | $^i$Pr | H | H | H | H | H |
| $L_A63$ | | $^i$Pr | H | $^i$Pr | H | H | H | H |
| $L_A64$ | | $^i$Pr | H | H | $^i$Pr | H | H | H |
| $L_A65$ | | $^i$Pr | H | H | H | $^i$Pr | H | H |
| $L_A66$ | | $^i$Pr | Ph | H | H | H | H | H |
| $L_A67$ | | $^i$Pr | H | Ph | H | H | H | H |
| $L_A68$ | | $^i$Pr | H | H | Ph | H | H | H |
| $L_A69$ | | $^i$Pr | H | H | H | Ph | H | H |
| $L_A70$ | | Ph | Me | H | H | H | H | H |
| $L_A71$ | | Ph | H | Me | H | H | H | H |
| $L_A72$ | | Ph | H | H | Me | H | H | H |
| $L_A73$ | | Ph | H | H | H | Me | H | H |
| $L_A74$ | | Ph | CD$_3$ | H | H | H | H | H |
| $L_A75$ | | Ph | H | CD$_3$ | H | H | H | H |
| $L_A76$ | | Ph | H | H | CD$_3$ | H | H | H |
| $L_A77$ | | Ph | H | H | H | CD$_3$ | H | H |
| $L_A78$ | | Ph | $^i$Pr | H | H | H | H | H |
| $L_A79$ | | Ph | H | $^i$Pr | H | H | H | H |
| $L_A80$ | | Ph | H | H | $^i$Pr | H | H | H |
| $L_A81$ | | Ph | H | H | H | $^i$Pr | H | H |
| $L_A82$ | | Ph | Ph | H | H | H | H | H |
| $L_A83$ | | Ph | H | Ph | H | H | H | H |
| $L_A84$ | | Ph | H | H | Ph | H | H | H |
| $L_A85$ | | Ph | H | H | H | Ph | H | H |
| $L_A86$ | | H | Me | Me | H | H | H | H |
| $L_A87$ | | H | Me | H | Me | H | H | H |
| $L_A88$ | | H | Me | H | H | Me | H | H |
| $L_A89$ | | H | Me | CD$_3$ | H | H | H | H |
| $L_A90$ | | H | Me | H | CD$_3$ | H | H | H |
| $L_A91$ | | H | Me | H | H | CD$_3$ | H | H |
| $L_A92$ | | H | Me | $^i$Pr | H | H | H | H |
| $L_A93$ | | H | Me | H | $^i$Pr | H | H | H |
| $L_A94$ | | H | Me | H | H | $^i$Pr | H | H |
| $L_A95$ | | H | Me | Ph | H | H | H | H |
| $L_A96$ | | H | Me | H | Ph | H | H | H |
| $L_A97$ | | H | Me | H | H | Ph | H | H |
| $L_A98$ | | H | CD$_3$ | Me | H | H | H | H |
| $L_A99$ | | H | CD$_3$ | H | Me | H | H | H |
| $L_A100$ | | H | CD$_3$ | H | H | Me | H | H |
| $L_A101$ | | H | CD$_3$ | CD$_3$ | H | H | H | H |
| $L_A102$ | | H | CD$_3$ | H | CD$_3$ | H | H | H |
| $L_A103$ | | H | CD$_3$ | H | H | CD$_3$ | H | H |
| $L_A104$ | (branched linker, C$^{1b}$···C$^{1e}$) | H | CD$_3$ | $^i$Pr | H | H | H | H |
| $L_A105$ | | H | CD$_3$ | H | $^i$Pr | H | H | H |
| $L_A106$ | | H | CD$_3$ | H | H | $^i$Pr | H | H |
| $L_A107$ | | H | CD$_3$ | Ph | H | H | H | H |
| $L_A108$ | | H | CD$_3$ | H | Ph | H | H | H |
| $L_A109$ | | H | CD$_3$ | H | H | Ph | H | H |
| $L_A110$ | | H | $^i$Pr | Me | H | H | H | H |
| $L_A111$ | | H | $^i$Pr | H | Me | H | H | H |
| $L_A112$ | | H | $^i$Pr | H | H | Me | H | H |
| $L_A113$ | | H | $^i$Pr | CD$_3$ | H | H | H | H |
| $L_A114$ | | H | $^i$Pr | H | CD$_3$ | H | H | H |
| $L_A115$ | | H | $^i$Pr | H | H | CD$_3$ | H | H |
| $L_A116$ | | H | $^i$Pr | $^i$Pr | H | H | H | H |
| $L_A117$ | | H | $^i$Pr | H | $^i$Pr | H | H | H |
| $L_A118$ | | H | $^i$Pr | H | H | $^i$Pr | H | H |
| $L_A119$ | | H | $^i$Pr | Ph | H | H | H | H |
| $L_A120$ | | H | $^i$Pr | H | Ph | H | H | H |
| $L_A121$ | | H | $^i$Pr | H | H | Ph | H | H |
| $L_A122$ | | H | Ph | Me | H | H | H | H |
| $L_A123$ | | H | Ph | H | Me | H | H | H |
| $L_A124$ | | H | Ph | H | H | Me | H | H |
| $L_A125$ | | H | Ph | CD$_3$ | H | H | H | H |
| $L_A126$ | | H | Ph | H | CD$_3$ | H | H | H |
| $L_A127$ | | H | Ph | H | H | CD$_3$ | H | H |
| $L_A128$ | | H | Ph | $^i$Pr | H | H | H | H |
| $L_A129$ | | H | Ph | H | $^i$Pr | H | H | H |
| $L_A130$ | | H | Ph | H | H | $^i$Pr | H | H |
| $L_A131$ | | H | Ph | Ph | H | H | H | H |
| $L_A132$ | | H | Ph | H | Ph | H | H | H |
| $L_A133$ | | H | Ph | H | H | Ph | H | H |
| $L_A134$ | | H | H | Me | Me | H | H | H |
| $L_A135$ | | H | H | CD$_3$ | Me | H | H | H |
| $L_A136$ | | H | H | $^i$Pr | Me | H | H | H |
| $L_A137$ | | H | H | Ph | Me | H | H | H |
| $L_A138$ | | H | H | Me | CD$_3$ | H | H | H |
| $L_A139$ | | H | H | CD$_3$ | CD$_3$ | H | H | H |
| $L_A140$ | | H | H | $^i$Pr | CD$_3$ | H | H | H |
| $L_A141$ | | H | H | Ph | CD$_3$ | H | H | H |
| $L_A142$ | | H | H | Me | $^i$Pr | H | H | H |
| $L_A143$ | | H | H | CD$_3$ | $^i$Pr | H | H | H |
| $L_A144$ | | H | H | $^i$Pr | $^i$Pr | H | H | H |
| $L_A145$ | | H | H | Ph | $^i$Pr | H | H | H |
| $L_A146$ | | H | H | Me | Ph | H | H | H |
| $L_A147$ | | H | H | CD$_3$ | Ph | H | H | H |
| $L_A148$ | | H | H | $^i$Pr | Ph | H | H | H |
| $L_A149$ | | H | H | Ph | Ph | H | H | H |
| $L_A150$ | | H | H | Me | H | Me | H | H |
| $L_A151$ | | H | H | CD$_3$ | H | Me | H | H |
| $L_A152$ | | H | H | $^i$Pr | H | Me | H | H |
| $L_A153$ | | H | H | Ph | H | Me | H | H |
| $L_A154$ | | H | H | Me | H | CD$_3$ | H | H |
| $L_A155$ | | H | H | CD$_3$ | H | CD$_3$ | H | H |
| $L_A156$ | | H | H | $^i$Pr | H | CD$_3$ | H | H |
| $L_A157$ | | H | H | Ph | H | CD$_3$ | H | H |
| $L_A158$ | (branched linker, C$^{1b}$···C$^{1e}$) | H | H | Me | H | $^i$Pr | H | H |
| $L_A159$ | | H | H | CD$_3$ | H | $^i$Pr | H | H |
| $L_A160$ | | H | H | $^i$Pr | H | $^i$Pr | H | H |
| $L_A161$ | | H | H | Ph | H | $^i$Pr | H | H |
| $L_A162$ | | H | H | Me | H | Ph | H | H |
| $L_A163$ | | H | H | CD$_3$ | H | Ph | H | H |

-continued

| L_A | Linker A | R^1a | R^1b | R^1c | R^1d | R^1e | R^1f | R^1g |
|---|---|---|---|---|---|---|---|---|
| L_A164 | | H | H | ^iPr | H | Ph | H | H |
| L_A165 | | H | H | Ph | H | Ph | H | H |
| L_A166 | | Me | Me | H | Me | H | H | H |
| L_A167 | | H | Me | Me | Me | H | H | H |
| L_A168 | | CD_3 | Me | H | Me | H | H | H |
| L_A169 | | H | Me | CD_3 | Me | H | H | H |
| L_A170 | | ^iPr | Me | H | Me | H | H | H |
| L_A171 | | H | Me | ^iPr | Me | H | H | H |
| L_A172 | | Ph | Me | H | Me | H | H | H |
| L_A173 | | H | Me | Ph | Me | H | H | H |
| L_A174 | | Me | CD_3 | H | CD_3 | H | H | H |
| L_A175 | | H | CD_3 | Me | CD_3 | H | H | H |
| L_A176 | | CD_3 | CD_3 | H | CD_3 | H | H | H |
| L_A177 | | H | CD_3 | CD_3 | CD_3 | H | H | H |
| L_A178 | | ^iPr | CD_3 | H | CD_3 | H | H | H |
| L_A179 | | H | CD_3 | ^iPr | CD_3 | H | H | H |
| L_A180 | | Ph | CD_3 | H | CD_3 | H | H | H |
| L_A181 | | H | CD_3 | Ph | CD_3 | H | H | H |
| L_A182 | | Me | ^iPr | H | ^iPr | H | H | H |
| L_A183 | | H | ^iPr | Me | ^iPr | H | H | H |
| L_A184 | | CD_3 | ^iPr | H | ^iPr | H | H | H |
| L_A185 | | H | ^iPr | CD_3 | ^iPr | H | H | H |
| L_A186 | | ^iPr | ^iPr | H | ^iPr | H | H | H |
| L_A187 | | H | ^iPr | ^iPr | ^iPr | H | H | H |
| L_A188 | | Ph | ^iPr | H | ^iPr | H | H | H |
| L_A189 | | H | ^iPr | Ph | ^iPr | H | H | H |
| L_A190 | | Me | Ph | H | Ph | H | H | H |
| L_A191 | | H | Ph | Me | Ph | H | H | H |
| L_A192 | | CD_3 | Ph | H | Ph | H | H | H |
| L_A193 | | H | Ph | CD_3 | Ph | H | H | H |
| L_A194 | | ^iPr | Ph | H | Ph | H | H | H |
| L_A195 | | H | Ph | ^iPr | Ph | H | H | H |
| L_A196 | | Ph | Ph | H | Ph | H | H | H |
| L_A197 | | H | Ph | Ph | Ph | H | H | H |
| L_A198 | Et,Et-C(−C^1b)(−C^1e) structure | H | H | H | H | H | H | H |
| L_A199 | | Me | H | H | H | H | H | H |
| L_A200 | | H | Me | H | H | H | H | H |
| L_A201 | | H | H | Me | H | H | H | H |
| L_A202 | | H | H | H | Me | H | H | H |
| L_A203 | | H | H | H | H | Me | H | H |
| L_A204 | | CD_3 | H | H | H | H | H | H |
| L_A205 | | H | CD_3 | H | H | H | H | H |
| L_A206 | | H | H | CD_3 | H | H | H | H |
| L_A207 | | H | H | H | CD_3 | H | H | H |
| L_A208 | | H | H | H | H | CD_3 | H | H |
| L_A209 | | ^iPr | H | H | H | H | H | H |
| L_A210 | | H | ^iPr | H | H | H | H | H |
| L_A211 | | H | H | ^iPr | H | H | H | H |
| L_A212 | | H | H | H | ^iPr | H | H | H |
| L_A213 | Et,Et-C(−C^1b)(−C^1e) structure | H | H | H | H | ^iPr | H | H |
| L_A214 | | Ph | H | H | H | H | H | H |
| L_A215 | | H | Ph | H | H | H | H | H |
| L_A216 | | H | H | Ph | H | H | H | H |
| L_A217 | | H | H | H | Ph | H | H | H |
| L_A218 | | H | H | H | H | Ph | H | H |
| L_A219 | | Me | Me | H | H | H | H | H |
| L_A220 | | Me | H | Me | H | H | H | H |
| L_A221 | | Me | H | H | Me | H | H | H |
| L_A222 | | Me | H | H | H | Me | H | H |
| L_A223 | | Me | CD_3 | H | H | H | H | H |
| L_A224 | | Me | H | CD_3 | H | H | H | H |
| L_A225 | | Me | H | H | CD_3 | H | H | H |
| L_A226 | | Me | H | H | H | CD_3 | H | H |
| L_A227 | | Me | ^iPr | H | H | H | H | H |
| L_A228 | | Me | H | ^iPr | H | H | H | H |
| L_A229 | | Me | H | H | ^iPr | H | H | H |
| L_A230 | | Me | H | H | H | ^iPr | H | H |
| L_A231 | | Me | Ph | H | H | H | H | H |
| L_A232 | | Me | H | Ph | H | H | H | H |
| L_A233 | | Me | H | H | Ph | H | H | H |
| L_A234 | | Me | H | H | H | Ph | H | H |
| L_A235 | | CD_3 | Me | H | H | H | H | H |
| L_A236 | | CD_3 | H | Me | H | H | H | H |
| L_A237 | | CD_3 | H | H | Me | H | H | H |
| L_A238 | | CD_3 | H | H | H | Me | H | H |
| L_A239 | | CD_3 | CD_3 | H | H | H | H | H |
| L_A240 | | CD_3 | H | CD_3 | H | H | H | H |
| L_A241 | | CD_3 | H | H | CD_3 | H | H | H |
| L_A242 | | CD_3 | H | H | H | CD_3 | H | H |
| L_A243 | | CD_3 | ^iPr | H | H | H | H | H |
| L_A244 | | CD_3 | H | ^iPr | H | H | H | H |
| L_A245 | | CD_3 | H | H | ^iPr | H | H | H |
| L_A246 | | CD_3 | H | H | H | ^iPr | H | H |
| L_A247 | | CD_3 | Ph | H | H | H | H | H |
| L_A248 | | CD_3 | H | Ph | H | H | H | H |
| L_A249 | | CD_3 | H | H | Ph | H | H | H |
| L_A250 | | CD_3 | H | H | H | Ph | H | H |
| L_A251 | | ^iPr | Me | H | H | H | H | H |
| L_A252 | | ^iPr | H | Me | H | H | H | H |
| L_A253 | | ^iPr | H | H | Me | H | H | H |
| L_A254 | | ^iPr | H | H | H | Me | H | H |
| L_A255 | | ^iPr | CD_3 | H | H | H | H | H |
| L_A256 | | ^iPr | H | CD_3 | H | H | H | H |
| L_A257 | | ^iPr | H | H | CD_3 | H | H | H |
| L_A258 | | ^iPr | H | H | H | CD_3 | H | H |
| L_A259 | | ^iPr | ^iPr | H | H | H | H | H |
| L_A260 | | ^iPr | H | ^iPr | H | H | H | H |
| L_A261 | | ^iPr | H | H | ^iPr | H | H | H |
| L_A262 | | ^iPr | H | H | H | ^iPr | H | H |
| L_A263 | | ^iPr | Ph | H | H | H | H | H |
| L_A264 | | ^iPr | H | Ph | H | H | H | H |
| L_A265 | | ^iPr | H | H | Ph | H | H | H |
| L_A266 | | ^iPr | H | H | H | Ph | H | H |
| L_A267 | | Ph | Me | H | H | H | H | H |
| L_A268 | Et,Et-C(−C^1b)(−C^1e) structure | Ph | H | Me | H | H | H | H |
| L_A269 | | Ph | H | H | Me | H | H | H |
| L_A270 | | Ph | H | H | H | Me | H | H |
| L_A271 | | Ph | CD_3 | H | H | H | H | H |
| L_A272 | | Ph | H | CD_3 | H | H | H | H |
| L_A273 | | Ph | H | H | CD_3 | H | H | H |
| L_A274 | | Ph | H | H | H | CD_3 | H | H |
| L_A275 | | Ph | ^iPr | H | H | H | H | H |
| L_A276 | | Ph | H | ^iPr | H | H | H | H |
| L_A277 | | Ph | H | H | ^iPr | H | H | H |
| L_A278 | | Ph | H | H | H | ^iPr | H | H |
| L_A279 | | Ph | Ph | H | H | H | H | H |
| L_A280 | | Ph | H | Ph | H | H | H | H |
| L_A281 | | Ph | H | H | Ph | H | H | H |
| L_A282 | | Ph | H | H | H | Ph | H | H |
| L_A283 | | H | Me | Me | H | H | H | H |
| L_A284 | | H | Me | H | Me | H | H | H |
| L_A285 | | H | Me | H | H | Me | H | H |
| L_A286 | | H | Me | CD_3 | H | H | H | H |
| L_A287 | | H | Me | H | CD_3 | H | H | H |
| L_A288 | | H | Me | H | H | CD_3 | H | H |
| L_A289 | | H | Me | ^iPr | H | H | H | H |
| L_A290 | | H | Me | H | ^iPr | H | H | H |
| L_A291 | | H | Me | H | H | ^iPr | H | H |
| L_A292 | | H | Me | Ph | H | H | H | H |
| L_A293 | | H | Me | H | Ph | H | H | H |
| L_A294 | | H | Me | H | H | Ph | H | H |
| L_A295 | | H | CD_3 | Me | H | H | H | H |
| L_A296 | | H | CD_3 | H | Me | H | H | H |
| L_A297 | | H | CD_3 | H | H | Me | H | H |
| L_A298 | | H | CD_3 | CD_3 | H | H | H | H |
| L_A299 | | H | CD_3 | H | CD_3 | H | H | H |
| L_A300 | | H | CD_3 | H | H | CD_3 | H | H |
| L_A301 | | H | CD_3 | ^iPr | H | H | H | H |
| L_A302 | | H | CD_3 | H | ^iPr | H | H | H |
| L_A303 | | H | CD_3 | H | H | ^iPr | H | H |
| L_A304 | | H | ^iPr | Ph | H | H | H | H |
| L_A305 | | H | CD_3 | H | Ph | H | H | H |
| L_A306 | | H | CD_3 | H | H | Ph | H | H |
| L_A307 | | H | ^iPr | Me | H | H | H | H |
| L_A308 | | H | ^iPr | H | Me | H | H | H |
| L_A309 | | H | ^iPr | H | H | Me | H | H |
| L_A310 | | H | ^iPr | CD_3 | H | H | H | H |
| L_A311 | | H | ^iPr | H | CD_3 | H | H | H |
| L_A312 | | H | ^iPr | H | H | CD_3 | H | H |
| L_A313 | | H | ^iPr | ^iPr | H | H | H | H |
| L_A314 | | H | ^iPr | H | ^iPr | H | H | H |
| L_A315 | | H | ^iPr | H | H | ^iPr | H | H |
| L_A316 | | H | ^iPr | Ph | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$317 | | H | $^i$Pr | H | Ph | H | H | H |
| $L_A$318 | | H | $^i$Pr | H | H | Ph | H | H |
| $L_A$319 | | H | Ph | Me | H | H | H | H |
| $L_A$320 | | H | Ph | H | Me | H | H | H |
| $L_A$321 | | H | Ph | H | H | Me | H | H |
| $L_A$322 | | H | Ph | CD$_3$ | H | H | H | H |
| $L_A$323 | 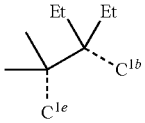 | H | Ph | H | CD$_3$ | H | H | H |
| $L_A$324 | | H | Ph | H | H | CD$_3$ | H | H |
| $L_A$325 | | H | Ph | $^i$Pr | H | H | H | H |
| $L_A$326 | | H | Ph | H | $^i$Pr | H | H | H |
| $L_A$327 | | H | Ph | H | H | $^i$Pr | H | H |
| $L_A$328 | | H | Ph | Ph | H | H | H | H |
| $L_A$329 | | H | Ph | H | Ph | H | H | H |
| $L_A$330 | | H | Ph | H | H | Ph | H | H |
| $L_A$331 | | H | H | Me | Me | H | H | H |
| $L_A$332 | | H | H | CD$_3$ | Me | H | H | H |
| $L_A$333 | | H | H | $^i$Pr | Me | H | H | H |
| $L_A$334 | | H | H | Ph | Me | H | H | H |
| $L_A$335 | | H | H | Me | CD$_3$ | H | H | H |
| $L_A$336 | | H | H | CD$_3$ | CD$_3$ | H | H | H |
| $L_A$337 | | H | H | $^i$Pr | CD$_3$ | H | H | H |
| $L_A$338 | | H | H | Ph | CD$_3$ | H | H | H |
| $L_A$339 | | H | H | Me | $^i$Pr | H | H | H |
| $L_A$340 | | H | H | CD$_3$ | $^i$Pr | H | H | H |
| $L_A$341 | | H | H | $^i$Pr | $^i$Pr | H | H | H |
| $L_A$342 | | H | H | $^i$Pr | $^i$Pr | H | H | H |
| $L_A$343 | | H | H | Me | Ph | H | H | H |
| $L_A$344 | | H | H | CD$_3$ | Ph | H | H | H |
| $L_A$345 | | H | H | $^i$Pr | Ph | H | H | H |
| $L_A$346 | | H | H | Ph | Ph | H | H | H |
| $L_A$347 | | H | H | Me | H | Me | H | H |
| $L_A$348 | | H | H | CD$_3$ | H | Me | H | H |
| $L_A$349 | | H | H | $^i$Pr | H | Me | H | H |
| $L_A$350 | | H | H | Ph | H | Me | H | H |
| $L_A$351 | | H | H | Me | H | CD$_3$ | H | H |
| $L_A$352 | | H | H | CD$_3$ | H | CD$_3$ | H | H |
| $L_A$353 | | H | H | $^i$Pr | H | CD$_3$ | H | H |
| $L_A$354 | | H | H | Ph | H | CD$_3$ | H | H |
| $L_A$355 | | H | H | Me | H | $^i$Pr | H | H |
| $L_A$356 | | H | H | CD$_3$ | H | $^i$Pr | H | H |
| $L_A$357 | | H | H | $^i$Pr | H | $^i$Pr | H | H |
| $L_A$358 | | H | H | Ph | H | $^i$Pr | H | H |
| $L_A$359 | | H | H | Me | H | Ph | H | H |
| $L_A$360 | | H | H | CD$_3$ | H | Ph | H | H |
| $L_A$361 | | H | H | $^i$Pr | H | Ph | H | H |
| $L_A$362 | | H | H | Ph | H | Ph | H | H |
| $L_A$363 | | Me | Me | H | Me | H | H | H |
| $L_A$364 | | H | Me | Me | Me | H | H | H |
| $L_A$365 | | CD$_3$ | Me | H | Me | H | H | H |
| $L_A$366 | | H | Me | CD$_3$ | Me | H | H | H |
| $L_A$367 | | $^i$Pr | Me | H | Me | H | H | H |
| $L_A$368 | | H | Me | $^i$Pr | Me | H | H | H |
| $L_A$369 | | Ph | Me | H | Me | H | H | H |
| $L_A$370 | | H | Me | Ph | Me | H | H | H |
| $L_A$371 | | Me | CD$_3$ | H | CD$_3$ | H | H | H |
| $L_A$372 | | H | CD$_3$ | Me | CD$_3$ | H | H | H |
| $L_A$373 | | CD$_3$ | CD$_3$ | H | CD$_3$ | H | H | H |
| $L_A$374 | | H | CD$_3$ | CD$_3$ | CD$_3$ | H | H | H |
| $L_A$375 | | $^i$Pr | CD$_3$ | H | CD$_3$ | H | H | H |
| $L_A$376 | | H | CD$_3$ | $^i$Pr | CD$_3$ | H | H | H |
| $L_A$377 | | Ph | CD$_3$ | H | CD$_3$ | H | H | H |
| $L_A$378 | 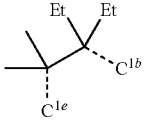 | H | CD$_3$ | Ph | CD$_3$ | H | H | H |
| $L_A$379 | | Me | $^i$Pr | H | $^i$Pr | H | H | H |
| $L_A$380 | | H | $^i$Pr | Me | $^i$Pr | H | H | H |
| $L_A$381 | | CD$_3$ | $^i$Pr | H | $^i$Pr | H | H | H |
| $L_A$382 | | H | $^i$Pr | CD$_3$ | $^i$Pr | H | H | H |
| $L_A$383 | | $^i$Pr | $^i$Pr | H | $^i$Pr | H | H | H |
| $L_A$384 | | H | $^i$Pr | $^i$Pr | $^i$Pr | H | H | H |
| $L_A$385 | | Ph | $^i$Pr | H | $^i$Pr | H | H | H |
| $L_A$386 | | H | $^i$Pr | Ph | $^i$Pr | H | H | H |
| $L_A$387 | | Me | Ph | H | Ph | H | H | H |
| $L_A$388 | | H | Ph | Me | Ph | H | H | H |
| $L_A$389 | | CD$_3$ | Ph | H | Ph | H | H | H |
| $L_A$390 | | H | Ph | CD$_3$ | Ph | H | H | H |
| $L_A$391 | | $^i$Pr | Ph | H | Ph | H | H | H |
| $L_A$392 | | H | Ph | $^i$Pr | Ph | H | H | H |
| $L_A$393 | | Ph | Ph | H | Ph | H | H | H |
| $L_A$394 | | H | Ph | Ph | Ph | H | H | H |
| $L_A$395 |  | H | H | H | H | H | H | H |
| $L_A$396 | | Me | H | H | H | H | H | H |
| $L_A$397 | | H | Me | H | H | H | H | H |
| $L_A$398 | | H | H | Me | H | H | H | H |
| $L_A$399 | | H | H | H | Me | H | H | H |
| $L_A$400 | | H | H | H | H | Me | H | H |
| $L_A$401 | | CD$_3$ | H | H | H | H | H | H |
| $L_A$402 | | H | CD$_3$ | H | H | H | H | H |
| $L_A$403 | | H | H | CD$_3$ | H | H | H | H |
| $L_A$404 | | H | H | H | CD$_3$ | H | H | H |
| $L_A$405 | | H | H | H | H | CD$_3$ | H | H |
| $L_A$406 | | $^i$Pr | H | H | H | H | H | H |
| $L_A$407 | | H | $^i$Pr | H | H | H | H | H |
| $L_A$408 | | H | H | $^i$Pr | H | H | H | H |
| $L_A$409 | | H | H | H | $^i$Pr | H | H | H |
| $L_A$410 | | H | H | H | H | $^i$Pr | H | H |
| $L_A$411 | | Ph | H | H | H | H | H | H |
| $L_A$412 | | H | Ph | H | H | H | H | H |
| $L_A$413 | | H | H | Ph | H | H | H | H |
| $L_A$414 | | H | H | H | Ph | H | H | H |
| $L_A$415 | | H | H | H | H | Ph | H | H |
| $L_A$416 | | Me | Me | H | H | H | H | H |
| $L_A$417 | | Me | H | Me | H | H | H | H |
| $L_A$418 | | Me | H | H | Me | H | H | H |
| $L_A$419 | | Me | H | H | H | Me | H | H |
| $L_A$420 | | Me | CD$_3$ | H | H | H | H | H |
| $L_A$421 | | Me | H | CD$_3$ | H | H | H | H |
| $L_A$422 | | Me | H | H | CD$_3$ | H | H | H |
| $L_A$423 | | Me | H | H | H | CD$_3$ | H | H |
| $L_A$424 | | Me | $^i$Pr | H | H | H | H | H |
| $L_A$425 | | Me | H | $^i$Pr | H | H | H | H |
| $L_A$426 | | Me | H | H | $^i$Pr | H | H | H |
| $L_A$427 | | Me | H | H | H | $^i$Pr | H | H |
| $L_A$428 | | Me | Ph | H | H | H | H | H |
| $L_A$429 | | Me | H | Ph | H | H | H | H |
| $L_A$430 | | Me | H | H | Ph | H | H | H |
| $L_A$431 | | Me | H | H | H | Ph | H | H |
| $L_A$432 | | CD$_3$ | Me | H | H | H | H | H |
| $L_A$433 | | CD$_3$ | H | Me | H | H | H | H |
| $L_A$434 | | CD$_3$ | H | H | Me | H | H | H |
| $L_A$435 | | CD$_3$ | H | H | H | Me | H | H |
| $L_A$436 | | CD$_3$ | CD$_3$ | H | H | H | H | H |
| $L_A$437 | | CD$_3$ | H | CD$_3$ | H | H | H | H |
| $L_A$438 | | CD$_3$ | H | H | CD$_3$ | H | H | H |
| $L_A$439 | | CD$_3$ | H | H | H | CD$_3$ | H | H |
| $L_A$440 | | CD$_3$ | $^i$Pr | H | H | H | H | H |
| $L_A$441 | | CD$_3$ | H | $^i$Pr | H | H | H | H |
| $L_A$442 | | CD$_3$ | H | H | $^i$Pr | H | H | H |
| $L_A$443 | | CD$_3$ | H | H | H | $^i$Pr | H | H |
| $L_A$444 | | CD$_3$ | Ph | H | H | H | H | H |
| $L_A$445 | | CD$_3$ | H | Ph | H | H | H | H |
| $L_A$446 | | CD$_3$ | H | H | Ph | H | H | H |
| $L_A$447 | | CD$_3$ | H | H | H | Ph | H | H |
| $L_A$448 | | $^i$Pr | Me | H | H | H | H | H |
| $L_A$449 | | $^i$Pr | H | Me | H | H | H | H |
| $L_A$450 | | $^i$Pr | H | H | Me | H | H | H |
| $L_A$451 | | $^i$Pr | H | H | H | Me | H | H |
| $L_A$452 | | $^i$Pr | CD$_3$ | H | H | H | H | H |
| $L_A$453 | | $^i$Pr | H | CD$_3$ | H | H | H | H |
| $L_A$454 | | $^i$Pr | H | H | CD$_3$ | H | H | H |
| $L_A$455 | | $^i$Pr | H | H | H | CD$_3$ | H | H |
| $L_A$456 | | $^i$Pr | $^i$Pr | H | H | H | H | H |
| $L_A$457 | | $^i$Pr | H | $^i$Pr | H | H | H | H |
| $L_A$458 | | $^i$Pr | H | H | $^i$Pr | H | H | H |
| $L_A$459 | | $^i$Pr | H | H | H | $^i$Pr | H | H |
| $L_A$460 | | $^i$Pr | Ph | H | H | H | H | H |
| $L_A$461 | | $^i$Pr | H | Ph | H | H | H | H |
| $L_A$462 | | $^i$Pr | H | H | Ph | H | H | H |
| $L_A$463 | | $^i$Pr | H | H | H | Ph | H | H |
| $L_A$464 | | Ph | Me | H | H | H | H | H |
| $L_A$465 | | Ph | H | Me | H | H | H | H |
| $L_A$466 | | Ph | H | H | Me | H | H | H |
| $L_A$467 | | Ph | H | H | H | Me | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A468$ | | Ph | CD₃ | H | H | H | H | H |
| $L_A469$ | | Ph | H | CD₃ | H | H | H | H |
| $L_A470$ | | Ph | H | H | CD₃ | H | H | H |
| $L_A471$ | | Ph | H | H | H | CD₃ | H | H |
| $L_A472$ | | Ph | ⁱPr | H | H | H | H | H |
| $L_A473$ | | Ph | H | ⁱPr | H | H | H | H |
| $L_A474$ | | Ph | H | H | ⁱPr | H | H | H |
| $L_A475$ | | Ph | H | H | H | ⁱPr | H | H |
| $L_A476$ | | Ph | Ph | H | H | H | H | H |
| $L_A477$ | | Ph | H | Ph | H | H | H | H |
| $L_A478$ | | Ph | H | H | Ph | H | H | H |
| $L_A479$ | | Ph | H | H | H | Ph | H | H |
| $L_A480$ | | H | Me | Me | H | H | H | H |
| $L_A481$ | | H | Me | H | Me | H | H | H |
| $L_A482$ | | H | Me | H | H | Me | H | H |
| $L_A483$ | | H | Me | CD₃ | H | H | H | H |
| $L_A484$ | | H | Me | H | CD₃ | H | H | H |
| $L_A485$ | | H | Me | H | H | CD₃ | H | H |
| $L_A486$ | | H | Me | ⁱPr | H | H | H | H |
| $L_A487$ | | H | Me | H | ⁱPr | H | H | H |
| $L_A488$ | | H | Me | H | H | ⁱPr | H | H |
| $L_A489$ | | H | Me | Ph | H | H | H | H |
| $L_A490$ | | H | Me | H | Ph | H | H | H |
| $L_A491$ | | H | Me | H | H | Ph | H | H |
| $L_A492$ | | H | CD₃ | Me | H | H | H | H |
| $L_A493$ | | H | CD₃ | H | Me | H | H | H |
| $L_A494$ | | H | CD₃ | H | H | Me | H | H |
| $L_A495$ | | H | CD | CD₃ | H | H | H | H |
| $L_A496$ | | H | CD₃ | H | CD₃ | H | H | H |
| $L_A497$ | | H | CD₃ | H | H | CD₃ | H | H |
| $L_A498$ | | H | CD₃ | ⁱPr | H | H | H | H |
| $L_A499$ | | H | ⁱPr | ⁱPr | H | H | H | H |
| $L_A500$ | | H | CD₃ | H | ⁱPr | H | H | H |
| $L_A501$ | | H | CD₃ | Ph | H | H | H | H |
| $L_A502$ | | H | CD₃ | H | Ph | H | H | H |
| $L_A503$ | | H | CD₃ | H | H | Ph | H | H |
| $L_A504$ | | H | ⁱPr | Me | H | H | H | H |
| $L_A505$ | | H | ⁱPr | H | Me | H | H | H |
| $L_A506$ | | H | ⁱPr | H | H | Me | H | H |
| $L_A507$ | | H | ⁱPr | CD₃ | H | H | H | H |
| $L_A508$ | | H | ⁱPr | H | CD₃ | H | H | H |
| $L_A509$ | | H | ⁱPr | H | H | CD₃ | H | H |
| $L_A510$ | | H | ⁱPr | ⁱPr | H | H | H | H |
| $L_A511$ | | H | ⁱPr | H | ⁱPr | H | H | H |
| $L_A512$ | | H | ⁱPr | H | H | ⁱPr | H | H |
| $L_A513$ | | H | ⁱPr | Ph | H | H | H | H |
| $L_A514$ | | H | ⁱPr | H | Ph | H | H | H |
| $L_A515$ | | H | ⁱPr | H | H | Ph | H | H |
| $L_A516$ | | H | Ph | Me | H | H | H | H |
| $L_A517$ | | H | Ph | H | Me | H | H | H |
| $L_A518$ | | H | Ph | H | H | Me | H | H |
| $L_A519$ | | H | Ph | CD₃ | H | H | H | H |
| $L_A520$ | | H | Ph | H | CD₃ | H | H | H |
| $L_A521$ | | H | Ph | H | H | CD₃ | H | H |
| $L_A522$ | | H | Ph | ⁱPr | H | H | H | H |
| $L_A523$ | | H | Ph | H | ⁱPr | H | H | H |
| $L_A524$ | | H | Ph | H | H | ⁱPr | H | H |
| $L_A525$ | | H | Ph | Ph | H | H | H | H |
| $L_A526$ | | H | Ph | H | Ph | H | H | H |
| $L_A527$ | | H | Ph | H | H | Ph | H | H |
| $L_A528$ | | H | Me | Me | H | H | H | H |
| $L_A529$ | | H | H | CD₃ | Me | H | H | H |
| $L_A530$ | | H | H | ⁱPr | Me | H | H | H |
| $L_A531$ | | H | H | Ph | Me | H | H | H |
| $L_A532$ | | H | H | Me | CD₃ | H | H | H |
| $L_A533$ | | H | H | CD₃ | CD₃ | H | H | H |
| $L_A534$ | | H | H | ⁱPr | CD₃ | H | H | H |
| $L_A535$ | | H | H | Ph | CD₃ | H | H | H |
| $L_A536$ | | H | H | Me | ⁱPr | H | H | H |
| $L_A537$ | | H | H | CD₃ | ⁱPr | H | H | H |
| $L_A538$ | | H | H | ⁱPr | ⁱPr | H | H | H |
| $L_A539$ | | H | H | Ph | ⁱPr | H | H | H |
| $L_A540$ | | H | H | Me | Ph | H | H | H |
| $L_A541$ | | H | H | CD₃ | Ph | H | H | H |
| $L_A542$ | | H | H | ⁱPr | Ph | H | H | H |
| $L_A543$ | cyclohexyl linker ($C^{1b}$, $C^{1e}$) | H | H | Ph | Ph | H | H | H |
| $L_A544$ | | H | H | Me | H | Me | H | H |
| $L_A545$ | | H | H | CD₃ | H | Me | H | H |
| $L_A546$ | | H | H | ⁱPr | H | Me | H | H |
| $L_A547$ | | H | H | Ph | H | Me | H | H |
| $L_A548$ | | H | H | Me | H | CD₃ | H | H |
| $L_A549$ | | H | H | CD₃ | H | CD₃ | H | H |
| $L_A550$ | | H | H | ⁱPr | H | CD₃ | H | H |
| $L_A551$ | | H | H | Ph | H | CD₃ | H | H |
| $L_A552$ | | H | H | Me | H | ⁱPr | H | H |
| $L_A553$ | | H | H | CD₃ | H | ⁱPr | H | H |
| $L_A554$ | | H | H | ⁱPr | H | ⁱPr | H | H |
| $L_A555$ | | H | H | Ph | H | ⁱPr | H | H |
| $L_A556$ | | H | H | Me | H | Ph | H | H |
| $L_A557$ | | H | H | CD₃ | H | Ph | H | H |
| $L_A558$ | | H | H | ⁱPr | H | Ph | H | H |
| $L_A559$ | | H | H | Ph | H | Ph | H | H |
| $L_A560$ | | Me | Me | H | Me | H | H | H |
| $L_A561$ | | H | Me | Me | Me | H | H | H |
| $L_A562$ | | CD₃ | Me | H | Me | H | H | H |
| $L_A563$ | | H | Me | CD₃ | Me | H | H | H |
| $L_A564$ | | ⁱPr | Me | H | Me | H | H | H |
| $L_A565$ | | H | Me | ⁱPr | Me | H | H | H |
| $L_A566$ | | Ph | Me | H | Me | H | H | H |
| $L_A567$ | | H | Me | Ph | Me | H | H | H |
| $L_A568$ | | Me | CD₃ | H | CD₃ | H | H | H |
| $L_A569$ | | H | CD₃ | Me | CD₃ | H | H | H |
| $L_A570$ | | CD₃ | CD₃ | H | CD₃ | H | H | H |
| $L_A571$ | | H | CD₃ | CD₃ | CD₃ | H | H | H |
| $L_A572$ | | ⁱPr | CD₃ | H | CD₃ | H | H | H |
| $L_A573$ | | H | CD₃ | ⁱPr | CD₃ | H | H | H |
| $L_A574$ | | Ph | CD₃ | H | CD₃ | H | H | H |
| $L_A575$ | | H | CD₃ | Ph | CD₃ | H | H | H |
| $L_A576$ | | Me | ⁱPr | H | ⁱPr | H | H | H |
| $L_A577$ | | H | ⁱPr | Me | ⁱPr | H | H | H |
| $L_A578$ | | CD₃ | ⁱPr | H | ⁱPr | H | H | H |
| $L_A579$ | | H | ⁱPr | CD₃ | ⁱPr | H | H | H |
| $L_A580$ | | ⁱPr | ⁱPr | H | ⁱPr | H | H | H |
| $L_A581$ | | H | ⁱPr | ⁱPr | ⁱPr | H | H | H |
| $L_A582$ | | Ph | ⁱPr | H | ⁱPr | H | H | H |
| $L_A583$ | | H | ⁱPr | Ph | ⁱPr | H | H | H |
| $L_A584$ | | Me | Ph | H | Ph | H | H | H |
| $L_A585$ | | H | Ph | Me | Ph | H | H | H |
| $L_A586$ | | CD₃ | Ph | H | Ph | H | H | H |
| $L_A587$ | | H | Ph | CD₃ | Ph | H | H | H |
| $L_A588$ | | ⁱPr | Ph | H | Ph | H | H | H |
| $L_A589$ | | H | Ph | ⁱPr | Ph | H | H | H |
| $L_A590$ | | Ph | Ph | H | Ph | H | H | H |
| $L_A591$ | | H | Ph | Ph | Ph | H | H | H |
| $L_A592$ | dibenzyl-substituted linker ($C^{1b}$, $C^{1e}$, Bn, Bn) | H | H | H | H | H | H | H |
| $L_A593$ | | Me | H | H | H | H | H | H |
| $L_A594$ | | H | Me | H | H | H | H | H |
| $L_A595$ | | H | H | Me | H | H | H | H |
| $L_A596$ | | H | H | H | Me | H | H | H |
| $L_A597$ | | H | H | H | H | Me | H | H |
| $L_A598$ | dibenzyl-substituted linker ($C^{1b}$, $C^{1e}$, Bn, Bn) | CD₃ | H | H | H | H | H | H |
| $L_A599$ | | H | CD₃ | H | H | H | H | H |
| $L_A600$ | | H | H | CD₃ | H | H | H | H |
| $L_A601$ | | H | H | H | CD₃ | H | H | H |
| $L_A602$ | | H | H | H | H | CD₃ | H | H |
| $L_A603$ | | ⁱPr | H | H | H | H | H | H |
| $L_A604$ | | H | ⁱPr | H | H | H | H | H |
| $L_A605$ | | H | H | ⁱPr | H | H | H | H |
| $L_A606$ | | H | H | H | ⁱPr | H | H | H |
| $L_A607$ | | H | H | H | H | ⁱPr | H | H |
| $L_A608$ | | Ph | H | H | H | H | H | H |
| $L_A609$ | | H | Ph | H | H | H | H | H |
| $L_A610$ | | H | H | Ph | H | H | H | H |
| $L_A611$ | | H | H | H | Ph | H | H | H |
| $L_A612$ | | H | H | H | H | Ph | H | H |
| $L_A613$ | | Me | Me | H | H | H | H | H |
| $L_A614$ | | Me | H | Me | H | H | H | H |
| $L_A615$ | | Me | H | H | Me | H | H | H |
| $L_A616$ | | Me | H | H | H | Me | H | H |
| $L_A617$ | | Me | CD₃ | H | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A618$ | | Me | H | CD$_3$ | H | H | H | H |
| $L_A619$ | | Me | H | H | CD$_3$ | H | H | H |
| $L_A620$ | | Me | H | H | H | CD$_3$ | H | H |
| $L_A621$ | | Me | $^i$Pr | H | H | H | H | H |
| $L_A622$ | | Me | H | $^i$Pr | H | H | H | H |
| $L_A623$ | | Me | H | H | $^i$Pr | H | H | H |
| $L_A624$ | | Me | H | H | H | $^i$Pr | H | H |
| $L_A625$ | | Me | Ph | H | H | H | H | H |
| $L_A626$ | | Me | H | Ph | H | H | H | H |
| $L_A627$ | | Me | H | H | Ph | H | H | H |
| $L_A628$ | | Me | H | H | H | Ph | H | H |
| $L_A629$ | | CD$_3$ | Me | H | H | H | H | H |
| $L_A630$ | | CD$_3$ | H | Me | H | H | H | H |
| $L_A631$ | | CD$_3$ | H | H | Me | H | H | H |
| $L_A632$ | | CD$_3$ | H | H | H | Me | H | H |
| $L_A633$ | | CD$_3$ | CD$_3$ | H | H | H | H | H |
| $L_A634$ | | CD$_3$ | H | CD$_3$ | H | H | H | H |
| $L_A635$ | | CD$_3$ | H | H | CD$_3$ | H | H | H |
| $L_A636$ | | CD$_3$ | H | H | H | CD$_3$ | H | H |
| $L_A637$ | | CD$_3$ | $^i$Pr | H | H | H | H | H |
| $L_A638$ | | CD$_3$ | H | $^i$Pr | H | H | H | H |
| $L_A639$ | | CD$_3$ | H | H | $^i$Pr | H | H | H |
| $L_A640$ | | CD$_3$ | H | H | H | $^i$Pr | H | H |
| $L_A641$ | | CD$_3$ | Ph | H | H | H | H | H |
| $L_A642$ | | CD$_3$ | H | Ph | H | H | H | H |
| $L_A643$ | | CD$_3$ | H | H | Ph | H | H | H |
| $L_A644$ | | CD$_3$ | H | H | H | Ph | H | H |
| $L_A645$ | | $^i$Pr | Me | H | H | H | H | H |
| $L_A646$ | | $^i$Pr | H | Me | H | H | H | H |
| $L_A647$ | | $^i$Pr | H | H | Me | H | H | H |
| $L_A648$ | | $^i$Pr | H | H | H | Me | H | H |
| $L_A649$ | | $^i$Pr | CD$_3$ | H | H | H | H | H |
| $L_A650$ | | $^i$Pr | H | CD$_3$ | H | H | H | H |
| $L_A651$ | | $^i$Pr | H | H | CD$_3$ | H | H | H |
| $L_A652$ | | $^i$Pr | H | H | H | CD$_3$ | H | H |
| $L_A653$ | Bn-C(Bn)($C^{1b}$)-$C^{1e}$ | $^i$Pr | $^i$Pr | H | H | H | H | H |
| $L_A654$ | | $^i$Pr | H | $^i$Pr | H | H | H | H |
| $L_A655$ | | $^i$Pr | H | H | $^i$Pr | H | H | H |
| $L_A656$ | | $^i$Pr | H | H | H | $^i$Pr | H | H |
| $L_A657$ | | $^i$Pr | Ph | H | H | H | H | H |
| $L_A658$ | | $^i$Pr | H | Ph | H | H | H | H |
| $L_A659$ | | $^i$Pr | H | H | Ph | H | H | H |
| $L_A660$ | | $^i$Pr | H | H | H | Ph | H | H |
| $L_A661$ | | Ph | Me | H | H | H | H | H |
| $L_A662$ | | Ph | H | Me | H | H | H | H |
| $L_A663$ | | Ph | H | H | Me | H | H | H |
| $L_A664$ | | Ph | H | H | H | Me | H | H |
| $L_A665$ | | Ph | CD$_3$ | H | H | H | H | H |
| $L_A666$ | | Ph | H | CD$_3$ | H | H | H | H |
| $L_A667$ | | Ph | H | H | CD$_3$ | H | H | H |
| $L_A668$ | | Ph | H | H | H | CD$_3$ | H | H |
| $L_A669$ | | Ph | $^i$Pr | H | H | H | H | H |
| $L_A670$ | | Ph | H | $^i$Pr | H | H | H | H |
| $L_A671$ | | Phh | H | H | $^i$Pr | H | H | H |
| $L_A672$ | | Ph | H | H | H | $^i$Pr | H | H |
| $L_A673$ | | Ph | Ph | H | H | H | H | H |
| $L_A674$ | | Ph | H | Ph | H | H | H | H |
| $L_A675$ | | Ph | H | H | Ph | H | H | H |
| $L_A676$ | | Ph | H | H | H | Ph | H | H |
| $L_A677$ | | H | Me | Me | H | H | H | H |
| $L_A678$ | | H | Me | H | Me | H | H | H |
| $L_A679$ | | H | Me | H | H | Me | H | H |
| $L_A680$ | | H | Me | CD$_3$ | H | H | H | H |
| $L_A681$ | | H | Me | H | CD$_3$ | H | H | H |
| $L_A682$ | | H | Me | H | H | CD$_3$ | H | H |
| $L_A683$ | | H | Me | $^i$Pr | H | H | H | H |
| $L_A684$ | | H | Me | H | $^i$Pr | H | H | H |
| $L_A685$ | | H | Me | H | H | $^i$Pr | H | H |
| $L_A686$ | | H | Me | Ph | H | H | H | H |
| $L_A687$ | | H | Me | H | Ph | H | H | H |
| $L_A688$ | | H | Me | H | H | Ph | H | H |
| $L_A689$ | | H | CD$_3$ | Me | H | H | H | H |
| $L_A690$ | | H | CD$_3$ | H | Me | H | H | H |
| $L_A691$ | | H | CD$_3$ | H | H | Me | H | H |
| $L_A692$ | | H | CD$_3$ | CD$_3$ | H | H | H | H |
| $L_A693$ | | H | CD$_3$ | H | CD$_3$ | H | H | H |
| $L_A694$ | | H | CD$_3$ | H | H | CD$_3$ | H | H |
| $L_A695$ | | H | CD$_3$ | $^i$Pr | H | H | H | H |
| $L_A696$ | | H | CD$_3$ | H | $^i$Pr | H | H | H |
| $L_A697$ | | H | CD$_3$ | H | H | $^i$Pr | H | H |
| $L_A698$ | | H | CD$_3$ | Ph | H | H | H | H |
| $L_A699$ | | H | CD$_3$ | H | Ph | H | H | H |
| $L_A700$ | | H | CD$_3$ | H | H | Ph | H | H |
| $L_A701$ | | H | $^i$Pr | Me | H | H | H | H |
| $L_A702$ | | H | $^i$Pr | H | Me | H | H | H |
| $L_A703$ | | H | $^i$Pr | H | H | Me | H | H |
| $L_A704$ | | H | $^i$Pr | CD$_3$ | H | H | H | H |
| $L_A705$ | | H | $^i$Pr | H | CD$_3$ | H | H | H |
| $L_A706$ | | H | $^i$Pr | H | H | CD$_3$ | H | H |
| $L_A707$ | | H | $^i$Pr | $^i$Pr | H | H | H | H |
| $L_A708$ | Bn-C(Bn)($C^{1b}$)-$C^{1e}$ | H | $^i$Pr | H | $^i$Pr | H | H | H |
| $L_A709$ | | H | $^i$Pr | H | H | $^i$Pr | H | H |
| $L_A710$ | | H | $^i$Pr | Ph | H | H | H | H |
| $L_A711$ | | H | $^i$Pr | H | Ph | H | H | H |
| $L_A712$ | | H | $^i$Pr | H | H | Ph | H | H |
| $L_A713$ | | H | Ph | Me | H | H | H | H |
| $L_A714$ | | H | Ph | H | Me | H | H | H |
| $L_A715$ | | H | Ph | H | H | Me | H | H |
| $L_A716$ | | H | Ph | CD$_3$ | H | H | H | H |
| $L_A717$ | | H | Ph | H | CD$_3$ | H | H | H |
| $L_A718$ | | H | Ph | H | H | CD$_3$ | H | H |
| $L_A719$ | | H | Ph | $^i$Pr | H | H | H | H |
| $L_A720$ | | H | Ph | H | $^i$Pr | H | H | H |
| $L_A721$ | | H | Ph | H | H | $^i$Pr | H | H |
| $L_A722$ | | H | Ph | Ph | H | H | H | H |
| $L_A723$ | | H | Ph | H | Ph | H | H | H |
| $L_A724$ | | H | Ph | H | H | Ph | H | H |
| $L_A725$ | | H | H | Me | Me | H | H | H |
| $L_A726$ | | H | H | CD$_3$ | Me | H | H | H |
| $L_A727$ | | H | H | $^i$Pr | Me | H | H | H |
| $L_A728$ | | H | H | Ph | Me | H | H | H |
| $L_A729$ | | H | H | Me | CD$_3$ | H | H | H |
| $L_A730$ | | H | H | CD$_3$ | CD$_3$ | H | H | H |
| $L_A731$ | | H | H | $^i$Pr | CD$_3$ | H | H | H |
| $L_A732$ | | H | H | Ph | CD$_3$ | H | H | H |
| $L_A733$ | | H | H | Me | $^i$Pr | H | H | H |
| $L_A734$ | | H | H | CD$_3$ | $^i$Pr | H | H | H |
| $L_A735$ | | H | H | $^i$Pr | $^i$Pr | H | H | H |
| $L_A736$ | | H | H | Ph | $^i$Pr | H | H | H |
| $L_A737$ | | H | H | Me | Ph | H | H | H |
| $L_A738$ | | H | H | CD$_3$ | Ph | H | H | H |
| $L_A739$ | | H | H | $^i$Pr | Ph | H | H | H |
| $L_A740$ | | H | H | Ph | Ph | H | H | H |
| $L_A741$ | | H | H | Me | H | Me | H | H |
| $L_A742$ | | H | H | CD$_3$ | H | Me | H | H |
| $L_A743$ | | H | H | $^i$Pr | H | Me | H | H |
| $L_A744$ | | H | H | Ph | H | Me | H | H |
| $L_A745$ | | H | H | Me | H | CD$_3$ | H | H |
| $L_A746$ | | H | H | CD$_3$ | H | CD$_3$ | H | H |
| $L_A747$ | | H | H | $^i$Pr | H | CD$_3$ | H | H |
| $L_A748$ | | H | H | Ph | H | CD$_3$ | H | H |
| $L_A749$ | | H | H | Me | H | $^i$Pr | H | H |
| $L_A750$ | | H | H | CD$_3$ | H | $^i$Pr | H | H |
| $L_A751$ | | H | H | $^i$Pr | H | $^i$Pr | H | H |
| $L_A752$ | | H | H | Ph | H | $^i$Pr | H | H |
| $L_A753$ | | H | H | Me | H | Ph | H | H |
| $L_A754$ | | H | H | CD$_3$ | H | Ph | H | H |
| $L_A755$ | | H | H | $^i$Pr | H | Ph | H | H |
| $L_A756$ | | H | H | Ph | H | Ph | H | H |
| $L_A757$ | | Me | Me | H | Me | H | H | H |
| $L_A758$ | | H | Me | Me | Me | H | H | H |
| $L_A759$ | | CD$_3$ | Me | H | Me | H | H | H |
| $L_A760$ | | H | Me | CD$_3$ | Me | H | H | H |
| $L_A761$ | | $^i$Pr | Me | H | Me | H | H | H |
| $L_A762$ | | H | Me | $^i$Pr | Me | H | H | H |
| $L_A763$ | Bn-C(Bn)($C^{1b}$)-$C^{1e}$ | Ph | Me | H | Me | H | H | H |
| $L_A764$ | | H | Me | Ph | Me | H | H | H |
| $L_A765$ | | Me | CD$_3$ | H | CD$_3$ | H | H | H |
| $L_A766$ | | H | CD$_3$ | Me | CD$_3$ | H | H | H |
| $L_A767$ | | CD$_3$ | CD$_3$ | H | CD$_3$ | H | H | H |
| $L_A768$ | | H | CD$_3$ | CD$_3$ | CD$_3$ | H | H | H |
| $L_A769$ | | $^i$Pr | CD$_3$ | H | CD$_3$ | H | H | H |
| $L_A770$ | | H | CD$_3$ | $^i$Pr | CD$_3$ | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$771 | | Ph | CD₃ | H | CD₃ | H | H | H |
| $L_A$772 | | H | CD₃ | Ph | CD₃ | H | H | H |
| $L_A$773 | | Me | ⁱPr | H | ⁱPr | H | H | H |
| $L_A$774 | | H | ⁱPr | Me | ⁱPr | H | H | H |
| $L_A$775 | | CD₃ | ⁱPr | H | ⁱPr | H | H | H |
| $L_A$776 | | H | ⁱPr | CD₃ | ⁱPr | H | H | H |
| $L_A$777 | | ⁱPr | ⁱPr | H | ⁱPr | H | H | H |
| $L_A$778 | | H | ⁱPr | ⁱPr | ⁱPr | H | H | H |
| $L_A$779 | | Ph | ⁱPr | H | ⁱPr | H | H | H |
| $L_A$780 | | H | ⁱPr | Ph | ⁱPr | H | H | H |
| $L_A$781 | | Me | Ph | H | Ph | H | H | H |
| $L_A$782 | | H | Ph | Me | Ph | H | H | H |
| $L_A$783 | | CD₃ | Ph | H | Ph | H | H | H |
| $L_A$784 | | H | Ph | CD₃ | Ph | H | H | H |
| $L_A$785 | | ⁱPr | Ph | H | Ph | H | H | H |
| $L_A$786 | | H | Ph | ⁱPr | Ph | H | H | H |
| $L_A$787 | | Ph | Ph | H | Ph | H | H | H |
| $L_A$788 | | H | Ph | Ph | Ph | H | H | H |
| $L_A$789 | Ph Ph C¹ᵇ C¹ᵉ | H | H | H | H | H | H | H |
| $L_A$790 | | Me | H | H | H | H | H | H |
| $L_A$791 | | H | Me | H | H | H | H | H |
| $L_A$792 | | H | H | Me | H | H | H | H |
| $L_A$793 | | H | H | H | Me | H | H | H |
| $L_A$794 | | H | H | H | H | Me | H | H |
| $L_A$795 | | CD₃ | H | H | H | H | H | H |
| $L_A$796 | | H | CD₃ | H | H | H | H | H |
| $L_A$797 | | H | H | CD₃ | H | H | H | H |
| $L_A$798 | | H | H | H | CD₃ | H | H | H |
| $L_A$799 | | H | H | H | H | CD₃ | H | H |
| $L_A$800 | | ⁱPr | H | H | H | H | H | H |
| $L_A$801 | | H | ⁱPr | H | H | H | H | H |
| $L_A$802 | | H | H | ⁱPr | H | H | H | H |
| $L_A$803 | | H | H | H | ⁱPr | H | H | H |
| $L_A$804 | | H | H | H | H | ⁱPr | H | H |
| $L_A$805 | | Ph | H | H | H | H | H | H |
| $L_A$806 | | H | Ph | H | H | H | H | H |
| $L_A$807 | | H | H | Ph | H | H | H | H |
| $L_A$808 | | H | H | H | Ph | H | H | H |
| $L_A$809 | | H | H | H | H | Ph | H | H |
| $L_A$810 | | Me | Me | H | H | H | H | H |
| $L_A$811 | | Me | H | Me | H | H | H | H |
| $L_A$812 | | Me | H | H | Me | H | H | H |
| $L_A$813 | | Me | H | H | H | Me | H | H |
| $L_A$814 | | Me | CD₃ | H | H | H | H | H |
| $L_A$815 | | Me | H | CD₃ | H | H | H | H |
| $L_A$816 | | Me | H | H | CD₃ | H | H | H |
| $L_A$817 | | Me | H | H | H | CD₃ | H | H |
| $L_A$818 | Ph Ph C¹ᵇ C¹ᵉ | Me | ⁱPr | H | H | H | H | H |
| $L_A$819 | | Me | H | ⁱPr | H | H | H | H |
| $L_A$820 | | Me | H | H | ⁱPr | H | H | H |
| $L_A$821 | | Me | H | H | H | ⁱPr | H | H |
| $L_A$822 | | Me | Ph | H | H | H | H | H |
| $L_A$823 | | Me | H | Ph | H | H | H | H |
| $L_A$824 | | Me | H | H | Ph | H | H | H |
| $L_A$825 | | Me | H | H | H | Ph | H | H |
| $L_A$826 | | CD₃ | Me | H | H | H | H | H |
| $L_A$827 | | CD₃ | H | Me | H | H | H | H |
| $L_A$828 | | CD₃ | H | H | Me | H | H | H |
| $L_A$829 | | CD₃ | H | H | H | Me | H | H |
| $L_A$830 | | CD₃ | CD₃ | H | H | H | H | H |
| $L_A$831 | | CD₃ | H | CD₃ | H | H | H | H |
| $L_A$832 | | CD₃ | H | H | CD₃ | H | H | H |
| $L_A$833 | | CD₃ | H | H | H | CD₃ | H | H |
| $L_A$834 | | CD₃ | ⁱPr | H | H | H | H | H |
| $L_A$835 | | CD₃ | H | ⁱPr | H | H | H | H |
| $L_A$836 | | CD₃ | H | H | ⁱPr | H | H | H |
| $L_A$837 | | CD₃ | H | H | H | ⁱPr | H | H |
| $L_A$838 | | CD₃ | Ph | H | H | H | H | H |
| $L_A$839 | | CD₃ | H | Ph | H | H | H | H |
| $L_A$840 | | CD₃ | H | H | Ph | H | H | H |
| $L_A$841 | | CD₃ | H | H | H | Ph | H | H |
| $L_A$842 | | ⁱPr | Me | H | H | H | H | H |
| $L_A$843 | | ⁱPr | H | Me | H | H | H | H |
| $L_A$844 | | ⁱPr | H | H | Me | H | H | H |
| $L_A$845 | | ⁱPr | H | H | H | Me | H | H |
| $L_A$846 | | ⁱPr | CD₃ | H | H | H | H | H |
| $L_A$847 | | ⁱPr | H | CD₃ | H | H | H | H |
| $L_A$848 | | ⁱPr | H | H | CD₃ | H | H | H |
| $L_A$849 | | ⁱPr | H | H | H | CD₃ | H | H |
| $L_A$850 | | ⁱPr | ⁱPr | H | H | H | H | H |
| $L_A$851 | | ⁱPr | H | ⁱPr | H | H | H | H |
| $L_A$852 | | ⁱPr | H | H | ⁱPr | H | H | H |
| $L_A$853 | | ⁱPr | H | H | H | ⁱPr | H | H |
| $L_A$854 | | ⁱPr | Ph | H | H | H | H | H |
| $L_A$855 | | ⁱPr | H | Ph | H | H | H | H |
| $L_A$856 | | ⁱPr | H | H | Ph | H | H | H |
| $L_A$857 | | ⁱPr | H | H | H | Ph | H | H |
| $L_A$858 | | Ph | Me | H | H | H | H | H |
| $L_A$859 | | Ph | H | Me | H | H | H | H |
| $L_A$860 | | Ph | H | H | Me | H | H | H |
| $L_A$861 | | Ph | H | H | H | Me | H | H |
| $L_A$862 | | Ph | CD₃ | H | H | H | H | H |
| $L_A$863 | | Ph | H | CD₃ | H | H | H | H |
| $L_A$864 | | Ph | H | H | CD₃ | H | H | H |
| $L_A$865 | | Ph | H | H | H | CD₃ | H | H |
| $L_A$866 | | Ph | ⁱPr | H | H | H | H | H |
| $L_A$867 | | Ph | H | ⁱPr | H | H | H | H |
| $L_A$868 | | Ph | H | H | ⁱPr | H | H | H |
| $L_A$869 | | Ph | H | H | H | ⁱPr | H | H |
| $L_A$870 | | Ph | Ph | H | H | H | H | H |
| $L_A$871 | | Ph | H | Ph | H | H | H | H |
| $L_A$872 | | Ph | H | H | Ph | H | H | H |
| $L_A$873 | Ph Ph C¹ᵇ C¹ᵉ | Ph | H | H | H | Ph | H | H |
| $L_A$874 | | H | Me | Me | H | H | H | H |
| $L_A$875 | | H | Me | H | Me | H | H | H |
| $L_A$876 | | H | Me | H | H | Me | H | H |
| $L_A$877 | | H | Me | CD₃ | H | H | H | H |
| $L_A$878 | | H | Me | H | CD₃ | H | H | H |
| $L_A$879 | | H | Me | H | H | CD₃ | H | H |
| $L_A$880 | | H | Me | ⁱPr | H | H | H | H |
| $L_A$881 | | H | Me | H | ⁱPr | H | H | H |
| $L_A$882 | | H | Me | H | H | ⁱPr | H | H |
| $L_A$883 | | H | Me | Ph | H | H | H | H |
| $L_A$884 | | H | Me | H | Ph | H | H | H |
| $L_A$885 | | H | Me | H | H | Ph | H | H |
| $L_A$886 | | H | CD₃ | Me | H | H | H | H |
| $L_A$887 | | H | CD₃ | H | Me | H | H | H |
| $L_A$888 | | H | CD₃ | H | H | Me | H | H |
| $L_A$889 | | H | CD₃ | CD₃ | H | H | H | H |
| $L_A$890 | | H | CD₃ | H | CD₃ | H | H | H |
| $L_A$891 | | H | CD₃ | H | H | CD₃ | H | H |
| $L_A$892 | | H | CD₃ | ⁱPr | H | H | H | H |
| $L_A$893 | | H | CD₃ | H | ⁱPr | H | H | H |
| $L_A$894 | | H | CD₃ | H | H | ⁱPr | H | H |
| $L_A$895 | | H | CD₃ | Ph | H | H | H | H |
| $L_A$896 | | H | CD₃ | H | Ph | H | H | H |
| $L_A$897 | | H | CD₃ | H | H | Ph | H | H |
| $L_A$898 | | H | ⁱPr | Me | H | H | H | H |
| $L_A$899 | | H | ⁱPr | H | Me | H | H | H |
| $L_A$900 | | H | ⁱPr | H | H | Me | H | H |
| $L_A$901 | | H | ⁱPr | CD₃ | H | H | H | H |
| $L_A$902 | | H | ⁱPr | H | CD₃ | H | H | H |
| $L_A$903 | | H | ⁱPr | H | H | CD₃ | H | H |
| $L_A$904 | | H | ⁱPr | ⁱPr | H | H | H | H |
| $L_A$905 | | H | ⁱPr | H | ⁱPr | H | H | H |
| $L_A$906 | | H | ⁱPr | H | H | ⁱPr | H | H |
| $L_A$907 | | H | ⁱPr | Ph | H | H | H | H |
| $L_A$908 | | H | ⁱPr | H | Ph | H | H | H |
| $L_A$909 | | H | ⁱPr | H | H | Ph | H | H |
| $L_A$910 | | H | Ph | Me | H | H | H | H |
| $L_A$911 | | H | Ph | H | Me | H | H | H |
| $L_A$912 | | H | Ph | H | H | Me | H | H |
| $L_A$913 | | H | Ph | CD₃ | H | H | H | H |
| $L_A$914 | | H | Ph | H | CD₃ | H | H | H |
| $L_A$915 | | H | Ph | H | H | CD₃ | H | H |
| $L_A$916 | | H | Ph | ⁱPr | H | H | H | H |
| $L_A$917 | | H | Ph | H | ⁱPr | H | H | H |
| $L_A$918 | | H | Ph | H | H | ⁱPr | H | H |
| $L_A$919 | | H | Ph | Ph | H | H | H | H |
| $L_A$920 | | H | Ph | H | Ph | H | H | H |
| $L_A$921 | | H | Ph | H | H | Ph | H | H |
| $L_A$922 | | H | H | Me | Me | H | H | H |
| $L_A$923 | | H | H | CD₃ | Me | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$924 | | H | H | $^i$Pr | Me | H | H | H |
| $L_A$925 | | H | H | Ph | Me | H | H | H |
| $L_A$926 | | H | H | Me | CD$_3$ | H | H | H |
| $L_A$927 | | H | H | CD$_3$ | CD$_3$ | H | H | H |
| $L_A$928 | Ph Ph / C$^{1b}$ / C$^{1e}$ | H | H | $^i$Pr | CD$_3$ | H | H | H |
| $L_A$929 | | H | H | Ph | CD$_3$ | H | H | H |
| $L_A$930 | | H | H | Me | $^i$Pr | H | H | H |
| $L_A$931 | | H | H | CD$_3$ | $^i$Pr | H | H | H |
| $L_A$932 | | H | H | $^i$Pr | $^i$Pr | H | H | H |
| $L_A$933 | | H | H | Ph | $^i$Pr | H | H | H |
| $L_A$934 | | H | H | Me | Ph | H | H | H |
| $L_A$935 | | H | H | CD$_3$ | Ph | H | H | H |
| $L_A$936 | | H | H | $^i$Pr | Ph | H | H | H |
| $L_A$937 | | H | H | Ph | Ph | H | H | H |
| $L_A$938 | | H | H | Me | H | Me | H | H |
| $L_A$939 | | H | H | CD$_3$ | H | Me | H | H |
| $L_A$940 | | H | H | $^i$Pr | H | Me | H | H |
| $L_A$941 | | H | H | Ph | H | Me | H | H |
| $L_A$942 | | H | H | Me | H | CD$_3$ | H | H |
| $L_A$943 | | H | H | CD$_3$ | H | CD$_3$ | H | H |
| $L_A$944 | | H | H | $^i$Pr | H | CD$_3$ | H | H |
| $L_A$945 | | H | H | Ph | H | CD$_3$ | H | H |
| $L_A$946 | | H | H | Me | H | $^i$Pr | H | H |
| $L_A$947 | | H | H | CD$_3$ | H | $^i$Pr | H | H |
| $L_A$948 | | H | H | $^i$Pr | H | $^i$Pr | H | H |
| $L_A$949 | | H | H | Ph | H | $^i$Pr | H | H |
| $L_A$950 | | H | H | Me | H | Ph | H | H |
| $L_A$951 | | H | H | CD$_3$ | H | Ph | H | H |
| $L_A$952 | | H | H | $^i$Pr | H | Ph | H | H |
| $L_A$953 | | H | H | Ph | H | Ph | H | H |
| $L_A$954 | | Me | Me | H | Me | H | H | H |
| $L_A$955 | | H | Me | Me | Me | H | H | H |
| $L_A$956 | | CD$_3$ | Me | H | Me | H | H | H |
| $L_A$957 | | H | Me | CD$_3$ | Me | H | H | H |
| $L_A$958 | | $^i$Pr | Me | H | Me | H | H | H |
| $L_A$959 | | H | Me | $^i$Pr | Me | H | H | H |
| $L_A$960 | | Ph | Me | H | Me | H | H | H |
| $L_A$961 | | H | Me | Ph | Me | H | H | H |
| $L_A$962 | | Me | CD$_3$ | H | CD$_3$ | H | H | H |
| $L_A$963 | | H | CD$_3$ | Me | CD$_3$ | H | H | H |
| $L_A$964 | | CD$_3$ | CD$_3$ | H | CD$_3$ | H | H | H |
| $L_A$965 | | H | CD$_3$ | CD$_3$ | CD$_3$ | H | H | H |
| $L_A$966 | | $^i$Pr | CD$_3$ | H | CD$_3$ | H | H | H |
| $L_A$967 | | H | CD$_3$ | $^i$Pr | CD$_3$ | H | H | H |
| $L_A$968 | | Ph | CD$_3$ | H | CD$_3$ | H | H | H |
| $L_A$969 | | H | CD$_3$ | Ph | CD$_3$ | H | H | H |
| $L_A$970 | | Me | $^i$Pr | H | $^i$Pr | H | H | H |
| $L_A$971 | | H | $^i$Pr | Me | $^i$Pr | H | H | H |
| $L_A$972 | | CD$_3$ | $^i$Pr | H | $^i$Pr | H | H | H |
| $L_A$973 | | H | $^i$Pr | CD$_3$ | $^i$Pr | H | H | H |
| $L_A$974 | | $^i$Pr | $^i$Pr | H | $^i$Pr | H | H | H |
| $L_A$975 | | H | $^i$Pr | $^i$Pr | $^i$Pr | H | H | H |
| $L_A$976 | | Ph | $^i$Pr | H | $^i$Pr | H | H | H |
| $L_A$977 | | H | $^i$Pr | Ph | $^i$Pr | H | H | H |
| $L_A$978 | | Me | Ph | H | Ph | H | H | H |
| $L_A$979 | | H | Ph | Me | Ph | H | H | H |
| $L_A$980 | | CD$_3$ | Ph | H | Ph | H | H | H |
| $L_A$981 | | H | Ph | CD$_3$ | Ph | H | H | H |
| $L_A$982 | | $^i$Pr | Ph | H | Ph | H | H | H |
| $L_A$983 | Ph Ph / C$^{1b}$ / C$^{1e}$ | H | Ph | $^i$Pr | Ph | H | H | H |
| $L_A$984 | | Ph | Ph | H | Ph | H | H | H |
| $L_A$985 | | H | Ph | Ph | Ph | H | H | H |
| $L_A$986 | D$_3$C CD$_3$ / D$_3$C / C$^{1b}$ / C$^{1e}$ | H | H | H | H | H | H | H |
| $L_A$987 | | Me | H | H | H | H | H | H |
| $L_A$988 | | H | Me | H | H | H | H | H |
| $L_A$989 | | H | H | Me | H | H | H | H |
| $L_A$990 | | H | H | H | Me | H | H | H |
| $L_A$991 | | H | H | H | H | Me | H | H |
| $L_A$992 | | CD$_3$ | H | H | H | H | H | H |
| $L_A$993 | | H | CD$_3$ | H | H | H | H | H |
| $L_A$994 | | H | H | CD$_3$ | H | H | H | H |
| $L_A$995 | | H | H | H | CD$_3$ | H | H | H |
| $L_A$996 | | H | H | H | H | CD$_3$ | H | H |
| $L_A$997 | | $^i$Pr | H | H | H | H | H | H |
| $L_A$998 | | H | $^i$Pr | H | H | H | H | H |
| $L_A$999 | | H | H | $^i$Pr | H | H | H | H |
| $L_A$1000 | | H | H | H | $^i$Pr | H | H | H |
| $L_A$1001 | | H | H | H | H | $^i$Pr | H | H |
| $L_A$1002 | | Ph | H | H | H | H | H | H |
| $L_A$1003 | | H | Ph | H | H | H | H | H |
| $L_A$1004 | | H | H | Ph | H | H | H | H |
| $L_A$1005 | | H | H | H | Ph | H | H | H |
| $L_A$1006 | | H | H | H | H | Ph | H | H |
| $L_A$1007 | | Me | Me | H | H | H | H | H |
| $L_A$1008 | | Me | H | Me | H | H | H | H |
| $L_A$1009 | | Me | H | H | Me | H | H | H |
| $L_A$1010 | | Me | H | H | H | Me | H | H |
| $L_A$1011 | | Me | CD$_3$ | H | H | H | H | H |
| $L_A$1012 | | Me | H | CD$_3$ | H | H | H | H |
| $L_A$1013 | | Me | H | H | CD$_3$ | H | H | H |
| $L_A$1014 | | Me | H | H | H | CD$_3$ | H | H |
| $L_A$1015 | | Me | $^i$Pr | H | H | H | H | H |
| $L_A$1016 | | Me | H | $^i$Pr | H | H | H | H |
| $L_A$1017 | | Me | H | H | $^i$Pr | H | H | H |
| $L_A$1018 | | Me | H | H | H | $^i$Pr | H | H |
| $L_A$1019 | | Me | Ph | H | H | H | H | H |
| $L_A$1020 | | Me | H | Ph | H | H | H | H |
| $L_A$1021 | | Me | H | H | Ph | H | H | H |
| $L_A$1022 | | Me | H | H | H | Ph | H | H |
| $L_A$1023 | | CD$_3$ | Me | H | H | H | H | H |
| $L_A$1024 | | CD$_3$ | H | Me | H | H | H | H |
| $L_A$1025 | | CD$_3$ | H | H | Me | H | H | H |
| $L_A$1026 | | CD$_3$ | H | H | H | Me | H | H |
| $L_A$1027 | | CD$_3$ | CD$_3$ | H | H | H | H | H |
| $L_A$1028 | | CD$_3$ | H | CD$_3$ | H | H | H | H |
| $L_A$1029 | | CD$_3$ | H | H | CD$_3$ | H | H | H |
| $L_A$1030 | | CD$_3$ | H | H | H | CD$_3$ | H | H |
| $L_A$1031 | | CD$_3$ | $^i$Pr | H | H | H | H | H |
| $L_A$1032 | | CD$_3$ | H | $^i$Pr | H | H | H | H |
| $L_A$1033 | | CD$_3$ | H | H | $^i$Pr | H | H | H |
| $L_A$1034 | | CD$_3$ | H | H | H | $^i$Pr | H | H |
| $L_A$1035 | | CD$_3$ | Ph | H | H | H | H | H |
| $L_A$1036 | | CD$_3$ | H | Ph | H | H | H | H |
| $L_A$1037 | | CD$_3$ | H | H | Ph | H | H | H |
| $L_A$1038 | D$_3$C CD$_3$ / D$_3$C / D$_3$C / C$^{1b}$ / C$^{1e}$ | CD$_3$ | H | H | H | Ph | H | H |
| $L_A$1039 | | $^i$Pr | Me | H | H | H | H | H |
| $L_A$1040 | | $^i$Pr | H | Me | H | H | H | H |
| $L_A$1041 | | $^i$Pr | H | H | Me | H | H | H |
| $L_A$1042 | | $^i$Pr | H | H | H | Me | H | H |
| $L_A$1043 | | $^i$Pr | CD$_3$ | H | H | H | H | H |
| $L_A$1044 | | $^i$Pr | H | CD$_3$ | H | H | H | H |
| $L_A$1045 | | $^i$Pr | H | H | CD$_3$ | H | H | H |
| $L_A$1046 | | $^i$Pr | H | H | H | CD$_3$ | H | H |
| $L_A$1047 | | $^i$Pr | $^i$Pr | H | H | H | H | H |
| $L_A$1048 | | $^i$Pr | H | $^i$Pr | H | H | H | H |
| $L_A$1049 | | $^i$Pr | H | H | $^i$Pr | H | H | H |
| $L_A$1050 | | $^i$Pr | H | H | H | $^i$Pr | H | H |
| $L_A$1051 | | $^i$Pr | Ph | H | H | H | H | H |
| $L_A$1052 | | $^i$Pr | H | Ph | H | H | H | H |
| $L_A$1053 | | $^i$Pr | H | H | Ph | H | H | H |
| $L_A$1054 | | $^i$Pr | H | H | H | Ph | H | H |
| $L_A$1055 | | Ph | Me | H | H | H | H | H |
| $L_A$1056 | | Ph | H | Me | H | H | H | H |
| $L_A$1057 | | Ph | H | H | Me | H | H | H |
| $L_A$1058 | | Ph | H | H | H | Me | H | H |
| $L_A$1059 | | Ph | CD$_3$ | H | H | H | H | H |
| $L_A$1060 | | Ph | H | CD$_3$ | H | H | H | H |
| $L_A$1061 | | Ph | H | H | CD$_3$ | H | H | H |
| $L_A$1062 | | Ph | H | H | H | CD$_3$ | H | H |
| $L_A$1063 | | Ph | $^i$Pr | H | H | H | H | H |
| $L_A$1064 | | Ph | H | $^i$Pr | H | H | H | H |
| $L_A$1065 | | Ph | H | H | $^i$Pr | H | H | H |
| $L_A$1066 | | Ph | H | H | H | $^i$Pr | H | H |
| $L_A$1067 | | Ph | Ph | H | H | H | H | H |
| $L_A$1068 | | Ph | H | Ph | H | H | H | H |
| $L_A$1069 | | Ph | H | H | Ph | H | H | H |
| $L_A$1070 | | Ph | H | H | H | Ph | H | H |
| $L_A$1071 | | H | Me | Me | H | H | H | H |

33
-continued

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1072 | | H | Me | H | Me | H | H | H |
| $L_A$1073 | | H | Me | H | H | Me | H | H |
| $L_A$1074 | | H | Me | $CD_3$ | H | H | H | H |
| $L_A$1075 | | H | Me | H | $CD_3$ | H | H | H |
| $L_A$1076 | | H | Me | H | H | $CD_3$ | H | H |
| $L_A$1077 | | H | Me | $^i$Pr | H | H | H | H |
| $L_A$1078 | | H | Me | H | $^i$Pr | H | H | H |
| $L_A$1079 | | H | Me | H | H | $^i$Pr | H | H |
| $L_A$1080 | | H | Me | Ph | H | H | H | H |
| $L_A$1081 | | H | Me | H | Ph | H | H | H |
| $L_A$1082 | | H | Me | H | H | Ph | H | H |
| $L_A$1083 | | H | $CD_3$ | Me | H | H | H | H |
| $L_A$1084 | | H | $CD_3$ | H | Me | H | H | H |
| $L_A$1085 | | H | $CD_3$ | H | H | Me | H | H |
| $L_A$1086 | | H | $CD_3$ | $CD_3$ | H | H | H | H |
| $L_A$1087 | | H | $CD_3$ | H | $CD_3$ | H | H | H |
| $L_A$1088 | | H | $CD_3$ | H | H | $CD_3$ | H | H |
| $L_A$1089 | | H | $CD_3$ | $^i$Pr | H | H | H | H |
| $L_A$1090 | | H | $CD_3$ | H | $^i$Pr | H | H | H |
| $L_A$1091 | | H | $CD_3$ | H | H | $^i$Pr | H | H |
| $L_A$1092 | | H | $CD_3$ | Ph | H | H | H | H |
| $L_A$1093 | $D_3C$-$C(CD_3)(D_3C)$-$C^{1b}$-$C^{1e}$ | H | $CD_3$ | H | Ph | H | H | H |
| $L_A$1094 | | H | $CD_3$ | H | H | Ph | H | H |
| $L_A$1095 | | H | $^i$Pr | Me | H | H | H | H |
| $L_A$1096 | | H | $^i$Pr | H | Me | H | H | H |
| $L_A$1097 | | H | $^i$Pr | H | H | Me | H | H |
| $L_A$1098 | | H | $^i$Pr | $CD_3$ | H | H | H | H |
| $L_A$1099 | | H | $^i$Pr | H | $CD_3$ | H | H | H |
| $L_A$1100 | | H | $^i$Pr | H | H | $CD_3$ | H | H |
| $L_A$1101 | | H | $^i$Pr | $^i$Pr | H | H | H | H |
| $L_A$1102 | | H | $^i$Pr | H | $^i$Pr | H | H | H |
| $L_A$1103 | | H | $^i$Pr | H | H | $^i$Pr | H | H |
| $L_A$1104 | | H | $^i$Pr | Ph | H | H | H | H |
| $L_A$1105 | | H | $^i$Pr | H | Ph | H | H | H |
| $L_A$1106 | | H | $^i$Pr | H | H | Ph | H | H |
| $L_A$1107 | | H | Ph | Me | H | H | H | H |
| $L_A$1108 | | H | Ph | H | Me | H | H | H |
| $L_A$1109 | | H | Ph | H | H | Me | H | H |
| $L_A$1110 | | H | Ph | $CD_3$ | H | H | H | H |
| $L_A$1111 | | H | Ph | H | $CD_3$ | H | H | H |
| $L_A$1112 | | H | Ph | H | H | $CD_3$ | H | H |
| $L_A$1113 | | H | Ph | $^i$Pr | H | H | H | H |
| $L_A$1114 | | H | Ph | H | $^i$Pr | H | H | H |
| $L_A$1115 | | H | Ph | H | H | $^i$Pr | H | H |
| $L_A$1116 | | H | Ph | Ph | H | H | H | H |
| $L_A$1117 | | H | Ph | H | Ph | H | H | H |
| $L_A$1118 | | H | Ph | H | H | Ph | H | H |
| $L_A$1119 | | H | H | Me | Me | H | H | H |
| $L_A$1120 | | H | H | $CD_3$ | Me | H | H | H |
| $L_A$1121 | | H | H | $^i$Pr | Me | H | H | H |
| $L_A$1122 | | H | H | Ph | Me | H | H | H |
| $L_A$1123 | | H | H | Me | $CD_3$ | H | H | H |
| $L_A$1124 | | H | H | $CD_3$ | $CD_3$ | H | H | H |
| $L_A$1125 | | H | H | $^i$Pr | $CD_3$ | H | H | H |
| $L_A$1126 | | H | H | Ph | $CD_3$ | H | H | H |
| $L_A$1127 | | H | H | Me | $^i$Pr | H | H | H |
| $L_A$1128 | | H | H | $CD_3$ | $^i$Pr | H | H | H |
| $L_A$1129 | | H | H | $^i$Pr | $^i$Pr | H | H | H |
| $L_A$1130 | | H | H | Ph | $^i$Pr | H | H | H |
| $L_A$1131 | | H | H | Me | Ph | H | H | H |
| $L_A$1132 | | H | H | $CD_3$ | Ph | H | H | H |
| $L_A$1133 | | H | H | $^i$Pr | Ph | H | H | H |
| $L_A$1134 | | H | H | Ph | Ph | H | H | H |
| $L_A$1135 | | H | H | Me | H | Me | H | H |
| $L_A$1136 | | H | H | $CD_3$ | H | Me | H | H |
| $L_A$1137 | | H | H | $^i$Pr | H | Me | H | H |
| $L_A$1138 | | H | H | Ph | H | Me | H | H |
| $L_A$1139 | | H | H | Me | H | $CD_3$ | H | H |
| $L_A$1140 | | H | H | $CD_3$ | H | $CD_3$ | H | H |
| $L_A$1141 | | H | H | $^i$Pr | H | $CD_3$ | H | H |
| $L_A$1142 | | H | H | Ph | H | $CD_3$ | H | H |
| $L_A$1143 | | H | H | Me | H | $^i$Pr | H | H |
| $L_A$1144 | | H | H | $CD_3$ | H | $^i$Pr | H | H |
| $L_A$1145 | | H | H | $^i$Pr | H | $^i$Pr | H | H |
| $L_A$1146 | | H | H | Ph | H | $^i$Pr | H | H |
| $L_A$1147 | | H | H | Me | H | Ph | H | H |
| $L_A$1148 | $D_3C$-$C(D_3C)(CD_3)$-$C^{1b}$-$C^{1e}$ | H | H | $CD_3$ | H | Ph | H | H |
| $L_A$1149 | | H | H | $^i$Pr | H | Ph | H | H |
| $L_A$1150 | | H | H | Ph | H | Ph | H | H |
| $L_A$1151 | | Me | Me | H | Me | H | H | H |
| $L_A$1152 | | H | Me | Me | Me | H | H | H |
| $L_A$1153 | | $CD_3$ | Me | H | Me | H | H | H |
| $L_A$1154 | | H | Me | $CD_3$ | Me | H | H | H |
| $L_A$1155 | | $^i$Pr | Me | H | Me | H | H | H |
| $L_A$1156 | | H | Me | $^i$Pr | Me | H | H | H |
| $L_A$1157 | | Ph | Me | H | Me | H | H | H |
| $L_A$1158 | | H | Me | Ph | Me | H | H | H |
| $L_A$1159 | | Me | $CD_3$ | H | $CD_3$ | H | H | H |
| $L_A$1160 | | H | $CD_3$ | Me | $CD_3$ | H | H | H |
| $L_A$1161 | | $CD_3$ | $CD_3$ | H | $CD_3$ | H | H | H |
| $L_A$1162 | | H | $CD_3$ | $CD_3$ | $CD_3$ | H | H | H |
| $L_A$1163 | | $^i$Pr | $CD_3$ | H | $CD_3$ | H | H | H |
| $L_A$1164 | | H | $CD_3$ | $^i$Pr | $CD_3$ | H | H | H |
| $L_A$1165 | | Ph | $CD_3$ | H | $CD_3$ | H | H | H |
| $L_A$1166 | | H | $CD_3$ | Ph | $CD_3$ | H | H | H |
| $L_A$1167 | | Me | $^i$Pr | H | $^i$Pr | H | H | H |
| $L_A$1168 | | H | $^i$Pr | Me | $^i$Pr | H | H | H |
| $L_A$1169 | | $CD_3$ | $^i$Pr | H | $^i$Pr | H | H | H |
| $L_A$1170 | | H | $^i$Pr | $CD_3$ | $^i$Pr | H | H | H |
| $L_A$1171 | | $^i$Pr | $^i$Pr | H | $^i$Pr | H | H | H |
| $L_A$1172 | | H | $^i$Pr | $^i$Pr | $^i$Pr | H | H | H |
| $L_A$1173 | | Ph | $^i$Pr | H | $^i$Pr | H | H | H |
| $L_A$1174 | | H | $^i$Pr | Ph | $^i$Pr | H | H | H |
| $L_A$1175 | | Me | Ph | H | Ph | H | H | H |
| $L_A$1176 | | H | Ph | Me | Ph | H | H | H |
| $L_A$1177 | | $CD_3$ | Ph | H | Ph | H | H | H |
| $L_A$1178 | | H | Ph | $CD_3$ | Ph | H | H | H |
| $L_A$1179 | | $^i$Pr | Ph | H | Ph | H | H | H |
| $L_A$1180 | | H | Ph | $^i$Pr | Ph | H | H | H |
| $L_A$1181 | | Ph | Ph | H | Ph | H | H | H |
| $L_A$1182 | | H | Ph | Ph | Ph | H | H | H |
| $L_A$1183 | $D_3C$-$C(Et)(Et)$-$C^{1b}$-$C^{1e}$ | H | H | H | H | H | H | H |
| $L_A$1184 | | Me | H | H | H | H | H | H |
| $L_A$1185 | | H | Me | H | H | H | H | H |
| $L_A$1186 | | H | H | Me | H | H | H | H |
| $L_A$1187 | | H | H | H | Me | H | H | H |
| $L_A$1188 | | H | H | H | H | Me | H | H |
| $L_A$1189 | | $CD_3$ | H | H | H | H | H | H |
| $L_A$1190 | | H | $CD_3$ | H | H | H | H | H |
| $L_A$1191 | | H | H | $CD_3$ | H | H | H | H |
| $L_A$1192 | | H | H | H | $CD_3$ | H | H | H |
| $L_A$1193 | | H | H | H | H | $CD_3$ | H | H |
| $L_A$1194 | | $^i$Pr | H | H | H | H | H | H |
| $L_A$1195 | | H | $^i$Pr | H | H | H | H | H |
| $L_A$1196 | | H | H | $^i$Pr | H | H | H | H |
| $L_A$1197 | | H | H | H | $^i$Pr | H | H | H |
| $L_A$1198 | | H | H | H | H | $^i$Pr | H | H |
| $L_A$1199 | | Ph | H | H | H | H | H | H |
| $L_A$1200 | | H | Ph | H | H | H | H | H |
| $L_A$1201 | | H | H | Ph | H | H | H | H |
| $L_A$1202 | | H | H | H | Ph | H | H | H |
| $L_A$1203 | $D_3C$-$C(Et)(Et)$-$C^{1b}$-$C^{1e}$ | H | H | H | H | Ph | H | H |
| $L_A$1204 | | Me | Me | H | H | H | H | H |
| $L_A$1205 | | Me | H | Me | H | H | H | H |
| $L_A$1206 | | Me | H | H | Me | H | H | H |
| $L_A$1207 | | Me | H | H | H | Me | H | H |
| $L_A$1208 | | Me | $CD_3$ | H | H | H | H | H |
| $L_A$1209 | | Me | H | $CD_3$ | H | H | H | H |
| $L_A$1210 | | Me | H | H | $CD_3$ | H | H | H |
| $L_A$1211 | | Me | H | H | H | $CD_3$ | H | H |
| $L_A$1212 | | Me | $^i$Pr | H | H | H | H | H |
| $L_A$1213 | | Me | H | $^i$Pr | H | H | H | H |
| $L_A$1214 | | Me | H | H | $^i$Pr | H | H | H |
| $L_A$1215 | | Me | H | H | H | $^i$Pr | H | H |
| $L_A$1216 | | Me | Ph | H | H | H | H | H |
| $L_A$1217 | | Me | H | Ph | H | H | H | H |
| $L_A$1218 | | Me | H | H | Ph | H | H | H |
| $L_A$1219 | | Me | H | H | H | Ph | H | H |
| $L_A$1220 | | $CD_3$ | Me | H | H | H | H | H |
| $L_A$1221 | | $CD_3$ | H | Me | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A1222$ | | $CD_3$ | H | H | Me | H | H | H |
| $L_A1223$ | | $CD_3$ | H | H | H | Me | H | H |
| $L_A1224$ | | $CD_3$ | $CD_3$ | H | H | H | H | H |
| $L_A1225$ | | $CD_3$ | H | $CD_3$ | H | H | H | H |
| $L_A1226$ | | $CD_3$ | H | H | $CD_3$ | H | H | H |
| $L_A1227$ | | $CD_3$ | H | H | H | $CD_3$ | H | H |
| $L_A1228$ | | $CD_3$ | $^i$Pr | H | H | H | H | H |
| $L_A1229$ | | $CD_3$ | H | $^i$Pr | H | H | H | H |
| $L_A1230$ | | $CD_3$ | H | H | $^i$Pr | H | H | H |
| $L_A1231$ | | $CD_3$ | H | H | H | $^i$Pr | H | H |
| $L_A1232$ | | $CD_3$ | Ph | H | H | H | H | H |
| $L_A1233$ | | $CD_3$ | H | Ph | H | H | H | H |
| $L_A1234$ | | $CD_3$ | H | H | Ph | H | H | H |
| $L_A1235$ | | $CD_3$ | H | H | H | Ph | H | H |
| $L_A1236$ | | $^i$Pr | Me | H | H | H | H | H |
| $L_A1237$ | | $^i$Pr | H | Me | H | H | H | H |
| $L_A1238$ | | $^i$Pr | H | H | Me | H | H | H |
| $L_A1239$ | | $^i$Pr | H | H | H | Me | H | H |
| $L_A1240$ | | $^i$Pr | $CD_3$ | H | H | H | H | H |
| $L_A1241$ | | $^i$Pr | H | $CD_3$ | H | H | H | H |
| $L_A1242$ | | $^i$Pr | H | H | $CD_3$ | H | H | H |
| $L_A1243$ | | $^i$Pr | H | H | H | $CD_3$ | H | H |
| $L_A1244$ | | $^i$Pr | $^i$Pr | H | H | H | H | H |
| $L_A1245$ | | $^i$Pr | H | $^i$Pr | H | H | H | H |
| $L_A1246$ | | $^i$Pr | H | H | $^i$Pr | H | H | H |
| $L_A1247$ | | $^i$Pr | H | H | H | $^i$Pr | H | H |
| $L_A1248$ | | $^i$Pr | Ph | H | H | H | H | H |
| $L_A1249$ | | $^i$Pr | H | Ph | H | H | H | H |
| $L_A1250$ | | $^i$Pr | H | H | Ph | H | H | H |
| $L_A1251$ | | $^i$Pr | H | H | H | Ph | H | H |
| $L_A1252$ | | Ph | Me | H | H | H | H | H |
| $L_A1253$ | | Ph | H | Me | H | H | H | H |
| $L_A1254$ | | Ph | H | H | Me | H | H | H |
| $L_A1255$ | | Ph | H | H | H | Me | H | H |
| $L_A1256$ | | Ph | $CD_3$ | H | H | H | H | H |
| $L_A1257$ | | Ph | H | $CD_3$ | H | H | H | H |
| $L_A1258$ | (Et, Et, $D_3C$, $D_3C$, $C^{1b}$, $C^{1e}$ structure) | Ph | H | H | $CD_3$ | H | H | H |
| $L_A1259$ | | Ph | H | H | H | $CD_3$ | H | H |
| $L_A1260$ | | Ph | $^i$Pr | H | H | H | H | H |
| $L_A1261$ | | Ph | H | $^i$Pr | H | H | H | H |
| $L_A1262$ | | Ph | H | H | $^i$Pr | H | H | H |
| $L_A1263$ | | Ph | H | H | H | $^i$Pr | H | H |
| $L_A1264$ | | Ph | Ph | H | H | H | H | H |
| $L_A1265$ | | Ph | H | Ph | H | H | H | H |
| $L_A1266$ | | Ph | H | H | Ph | H | H | H |
| $L_A1267$ | | Ph | H | H | H | Ph | H | H |
| $L_A1268$ | | H | Me | Me | H | H | H | H |
| $L_A1269$ | | H | Me | H | Me | H | H | H |
| $L_A1270$ | | H | Me | H | H | Me | H | H |
| $L_A1271$ | | H | Me | $CD_3$ | H | H | H | H |
| $L_A1272$ | | H | Me | H | $CD_3$ | H | H | H |
| $L_A1273$ | | H | Me | H | H | $CD_3$ | H | H |
| $L_A1274$ | | H | Me | $^i$Pr | H | H | H | H |
| $L_A1275$ | | H | Me | H | $^i$Pr | H | H | H |
| $L_A1276$ | | H | Me | H | H | $^i$Pr | H | H |
| $L_A1277$ | | H | Me | Ph | H | H | H | H |
| $L_A1278$ | | H | Me | H | Ph | H | H | H |
| $L_A1279$ | | H | Me | H | H | Ph | H | H |
| $L_A1280$ | | H | $CD_3$ | Me | H | H | H | H |
| $L_A1281$ | | H | $CD_3$ | H | Me | H | H | H |
| $L_A1282$ | | H | $CD_3$ | H | H | Me | H | H |
| $L_A1283$ | | H | $CD_3$ | $CD_3$ | H | H | H | H |
| $L_A1284$ | | H | $CD_3$ | H | $CD_3$ | H | H | H |
| $L_A1285$ | | H | $CD_3$ | H | H | $CD_3$ | H | H |
| $L_A1286$ | | H | $CD_3$ | $^i$Pr | H | H | H | H |
| $L_A1287$ | | H | $CD_3$ | H | $^i$Pr | H | H | H |
| $L_A1288$ | | H | $CD_3$ | H | H | $^i$Pr | H | H |
| $L_A1289$ | | H | $CD_3$ | Ph | H | H | H | H |
| $L_A1290$ | | H | $CD_3$ | H | Ph | H | H | H |
| $L_A1291$ | | H | $CD_3$ | H | H | Ph | H | H |
| $L_A1292$ | | H | $^i$Pr | Me | H | H | H | H |
| $L_A1293$ | | H | $^i$Pr | H | Me | H | H | H |
| $L_A1294$ | | H | $^i$Pr | H | H | Me | H | H |
| $L_A1295$ | | H | $^i$Pr | $CD_3$ | H | H | H | H |
| $L_A1296$ | | H | $^i$Pr | H | $CD_3$ | H | H | H |
| $L_A1297$ | | H | $^i$Pr | H | H | $CD_3$ | H | H |
| $L_A1298$ | | H | $^i$Pr | $^i$Pr | H | H | H | H |
| $L_A1299$ | | H | $^i$Pr | H | $^i$Pr | H | H | H |
| $L_A1300$ | | H | $^i$Pr | H | H | $^i$Pr | H | H |
| $L_A1301$ | | H | $^i$Pr | Ph | H | H | H | H |
| $L_A1302$ | | H | $^i$Pr | H | Ph | H | H | H |
| $L_A1303$ | | H | $^i$Pr | H | H | Ph | H | H |
| $L_A1304$ | | H | Ph | Me | H | H | H | H |
| $L_A1305$ | | H | Ph | H | Me | H | H | H |
| $L_A1306$ | | H | Ph | H | H | Me | H | H |
| $L_A1307$ | | H | Ph | $CD_3$ | H | H | H | H |
| $L_A1308$ | | H | Ph | H | $CD_3$ | H | H | H |
| $L_A1309$ | | H | Ph | H | H | $CD_3$ | H | H |
| $L_A1310$ | | H | Ph | $^i$Pr | H | H | H | H |
| $L_A1311$ | | H | Ph | H | $^i$Pr | H | H | H |
| $L_A1312$ | | H | Ph | H | H | $^i$Pr | H | H |
| $L_A1313$ | | H | Ph | Ph | H | H | H | H |
| $L_A1314$ | (Et, Et, $D_3C$, $D_3C$, $C^{1b}$, $C^{1e}$ structure) | H | Ph | H | Ph | H | H | H |
| $L_A1315$ | | H | Ph | H | H | Ph | H | H |
| $L_A1316$ | | H | H | Me | Me | H | H | H |
| $L_A1317$ | | H | H | $CD_3$ | Me | H | H | H |
| $L_A1318$ | | H | H | $^i$Pr | Me | H | H | H |
| $L_A1319$ | | H | H | Ph | Me | H | H | H |
| $L_A1320$ | | H | H | Me | $CD_3$ | H | H | H |
| $L_A1321$ | | H | H | $CD_3$ | $CD_3$ | H | H | H |
| $L_A1322$ | | H | H | $^i$Pr | $CD_3$ | H | H | H |
| $L_A1323$ | | H | H | Ph | $CD_3$ | H | H | H |
| $L_A1324$ | | H | H | Me | $^i$Pr | H | H | H |
| $L_A1325$ | | H | H | $CD_3$ | $^i$Pr | H | H | H |
| $L_A1326$ | | H | H | $^i$Pr | $^i$Pr | H | H | H |
| $L_A1327$ | | H | H | Ph | $^i$Pr | H | H | H |
| $L_A1328$ | | H | H | Me | Ph | H | H | H |
| $L_A1329$ | | H | H | $CD_3$ | Ph | H | H | H |
| $L_A1330$ | | H | H | $^i$Pr | Ph | H | H | H |
| $L_A1331$ | | H | H | Ph | Ph | H | H | H |
| $L_A1332$ | | H | H | Me | H | Me | H | H |
| $L_A1333$ | | H | H | $CD_3$ | H | Me | H | H |
| $L_A1334$ | | H | H | $^i$Pr | H | Me | H | H |
| $L_A1335$ | | H | H | Ph | H | Me | H | H |
| $L_A1336$ | | H | H | Me | H | $CD_3$ | H | H |
| $L_A1337$ | | H | H | $CD_3$ | H | $CD_3$ | H | H |
| $L_A1338$ | | H | H | $^i$Pr | H | $CD_3$ | H | H |
| $L_A1339$ | | H | H | Ph | H | $CD_3$ | H | H |
| $L_A1340$ | | H | H | Me | H | $^i$Pr | H | H |
| $L_A1341$ | | H | H | $CD_3$ | H | $^i$Pr | H | H |
| $L_A1342$ | | H | H | $^i$Pr | H | $^i$Pr | H | H |
| $L_A1343$ | | H | H | Ph | H | $^i$Pr | H | H |
| $L_A1344$ | | H | H | Me | H | Ph | H | H |
| $L_A1345$ | | H | H | $CD_3$ | H | Ph | H | H |
| $L_A1346$ | | H | H | $^i$Pr | H | Ph | H | H |
| $L_A1347$ | | H | H | Ph | H | Ph | H | H |
| $L_A1348$ | | Me | Me | H | Me | H | H | H |
| $L_A1349$ | | H | Me | Me | Me | H | H | H |
| $L_A1350$ | | $CD_3$ | Me | H | Me | H | H | H |
| $L_A1351$ | | H | Me | $CD_3$ | Me | H | H | H |
| $L_A1352$ | | $^i$Pr | Me | H | Me | H | H | H |
| $L_A1353$ | | H | Me | $^i$Pr | Me | H | H | H |
| $L_A1354$ | | Ph | Me | H | Me | H | H | H |
| $L_A1355$ | | H | Me | Ph | Me | H | H | H |
| $L_A1356$ | | Me | $CD_3$ | H | $CD_3$ | H | H | H |
| $L_A1357$ | | H | $CD_3$ | Me | $CD_3$ | H | H | H |
| $L_A1358$ | | $CD_3$ | $CD_3$ | H | $CD_3$ | H | H | H |
| $L_A1359$ | | H | $CD_3$ | $CD_3$ | $CD_3$ | H | H | H |
| $L_A1360$ | | $^i$Pr | $CD_3$ | H | $CD_3$ | H | H | H |
| $L_A1361$ | | H | $CD_3$ | $^i$Pr | $CD_3$ | H | H | H |
| $L_A1362$ | | Ph | $CD_3$ | H | $CD_3$ | H | H | H |
| $L_A1363$ | | H | $CD_3$ | Ph | $CD_3$ | H | H | H |
| $L_A1364$ | | Me | $^i$Pr | H | $^i$Pr | H | H | H |
| $L_A1365$ | | H | $^i$Pr | Me | $^i$Pr | H | H | H |
| $L_A1366$ | | $CD_3$ | $^i$Pr | H | $^i$Pr | H | H | H |
| $L_A1367$ | | H | $^i$Pr | $CD_3$ | $^i$Pr | H | H | H |
| $L_A1368$ | | $^i$Pr | $^i$Pr | H | $^i$Pr | H | H | H |
| $L_A1369$ | (Et, Et, $D_3C$, $D_3C$, $C^{1b}$, $C^{1e}$ structure) | H | $^i$Pr | $^i$Pr | $^i$Pr | H | H | H |
| $L_A1370$ | | Ph | $^i$Pr | H | $^i$Pr | H | H | H |
| $L_A1371$ | | H | $^i$Pr | Ph | $^i$Pr | H | H | H |
| $L_A1372$ | | Me | Ph | H | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1373 | | H | Ph | Me | Ph | H | H | H |
| $L_A$1374 | | CD₃ | Ph | H | Ph | H | H | H |
| $L_A$1375 | | H | Ph | CD₃ | Ph | H | H | H |
| $L_A$1376 | | ⁱPr | Ph | H | Ph | H | H | H |
| $L_A$1377 | | H | Ph | ⁱPr | Ph | H | H | H |
| $L_A$1378 | | Ph | Ph | H | Ph | H | H | H |
| $L_A$1379 | | H | Ph | Ph | Ph | H | H | H |
| $L_A$1380 | cyclohexane with D₃C, D₃C, C¹ᵇ, C¹ᵉ | H | H | H | H | H | H | H |
| $L_A$1381 | | Me | H | H | H | H | H | H |
| $L_A$1382 | | H | Me | H | H | H | H | H |
| $L_A$1383 | | H | H | Me | H | H | H | H |
| $L_A$1384 | | H | H | H | Me | H | H | H |
| $L_A$1385 | | H | H | H | H | Me | H | H |
| $L_A$1386 | | CD₃ | H | H | H | H | H | H |
| $L_A$1387 | | H | CD₃ | H | H | H | H | H |
| $L_A$1388 | | H | H | CD₃ | H | H | H | H |
| $L_A$1389 | | H | H | H | CD₃ | H | H | H |
| $L_A$1390 | | H | H | H | H | CD₃ | H | H |
| $L_A$1391 | | ⁱPr | H | H | H | H | H | H |
| $L_A$1392 | | H | ⁱPr | H | H | H | H | H |
| $L_A$1393 | | H | H | ⁱPr | H | H | H | H |
| $L_A$1394 | | H | H | H | ⁱPr | H | H | H |
| $L_A$1395 | | H | H | H | H | ⁱPr | H | H |
| $L_A$1396 | | Ph | H | H | H | H | H | H |
| $L_A$1397 | | H | Ph | H | H | H | H | H |
| $L_A$1398 | | H | H | Ph | H | H | H | H |
| $L_A$1399 | | H | H | H | Ph | H | H | H |
| $L_A$1400 | | H | H | H | H | Ph | H | H |
| $L_A$1401 | | Me | Me | H | H | H | H | H |
| $L_A$1402 | | Me | H | Me | H | H | H | H |
| $L_A$1403 | | Me | H | H | Me | H | H | H |
| $L_A$1404 | | Me | H | H | H | Me | H | H |
| $L_A$1405 | | Me | CD₃ | H | H | H | H | H |
| $L_A$1406 | | Me | H | CD₃ | H | H | H | H |
| $L_A$1407 | | Me | H | H | CD₃ | H | H | H |
| $L_A$1408 | | Me | H | H | H | CD₃ | H | H |
| $L_A$1409 | | Me | ⁱPr | H | H | H | H | H |
| $L_A$1410 | | Me | H | ⁱPr | H | H | H | H |
| $L_A$1411 | | Me | H | H | ⁱPr | H | H | H |
| $L_A$1412 | | Me | H | H | H | ⁱPr | H | H |
| $L_A$1413 | | Me | Ph | H | H | H | H | H |
| $L_A$1414 | | Me | H | Ph | H | H | H | H |
| $L_A$1415 | | Me | H | H | Ph | H | H | H |
| $L_A$1416 | | Me | H | H | H | Ph | H | H |
| $L_A$1417 | | CD₃ | Me | H | H | H | H | H |
| $L_A$1418 | | CD₃ | H | Me | H | H | H | H |
| $L_A$1419 | | CD₃ | H | H | Me | H | H | H |
| $L_A$1420 | | CD₃ | H | H | H | Me | H | H |
| $L_A$1421 | | CD₃ | CD₃ | H | H | H | H | H |
| $L_A$1422 | | CD₃ | H | CD₃ | H | H | H | H |
| $L_A$1423 | cyclohexane with D₃C, D₃C, C¹ᵇ, C¹ᵉ | CD₃ | H | H | CD₃ | H | H | H |
| $L_A$1424 | | CD₃ | H | H | H | CD₃ | H | H |
| $L_A$1425 | | CD₃ | ⁱPr | H | H | H | H | H |
| $L_A$1426 | | CD₃ | H | ⁱPr | H | H | H | H |
| $L_A$1427 | | CD₃ | H | H | ⁱPr | H | H | H |
| $L_A$1428 | | CD₃ | H | H | H | ⁱPr | H | H |
| $L_A$1429 | | CD₃ | Ph | H | H | H | H | H |
| $L_A$1430 | | CD₃ | H | Ph | H | H | H | H |
| $L_A$1431 | | CD₃ | H | H | Ph | H | H | H |
| $L_A$1432 | | CD₃ | H | H | H | Ph | H | H |
| $L_A$1433 | | ⁱPr | Me | H | H | H | H | H |
| $L_A$1434 | | ⁱPr | H | Me | H | H | H | H |
| $L_A$1435 | | ⁱPr | H | H | Me | H | H | H |
| $L_A$1436 | | ⁱPr | H | H | H | Me | H | H |
| $L_A$1437 | | ⁱPr | CD₃ | H | H | H | H | H |
| $L_A$1438 | | ⁱPr | H | CD₃ | H | H | H | H |
| $L_A$1439 | | ⁱPr | H | H | CD₃ | H | H | H |
| $L_A$1440 | | ⁱPr | H | H | H | CD₃ | H | H |
| $L_A$1441 | | ⁱPr | ⁱPr | H | H | H | H | H |
| $L_A$1442 | | ⁱPr | H | ⁱPr | H | H | H | H |
| $L_A$1443 | | ⁱPr | H | H | ⁱPr | H | H | H |
| $L_A$1444 | | ⁱPr | H | H | H | ⁱPr | H | H |
| $L_A$1445 | | ⁱPr | Ph | H | H | H | H | H |
| $L_A$1446 | | ⁱPr | H | Ph | H | H | H | H |
| $L_A$1447 | | ⁱPr | H | H | Ph | H | H | H |
| $L_A$1448 | | ⁱPr | H | H | H | Ph | H | H |
| $L_A$1449 | | Ph | Me | H | H | H | H | H |
| $L_A$1450 | | Ph | H | Me | H | H | H | H |
| $L_A$1451 | | Ph | H | H | Me | H | H | H |
| $L_A$1452 | | Ph | H | H | H | Me | H | H |
| $L_A$1453 | | Ph | CD₃ | H | H | H | H | H |
| $L_A$1454 | | Ph | H | CD₃ | H | H | H | H |
| $L_A$1455 | | Ph | H | H | CD₃ | H | H | H |
| $L_A$1456 | | Ph | H | H | H | CD₃ | H | H |
| $L_A$1457 | | Ph | ⁱPr | H | H | H | H | H |
| $L_A$1458 | | Ph | H | ⁱPr | H | H | H | H |
| $L_A$1459 | | Ph | H | H | ⁱPr | H | H | H |
| $L_A$1460 | | Ph | H | H | H | ⁱPr | H | H |
| $L_A$1461 | | Ph | Ph | H | H | H | H | H |
| $L_A$1462 | | Ph | H | Ph | H | H | H | H |
| $L_A$1463 | | Ph | H | H | Ph | H | H | H |
| $L_A$1464 | | Ph | H | H | H | Ph | H | H |
| $L_A$1465 | | H | Me | Me | H | H | H | H |
| $L_A$1466 | | H | Me | H | Me | H | H | H |
| $L_A$1467 | | H | Me | H | H | Me | H | H |
| $L_A$1468 | | H | Me | CD₃ | H | H | H | H |
| $L_A$1469 | | H | Me | H | CD₃ | H | H | H |
| $L_A$1470 | | H | Me | H | H | CD₃ | H | H |
| $L_A$1471 | | H | Me | ⁱPr | H | H | H | H |
| $L_A$1472 | | H | Me | H | ⁱPr | H | H | H |
| $L_A$1473 | | H | Me | H | H | ⁱPr | H | H |
| $L_A$1474 | | H | Me | Ph | H | H | H | H |
| $L_A$1475 | | H | Me | H | Ph | H | H | H |
| $L_A$1476 | | H | Me | H | H | Ph | H | H |
| $L_A$1477 | | H | CD₃ | Me | H | H | H | H |
| $L_A$1478 | cyclohexane with D₃C, D₃C, C¹ᵇ, C¹ᵉ | H | CD₃ | H | Me | H | H | H |
| $L_A$1479 | | H | CD₃ | H | H | Me | H | H |
| $L_A$1480 | | H | CD₃ | CD₃ | H | H | H | H |
| $L_A$1481 | | H | CD₃ | H | CD₃ | H | H | H |
| $L_A$1482 | | H | CD₃ | H | H | CD₃ | H | H |
| $L_A$1483 | | H | CD₃ | ⁱPr | H | H | H | H |
| $L_A$1484 | | H | CD₃ | H | ⁱPr | H | H | H |
| $L_A$1485 | | H | CD₃ | H | H | ⁱPr | H | H |
| $L_A$1486 | | H | CD₃ | Ph | H | H | H | H |
| $L_A$1487 | | H | CD₃ | H | Ph | H | H | H |
| $L_A$1488 | | H | CD₃ | H | H | Ph | H | H |
| $L_A$1489 | | H | ⁱPr | Me | H | H | H | H |
| $L_A$1490 | | H | ⁱPr | H | Me | H | H | H |
| $L_A$1491 | | H | ⁱPr | H | H | Me | H | H |
| $L_A$1492 | | H | ⁱPr | CD₃ | H | H | H | H |
| $L_A$1493 | | H | ⁱPr | H | CD₃ | H | H | H |
| $L_A$1494 | | H | ⁱPr | H | H | CD₃ | H | H |
| $L_A$1495 | | H | ⁱPr | ⁱPr | H | H | H | H |
| $L_A$1496 | | H | ⁱPr | H | ⁱPr | H | H | H |
| $L_A$1497 | | H | ⁱPr | H | H | ⁱPr | H | H |
| $L_A$1498 | | H | ⁱPr | Ph | H | H | H | H |
| $L_A$1499 | | H | ⁱPr | H | Ph | H | H | H |
| $L_A$1500 | | H | ⁱPr | H | H | Ph | H | H |
| $L_A$1501 | | H | Ph | Me | H | H | H | H |
| $L_A$1502 | | H | Ph | H | Me | H | H | H |
| $L_A$1503 | | H | Ph | H | H | Me | H | H |
| $L_A$1504 | | H | Ph | CD₃ | H | H | H | H |
| $L_A$1505 | | H | Ph | H | CD₃ | H | H | H |
| $L_A$1506 | | H | Ph | H | H | CD₃ | H | H |
| $L_A$1507 | | H | Ph | ⁱPr | H | H | H | H |
| $L_A$1508 | | H | Ph | H | ⁱPr | H | H | H |
| $L_A$1509 | | H | Ph | H | H | ⁱPr | H | H |
| $L_A$1510 | | H | Ph | Ph | H | H | H | H |
| $L_A$1511 | | H | Ph | H | Ph | H | H | H |
| $L_A$1512 | | H | Ph | H | H | Ph | H | H |
| $L_A$1513 | | H | H | Me | Me | H | H | H |
| $L_A$1514 | | H | H | CD₃ | Me | H | H | H |
| $L_A$1515 | | H | H | ⁱPr | Me | H | H | H |
| $L_A$1516 | | H | H | Ph | Me | H | H | H |
| $L_A$1517 | | H | H | Me | CD₃ | H | H | H |
| $L_A$1518 | | H | H | CD₃ | CD₃ | H | H | H |
| $L_A$1519 | | H | H | ⁱPr | CD₃ | H | H | H |
| $L_A$1520 | | H | H | Ph | CD₃ | H | H | H |
| $L_A$1521 | | H | H | Me | ⁱPr | H | H | H |
| $L_A$1522 | | H | H | CD₃ | ⁱPr | H | H | H |
| $L_A$1523 | | H | H | ⁱPr | ⁱPr | H | H | H |
| $L_A$1524 | | H | H | Ph | ⁱPr | H | H | H |
| $L_A$1525 | | H | H | Me | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1526 |  | H | H | CD₃ | Ph | H | H | H |
| $L_A$1527 |  | H | H | ⁱPr | Ph | H | H | H |
| $L_A$1528 |  | H | H | Ph | Ph | H | H | H |
| $L_A$1529 |  | H | H | Me | H | Me | H | H |
| $L_A$1530 |  | H | H | CD₃ | H | Me | H | H |
| $L_A$1531 |  | H | H | ⁱPr | H | Me | H | H |
| $L_A$1532 |  | H | H | Ph | H | Me | H | H |
| $L_A$1533 | [cyclohexyl linker with two D₃C groups, C¹ᵇ, C¹ᵉ substituents] | H | H | Me | H | CD₃ | H | H |
| $L_A$1534 |  | H | H | CD₃ | H | CD₃ | H | H |
| $L_A$1535 |  | H | H | ⁱPr | H | CD₃ | H | H |
| $L_A$1536 |  | H | H | Ph | H | CD₃ | H | H |
| $L_A$1537 |  | H | H | Me | H | ⁱPr | H | H |
| $L_A$1538 |  | H | H | CD₃ | H | ⁱPr | H | H |
| $L_A$1539 |  | H | H | ⁱPr | H | ⁱPr | H | H |
| $L_A$1540 |  | H | H | Ph | H | ⁱPr | H | H |
| $L_A$1541 |  | H | H | Me | H | Ph | H | H |
| $L_A$1542 |  | H | H | CD₃ | H | Ph | H | H |
| $L_A$1543 |  | H | H | ⁱPr | H | Ph | H | H |
| $L_A$1544 |  | H | H | Ph | H | Ph | H | H |
| $L_A$1545 |  | Me | Me | H | Me | H | H | H |
| $L_A$1546 |  | H | Me | Me | Me | H | H | H |
| $L_A$1547 |  | CD₃ | Me | H | Me | H | H | H |
| $L_A$1548 |  | H | Me | CD₃ | Me | H | H | H |
| $L_A$1549 |  | ⁱPr | Me | H | Me | H | H | H |
| $L_A$1550 |  | H | Me | ⁱPr | Me | H | H | H |
| $L_A$1551 |  | Ph | Me | H | Me | H | H | H |
| $L_A$1552 |  | H | Me | Ph | Me | H | H | H |
| $L_A$1553 |  | Me | CD₃ | H | CD₃ | H | H | H |
| $L_A$1554 |  | H | CD₃ | Me | CD₃ | H | H | H |
| $L_A$1555 |  | CD₃ | CD₃ | H | CD₃ | H | H | H |
| $L_A$1556 |  | H | CD₃ | CD₃ | CD₃ | H | H | H |
| $L_A$1557 |  | ⁱPr | CD₃ | H | CD₃ | H | H | H |
| $L_A$1558 |  | H | CD₃ | ⁱPr | CD₃ | H | H | H |
| $L_A$1559 |  | Ph | CD₃ | H | CD₃ | H | H | H |
| $L_A$1560 |  | H | CD₃ | Ph | CD₃ | H | H | H |
| $L_A$1561 |  | Me | ⁱPr | H | ⁱPr | H | H | H |
| $L_A$1562 |  | H | ⁱPr | Me | ⁱPr | H | H | H |
| $L_A$1563 |  | CD₃ | ⁱPr | H | ⁱPr | H | H | H |
| $L_A$1564 |  | H | ⁱPr | CD₃ | ⁱPr | H | H | H |
| $L_A$1565 |  | ⁱPr | ⁱPr | H | ⁱPr | H | H | H |
| $L_A$1566 |  | H | ⁱPr | ⁱPr | ⁱPr | H | H | H |
| $L_A$1567 |  | Ph | ⁱPr | H | ⁱPr | H | H | H |
| $L_A$1568 |  | H | ⁱPr | Ph | ⁱPr | H | H | H |
| $L_A$1569 |  | Me | Ph | H | Ph | H | H | H |
| $L_A$1570 |  | H | Ph | Me | Ph | H | H | H |
| $L_A$1571 |  | CD₃ | Ph | H | Ph | H | H | H |
| $L_A$1572 |  | H | Ph | CD₃ | Ph | H | H | H |
| $L_A$1573 |  | ⁱPr | Ph | H | Ph | H | H | H |
| $L_A$1574 |  | H | Ph | ⁱPr | Ph | H | H | H |
| $L_A$1575 |  | Ph | Ph | H | Ph | H | H | H |
| $L_A$1576 |  | H | Ph | Ph | Ph | H | H | H |
| $L_A$1577 | [cyclohexyl linker with C¹ᵇ, C¹ᵉ substituents] | H | H | H | H | H | H | H |
| $L_A$1578 |  | Me | H | H | H | H | H | H |
| $L_A$1579 |  | H | Me | H | H | H | H | H |
| $L_A$1580 |  | H | H | Me | H | H | H | H |
| $L_A$1581 |  | H | H | H | Me | H | H | H |
| $L_A$1582 |  | H | H | H | H | Me | H | H |
| $L_A$1583 |  | CD₃ | H | H | H | H | H | H |
| $L_A$1584 |  | H | CD₃ | H | H | H | H | H |
| $L_A$1585 |  | H | H | CD₃ | H | H | H | H |
| $L_A$1586 |  | H | H | H | CD₃ | H | H | H |
| $L_A$1587 |  | H | H | H | H | CD₃ | H | H |
| $L_A$1588 | [cyclohexyl linker with C¹ᵇ, C¹ᵉ substituents] | ⁱPr | H | H | H | H | H | H |
| $L_A$1589 |  | H | ⁱPr | H | H | H | H | H |
| $L_A$1590 |  | H | H | ⁱPr | H | H | H | H |
| $L_A$1591 |  | H | H | H | ⁱPr | H | H | H |
| $L_A$1592 |  | H | H | H | H | ⁱPr | H | H |
| $L_A$1593 |  | Ph | H | H | H | H | H | H |
| $L_A$1594 |  | H | Ph | H | H | H | H | H |
| $L_A$1595 |  | H | H | Ph | H | H | H | H |
| $L_A$1596 |  | H | H | H | Ph | H | H | H |
| $L_A$1597 |  | H | H | H | H | Ph | H | H |
| $L_A$1598 |  | Me | Me | H | H | H | H | H |
| $L_A$1599 |  | Me | H | Me | H | H | H | H |
| $L_A$1600 |  | Me | H | H | Me | H | H | H |
| $L_A$1601 |  | Me | H | H | H | Me | H | H |
| $L_A$1602 |  | Me | CD₃ | H | H | H | H | H |
| $L_A$1603 |  | Me | H | CD₃ | H | H | H | H |
| $L_A$1604 |  | Me | H | H | CD₃ | H | H | H |
| $L_A$1605 |  | Me | H | H | H | CD₃ | H | H |
| $L_A$1606 |  | Me | ⁱPr | H | H | H | H | H |
| $L_A$1607 |  | Me | H | ⁱPr | H | H | H | H |
| $L_A$1608 |  | Me | H | H | ⁱPr | H | H | H |
| $L_A$1609 |  | Me | H | H | H | ⁱPr | H | H |
| $L_A$1610 |  | Me | Ph | H | H | H | H | H |
| $L_A$1611 |  | Me | H | Ph | H | H | H | H |
| $L_A$1612 |  | Me | H | H | Ph | H | H | H |
| $L_A$1613 |  | Me | H | H | H | Ph | H | H |
| $L_A$1614 |  | CD₃ | Me | H | H | H | H | H |
| $L_A$1615 |  | CD₃ | H | Me | H | H | H | H |
| $L_A$1616 |  | CD₃ | H | H | Me | H | H | H |
| $L_A$1617 |  | CD₃ | H | H | H | Me | H | H |
| $L_A$1618 |  | CD₃ | CD₃ | H | H | H | H | H |
| $L_A$1619 |  | CD₃ | H | CD₃ | H | H | H | H |
| $L_A$1620 |  | CD₃ | H | H | CD₃ | H | H | H |
| $L_A$1621 |  | CD₃ | H | H | H | CD₃ | H | H |
| $L_A$1622 |  | CD₃ | ⁱPr | H | H | H | H | H |
| $L_A$1623 |  | CD₃ | H | ⁱPr | H | H | H | H |
| $L_A$1624 |  | CD₃ | H | H | ⁱPr | H | H | H |
| $L_A$1625 |  | CD₃ | H | H | H | ⁱPr | H | H |
| $L_A$1626 |  | CD₃ | Ph | H | H | H | H | H |
| $L_A$1627 |  | CD₃ | H | Ph | H | H | H | H |
| $L_A$1628 |  | CD₃ | H | H | Ph | H | H | H |
| $L_A$1629 |  | CD₃ | H | H | H | Ph | H | H |
| $L_A$1630 |  | ⁱPr | Me | H | H | H | H | H |
| $L_A$1631 |  | ⁱPr | H | Me | H | H | H | H |
| $L_A$1632 |  | ⁱPr | H | H | Me | H | H | H |
| $L_A$1633 |  | ⁱPr | H | H | H | Me | H | H |
| $L_A$1634 |  | ⁱPr | CD₃ | H | H | H | H | H |
| $L_A$1635 |  | ⁱPr | H | CD₃ | H | H | H | H |
| $L_A$1636 |  | ⁱPr | H | H | CD₃ | H | H | H |
| $L_A$1637 |  | ⁱPr | H | H | H | CD₃ | H | H |
| $L_A$1638 |  | ⁱPr | ⁱPr | H | H | H | H | H |
| $L_A$1639 |  | ⁱPr | H | ⁱPr | H | H | H | H |
| $L_A$1640 |  | ⁱPr | H | H | ⁱPr | H | H | H |
| $L_A$1641 |  | ⁱPr | H | H | H | ⁱPr | H | H |
| $L_A$1642 |  | ⁱPr | Ph | H | H | H | H | H |
| $L_A$1643 | [cyclohexyl linker with C¹ᵇ, C¹ᵉ substituents] | ⁱPr | H | Ph | H | H | H | H |
| $L_A$1644 |  | ⁱPr | H | H | Ph | H | H | H |
| $L_A$1645 |  | ⁱPr | H | H | H | Ph | H | H |
| $L_A$1646 |  | Ph | Me | H | H | H | H | H |
| $L_A$1647 |  | Ph | H | Me | H | H | H | H |
| $L_A$1648 |  | Ph | H | H | Me | H | H | H |
| $L_A$1649 |  | Ph | H | H | H | Me | H | H |
| $L_A$1650 |  | Ph | CD₃ | H | H | H | H | H |
| $L_A$1651 |  | Ph | H | CD₃ | H | H | H | H |
| $L_A$1652 |  | Ph | H | H | CD₃ | H | H | H |
| $L_A$1653 |  | Ph | H | H | H | CD₃ | H | H |
| $L_A$1654 |  | Ph | ⁱPr | H | H | H | H | H |
| $L_A$1655 |  | Ph | H | ⁱPr | H | H | H | H |
| $L_A$1656 |  | Ph | H | H | ⁱPr | H | H | H |
| $L_A$1657 |  | Ph | H | H | H | ⁱPr | H | H |
| $L_A$1658 |  | Ph | Ph | H | H | H | H | H |
| $L_A$1659 |  | Ph | H | Ph | H | H | H | H |
| $L_A$1660 |  | Ph | H | H | Ph | H | H | H |
| $L_A$1661 |  | Ph | H | H | H | Ph | H | H |
| $L_A$1662 |  | H | Me | Me | H | H | H | H |
| $L_A$1663 |  | H | Me | H | Me | H | H | H |
| $L_A$1664 |  | H | Me | H | H | Me | H | H |
| $L_A$1665 |  | H | Me | CD₃ | H | H | H | H |
| $L_A$1666 |  | H | Me | H | CD₃ | H | H | H |
| $L_A$1667 |  | H | Me | H | H | CD₃ | H | H |
| $L_A$1668 |  | H | Me | ⁱPr | H | H | H | H |
| $L_A$1669 |  | H | Me | H | ⁱPr | H | H | H |
| $L_A$1670 |  | H | Me | H | H | ⁱPr | H | H |
| $L_A$1671 |  | H | Me | Ph | H | H | H | H |
| $L_A$1672 |  | H | Me | H | Ph | H | H | H |
| $L_A$1673 |  | H | Me | H | H | Ph | H | H |
| $L_A$1674 |  | H | CD₃ | Me | H | H | H | H |
| $L_A$1675 |  | H | CD₃ | H | Me | H | H | H |
| $L_A$1676 |  | H | CD₃ | H | H | Me | H | H |
| $L_A$1677 |  | H | CD₃ | CD₃ | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A1678$ | | H | $CD_3$ | H | $CD_3$ | H | H | H |
| $L_A1679$ | | H | $CD_3$ | H | H | $CD_3$ | H | H |
| $L_A1680$ | | H | $CD_3$ | $^i$Pr | H | H | H | H |
| $L_A1681$ | | H | $CD_3$ | H | $^i$Pr | H | H | H |
| $L_A1682$ | | H | $CD_3$ | H | H | $^i$Pr | H | H |
| $L_A1683$ | | H | $CD_3$ | Ph | H | H | H | H |
| $L_A1684$ | | H | $CD_3$ | H | Ph | H | H | H |
| $L_A1685$ | | H | $CD_3$ | H | H | Ph | H | H |
| $L_A1686$ | | H | $^i$Pr | Me | H | H | H | H |
| $L_A1687$ | | H | $^i$Pr | H | Me | H | H | H |
| $L_A1688$ | | H | $^i$Pr | H | H | Me | H | H |
| $L_A1689$ | | H | $^i$Pr | $CD_3$ | H | H | H | H |
| $L_A1690$ | | H | $^i$Pr | H | $CD_3$ | H | H | H |
| $L_A1691$ | | H | $^i$Pr | H | H | $CD_3$ | H | H |
| $L_A1692$ | | H | $^i$Pr | $^i$Pr | H | H | H | H |
| $L_A1693$ | | H | $^i$Pr | H | $^i$Pr | H | H | H |
| $L_A1694$ | | H | $^i$Pr | H | H | $^i$Pr | H | H |
| $L_A1695$ | | H | $^i$Pr | Ph | H | H | H | H |
| $L_A1696$ | | H | $^i$Pr | H | Ph | H | H | H |
| $L_A1697$ | | H | $^i$Pr | H | H | Ph | H | H |
| $L_A1698$ | 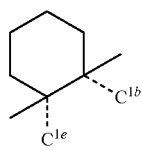 | H | Ph | Me | H | H | H | H |
| $L_A1699$ | | H | Ph | H | Me | H | H | H |
| $L_A1700$ | | H | Ph | H | H | Me | H | H |
| $L_A1701$ | | H | Ph | $CD_3$ | H | H | H | H |
| $L_A1702$ | | H | Ph | H | $CD_3$ | H | H | H |
| $L_A1703$ | | H | Ph | H | H | $CD_3$ | H | H |
| $L_A1704$ | | H | Ph | $^i$Pr | H | H | H | H |
| $L_A1705$ | | H | Ph | H | $^i$Pr | H | H | H |
| $L_A1706$ | | H | H | Ph | H | $^i$Pr | H | H |
| $L_A1707$ | | H | Ph | Ph | H | H | H | H |
| $L_A1708$ | | H | Ph | H | Ph | H | H | H |
| $L_A1709$ | | H | Ph | H | H | Ph | H | H |
| $L_A1710$ | | H | H | Me | Me | H | H | H |
| $L_A1711$ | | H | H | $CD_3$ | Me | H | H | H |
| $L_A1712$ | | H | H | $^i$Pr | Me | H | H | H |
| $L_A1713$ | | H | H | Ph | Me | H | H | H |
| $L_A1714$ | | H | H | Me | $CD_3$ | H | H | H |
| $L_A1715$ | | H | H | $CD_3$ | $CD_3$ | H | H | H |
| $L_A1716$ | | H | H | $^i$Pr | $CD_3$ | H | H | H |
| $L_A1717$ | | H | H | Ph | $CD_3$ | H | H | H |
| $L_A1718$ | | H | H | Me | $^i$Pr | H | H | H |
| $L_A1719$ | | H | H | $CD_3$ | $^i$Pr | H | H | H |
| $L_A1720$ | | H | H | $^i$Pr | $^i$Pr | H | H | H |
| $L_A1721$ | | H | H | Ph | $^i$Pr | H | H | H |
| $L_A1722$ | | H | H | Me | Ph | H | H | H |
| $L_A1723$ | | H | H | $CD_3$ | Ph | H | H | H |
| $L_A1724$ | | H | H | $^i$Pr | Ph | H | H | H |
| $L_A1725$ | | H | H | Ph | Ph | H | H | H |
| $L_A1726$ | | H | H | Me | H | Me | H | H |
| $L_A1727$ | | H | H | $CD_3$ | H | Me | H | H |
| $L_A1728$ | | H | H | $^i$Pr | H | Me | H | H |
| $L_A1729$ | | H | H | Ph | H | Me | H | H |
| $L_A1730$ | | H | H | Me | H | $CD_3$ | H | H |
| $L_A1731$ | | H | H | $CD_3$ | H | $CD_3$ | H | H |
| $L_A1732$ | | H | H | $^i$Pr | H | $CD_3$ | H | H |
| $L_A1733$ | | H | H | Ph | H | $CD_3$ | H | H |
| $L_A1734$ | | H | H | Me | H | $^i$Pr | H | H |
| $L_A1735$ | | H | H | $CD_3$ | H | $^i$Pr | H | H |
| $L_A1736$ | | H | H | $^i$Pr | H | $^i$Pr | H | H |
| $L_A1737$ | | H | H | Ph | H | $^i$Pr | H | H |
| $L_A1738$ | | H | H | Me | H | Ph | H | H |
| $L_A1739$ | | H | H | $CD_3$ | H | Ph | H | H |
| $L_A1740$ | | H | H | $^i$Pr | H | Ph | H | H |
| $L_A1741$ | | H | H | Ph | H | Ph | H | H |
| $L_A1742$ | | Me | Me | H | Me | H | H | H |
| $L_A1743$ | | H | Me | Me | Me | H | H | H |
| $L_A1744$ | | $CD_3$ | Me | H | Me | H | H | H |
| $L_A1745$ | | H | Me | $CD_3$ | Me | H | H | H |
| $L_A1746$ | | $^i$Pr | Me | H | Me | H | H | H |
| $L_A1747$ | | H | Me | $^i$Pr | Me | H | H | H |
| $L_A1748$ | | Ph | Me | H | Me | H | H | H |
| $L_A1749$ | | H | Me | Ph | Me | H | H | H |
| $L_A1750$ | | Me | $CD_3$ | H | $CD_3$ | H | H | H |
| $L_A1751$ | | H | $CD_3$ | Me | $CD_3$ | H | H | H |
| $L_A1752$ | | $CD_3$ | $CD_3$ | H | $CD_3$ | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A1753$ | 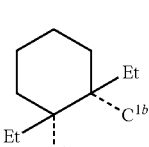 | H | $CD_3$ | $CD_3$ | $CD_3$ | H | H | H |
| $L_A1754$ | | $^i$Pr | $CD_3$ | H | $CD_3$ | H | H | H |
| $L_A1755$ | | H | $CD_3$ | $^i$Pr | $CD_3$ | H | H | H |
| $L_A1756$ | | Ph | $CD_3$ | H | $CD_3$ | H | H | H |
| $L_A1757$ | | H | $CD_3$ | Ph | $CD_3$ | H | H | H |
| $L_A1758$ | | Me | $^i$Pr | H | $^i$Pr | H | H | H |
| $L_A1759$ | | H | $^i$Pr | Me | $^i$Pr | H | H | H |
| $L_A1760$ | | $CD_3$ | $^i$Pr | H | $^i$Pr | H | H | H |
| $L_A1761$ | | H | $^i$Pr | $CD_3$ | $^i$Pr | H | H | H |
| $L_A1762$ | | $^i$Pr | $^i$Pr | H | $^i$Pr | H | H | H |
| $L_A1763$ | | H | $^i$Pr | $^i$Pr | $^i$Pr | H | H | H |
| $L_A1764$ | | Ph | $^i$Pr | H | $^i$Pr | H | H | H |
| $L_A1765$ | | H | $^i$Pr | Ph | $^i$Pr | H | H | H |
| $L_A1766$ | | Me | Ph | H | Ph | H | H | H |
| $L_A1767$ | | H | Ph | Me | Ph | H | H | H |
| $L_A1768$ | | $CD_3$ | Ph | H | Ph | H | H | H |
| $L_A1769$ | | H | Ph | $CD_3$ | Ph | H | H | H |
| $L_A1770$ | | $^i$Pr | Ph | H | Ph | H | H | H |
| $L_A1771$ | | H | Ph | $^i$Pr | Ph | H | H | H |
| $L_A1772$ | | Ph | Ph | H | Ph | H | H | H |
| $L_A1773$ | | H | Ph | Ph | Ph | H | H | H |
| $L_A1774$ | | H | H | H | H | H | H | H |
| $L_A1775$ | | Me | H | H | H | H | H | H |
| $L_A1776$ | | H | Me | H | H | H | H | H |
| $L_A1777$ | | H | H | Me | H | H | H | H |
| $L_A1778$ | | H | H | H | Me | H | H | H |
| $L_A1779$ | | H | H | H | H | Me | H | H |
| $L_A1780$ | | $CD_3$ | H | H | H | H | H | H |
| $L_A1781$ | | H | $CD_3$ | H | H | H | H | H |
| $L_A1782$ | | H | H | $CD_3$ | H | H | H | H |
| $L_A1783$ | | H | H | H | $CD_3$ | H | H | H |
| $L_A1784$ | | H | H | H | H | $CD_3$ | H | H |
| $L_A1785$ | | $^i$Pr | H | H | H | H | H | H |
| $L_A1786$ | | H | $^i$Pr | H | H | H | H | H |
| $L_A1787$ | | H | H | $^i$Pr | H | H | H | H |
| $L_A1788$ | | H | H | H | $^i$Pr | H | H | H |
| $L_A1789$ | | H | H | H | $^i$Pr | H | H | H |
| $L_A1790$ | | Ph | H | H | H | H | H | H |
| $L_A1791$ | | H | Ph | H | H | H | H | H |
| $L_A1792$ | | H | H | Ph | H | H | H | H |
| $L_A1793$ | | H | H | H | Ph | H | H | H |
| $L_A1794$ | | H | H | H | H | Ph | H | H |
| $L_A1795$ | | Me | Me | H | H | H | H | H |
| $L_A1796$ | | Me | H | Me | H | H | H | H |
| $L_A1797$ | | Me | H | H | Me | H | H | H |
| $L_A1798$ | | Me | H | H | H | Me | H | H |
| $L_A1799$ | | Me | $CD_3$ | H | H | H | H | H |
| $L_A1800$ | | Me | H | $CD_3$ | H | H | H | H |
| $L_A1801$ | | Me | H | H | $CD_3$ | H | H | H |
| $L_A1802$ | | Me | H | H | H | $CD_3$ | H | H |
| $L_A1803$ | | Me | $^i$Pr | H | H | H | H | H |
| $L_A1804$ | | Me | H | $^i$Pr | H | H | H | H |
| $L_A1805$ | | Me | H | H | $^i$Pr | H | H | H |
| $L_A1806$ | | Me | H | H | H | $^i$Pr | H | H |
| $L_A1807$ | | Me | Ph | H | H | H | H | H |
| $L_A1808$ | | Me | H | Ph | H | H | H | H |
| $L_A1809$ | | Me | H | H | Ph | H | H | H |
| $L_A1810$ | | Me | H | H | H | Ph | H | H |
| $L_A1811$ | | $CD_3$ | Me | H | H | H | H | H |
| $L_A1812$ | | $CD_3$ | Me | H | H | H | H | H |
| $L_A1813$ | | $CD_3$ | H | Me | H | H | H | H |
| $L_A1814$ | | $CD_3$ | H | H | Me | H | H | H |
| $L_A1815$ | | $CD_3$ | H | H | H | Me | H | H |
| $L_A1816$ | | $CD_3$ | $CD_3$ | H | H | H | H | H |
| $L_A1817$ | | $CD_3$ | H | $CD_3$ | H | H | H | H |
| $L_A1818$ | | $CD_3$ | H | H | $CD_3$ | H | H | H |
| $L_A1819$ | | $CD_3$ | $^i$Pr | H | H | H | H | H |
| $L_A1820$ | | $CD_3$ | H | $^i$Pr | H | H | H | H |
| $L_A1821$ | | $CD_3$ | H | H | $^i$Pr | H | H | H |
| $L_A1822$ | | $CD_3$ | H | H | H | $^i$Pr | H | H |
| $L_A1823$ | | $CD_3$ | Ph | H | H | H | H | H |
| $L_A1824$ | | $CD_3$ | H | Ph | H | H | H | H |
| $L_A1825$ | | $CD_3$ | H | H | Ph | H | H | H |
| $L_A1826$ | | $CD_3$ | H | H | H | Ph | H | H |
| $L_A1827$ | | $^i$Pr | Me | H | H | H | H | H |
| $L_A1828$ | | $^i$Pr | H | Me | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1829 | | $^i$Pr | H | H | Me | H | H | H |
| $L_A$1830 | | $^i$Pr | H | H | H | Me | H | H |
| $L_A$1831 | | $^i$Pr | CD$_3$ | H | H | H | H | H |
| $L_A$1832 | | $^i$Pr | H | CD$_3$ | H | H | H | H |
| $L_A$1833 | | $^i$Pr | H | H | CD$_3$ | H | H | H |
| $L_A$1834 | | $^i$Pr | H | H | H | CD$_3$ | H | H |
| $L_A$1835 | | $^i$Pr | $^i$Pr | H | H | H | H | H |
| $L_A$1836 | | $^i$Pr | H | $^i$Pr | H | H | H | H |
| $L_A$1837 | | $^i$Pr | H | H | $^i$Pr | H | H | H |
| $L_A$1838 | | $^i$Pr | H | H | H | $^i$Pr | H | H |
| $L_A$1839 | | $^i$Pr | Ph | H | H | H | H | H |
| $L_A$1840 | | $^i$Pr | H | Ph | H | H | H | H |
| $L_A$1841 | | $^i$Pr | H | H | Ph | H | H | H |
| $L_A$1842 | | $^i$Pr | H | H | H | Ph | H | H |
| $L_A$1843 | | Ph | Me | H | H | H | H | H |
| $L_A$1844 | | Ph | H | Me | H | H | H | H |
| $L_A$1845 | | Ph | H | H | Me | H | H | H |
| $L_A$1846 | | Ph | H | H | H | Me | H | H |
| $L_A$1847 | | Ph | CD$_3$ | H | H | H | H | H |
| $L_A$1848 | | Ph | H | CD$_3$ | H | H | H | H |
| $L_A$1849 | | Ph | H | H | CD$_3$ | H | H | H |
| $L_A$1850 | | Ph | H | H | H | CD$_3$ | H | H |
| $L_A$1851 | | Ph | $^i$Pr | H | H | H | H | H |
| $L_A$1852 | | Ph | H | $^i$Pr | H | H | H | H |
| $L_A$1853 | | Ph | H | H | $^i$Pr | H | H | H |
| $L_A$1854 | | Ph | H | H | H | $^i$Pr | H | H |
| $L_A$1855 | | Ph | Ph | H | H | H | H | H |
| $L_A$1856 | | Ph | H | Ph | H | H | H | H |
| $L_A$1857 | | Ph | H | H | Ph | H | H | H |
| $L_A$1858 | | Ph | H | H | H | Ph | H | H |
| $L_A$1859 | | H | Me | Me | H | H | H | H |
| $L_A$1860 | | H | Me | H | Me | H | H | H |
| $L_A$1861 | | H | Me | H | H | Me | H | H |
| $L_A$1862 | | H | Me | CD$_3$ | H | H | H | H |
| $L_A$1863 | cyclohexyl-Et-C$^{1b}$/Et-C$^{1e}$ | H | Me | H | CD$_3$ | H | H | H |
| $L_A$1864 | | H | Me | H | H | CD$_3$ | H | H |
| $L_A$1865 | | H | Me | $^i$Pr | H | H | H | H |
| $L_A$1866 | | H | Me | H | $^i$Pr | H | H | H |
| $L_A$1867 | | H | Me | H | H | $^i$Pr | H | H |
| $L_A$1868 | | H | Me | Ph | H | H | H | H |
| $L_A$1869 | | H | Me | H | Ph | H | H | H |
| $L_A$1870 | | H | Me | H | H | Ph | H | H |
| $L_A$1871 | | H | CD$_3$ | Me | H | H | H | H |
| $L_A$1872 | | H | CD$_3$ | H | Me | H | H | H |
| $L_A$1873 | | H | CD$_3$ | H | H | Me | H | H |
| $L_A$1874 | | H | CD$_3$ | CD$_3$ | H | H | H | H |
| $L_A$1875 | | H | CD$_3$ | H | CD$_3$ | H | H | H |
| $L_A$1876 | | H | CD$_3$ | H | H | CD$_3$ | H | H |
| $L_A$1877 | | H | CD$_3$ | $^i$Pr | H | H | H | H |
| $L_A$1878 | | H | CD$_3$ | H | $^i$Pr | H | H | H |
| $L_A$1879 | | H | CD$_3$ | H | H | $^i$Pr | H | H |
| $L_A$1880 | | H | CD$_3$ | Ph | H | H | H | H |
| $L_A$1881 | | H | CD$_3$ | H | Ph | H | H | H |
| $L_A$1882 | | H | CD$_3$ | H | H | Ph | H | H |
| $L_A$1883 | | H | $^i$Pr | Me | H | H | H | H |
| $L_A$1884 | | H | $^i$Pr | H | Me | H | H | H |
| $L_A$1885 | | H | $^i$Pr | H | H | Me | H | H |
| $L_A$1886 | | H | $^i$Pr | CD$_3$ | H | H | H | H |
| $L_A$1887 | | H | $^i$Pr | H | CD$_3$ | H | H | H |
| $L_A$1888 | | H | $^i$Pr | H | H | CD$_3$ | H | H |
| $L_A$1889 | | H | $^i$Pr | $^i$Pr | H | H | H | H |
| $L_A$1890 | | H | $^i$Pr | H | $^i$Pr | H | H | H |
| $L_A$1891 | | H | $^i$Pr | H | H | $^i$Pr | H | H |
| $L_A$1892 | | H | $^i$Pr | Ph | H | H | H | H |
| $L_A$1893 | | H | $^i$Pr | H | Ph | H | H | H |
| $L_A$1894 | | H | $^i$Pr | H | H | Ph | H | H |
| $L_A$1895 | | H | Ph | Me | H | H | H | H |
| $L_A$1896 | | H | Ph | H | Me | H | H | H |
| $L_A$1897 | | H | Ph | H | H | Me | H | H |
| $L_A$1898 | | H | Ph | CD$_3$ | H | H | H | H |
| $L_A$1899 | | H | Ph | H | CD$_3$ | H | H | H |
| $L_A$1900 | | H | Ph | H | H | CD$_3$ | H | H |
| $L_A$1901 | | H | Ph | $^i$Pr | H | H | H | H |
| $L_A$1902 | | H | Ph | H | $^i$Pr | H | H | H |
| $L_A$1903 | | H | Ph | H | H | $^i$Pr | H | H |
| $L_A$1904 | | H | Ph | Ph | H | H | H | H |
| $L_A$1905 | | H | Ph | H | Ph | H | H | H |
| $L_A$1906 | | H | Ph | H | H | Ph | H | H |
| $L_A$1907 | | H | H | Me | Me | H | H | H |
| $L_A$1908 | | H | H | CD$_3$ | Me | H | H | H |
| $L_A$1909 | | H | H | $^i$Pr | Me | H | H | H |
| $L_A$1910 | | H | H | Ph | Me | H | H | H |
| $L_A$1911 | | H | H | Me | CD$_3$ | H | H | H |
| $L_A$1912 | | H | H | CD$_3$ | CD$_3$ | H | H | H |
| $L_A$1913 | | H | H | $^i$Pr | CD$_3$ | H | H | H |
| $L_A$1914 | | H | H | Ph | CD$_3$ | H | H | H |
| $L_A$1915 | | H | H | Me | $^i$Pr | H | H | H |
| $L_A$1916 | | H | H | CD$_3$ | $^i$Pr | H | H | H |
| $L_A$1917 | | H | H | $^i$Pr | $^i$Pr | H | H | H |
| $L_A$1918 | cyclohexyl-Et-C$^{1b}$/Et-C$^{1e}$ | H | H | Ph | $^i$Pr | H | H | H |
| $L_A$1919 | | H | H | Me | Ph | H | H | H |
| $L_A$1920 | | H | H | CD$_3$ | Ph | H | H | H |
| $L_A$1921 | | H | H | $^i$Pr | Ph | H | H | H |
| $L_A$1922 | | H | H | Ph | Ph | H | H | H |
| $L_A$1923 | | H | H | Me | H | Me | H | H |
| $L_A$1924 | | H | H | CD$_3$ | H | Me | H | H |
| $L_A$1925 | | H | H | $^i$Pr | H | Me | H | H |
| $L_A$1926 | | H | H | Ph | H | Me | H | H |
| $L_A$1927 | | H | H | Me | H | CD$_3$ | H | H |
| $L_A$1928 | | H | H | CD$_3$ | H | CD$_3$ | H | H |
| $L_A$1929 | | H | H | $^i$Pr | H | CD$_3$ | H | H |
| $L_A$1930 | | H | H | Ph | H | CD$_3$ | H | H |
| $L_A$1931 | | H | H | Me | H | $^i$Pr | H | H |
| $L_A$1932 | | H | H | CD$_3$ | H | $^i$Pr | H | H |
| $L_A$1933 | | H | H | $^i$Pr | H | $^i$Pr | H | H |
| $L_A$1934 | | H | H | Ph | H | $^i$Pr | H | H |
| $L_A$1935 | | H | H | Me | H | Ph | H | H |
| $L_A$1936 | | H | H | CD$_3$ | H | Ph | H | H |
| $L_A$1937 | | H | H | $^i$Pr | H | Ph | H | H |
| $L_A$1938 | | H | H | Ph | H | Ph | H | H |
| $L_A$1939 | | Me | Me | Me | Me | H | H | H |
| $L_A$1940 | | H | Me | Me | Me | H | H | H |
| $L_A$1941 | | CD$_3$ | Me | H | Me | H | H | H |
| $L_A$1942 | | H | Me | CD$_3$ | Me | H | H | H |
| $L_A$1943 | | $^i$Pr | Me | H | Me | H | H | H |
| $L_A$1944 | | H | Me | $^i$Pr | Me | H | H | H |
| $L_A$1945 | | Ph | Me | H | Me | H | H | H |
| $L_A$1946 | | H | Me | Ph | Me | H | H | H |
| $L_A$1947 | | Me | CD$_3$ | H | CD$_3$ | H | H | H |
| $L_A$1948 | | H | CD$_3$ | Me | CD$_3$ | H | H | H |
| $L_A$1949 | | CD$_3$ | CD$_3$ | H | CD$_3$ | H | H | H |
| $L_A$1950 | | H | CD$_3$ | CD$_3$ | CD$_3$ | H | H | H |
| $L_A$1951 | | $^i$Pr | CD$_3$ | H | CD$_3$ | H | H | H |
| $L_A$1952 | | H | CD$_3$ | $^i$Pr | CD$_3$ | H | H | H |
| $L_A$1953 | | Ph | CD$_3$ | H | CD$_3$ | H | H | H |
| $L_A$1954 | | H | CD$_3$ | Ph | CD$_3$ | H | H | H |
| $L_A$1955 | | Me | $^i$Pr | H | $^i$Pr | H | H | H |
| $L_A$1956 | | H | $^i$Pr | Me | $^i$Pr | H | H | H |
| $L_A$1957 | | CD$_3$ | $^i$Pr | H | $^i$Pr | H | H | H |
| $L_A$1958 | | H | $^i$Pr | CD$_3$ | $^i$Pr | H | H | H |
| $L_A$1959 | | $^i$Pr | $^i$Pr | H | $^i$Pr | H | H | H |
| $L_A$1960 | | H | $^i$Pr | $^i$Pr | $^i$Pr | H | H | H |
| $L_A$1961 | | Ph | $^i$Pr | H | $^i$Pr | H | H | H |
| $L_A$1962 | | H | $^i$Pr | Ph | $^i$Pr | H | H | H |
| $L_A$1963 | | Me | Ph | H | Ph | H | H | H |
| $L_A$1964 | | H | Pe | Me | Ph | H | H | H |
| $L_A$1965 | | CD$_3$ | Ph | H | Ph | H | H | H |
| $L_A$1966 | | H | Ph | CD$_3$ | Ph | H | H | H |
| $L_A$1967 | | $^i$Pr | Ph | H | Ph | H | H | H |
| $L_A$1968 | | H | Ph | $^i$Pr | Ph | H | H | H |
| $L_A$1969 | | Ph | Ph | H | Ph | H | H | H |
| $L_A$1970 | | H | Ph | Ph | Ph | H | H | H |
| $L_A$1971 | cyclohexyl-iPr-C$^{1b}$/iPr-C$^{1e}$ | H | H | H | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1972 | (cyclohexane, iPr–C1b, iPr–C1e) | Me | H | H | H | H | H | H |
| $L_A$1973 | | H | Me | H | H | H | H | H |
| $L_A$1974 | | H | H | Me | H | H | H | H |
| $L_A$1975 | | H | H | H | Me | H | H | H |
| $L_A$1976 | | H | H | H | H | Me | H | H |
| $L_A$1977 | | CD$_3$ | H | H | H | H | H | H |
| $L_A$1978 | | H | CD$_3$ | H | H | H | H | H |
| $L_A$1979 | | H | H | CD$_3$ | H | H | H | H |
| $L_A$1980 | | H | H | H | CD$_3$ | H | H | H |
| $L_A$1981 | | H | H | H | H | CD$_3$ | H | H |
| $L_A$1982 | | $^i$Pr | H | H | H | H | H | H |
| $L_A$1983 | | H | $^i$Pr | H | H | H | H | H |
| $L_A$1984 | | H | H | $^i$Pr | H | H | H | H |
| $L_A$1985 | | H | H | H | $^i$Pr | H | H | H |
| $L_A$1986 | | H | H | H | H | $^i$Pr | H | H |
| $L_A$1987 | | Ph | H | H | H | H | H | H |
| $L_A$1988 | | H | Ph | H | H | H | H | H |
| $L_A$1989 | | H | H | Ph | H | H | H | H |
| $L_A$1990 | | H | H | H | Ph | H | H | H |
| $L_A$1991 | | H | H | H | H | Ph | H | H |
| $L_A$1992 | | Me | Me | H | H | H | H | H |
| $L_A$1993 | | Me | H | Me | H | H | H | H |
| $L_A$1994 | | Me | H | H | Me | H | H | H |
| $L_A$1995 | | Me | H | H | H | Me | H | H |
| $L_A$1996 | | Me | CD$_3$ | H | H | H | H | H |
| $L_A$1997 | | Me | H | CD$_3$ | H | H | H | H |
| $L_A$1998 | | Me | H | H | CD$_3$ | H | H | H |
| $L_A$1999 | | Me | H | H | H | CD$_3$ | H | H |
| $L_A$2000 | | Me | $^i$Pr | H | H | H | H | H |
| $L_A$2001 | | Me | H | $^i$Pr | H | H | H | H |
| $L_A$2002 | | Me | H | H | $^i$Pr | H | H | H |
| $L_A$2003 | | Me | H | H | H | $^i$Pr | H | H |
| $L_A$2004 | | Me | Ph | H | H | H | H | H |
| $L_A$2005 | | Me | H | Ph | H | H | H | H |
| $L_A$2006 | | Me | H | H | Ph | H | H | H |
| $L_A$2007 | | Me | H | H | H | Ph | H | H |
| $L_A$2008 | | CD$_3$ | Me | H | H | H | H | H |
| $L_A$2009 | | CD$_3$ | H | Me | H | H | H | H |
| $L_A$2010 | | CD$_3$ | H | H | Me | H | H | H |
| $L_A$2011 | | CD$_3$ | H | H | H | Me | H | H |
| $L_A$2012 | | CD$_3$ | CD$_3$ | H | H | H | H | H |
| $L_A$2013 | | CD$_3$ | H | CD$_3$ | H | H | H | H |
| $L_A$2014 | | CD$_3$ | H | H | CD$_3$ | H | H | H |
| $L_A$2015 | | CD$_3$ | H | H | H | CD$_3$ | H | H |
| $L_A$2016 | | CD$_3$ | $^i$Pr | H | H | H | H | H |
| $L_A$2017 | | CD$_3$ | H | $^i$Pr | H | H | H | H |
| $L_A$2018 | | CD$_3$ | H | H | $^i$Pr | H | H | H |
| $L_A$2019 | | CD$_3$ | H | H | H | $^i$Pr | H | H |
| $L_A$2020 | | CD$_3$ | Ph | H | H | H | H | H |
| $L_A$2021 | | CD$_3$ | H | Ph | H | H | H | H |
| $L_A$2022 | | CD$_3$ | H | H | Ph | H | H | H |
| $L_A$2023 | | CD$_3$ | H | H | H | Ph | H | H |
| $L_A$2024 | | $^i$Pr | Me | H | H | H | H | H |
| $L_A$2025 | | $^i$Pr | H | Me | H | H | H | H |
| $L_A$2026 | | $^i$Pr | H | H | Me | H | H | H |
| $L_A$2027 | (cyclohexane, iPr–C1b, iPr–C1e) | $^i$Pr | H | H | H | Me | H | H |
| $L_A$2028 | | $^i$Pr | CD$_3$ | H | H | H | H | H |
| $L_A$2029 | | $^i$Pr | H | CD$_3$ | H | H | H | H |
| $L_A$2030 | | $^i$Pr | H | H | CD$_3$ | H | H | H |
| $L_A$2031 | | $^i$Pr | H | H | H | CD$_3$ | H | H |
| $L_A$2032 | | $^i$Pr | $^i$Pr | H | H | H | H | H |
| $L_A$2033 | | $^i$Pr | H | $^i$Pr | H | H | H | H |
| $L_A$2034 | | $^i$Pr | H | H | $^i$Pr | H | H | H |
| $L_A$2035 | | $^i$Pr | H | H | H | $^i$Pr | H | H |
| $L_A$2036 | | $^i$Pr | Ph | H | H | H | H | H |
| $L_A$2037 | | $^i$Pr | H | Ph | H | H | H | H |
| $L_A$2038 | | $^i$Pr | H | H | Ph | H | H | H |
| $L_A$2039 | | $^i$Pr | H | H | H | Ph | H | H |
| $L_A$2040 | | Ph | Me | H | H | H | H | H |
| $L_A$2041 | | Ph | H | Me | H | H | H | H |
| $L_A$2042 | | Ph | H | H | Me | H | H | H |
| $L_A$2043 | | Ph | H | H | H | Me | H | H |
| $L_A$2044 | | Ph | CD$_3$ | H | H | H | H | H |
| $L_A$2045 | | Ph | H | CD$_3$ | H | H | H | H |
| $L_A$2046 | | Ph | H | H | CD$_3$ | H | H | H |
| $L_A$2047 | | Ph | H | H | H | CD$_3$ | H | H |
| $L_A$2048 | | Ph | $^i$Pr | H | H | H | H | H |
| $L_A$2049 | | Ph | H | $^i$Pr | H | H | H | H |
| $L_A$2050 | | Ph | H | H | $^i$Pr | H | H | H |
| $L_A$2051 | | Ph | H | H | H | $^i$Pr | H | H |
| $L_A$2052 | | Ph | Ph | H | H | H | H | H |
| $L_A$2053 | | Ph | H | Ph | H | H | H | H |
| $L_A$2054 | | Ph | H | H | Ph | H | H | H |
| $L_A$2055 | | Ph | H | H | H | Ph | H | H |
| $L_A$2056 | | H | Me | Me | H | H | H | H |
| $L_A$2057 | | H | Me | H | Me | H | H | H |
| $L_A$2058 | | H | Me | H | H | Me | H | H |
| $L_A$2059 | | H | Me | CD$_3$ | H | H | H | H |
| $L_A$2060 | | H | Me | H | CD$_3$ | H | H | H |
| $L_A$2061 | | H | Me | H | H | CD$_3$ | H | H |
| $L_A$2062 | | H | Me | $^i$Pr | H | H | H | H |
| $L_A$2063 | | H | Me | H | $^i$Pr | H | H | H |
| $L_A$2064 | | H | Me | H | H | $^i$Pr | H | H |
| $L_A$2065 | | H | Me | Ph | H | H | H | H |
| $L_A$2066 | | H | Me | H | Ph | H | H | H |
| $L_A$2067 | | H | Me | H | H | Ph | H | H |
| $L_A$2068 | | H | CD$_3$ | Me | H | H | H | H |
| $L_A$2069 | | H | CD$_3$ | H | Me | H | H | H |
| $L_A$2070 | | H | CD$_3$ | H | H | Me | H | H |
| $L_A$2071 | | H | CD$_3$ | CD$_3$ | H | H | H | H |
| $L_A$2072 | | H | CD$_3$ | H | CD$_3$ | H | H | H |
| $L_A$2073 | | H | CD$_3$ | H | H | CD$_3$ | H | H |
| $L_A$2074 | | H | CD$_3$ | $^i$Pr | H | H | H | H |
| $L_A$2075 | | H | CD$_3$ | H | $^i$Pr | H | H | H |
| $L_A$2076 | | H | CD$_3$ | H | H | $^i$Pr | H | H |
| $L_A$2077 | | H | CD$_3$ | Ph | H | H | H | H |
| $L_A$2078 | | H | CD$_3$ | H | Ph | H | H | H |
| $L_A$2079 | | H | CD$_3$ | H | H | Ph | H | H |
| $L_A$2080 | | H | $^i$Pr | Me | H | H | H | H |
| $L_A$2081 | | H | $^i$Pr | H | Me | H | H | H |
| $L_A$2082 | (cyclohexane, iPr–C1b, iPr–C1e) | H | $^i$Pr | H | H | Me | H | H |
| $L_A$2083 | | H | $^i$Pr | CD$_3$ | H | H | H | H |
| $L_A$2084 | | H | $^i$Pr | H | CD$_3$ | H | H | H |
| $L_A$2085 | | H | $^i$Pr | H | H | CD$_3$ | H | H |
| $L_A$2086 | | H | $^i$Pr | $^i$Pr | H | H | H | H |
| $L_A$2087 | | H | $^i$Pr | H | $^i$Pr | H | H | H |
| $L_A$2088 | | H | $^i$Pr | H | H | $^i$Pr | H | H |
| $L_A$2089 | | H | $^i$Pr | Ph | H | H | H | H |
| $L_A$2090 | | H | $^i$Pr | H | Ph | H | H | H |
| $L_A$2091 | | H | $^i$Pr | H | H | Ph | H | H |
| $L_A$2092 | | H | Ph | Me | H | H | H | H |
| $L_A$2093 | | H | Ph | H | Me | H | H | H |
| $L_A$2094 | | H | Ph | H | H | Me | H | H |
| $L_A$2095 | | H | Ph | CD$_3$ | H | H | H | H |
| $L_A$2096 | | H | Ph | H | CD$_3$ | H | H | H |
| $L_A$2097 | | H | Ph | H | H | CD$_3$ | H | H |
| $L_A$2098 | | H | Ph | $^i$Pr | H | H | H | H |
| $L_A$2099 | | H | Ph | H | $^i$Pr | H | H | H |
| $L_A$2100 | | H | Ph | H | H | $^i$Pr | H | H |
| $L_A$2101 | | H | Ph | Ph | H | H | H | H |
| $L_A$2102 | | H | Ph | H | Ph | H | H | H |
| $L_A$2103 | | H | Ph | H | H | Ph | H | H |
| $L_A$2104 | | H | H | Me | Me | H | H | H |
| $L_A$2105 | | H | H | CD$_3$ | Me | H | H | H |
| $L_A$2106 | | H | H | $^i$Pr | Me | H | H | H |
| $L_A$2107 | | H | H | Ph | Me | H | H | H |
| $L_A$2108 | | H | H | Me | CD$_3$ | H | H | H |
| $L_A$2109 | | H | H | CD$_3$ | CD$_3$ | H | H | H |
| $L_A$2110 | | H | H | $^i$Pr | CD$_3$ | H | H | H |
| $L_A$2111 | | H | H | Ph | CD$_3$ | H | H | H |
| $L_A$2112 | | H | H | Me | $^i$Pr | H | H | H |
| $L_A$2113 | | H | H | CD$_3$ | $^i$Pr | H | H | H |
| $L_A$2114 | | H | H | $^i$Pr | $^i$Pr | H | H | H |
| $L_A$2115 | | H | H | Ph | $^i$Pr | H | H | H |
| $L_A$2116 | | H | H | Me | Ph | H | H | H |
| $L_A$2117 | | H | H | CD$_3$ | Ph | H | H | H |
| $L_A$2118 | | H | H | $^i$Pr | Ph | H | H | H |
| $L_A$2119 | | H | H | Ph | Ph | H | H | H |
| $L_A$2120 | | H | H | Me | H | Me | H | H |
| $L_A$2121 | | H | H | CD$_3$ | H | Me | H | H |
| $L_A$2122 | | H | H | $^i$Pr | H | Me | H | H |
| $L_A$2123 | | H | H | Ph | H | Me | H | H |
| $L_A$2124 | | H | H | Me | H | CD$_3$ | H | H |
| $L_A$2125 | | H | H | CD$_3$ | H | CD$_3$ | H | H |

-continued

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A2126$ | | H | H | $^i$Pr | H | CD$_3$ | H | H |
| $L_A2127$ | | H | H | Ph | H | CD$_3$ | H | H |
| $L_A2128$ | | H | H | Me | H | $^i$Pr | H | H |
| $L_A2129$ | | H | H | CD$_3$ | H | $^i$Pr | H | H |
| $L_A2130$ | | H | H | $^i$Pr | H | $^i$Pr | H | H |
| $L_A2131$ | | H | H | Ph | H | $^i$Pr | H | H |
| $L_A2132$ | | H | H | Me | H | Ph | H | H |
| $L_A2133$ | | H | H | CD$_3$ | H | Ph | H | H |
| $L_A2134$ | | H | H | $^i$Pr | H | Ph | H | H |
| $L_A2135$ | | H | H | Ph | H | Ph | H | H |
| $L_A2136$ | | Me | Me | H | Me | H | H | H |
| $L_A2137$ | (cyclohexane linker) | H | Me | Me | Me | H | H | H |
| $L_A2138$ | | CD$_3$ | Me | H | Me | H | H | H |
| $L_A2139$ | | H | Me | CD$_3$ | Me | H | H | H |
| $L_A2140$ | | $^i$Pr | Me | H | Me | H | H | H |
| $L_A2141$ | | H | Me | $^i$Pr | Me | H | H | H |
| $L_A2142$ | | Ph | Me | H | Me | H | H | H |
| $L_A2143$ | | H | Me | Ph | Me | H | H | H |
| $L_A2144$ | | Me | CD$_3$ | H | CD$_3$ | H | H | H |
| $L_A2145$ | | H | CD$_3$ | Me | CD$_3$ | H | H | H |
| $L_A2146$ | | CD$_3$ | CD$_3$ | H | CD$_3$ | H | H | H |
| $L_A2147$ | | H | CD$_3$ | CD$_3$ | CD$_3$ | H | H | H |
| $L_A2148$ | | $^i$Pr | CD$_3$ | H | CD$_3$ | H | H | H |
| $L_A2149$ | | H | CD$_3$ | $^i$Pr | CD$_3$ | H | H | H |
| $L_A2150$ | | Ph | CD$_3$ | H | CD$_3$ | H | H | H |
| $L_A2151$ | | H | CD$_3$ | Ph | CD$_3$ | H | H | H |
| $L_A2152$ | | Me | $^i$Pr | H | $^i$Pr | H | H | H |
| $L_A2153$ | | H | $^i$Pr | Me | $^i$Pr | H | H | H |
| $L_A2154$ | | CD$_3$ | $^i$Pr | H | $^i$Pr | H | H | H |
| $L_A2155$ | | H | $^i$Pr | CD$_3$ | $^i$Pr | H | H | H |
| $L_A2156$ | | $^i$Pr | $^i$Pr | H | $^i$Pr | H | H | H |
| $L_A2157$ | | H | $^i$Pr | $^i$Pr | $^i$Pr | H | H | H |
| $L_A2158$ | | Ph | $^i$Pr | H | $^i$Pr | H | H | H |
| $L_A2159$ | | H | $^i$Pr | Ph | $^i$Pr | H | H | H |
| $L_A2160$ | | Me | Ph | H | Ph | H | H | H |
| $L_A2161$ | | H | Ph | Me | Ph | H | H | H |
| $L_A2162$ | | CD$_3$ | Ph | H | Ph | H | H | H |
| $L_A2163$ | | H | Ph | CD$_3$ | Ph | H | H | H |
| $L_A2164$ | | $^i$Pr | Ph | H | Ph | H | H | H |
| $L_A2165$ | | H | Ph | $^i$Pr | Ph | H | H | H |
| $L_A2166$ | | Ph | Ph | H | Ph | H | H | H |
| $L_A2167$ | | H | Ph | Ph | Ph | H | H | H |
| $L_A2168$ | (decalin linker) | H | H | H | H | H | H | H |
| $L_A2169$ | | Me | H | H | H | H | H | H |
| $L_A2170$ | | H | Me | H | H | H | H | H |
| $L_A2171$ | | H | H | Me | H | H | H | H |
| $L_A2172$ | | H | H | H | Me | H | H | H |
| $L_A2173$ | | H | H | H | H | Me | H | H |
| $L_A2174$ | | CD$_3$ | H | H | H | H | H | H |
| $L_A2175$ | | H | CD$_3$ | H | H | H | H | H |
| $L_A2176$ | | H | H | CD$_3$ | H | H | H | H |
| $L_A2177$ | | H | H | H | CD$_3$ | H | H | H |
| $L_A2178$ | | H | H | H | H | CD$_3$ | H | H |
| $L_A2179$ | | $^i$Pr | H | H | H | H | H | H |
| $L_A2180$ | | H | $^i$Pr | H | H | H | H | H |
| $L_A2181$ | | H | H | $^i$Pr | H | H | H | H |
| $L_A2182$ | | H | H | H | $^i$Pr | H | H | H |
| $L_A2183$ | | H | H | H | H | $^i$Pr | H | H |
| $L_A2184$ | | Ph | H | H | H | H | H | H |
| $L_A2185$ | | H | Ph | H | H | H | H | H |
| $L_A2186$ | | H | H | Ph | H | H | H | H |
| $L_A2187$ | | H | H | H | Ph | H | H | H |
| $L_A2188$ | | H | H | H | H | Ph | H | H |
| $L_A2189$ | | Me | Me | H | H | H | H | H |
| $L_A2190$ | | Me | H | Me | H | H | H | H |
| $L_A2191$ | | Me | H | H | Me | H | H | H |
| $L_A2192$ | (decalin linker) | Me | H | H | H | Me | H | H |
| $L_A2193$ | | Me | CD$_3$ | H | H | H | H | H |
| $L_A2194$ | | Me | H | CD$_3$ | H | H | H | H |
| $L_A2195$ | | Me | H | H | CD$_3$ | H | H | H |
| $L_A2196$ | | Me | H | H | H | CD$_3$ | H | H |
| $L_A2197$ | | Me | $^i$Pr | H | H | H | H | H |
| $L_A2198$ | | Me | H | $^i$Pr | H | H | H | H |
| $L_A2199$ | | Me | H | H | $^i$Pr | H | H | H |
| $L_A2200$ | | Me | H | H | H | $^i$Pr | H | H |
| $L_A2201$ | | Me | Ph | H | H | H | H | H |
| $L_A2202$ | | Me | H | Ph | H | H | H | H |
| $L_A2203$ | | Me | H | H | Ph | H | H | H |
| $L_A2204$ | | Me | H | H | H | Ph | H | H |
| $L_A2205$ | | CD$_3$ | Me | H | H | H | H | H |
| $L_A2206$ | | CD$_3$ | H | Me | H | H | H | H |
| $L_A2207$ | | CD$_3$ | H | H | Me | H | H | H |
| $L_A2208$ | | CD$_3$ | H | H | H | Me | H | H |
| $L_A2209$ | | CD$_3$ | CD$_3$ | H | H | H | H | H |
| $L_A2210$ | | CD$_3$ | H | CD$_3$ | H | H | H | H |
| $L_A2211$ | | CD$_3$ | H | H | CD$_3$ | H | H | H |
| $L_A2212$ | | CD$_3$ | H | H | H | CD$_3$ | H | H |
| $L_A2213$ | | CD$_3$ | $^i$Pr | H | H | H | H | H |
| $L_A2214$ | | CD$_3$ | H | $^i$Pr | H | H | H | H |
| $L_A2215$ | | CD$_3$ | H | H | $^i$Pr | H | H | H |
| $L_A2216$ | | CD$_3$ | H | H | H | $^i$Pr | H | H |
| $L_A2217$ | | CD$_3$ | Ph | H | H | H | H | H |
| $L_A2218$ | | CD$_3$ | H | Ph | H | H | H | H |
| $L_A2219$ | | CD$_3$ | H | H | Ph | H | H | H |
| $L_A2220$ | | CD$_3$ | H | H | H | Ph | H | H |
| $L_A2221$ | | $^i$Pr | Me | H | H | H | H | H |
| $L_A2222$ | | $^i$Pr | H | Me | H | H | H | H |
| $L_A2223$ | | $^i$Pr | H | H | Me | H | H | H |
| $L_A2224$ | | $^i$Pr | H | H | H | Me | H | H |
| $L_A2225$ | | $^i$Pr | CD$_3$ | H | H | H | H | H |
| $L_A2226$ | | $^i$Pr | H | CD$_3$ | H | H | H | H |
| $L_A2227$ | | $^i$Pr | H | H | CD$_3$ | H | H | H |
| $L_A2228$ | | $^i$Pr | H | H | H | CD$_3$ | H | H |
| $L_A2229$ | | $^i$Pr | $^i$Pr | H | H | H | H | H |
| $L_A2230$ | | $^i$Pr | H | $^i$Pr | H | H | H | H |
| $L_A2231$ | | $^i$Pr | H | H | $^i$Pr | H | H | H |
| $L_A2232$ | | $^i$Pr | H | H | H | $^i$Pr | H | H |
| $L_A2233$ | | $^i$Pr | Ph | H | H | H | H | H |
| $L_A2234$ | | $^i$Pr | H | Ph | H | H | H | H |
| $L_A2235$ | | $^i$Pr | H | H | Ph | H | H | H |
| $L_A2236$ | | $^i$Pr | H | H | H | Ph | H | H |
| $L_A2237$ | | Ph | Me | H | H | H | H | H |
| $L_A2238$ | | Ph | H | Me | H | H | H | H |
| $L_A2239$ | | Ph | H | H | Me | H | H | H |
| $L_A2240$ | | Ph | H | H | H | Me | H | H |
| $L_A2241$ | | Ph | CD$_3$ | H | H | H | H | H |
| $L_A2242$ | | Ph | H | CD$_3$ | H | H | H | H |
| $L_A2243$ | | Ph | H | H | CD$_3$ | H | H | H |
| $L_A2244$ | | Ph | H | H | H | CD$_3$ | H | H |
| $L_A2245$ | | Ph | $^i$Pr | H | H | H | H | H |
| $L_A2246$ | | Ph | H | $^i$Pr | H | H | H | H |
| $L_A2247$ | | Ph | H | H | $^i$Pr | H | H | H |
| $L_A2248$ | | Ph | H | H | H | $^i$Pr | H | H |
| $L_A2249$ | (decalin linker) | Ph | Ph | H | H | H | H | H |
| $L_A2250$ | | Ph | H | Ph | H | H | H | H |
| $L_A2251$ | | Ph | H | H | Ph | H | H | H |
| $L_A2252$ | | Ph | H | H | H | Ph | H | H |
| $L_A2253$ | | H | Me | Me | H | H | H | H |
| $L_A2254$ | | H | Me | H | Me | H | H | H |
| $L_A2255$ | | H | Me | H | H | Me | H | H |
| $L_A2256$ | | H | Me | CD$_3$ | H | H | H | H |
| $L_A2257$ | | H | Me | H | CD$_3$ | H | H | H |
| $L_A2258$ | | H | Me | H | H | CD$_3$ | H | H |
| $L_A2259$ | | H | Me | $^i$Pr | H | H | H | H |
| $L_A2260$ | | H | Me | H | $^i$Pr | H | H | H |
| $L_A2261$ | | H | Me | H | H | $^i$Pr | H | H |
| $L_A2262$ | | H | Me | Ph | H | H | H | H |
| $L_A2263$ | | H | Me | H | Ph | H | H | H |
| $L_A2264$ | | H | Me | H | H | Ph | H | H |
| $L_A2265$ | | H | CD$_3$ | Me | H | H | H | H |
| $L_A2266$ | | H | CD$_3$ | H | Me | H | H | H |
| $L_A2267$ | | H | CD$_3$ | H | H | Me | H | H |
| $L_A2268$ | | H | CD$_3$ | CD$_3$ | H | H | H | H |
| $L_A2269$ | | H | CD$_3$ | H | CD$_3$ | H | H | H |
| $L_A2270$ | | H | CD$_3$ | H | H | CD$_3$ | H | H |
| $L_A2271$ | | H | CD$_3$ | $^i$Pr | H | H | H | H |
| $L_A2272$ | | H | CD$_3$ | H | $^i$Pr | H | H | H |
| $L_A2273$ | | H | CD$_3$ | H | H | $^i$Pr | H | H |
| $L_A2274$ | | H | CD$_3$ | Ph | H | H | H | H |
| $L_A2275$ | | H | CD$_3$ | H | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A2276$ | | H | $CD_3$ | H | H | Ph | H | H |
| $L_A2277$ | | H | $^iPr$ | Me | H | H | H | H |
| $L_A2278$ | | H | $^iPr$ | H | Me | H | H | H |
| $L_A2279$ | | H | $^iPr$ | H | H | Me | H | H |
| $L_A2280$ | | H | $^iPr$ | $CD_3$ | H | H | H | H |
| $L_A2281$ | | H | $^iPr$ | H | $CD_3$ | H | H | H |
| $L_A2282$ | | H | $^iPr$ | H | H | $CD_3$ | H | H |
| $L_A2283$ | | H | $^iPr$ | $^iPr$ | H | H | H | H |
| $L_A2284$ | | H | $^iPr$ | H | $^iPr$ | H | H | H |
| $L_A2285$ | | H | $^iPr$ | H | H | $^iPr$ | H | H |
| $L_A2286$ | | H | $^iPr$ | Ph | H | H | H | H |
| $L_A2287$ | | H | $^iPr$ | H | Ph | H | H | H |
| $L_A2288$ | | H | $^iPr$ | H | H | Ph | H | H |
| $L_A2289$ | | H | Ph | Me | H | H | H | H |
| $L_A2290$ | | H | Ph | H | Me | H | H | H |
| $L_A2291$ | | H | Ph | H | H | Me | H | H |
| $L_A2292$ | | H | Ph | $CD_3$ | H | H | H | H |
| $L_A2293$ | | H | Ph | H | $CD_3$ | H | H | H |
| $L_A2294$ | | H | Ph | H | H | $CD_3$ | H | H |
| $L_A2295$ | | H | Ph | $^iPr$ | H | H | H | H |
| $L_A2296$ | | H | Ph | H | $^iPr$ | H | H | H |
| $L_A2297$ | | H | Ph | H | H | $^iPr$ | H | H |
| $L_A2298$ | | H | Ph | Ph | H | H | H | H |
| $L_A2299$ | | H | Ph | H | Ph | H | H | H |
| $L_A2300$ | | H | Ph | H | H | Ph | H | H |
| $L_A2301$ | | H | H | Me | Me | H | H | H |
| $L_A2302$ | 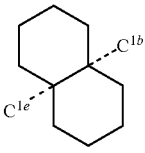 | H | H | $CD_3$ | Me | H | H | H |
| $L_A2303$ | | H | H | $^iPr$ | Me | H | H | H |
| $L_A2304$ | | H | H | Ph | Me | H | H | H |
| $L_A2305$ | | H | H | Me | $CD_3$ | H | H | H |
| $L_A2306$ | | H | H | $CD_3$ | $CD_3$ | H | H | H |
| $L_A2307$ | | H | H | $^iPr$ | $CD_3$ | H | H | H |
| $L_A2308$ | | H | H | Ph | $CD_3$ | H | H | H |
| $L_A2309$ | | H | H | Me | $^iPr$ | H | H | H |
| $L_A2310$ | | H | H | $CD_3$ | $^iPr$ | H | H | H |
| $L_A2311$ | | H | H | $^iPr$ | $^iPr$ | H | H | H |
| $L_A2312$ | | H | H | Ph | $^iPr$ | H | H | H |
| $L_A2313$ | | H | H | Me | Ph | H | H | H |
| $L_A2314$ | | H | H | $CD_3$ | Ph | H | H | H |
| $L_A2315$ | | H | H | $^iPr$ | Ph | H | H | H |
| $L_A2316$ | | H | H | Ph | Ph | H | H | H |
| $L_A2317$ | | H | H | Me | H | Me | H | H |
| $L_A2318$ | | H | H | $CD_3$ | H | Me | H | H |
| $L_A2319$ | | H | H | $^iPr$ | H | Me | H | H |
| $L_A2320$ | | H | H | Ph | H | Me | H | H |
| $L_A2321$ | | H | H | Me | H | $CD_3$ | H | H |
| $L_A2322$ | | H | H | $CD_3$ | H | $CD_3$ | H | H |
| $L_A2323$ | | H | H | $^iPr$ | H | $CD_3$ | H | H |
| $L_A2324$ | | H | H | Ph | H | $CD_3$ | H | H |
| $L_A2325$ | | H | H | Me | H | $^iPr$ | H | H |
| $L_A2326$ | | H | H | $CD_3$ | H | $^iPr$ | H | H |
| $L_A2327$ | | H | H | $^iPr$ | H | $^iPr$ | H | H |
| $L_A2328$ | | H | H | Ph | H | $^iPr$ | H | H |
| $L_A2329$ | | H | H | Me | H | Ph | H | H |
| $L_A2330$ | | H | H | $CD_3$ | H | Ph | H | H |
| $L_A2331$ | | H | H | $^iPr$ | H | Ph | H | H |
| $L_A2332$ | | H | H | Ph | H | Ph | H | H |
| $L_A2333$ | | Me | Me | H | Me | H | H | H |
| $L_A2334$ | | H | Me | Me | Me | H | H | H |
| $L_A2335$ | | $CD_3$ | Me | H | Me | H | H | H |
| $L_A2336$ | | H | Me | $CD_3$ | Me | H | H | H |
| $L_A2337$ | | $^iPr$ | Me | H | Me | H | H | H |
| $L_A2338$ | | H | Me | $^iPr$ | Me | H | H | H |
| $L_A2339$ | | Ph | Me | H | Me | H | H | H |
| $L_A2340$ | | H | Me | Ph | Me | H | H | H |
| $L_A2341$ | | Me | $CD_3$ | H | $CD_3$ | H | H | H |
| $L_A2342$ | | H | $CD_3$ | Me | $CD_3$ | H | H | H |
| $L_A2343$ | | $CD_3$ | $CD_3$ | H | $CD_3$ | H | H | H |
| $L_A2344$ | | H | $CD_3$ | $CD_3$ | $CD_3$ | H | H | H |
| $L_A2345$ | | $^iPr$ | $CD_3$ | H | $CD_3$ | H | H | H |
| $L_A2346$ | | H | $CD_3$ | $^iPr$ | $CD_3$ | H | H | H |
| $L_A2347$ | | Ph | $CD_3$ | H | $CD_3$ | H | H | H |
| $L_A2348$ | | H | $CD_3$ | Ph | $CD_3$ | H | H | H |
| $L_A2349$ | | Me | $^iPr$ | H | $^iPr$ | H | H | H |
| $L_A2350$ | | H | $^iPr$ | Me | $^iPr$ | H | H | H |
| $L_A2351$ | | $CD_3$ | $^iPr$ | H | $^iPr$ | H | H | H |
| $L_A2352$ | | H | $^iPr$ | $CD_3$ | $^iPr$ | H | H | H |
| $L_A2353$ | | $^iPr$ | $^iPr$ | H | $^iPr$ | H | H | H |
| $L_A2354$ | | H | $^iPr$ | $^iPr$ | $^iPr$ | H | H | H |
| $L_A2355$ | | Ph | $^iPr$ | H | $^iPr$ | H | H | H |
| $L_A2356$ | | H | $^iPr$ | Ph | $^iPr$ | H | H | H |
| $L_A2357$ | | Me | Ph | H | Ph | H | H | H |
| $L_A2358$ | | H | Ph | Me | Ph | H | H | H |
| $L_A2359$ | | $CD_3$ | Ph | H | Ph | H | H | H |
| $L_A2360$ | | H | Ph | $CD_3$ | Ph | H | H | H |
| $L_A2361$ | | $^iPr$ | Ph | H | Ph | H | H | H |
| $L_A2362$ | | H | Ph | $^iPr$ | Ph | H | H | H |
| $L_A2363$ | | Ph | Ph | H | Ph | H | H | H |
| $L_A2364$ | | H | Ph | Ph | Ph | H | H | H |
| $L_A2365$ | | H | H | H | H | H | H | H |
| $L_A2366$ | | Me | H | H | H | H | H | H |
| $L_A2367$ | | H | Me | H | H | H | H | H |
| $L_A2368$ | | H | H | Me | H | H | H | H |
| $L_A2369$ | | H | H | H | Me | H | H | H |
| $L_A2370$ | | H | H | H | H | Me | H | H |
| $L_A2371$ | | $CD_3$ | H | H | H | H | H | H |
| $L_A2372$ | | H | $CD_3$ | H | H | H | H | H |
| $L_A2373$ | | H | H | $CD_3$ | H | H | H | H |
| $L_A2374$ | | H | H | H | $CD_3$ | H | H | H |
| $L_A2375$ | | H | H | H | H | $CD_3$ | H | H |
| $L_A2376$ | | $^iPr$ | H | H | H | H | H | H |
| $L_A2377$ | | H | $^iPr$ | H | H | H | H | H |
| $L_A2378$ | | H | H | $^iPr$ | H | H | H | H |
| $L_A2379$ | | H | H | H | $^iPr$ | H | H | H |
| $L_A2380$ | | H | H | H | H | $^iPr$ | H | H |
| $L_A2381$ | | Ph | H | H | H | H | H | H |
| $L_A2382$ | | H | Ph | H | H | H | H | H |
| $L_A2383$ | | H | H | Ph | H | H | H | H |
| $L_A2384$ | | H | H | H | Ph | H | H | H |
| $L_A2385$ | | H | H | H | H | Ph | H | H |
| $L_A2386$ | | Me | Me | H | H | H | H | H |
| $L_A2387$ | | Me | H | Me | H | H | H | H |
| $L_A2388$ | | Me | H | H | Me | H | H | H |
| $L_A2389$ | | Me | H | H | H | Me | H | H |
| $L_A2390$ | | Me | $CD_3$ | H | H | H | H | H |
| $L_A2391$ | | Me | H | $CD_3$ | H | H | H | H |
| $L_A2392$ | | Me | H | H | $CD_3$ | H | H | H |
| $L_A2393$ | | Me | H | H | H | $CD_3$ | H | H |
| $L_A2394$ | | Me | $^iPr$ | H | H | H | H | H |
| $L_A2395$ | | Me | H | $^iPr$ | H | H | H | H |
| $L_A2396$ | | Me | H | H | $^iPr$ | H | H | H |
| $L_A2397$ | | Me | H | H | H | $^iPr$ | H | H |
| $L_A2398$ | | Me | Ph | H | H | H | H | H |
| $L_A2399$ | | Me | H | Ph | H | H | H | H |
| $L_A2400$ | | Me | H | H | Ph | H | H | H |
| $L_A2401$ | | Me | H | H | H | Ph | H | H |
| $L_A2402$ | | $CD_3$ | Me | H | H | H | H | H |
| $L_A2403$ | | $CD_3$ | H | Me | H | H | H | H |
| $L_A2404$ | | $CD_3$ | H | H | Me | H | H | H |
| $L_A2405$ | | $CD_3$ | H | H | H | Me | H | H |
| $L_A2406$ | | $CD_3$ | $CD_3$ | H | H | H | H | H |
| $L_A2407$ | | $CD_3$ | H | $CD_3$ | H | H | H | H |
| $L_A2408$ | | $CD_3$ | H | H | $CD_3$ | H | H | H |
| $L_A2409$ | | $CD_3$ | H | H | H | $CD_3$ | H | H |
| $L_A2410$ | | $CD_3$ | $^iPr$ | H | H | H | H | H |
| $L_A2411$ | | $CD_3$ | H | $^iPr$ | H | H | H | H |
| $L_A2412$ | | $CD_3$ | H | H | $^iPr$ | H | H | H |
| $L_A2413$ | | $CD_3$ | H | H | H | $^iPr$ | H | H |
| $L_A2414$ | | $CD_3$ | Ph | H | H | H | H | H |
| $L_A2415$ | | $CD_3$ | H | Ph | H | H | H | H |
| $L_A2416$ | | $CD_3$ | H | H | Ph | H | H | H |
| $L_A2417$ | | $CD_3$ | H | H | H | Ph | H | H |
| $L_A2418$ | | $^iPr$ | Me | H | H | H | H | H |
| $L_A2419$ | | $^iPr$ | H | Me | H | H | H | H |
| $L_A2420$ | | $^iPr$ | H | H | Me | H | H | H |
| $L_A2421$ | | $^iPr$ | H | H | H | Me | H | H |
| $L_A2422$ | | $^iPr$ | $CD_3$ | H | H | H | H | H |
| $L_A2423$ | | $^iPr$ | H | $CD_3$ | H | H | H | H |
| $L_A2424$ | | $^iPr$ | H | H | $CD_3$ | H | H | H |
| $L_A2425$ | | $^iPr$ | H | H | H | $CD_3$ | H | H |

-continued

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$2426 | | $^i$Pr | $^i$Pr | H | H | H | H | H |
| $L_A$2427 | | $^i$Pr | H | $^i$Pr | H | H | H | H |
| $L_A$2428 | | $^i$Pr | H | H | $^i$Pr | H | H | H |
| $L_A$2429 | | $^i$Pr | H | H | H | $^i$Pr | H | H |
| $L_A$2430 | | $^i$Pr | Ph | H | H | H | H | H |
| $L_A$2431 | | $^i$Pr | H | Ph | H | H | H | H |
| $L_A$2432 | | $^i$Pr | H | H | Ph | H | H | H |
| $L_A$2433 | | $^i$Pr | H | H | H | Ph | H | H |
| $L_A$2434 | | Ph | Me | H | H | H | H | H |
| $L_A$2435 | | Ph | H | Me | H | H | H | H |
| $L_A$2436 | | Ph | H | H | Me | H | H | H |
| $L_A$2437 | | Ph | H | H | H | Me | H | H |
| $L_A$2438 | | Ph | CD$_3$ | H | H | H | H | H |
| $L_A$2439 | | Ph | H | CD$_3$ | H | H | H | H |
| $L_A$2440 | | Ph | H | H | CD$_3$ | H | H | H |
| $L_A$2441 | | Ph | H | H | H | CD$_3$ | H | H |
| $L_A$2442 | | Ph | $^i$Pr | H | H | H | H | H |
| $L_A$2443 | | Ph | H | $^i$Pr | H | H | H | H |
| $L_A$2444 | | Ph | H | H | $^i$Pr | H | H | H |
| $L_A$2445 | | Ph | H | H | H | $^i$Pr | H | H |
| $L_A$2446 | | Ph | Ph | H | H | H | H | H |
| $L_A$2447 | | Ph | H | Ph | H | H | H | H |
| $L_A$2448 | | Ph | H | H | Ph | H | H | H |
| $L_A$2449 | | Ph | H | H | H | Ph | H | H |
| $L_A$2450 | | H | Me | Me | H | H | H | H |
| $L_A$2451 | | H | Me | H | Me | H | H | H |
| $L_A$2452 | | H | Me | H | H | Me | H | H |
| $L_A$2453 | | H | Me | CD$_3$ | H | H | H | H |
| $L_A$2454 | | H | Me | H | CD$_3$ | H | H | H |
| $L_A$2455 | | H | Me | H | H | CD$_3$ | H | H |
| $L_A$2456 | | H | Me | $^i$Pr | H | H | H | H |
| $L_A$2457 | | H | Me | H | $^i$Pr | H | H | H |
| $L_A$2458 | | H | Me | H | H | $^i$Pr | H | H |
| $L_A$2459 | | H | Me | Ph | H | H | H | H |
| $L_A$2460 | | H | Me | H | Ph | H | H | H |
| $L_A$2461 | | H | Me | H | H | Ph | H | H |
| $L_A$2462 | | H | CD$_3$ | Me | H | H | H | H |
| $L_A$2463 | | H | CD$_3$ | H | Me | H | H | H |
| $L_A$2464 | | H | CD$_3$ | H | H | Me | H | H |
| $L_A$2465 | | H | CD$_3$ | CD$_3$ | H | H | H | H |
| $L_A$2466 | 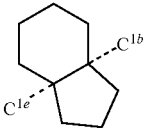 | H | CD$_3$ | H | CD$_3$ | H | H | H |
| $L_A$2467 | | H | CD$_3$ | H | H | CD$_3$ | H | H |
| $L_A$2468 | | H | CD$_3$ | $^i$Pr | H | H | H | H |
| $L_A$2469 | | H | CD$_3$ | H | $^i$Pr | H | H | H |
| $L_A$2470 | | H | CD$_3$ | H | H | $^i$Pr | H | H |
| $L_A$2471 | | H | CD$_3$ | Ph | H | H | H | H |
| $L_A$2472 | | H | CD$_3$ | H | Ph | H | H | H |
| $L_A$2473 | | H | CD$_3$ | H | H | Ph | H | H |
| $L_A$2474 | | H | $^i$Pr | Me | H | H | H | H |
| $L_A$2475 | | H | $^i$Pr | H | Me | H | H | H |
| $L_A$2476 | | H | $^i$Pr | H | H | Me | H | H |
| $L_A$2477 | | H | $^i$Pr | CD$_3$ | H | H | H | H |
| $L_A$2478 | | H | $^i$Pr | H | CD$_3$ | H | H | H |
| $L_A$2479 | | H | $^i$Pr | H | H | CD$_3$ | H | H |
| $L_A$2480 | | H | $^i$Pr | $^i$Pr | H | H | H | H |
| $L_A$2481 | | H | $^i$Pr | H | $^i$Pr | H | H | H |
| $L_A$2482 | | H | $^i$Pr | H | H | $^i$Pr | H | H |
| $L_A$2483 | | H | $^i$Pr | Ph | H | H | H | H |
| $L_A$2484 | | H | $^i$Pr | H | Ph | H | H | H |
| $L_A$2485 | | H | $^i$Pr | H | H | Ph | H | H |
| $L_A$2486 | | H | Ph | Me | H | H | H | H |
| $L_A$2487 | | H | Ph | H | Me | H | H | H |
| $L_A$2488 | | H | Ph | H | H | Me | H | H |
| $L_A$2489 | | H | Ph | CD$_3$ | H | H | H | H |
| $L_A$2490 | | H | Ph | H | CD$_3$ | H | H | H |
| $L_A$2491 | | H | Ph | H | H | CD$_3$ | H | H |
| $L_A$2492 | | H | Ph | $^i$Pr | H | H | H | H |
| $L_A$2493 | | H | Ph | H | $^i$Pr | H | H | H |
| $L_A$2494 | | H | Ph | H | H | $^i$Pr | H | H |
| $L_A$2495 | | H | Ph | Ph | H | H | H | H |
| $L_A$2496 | | H | Ph | H | Ph | H | H | H |
| $L_A$2497 | | H | Ph | H | H | Ph | H | H |
| $L_A$2498 | | H | H | Me | Me | H | H | H |
| $L_A$2499 | | H | H | CD$_3$ | Me | H | H | H |
| $L_A$2500 | | H | H | $^i$Pr | Me | H | H | H |
| $L_A$2501 | | H | H | Ph | Me | H | H | H |
| $L_A$2502 | | H | H | Me | CD$_3$ | H | H | H |
| $L_A$2503 | | H | H | CD$_3$ | CD$_3$ | H | H | H |
| $L_A$2504 | | H | H | $^i$Pr | CD$_3$ | H | H | H |
| $L_A$2505 | | H | H | Ph | CD$_3$ | H | H | H |
| $L_A$2506 | | H | H | Me | $^i$Pr | H | H | H |
| $L_A$2507 | | H | H | CD$_3$ | $^i$Pr | H | H | H |
| $L_A$2508 | | H | H | $^i$Pr | $^i$Pr | H | H | H |
| $L_A$2509 | | H | H | Ph | $^i$Pr | H | H | H |
| $L_A$2510 | | H | H | Me | Ph | H | H | H |
| $L_A$2511 | | H | H | CD$_3$ | Ph | H | H | H |
| $L_A$2512 | | H | H | $^i$Pr | Ph | H | H | H |
| $L_A$2513 | | H | H | Ph | Ph | H | H | H |
| $L_A$2514 | | H | H | Me | H | Me | H | H |
| $L_A$2515 | | H | H | CD$_3$ | H | Me | H | H |
| $L_A$2516 | | H | H | $^i$Pr | H | Me | H | H |
| $L_A$2517 | | H | H | Ph | H | Me | H | H |
| $L_A$2518 | | H | H | Me | H | CD$_3$ | H | H |
| $L_A$2519 | | H | H | CD$_3$ | H | CD$_3$ | H | H |
| $L_A$2520 | | H | H | $^i$Pr | H | CD$_3$ | H | H |
| $L_A$2521 | | H | H | Ph | H | CD$_3$ | H | H |
| $L_A$2522 | | H | H | Me | H | $^i$Pr | H | H |
| $L_A$2523 | | H | H | CD$_3$ | H | $^i$Pr | H | H |
| $L_A$2524 | | H | H | $^i$Pr | H | $^i$Pr | H | H |
| $L_A$2525 | | H | H | Ph | H | $^i$Pr | H | H |
| $L_A$2526 | | H | H | Me | H | $^i$Pr | H | H |
| $L_A$2527 | | H | H | CD$_3$ | H | $^i$Pr | H | H |
| $L_A$2528 | | H | H | $^i$Pr | H | Ph | H | H |
| $L_A$2529 | | H | H | Ph | H | Ph | H | H |
| $L_A$2530 | | Me | Me | H | Me | H | H | H |
| $L_A$2531 | | H | Me | Me | Me | H | H | H |
| $L_A$2532 | | CD$_3$ | Me | H | Me | H | H | H |
| $L_A$2533 | | H | Me | CD$_3$ | Me | H | H | H |
| $L_A$2534 | | $^i$Pr | Me | H | Me | H | H | H |
| $L_A$2535 | | H | Me | $^i$Pr | Me | H | H | H |
| $L_A$2536 | | Ph | Me | H | Me | H | H | H |
| $L_A$2537 | | H | Me | Ph | Me | H | H | H |
| $L_A$2538 | | Me | CD$_3$ | H | CD$_3$ | H | H | H |
| $L_A$2539 | | H | CD$_3$ | Me | CD$_3$ | H | H | H |
| $L_A$2540 | | CD$_3$ | CD$_3$ | H | CD$_3$ | H | H | H |
| $L_A$2541 | | H | CD$_3$ | CD$_3$ | CD$_3$ | H | H | H |
| $L_A$2542 | | $^i$Pr | CD$_3$ | H | CD$_3$ | H | H | H |
| $L_A$2543 | | H | CD$_3$ | $^i$Pr | CD$_3$ | H | H | H |
| $L_A$2544 | | Ph | CD$_3$ | H | CD$_3$ | H | H | H |
| $L_A$2545 | | H | CD$_3$ | Ph | CD$_3$ | H | H | H |
| $L_A$2546 | | Me | $^i$Pr | H | $^i$Pr | H | H | H |
| $L_A$2547 | | H | $^i$Pr | Me | $^i$Pr | H | H | H |
| $L_A$2548 | | CD$_3$ | $^i$Pr | H | $^i$Pr | H | H | H |
| $L_A$2549 | | H | $^i$Pr | CD$_3$ | $^i$Pr | H | H | H |
| $L_A$2550 | | $^i$Pr | $^i$Pr | H | $^i$Pr | H | H | H |
| $L_A$2551 | | H | $^i$Pr | $^i$Pr | $^i$Pr | H | H | H |
| $L_A$2552 | | Ph | $^i$Pr | H | $^i$Pr | H | H | H |
| $L_A$2553 | | H | $^i$Pr | Ph | $^i$Pr | H | H | H |
| $L_A$2554 | | Me | Ph | H | Ph | H | H | H |
| $L_A$2555 | | H | Ph | Me | Ph | H | H | H |
| $L_A$2556 | | CD$_3$ | Ph | H | Ph | H | H | H |
| $L_A$2557 | | H | Ph | CD$_3$ | Ph | H | H | H |
| $L_A$2558 | | $^i$Pr | Ph | H | Ph | H | H | H |
| $L_A$2559 | | H | Ph | $^i$Pr | Ph | H | H | H |
| $L_A$2560 | | Ph | Ph | H | Ph | H | H | H |
| $L_A$2561 | | H | Ph | Ph | Ph | H | H | H |
| $L_A$2562 | | H | H | H | H | H | H | H |
| $L_A$2563 | | Me | H | H | H | H | H | H |
| $L_A$2564 | | H | Me | H | H | H | H | H |
| $L_A$2565 | | H | H | Me | H | H | H | H |
| $L_A$2566 | | H | H | H | Me | H | H | H |
| $L_A$2567 | | H | H | H | H | Me | H | H |
| $L_A$2568 | | CD$_3$ | H | H | H | H | H | H |
| $L_A$2569 | | H | CD$_3$ | H | H | H | H | H |
| $L_A$2570 | | H | H | CD$_3$ | H | H | H | H |
| $L_A$2571 | | H | H | H | CD$_3$ | H | H | H |
| $L_A$2572 | | H | H | H | H | CD$_3$ | H | H |
| $L_A$2573 | | $^i$Pr | H | H | H | H | H | H |
| $L_A$2574 | | H | $^i$Pr | H | H | H | H | H |
| $L_A$2575 | | H | H | $^i$Pr | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A2576$ | | H | H | H | $^i$Pr | H | H | H |
| $L_A2577$ | | H | H | H | H | $^i$Pr | H | H |
| $L_A2578$ | | Ph | H | H | H | H | H | H |
| $L_A2579$ | | H | Ph | H | H | H | H | H |
| $L_A2580$ | | H | H | Ph | H | H | H | H |
| $L_A2581$ | | H | H | H | Ph | H | H | H |
| $L_A2582$ | | H | H | H | H | Ph | H | H |
| $L_A2583$ | | Me | Me | H | H | H | H | H |
| $L_A2584$ | | Me | H | Me | H | H | H | H |
| $L_A2585$ | | Me | H | H | Me | H | H | H |
| $L_A2586$ | | Me | H | H | H | Me | H | H |
| $L_A2587$ | | Me | $CD_3$ | H | H | H | H | H |
| $L_A2588$ | | Me | H | $CD_3$ | H | H | H | H |
| $L_A2589$ | | Me | H | H | $CD_3$ | H | H | H |
| $L_A2590$ | | Me | H | H | H | $CD_3$ | H | H |
| $L_A2591$ | | Me | $^i$Pr | H | H | H | H | H |
| $L_A2592$ | | Me | H | $^i$Pr | H | H | H | H |
| $L_A2593$ | | Me | H | H | $^i$Pr | H | H | H |
| $L_A2594$ | | Me | H | H | H | $^i$Pr | H | H |
| $L_A2595$ | | Me | Ph | H | H | H | H | H |
| $L_A2596$ | | Me | H | Ph | H | H | H | H |
| $L_A2597$ | | Me | H | H | Ph | H | H | H |
| $L_A2598$ | | Me | H | H | H | Ph | H | H |
| $L_A2599$ | | $CD_3$ | Me | H | H | H | H | H |
| $L_A2600$ | | $CD_3$ | H | Me | H | H | H | H |
| $L_A2601$ | | $CD_3$ | H | H | Me | H | H | H |
| $L_A2602$ | | $CD_3$ | H | H | H | Me | H | H |
| $L_A2603$ | | $CD_3$ | $CD_3$ | H | H | H | H | H |
| $L_A2604$ | | $CD_3$ | H | $CD_3$ | H | H | H | H |
| $L_A2605$ | | $CD_3$ | H | H | $CD_3$ | H | H | H |
| $L_A2606$ | | $CD_3$ | H | H | H | $CD_3$ | H | H |
| $L_A2607$ | | $CD_3$ | $^i$Pr | H | H | H | H | H |
| $L_A2608$ | | $CD_3$ | H | $^i$Pr | H | H | H | H |
| $L_A2609$ | | $CD_3$ | H | H | $^i$Pr | H | H | H |
| $L_A2610$ | | $CD_3$ | H | H | H | $^i$Pr | H | H |
| $L_A2611$ | | $CD_3$ | Ph | H | H | H | H | H |
| $L_A2612$ | | $CD_3$ | H | Ph | H | H | H | H |
| $L_A2613$ | | $CD_3$ | H | H | Ph | H | H | H |
| $L_A2614$ | | $CD_3$ | H | H | H | Ph | H | H |
| $L_A2615$ | | $^i$Pr | Me | H | H | H | H | H |
| $L_A2616$ | | $^i$Pr | H | Me | H | H | H | H |
| $L_A2617$ | | $^i$Pr | H | H | Me | H | H | H |
| $L_A2618$ | | $^i$Pr | H | H | H | Me | H | H |
| $L_A2619$ | | $^i$Pr | $CD_3$ | H | H | H | H | H |
| $L_A2620$ | | $^i$Pr | H | $CD_3$ | H | H | H | H |
| $L_A2621$ | | $^i$Pr | H | H | $CD_3$ | H | H | H |
| $L_A2622$ | | $^i$Pr | H | H | H | $CD_3$ | H | H |
| $L_A2623$ | | $^i$Pr | $^i$Pr | H | H | H | H | H |
| $L_A2624$ | | $^i$Pr | H | $^i$Pr | H | H | H | H |
| $L_A2625$ | | $^i$Pr | H | H | $^i$Pr | H | H | H |
| $L_A2626$ | | $^i$Pr | H | H | H | $^i$Pr | H | H |
| $L_A2627$ | | $^i$Pr | Ph | H | H | H | H | H |
| $L_A2628$ | | $^i$Pr | H | Ph | H | H | H | H |
| $L_A2629$ | | $^i$Pr | H | H | Ph | H | H | H |
| $L_A2630$ | | $^i$Pr | H | H | H | Ph | H | H |
| $L_A2631$ | | Ph | Me | H | H | H | H | H |
| $L_A2632$ | | Ph | H | Me | H | H | H | H |
| $L_A2633$ | | Ph | H | H | Me | H | H | H |
| $L_A2634$ | | Ph | H | H | H | Me | H | H |
| $L_A2635$ | | Ph | $CD_3$ | H | H | H | H | H |
| $L_A2636$ | | Ph | H | $CD_3$ | H | H | H | H |
| $L_A2637$ | | Ph | H | H | $CD_3$ | H | H | H |
| $L_A2638$ | | Ph | H | H | H | $CD_3$ | H | H |
| $L_A2639$ | | Ph | $^i$Pr | H | H | H | H | H |
| $L_A2640$ | | Ph | H | $^i$Pr | H | H | H | H |
| $L_A2641$ | | Ph | H | H | $^i$Pr | H | H | H |
| $L_A2642$ | | Ph | H | H | H | $^i$Pr | H | H |
| $L_A2643$ | | Ph | Ph | H | H | H | H | H |
| $L_A2644$ | | Ph | H | Ph | H | H | H | H |
| $L_A2645$ | | Ph | H | H | Ph | H | H | H |
| $L_A2646$ | | Ph | H | H | H | Ph | H | H |
| $L_A2647$ | | H | Me | Me | H | H | H | H |
| $L_A2648$ | | H | Me | H | Me | H | H | H |
| $L_A2649$ | | H | Me | H | H | Me | H | H |
| $L_A2650$ | | H | Me | $CD_3$ | H | H | H | H |
| $L_A2651$ | | H | Me | H | $CD_3$ | H | H | H |
| $L_A2652$ | | H | Me | H | H | $CD_3$ | H | H |
| $L_A2653$ | | H | Me | $^i$Pr | H | H | H | H |
| $L_A2654$ | | H | Me | H | $^i$Pr | H | H | H |
| $L_A2655$ | | H | Me | H | H | $^i$Pr | H | H |
| $L_A2656$ | | H | Me | Ph | H | H | H | H |
| $L_A2657$ | | H | Me | H | Ph | H | H | H |
| $L_A2658$ | | H | Me | H | H | Ph | H | H |
| $L_A2659$ | | H | $CD_3$ | Me | H | H | H | H |
| $L_A2660$ | | H | $CD_3$ | H | Me | H | H | H |
| $L_A2661$ | | H | $CD_3$ | H | H | Me | H | H |
| $L_A2662$ | | H | $CD_3$ | $CD_3$ | H | H | H | H |
| $L_A2663$ | | H | $CD_3$ | H | $CD_3$ | H | H | H |
| $L_A2664$ | | H | $CD_3$ | H | H | $CD_3$ | H | H |
| $L_A2665$ | | H | $CD_3$ | $^i$Pr | H | H | H | H |
| $L_A2666$ | | H | $CD_3$ | H | $^i$Pr | H | H | H |
| $L_A2667$ | | H | $CD_3$ | H | H | $^i$Pr | H | H |
| $L_A2668$ | | H | $CD_3$ | Ph | H | H | H | H |
| $L_A2669$ | | H | $CD_3$ | H | Ph | H | H | H |
| $L_A2670$ | | H | $CD_3$ | H | H | Ph | H | H |
| $L_A2671$ | | H | $^i$Pr | Me | H | H | H | H |
| $L_A2672$ | | H | $^i$Pr | H | Me | H | H | H |
| $L_A2673$ | | H | $^i$Pr | H | H | Me | H | H |
| $L_A2674$ | | H | $^i$Pr | $CD_3$ | H | H | H | H |
| $L_A2675$ | | H | $^i$Pr | H | $CD_3$ | H | H | H |
| $L_A2676$ | | H | $^i$Pr | H | H | $CD_3$ | H | H |
| $L_A2677$ | | H | $^i$Pr | $^i$Pr | H | H | H | H |
| $L_A2678$ | | H | $^i$Pr | H | $^i$Pr | H | H | H |
| $L_A2679$ | | H | $^i$Pr | H | H | $^i$Pr | H | H |
| $L_A2680$ | | H | $^i$Pr | Ph | H | H | H | H |
| $L_A2681$ | | H | $^i$Pr | H | Ph | H | H | H |
| $L_A2682$ | | H | $^i$Pr | H | H | Ph | H | H |
| $L_A2683$ | | H | Ph | Me | H | H | H | H |
| $L_A2684$ | | H | Ph | H | Me | H | H | H |
| $L_A2685$ | | H | Ph | H | H | Me | H | H |
| $L_A2686$ | | H | Ph | $CD_3$ | H | H | H | H |
| $L_A2687$ | | H | Ph | H | $CD_3$ | H | H | H |
| $L_A2688$ | | H | Ph | H | H | $CD_3$ | H | H |
| $L_A2689$ | | H | Ph | $^i$Pr | H | H | H | H |
| $L_A2690$ | | H | Ph | H | $^i$Pr | H | H | H |
| $L_A2691$ | | H | Ph | H | H | $^i$Pr | H | H |
| $L_A2692$ | | H | Ph | Ph | H | H | H | H |
| $L_A2693$ | | H | Ph | H | Ph | H | H | H |
| $L_A2694$ | | H | Ph | H | H | Ph | H | H |
| $L_A2695$ | | H | H | Me | Me | H | H | H |
| $L_A2696$ | | H | H | $CD_3$ | Me | H | H | H |
| $L_A2697$ | | H | H | $^i$Pr | Me | H | H | H |
| $L_A2698$ | | H | H | Ph | Me | H | H | H |
| $L_A2699$ | | H | H | Me | $CD_3$ | H | H | H |
| $L_A2700$ | | H | H | $CD_3$ | $CD_3$ | H | H | H |
| $L_A2701$ | | H | H | $^i$Pr | $CD_3$ | H | H | H |
| $L_A2702$ | | H | H | Ph | $CD_3$ | H | H | H |
| $L_A2703$ | | H | H | Me | $^i$Pr | H | H | H |
| $L_A2704$ | | H | H | $CD_3$ | $^i$Pr | H | H | H |
| $L_A2705$ | | H | H | $^i$Pr | $^i$Pr | H | H | H |
| $L_A2706$ | | H | H | Ph | $^i$Pr | H | H | H |
| $L_A2707$ | | H | H | Me | Ph | H | H | H |
| $L_A2708$ | | H | H | $CD_3$ | Ph | H | H | H |
| $L_A2709$ | | H | H | $^i$Pr | Ph | H | H | H |
| $L_A2710$ | | H | H | Ph | Ph | H | H | H |
| $L_A2711$ | | H | H | Me | H | Me | H | H |
| $L_A2712$ | | H | H | $CD_3$ | H | Me | H | H |
| $L_A2713$ | | H | H | $^i$Pr | H | Me | H | H |
| $L_A2714$ | | H | H | Ph | H | Me | H | H |
| $L_A2715$ | | H | H | Me | H | $CD_3$ | H | H |
| $L_A2716$ | | H | H | $CD_3$ | H | $CD_3$ | H | H |
| $L_A2717$ | | H | H | $^i$Pr | H | $CD_3$ | H | H |
| $L_A2718$ | | H | H | Ph | H | $CD_3$ | H | H |
| $L_A2719$ | | H | H | Me | H | $^i$Pr | H | H |
| $L_A2720$ | | H | H | $CD_3$ | H | $^i$Pr | H | H |
| $L_A2721$ | | H | H | $^i$Pr | H | $^i$Pr | H | H |
| $L_A2722$ | | H | H | Ph | H | $^i$Pr | H | H |
| $L_A2723$ | | H | H | Me | H | Ph | H | H |
| $L_A2724$ | | H | H | $CD_3$ | H | Ph | H | H |
| $L_A2725$ | | H | H | $^i$Pr | H | Ph | H | H |
| $L_A2726$ | | H | H | Ph | H | Ph | H | H |
| $L_A2727$ | | Me | Me | H | Me | H | H | H |

-continued

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$2728 | | H | Me | Me | Me | H | H | H |
| $L_A$2729 | | CD$_3$ | Me | H | Me | H | H | H |
| $L_A$2730 | | H | Me | CD$_3$ | Me | H | H | H |
| $L_A$2731 | | $^i$Pr | Me | H | Me | H | H | H |
| $L_A$2732 | | H | Me | $^i$Pr | Me | H | H | H |
| $L_A$2733 | | Ph | Me | H | Me | H | H | H |
| $L_A$2734 | | H | Me | Ph | Me | H | H | H |
| $L_A$2735 | | Me | CD$_3$ | H | CD$_3$ | H | H | H |
| $L_A$2736 | | H | CD$_3$ | Me | CD$_3$ | H | H | H |
| $L_A$2737 | | CD$_3$ | CD$_3$ | H | CD$_3$ | H | H | H |
| $L_A$2738 | | H | CD$_3$ | CD$_3$ | CD$_3$ | H | H | H |
| $L_A$2739 | | $^i$Pr | CD$_3$ | H | CD$_3$ | H | H | H |
| $L_A$2740 | | H | CD$_3$ | $^i$Pr | CD$_3$ | H | H | H |
| $L_A$2741 | | Ph | CD$_3$ | H | CD$_3$ | H | H | H |
| $L_A$2742 | | H | CD$_3$ | Ph | CD$_3$ | H | H | H |
| $L_A$2743 | | Me | $^i$Pr | H | $^i$Pr | H | H | H |
| $L_A$2744 | | H | $^i$Pr | Me | $^i$Pr | H | H | H |
| $L_A$2745 | | CD$_3$ | $^i$Pr | H | $^i$Pr | H | H | H |
| $L_A$2746 | | H | $^i$Pr | CD$_3$ | $^i$Pr | H | H | H |
| $L_A$2747 | | $^i$Pr | $^i$Pr | H | $^i$Pr | H | H | H |
| $L_A$2748 | | H | $^i$Pr | $^i$Pr | $^i$Pr | H | H | H |
| $L_A$2749 | | Ph | $^i$Pr | H | $^i$Pr | H | H | H |
| $L_A$2750 | | H | $^i$Pr | Ph | $^i$Pr | H | H | H |
| $L_A$2751 | | Me | Ph | H | Ph | H | H | H |
| $L_A$2752 | | H | Ph | Me | Ph | H | H | H |
| $L_A$2753 | | CD$_3$ | Ph | H | Ph | H | H | H |
| $L_A$2754 | | H | Ph | CD$_3$ | Ph | H | H | H |
| $L_A$2755 | | $^i$Pr | Ph | H | Ph | H | H | H |
| $L_A$2756 | | H | Ph | $^i$Pr | Ph | H | H | H |
| $L_A$2757 | | Ph | Ph | H | Ph | H | H | H |
| $L_A$2758 | | H | Ph | Ph | Ph | H | H | H |

In some embodiments of the compound of Formula 1, the ligand L is selected from the group consisting of:

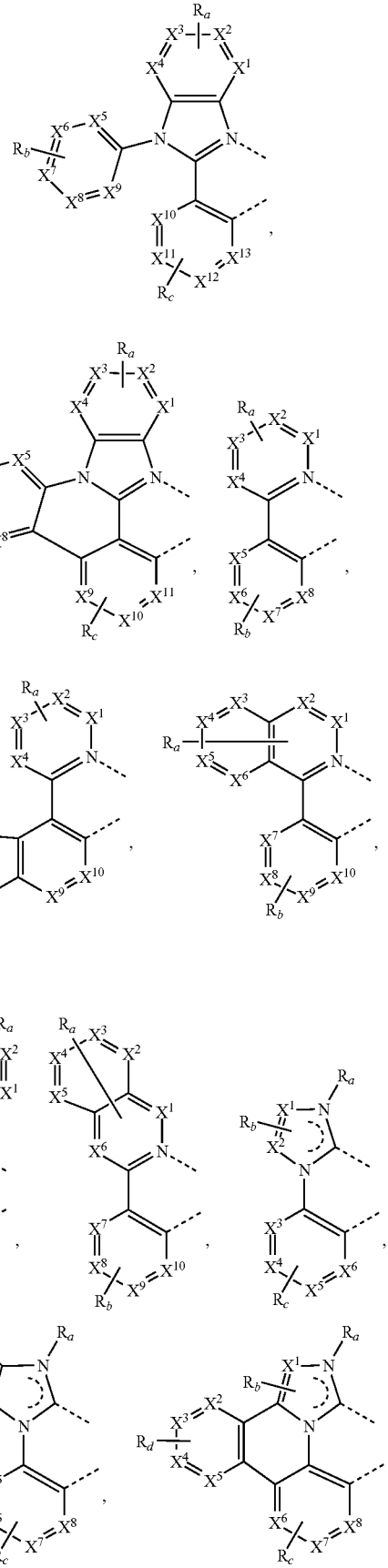

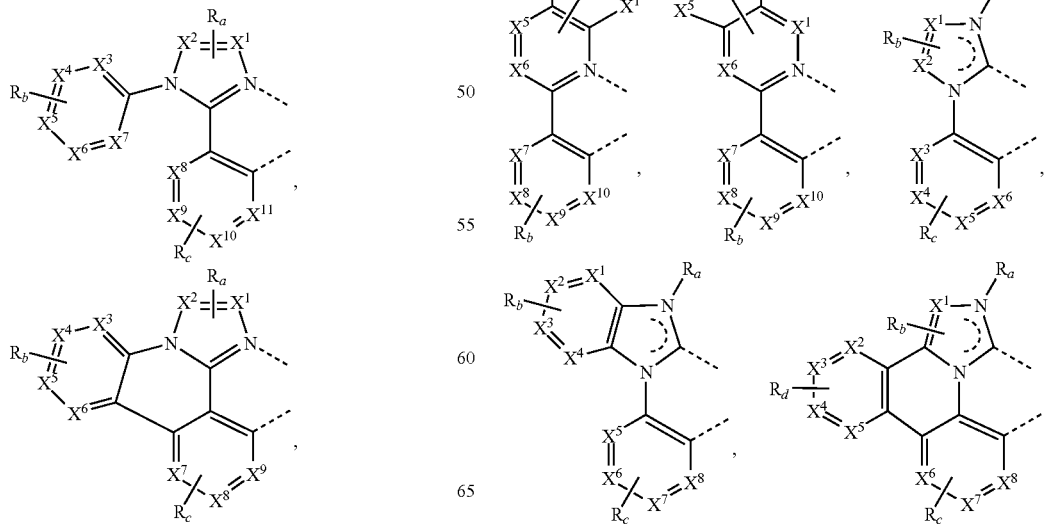

-continued

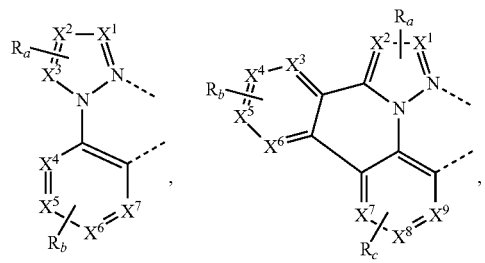

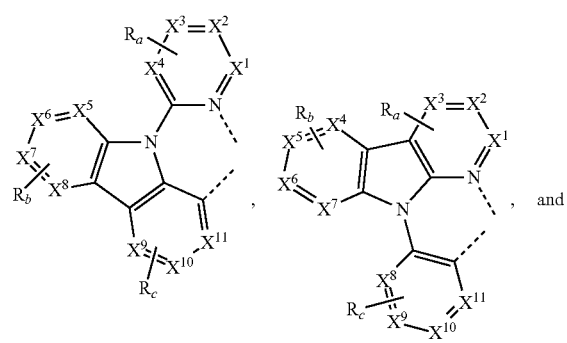

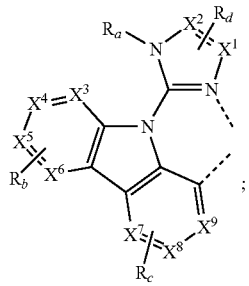

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In some embodiments of the compound of Formula 1, the ligand L is selected from the group consisting of:

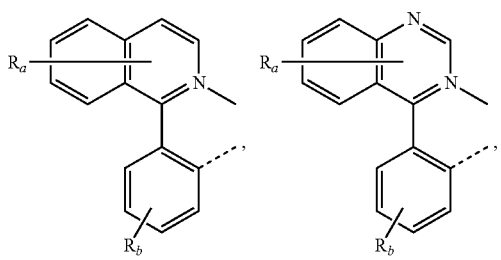

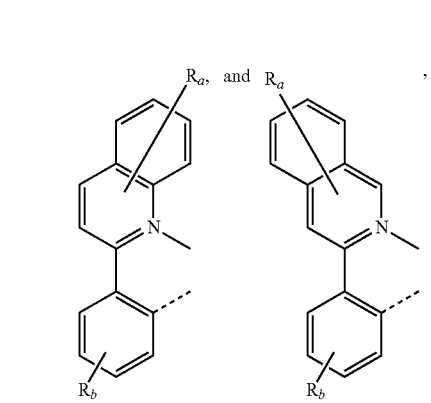

wherein $R_a$ and $R_b$ are as defined above.

In some embodiments of the compound of Formula 1, the ligand L is selected from the group consisting of:

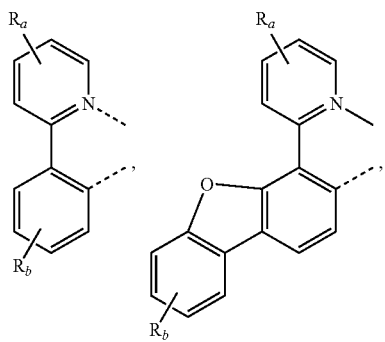

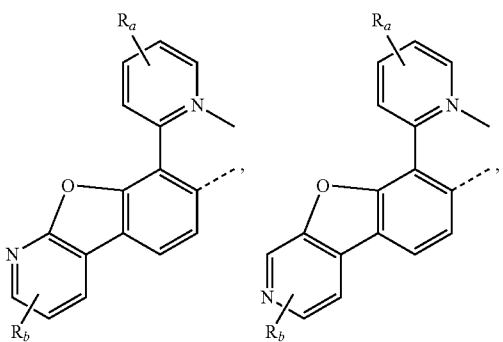

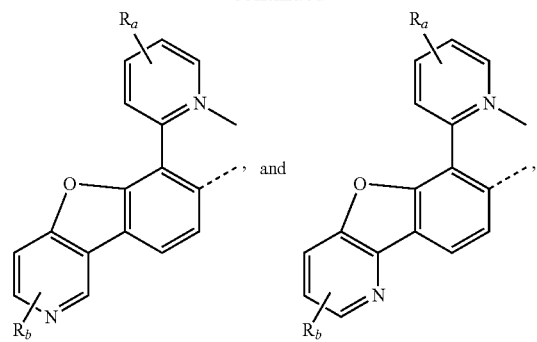
wherein $R_a$ and $R_b$ are as defined above.
In some embodiments of the compound of Formula 1, the ligand L is selected from the group consisting of:
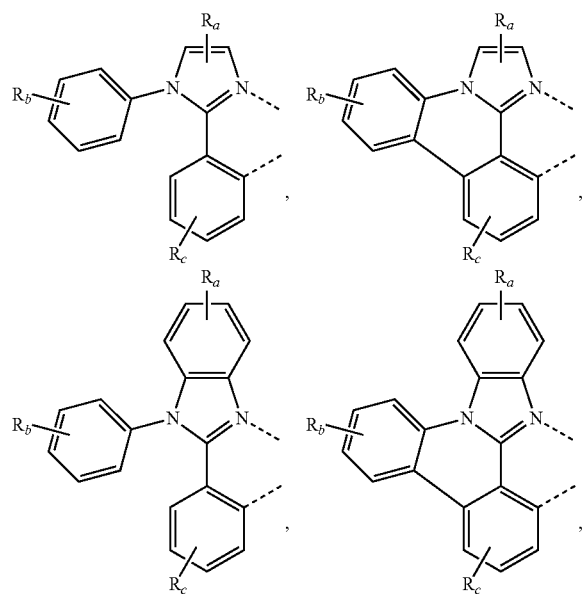
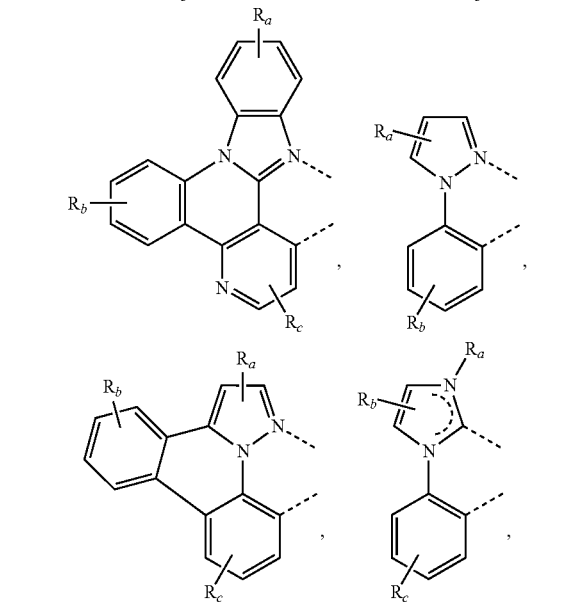
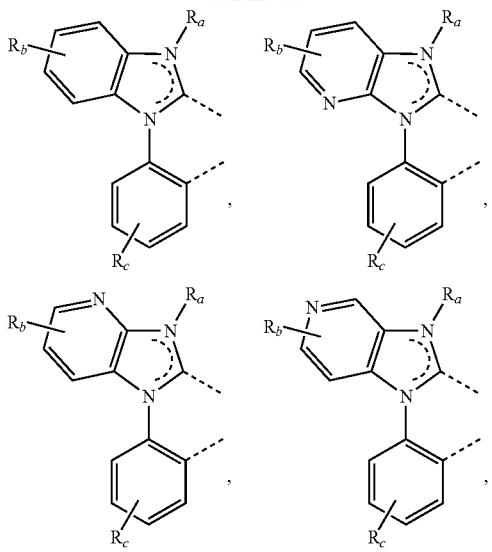
wherein $R_a$, $R_b$, and $R_c$ are as defined above.
In some embodiments of the compound of Formula 1, ligand L is selected from the group consisting of:
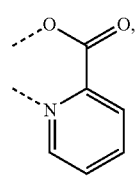
L₁
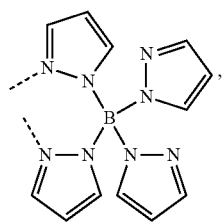
L₂

-continued
| | |
|---|---|
| 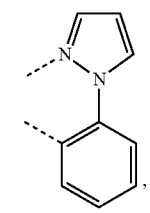 | L₃ |
| 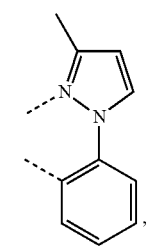 | L₄ |
| 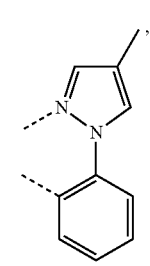 | L₅ |
| 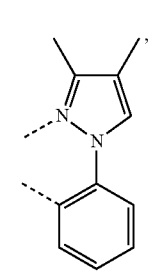 | L₆ |
| 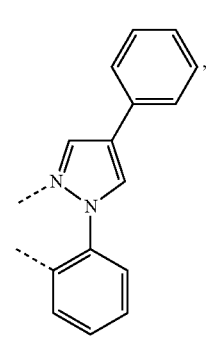 | L₇ |
| 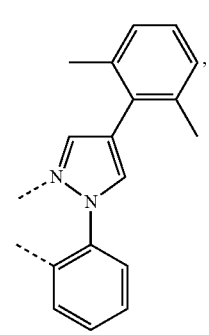 | L₈ |
-continued
| | |
|---|---|
| 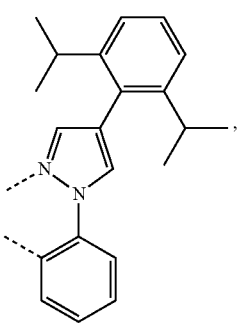 | L₉ |
| 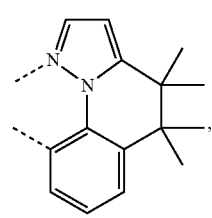 | L₁₀ |
| 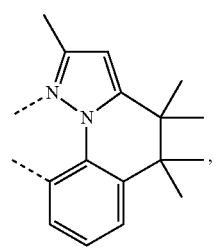 | L₁₁ |
| 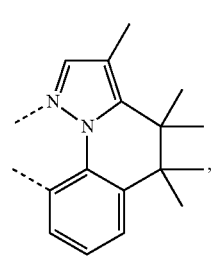 | L₁₂ |
| 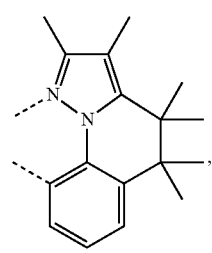 | L₁₃ |
| 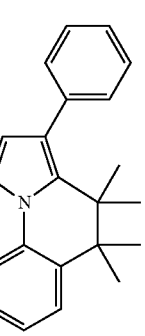 | L₁₄ |

-continued
L15
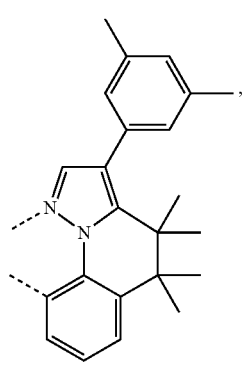
L16
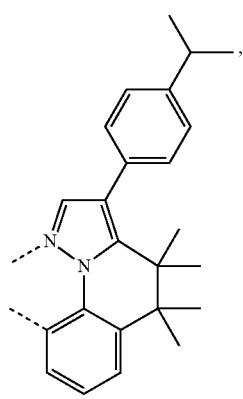
L17
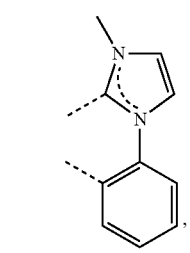
L18
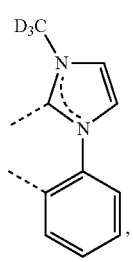
L19
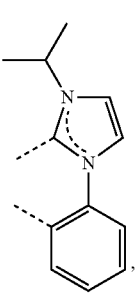
-continued
L20
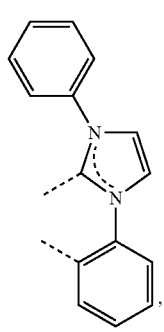
L21
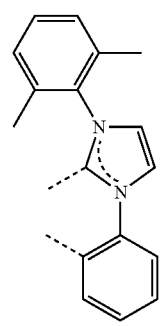
L22
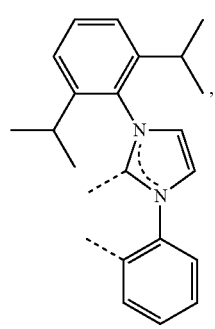
L23
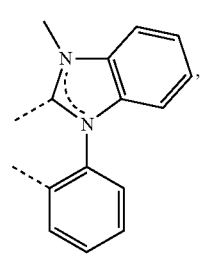
L24
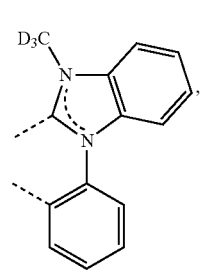

L25 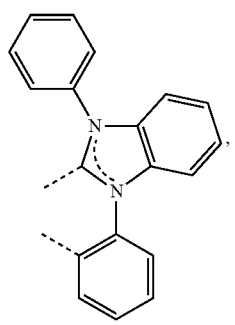
L26 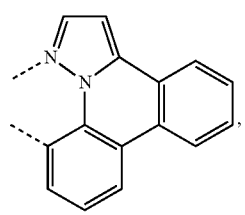
L27 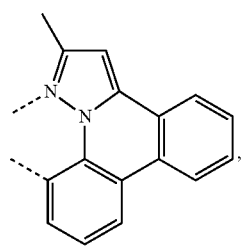
L28 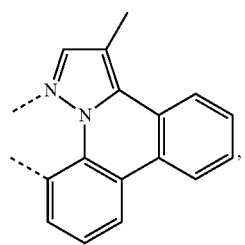
L29 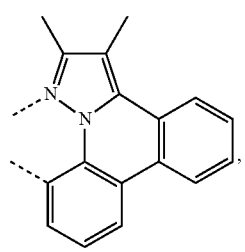
L30 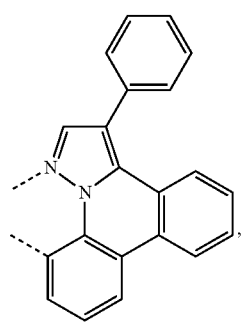
L31 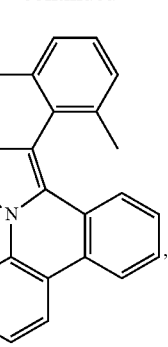
L32 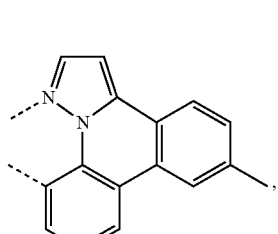
L33 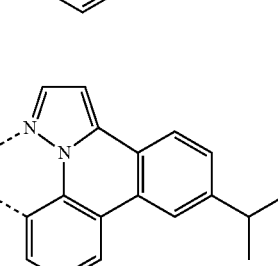
L34 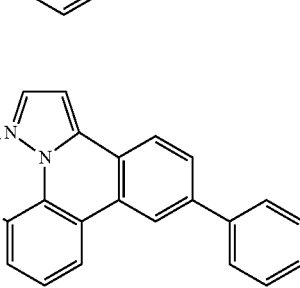
L35 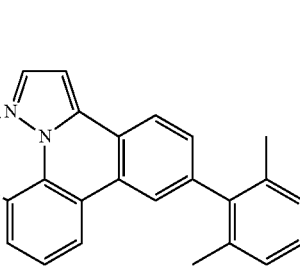
L36 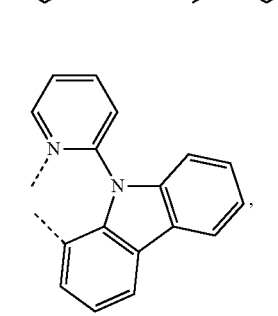

-continued

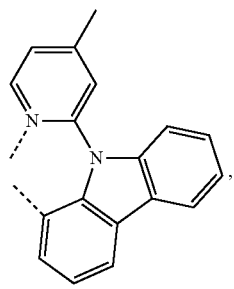
L37

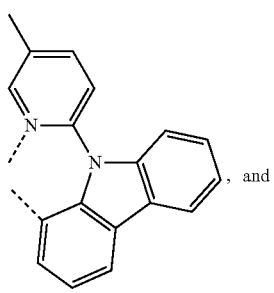
L38, and

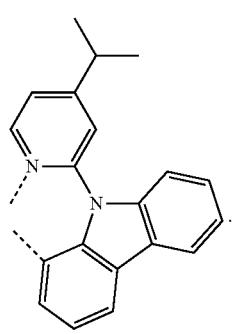
L39

In some embodiments of the compound of Formula 1, the compound is $(L_A)_3Ir$, wherein $L_A$ is as defined above.

In some embodiments of the compound of Formula 1, the compound is $(L_A)Ir(L)_2$ or $(L_A)_2Ir(L)$, wherein $L_A$ and L are as defined above.

In some embodiments of the compound of Formula 1, where $L_A$ is as defined above, the compound is Compound Ax having the formula $Ir(L_{Ai})_3$; wherein x=i, i is an integer from 1 to 2758.

In some embodiments of the compound of Formula 1, where $L_A$ is as defined above, the compound is Compound By having the formula $Ir(L_{Ai})(L_j)_2$ or Compound Cz having the formula $Ir(L_{Ai})_2(L_j)$;

wherein y=39i+j−39, i is an integer from 1 to 2758, and j is an integer from 1 to 39;

wherein z=39i+j−39, i is an integer from 1 to 2758, and j is an integer from 1 to 39; and wherein $L_1$ to $L_{39}$ have the following structure:

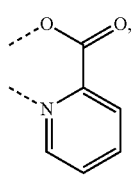
L1

-continued

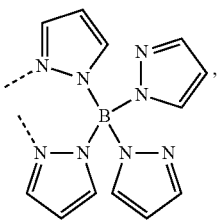
L2

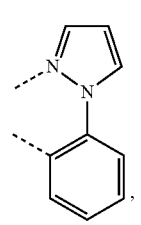
L3

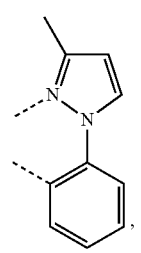
L4

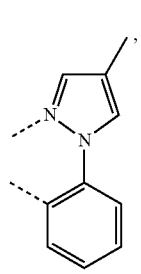
L5

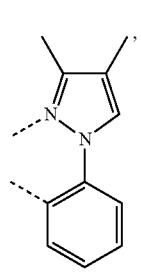
L6

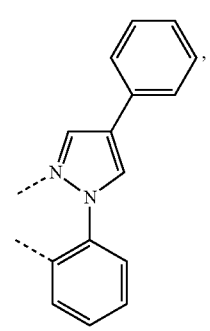
L7

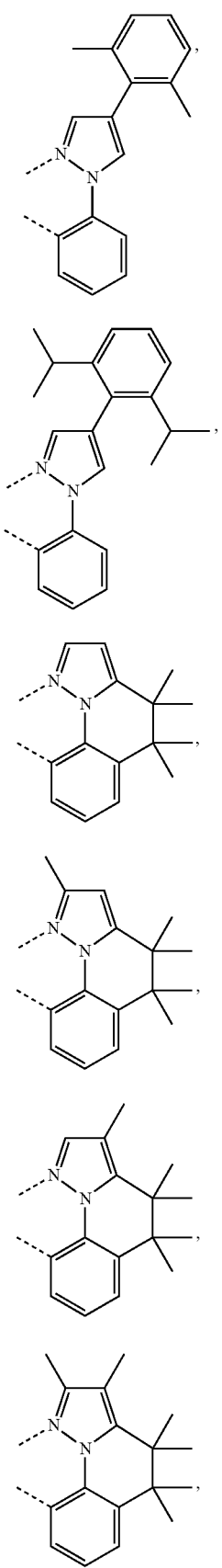
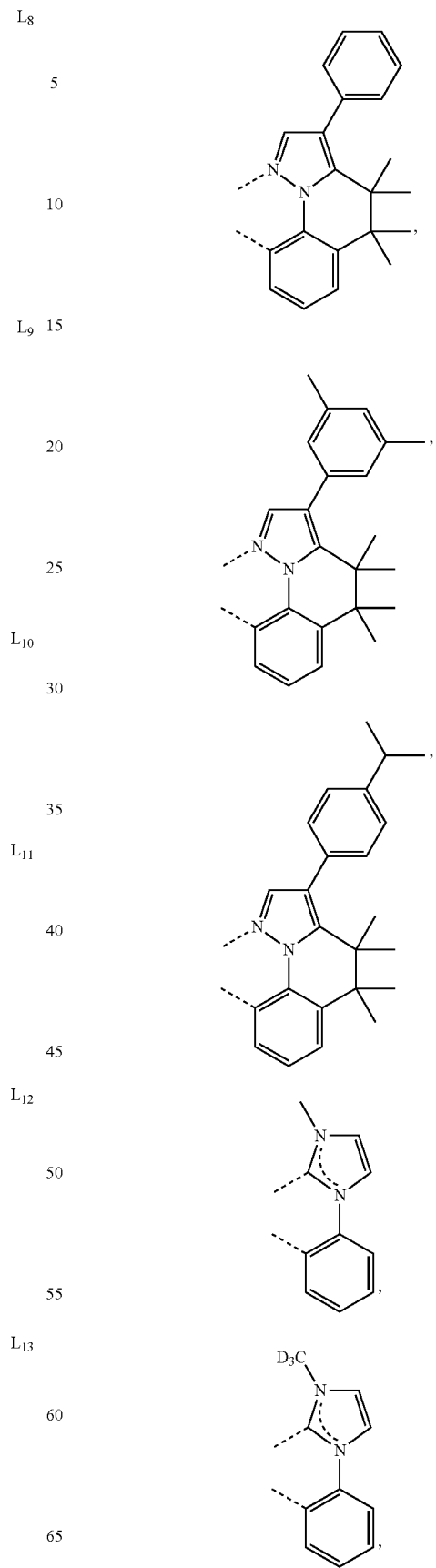

L19 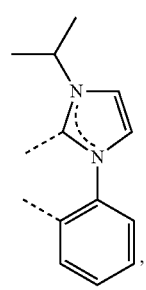
L20 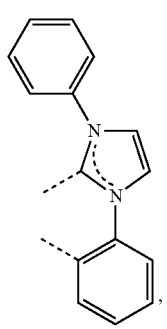
L21 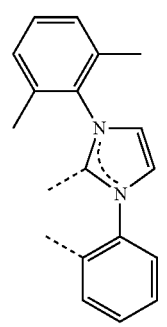
L22 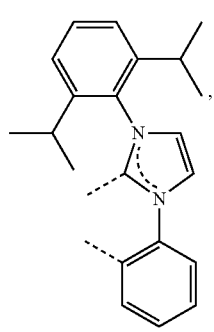
L23 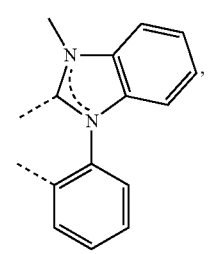
L24 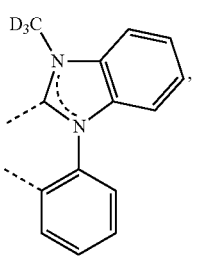
L25 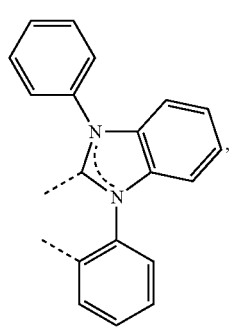
L26 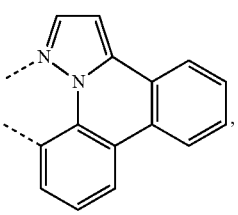
L27 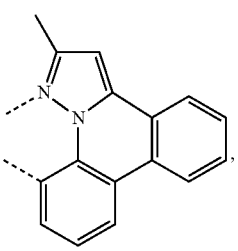
L28 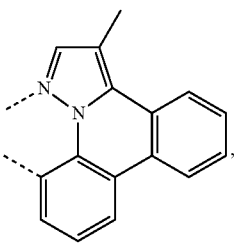
L29 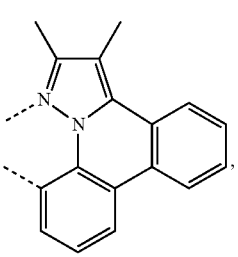

-continued
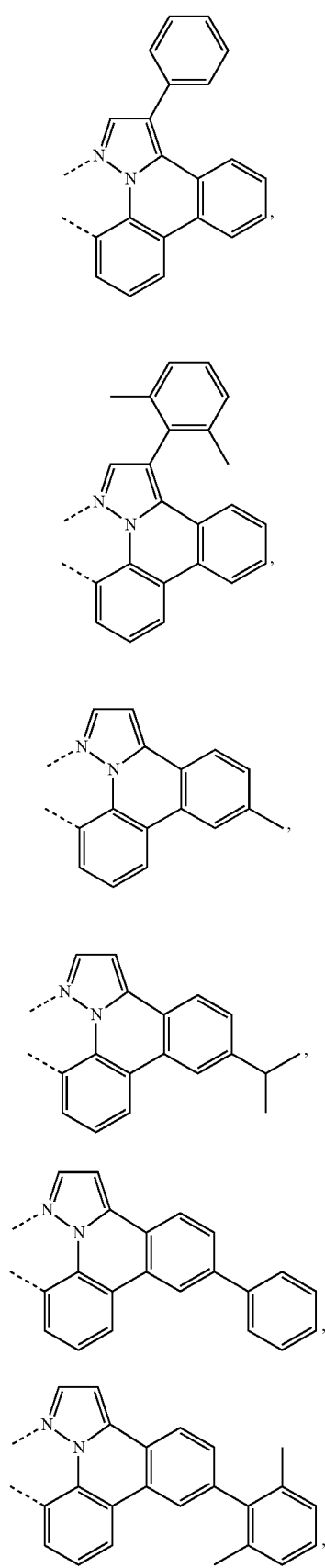
L30
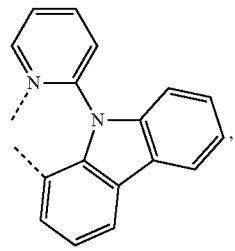
L31
L32
L33
L34
L35
-continued
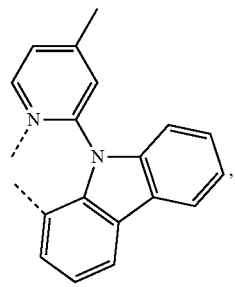
L36
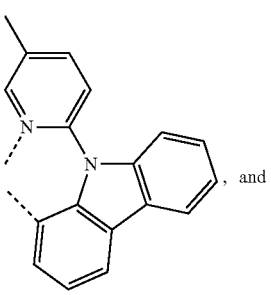
L37
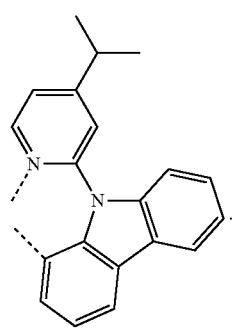
L38
, and
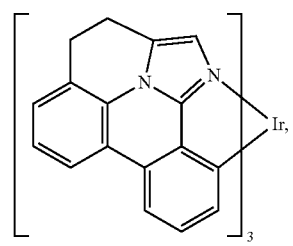
L39
.
In some embodiments of the compound of Formula 1, the compound is selected from the group consisting of:
Compound 1

Compound 2
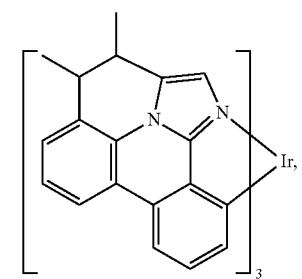
Compound 3
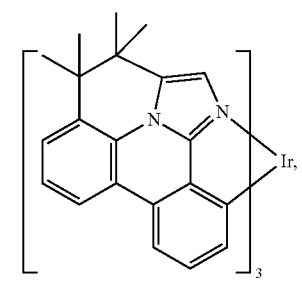
Compound 4
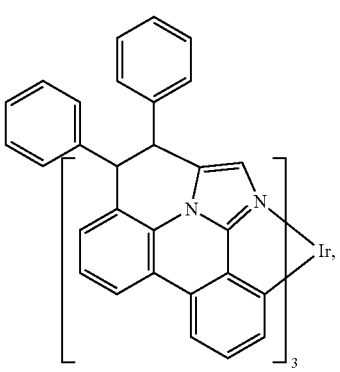
Compound 5
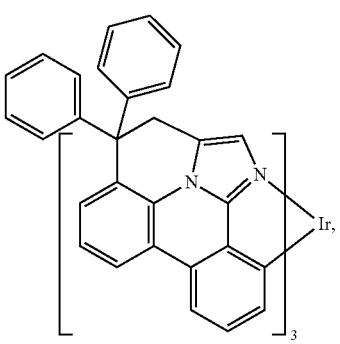
Compound 6
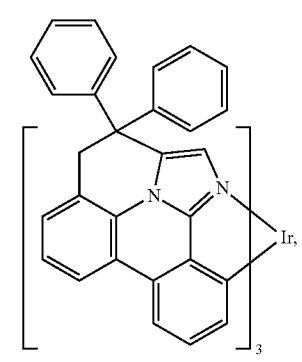
Compound 7
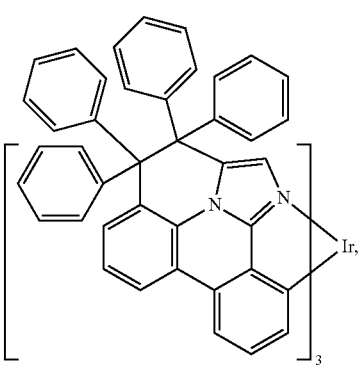
Compound 8
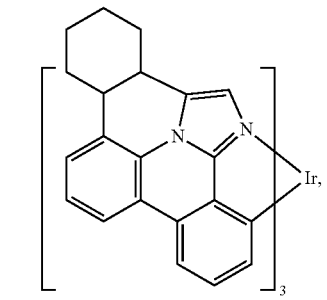
Compound 9
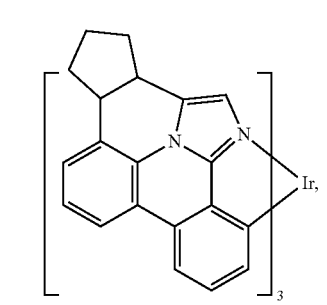
Compound 10
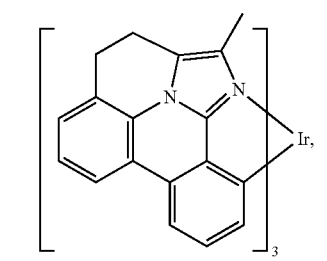
Compound 11
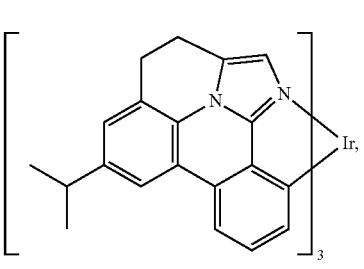

-continued
Compound 12
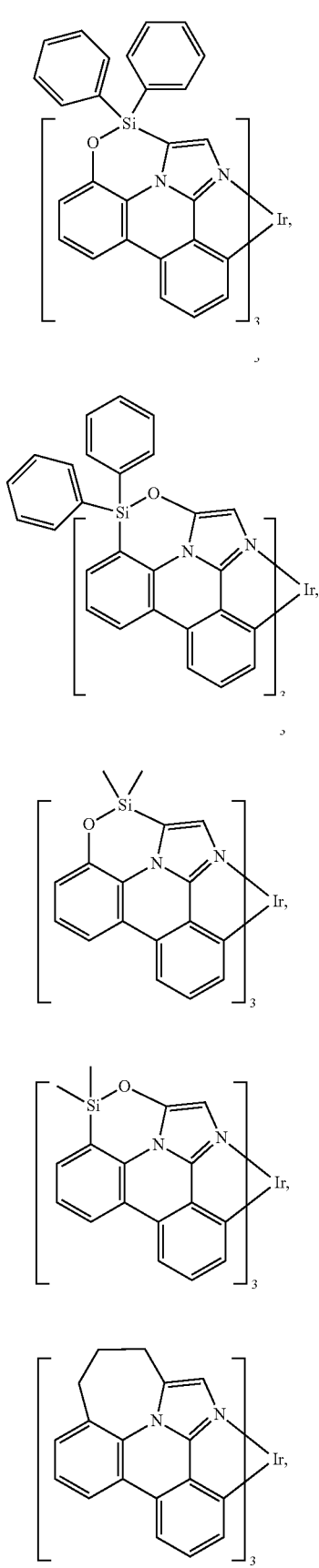
Compound 13
Compound 14
Compound 15
Compound 16
-continued
Compound 17
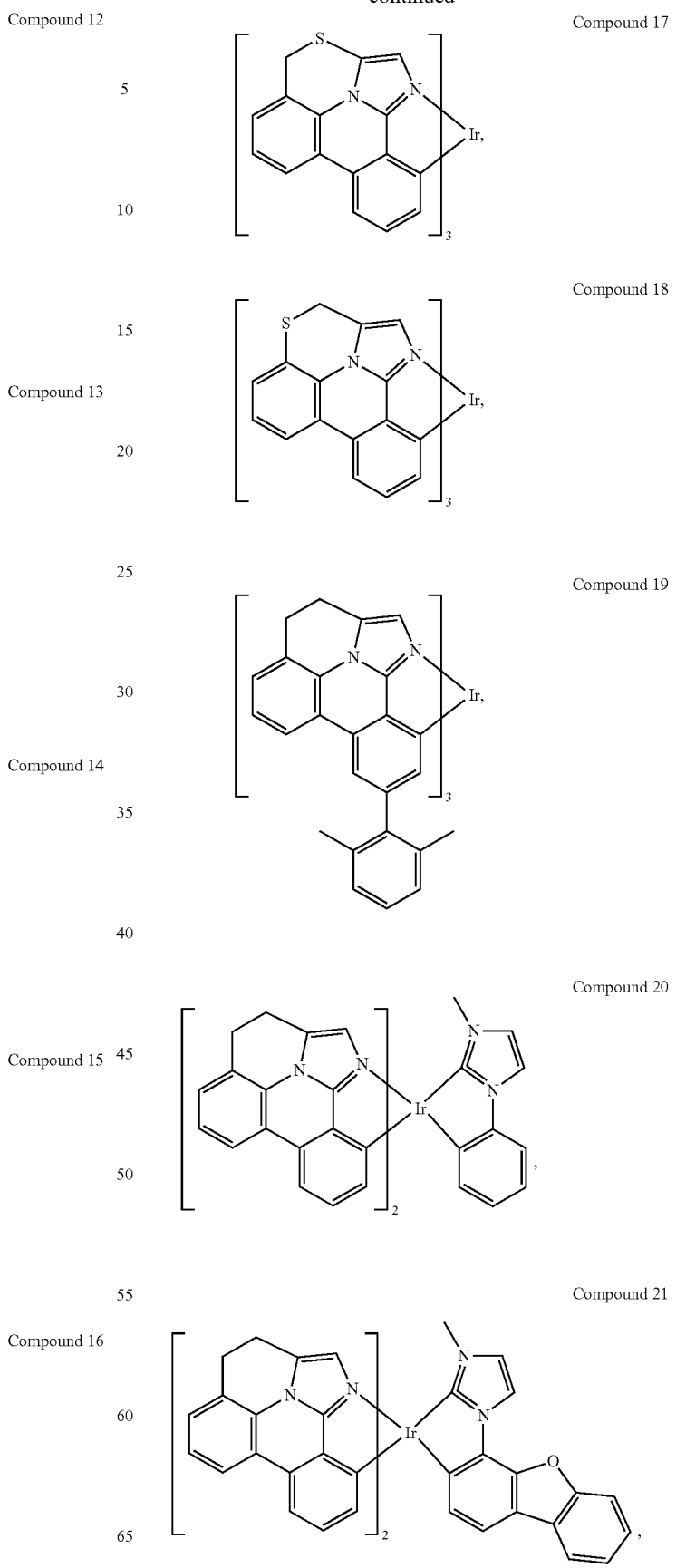
Compound 18
Compound 19
Compound 20
Compound 21

Compound 22
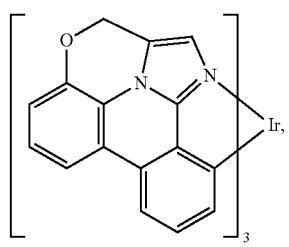
Compound 23
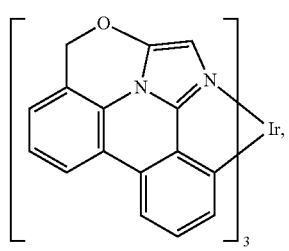
Compound 24
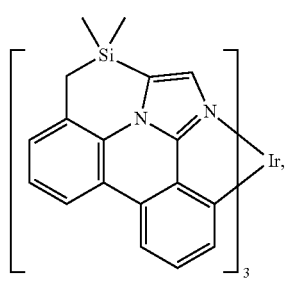
Compound 25
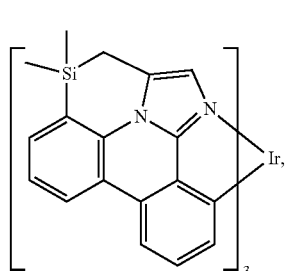
Compound 26
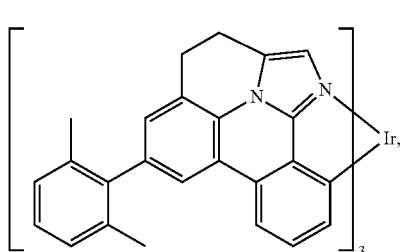
Compound 27
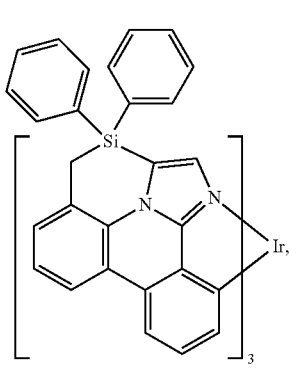
Compound 28
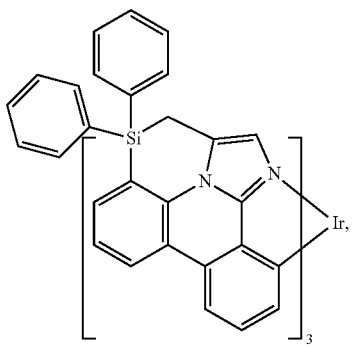
Compound 29
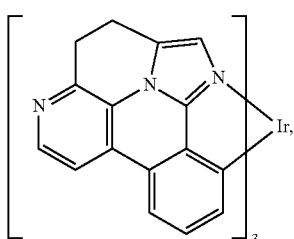
Compound 30
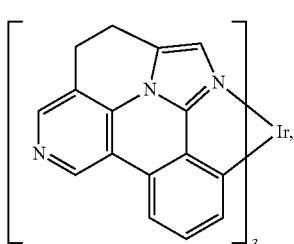
Compound 31
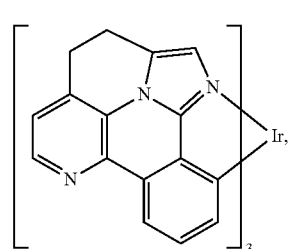
Compound 32
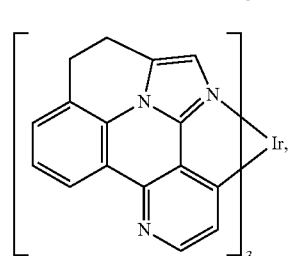
Compound 33
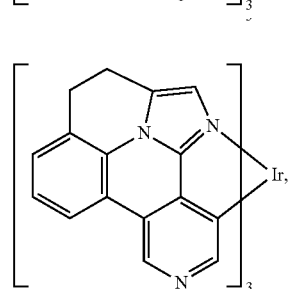

Compound 34
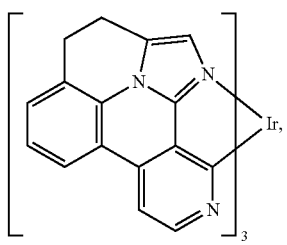
Compound 35
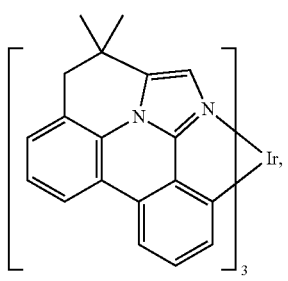
Compound 36
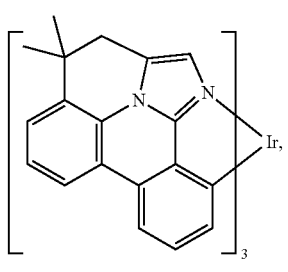
Compound 37
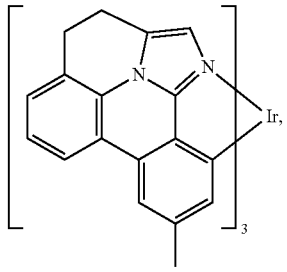
Compound 38
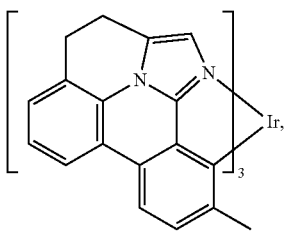
Compound 39
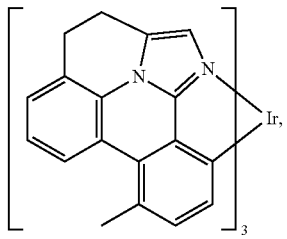
Compound 40
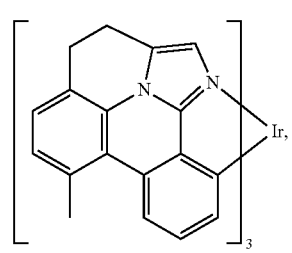
Compound 41
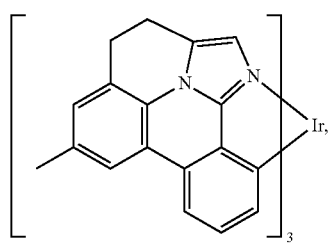
Compound 42
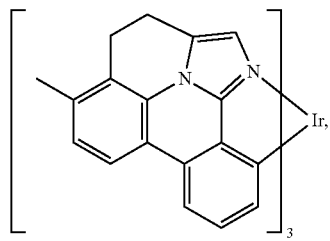
Compound 43
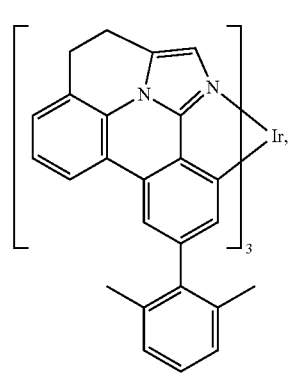
Compound 44
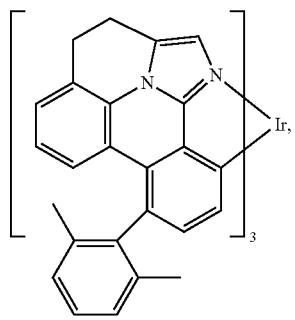

Compound 45
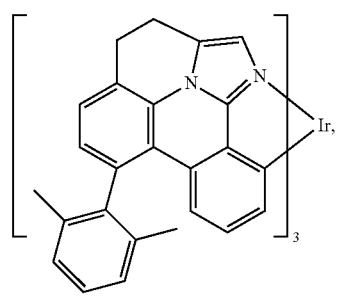
Compound 46
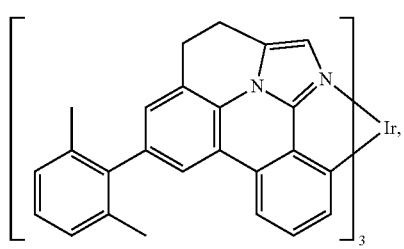
Compound 47
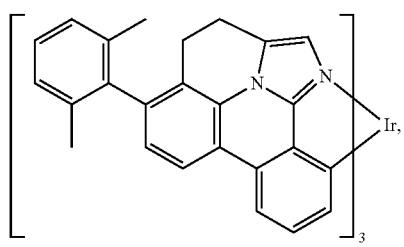
Compound 48
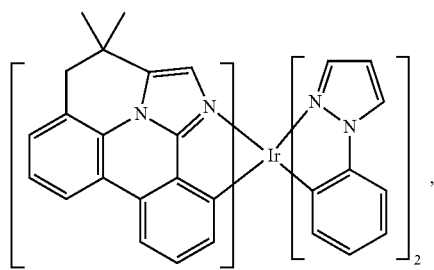
Compound 49
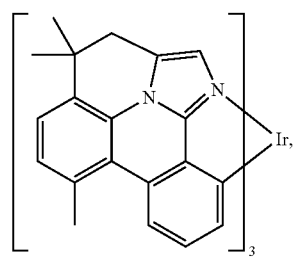
Compound 50
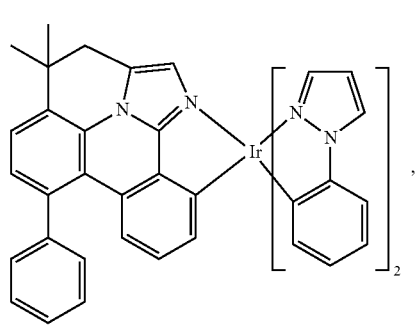
Compound 51
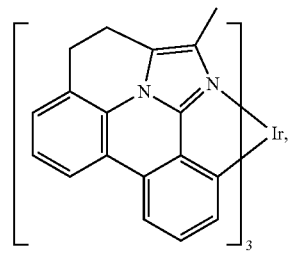
Compound 52
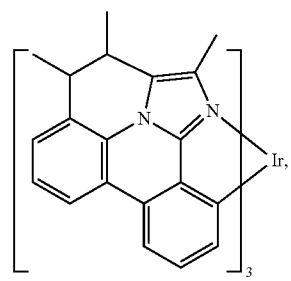
Compound 53
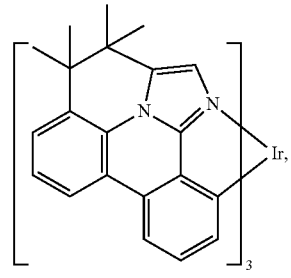
Compound 54
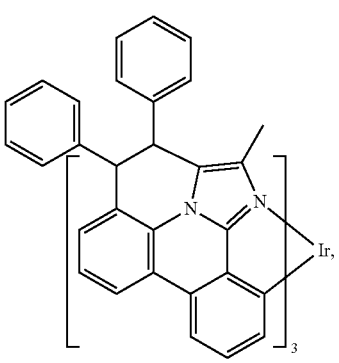
Compound 55
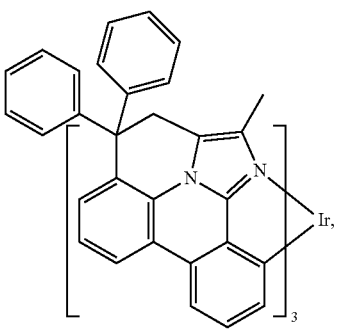

Compound 56
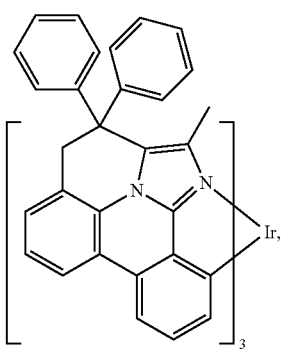
Compound 61
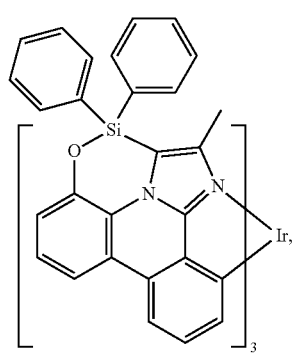
Compound 57
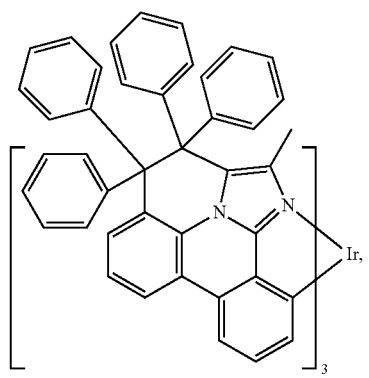
Compound 62
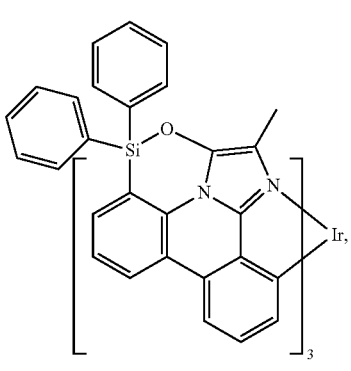
Compound 58
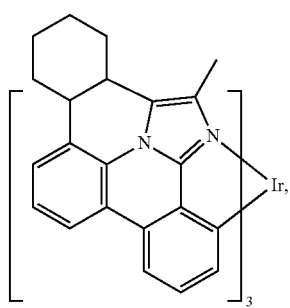
Compound 63
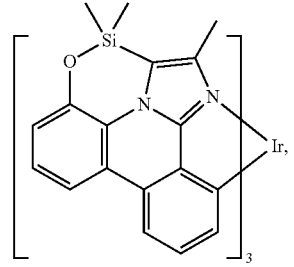
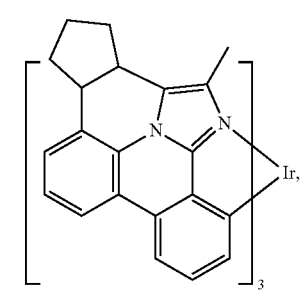
Compound 64
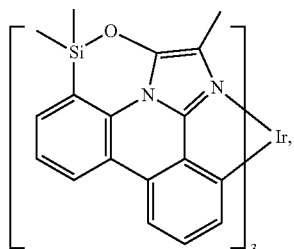
Compound 60
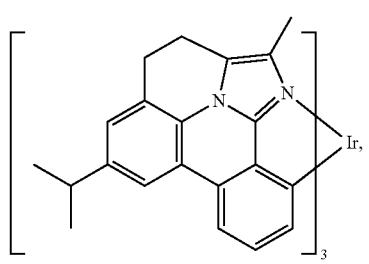
Compound 65
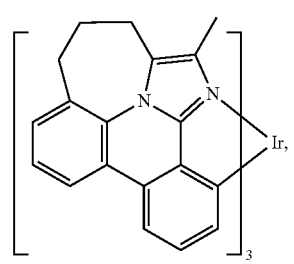

-continued
Compound 66
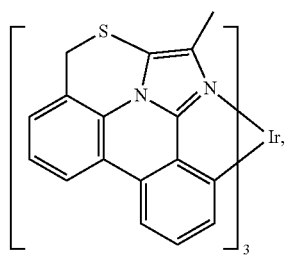
Compound 67
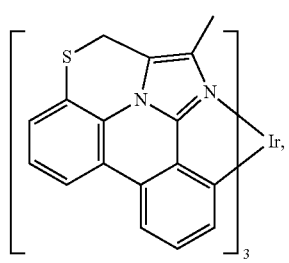
Compound 68
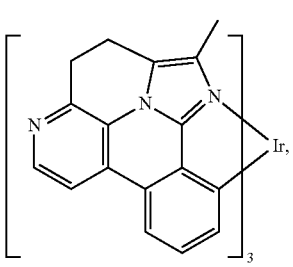
Compound 69
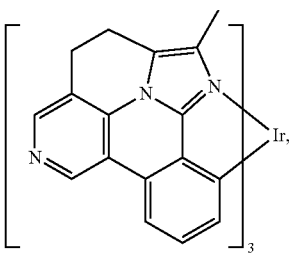
Compound 70
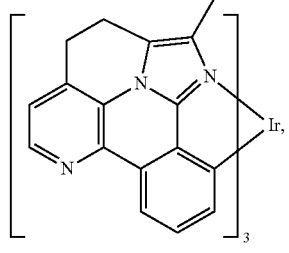
Compound 71
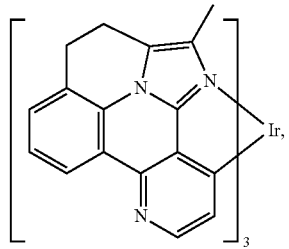
-continued
Compound 72
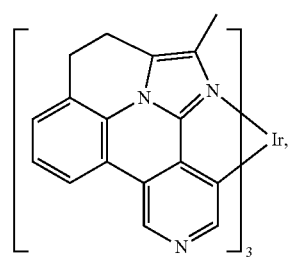
Compound 73
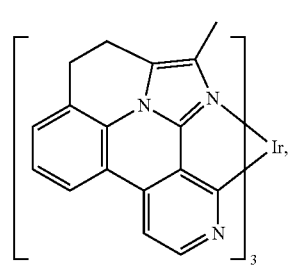
Compound 74
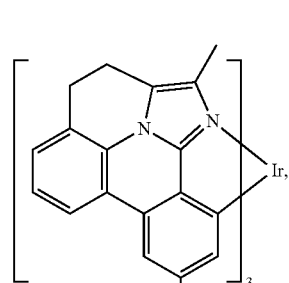
Compound 75
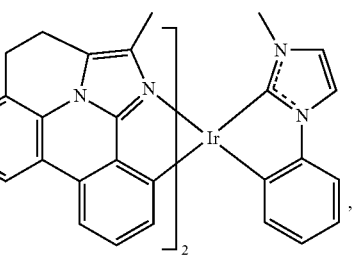
Compound 76
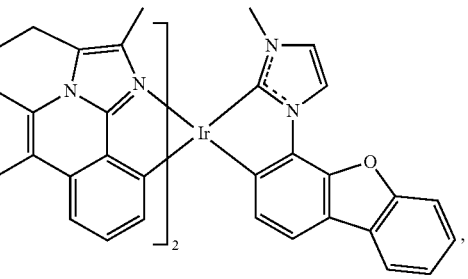

Compound 77
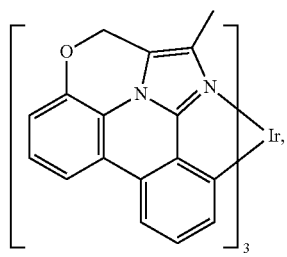
Compound 78
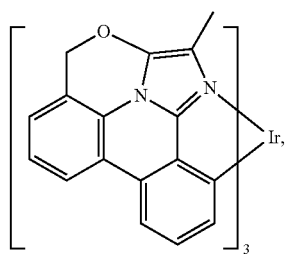
Compound 79
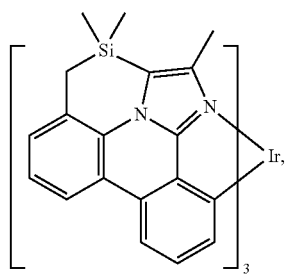
Compound 80
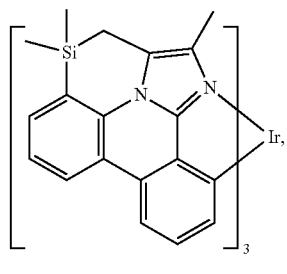
Compound 81
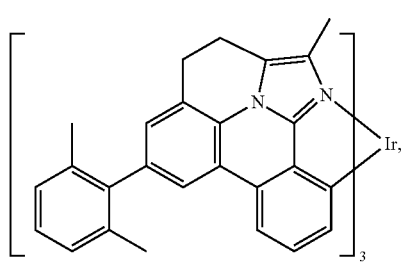
Compound 82
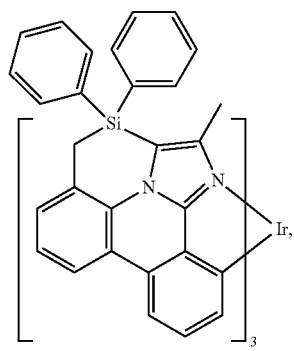
Compound 83
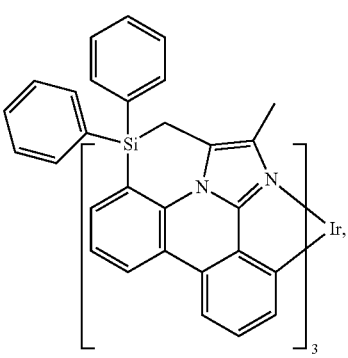
Compound 84
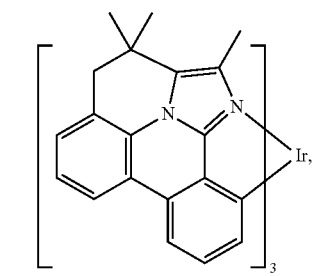
Compound 85
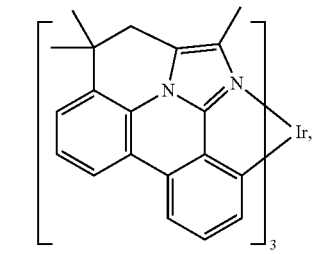
Compound 86
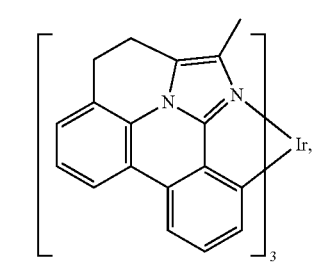

Compound 87
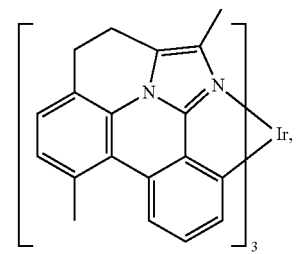
Compound 88
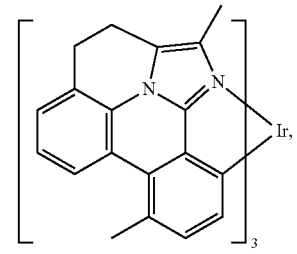
Compound 89
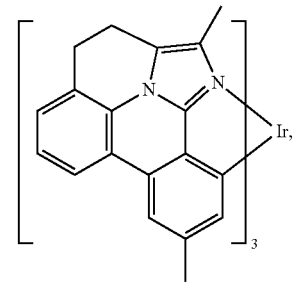
Compound 90
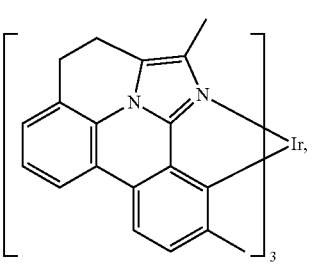
Compound 91
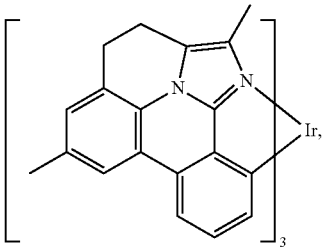
Compound 92
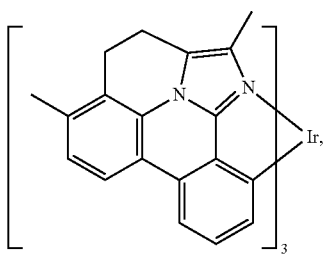
Compound 93
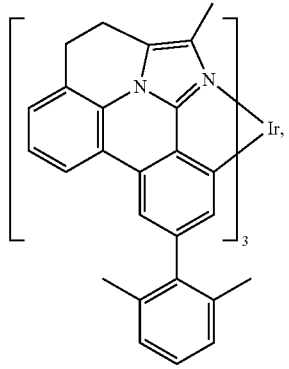
Compound 94
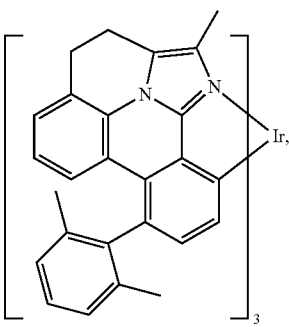
Compound 95
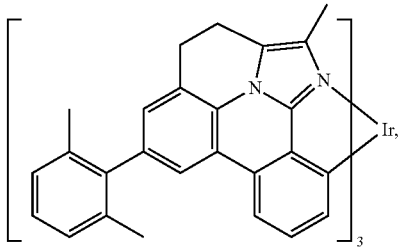
Compound 96
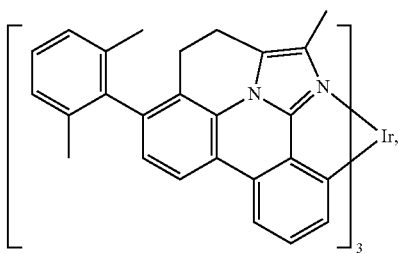
Comound 97
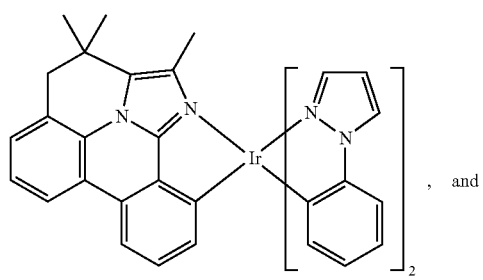
, and Compound 98

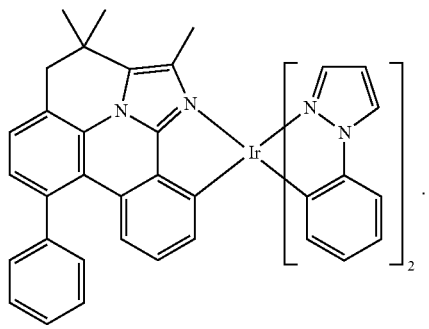

In some embodiments of the compound of Formula 1, the compound has a structure of Formula 2:

Formula 2

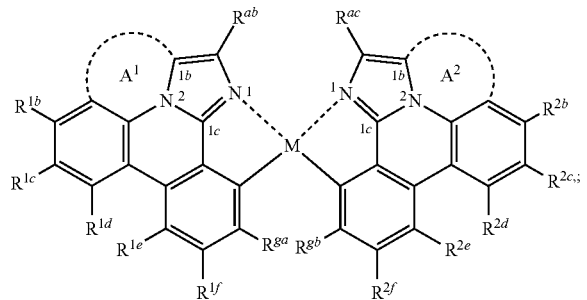

wherein M is Pt;

wherein $A^1$ and $A^2$ are each independently a first linking group having two to three linking atoms, wherein the linking atoms are each independently selected from the group consisting of C, Si, O, S, N, B or combinations thereof;

wherein $R^{1b}$ to $R^{1f}$ and $R^{2b}$ to $R^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1f}$ and $R^{2b}$ to $R^{2f}$ are attached may be replaced with a nitrogen atom, wherein when the ring atom is replaced with a nitrogen atom the corresponding R group is not present; and wherein $R^{ab}$ and $R^{ac}$ and/or $R^{ga}$ and $R^{gb}$ may bond to form a second linking group having one to three linking atoms each independently selected from the group consisting of B, N, P, O, S, Se, C, Si, Ge or combinations thereof.

In some embodiments of the compound of Formula 2, each of the first linking groups $A^1$ and $A^2$ is independently selected from the group consisting of —$CR^1R^2$—$CR^3R^4$—, —$CR^1R^2$—$CR^3R^4$—$CR^5R^6$—, —$CR^1R^2$—$NR^3$—, —$CR^1$=$CR^2$—$CR^3R^4$—, —O—$SiR^1R^2$—, —$CR^1R^2$—S—, —$CR^1R^2$—O—, and —C—$SiR^1R^2$—, wherein each $R^1$ to $R^6$ can be same or different, and are independently selected from the group consisting of hydrogen, deuterium, alkyl, cycloalkyl, aryl, heteroaryl, and combinations thereof; and wherein any adjacent $R^1$ to $R^6$ are optionally connected to form a saturated five membered ring or a saturated six membered ring.

In some embodiments of the compound of Formula 2, the compound has a triplet excited state and wherein the linking group stabilizes the bond between $N^2$ and $C^{1b}$ from cleavage when the compound is in the triplet excited state.

In some embodiments of the compound of Formula 2, the compound has a peak emissive wavelength less than 500 nm. In some embodiments, the compound has a peak emissive wavelength less than 480 nm. In some embodiments, the compound has a peak emissive wavelength ranging from 400 nm to 500 nm.

In some embodiments of the compound of Formula 2, each of the first linking groups $A^1$ and $A^2$ is independently selected from the Linker Group consisting of:

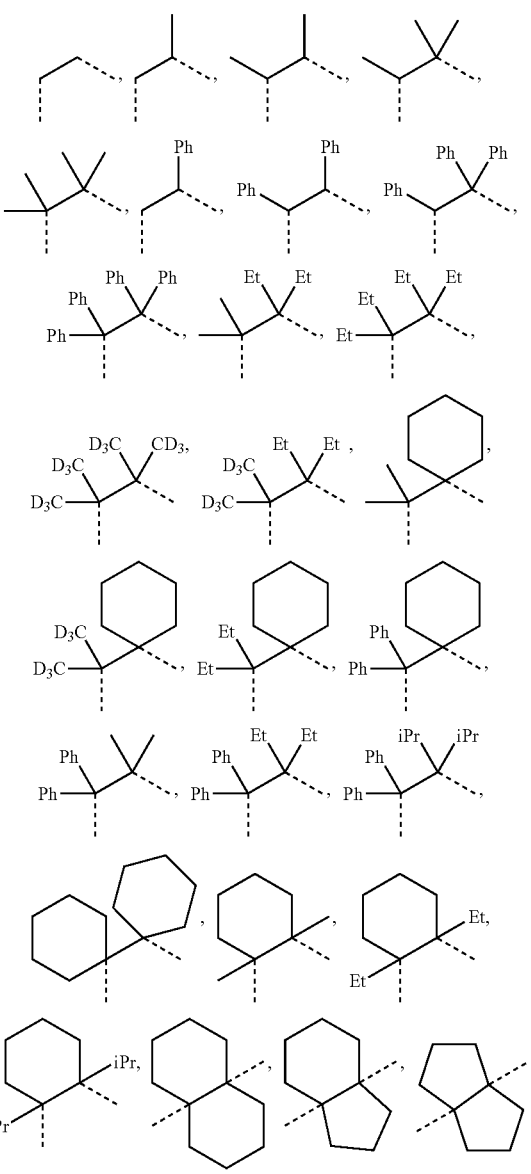

-continued

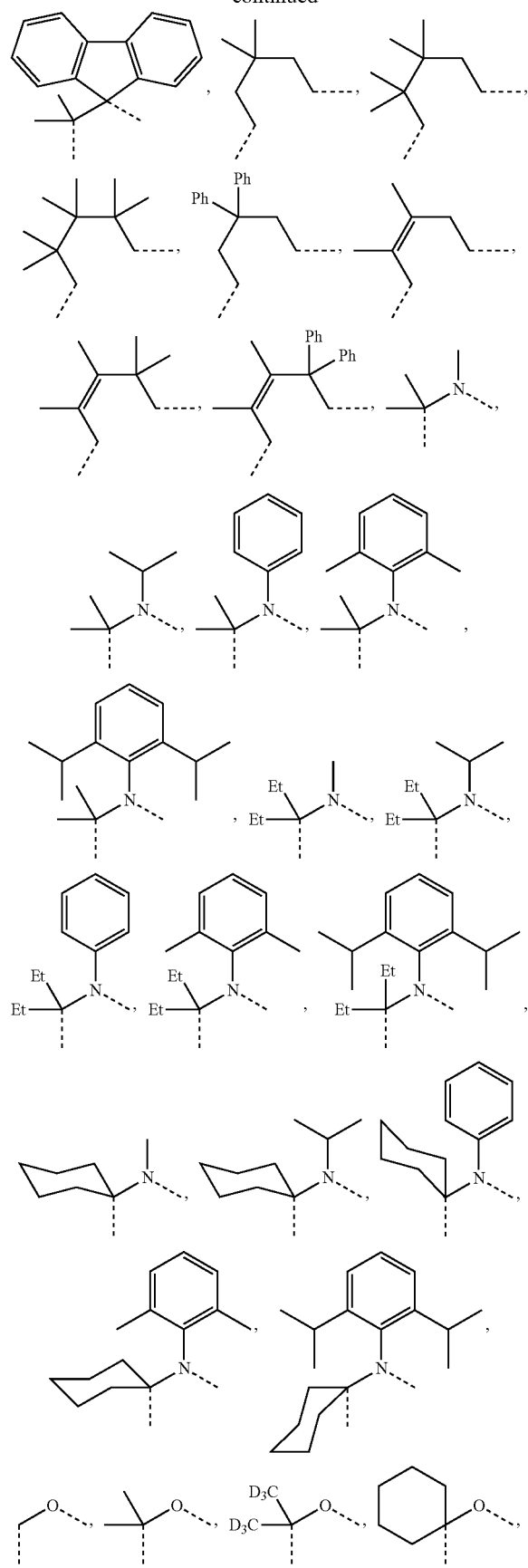

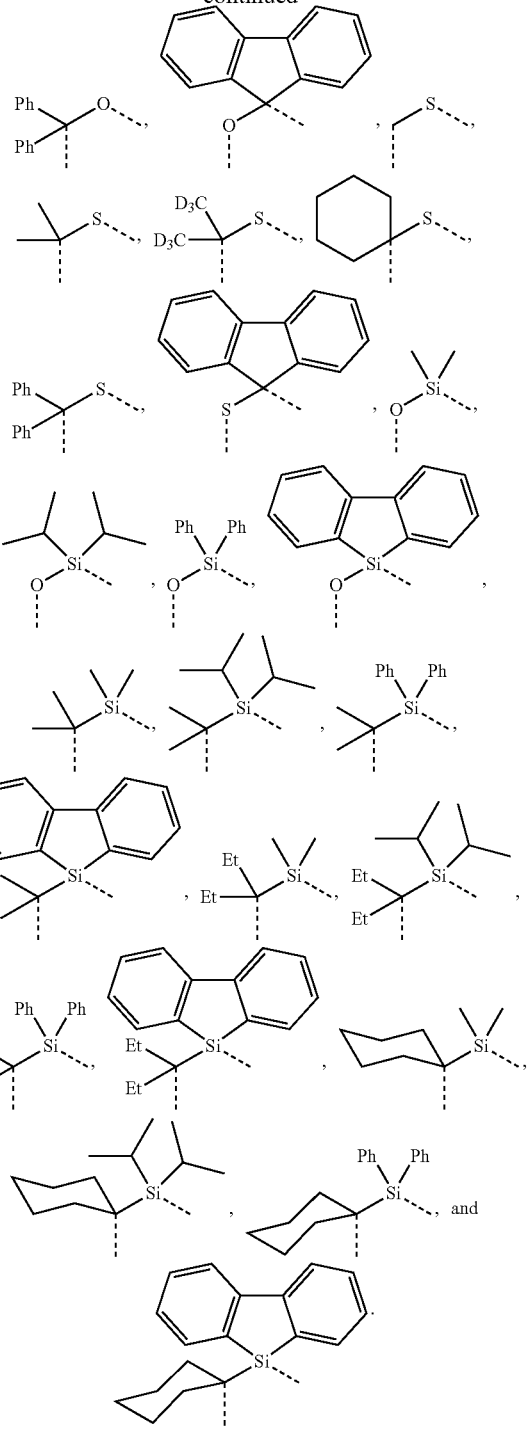

In some embodiments of the compound of Formula 2, the second linking group is independently selected from the group consisting of: $BR^1$, $NR^1$, $PR^1$, O, S, Se, C=O, S=O, $SO_2$, $CR^1R^2$, $-CR^1R^2-CR^3R^4-$, $-CR^1R^2-CR^3R^4-CR^5R^6-$, $-CR^1R^2-NR^3-$, $-CR^1=CR^2-CR^3R^4-$, $-O-SiR^1R^2-$, $-CR^1R^2-S-$, $-CR^1R^2-O-$, $-C-SiR^1R^2-$, $SiR^1R^2$, and $GeR^1R^2$, wherein each $R^1$ to $R^6$ can be same or different, and are independently selected from the group consisting of hydrogen, deuterium, alkyl, cycloalkyl, alkenyl, alkenyl, alkynyl, heteroalkyl, aralkyl, aryl, heteroaryl, and combinations thereof; and wherein any adjacent $R^1$ to $R^6$ are optionally connected to form a saturated five membered ring or a saturated six membered ring.

In some embodiments of the compound of Formula 2, the compound is selected from the group consisting of:

Compound 99

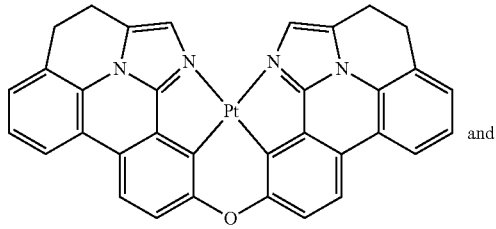

and

Compound 100

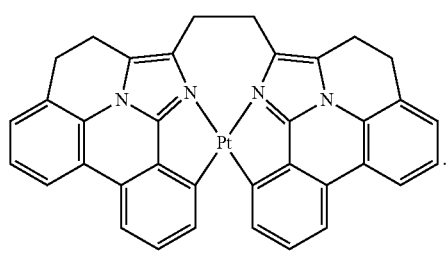

In some embodiments of the compound of Formula 1, the compound has Formula 3:

Formula 3

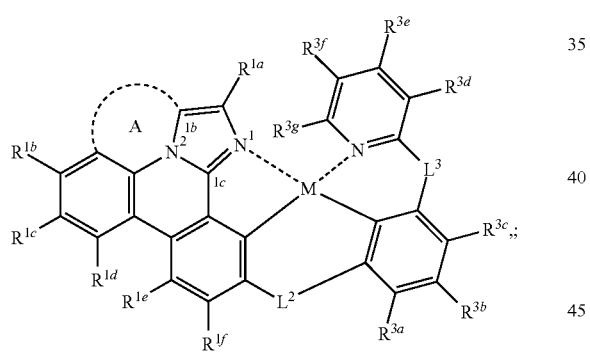

wherein M is Pt;

wherein $L^2$ and $L^3$ are each independently selected from the group consisting of a single bond, BR, NR, PR, O, S, Se, C=O, S=O, SO$_2$, CR$^1$R$^2$, SiR$^1$R$^2$, and GeR$^1$R$^2$;

wherein $R^{3a}$ to $R^{3f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any two adjacent $R^{1f}$, $R^{3a}$, $R^{3c}$, $R^{3d}$, $R^1$ and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings; and wherein $L^3$ and $R^{3c}$, $L^3$ and $R^{3d}$, or $L^3$ and both $R^{3c}$ and $R^{3d}$ are optionally joined to form one or more rings.

In some embodiments of the compound of Formula 3, $L^2$ and $L^3$ are each independently selected from the group consisting of BR$^1$, NR$^1$, PR$^1$, O, S, Se, C=O, S=O, SO$_2$, CR$^1$R$^2$, SiR$^1$R$^2$, and GeR$^1$R$^2$. In some embodiments of the compound of Formula 3, $R^{1f}$ or $R^{3a}$ and $R^1$ or $R^2$ are joined to form a ring. In some embodiments of the compound of Formula 3, $R^{3c}$ or $R^{3d}$ and $R^1$ or $R^2$ are joined to form a ring.

In some embodiments of the compound of Formula 3, the compound is selected from the group consisting of:

Compound 101

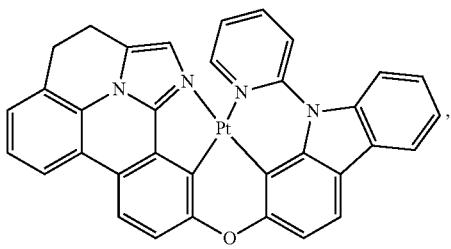

,

Compound 102

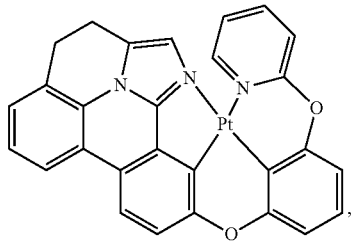

,

Compound 103

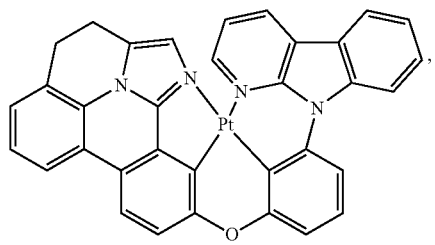

,

Compound 104

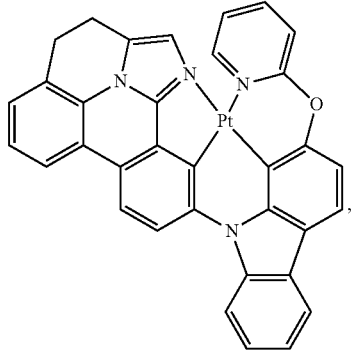

,

Compound 105

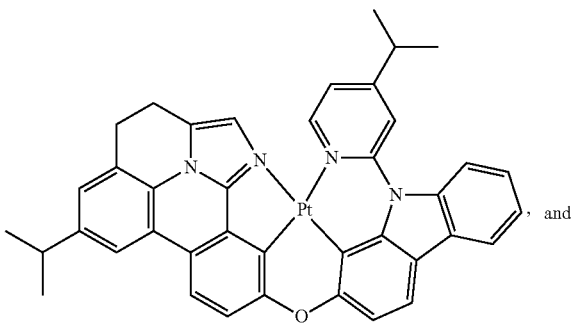

Compound 106

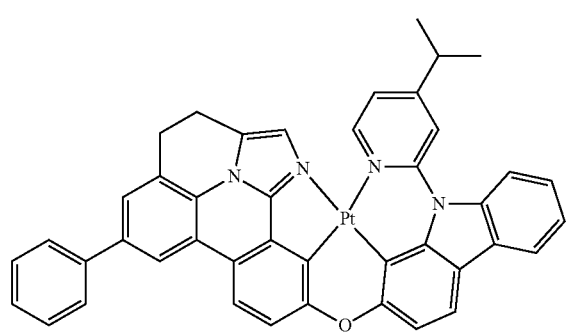

According to another aspect of the present disclosure, an organic light emitting device (OLED) is disclosed. The OLED comprises an anode; a cathode; and an organic layer disposed between the anode and the cathode, wherein the organic layer comprising a compound having a structure $(L_A)_n ML_m$ according to Formula 1:

Formula 1

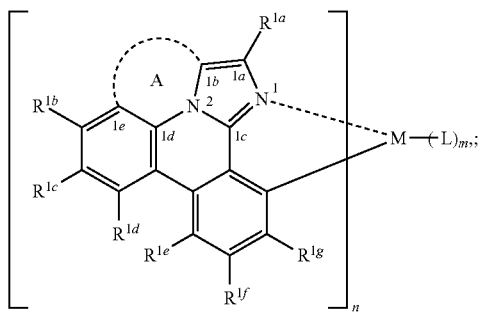

wherein M is a metal having an atomic weight greater than 40, n has a value of at least 1 and m+n is the maximum number of ligands that may be attached to the metal;

wherein A is a linking group having two to three linking atoms, wherein the linking atoms are each independently selected from the group consisting of C, Si, O, S, N, B or combinations thereof;

wherein the linking atoms form at least one single bond between two linking atoms; wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

In some embodiments of the OLED, the OLED is incorporated into a device selected from the group consisting of a consumer product, an electronic component module, and a lighting panel.

In some embodiments of the OLED, the organic layer is an emissive layer and the compound is an emissive dopant or a non-emissive dopant.

In some embodiments of the OLED, the organic layer further comprises a host, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments of the OLED, the organic layer further comprises a host, wherein host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

In some embodiments of the OLED, the organic layer further comprises a host, wherein the host is selected from the group consisting of:

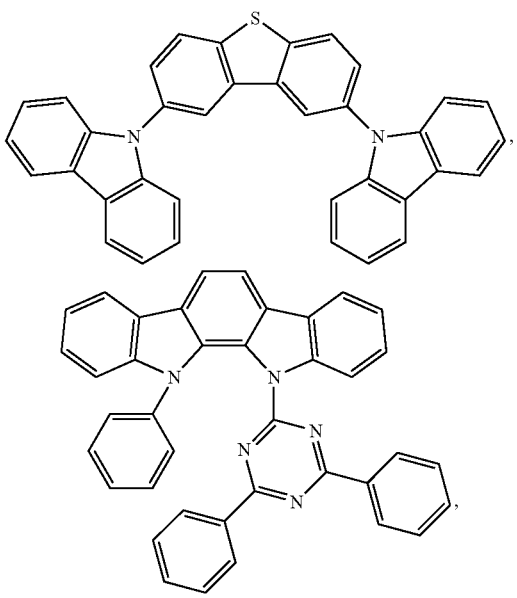

101
-continued
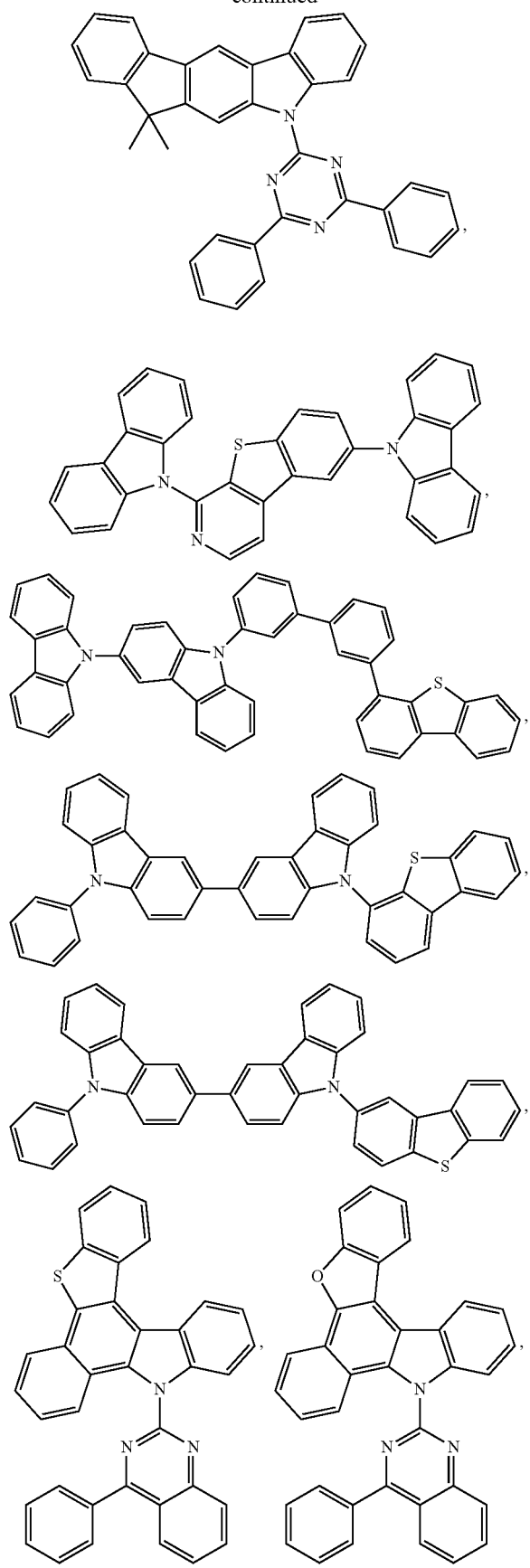
102
-continued
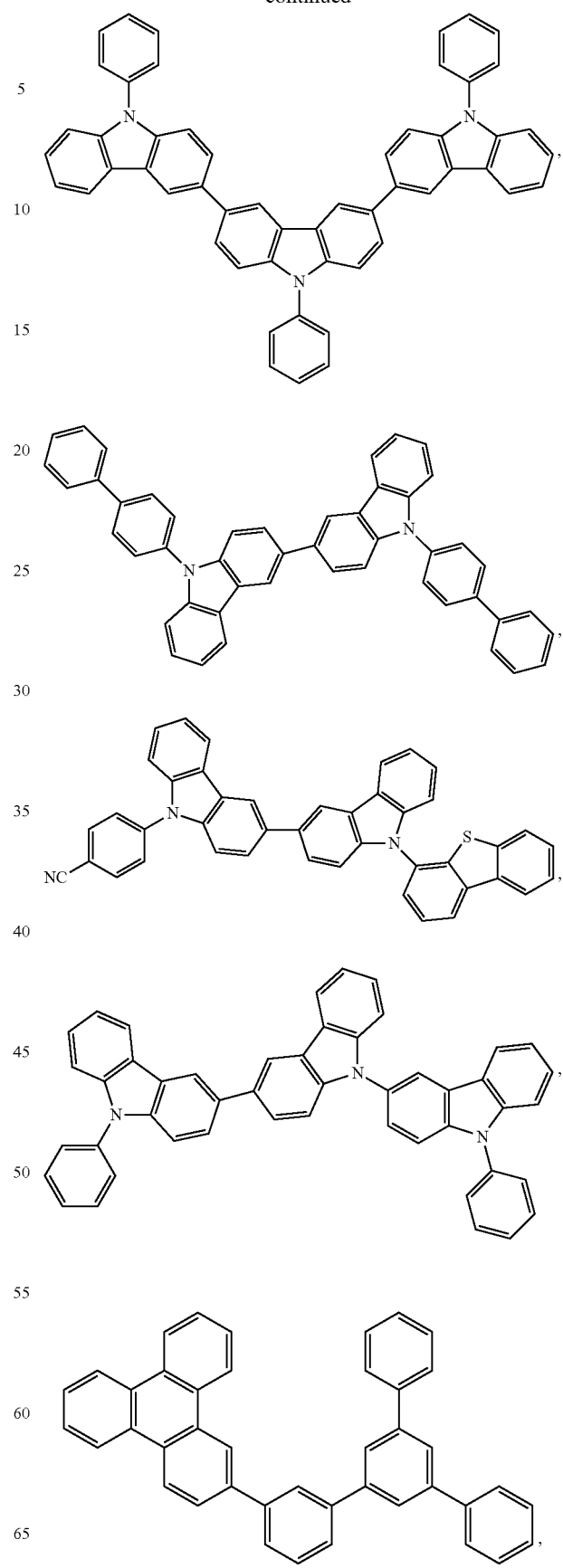

-continued

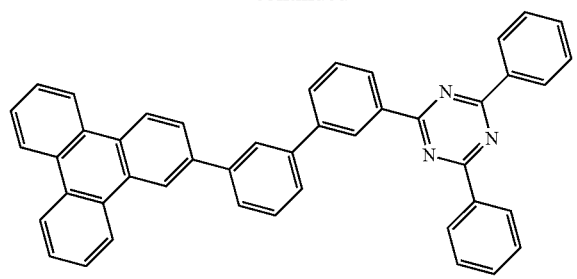

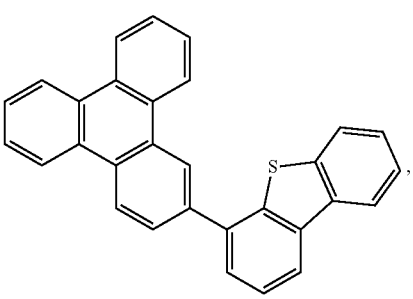

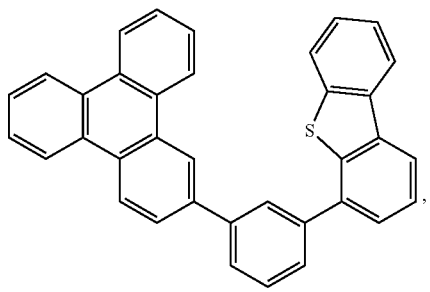

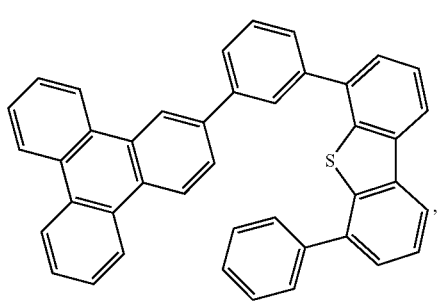

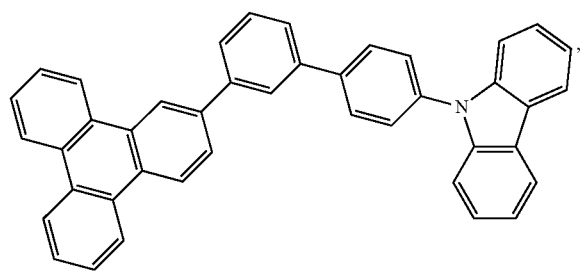

-continued

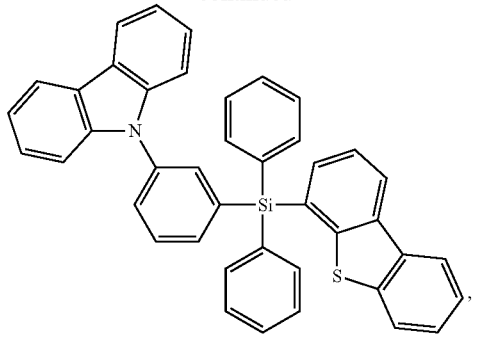

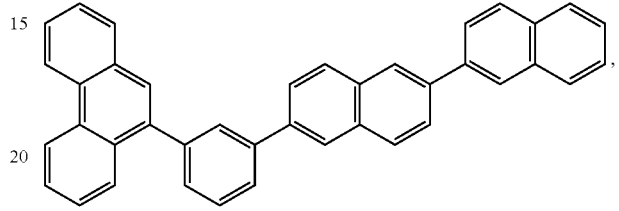

and combinations thereof.

In some embodiments of the OLED, the organic layer further comprises a host, wherein the host comprises a metal complex.

According to another aspect of the present disclosure, a formulation comprising a compound of Formula 1 is also disclosed. The formulation can include one or more components selected from the group consisting of a solvent, a host, a hole injection material, hole transport material, and an electron transport layer material, disclosed herein.

According to another aspect of the present disclosure, a compound having Formula (1a) shown below is disclosed.

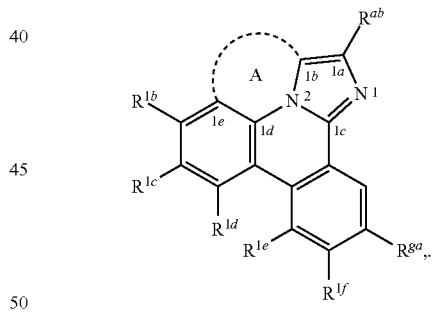

Formula (1a)

In Formula (1a), A is a linking group having two to three linking atoms, wherein the linking atoms are each independently selected from the group consisting of C, Si, O, S, N, B or combinations thereof;

wherein $R^{ab}$, $R^{ga}$, $R^{1b}$ to $R^{1f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof; and wherein any one of the ring atoms to which $R^{ab}$, $R^{ga}$, $R^{1b}$ to $R^{1f}$ are attached may be replaced with a nitrogen atom, wherein when the ring atom is replaced with a nitrogen atom the corresponding R group is not present.

In some embodiments of the compound of Formula 1a, the linking group A is independently selected from the group consisting of —$CR^1R^2$—$CR^3R^4$—, —$CR^1R^2$—$CR^3R^4$—$CR^5R^6$—, —$CR^1R^2$—$NR^3$—, —$CR^1$=$CR^2$—$CR^3R^4$—, —O—$SiR^1R^2$—, —$CR^1R^2$—S—, —$CR^1R^2$—O—, and —C—$SiR^1R^2$—, wherein each $R^1$ to $R^6$ can be same or different, and are independently selected from the group consisting of hydrogen, deuterium, alkyl, cycloalkyl, aryl, heteroaryl, and combinations thereof; wherein any adjacent $R^1$ to $R^6$ are optionally connected to form a saturated five membered ring or a saturated six membered ring.

In some embodiments of the compound of Formula (1a), the compound has a triplet excited state and wherein the linking group stabilizes the bond between $N^2$ and $C^{1b}$ from cleavage when the compound is in the triplet excited state.

In some embodiments of the compound of Formula (1a), the linking group A is selected from the Linker Group defined above.

In some embodiments of the compound of Formula (1a), the compound is selected from the group consisting of:

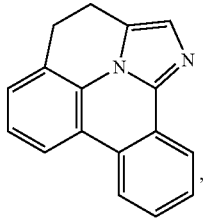

Compound (1-1)

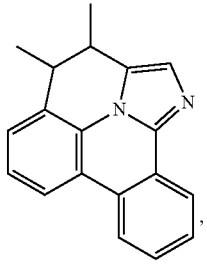

Compound (1-2)

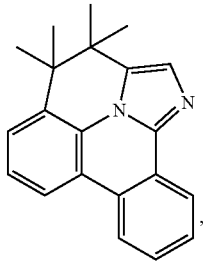

Compound (1-3)

-continued

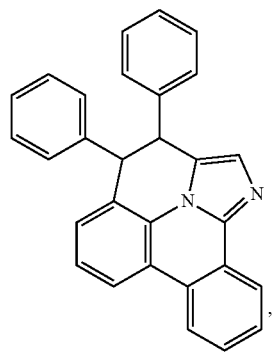

Compound (1-4)

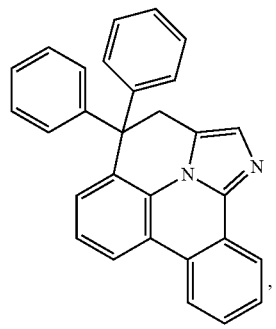

Compound (1-5)

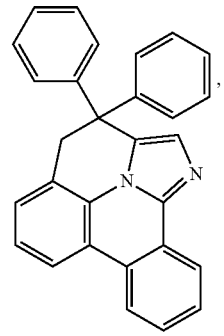

Compound (1-6)

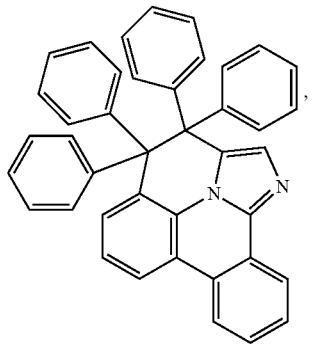

Compound (1-7)

Compound (1-8)
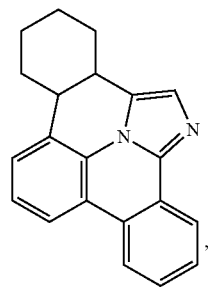
Compound (1-9)
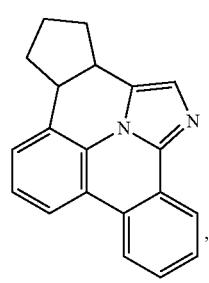
Compound (1-10)
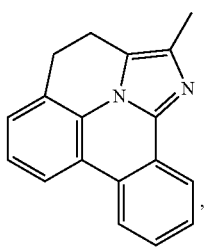
Compound (1-11)
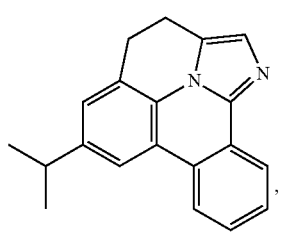
Compound (1-12)
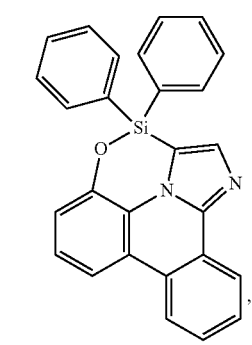
Compound (1-13)
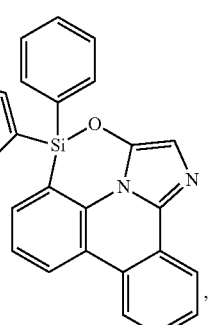
Compound (1-14)
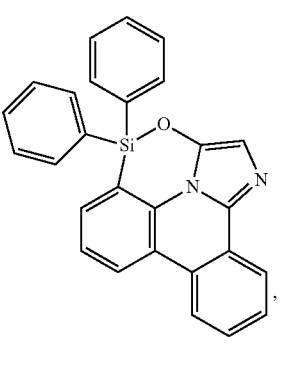
Compound (1-15)
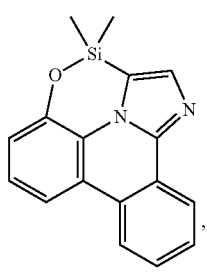
Compound (1-16)
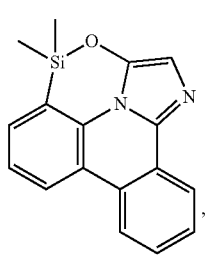
Compound (1-17)
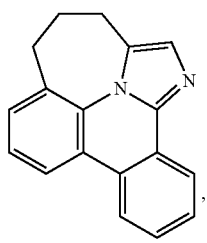
Compound (1-18)
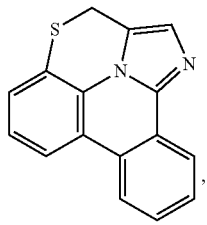

Compound (1-19)
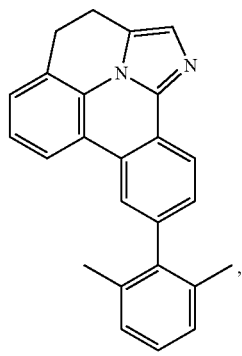
Compound (1-20)
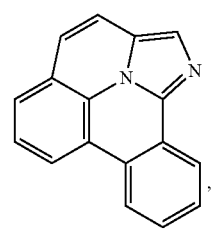
Compound (1-21)
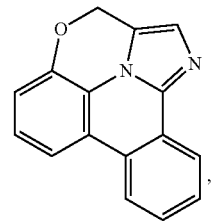
Compound (1-22)
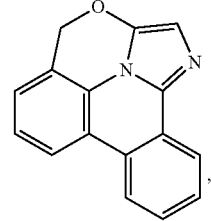
Compound (1-23)
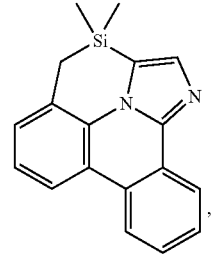
Compound (1-24)
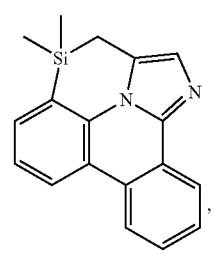
Compound (1-25)
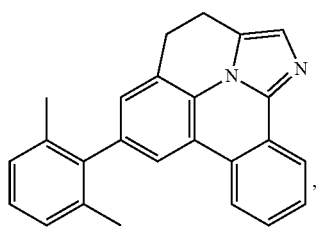
Compound (1-26)
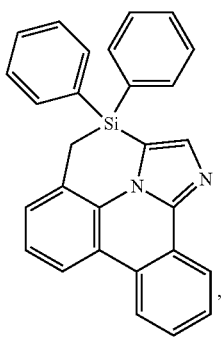
Compound (1-27)
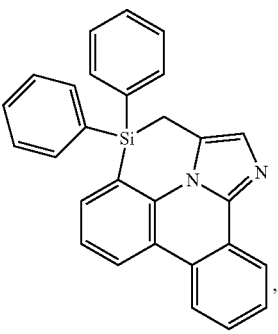
Compound (1-28)
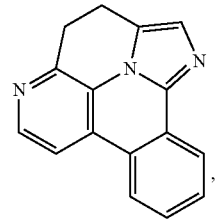
Compound (1-29)
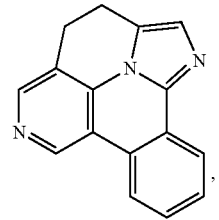
Compound (1-30)
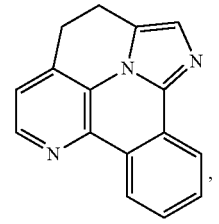

Compound (1-31)
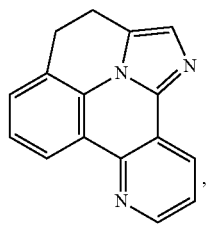
Compound (1-37)
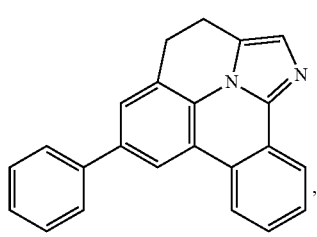
Compound (1-32)
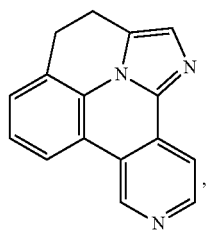
Compound (1-38)
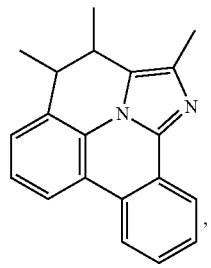
Compound (1-33)
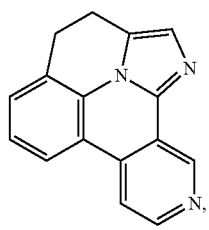
Compound (1-39)
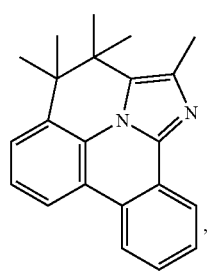
Compound (1-34)
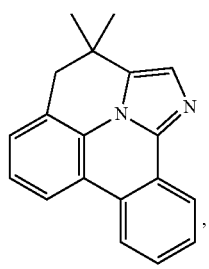
Compound (1-35)
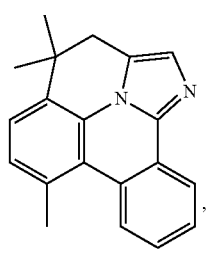
Compound (1-40)
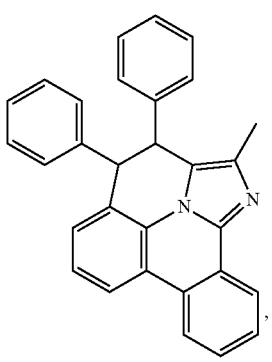
Compound (1-36)
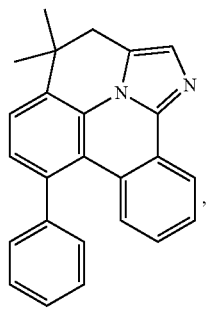
Compound (1-41)
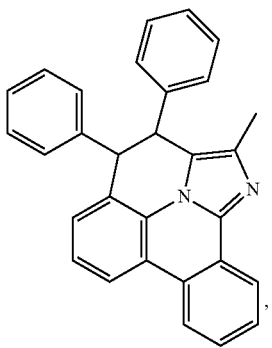

Compound (1-42)
Compound (1-43)
Compound (1-44)
Compound (1-45)
Compound (1-46)
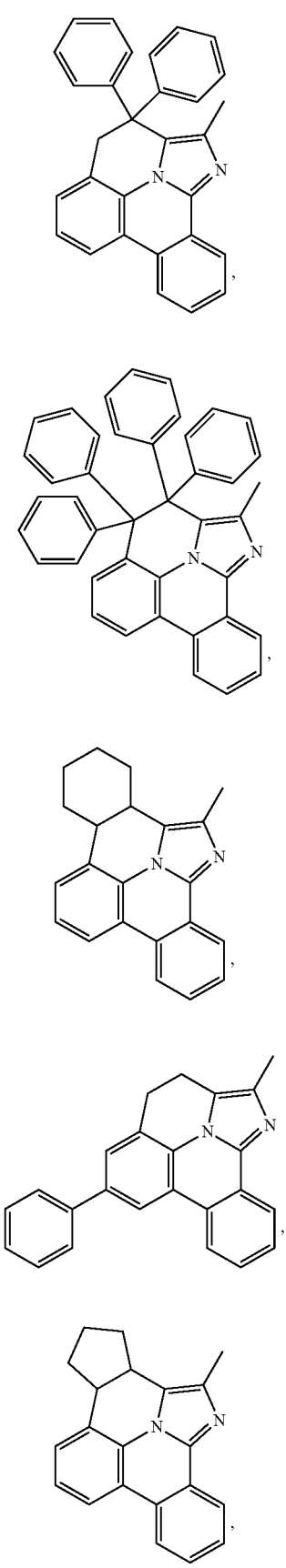
Compound (1-47)
Compound (1-48)
Compound (1-49)
Compound (1-50)
Compound (1-51)
Compound (1-52)
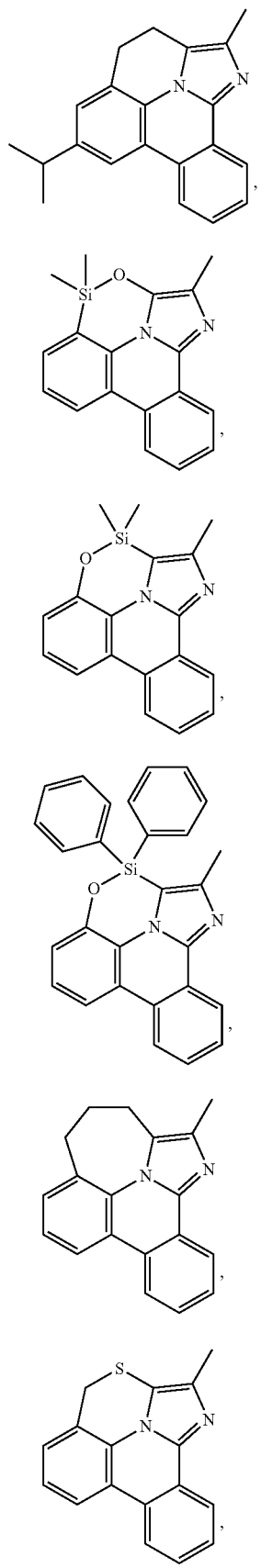

Compound (1-53)
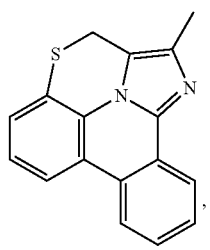
Compound (1-54)
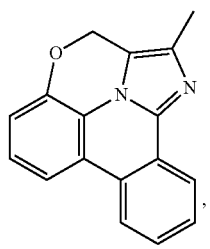
Compound (1-55)
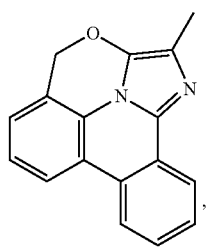
Compound (1-56)
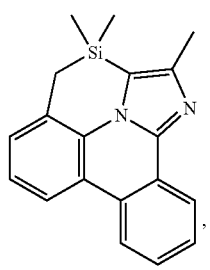
Compound (1-57)
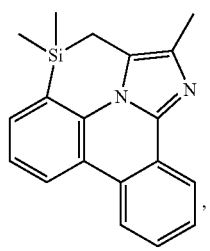
Compound (1-58)
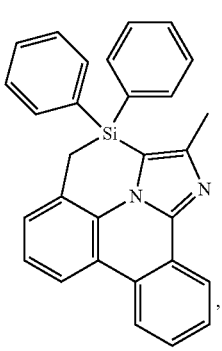
Compound (1-59)
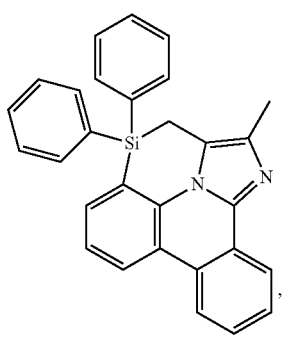
Compound (1-60)
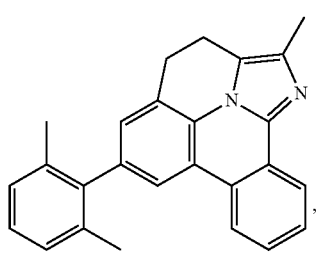
Compound (1-61)
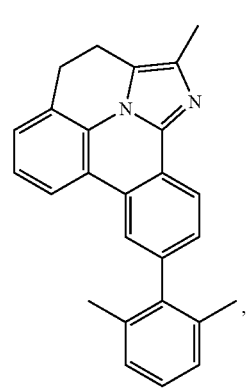
Compound (1-62)
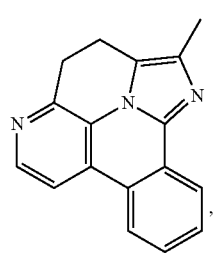
Compound (1-63)
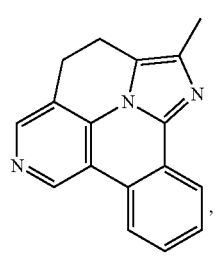

Compound (1-64)
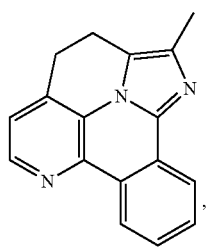
Compound (1-65)
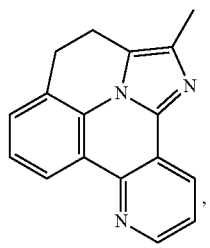
Compound (1-66)
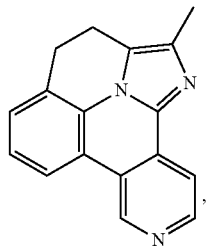
Compound (1-67)
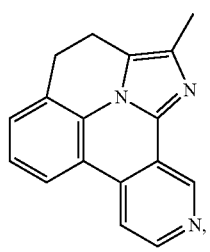
Compound (1-68)
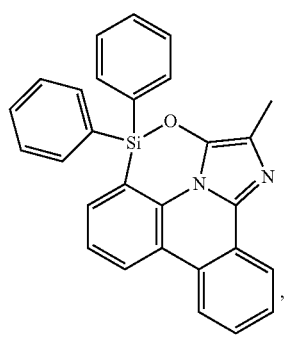
Compound (1-69)
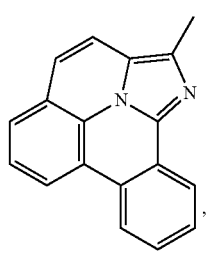
Compound (1-70)
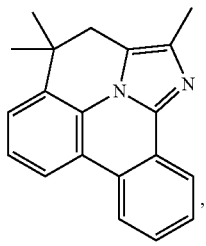
Compound (1-71)
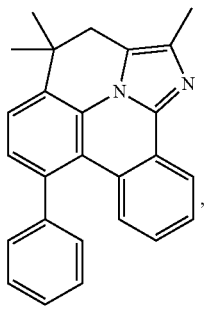
Compound (1-72)
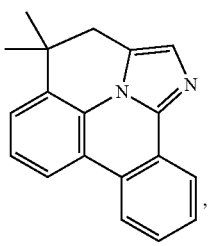
Compound (1-73)
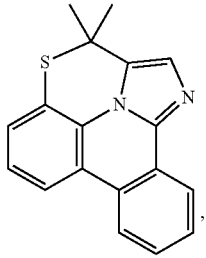
Compound (1-74)
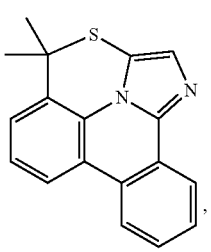

Compound (1-75)
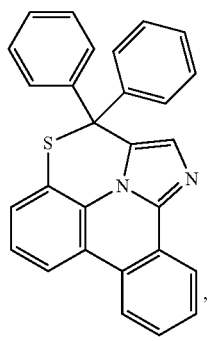
Compound (1-76)
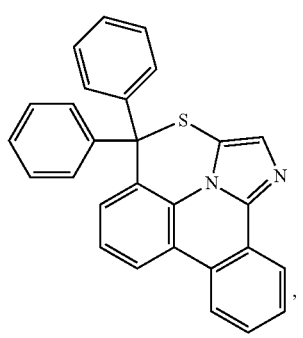
Compound (1-77)
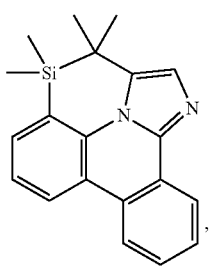
Compound (1-78)
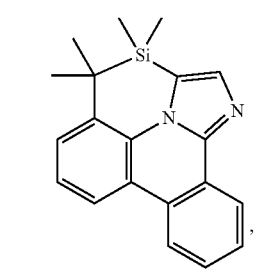
Compound (1-79)
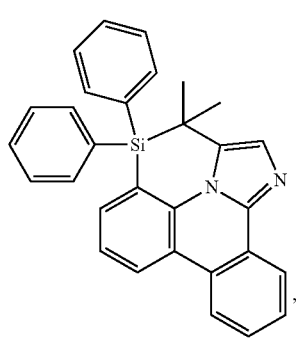
Compound (1-80)
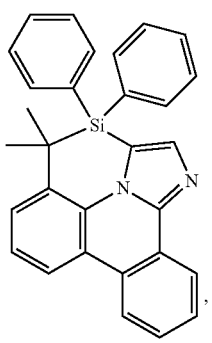
Compound (1-81)
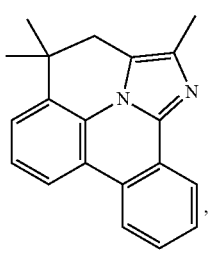
Compound (1-82)
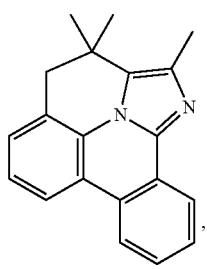
Compound (1-83)
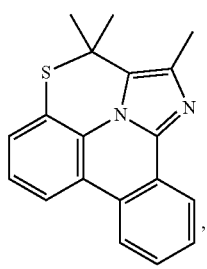
Compound (1-84)
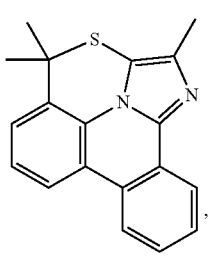

-continued
Compound (1-85)
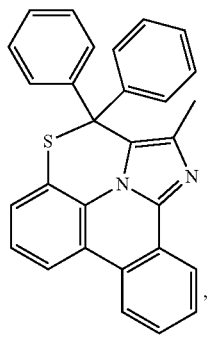
Compound (1-86)
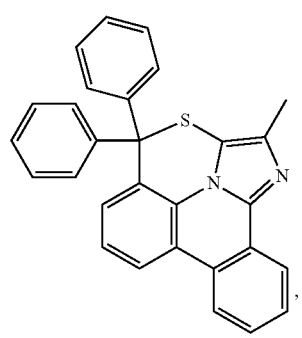
Compound (1-87)
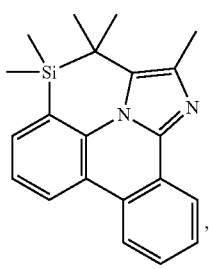
Compound (1-88)
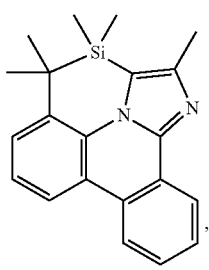
Compound (1-89)
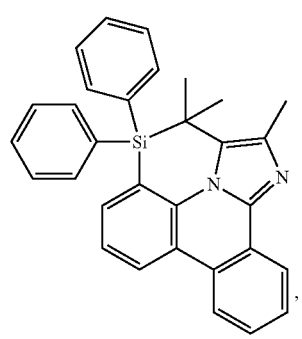
-continued
Compound (1-90)
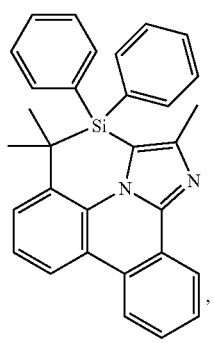
Compound (1-91)
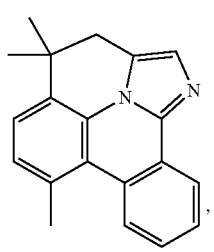
Compound (1-92)
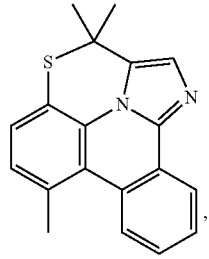
Compound (1-93)
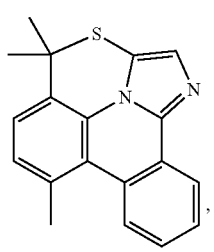
Compound (1-94)
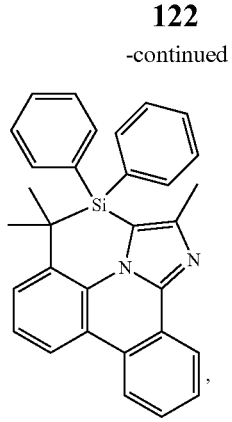

Compound (1-95)
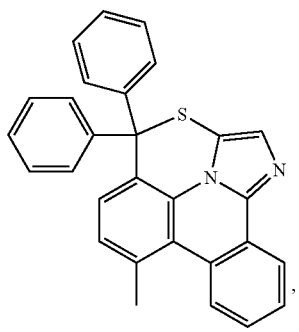
Compound (1-96)
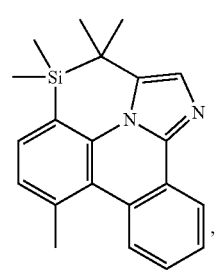
Compound (1-97)
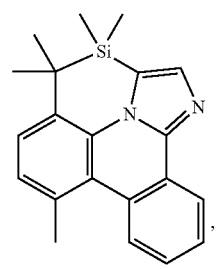
Compound (1-98)
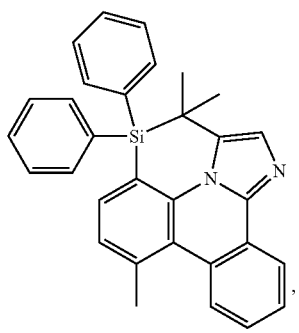
Compound (1-99)
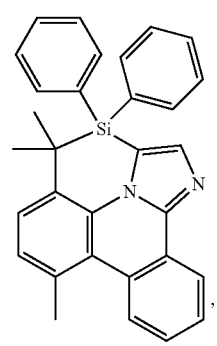
Compound (1-100)
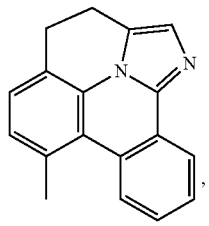
Compound (1-101)
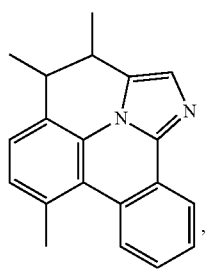
Compound (1-102)
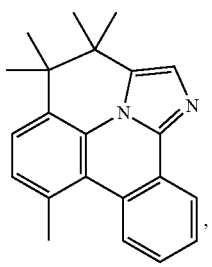
Compound (1-103)
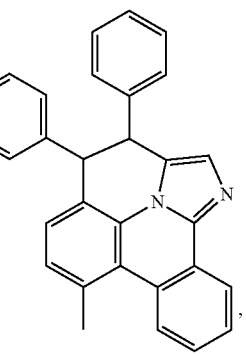
Compound (1-104)
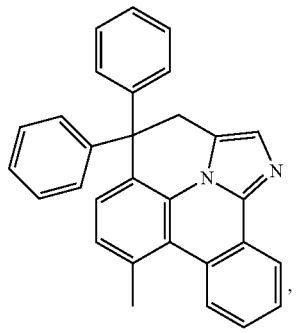

Compound (1-105)
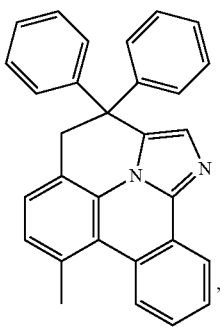
Compound (1-106)
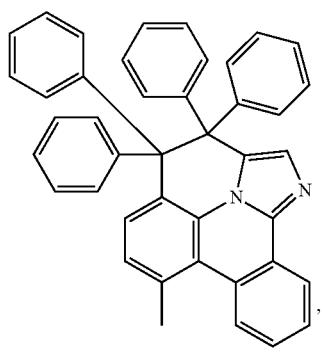
Compound (1-107)
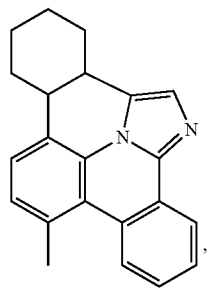
Compound (1-108)
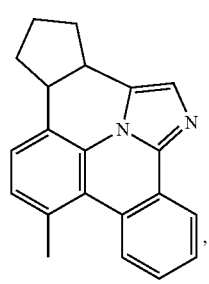
Compound (1-109)
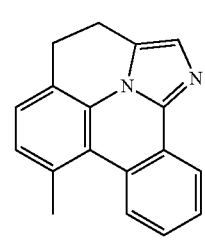
Compound (1-110)
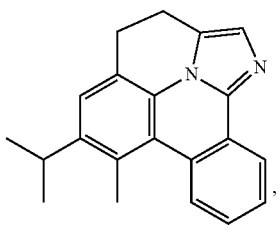
Compound (1-111)
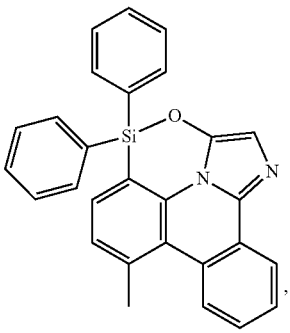
Compound (1-112)
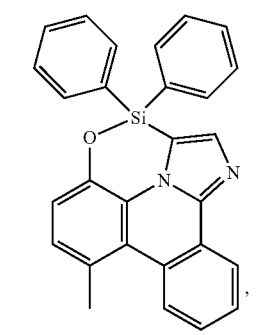
Compound (1-113)
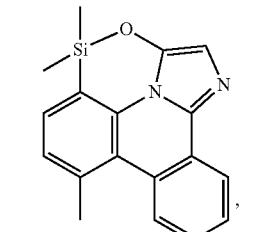
Compound (1-115)
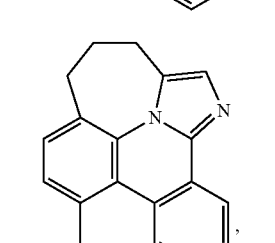
Compound (1-116)
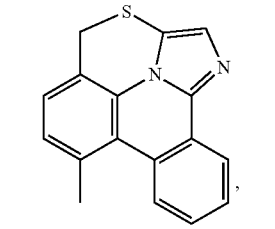

Compound (1-117)
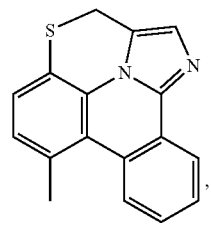
Compound (1-118)
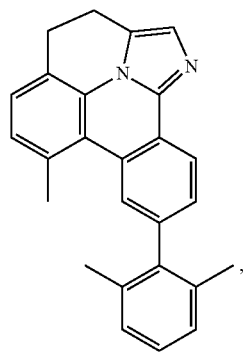
Compound (1-119)
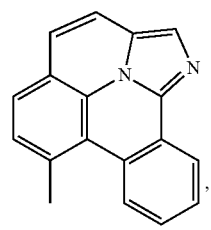
Compound (1-120)
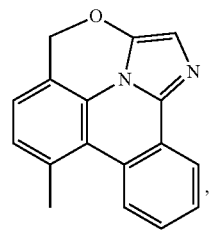
Compound (1-121)
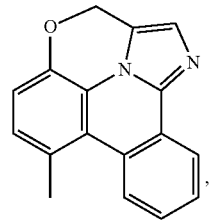
Compound (1-122)
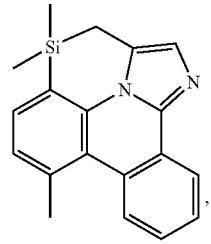
Compound (1-123)
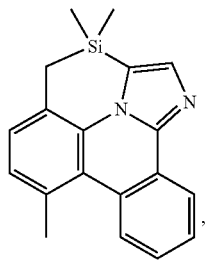
Compound (1-124)
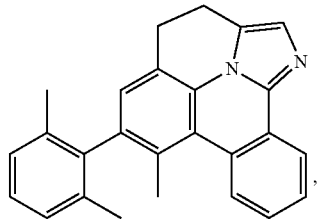
Compound (1-125)
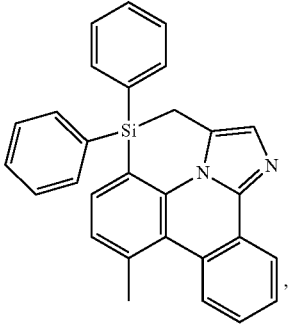
Compound (1-126)
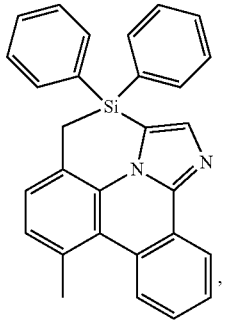
Compound (1-127)
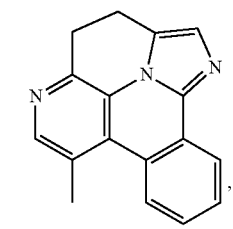
Compound (1-128)
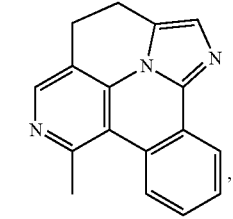

-continued
Compound (1-130)
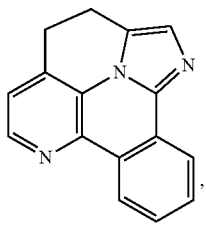
Compound (1-131)
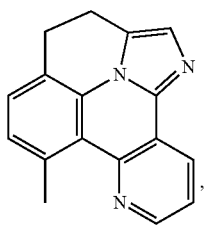
Compound (1-132)
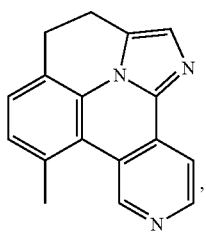
Compound (1-133)
Compound (1-134)
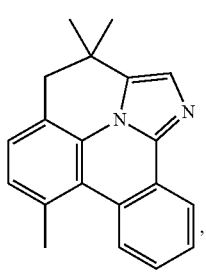
Compound (1-135)
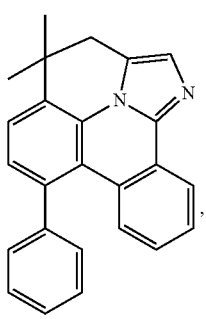
-continued
Compound (1-136)
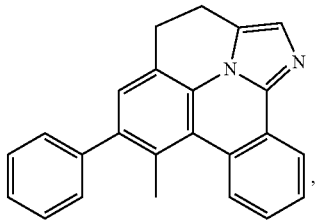
Compound (1-137)
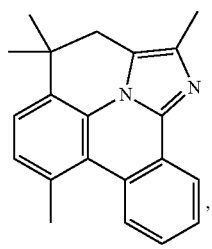
Compound (1-138)
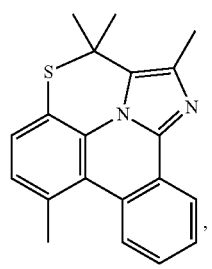
Compound (1-139)
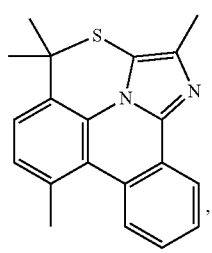
Compound (1-140)
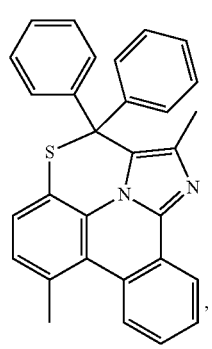

Compound (1-141)
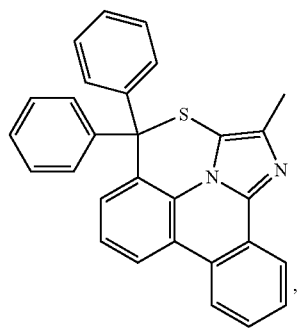
Compound (1-142)
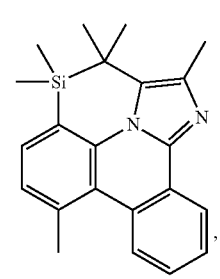
Compound (1-143)
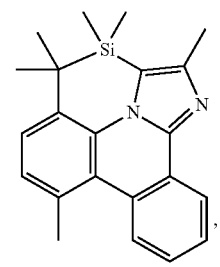
Compound (1-144)
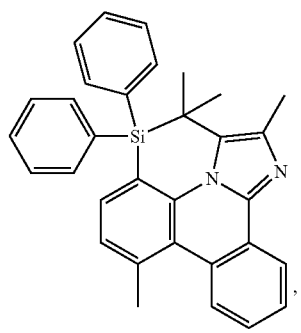
Compound (1-145)
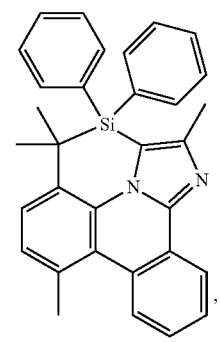
Compound (1-146)
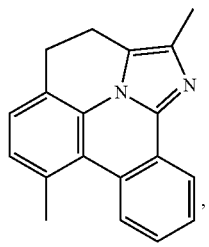
Compound (1-147)
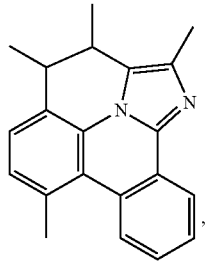
Compound (1-148)
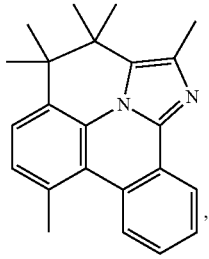
Compound (1-149)
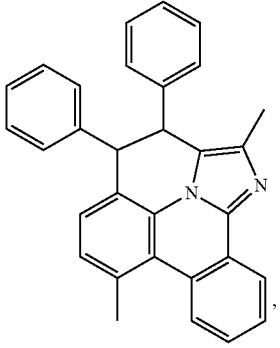
Compound (1-150)
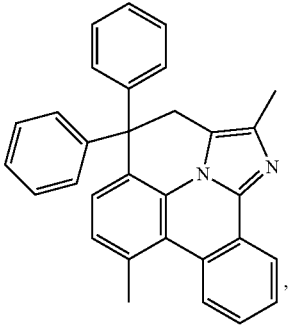

Compound (1-151)
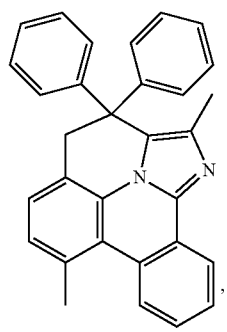
Compound (1-152)
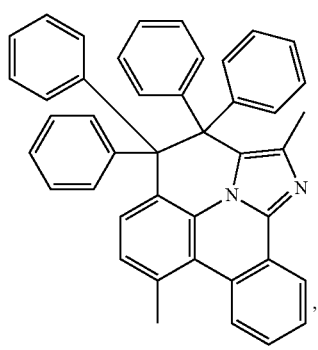
Compound (1-153)
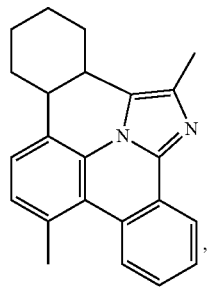
Compound (1-154)
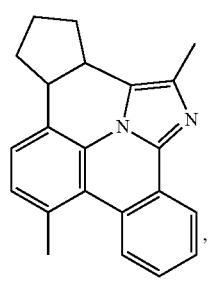
Compound (1-155)
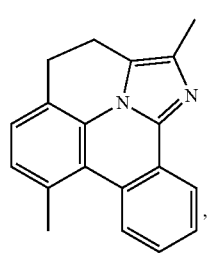
Compound (1-156)
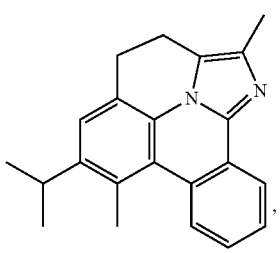
Compound (1-157)
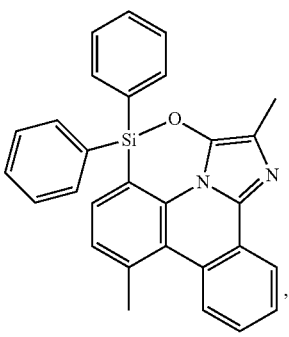
Compound (1-158)
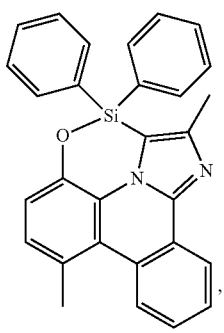
Compound (1-159)
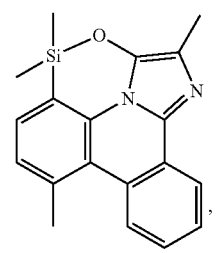
Compound (1-160)
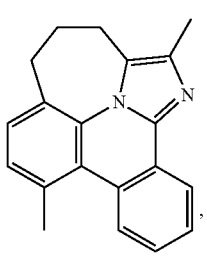

Compound (1-161)
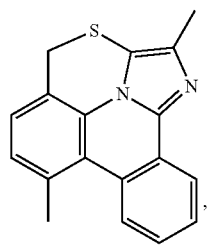
Compound (1-162)
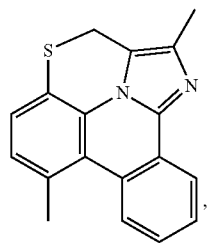
Compound (1-163)
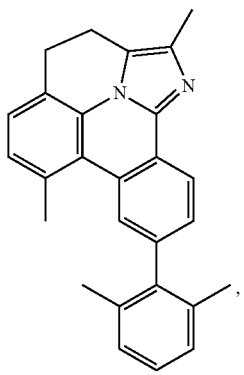
Compound (1-164)
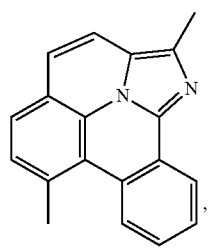
Compound (1-165)
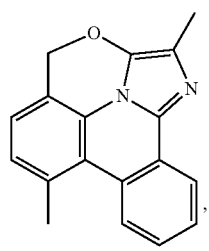
Compound (1-166)
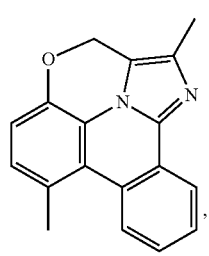
Compound (1-167)
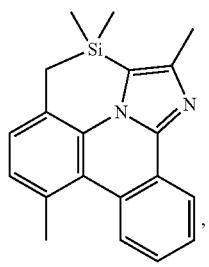
Compound (1-168)
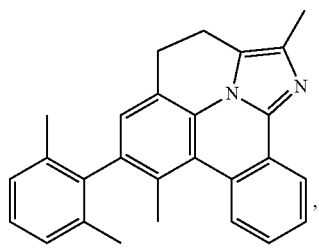
Compound (1-169)
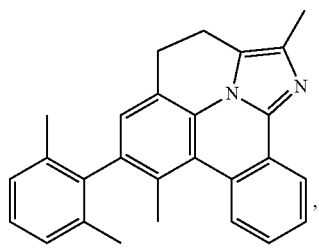
Compound (1-170)
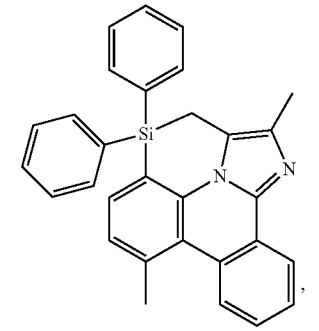
Compound (1-171)
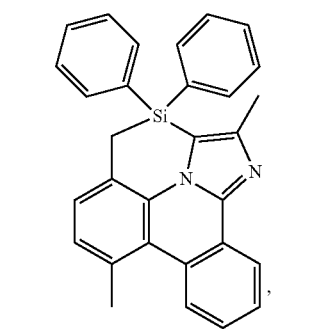

-continued
Compound (1-172)
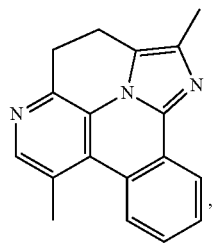
Compound (1-173)
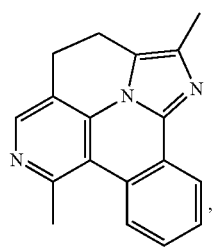
Compound (1-174)
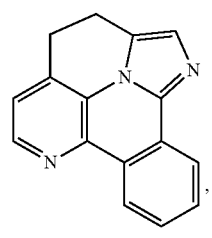
Compound (1-175)
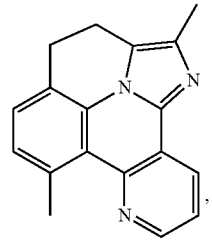
Compound (1-176)
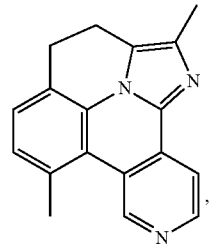
Compound (1-177)
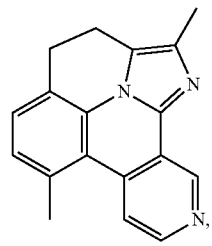
-continued
Compound (1-178)
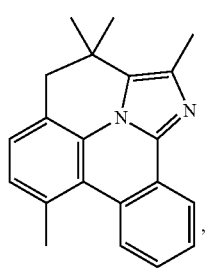
Compound (1-179)
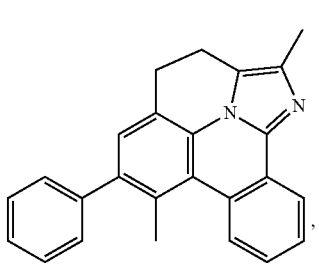
Compound (1-180)
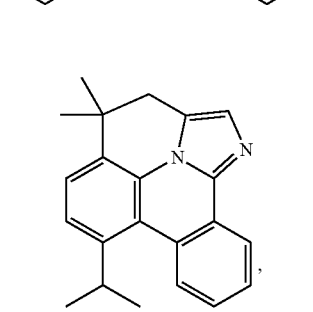
Compound (1-181)
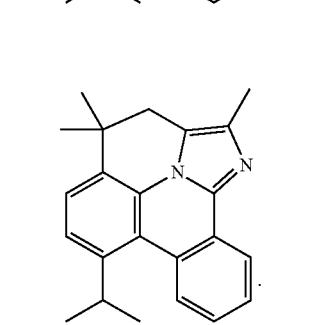
In some embodiments of the compound having Formula (1a), the compound has the structure of Formula (2a) and Formula (2b) tethered together as defined below:
Formula (2a)
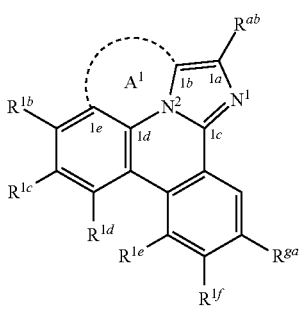

-continued

Formula (2b)

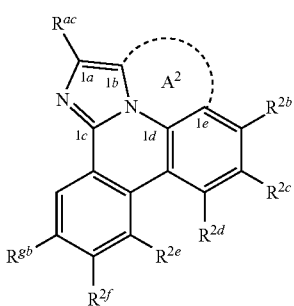

wherein $A^1$ and $A^2$ are each a first linking group having two to three linking atoms, wherein the linking atoms are each independently selected from the group consisting of C, Si, O, S, N, B and combinations thereof, and wherein $R^{ac}$, $R^{gb}$, and $R^{2b}$ to $R^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;

wherein the compound is tethered together via at least one second linking group formed between $R^{ab}$ and $R^{ac}$ and/or $R^{ga}$ and $R^{gb}$, wherein at least one second linking group has one to three linking atoms and each linking atom is independently selected from the group consisting of B, N, P, O, S, Se, C, Si, Ge and combinations thereof; and any one of the ring atoms to which $R^{1b}$ to $R^{1f}$ and $R^{2b}$ to $R^{2f}$ are attached may be replaced with a nitrogen atom, wherein when the ring atom is replaced with a nitrogen atom the corresponding R group is not present.

In some embodiments of the compound having the structure of Formula (2a) and Formula (2b) tethered together as defined above, the at least one second linking group is formed between $R^{ab}$ and $R^{ac}$.

In some embodiments of the compound having the structure of Formula (2a) and Formula (2b) tethered together as defined above, the at least one second linking group is formed between $R^{ga}$ and $R^{gb}$.

In some embodiments of the compound having the structure of Formula (2a) and Formula (2b) tethered together as defined above, the at least one second linking group are formed between $R^{ga}$ and $R^{gb}$ and $R^{ab}$ and $R^{ac}$.

In some embodiments of the compound having the structure of Formula (2a) and Formula (2b) tethered together as defined above, each of the first linking groups $A^1$ and $A^2$ is independently selected from the group consisting of $-CR^1R^2-R^3R^4-$, $-CR^1R^2-CR^3R-CR^5R^6-$, $-CR^1R^2-NR^3-$, $-CR^1=CR^2-CR^3R^4-$, $-O-SiR^1R^2-$, $-CR^1R^2-S-$, $-CR^1R^2-O-$, and $-C-SiR^1R^2-$, wherein each $R^1$ to $R^6$ can be same or different, and are independently selected from the group consisting of hydrogen, deuterium, alkyl, cycloalkyl, aryl, heteroaryl, and combinations thereof; wherein any adjacent $R^1$ to $R^6$ are optionally connected to form a saturated five membered ring or a saturated six membered ring.

In some embodiments of the compound having the structure of Formula (2a) and Formula (2b) tethered together as defined above, each of the first linking groups $A^1$ and $A^2$ is independently selected from the Linker Group defined above.

In some embodiments of the compound having the structure of Formula (2a) and Formula (2b) tethered together as defined above, the second linking group is independently selected from the group consisting of $BR^1$, $NR^1$, $PR^1$, O, S, Se, C=O, S=O, $SO_2$, $CR^1R^2$, $-CR^1R^2-CR^3R^4-$, $-CR^1R^2-CR^3R^4-CR^5R^6-$, $-CR^1R^2-NR^3-$, $-CR^1=CR^2-CR^3R^4-$, $-O-SiR^1R^2-$, $-CR^1R^2-S-$, $-CR^1R^2-O-$, $-C-SiR^1R^2-$, $SiR^1R^2$, and $GeR^1R^2$, wherein each $R^1$ to $R^6$ can be same or different, and are independently selected from the group consisting of hydrogen, deuterium, alkyl, cycloalkyl, aryl, heteroaryl, and combinations thereof; wherein any adjacent $R^1$ to $R^6$ are optionally connected to form a saturated five membered ring or a saturated six membered ring.

In some embodiments of the compound having the structure of Formula (2a) and Formula (2b) tethered together as defined above, the compound is selected from the group consisting of:

Compound (2-1)

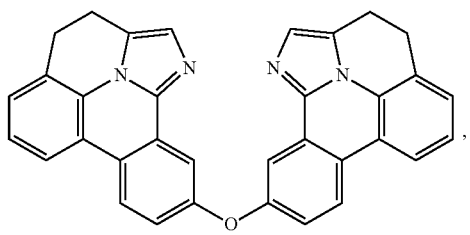

Compound (2-2)

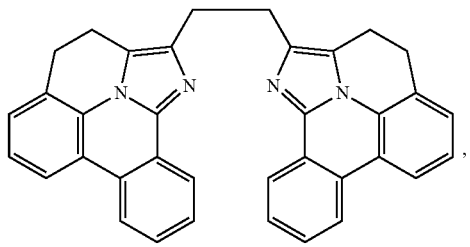

Compound (2-3)

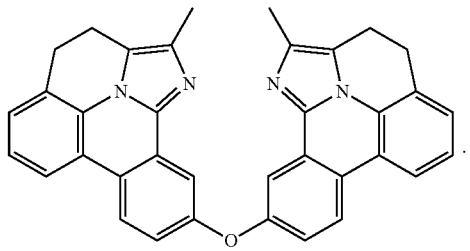

In some embodiments of the compound having the structure of Formula (2a) and Formula (2b) tethered together as defined above, the compound has Formula (3a):

Formula (3a)

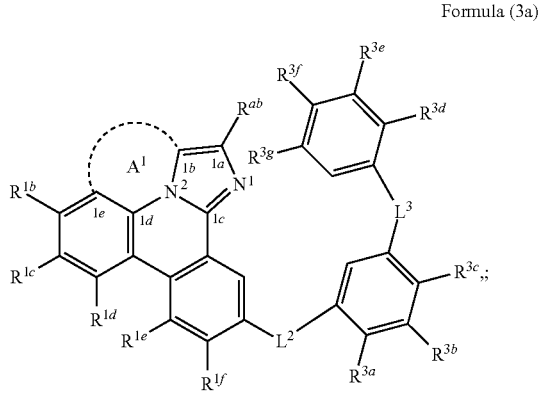

wherein $L^2$ and $L^3$ are each independently selected from the group consisting of a single bond, $BR^1$, $NR^1$, $PR^1$, O, S, Se, C=O, S=O, $SO_2$, $CR^1R^2$, $SiR^1R^2$, and $GeR^1R^2$;

wherein $R^{3a}$-$R^{3f}$, are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein each $R^1$ and $R^2$ is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any two adjacent $R^{1f}$, $R^{3a}$, $R^{3c}$, $R^{3d}$, $R^1$, and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings; and wherein $L^3$ and $R^{3c}$, $L^3$ and $R^{3d}$, or $L^3$ and both $R^{3c}$ and $R^{3d}$ are optionally joined to form one or more rings.

In some embodiments of the compound having Formula (3a), $L^2$ and $L^3$ are independently selected from the group consisting of $BR^1$, $NR^1$, $PR^1$, O, S, Se, C=O, S=O, $SO_2$, $CR^1R^2$, $SiR^1R^2$, and $GeR^1R^2$.

In some embodiments of the compound having Formula (3a), $R^{1f}$ or $R^{3a}$ and $R^1$ or $R^2$ are joined to form a ring.

In some embodiments of the compound having Formula (3a), $R^{3c}$ or $R^{3d}$ and $R^1$ or $R^2$ are joined to form a ring.

In some embodiments of the compound having Formula (3a), the compound is selected from the group consisting of:

Compound (3-1)

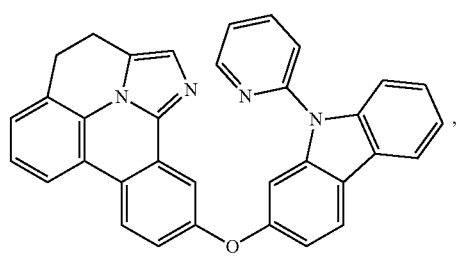

Compound (3-2)

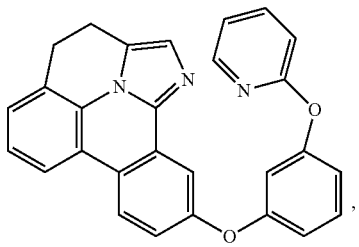

Compound (3-3)

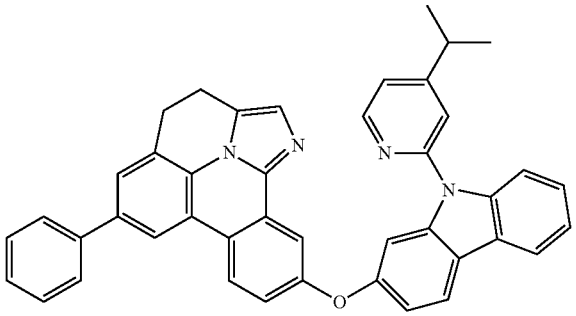

Compound (3-4)

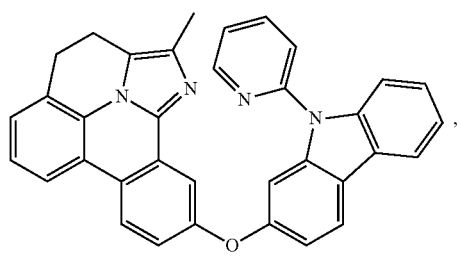

Compound (3-5)

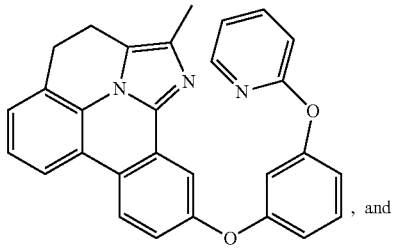

, and

Compound (3-6)

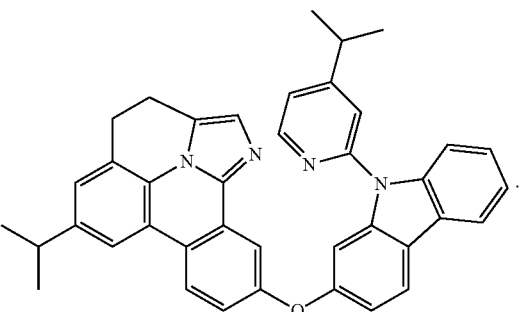

The metal complexes according to various embodiments of the present invention can exhibit a number of desirable characteristics. In some embodiments, the metal complexes having the structures of Formula 1, Formula 2, or Formula 3 can exhibit photoluminescence with a high quantum efficiency, with a narrow spectral width, and/or with a peak emission wavelength located within a desirable range of wavelengths, such as the visible range or the near infrared range. Also, these photoluminescent characteristics can be relatively invariant over a wide range of excitation wavelengths. In some embodiments, the metal complexes of Formula 1, Formula 2, or Formula 3 can have other desirable characteristics, such as relating to their band gap energies and electrical conductivities. Also, advantageously, the metal complexes of Formula 1, Formula 2, or Formula 3 can be inexpensively and readily synthesized from commercially available starting materials. In some embodiments, the metal complexes of Formula 1, Formula 2, or Formula 3 can exhibit photoluminescence with a relatively low quantum efficiency but this may still be sufficient for certain applications.

In some embodiments, a metal complex having the structure of Formula 1, Formula 2, or Formula 3 has a peak emissive wavelength less than 500 nm. In some embodiments, a metal complexes having the structure of Formula 1, Formula 2, or Formula 3 has a peak emissive wavelength less than 480 nm. In some embodiments, a metal complex having the structure of Formula 1, Formula 2, or Formula 3 has a peak emissive wavelength of 400 nm to 500 nm inclusive.

In some embodiments, metal complexes having the structure of Formula 1, Formula 2, or Formula 3 have a triplet excited state and the linking group A that stabilizes the bond between $N^2$ and $C^{1b}$, shown below, from cleavage when the compound is in the triplet excited state.

Formula 1

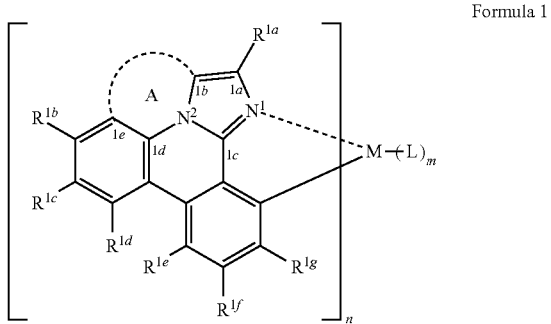

Formula 2

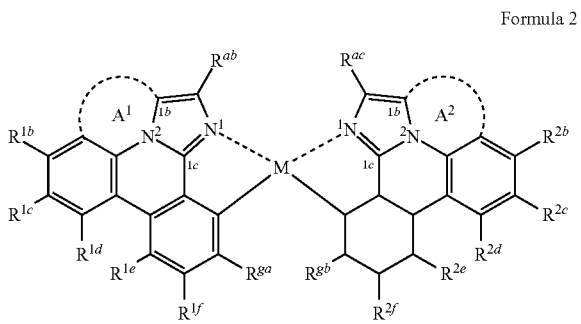

-continued

Formula 3

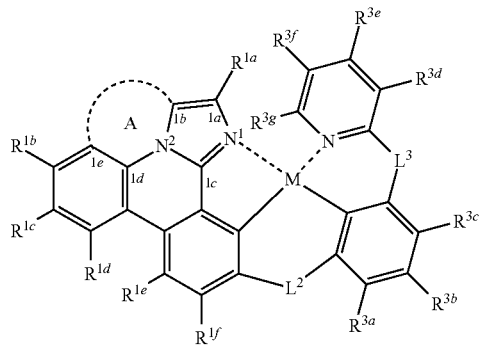

Accordingly, in some embodiments, the metal complex having the structure of Formula 1, Formula 2, or Formula 3 is a phosphorescent light emitting substance. In some embodiments, the metal complex having the structure of Formula 1, Formula 2, or Formula 3 is a fluorescent light emitting substance. In some embodiments, the metal complex having the structure of Formula 1, Formula 2, or Formula 3 is both a fluorescent and a phosphorescent light emitting substance.

Metal complexes having the structure of Formula 1, Formula 2, or Formula 3 are suitable, for example, for use in OLEDs, which exploit the propensity of materials to emit light when they are excited by an electrical current. Accordingly, in some aspects, the present invention provides an organic light-emitting material comprising at least one metal complex having the structure of Formula 1, Formula 2, or Formula 3. In some embodiments, the present invention provides an organic light-emitting material comprising at least two metal complexes selected from compounds having the structure of Formula 1. Formula 2, or Formula 3.

Organic light-emitting materials according to various embodiments of the invention can exhibit a number of desirable characteristics. In some embodiments, the organic light-emitting materials can exhibit photoluminescence with a high quantum efficiency, with a narrow spectral width, and with a peak emission wavelength located within a desirable range of wavelengths, such as the visible range or the near infrared range. Also, these photoluminescent characteristics can be relatively invariant over a wide range of excitation wavelengths. The organic light-emitting materials can have other desirable characteristics, such as relating to their band gap energies and electrical conductivities. Advantageously, the organic light-emitting materials can be inexpensively and readily formed for use in various applications, including consumer products and lighting panels.

In some embodiments, the content of a photoluminescent substance in a light emitting material according to the present invention (e.g., one or more metal complexes having the structure of Formula 1. Formula 2, or Formula 3) is between 0.1% by mass to 50% by mass inclusive with respect to the total mass of a light emitting layer comprising the light emitting material. In some embodiments, the content of a photoluminescent substance in a light emitting material according to the present invention is between 0.3% by mass to 40% by mass inclusive with respect to the total mass of a light emitting layer comprising the light emitting material. In some embodiments, the content of a photoluminescent substance in a light emitting material according to the present invention is between 0.5% by mass to 30% by mass inclusive with respect to the total mass of a light emitting layer comprising the light emitting material. In some embodiments, the photoluminescent substance in a light emitting material according to the present invention is appended to a polymer chain or incorporated in a denrimer material.

IV. Devices

In some aspects, the present invention provides an organic electroluminescence device which comprises at least one metal complex having the structure of Formula 1, Formula 2, or Formula 3. In some embodiments, an organic electroluminescence device according to the present invention comprises a first organic light emitting device, which further comprises an anode; a cathode; an organic layer disposed between the anode and the cathode, and comprising at least one metal complex having the structure of Formula 1, Formula 2, or Formula 3. In some preferred embodiments of the organic electroluminescence device, the organic layer further comprises a host material. In some preferred embodiments of the organic electroluminescence device, the host material comprises an organic compound. In some preferred embodiments of the organic electroluminescence device, the host material comprises an organic compound having a molecule containing at least one group selected from the group consisting of carbazole, dibenzothiphene, dibenzofuran, azacarbazole, aza-dibenzothiophene, and aza-dibenzofuran.

Generally, an organic layer suitable for use in the organic electroluminescence device of the present may have any suitable configuration of layer depending, for example, on application and purpose of the organic electroluminescence device. Accordingly, in some embodiments of the organic electroluminescence device, the organic layer is formed on a transparent electrode or a semitransparent electrode. In some such embodiments, the organic layer is formed on a top surface or any suitable surface of the transparent electrode or the semitransparent electrode. Also, suitable shape, size and/or thickness of the organic layer may be employed depending, for example, on application and the purpose of the organic electroluminescence device. Specific examples of configurations of an organic electroluminescence device of the present invention, having a substrate, a cathode, an anode and an organic layer include, but are not limited to, the following:

(A) Anode/hole transporting layer/light emitting layer/electron transporting layer/cathode;

(B) Anode/hole transporting layer/light emitting layer/block layer/electron transporting layer/cathode;

(C) Anode/hole transporting layer/light emitting layer/block layer/electron transporting layer/electron injection layer/cathode;

(D) Anode/hole injection layer/hole transporting layer/light emitting layer/block layer/electron transporting layer/cathode; and (E) Anode/hole injection layer/hole transporting layer/light emitting layer/block layer/electron transporting layer/electron injection layer/cathode.

(F) Anode/hole injection layer/electron blocking layer/hole transporting layer/light emitting layer/block layer/electron transporting layer/electron injection layer/cathode.

Additional device configuration, including substrate, cathode and anode of an organic electroluminescence device, is described in Japanese Patent Publication No. 2008-270736.

<Substrate>

A suitable substrate usable in an organic electroluminescence device of the present invention is preferably a substrate which does not scatter or decrease light emitted from an organic layer when used for display applications. When used for lighting or certain display applications, substrates that scatter light are acceptable. In some embodiments, the substrate preferably is composed of an organic material which exhibits superior heat resistance, dimensional stability, solvent resistance, electrical insulating property and/or processability.

The substrate suitable for use in the present invention is preferably one which does not scatter or attenuate light emitted from the organic compound layer. Specific examples of materials for the substrate, include but are not limited to, inorganic materials such as zirconia-stabilized yttrium (YSZ) and glass; polyesters such as polyethylene terephthalate, polybutylene phthalate, and polyethylene naphthalate; and organic materials such as polystyrene, polycarbonate, polyethersulfone, polyarylate, polyimide, polycycloolefin, norbornene resin, polychlorotrifluoroethylene, and the like.

In some embodiments, when glass is used as the substrate, alkali free glass is preferably used. Specific examples of suitable alkali free glass are found in US patent application publication no. 2013/0237401 by Takahiro Kawaguchi, which published Sep. 12, 2013. In some embodiments, when soda-lime glass is used as the substrate, it is preferred to use glass on which a barrier coat of silica or the like has been applied. In some embodiments, when an organic material is used as the substrate, it is preferred to use a material having one or more of the attributes: excellent in heat resistance, dimensional stability, solvent resistance, electric insulation performance, and workability.

Generally, there is no particular limitation as to the shape, the structure, the size or the like of the substrate, but any of these attributes may be suitably selected according to the application, purposes and the like of the light-emitting element. n general, a plate-like substrate is preferred as the shape of the substrate. A structure of the substrate may be a monolayer structure or a laminate structure. Furthermore, the substrate may be formed from a single member or two or more members.

Although the substrate may be transparent and colorless, or transparent and colored, it is preferred that the substrate is transparent and colorless from the viewpoint that the substrate does not scatter or attenuate light emitted from the organic light-emitting layer. In some embodiments, a moisture permeation preventive layer (gas barrier layer) may be provided on the top surface or the bottom surface of the substrate. Examples of a material of the moisture permeation preventive layer (gas barrier layer), include, but are not limited to, inorganic substances such as silicon nitride and silicon oxide. The moisture permeation preventive layer (gas barrier layer) may be formed in accordance with, for example, a high-frequency sputtering method or the like.

In the case of applying a thermoplastic substrate, a hard-coat layer or an under-coat layer may be further provided as needed.

<Anode>

Any anode may be used in an organic electroluminescence device of the present invention so long as it serves as an electrode supplying holes into an organic layer. In some embodiments of the organic electroluminescence device of the present invention, any suitable shape, structure and/or size of known electrode material may be used depending, for example, on the application and purpose of the organic electroluminescence device. In some embodiments, a transparent anode is preferred.

The anode may generally be any material as long as it has a function as an electrode for supplying holes to the organic compound layer, and there is no particular limitation as to the shape, the structure, the size or the like. However, it may be suitably selected from among well-known electrode materials according to the application and purpose of the light-emitting element. In some embodiments, the anode is provided as a transparent anode.

Materials for the anode preferably include, for example, metals, alloys, metal oxides, electric conductive compounds, and mixtures thereof. Materials having a work function of 4.0 eV or more are preferable. Specific examples of the anode materials include electric conductive metal oxides such as tin oxides doped with antimony, fluorine or the like (ATO and FTO), tin oxide, zinc oxide, indium oxide, indium tin oxide (ITO), and indium zinc oxide (IZO); metals such as gold, silver, chromium, aluminum, copper, and nickel; mixtures or laminates of these metals and the electric conductive metal oxides; inorganic electric conductive materials such as copper iodide and copper sulfide; organic electric conductive materials such as polyaniline, polythiophene, and polypyrrole; and laminates of these inorganic or organic electron-conductive materials with ITO. Among these, the electric conductive metal oxides are preferred, and particularly, ITO is preferable in view of productivity, high electric conductivity, transparency and the like.

The anode may be formed on the substrate in accordance with a method which is appropriately selected from among wet methods such as printing methods, coating methods and the like; physical methods such as vacuum deposition methods, sputtering methods, ion plating methods and the like; and chemical methods such as CVD (chemical vapor deposition) and plasma CVD methods and the like, in consideration of the suitability to a material constituting the anode. For instance, when ITO is selected as a material for the anode, the anode may be formed in accordance with a DC or high-frequency sputtering method, a vacuum deposition method, an ion plating method or the like.

In the organic electroluminescence element of the present invention, a position at which the anode is to be formed is not particularly limited, but it may be suitably selected according to the application and purpose of the light-emitting element. The anode may be formed on either the whole surface or a part of the surface on either side of the substrate.

For patterning to form the anode, a chemical etching method such as photolithography, a physical etching method such as etching by laser, a method of vacuum deposition or sputtering through superposing masks, or a lift-off method or a printing method may be applied.

A thickness of the anode may be suitably selected according to the material constituting the anode and is therefore not definitely decided, but it is usually in a range of from 10 nm to 50 µm, and preferably from 50 nm to 20 µm. The thickness of the anode layer may be properly controlled depending on the material used therefor. The resistance of the anode is preferably $10^3 \Omega$/square or less, and more preferably $10^2 \Omega$/square or less, more preferably 30 $\Omega$/square or less. In the case where the anode is transparent, it may be either transparent and colorless, or transparent and colored. For extracting luminescence from the transparent anode side, it is preferred that a light transmittance of the anode is 60% or higher, and more preferably 70% or higher. A detailed description of transparent anodes can be found in "TOUMEI DENNKYOKU-MAKU NO SHINTENKAI (Novel Developments in Transparent Electrode Films)" edited by Yutaka Sawada, published by C.M.C. in 1999.

In the case where a plastic substrate having a low heat resistance is used in the present invention, it is preferred that ITO or IZO is used to obtain a transparent anode prepared by forming the film at a low temperature of 150° C. or lower.

<Cathode>

Any cathode may be used in an organic electroluminescence device of the present invention so long as it serves as an electrode supplying electrons into the organic layer. In some embodiments of the organic electroluminescence device of the present invention, any suitable shape, structure and/or size of known electrode material may be used depending, for example, on the application and purpose of the organic electroluminescence device. In some embodiments, a transparent cathode is preferred.

The cathode may generally be any material as long as it has a function as an electrode for injecting electrons to the organic compound layer, and there is no particular limitation as to the shape, the structure, the size or the like. However it may be suitably selected from among well-known electrode materials according to the application and purpose of the light-emitting element.

Materials constituting the cathode include, for example, metals, alloys, metal oxides, electric conductive compounds, and mixtures thereof. Materials having a work function of 4.0 eV or more are preferable. Specific examples thereof include alkali metals (e.g., Li, Na, K, Cs or the like), alkaline earth metals (e.g., Mg, Ca or the like), gold, silver, lead, aluminum, sodium-potassium alloys, lithium-aluminum alloys, magnesium-silver alloys, rare earth metals such as indium, and ytterbium, and the like. They may be used alone, but it is preferred that two or more of them are used in combination from the viewpoint of satisfying both stability and electron injectability.

In some embodiments, as the materials for constituting the cathode, alkaline metals or alkaline earth metals are preferred in view of electron injectability, and materials containing aluminum as a major component are preferred in view of excellent preservation stability.

The term "material containing aluminum as a major component" refers to a material constituted by aluminum alone; alloys comprising aluminum and 0.01% by weight to 10% by weight of an alkaline metal or an alkaline earth metal; or mixtures thereof (e.g., lithium-aluminum alloys, magnesium-aluminum alloys and the like). Exemplary materials for the cathode are described in detail in JP-A Nos. 2-15595 and 5-121172.

A method for forming the cathode is not particularly limited, but it may be formed in accordance with a well-known method. For instance, the cathode may be formed in accordance with a method which is appropriately selected from among wet methods such as printing methods, coating methods and the like; physical methods such as vacuum deposition methods, sputtering methods, ion plating methods and the like; and chemical methods such as CVD and plasma CVD methods and the like, in consideration of the suitability to a material constituting the cathode. For example, when a metal (or metals) is (are) selected as a material (or materials) for the cathode, one or two or more of them may be applied at the same time or sequentially in accordance with a sputtering method or the like.

For patterning to form the cathode, a chemical etching method such as photolithography, a physical etching method such as etching by laser, a method of vacuum deposition or sputtering through superposing masks, or a lift-off method or a printing method may be applied.

In the present invention, a position at which the cathode is to be formed is not particularly limited, and it may be formed on either the whole or a part of the organic compound layer.

Furthermore, a dielectric material layer made of fluorides, oxides or the like of an alkaline metal or an alkaline earth metal may be inserted between the cathode and the organic compound layer with a thickness of from 0.1 nm to 5 nm. The dielectric material layer may be considered to be a kind of electron injection layer. The dielectric material layer may be formed in accordance with, for example, a vacuum deposition method, a sputtering method, an ionplating method or the like.

A thickness of the cathode may be suitably selected according to materials for constituting the cathode and is therefore not definitely decided, but it is usually in a range of from 10 nm to 5 µm, and preferably from 50 nm to 1 µm.

Moreover, the cathode may be transparent or opaque. A transparent cathode may be formed by preparing a material for the cathode with a small thickness of from 1 nm to 10 nm, and further laminating a transparent electric conductive material such as ITO or IZO thereon.

<Protective Layer>

A whole body of the organic EL element of the present invention may be protected by a protective layer. Any materials may be applied in the protective layer as long as the materials have a function to protect a penetration of ingredients such as moisture, oxygen or the like which accelerates deterioration of the element into the element. Specific examples of materials for the protective layer include metals such as In, Sn, Pb, Au, Cu, Ag, Al, Ti, Ni and the like; metal oxides such as MgO, SiO, $SiO_2$, $Al_2O_3$, GeO, NiO, CaO, BaO, $Fe_2O_3$, $Y_2O_3$, $TiO_2$ and the like; metal nitrides such as $SiN_x$, $SiN_xO_y$, and the like; metal fluorides such as $MgF_2$, LiF, $AlF_3$, $CaF_2$ and the like; polyethylene; polypropylene; polymethyl methacrylate; polyimide; polyurea; polytetrafluoroethylene; polychlorotrifluoroethylene; polydichlorodifluoroethylene; a copolymer of chlorotrifluoroethylene and dichlorodifluoroethylene; copolymers obtained by copolymerizing a monomer mixture containing tetrafluoroethylene and at least one comonomer; fluorine-containing copolymers each having a cyclic structure in the copolymerization main chain; water-absorbing materials each having a coefficient of water absorption of 1% or more; moisture permeation preventive substances each having a coefficient of water absorption of 0.1% or less; and the like.

There is no particular limitation as to a method for forming the protective layer. For instance, a vacuum deposition method, a sputtering method, a reactive sputtering method, an MBE (molecular beam epitaxial) method, a cluster ion beam method, an ion plating method, a plasma polymerization method (high-frequency excitation ion plating method), a plasma CVD method, a laser CVD method, a thermal CVD method, a gas source CVD method, a coating method, a printing method, or a transfer method may be applied.

<Sealing>

The whole organic electroluminescence element of the present invention may be sealed with a sealing cap. Furthermore, a moisture absorbent or an inert liquid may be used to seal a space defined between the sealing cap and the light-emitting element. Although the moisture absorbent is not particularly limited, specific examples thereof include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, molecular sieve, zeolite, magnesium oxide and the like. Although the inert liquid is not particularly limited, specific examples thereof include paraffins; liquid paraffins; fluorine-based solvents such as perfluoroalkanes, perfluoroamines, perfluoroethers and the like; chlorine-based solvents; silicone oils; and the like.

<Driving>

In the organic electroluminescence element of the present invention, when a DC (AC components may be contained as needed) voltage (usually 2 volts to 15 volts) or DC is applied across the anode and the cathode, luminescence can be obtained. For the driving method of the organic electroluminescence element of the present invention, driving methods described in JP-A Nos. 2-148687, 6-301355, 5-29080, 7-134558, 8-234685, and 8-241047; Japanese Patent No. 2784615, U.S. Pat. Nos. 5,828,429 and 6,023,308 are applicable.

<Applications>

Devices fabricated in accordance with embodiments of the inventions described herein may be incorporated into a wide variety of consumer products, including but not limited to flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign.

<Organic Layer>

An organic layer suitable for use in an organic electroluminescence device of the present invention may comprise a plurality of layers, including, for example, light emitting layer, host material, electric charge transporting layer, hole injection layer, and hole transporting layer. Blocking layers may also be included e.g. hole (and or exciton) blocking layers (HBL) or electron (and or exciton) blocking layers (EBL). In some embodiments of an organic electroluminescence device of the present invention, each organic layer may be formed by a dry-type film formation method such as a deposition method or a sputtering method, or a solution coating process such as a transfer method, a printing method, a spin coating method, or a bar coating method. In some embodiments of an organic electroluminescence device of the present invention, at least one layer of the organic layer is preferably formed by a solution coating process.

A. Light Emitting Layer

Light Emitting Material:

A light emitting material in accordance with the present invention preferably includes at least one metal complex having the structure of Formula 1, Formula 2, or Formula 3. Some embodiments of an organic electroluminescence device of the present invention comprises the light emitting material in an amount of about 0.1% by mass to about 50% by mass with respect to the total mass of the compound constituting the light emitting layer. In some embodiments, an organic electroluminescence device of the present invention comprises the light emitting material in an amount of about 1% by mass to about 50% by mass with respect to the total mass of the compound constituting the light emitting layer. In some embodiments, an organic electroluminescence device of the present invention comprises the light emitting material in an amount of about 2% by mass to about 40% by mass with respect to the total mass of the compound constituting the light emitting layer. In some embodiments, a total amount of the light-emitting materials in the light-emitting layer is preferably from about 0.1% by weight to about 30% by weight with respect to the entire amount of compounds contained in the light-emitting layer. In some embodiments, a total amount of the light-emitting materials in the light-emitting layer is preferably from about 1% by weight to about 20% by weight in view of durability and external quantum efficiency. In some embodiments, a total amount of the host materials in the light-emitting layer is preferably from about 70% by weight to about 99.9% by weight. In some embodiments, a total amount of the host materials in the light-emitting layer is preferably from about 80% by weight to 99% by weight in view of durability and external quantum efficiency. In some embodiments, graded light emitting layers or graded interfaces within the light emitting layer may be used. Grading may be formed, for example, by mixing two or more distinct materials in a fashion that an abrupt change from one layer to another is not formed. Graded light emitting layers and or interfaces have been shown to improve device lifetime and this device architecture may be beneficial to improving PHOLED lifetime and general performance. In this instance the light emitting material may be present in an amount of about 0% by mass to about 100% by mass at any given position within the light emitting layer.

In some embodiments, a light-emitting layer in the present invention may include the light-emitting materials and a host material contained in the light-emitting layer as a combination of a fluorescent light-emitting material which emits light (fluorescence) through a singlet exciton and a host material, or a combination of a phosphorescent light-emitting material which emits light (phosphorescence) through a triplet exciton and a host material. In some embodiments, a light-emitting layer in the present invention may include the light-emitting materials and a host material contained in the light-emitting layer as a combination of a phosphorescent light-emitting material and a host material.

In some embodiments, the first compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

B. Host Material

A suitable host material for use in the present invention, may be a hole transporting host material (sometimes referred to as a hole transporting host), and/or an electron transporting host material (sometimes referred to as an electron transporting host).

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. In some embodiment, the host can also be an inorganic compound. For example a Zn containing inorganic material, e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be a specific compound selected from the group consisting of:

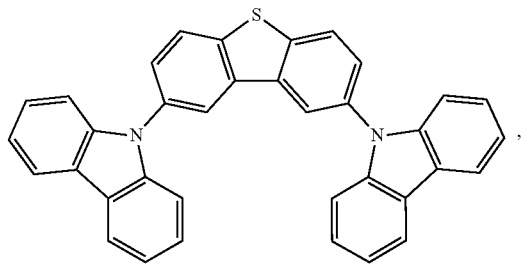

,

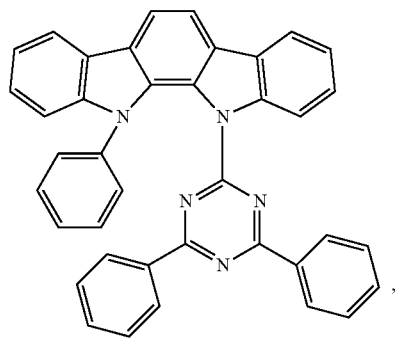

,

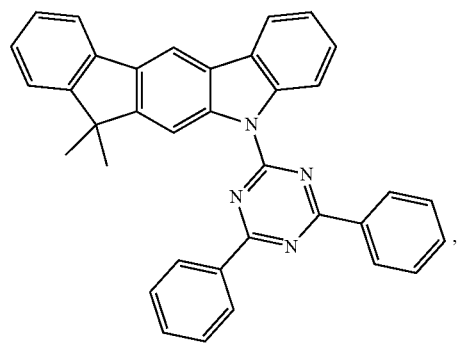

,

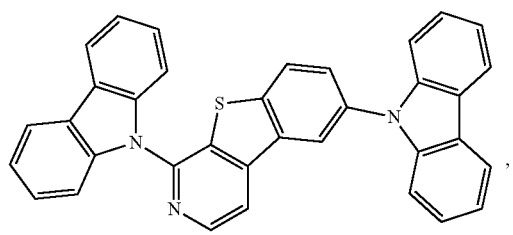

,

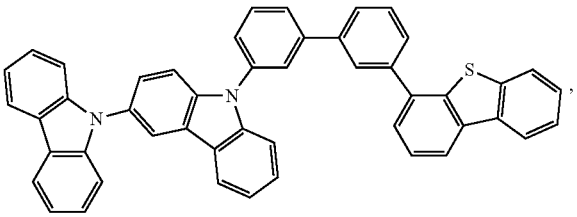

,

153
-continued
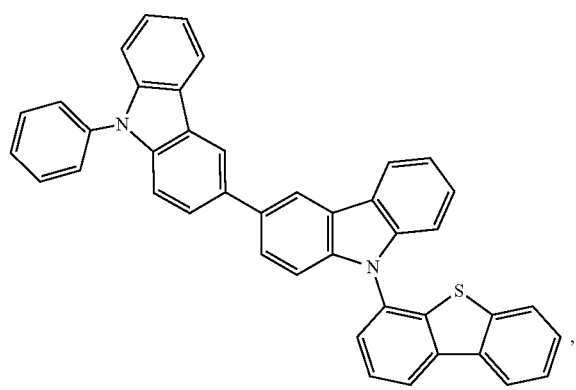
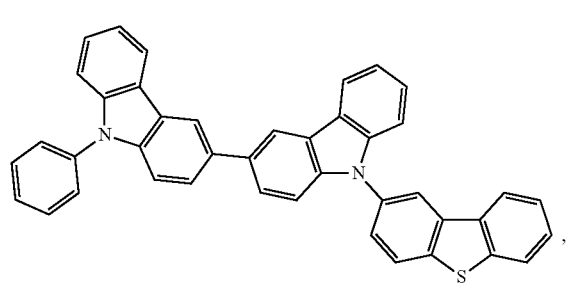
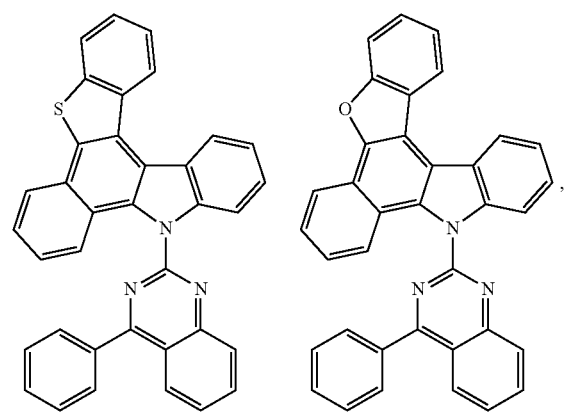
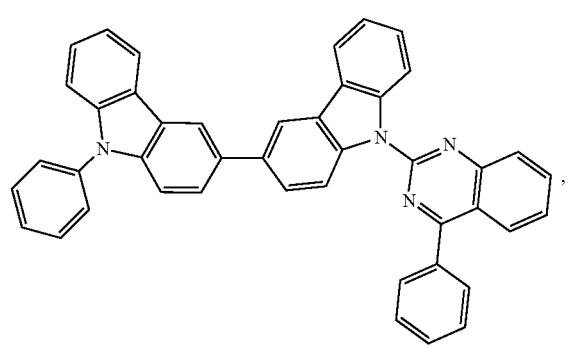
154
-continued
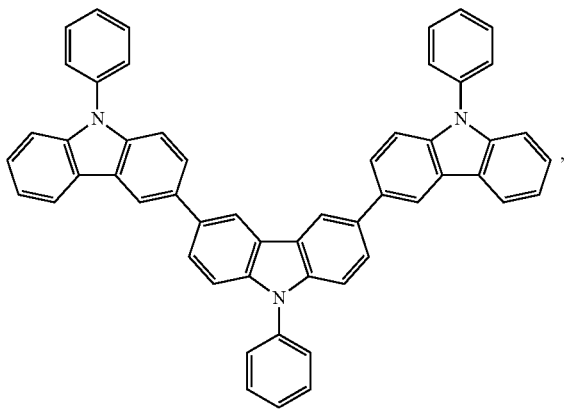
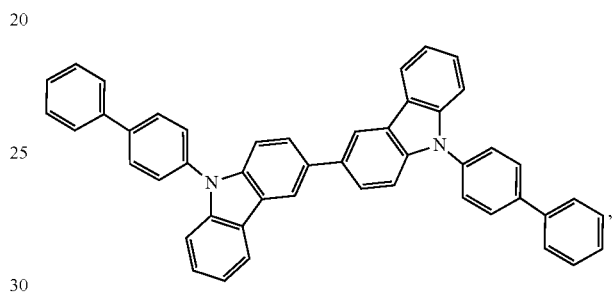
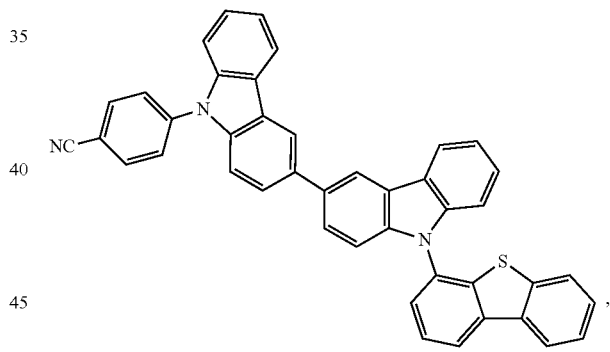
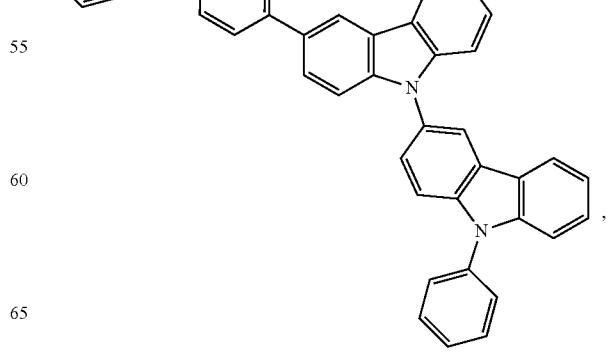

-continued

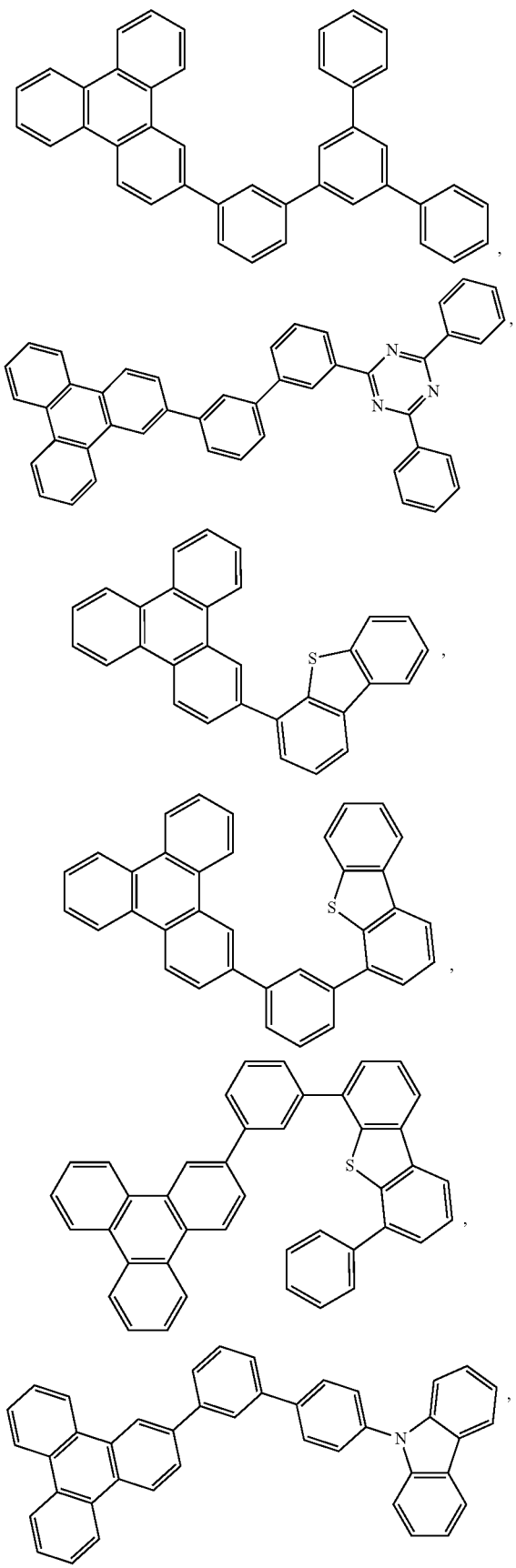

-continued

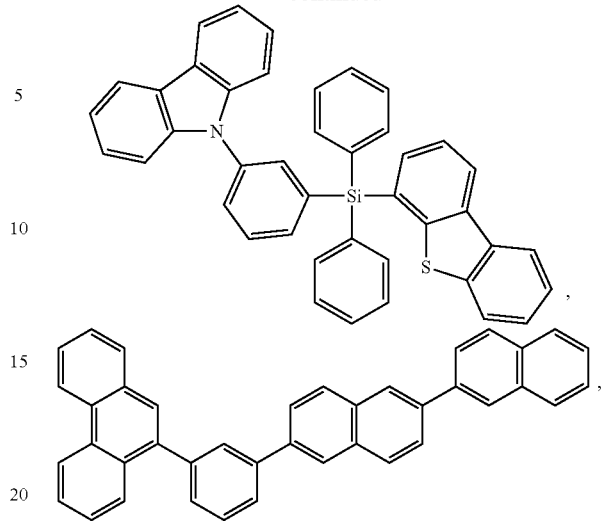

and combinations thereof.

Hole Transporting Host Material

Specific examples of the hole transporting host materials include, but are not limited to pyrrole, carbazole, azacarbazole, pyrazole, indole, azaindole, imidazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, aromatic dimethylidine compounds, porphyrin compounds, polysilane compounds, poly(N-vinylcarbazole), aniline copolymers, electric conductive high-molecular oligomers such as thiophene oligomers, polythiophenes and the like, organic silanes, carbon films, derivatives thereof, and the like. Some preferred host materials include carbazole derivatives, indole derivatives, imidazole derivatives, aromatic tertiary amine compounds, and thiophene derivatives.

Specific examples of the electron transporting host materials include, but are not limited to pyridine, pyrimidine, triazine, imidazole, pyrazole, triazole, oxazole, oxadiazole, fluorenone, anthraquinonedimethane, anthrone, diphenylquinone, thiopyrandioxide, carbodiimide, fluorenylidenemethane, distyrylpyrazine, fluorine-substituted aromatic compounds, aromacyclic tetracarboxylic anhydrides of naphthalene, perylene or the like, phthalocyanine, derivatives thereof, including a variety of metal complexes represented by metal complexes of 8-quinolinol derivatives, metal phthalocyanine, and metal complexes having benzoxazole or benzothiazole as the ligand.

Preferable electron transporting hosts are metal complexes, azole derivatives (benzimidazole derivatives, imidazopyridine derivatives and the like), and azine derivatives (pyridine derivatives, pyrimidine derivatives, triazine derivatives and the like).

C. Film Thickness

In some embodiments, the film thickness of the light-emitting layer is preferably from about 10 nm to about 500 nm. In some embodiments, the film thickness of the light-emitting layer is preferably from about 20 nm to about 100 nm depending, for example, on desired brightness uniformity, driving voltage and brightness. In some embodiments, the light-emitting layer is configured to have a thickness that optimizes passage of charges from the light-emitting layer to adjacent layers without lowering light-emission efficiency.

In some embodiments, the light-emitting layer is configured to have a thickness that maintains minimum driving voltage maximum light-emission efficiency.

D. Layer Configuration

The light-emitting layer may be composed of a single layer or two or more layers, and the respective layers may cause light emission in different light-emitting colors. Also, in the case where the light-emitting layer has a laminate structure, though the film thickness of each of the layers configuring the laminate structure is not particularly limited, it is preferable that a total film thickness of each of the light-emitting layers falls within the foregoing range. In some embodiments, graded layers or graded interfaces within the layers may be used.

E. Hole Injection Layer and Hole Transport Layer

The hole injection layer and hole transport layer are layers functioning to receive holes from an anode or from an anode side and to transport the holes to the emitting layer. Materials to be introduced into a hole injection layer or a hole transport layer is not particularly limited, but either of a low molecular compound or a high molecular compound may be used.

Specific examples of the material contained in the hole injection layer and the hole transport layer include, but are not limited to, pyrrole derivatives, carbazole derivatives, azacarbazole derivatives, indole derivatives, azaindole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidine compounds, phthalocyanine compounds, porphyrin compounds, organosilane derivatives, carbon, and the like.

An electron-accepting dopant may be introduced into the hole injection layer or the hole transport layer in the organic EL element of the present invention. As the electron-accepting dopant to be introduced into the hole injection layer or the hole transport layer, either of an inorganic compound or an organic compound may be used as long as the compound has electron accepting property and a function for oxidizing an organic compound.

Specifically, the inorganic compound includes metal halides such as ferric chloride, aluminum chloride, gallium chloride, indium chloride, antimony pentachloride and the like, and metal oxides such as vanadium pentaoxide, molybdenum trioxide and the like.

In case of employing the organic compounds, compounds having a substituent such as a nitro group, a halogen, a cyano group, a trifluoromethyl group or the like; quinone compounds; acid anhydride compounds; fullerenes; and the like may be preferably applied.

Specific examples hole injection and hole transport materials include compounds described in patent documents such as JP-A Nos. 6-212153, 11-111463, 11-251067, 2000-196140, 2000-286054, 2000-315580, 2001-102175, 2001-160493, 2002-252085, 2002-56985, 2003-157981, 2003-217862, 2003-229278, 2004-342614, 2005-72012, 2005-166637, 2005-209643 and the like.

Specific examples of hole injection and hole transport materials include the organic compounds: hexacyanobutadiene, hexacyanobenzene, tetracyanoethylene, tetracyanoquinodimethane, tetrafluorotetracyanoquinodimethane, p-fluoranil, p-chloranil, p-bromanil, p-benzoquinone, 2,6-dichlorobenzoquinone, 2,5-dichlorobenzoquinone, 1,2,4,5-tetracyanobenzene, 1,4-dicyanotetrafluorobenzene, 2,3-dichloro-5,6-dicyanobenzoquinone, p-dinitrobenzene, m-dinitrobenzene, o-dinitrobenzene, 1,4-naphthoquinone, 2,3-dichloronaphthoquinone, 1,3-dinitronaphthalene, 1,5-dinitronaphthalene, 9,10-anthraquinone, 1,3,6,8-tetranitrocarbazole, 2,4,7-trinitro-9-fluorenone, 2,3,5,6-tetracyanopyridine and fullerene C60. Among these, hexacyanobutadiene, hexacyanobenzene, tetracyanoethylene, tetracyanoquinodimethane, tetrafluorotetracyanoquinodimethane, p-fluoranil, p-chloranil, p-bromanil, 2,6-dichlorobenzoquinone, 2,5-dichlorobenzoquinone, 2,3-dichloronaphthoquinone, 1,2,4,5-tetracyanobenzene, 2,3-dichloro-5,6-dicyanobenzoquinone and 2,3,5,6-tetracyanopyridine are more preferable, and tetrafluorotetracyanoquinodimethane.

As one or more electron-accepting dopants may be introduced into the hole injection layer or the hole transport layer in the organic EL element of the present invention, these electron-accepting dopants may be used alone or in combinations of two or more. Although precise amount of these electron-accepting dopants used will depend on the type of material, about 0.01% by weight to about 50% by weight of the total weight of the hole transport layer or the hole injection layer is preferred. In some embodiments, the amount of these electron-accepting dopants range from about 0.05% by weight to about 20% by weight of the total weight of the hole transport layer or the hole injection layer. In some embodiments, the amount of these electron-accepting dopants range from about 0.1% by weight to about 10% by weight of the total weight of the hole transport layer or the hole injection layer.

In some embodiments, a thickness of the hole injection layer and a thickness of the hole transport layer are each preferably about 500 nm or less in view of decreasing driving voltage or optimizing for optical outcoupling. In some embodiments, the thickness of the hole transport layer is preferably from about 1 nm to about 500 nm. In some embodiments, the thickness of the hole transport layer is preferably from about 5 nm to about 50 nm. In some embodiments, the thickness of the hole transport layer is preferably from about 10 nm to about 40 nm. In some embodiments, the thickness of the hole injection layer is preferably from about 0.1 nm to about 500 nm. In some embodiments, the thickness of the hole injection layer is preferably from about 0.5 nm to about 300 nm. In some embodiments, the thickness of the hole injection layer is preferably from about 1 nm to about 200 nm.

The hole injection layer and the hole transport layer may be composed of a monolayer structure comprising one or two or more of the above-mentioned materials, or a multilayer structure composed of plural layers of a homogeneous composition or a heterogeneous composition.

F. Electron Injection Layer and Electron Transport Layer

The electron injection layer and the electron transport layer are layers having functions for receiving electrons from a cathode or a cathode side, and transporting electrons to the light emitting layer. An electron injection material or an electron transporting material used for these layers may be a low molecular compound or a high molecular compound. Specific examples of the materials suitable for use in electron injection and electron transport layers include, but are not limited to, pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, aromacyclic tetracarboxylic anhydrides of perylene, naphthalene or the like, phthalocyanine derivatives, metal complexes represented by metal complexes of 8-quinolinol derivatives, metal phthalocyanine, and metal complexes containing benzoxazole, or benzothiazole as the ligand, organic silane derivatives exemplified by silole, and the like.

The electron injection layer or the electron transport layer may contain an electron donating dopant. Suitable electron donating dopant for use in the electron injection layer or the electron transport layer, include any suitable material that may be used as long as it has an electron-donating property and a property for reducing an organic compound. Specific examples of electron donating dopants include an alkaline metal such as Li, an alkaline earth metal such as Mg, a transition metal including a rare-earth metal, and a reducing organic compound. Other examples of metal donating dopants include, metals having a work function of 4.2 V or less, for example, Li, Na, K, Be, Mg, Ca, Sr, Ba, Y, Cs, La, Sm, Gd, Yb, and the like. Specific examples of the reducing organic compounds include nitrogen-containing compounds, sulfur-containing compounds, phosphorus-containing compounds, and the like.

The electron donating dopants may be used alone or in combinations of two or more. In some embodiments, an electron donating dopant is contained in the electron injection layer or the electron transport layer in an amount ranging from about 0.1% by weight to about 99% by weight of the total weight of the electron transport layer material or the electron injecting layer mater. In some embodiments, an electron donating dopant is contained in the electron injection layer or the electron transport layer in an amount ranging from about 1.0% by weight to about 80% by weight of the total weight of the electron transport layer material or the electron injecting layer material. In some embodiments, an electron donating dopant is contained in the electron injection layer or the electron transport layer in an amount ranging from about 2.0% by weight to about 70% by weight of the total weight of the electron transport layer material or the electron injecting layer material.

A thickness of the electron injection layer and a thickness of the electron transport layer are each preferably 500 nm or less in view of decrease in driving voltage. The thickness of the electron transport layer is preferably from 1 nm to 500 nm, more preferably from 5 nm to 200 nm, and even more preferably from 10 nm to 100 nm. A thickness of the electron injection layer is preferably from 0.1 nm to 200 nm, more preferably from 0.2 nm to 100 nm, and even more preferably from 0.5 nm to 50 nm.

The electron injection layer and the electron-transport may be composed of a monolayer structure comprising one or two or more of the above-mentioned materials, or a multilayer structure composed of plural layers of a homogeneous composition or a heterogeneous composition.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

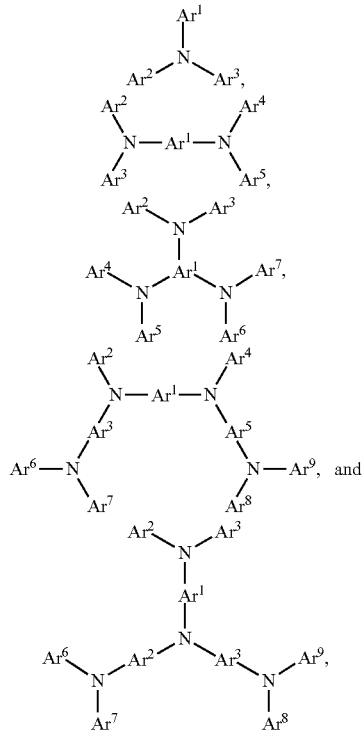

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

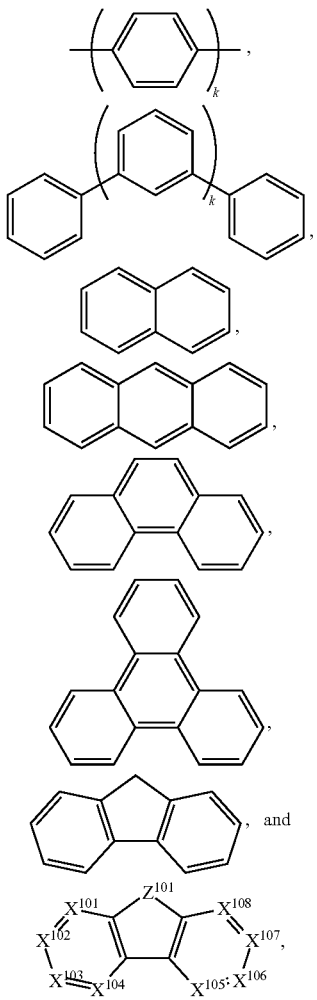

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

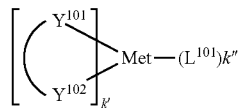

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc+/Fc couple less than about 0.6 V.

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and or higher triplet energy than the emitter closest to the EBL interface. In some embodiments, the EBL material has a higher LUMO (closer to the vacuum level) and or higher triplet energy than one or more of the hosts closest to the EBL interface. In one aspect, compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. In some embodiments, two or more hosts are preferred. In some embodiments, the hosts used maybe a) bipolar, b) electron transporting, c) hole transporting or d) wide band gap materials that play little role in charge transport. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

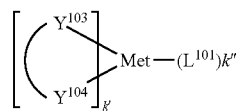

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

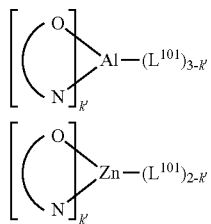

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

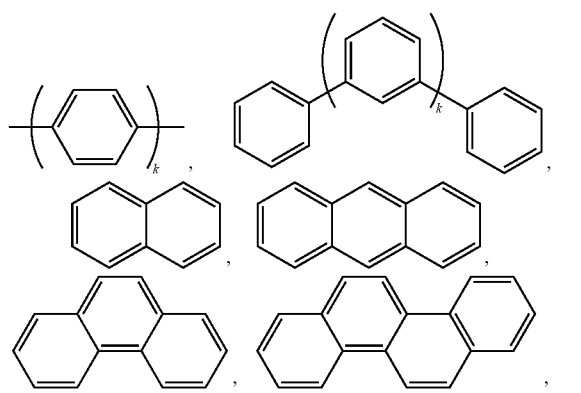

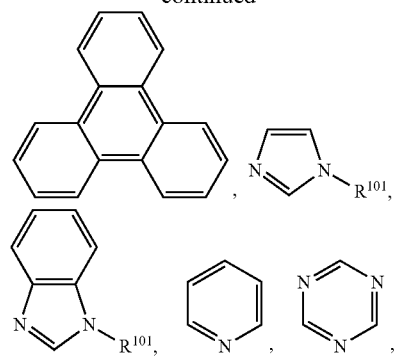

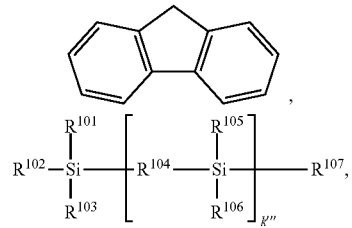

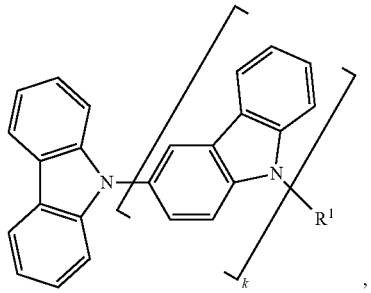

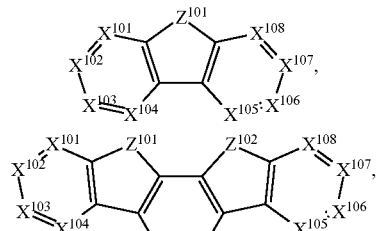

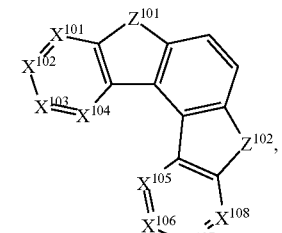

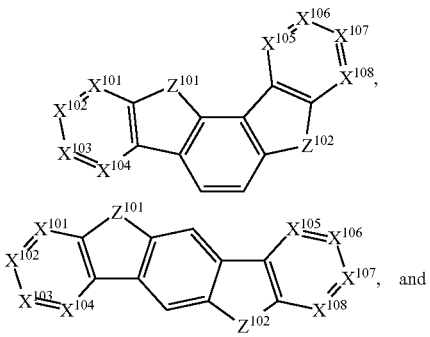

and

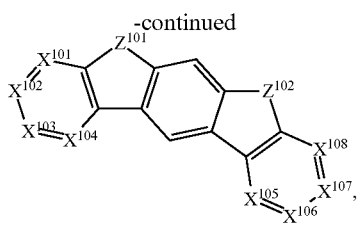

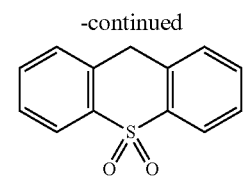

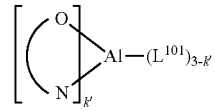

wherein $R^{101}$ to $R^{107}$ is independently selected from the group consisting of hydrogen deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO and or higher triplet energy than the emitter closest to the HBL interface.

In one aspect, compound used in HBL contains the same molecule or the same functional groups used as host described above.

In another aspect, compound used in HBL contains at least one of the following groups in the molecule:

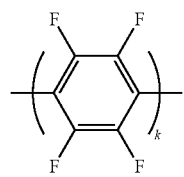

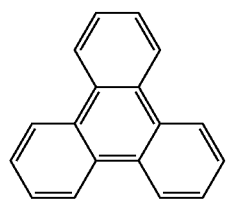

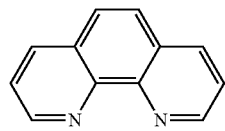

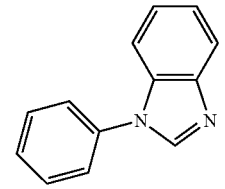

wherein k is an integer from 1 to 20; $L^{101}$ is an another ligand, k' is an integer from 1 to 3.

ETL:

Electron transport layer (ETL) may include a material capable of transporting electrons.

Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

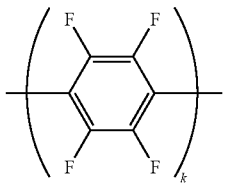

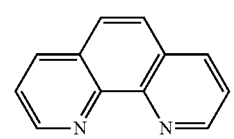

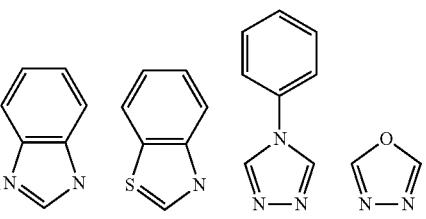

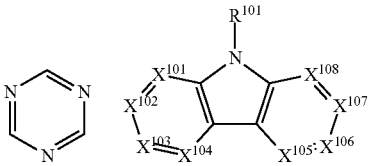

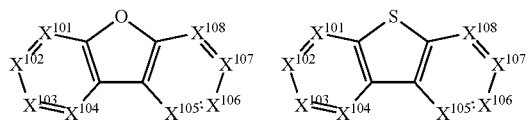

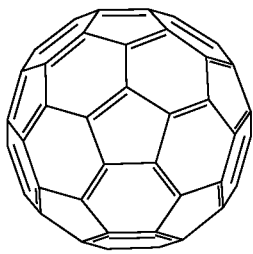

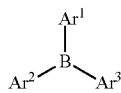

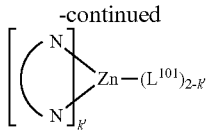

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

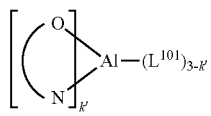

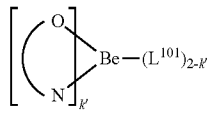

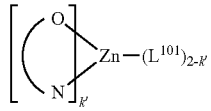

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Charge Generation Layer (CGL):

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphyrin compounds | | Appl. Phys. Lett. 69, 2160 (1996) |

TABLE A-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20060162053 |

| MATERIAL | EXAMPLES OF MATERIAL | PUBLICATIONS |
|---|---|---|
| Triarylamine or polythiophene polymers with conductivity dopants | 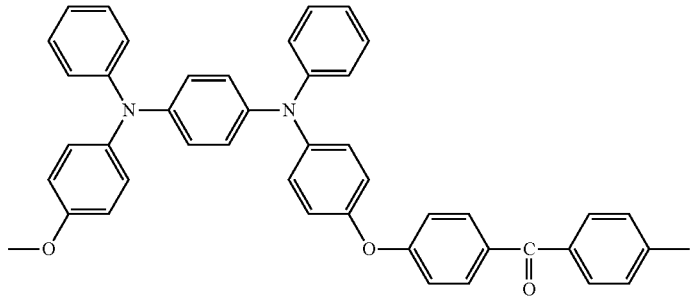 and 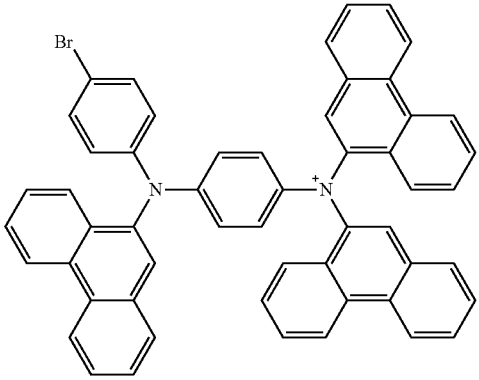 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 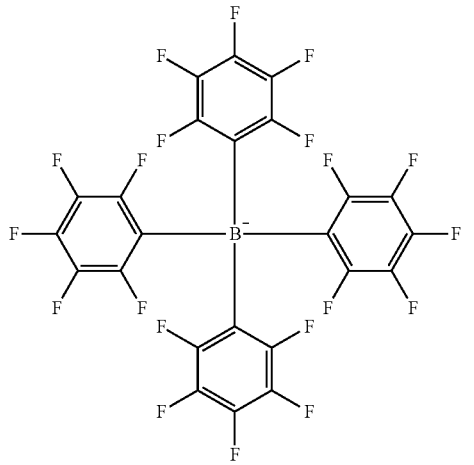 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 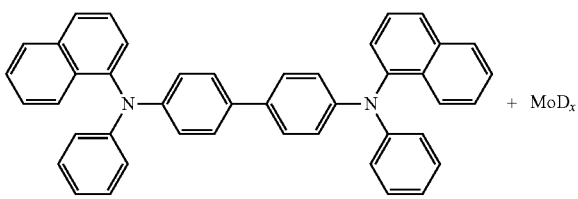 [SMILES: c1ccc(N(c2ccc(-c3ccc(N(c4ccccc4)c4cccc5ccccc45)cc3)cc2)c2cccc3ccccc23)cc1] | US20050123751 SID Symposium Digest, 37, 923 (2006) WO2009018009 |

TABLE A-continued

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

Hole transporting materials

| MATERIAL | EXAMPLES OF MATERIAL | PUBLICATIONS |
|---|---|---|
| Triarylamines (e.g., TPD, α-NPD) | 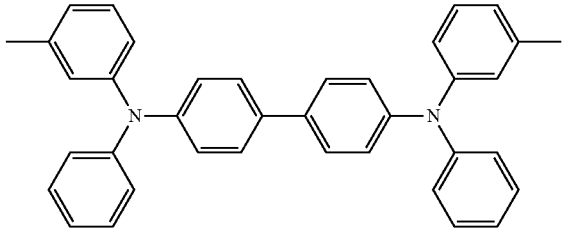 | Appl. Phys. Lett. 51, 913 (1987) |
| | 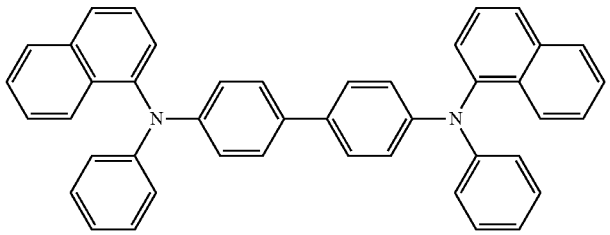 [SMILES: c1ccc(N(c2ccc(-c3ccc(N(c4ccccc4)c4cccc5ccccc45)cc3)cc2)c2cccc3ccccc23)cc1] | US5061569 |
| | 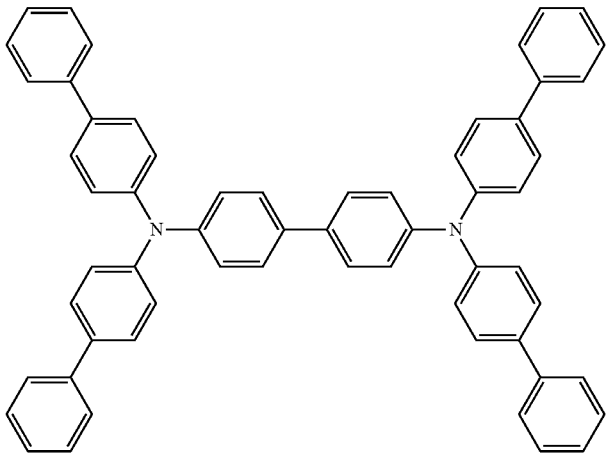 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 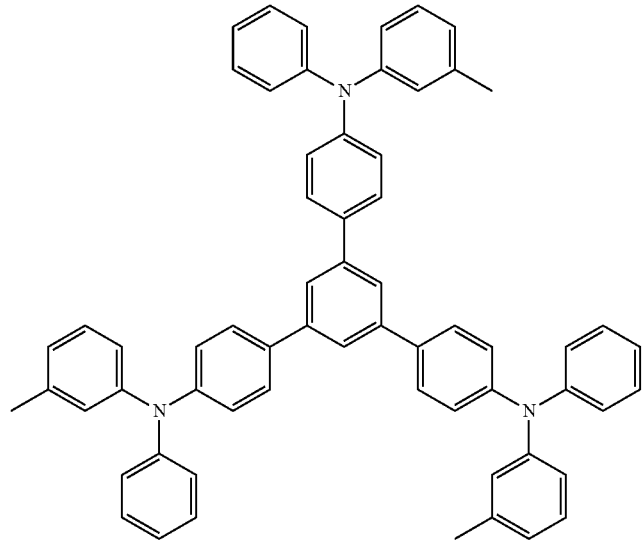 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triarylamine on spirofluorene core | | Synth. Met. 91, 209 (1997) |
| Arylamine cabazole compounds | | Adv. Mater. 6, 677 (1994), US20080124572 |

TABLE A-continued
| MATERIAL | EXAMPLES OF MATERIAL | PUBLICATIONS |
|---|---|---|
| Triarylamine with (di)benzothiophene/ (di)benzofuran | 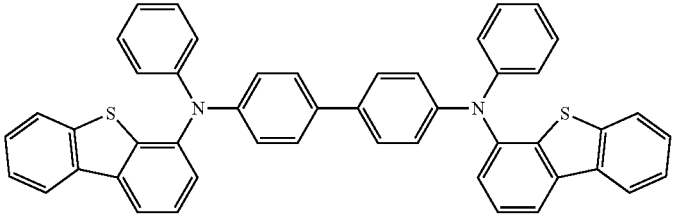 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938<br>US20080106190<br>US20110163302 |
| Indolocarbazoles | 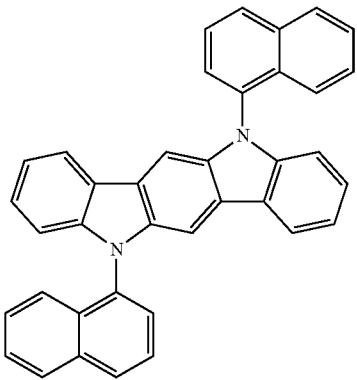 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 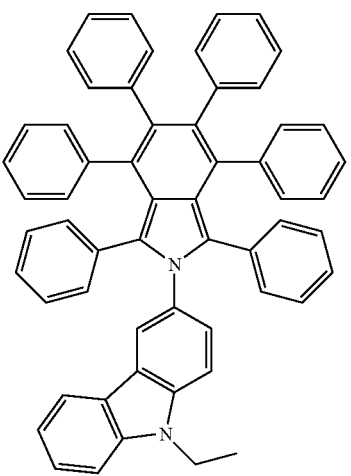 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 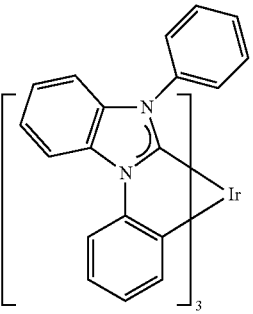 | US20080018221 |
Phosphorescent OLED host materials TABLE A-continued
| MATERIAL | EXAMPLES OF MATERIAL | PUBLICATIONS |
|---|---|---|
| Red hosts | | |
| Arylcarbazoles | 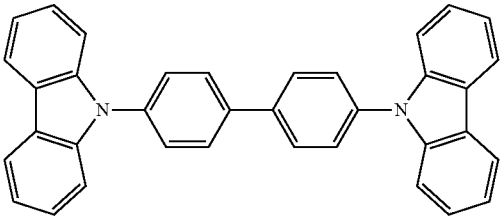 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BAlq) | 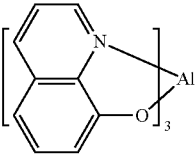 | Nature 395, 151 (1998) |
| | 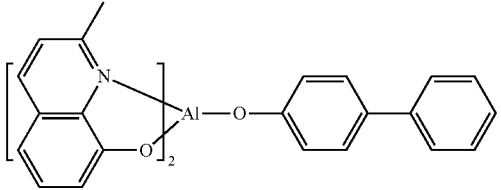 | US20060202194 |
| | 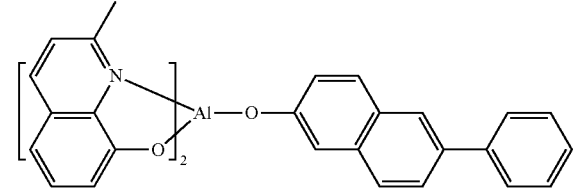 | WO2005014551 |
| | 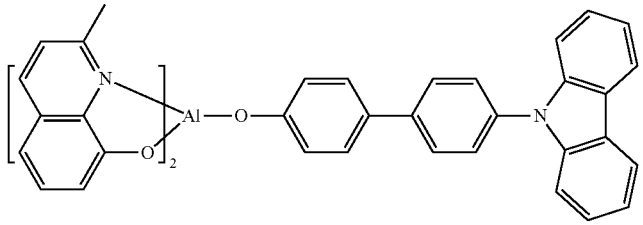 | WO2006072002 |
| Metal phenoxybenzothiazole compounds | 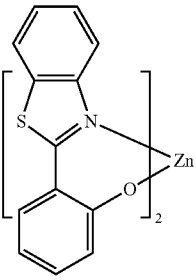 | Appl. Phys. Lett. 90, 123509 (2007) |
| Conjugated oligomers and polymers (e.g., polyfluorene) | 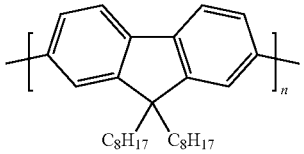 | Org. Electron. 1, 15 (2000) |

TABLE A-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |
| | | US20030175553 |
| | | WO2001039234 |

TABLE A-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

| MATERIAL | EXAMPLES OF MATERIAL | PUBLICATIONS |
|---|---|---|
| | 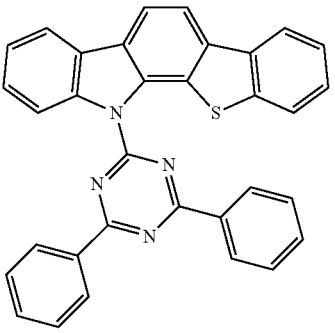 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 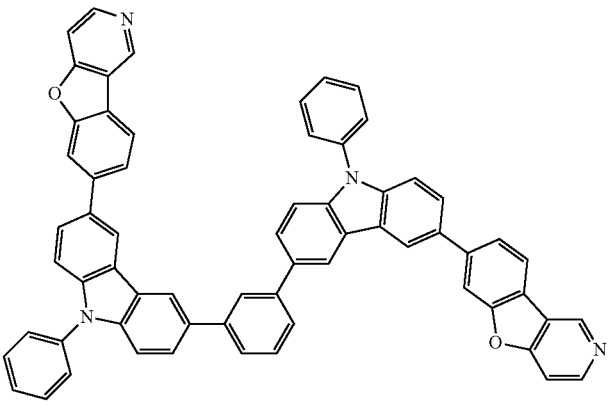 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 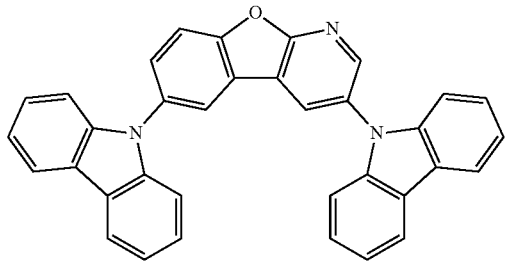 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 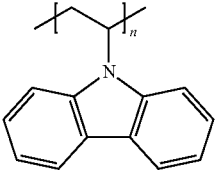 | Appl. Phys. Lett. 77, 2280 (2000) |
| Spirofluorene compounds | 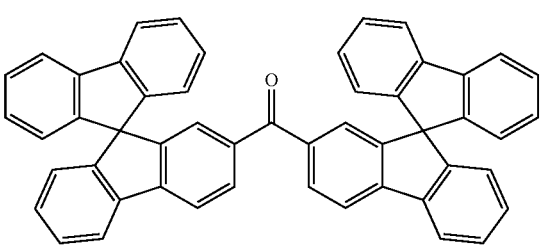 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE A-continued

| MATERIAL | EXAMPLES OF MATERIAL | PUBLICATIONS |
| --- | --- | --- |
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE A-continued

| MATERIAL | EXAMPLES OF MATERIAL | PUBLICATIONS |
|---|---|---|
| Indolocarbazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE A-continued

| MATERIAL | EXAMPLES OF MATERIAL | PUBLICATIONS |
| --- | --- | --- |
| Metal phenoxypyridine | | WO2005030900 |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE A-continued

| MATERIAL | EXAMPLES OF MATERIAL | PUBLICATIONS |
|---|---|---|
| | | WO2009086028 |
| | | US20090030202, US20090017330 |
| | | US20100084966 |
| Silicon aryl compounds | | US20050238919 |
| | | WO2009003898 |
| Silicon/Germanium aryl compounds | | EP2034538A |

TABLE A-continued

| MATERIAL | EXAMPLES OF MATERIAL | PUBLICATIONS |
| --- | --- | --- |
| Aryl benzoyl ester | | WO2006100298 |
| Carbazole linked by non-conjugated groups | | US20040115476 |
| Aza-carbazoles | | US20060121308 |
| High triplet metal organometallic complex | | US7154114 |
| Phosphorescent dopants | | |
| Red dopants | | |
| Heavy metal porphyrins (e.g., PtOEP) | | Nature 395, 151 (1998) |

TABLE A-continued

| MATERIAL | EXAMPLES OF MATERIAL | PUBLICATIONS |
| --- | --- | --- |
| Iridium (III) organometallic complexes | | Appl. Phys. Lett. 78, 1622 (2001) |
| | | US20030072964 |
| | | US20030072964 |
| | | US20060202194 |
| | | US20060202194 |

TABLE A-continued
| MATERIAL | EXAMPLES OF MATERIAL | PUBLICATIONS |
|---|---|---|
| | 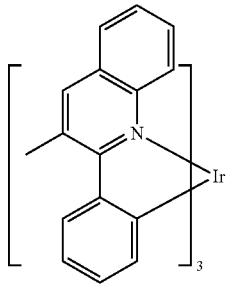 | US20070087321 |
| | 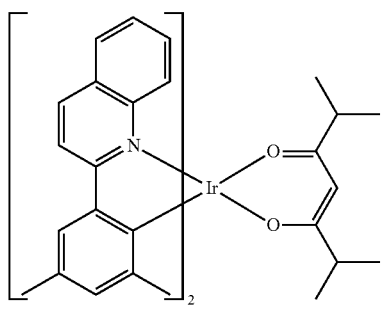 | US20080261076<br>US20100090591 |
| | 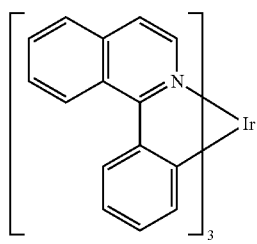 | US20070087321 |
| | 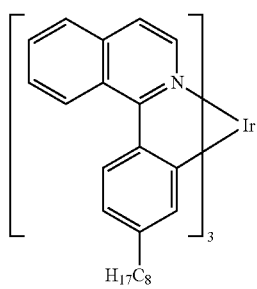 | Adv. Mater. 19, 739 (2007) |
| | 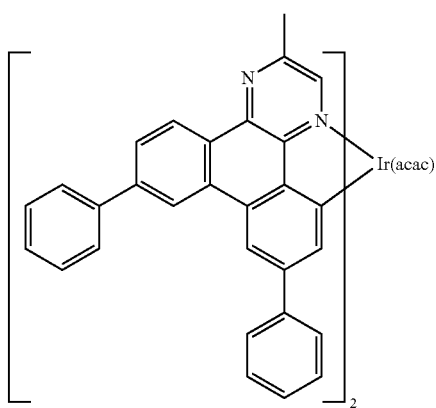 | WO2009100991 |

TABLE A-continued
| MATERIAL | EXAMPLES OF MATERIAL | PUBLICATIONS |
|---|---|---|
| | 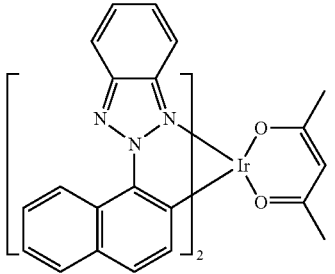 | WO2008101842 |
| | 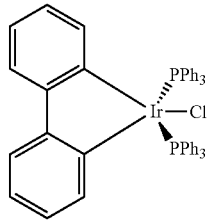 | US7232618 |
| Platinum (II) organometallic complexes | | WO2003040257 |
| | 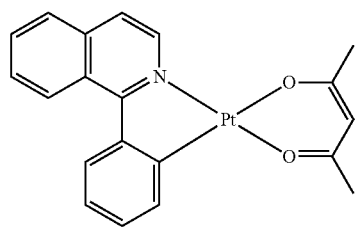 | |
| | 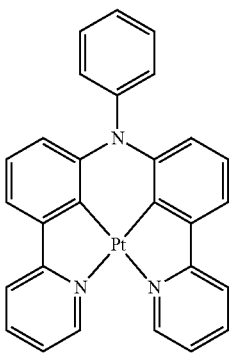 | US20070103060 |
| Osmium (III) complexes | 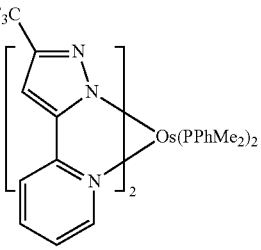 | Chem. Mater. 17, 3532 (2005) |

TABLE A-continued

| MATERIAL | EXAMPLES OF MATERIAL | PUBLICATIONS |
|---|---|---|
| Ruthenium (II) complexes | | Adv. Mater. 17, 1059 (2005) |
| Rhenium (I), (II), and (III) complexes | | US20050244673 |
| Green dopants | | |
| Iridium (III) organometallic complexes | and its derivatives | Inorg. Chem. 40, 1704 (2001)<br><br>US20020034656 |

TABLE A-continued
| MATERIAL | EXAMPLES OF MATERIAL | PUBLICATIONS |
|---|---|---|
| | 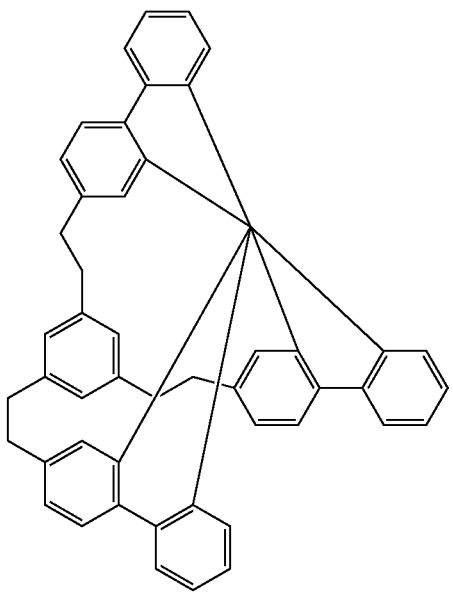 | US7332232 |
| | 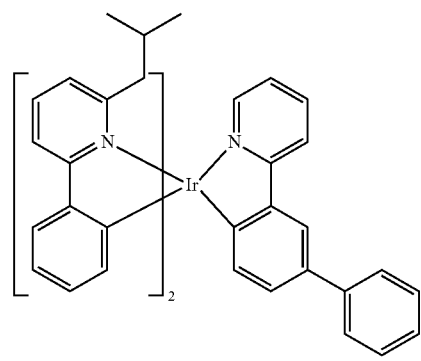 | US20090108737 |
| | 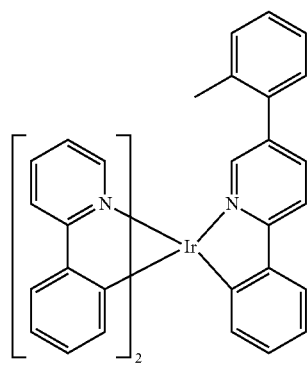 | WO2010028151 |

TABLE A-continued

| MATERIAL | EXAMPLES OF MATERIAL | PUBLICATIONS |
|---|---|---|
| | | EP1841834B |
| | | US20060127696 |
| | | US20090039776 |
| | | US6921915 |
| | | US20100244004 |

| MATERIAL | EXAMPLES OF MATERIAL | PUBLICATIONS |
|---|---|---|
| | | US6687266 |
| | | Chem. Mater. 16, 2480 (2004) |
| | | US20070190359 |
| | | US 20060008670 JP2007123392 |
| | | WO2010086089, WO2011044988 |
| | | Adv. Mater. 16, 2003 (2004) |

TABLE A-continued
| MATERIAL | EXAMPLES OF MATERIAL | PUBLICATIONS |
|---|---|---|
| | 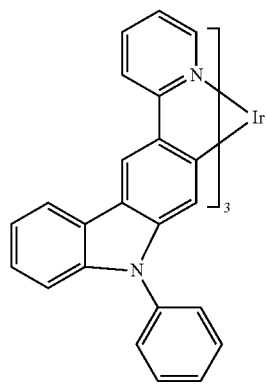 | Angew. Chem. Int. Ed. 2006, 45, 7800 |
| | 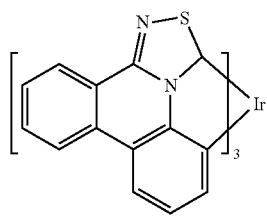 | WO2009050290 |
| | 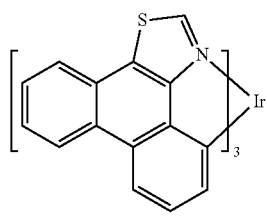 | US20090165846 |
| | 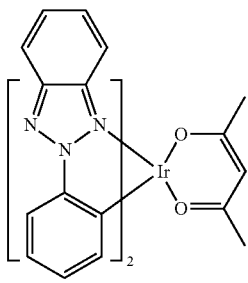 | US20080015355 |
| | 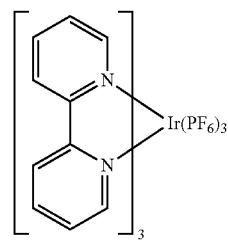 | US20010015432 |
| | 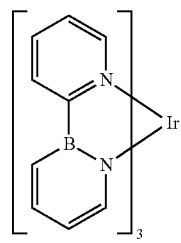 | US20100295032 |

TABLE A-continued

| MATERIAL | EXAMPLES OF MATERIAL | PUBLICATIONS |
|---|---|---|
| Monomer for polymeric metal organometallic compounds | | US7250226, US7396598 |
| Pt (II) organometallic complexes, including polydentate ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

| MATERIAL | EXAMPLES OF MATERIAL | PUBLICATIONS |
|---|---|---|
| | 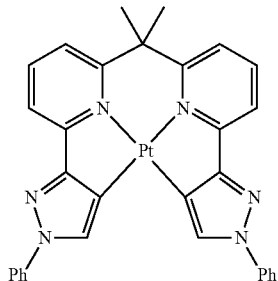 | US20060263635 |
| | 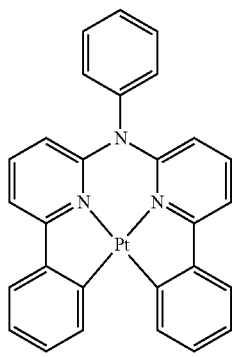 | US20060182992<br>US20070103060 |
| Cu complexes | 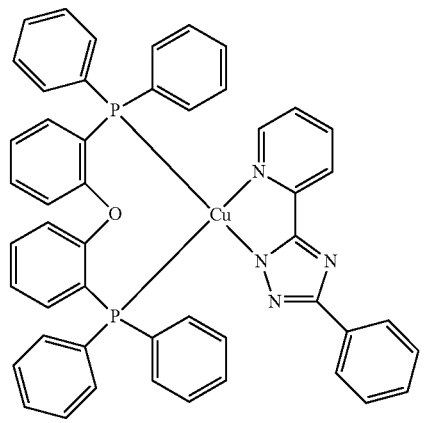 | WO2009000673 |
| | 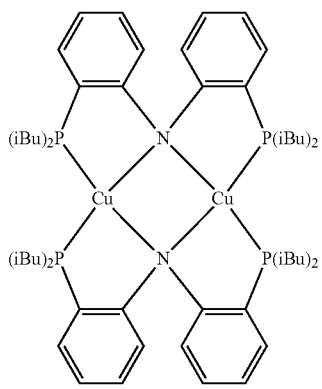 | US20070111026 |

| MATERIAL | EXAMPLES OF MATERIAL | PUBLICATIONS |
|---|---|---|
| Gold complexes | | Chem. Commun. 2906 (2005) |
| Rhenium (III) complexes | | Inorg. Chem. 42, 1248 (2003) |
| Osmium (II) complexes | | US7279704 |
| Deuterated organometallic complexes | | US20030138657 |

| MATERIAL | EXAMPLES OF MATERIAL | PUBLICATIONS |
|---|---|---|
| Organometallic complexes with two or more metal centers | 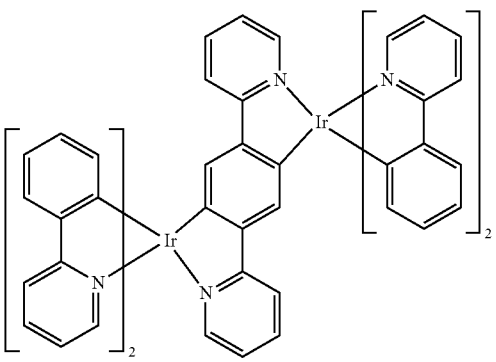 | US20030152802 |
| | 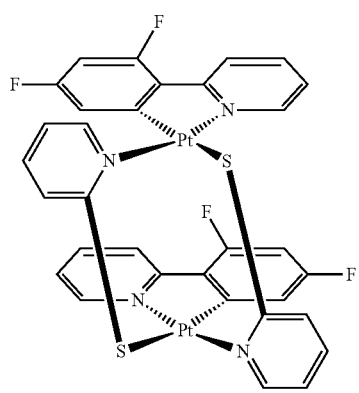 | US7090928 |
| Blue dopants | | |
| Iridium (III) organometallic complexes | 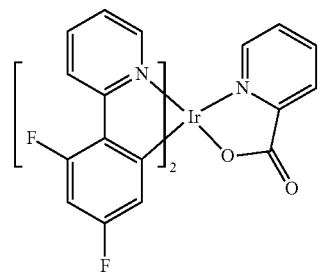 | WO2002002714 |
| | 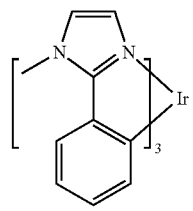 | WO2006007024 |
| | 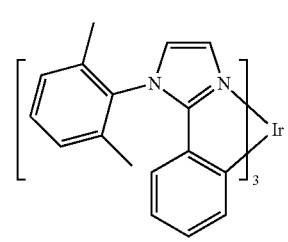 | US20060251923<br>US20112257559<br>US20110204333 |

TABLE A-continued

| MATERIAL | EXAMPLES OF MATERIAL | PUBLICATIONS |
|---|---|---|
| | | US7393599, WO2006053418, US20050260441, WO2005019373 |
| | | US7534505 |
| | | WO2011051404 |
| | | US7445855 |
| | | US20070191359, US20080297033 US20100148663 |

| MATERIAL | EXAMPLES OF MATERIAL | PUBLICATIONS |
|---|---|---|
| | | US7338722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

TABLE A-continued
| MATERIAL | EXAMPLES OF MATERIAL | PUBLICATIONS |
|---|---|---|
| | 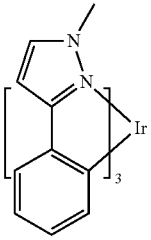 | WO2005123873 |
| | 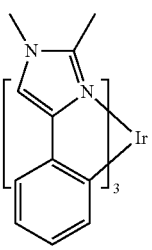 | WO2005123873 |
| | 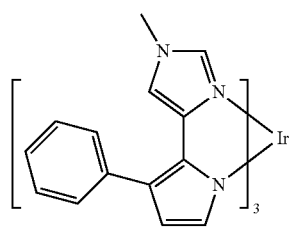 | WO2007004380 |
| | 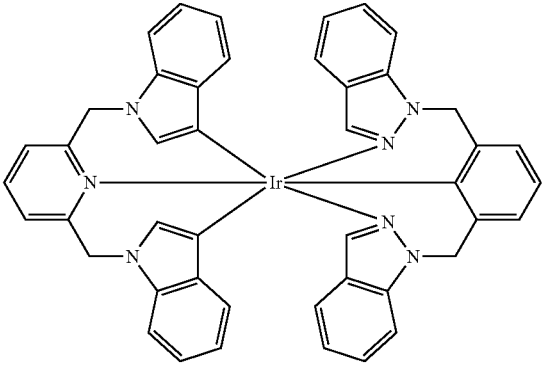 | WO2006082742 |
| Osmium (II) complexes | 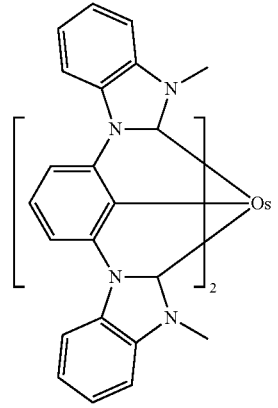 | US7279704 |

TABLE A-continued

| MATERIAL | EXAMPLES OF MATERIAL | PUBLICATIONS |
| --- | --- | --- |
| | | Organometallics 23, 3745 (2004) |
| Gold complexes | | Appl. Phys. Lett. 74, 1361 (1999) |
| Platinum (II) complexes | | WO2006098120, WO2006103874 |
| Pt tetradentate complexes with at least one metal-carbene bond | | US7655323 |
| Exciton/hole blocking layer materials | | |
| Bathocuproine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE A-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 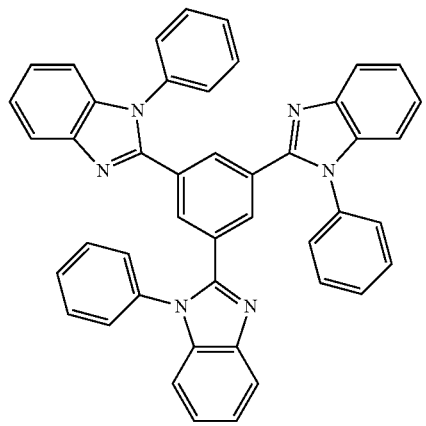 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 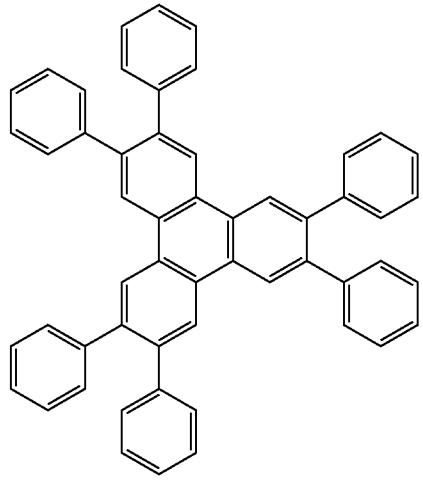 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 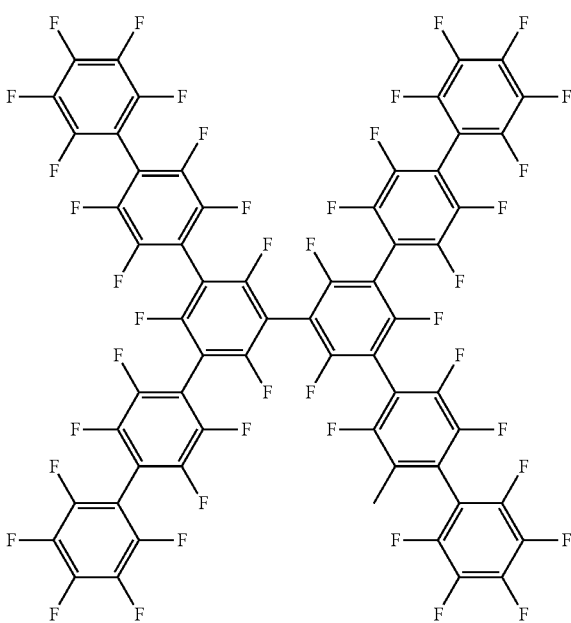 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE A-continued

| MATERIAL | EXAMPLES OF MATERIAL | PUBLICATIONS |
| --- | --- | --- |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE A-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) US7230107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE A-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 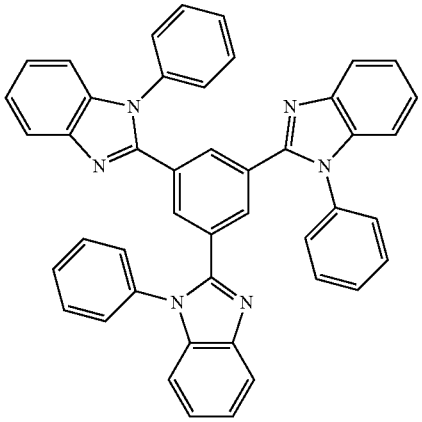 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 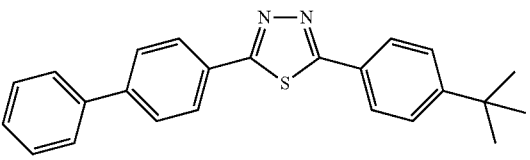 [SMILES: CC(C)(C)c1ccc(-c2nnc(-c3ccc(-c4ccccc4)cc3)s2)cc1] | Appl. Phys. Lett. 55, 1489 (1989) |
| | 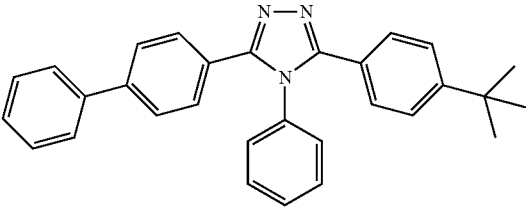 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 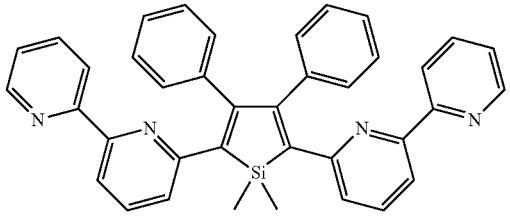 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 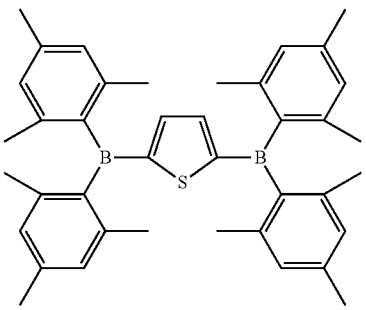 | J. Am. Chem. Soc. 120, 9714 (1998) |
| Fluorinated aromatic compounds | 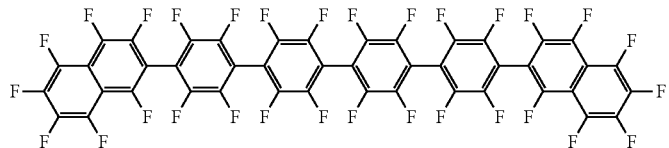 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE A-continued

| MATERIAL | EXAMPLES OF MATERIAL | PUBLICATIONS |
|---|---|---|
| Fullerene (e.g., $C_{60}$) | 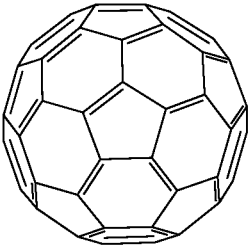 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 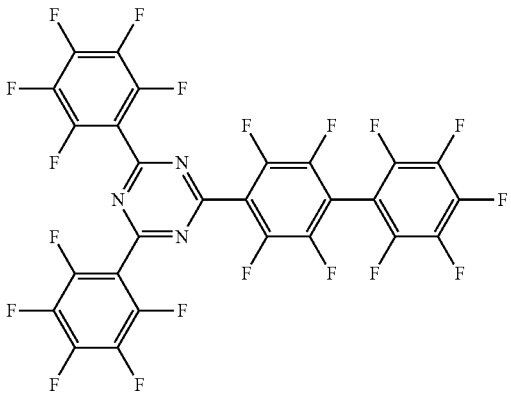 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 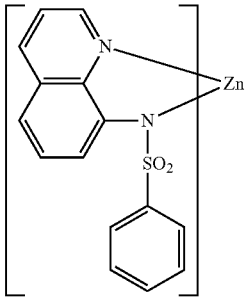 | US6528187 |

The invention is explained in greater detail by the following examples, without wishing to restrict it thereby. The person skilled in the art will be able to produce further electronic devices on the basis of the descriptions without inventive step and will thus be able to carry out the invention throughout the range claimed.

Examples

The following syntheses are carried out, unless indicated otherwise, in dried solvents under a protective-gas atmosphere. The metal complexes are additionally handled with exclusion of light. The solvents and reagents can be purchased, for example, from Sigma-ALDRICH or ABCR.

Example 1: Synthesis of 3,4-dihydrodibenzo[b,ij] imidazo[2,1,5-de]quinolizine was Prepared in Accordance with Scheme 1
Scheme 1
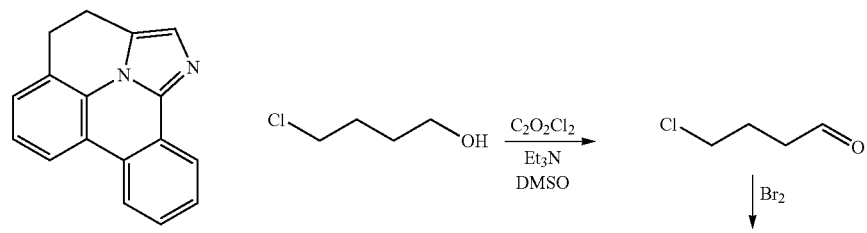
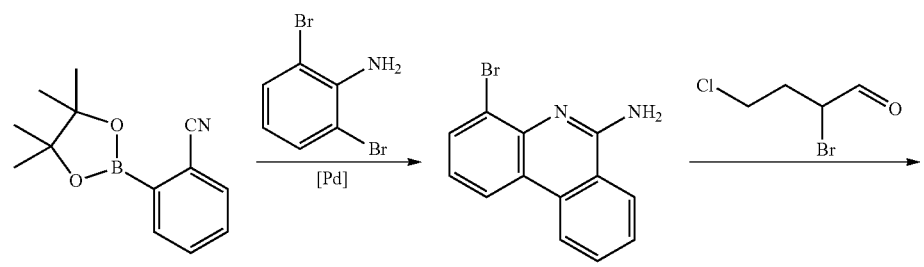
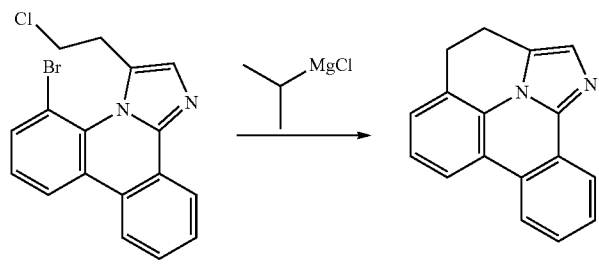

A. Synthesis of 4-chlorobutanal

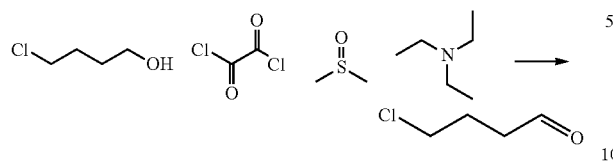

A solution of oxalyl chloride (22.54 ml, 263 mmol) in DCM (400 ml) was cooled in an $^i$PrOH/CO$_2$ bath. DMSO (37.3 ml, 525 mmol) was slowly via syringe and stirred cold for 1 hour. A solution of 4-chlorobutan-1-ol (19 g, 175 mmol) in 50 mL DCM was added dropwise. The col mixture was stirred for one hour, then, triethylamine (110 ml, 788 mmol) was slowly added. The suspension was stirred cold for 30 minutes, then allowed to warm to room temperature. The reaction was quenched with water, acidified and organics separated. Solvent removal followed by distillation yielded the product as a colorless oil, 8 g.

B. Synthesis of 2-bromo-4-chlorobutanal

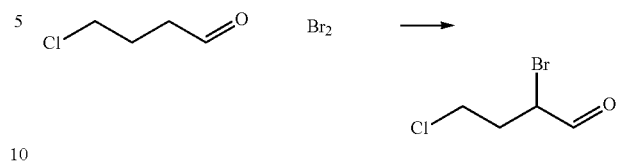

4-chlorobutanal (7.939 g, 74.5 mmol) was dissolved in DCM (300 ml) and cooled in an ice bath. A solution of dibromine (4.00 ml, 78 mmol) in DCM (50 ml) was added over about 1 hr. After addition the red solution was stirred cold for 30 minutes, then warmed slowly to room temperature and stirred one more hour. Water was added, the organics were separated, and drying and solvent removal yielded the crude product as a pale yellow oil, 1.57 g (80%).

C. Synthesis of 4-bromophenanthridin-6-amine

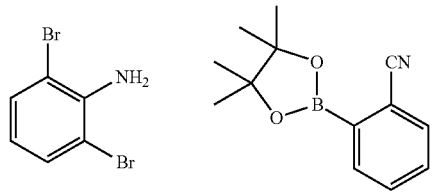 K$_3$PO$_4$(H$_2$O) 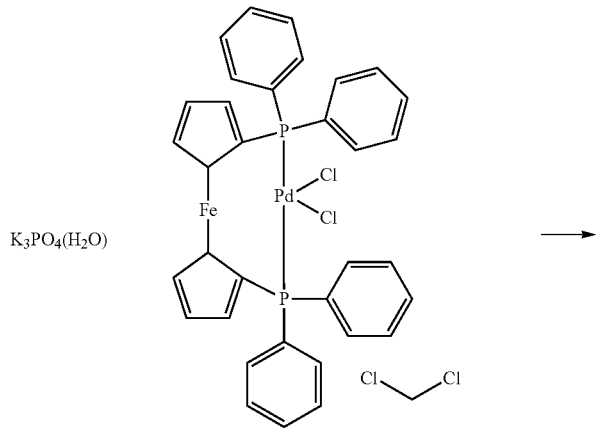

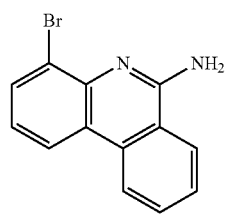

2,6-dibromoaniline (15.33 g, 61.1 mmol), 2-(4,4,5,5-tetramethyl-1,3,2-dioxaborolan-2-yl)benzonitrile (7.0 g, 30.6 mmol), and potassium phosphate monohydrate (21.11 g, 92 mmol) were combined in dioxane (120 ml) and water (7.49 ml). The mixture was degassed, then added (dppf)PdCl$_2$ complex with DCM (0.749 g, 0.917 mmol) was added and the mixture was refluxed for 4 hours. The black mixture was partitioned between EtOAc and water/brine. The organic layer was washed with brine, dried, and solvent was removed. Dissolution in 500 mL EtOAc followed by elution through a silica plug using EtOAc and solvent removal yielded an orange residue that was purified by column chromatography to yield the product as a yellow/orange solid, 5.86 g, 70%.

D. Synthesis of 5-bromo-3-(2-chloroethyl)imidazo[1,2-f]phenanthridine

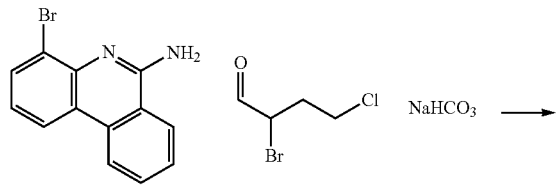

4-bromophenanthridin-6-amine (5.86, 21.46 mmol), 2-bromo-4-chlorobutanal (5.36 g, 28.9 mmol), and sodium bicarbonate (3.60 g, 42.9 mmol) were combined in 2-propanol (102 ml) and water (5.11 ml). The suspension was stirred at room temperature for 4 hours, then at reflux for 16 hours. Solvent was removed under vacuum and the residue coated on celite. Column chromatography yielded a mixture of the product and starting amidine, which was treated with excess acetyl chloride and triethylamine in DCM. After workup the desired product was extracted from the acetamide by repeated extraction into heptanes, yielding 3.93 g of yellow, tacky residue (51%).

E. Synthesis of 3,4-dihydrodibenzo[b,ij]imidazo[2,1,5-de]quinolizine

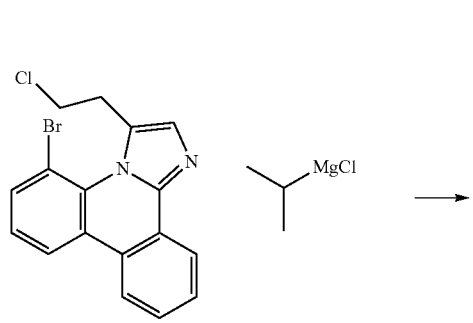

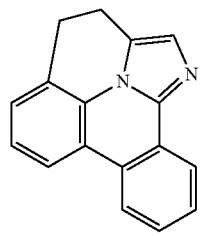

5-bromo-3-((2-chloroethyl)imidazo[1,2-f]phenanthridine (3.93 g, 10.93 mmol) was dissolved in THF (200 ml), cooled in an ice bath, and isopropylmagnesium chloride solution in THF (2.0M, 6.01 ml, 12.02 mmol) was slowly added. The solution was stirred for 30 minutes cold, then warmed to room temperature and stirred for 2 more hours. The reaction was quenched, extracted into DCM, and the reaction product was purified using column chromatography to yield 1.90 g of a pale beige, crystalline solid (71%).

Figure 5:
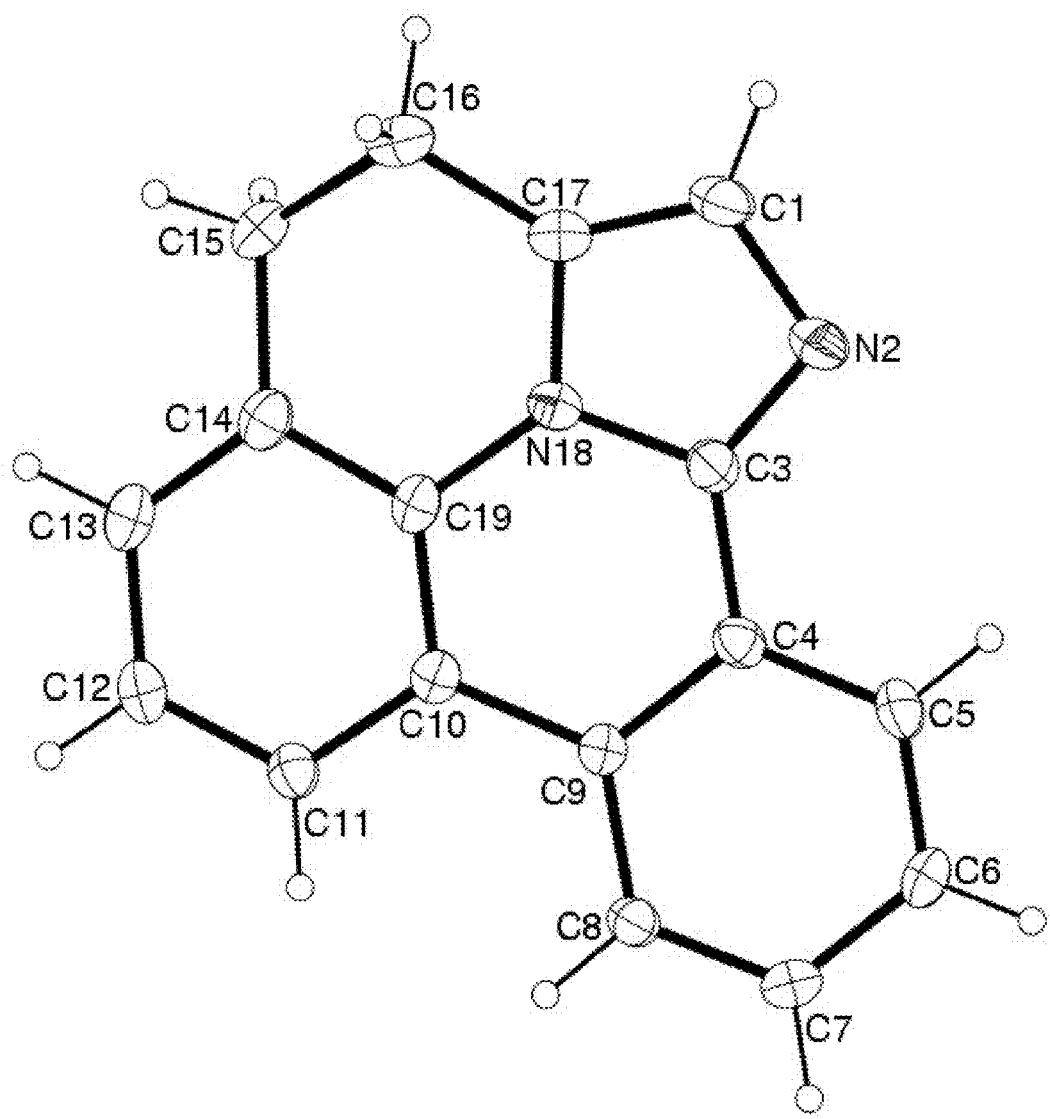
FIG. 5 illustrates the x-ray crystal structure of 3,4-dihydrodibenzo[b,ij]imidazo[2,1,5-de]quinolizine.

An X-ray structure of 3,4-dihydrodibenzo[b,ij]imidazo[2,1,5-de]quinolizine is shown in FIG. 5. The crystal structure of 3,4-dihydrodibenzo[b,ij]imidazo[2,1,5-de]quinolizine may be defined by one or more of the characteristics listed in the following table.

| Formula | $C_{17}H_{12}N_2$ | Data/restr./param. | 2107/0/173 |
|---|---|---|---|
| MW | 244.29 | T [K] | 100(1) |
| Crystal system | Orthorhombic | $\rho_{calcd}$ [g cm$^{-3}$] | 1.410 |
| Space group | $P2_12_12_1$ | $\mu_{calcd}$ [mm$^{-1}$] | 0.084 |
| Color | Colorless | Total reflections | 22768 |
| a [Å] | 6.6974(5) | Z | 4 |
| b [Å] | 11.0502(8) | F(000) | 512 |
| c [Å] | 15.5459(10) | $T_{min}/T_{max}$ | 0.894 |
| α [°] | 90 | Cryst. Size [mm$^3$] | 0.42 × 0.22 × 0.08 |
| β [°] | 90 | $R_1$ [I > 2σ(I)]$^a$ | 0.0405 |
| γ [°] | 90 | $wR_2$ (all data)$^a$ | 0.1173 |
| V [Å$^3$] | 1150.52(14) | GOF$^a$ | 1.075 |

$^a R_1 = \Sigma||F_o| - |F_c||/\Sigma|F_o|$; $wR_2 = [\Sigma[w(F_o^2 - F_c^2)^2]/\Sigma[w(F_o^2)^2]]^{1/2}$; GOF = $[\Sigma w(|F_o| - |F_c|)^2/(n - m)]^{1/2}$ Example 2: Synthesis of 4,4-dimethyl-3,4-dihydro-1,2a1-diaza-4-silabenzo[fg]aceanthrylene and 3,3-dimethyl-3,4-dihydro-1,2a1-diaza-3-silabenzo[fg]aceanthrylene

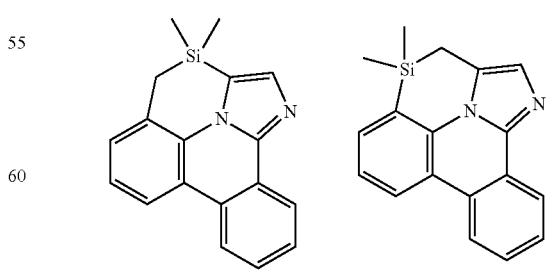

The ligands above are prepared in accordance with Scheme 2 below.

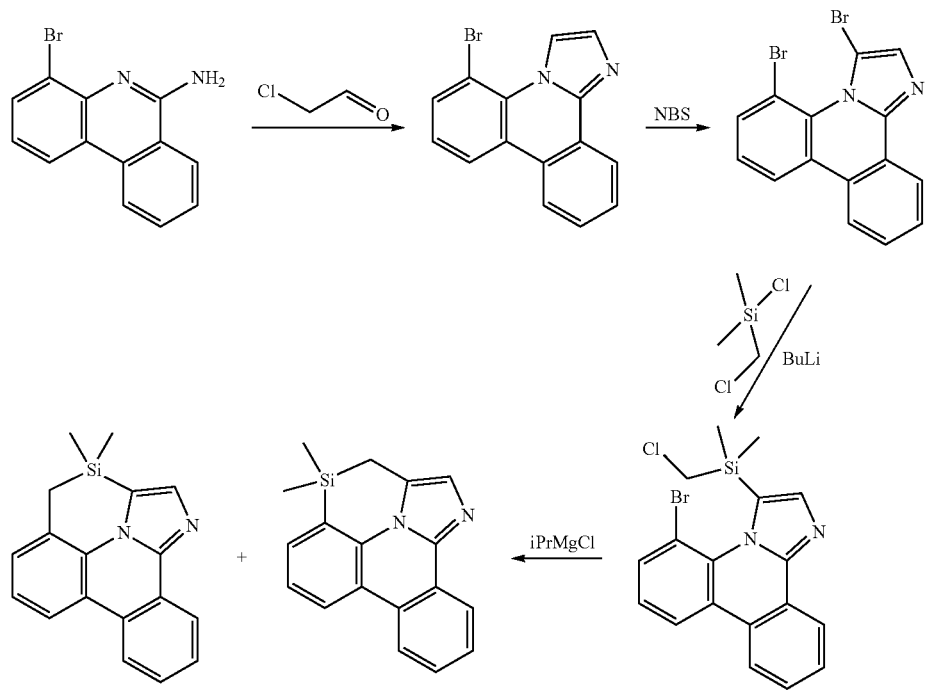

Scheme 2

A. Synthesis of 5-bromoimidazo[1,2-f]phenanthridine

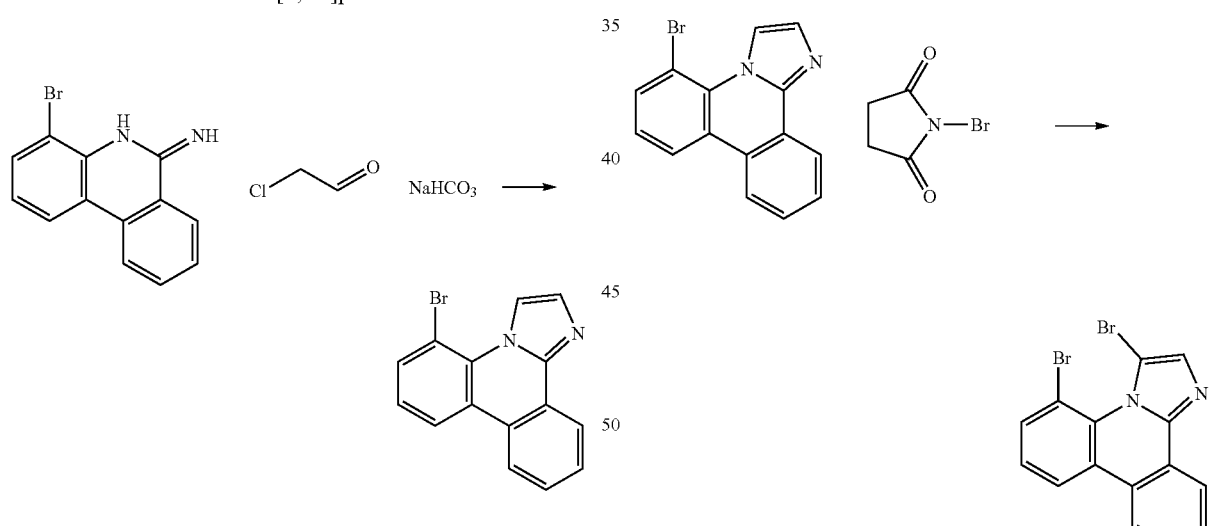

B. Synthesis of 3,5-dibromoimidazo[1,2-f]phenanthridine 4-bromophenanthridin-6-amine (4.0 g, 14.7 mmol) was dissolved in 100 mL of iPrOH. Chloroacetaldehyde (50% in water, 3.6 g, 22 mmol, 1.5 equiv.) was added, followed by NaHCO₃ (2.5 g, 2 equiv.), and the mixture was refluxed for 2 hours, then cooled in an ice bath. The tan solid was filtered off, washing with MeOH. The receiving flask was changed and the solid was washed with water, resulting in clean, off-white product, 3.2 g. The aqueous washes were extracted with EtOAc and these extracts were combined with the alcoholic washes from the initial filtration. Solvent was removed to yield 1.3 g of an orange solid which was recrystallized from EtOAc, yielding more clean product as tan needles, 0.46 g. Total yield: 3.5 g (80%).

Dissolved 5-bromoimidazo[1,2-f]phenanthridine (2.0 g, 6.73 mmol) in DMF (125 ml), then added a solution of NBS (1.318 g, 7.40 mmol) in 10 mL of DMF slowly under nitrogen. After stirring for 3 hours at room temperature, then gentle heating for 16 hours, the reaction mixture was partitioned between 300 mL of water and EtOAc. The aqueous layer was further extracted with EtOAc, the organics washed with water, and the product was isolated by column chromatography as a pale yellow solid, 1.99 g (79%).

C. Synthesis of 5-bromo-3-((chloromethyl)dimethylsilyl)imidazo[1,2-f]phenanthridine

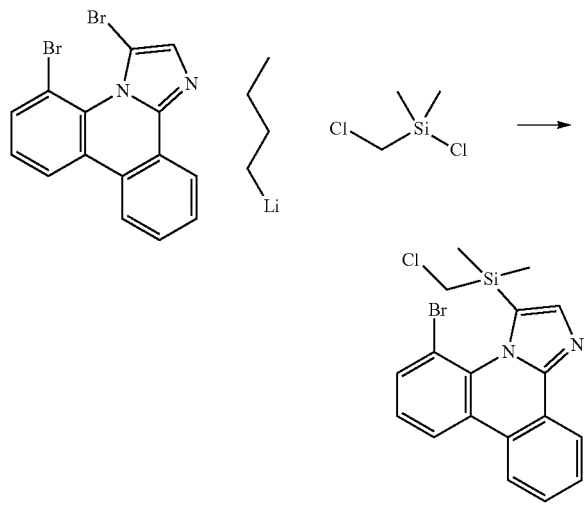

3,5-dibromoimidazo[1,2-f]phenanthridine (0.48 g, 1.28 mmol) and chloro(chloromethyl)dimethylsilane (0.17 ml, 1.28 mmol) were dissolved in THF (25 ml) and cooled in iPrOH/CO2 bath. Butyllithium solution in hexanes (2.5 M, 0.51 ml, 1.28 mmol) was added slowly, the mixture was stirred cold for 30 minutes, then allowed to warm to room temperature. Brine was added to quench the reaction, the organics were extracted into EtOAc and purified by column chromatography to yield the product as a colorless, tacky residue, 0.16 g (31%).

D. Synthesis of 4,4-dimethyl-3,4-dihydro-1,2a1-diaza-4-silabenzo[fg]aceanthrylene and 3,3-dimethyl-3,4-dihydro-1,2a1-diaza-3-silabenzo[fg]aceanthrylene

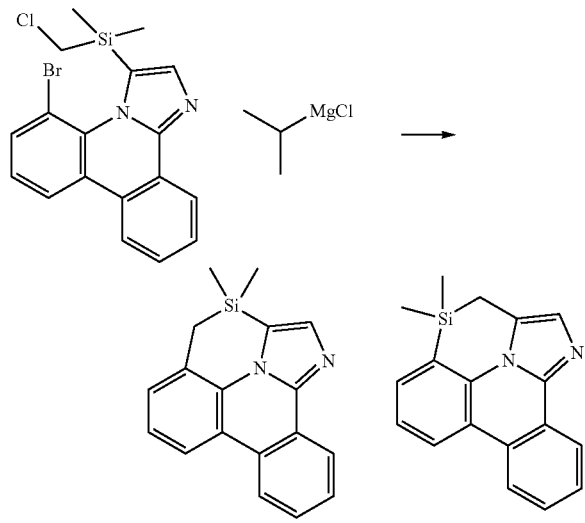

5-bromo-3-((chloromethyl)dimethylsilyl)imidazo[1,2-f]phenanthridine (0.13 g, 0.322 mmol) was dissolved in THF (25 ml) and cooled in an ice bath. Isopropylmagnesium chloride solution in THF (2.0 M, 0.18 ml, 0.36 mmol) was added slowly, then warmed to room temperature. The reaction was quenched with brine, organics were extracted with DCM, and the mixture chromatographed to yield 16 mg of 4,4-dimethyl-3,4-dihydro-1,2a1-diaza-4-silabenzo[fg] aceanthrylene as a tacky residue (17%), and 33 mg of 3,3-dimethyl-3,4-dihydro-1,2a1-diaza-3-silabenzo[fg] aceanthrylene as a crystalline solid (36%).

Furthermore, all organic materials used in this example were sublimation-purified and analyzed by high-performance liquid chromatography (Tosoh TSKgel ODS-100Z), and materials having 99.9% or higher of an absorption intensity area ratio at 254 nm were used.

Figure 6:
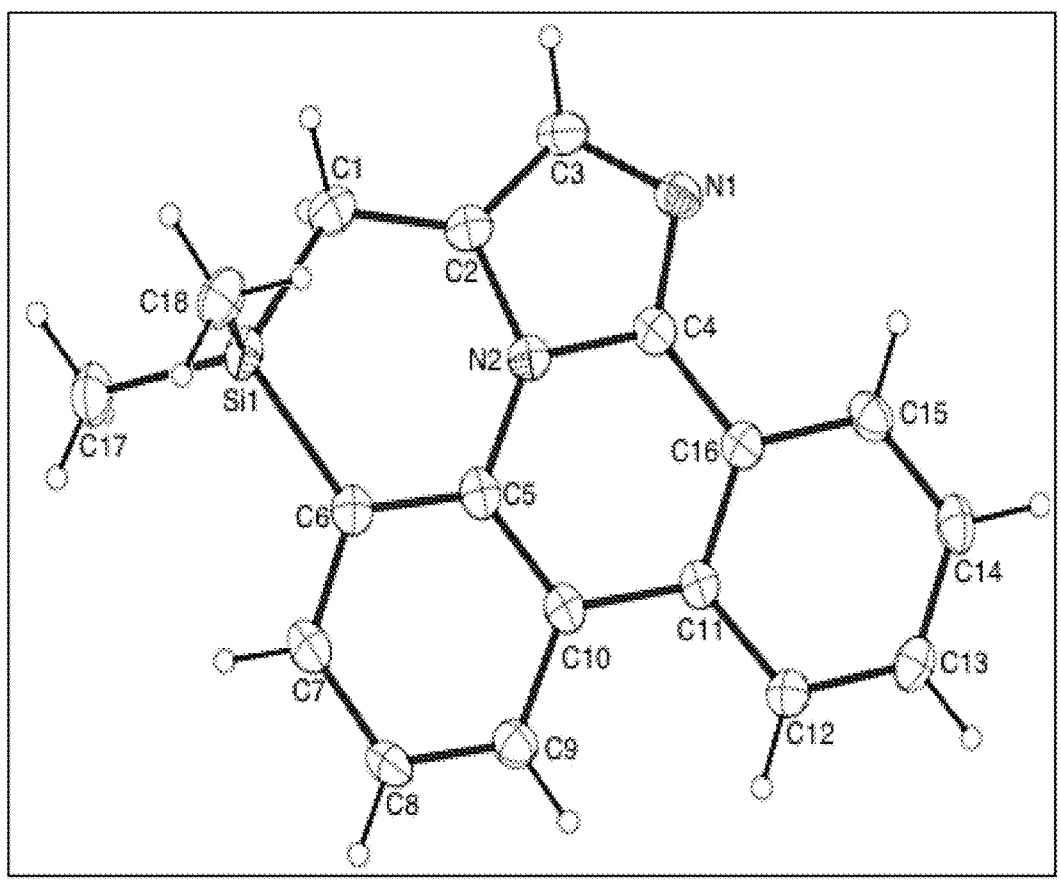
FIG. 6 illustrates the x-ray crystal structure of 3,3-dimethyl-3,4-dihydro-1,2a1-diaza-3-silabenzo[fg]aceanthrylene.
Figure 7:
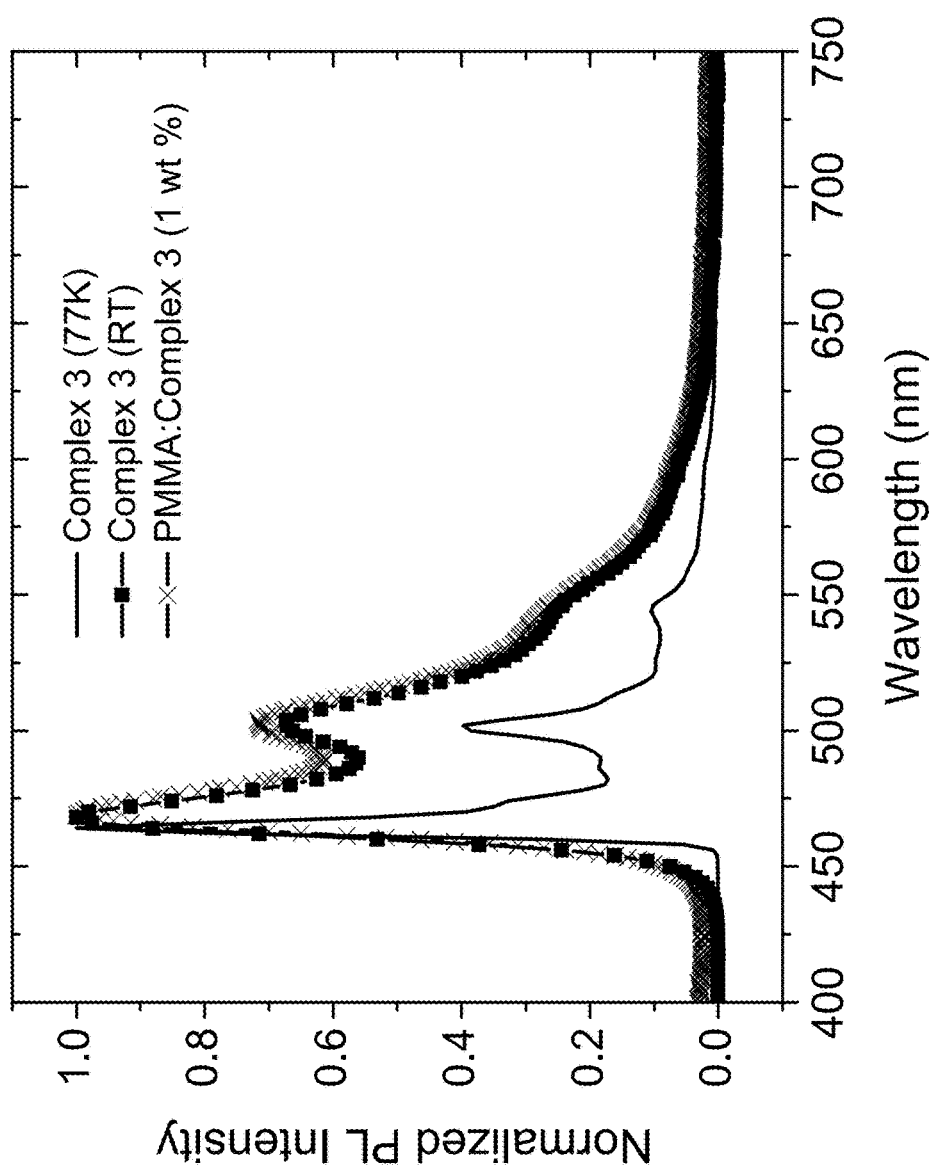
FIG. 7 depicts Emission spectrum of Compound 49 in 77 K and room temperature 2-methyl THF solvent and solid state PMMA matrix.

An X-ray structure of 3,3-dimethyl-3,4-dihydro-1,2a1-diaza-3-silabenzo[fg]aceanthrylene is shown in FIG. 6. The crystal structure of 3,3-dimethyl-3,4-dihydro-1,2a1-diaza-3-silabenzo[fg]aceanthrylene may be defined by one or more of the characteristics listed in the following table.

| Formula | $C_{18}H_{16}N_2Si$ | Data/restr./param. | 5211/0/384 |
|---|---|---|---|
| MW | 288.42 | T [K] | 100(1) |
| Crystal system | Triclinic | $\rho_{cald}$ [g cm$^{-3}$] | 1.341 |
| Space group | P-1 | $\mu_{calcd}$ [mm$^{-1}$] | 0.159 |
| Color | Colorless | Total reflections | 54823 |
| a [Å] | 9.1888(8) | Z | 4 |
| b [Å] | 12.5217(11) | F(000) | 608 |
| c [Å] | 12.5428(12) | $T_{min}/T_{max}$ | 0.954 |
| α [°] | 82.769(4) | Cryst. Size [mm$^3$] | 0.28 × 0.18 × 0.15 |
| β [°] | 89.062(4) | $R_1$ [I > 2σ(I)]$^a$ | 0.0324 |
| γ [°] | 86.121(2) | $wR_2$ (all data)$^a$ | 0.0892 |
| V [Å$^3$] | 1428.4(2) | GOF$^a$ | 1.055 |

$^a R_1 = \Sigma||F_o| - |F_c||/\Sigma|F_o|$; $wR_2 = [\Sigma[w(F_o^2 - F_c^2)^2]/\Sigma[w(F_o^2)^2]]^{1/2}$; GOF = $[\Sigma w(|F_o| - |F_c|)^2/(n - m)]^{1/2}$

Example 3: Synthesis of platinum(II) complex of 6-isopropyl-10-((9-(4-isopropylpyridin-2-yl)-9H-carbazol-2-yl)oxy)-3,4-dihydrodibenzo[b,ij]imidazo[2,1,5-de]quinolizine Scheme 3

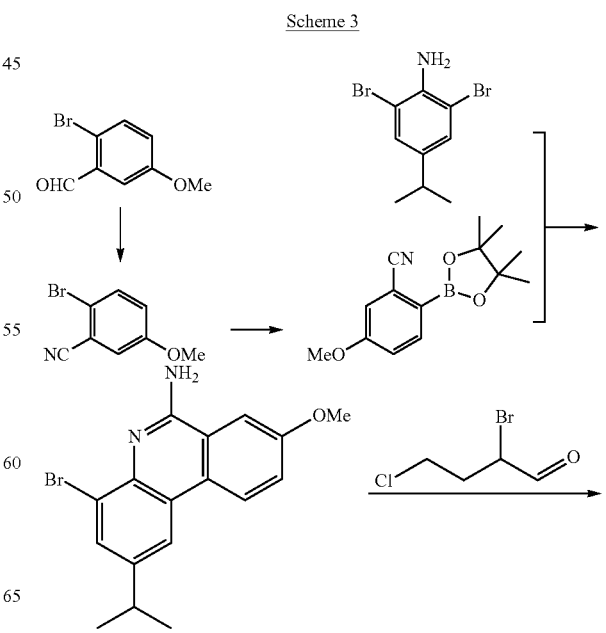

251
-continued

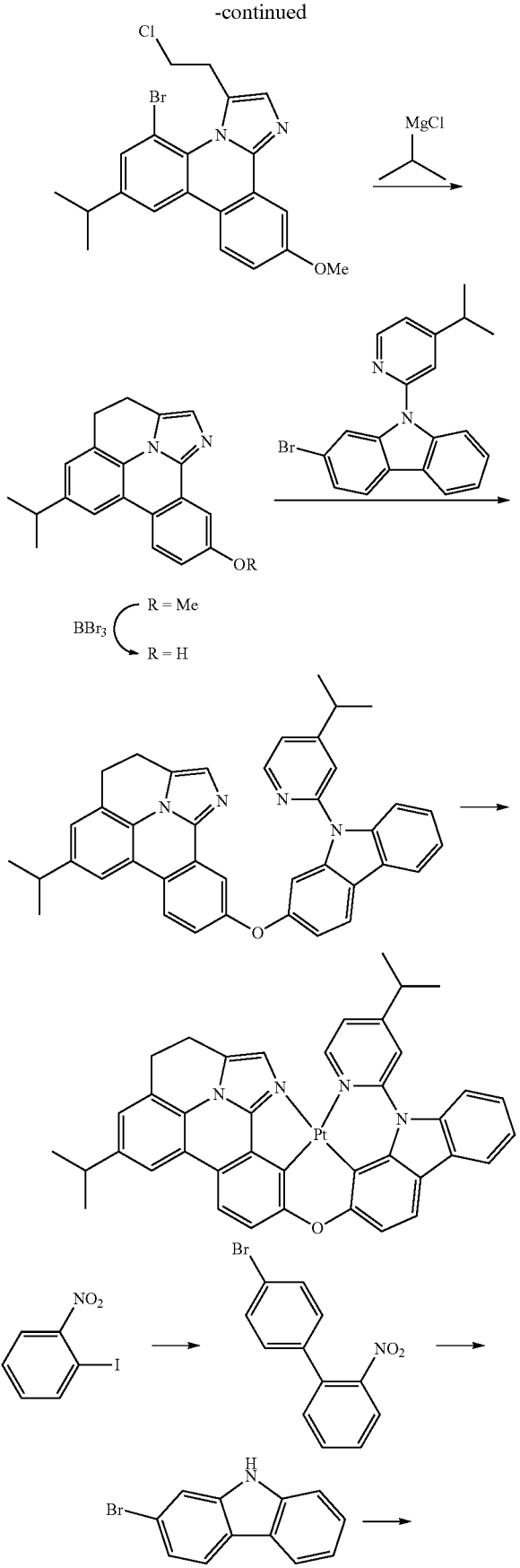

252
-continued

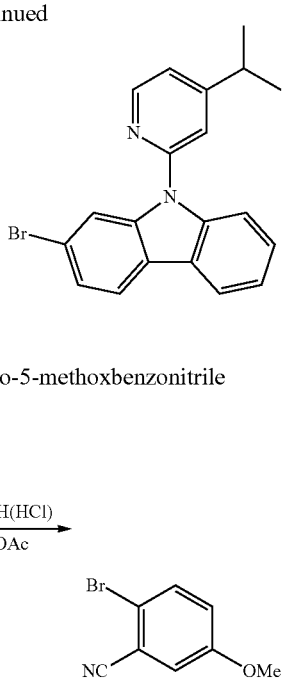

A. Synthesis of 2-Bromo-5-methoxbenzonitrile

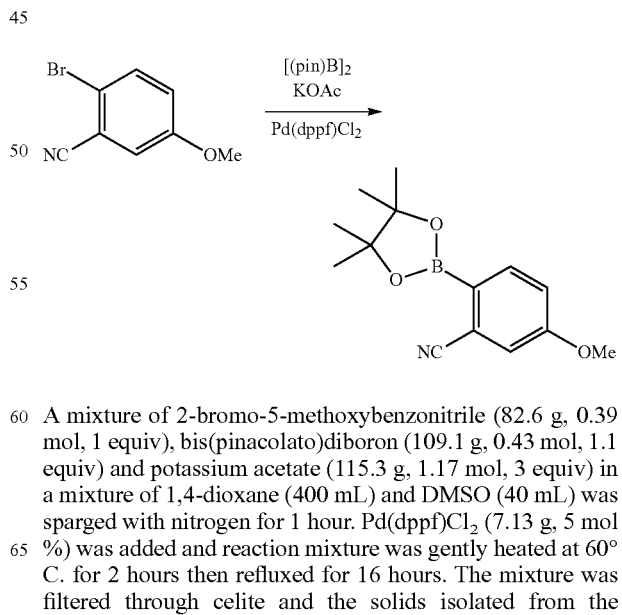

A mixture of 2-bromo-5-methoxybenzaldehyde (100 g, 0.47 mol, 1 equiv), hydroxylamine hydrochloride (64.8 g, 0.93 mol, 2 equiv), sodium acetate (76.42 g, 0.93 mol, 2 equiv) and glacial acetic acid (500 mL) was refluxed for 16 hours. The acetic acid was removed under reduced pressure and the residue was extracted with dichloromethane (~400 mL). The organic layer was washed with saturated brine (3×200 mL), dried over sodium sulfate and concentrated under reduced pressure. The resulting residue was triturated with heptanes (50 mL) and solids washed with additional heptanes (2×50 mL) to give the desired product as a white powder (82.6 g, 86% yield).

B. Synthesis of 5-Methoxy-2-(4,4,5,5-tetramethyl-1,3,2-dioxaborolan-2-yl)benzonitrile A mixture of 2-bromo-5-methoxybenzonitrile (82.6 g, 0.39 mol, 1 equiv), bis(pinacolato)diboron (109.1 g, 0.43 mol, 1.1 equiv) and potassium acetate (115.3 g, 1.17 mol, 3 equiv) in a mixture of 1,4-dioxane (400 mL) and DMSO (40 mL) was sparged with nitrogen for 1 hour. Pd(dppf)Cl$_2$ (7.13 g, 5 mol %) was added and reaction mixture was gently heated at 60° C. for 2 hours then refluxed for 16 hours. The mixture was filtered through celite and the solids isolated from the filtrates were washed with isopropanol and heptanes to give the desired product as an off-white solid (57.41 g, 57% yield). Additional product (~10 g) was isolated from the filtrates.

C. Synthesis of 4-Bromo-2-isopropyl-8-methoxyphenanthridin-6-amine

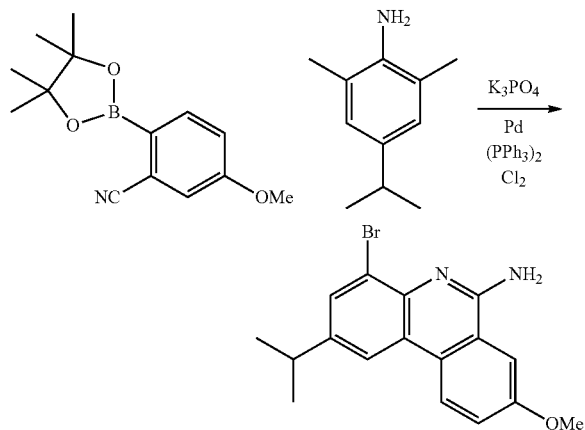

A mixture of 5-methoxy-2-(4,4,5,5-tetramethyl-1,3,2-dioxaborolan-2-yl)benzo-nitrile (57.41 g, 0.22 mol, 1 equiv), 2,6-dibromo-4-iso-propylaniline (64.92 g, 0.22 mol, 1 equiv) and potassium phosphate (153.1 g, 0.66 mol, 3 equiv) in a 4:1 mixture of toluene and water (1250 mL) was sparged with nitrogen for 1 hour. trans-Pd(PPh$_3$)$_2$Cl$_2$ (7.8 g, 11 mmol, 0.05 equiv) was added and the reaction mixture was refluxed for 20 hours. Additional potassium phosphate (77 g, 0.33 mol, 1.5 equiv) and trans-Pd(PPh$_3$)$_2$Cl$_2$ (1 g, 1.43 mmol, 0.0065 equiv) were added and the reaction mixture was refluxed for an additional 3 hours. The layers were separated and the organic layer was washed with hot water (2×400 mL). The organic layer was dried over sodium sulfate and concentrated under reduced pressure. The resulting solid was triturated sequentially with dichloromethane and heptanes. Column chromatography gave the desired product (30 g).

D. Synthesis of 6-Isopropyl-10-((9-(4-isopropylpyridin-2-yl)-9H-carbazol-2-yl)oxy)-3,4dihydro-dibenzo[b,ij]imidazo[2,1,5-de]quinolizine

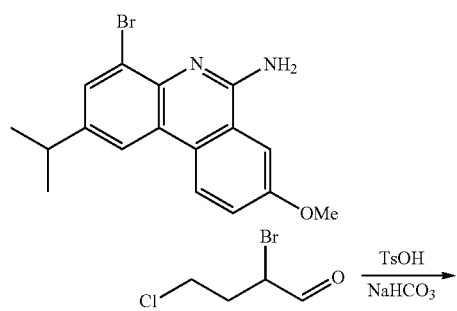

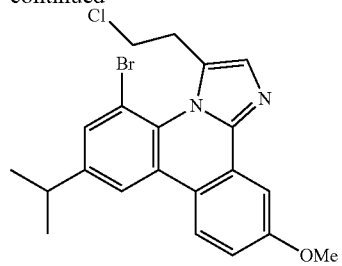

A suspension of 4-bromo-2-isopropyl-8-methoxyphenanthridin-6-amine (8.9 g, 25.8 mmol, 1 equiv), p-toluenesulfonic acid monohydrate (348 mg), freshly prepared 2-bromo-4-chlorobutanal (24 g, 129 mmol, 5 equiv) and iso-propanol (500 mL) was stirred at room temperature for 2.5 hours. Sodium carbonate (6.5 g, 77.4 mmol, 3 equiv) and deionized water (32 ml) were added, and the reaction mixture was refluxed for 16 hours. After cooling to room temperature, the volume of reaction mixture was reduced to ~100 mL under reduced pressure. The mixture was diluted with ethyl acetate (350 mL) and washed with saturated brine (200 mL). The organic layer was dried over sodium sulfate and concentrated under reduced pressure. The crude product was purified by column chromatography to yield 8.44 g of product (76% yield).

E. Synthesis of 6-Isopropyl-10-methoxy-3,4-dihydrodibenzo[b,j]imidazo[2,1,5-de]quinolizine

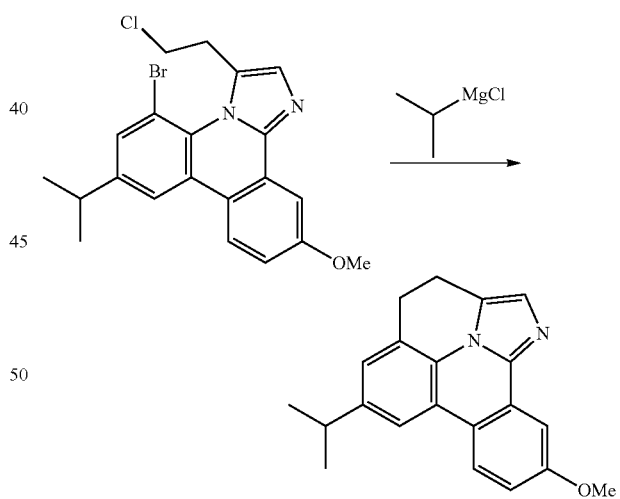

A solution of 6-Isopropyl-10-((9-(4-isopropylpyridin-2-yl)-9H-carbazol-2-yl)oxy)-3,4dihydro-dibenzo[b,ij]imidazo[2,1,5-de]quinolizine (8.44 g, 19.6 mmol, 1.0 equiv) in dry THF (250 mL) was sparged with nitrogen for 30 minutes). After cooling to 0° C., 2M isopropylmagnesium chloride (14.7 mL, 29.4 mmol, 1.5 equiv) in THF was added dropwise. The reaction mixture was warmed up to room temperature and stirred for 16 hours. The reaction was quenched with water (10 mL) and the THF was removed under reduced pressure. The residue was diluted with ethyl acetate (400 mL) and washed with saturated brine (2×200 mL). The organic layer was dried over sodium sulfate and the residue was purified by column chromatography to give 3.6 g of product (58% yield).

F. Synthesis of 6-Isopropyl-3,4-dihydrodibenzo[b,ij]imidazo[2,1,5-de]quinolizin-10-ol

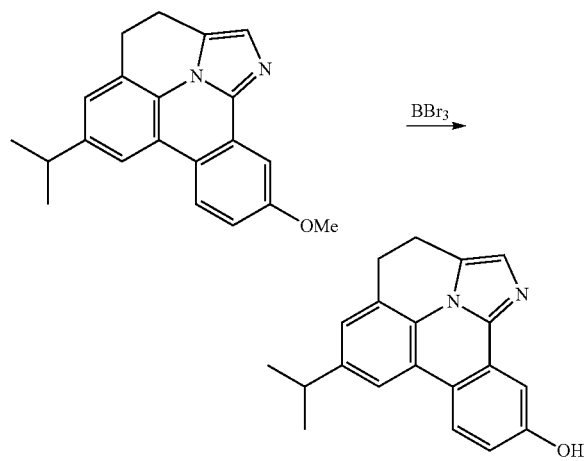

Boron tribromide (5.4 mL, 56.78 mmol, 5 equiv) was added dropwise at −78° C. to a solution of 6-Isopropyl-10-methoxy-3,4-dihydrodibenzo[b, ij]imidazo[2,1,5-de]quinolizine (3.6 g, 11.36 mmol, 1 equiv) in dichloromethane (200 mL). The reaction was warmed to room temperature and stirred for 16 hours. The reaction mixture was carefully poured into 300 ml of ice water and the resulting solid was filtered and washed sequentially with water (70 mL), ethyl acetate (40 mL) and heptanes (40 mL) to give 3.6 g of product (quantitative yield).

G. Synthesis of 4'-Bromo-2-nitro-1,1'-biphenyl:

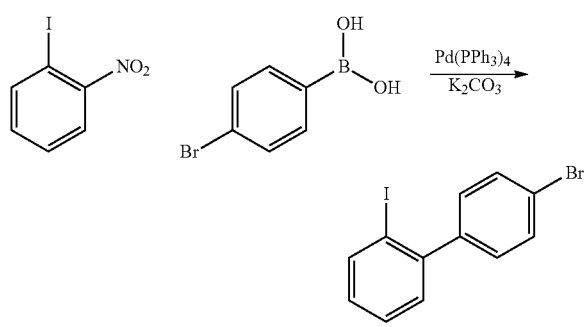

A solution of potassium carbonate (84 g, 608 mmol, 3.0 equiv) in water (450 mL) was added to a mixture of 2-iodo-nitrobenzene (50 g, 200 mmol, 1.0 equiv) and 4-bromobenzeneboronic acid (40.7 g, 202 mol, 1.0 equiv) in 1,2-dimethoxyethane (660 mL). The reaction was sparged with nitrogen for 5.0 minutes. Tetrakis(triphenylphosphine)palladium(0) (2.32 g, 2 mmol, 1 mol %) was added and the mixture was sparged with nitrogen for an additional 10 minutes. After refluxing for 16 hours, the reaction was cooled to room temperature and the layers were separated. The aqueous layer was extracted with ethyl acetate (500 mL). The combined organic extracts were washed with saturated brine (500 mL), dried over sodium sulfate, filtered and concentrated under reduced pressure. The residue was dissolved in 25% ethyl acetate in heptanes (300 mL) and vacuum filtered through a pad of silica gel (135 g). The pad was rinsed with 25% ethyl acetate in heptanes (3×350 mL). The combined filtrates were concentrated under reduced pressure giving an orange solid. This residue was suspended in heptanes (150 mL) and heated to 40° C. for 20 minutes. The suspension was allowed to cool to room temperature for 1.0 hour. The solid was collected by vacuum filtration, washed with heptanes (50 mL) and dried to give 4'-bromo-2-nitro-1,1'-biphenyl as a yellow solid (49.16 g, 88.4% yield).

H. Synthesis of 2-Bromo-9H-carbazole

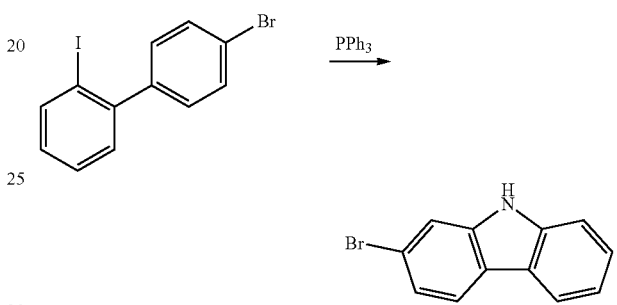

Triphenylphosphine (156.3 g, 596 mmol, 2.5 equiv) was added over 5 minutes to a solution 4'-bromo-2-nitro-1,1'-biphenyl (66.25 g, 238 mmol, 1.0 equiv) in 1,2-dichlorobenzene (460 mL). The reaction was sparged with nitrogen 5 minutes, then refluxed for 16 hours. The reaction was cooled to room temperature and vacuum distilled to remove most of the 1,2-dichlorobenzene (450 mL). This dark residue was dissolved in ethyl acetate (1.5 L) and treated with decolorizing carbon (50 g) at 50° C. for 30 minutes. After cooling, the mixture was filtered through Celite (200 g), then washed with ethyl acetate washes (2×650 mL). The combined filtrates were concentrated under reduced pressure to a volume of ~500 mL. The solution was cooled to room temperature and after 1.5 hours, the resulting pale tan solid (triphenylphosphine oxide) was removed by filtration and discarded. The filtrate was concentrated under reduced pressure. The residue was dissolved in methanol (600 m L) and stored at room temperature for 16 hours. The resulting tan solid was filtered, washed with methanol (2×100 mL) and dried under vacuum at 40° C. to give 2-bromo-9H-carbazole as a pale tan solid (33.5 g, 57.2% yield).

I. Synthesis of 2-Bromo-9-(4-isopropylpyridin-2-yl)-9H-carbazole

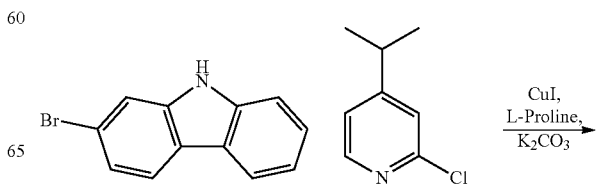

-continued

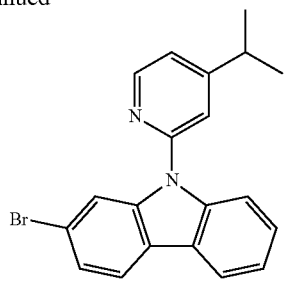

A suspension of 2-bromo-9H-carbazole (13.9 g, 56.5 mmol, 1 equiv), 4-isopropyl-2-chloropyridine (15.86 g, 101.7 mmol, 1.8 equiv), L-proline (1.3 g, 11.3 mmol, 0.2 equiv), copper (1) iodide (0.95 g, 5.65 mmol, 0.1 equiv), potassium carbonate (19.48 g, 141.25 mmol, 2.5 equiv) and DMSO (80 mL) was sparged with nitrogen for 5 minutes. The mixture was heated at 95° C. for 16 hours. Additional 4-isopropyl-2-chloropyridine (1.58 g, 10.12 mmol, 0.18 equiv) was added, the reaction mixture was heated at 155° C. for an additional 24 hours. The reaction mixture was cooled to room temperature, diluted with ethyl acetate (750 mL), and vacuum filtered through celite (70 g). The celite pad was washed with ethyl acetate washes (2×100 mL). The combined filtrates were washed with saturated brine (3×500 mL), dried over sodium sulfate, filtered and concentrated under reduced pressure. This residue was purified by column chromatography to give 1.8 g of product as a brown oil (8.6% yield).

J. Synthesis of 6-Isopropyl-10-((9-(4-isopropylpyridin-2-yl)-9H-carbazol-2-yl)oxy)-3,4-dihydrodibenzo[b,ij]imidazo[2,1,5-de]quinolizine A mixture of 6-Isopropyl-3,4-dihydrodibenzo[b,ij]imidazo[2,1,5-de]quinolizin-10-ol (1.5 g, 4.93 mmol, 1 equiv), 2-Bromo-9-(4-isopropylpyridin-2-yl)-9H-carbazole (1.8 g, 4.93 mmol, 1 equiv), potassium phosphate (5.68 g, 24.65 mmol, 5 equiv), copper(I) iodide (0.47 g, 2.47 mmol, 0.5 equiv), picolinic acid (1.52 g, 12.33 mmol, 2.5 equiv) and DMSO (150 mL) was heated at 150° C. for 4.5 hours. After cooling to room temperature, the reaction mixture was poured into water (700 mL) and extracted with ethyl acetate (4×150 mL). The combined organic layers were dried over sodium sulfate and concentrated in under reduced pressure. The crude product was purified by column chromatography to yield product as a tan solid, 1.25 g (43% yield).

K. Synthesis of platinum(II) complex of 6-isopropyl-10-((9-(4-isopropylpyridin-2-yl)-9H-carbazol-2-yl)oxy)-3,4-dihydrodibenzo[b,ij]imidazo[2,1,5-de]quinolizine

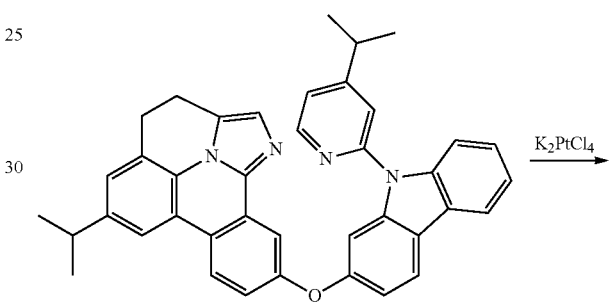

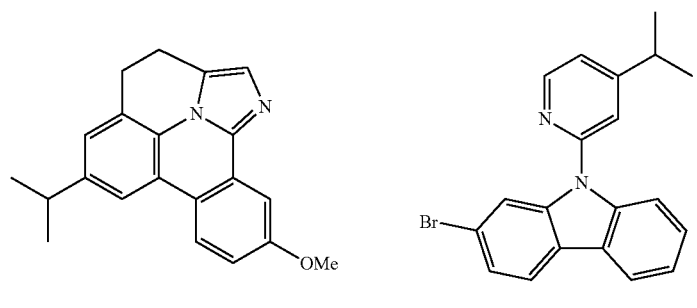

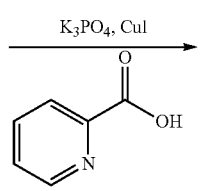

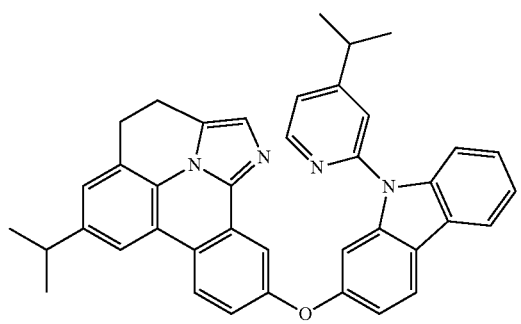

259
-continued

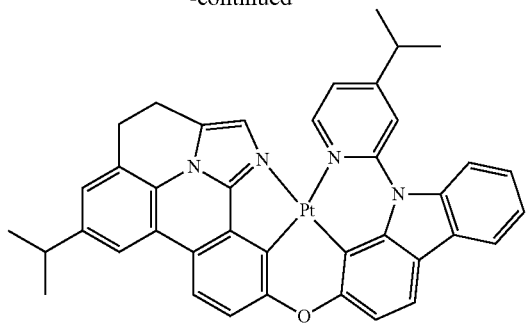

6-Isopropyl-10-((9-(4-isopropylpyridin-2-yl)-9H-carbazol-2-yl)oxy)-3,4-dihydrodibenzo[b,ij]imidazo[2,1,5-de]quinolizine (400 mg, 0.68 mmol, 1 equiv) was dissolved in 60 ml of glacial acetic acid and sparged with nitrogen for 30 minutes. Then $K_2PtCl_4$ (283 mg, 0.68 mmol, 1 equiv) was added, and the reaction mixture was refluxed for 40 hours. After cooling to room temperature, the orange precipitate was filtered and washed sequentially with water (3×15 mL) and heptanes (10 ml×2 times). The crude product (340 mg) was dissolved in 10 ml of dichloromethane and filtered through a plug of silica gel to remove residual $K_2PtCl_4$, eluting with additional dichloromethane (10 mL). The filtrate was reduced to half its volume and diluted with heptanes (10 mL). The product was filtered and triturated with a 10% solution of dichloromethane in heptanes (10 mL) to give product as a light yellow solid (140 mg, 26% yield). Additional product was isolated from the acetic acid and dichloromethane/heptane filtrates.

Example 4: Synthesis of (3-phenyl-1H-pyrazole)$_2$Ir(MeOH)$_2$(OTf)

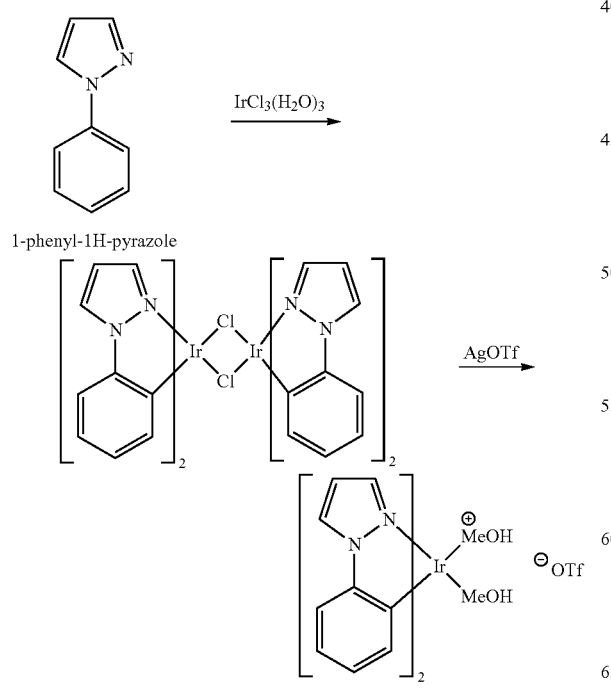

260

A. Synthesis of (3-phenyl-1H-pyrazole)$_2$IrCl$_2$ dimer

Iridium chloride hydrate (6.00 g, 17.02 mmol) and 1-phenyl-1H-pyrazole (5.89 g, 40.9 mmol) were combined in 2-ethoxyethanol (120 ml) and water (40 ml). The reaction mixture was heated to reflux for 16 hours under nitrogen. The resulting solid was filtered off and washed with methanol and dried to yield 8.3 g of the iridium dimer.

The iridium dimer of Example 4A (8.3 g, 8.07 mmol) was dissolved in 100 mL of DCM and a solution of silver triflate (4.36 g, 16.96 mmol) in 20 mL of methanol was added. The reaction mixture was stirred at room temperature under nitrogen for 1 hour. The mixture was filtered through celite and the cake was washed with DCM. The filtrates were evaporated to yield 10.85 g of (3-phenyl-1H-pyrazole)$_2$Ir(MeOH)$_2$(OTf) (97%).

Example 5: Exemplary Compound 35 was Prepared According to Scheme 5

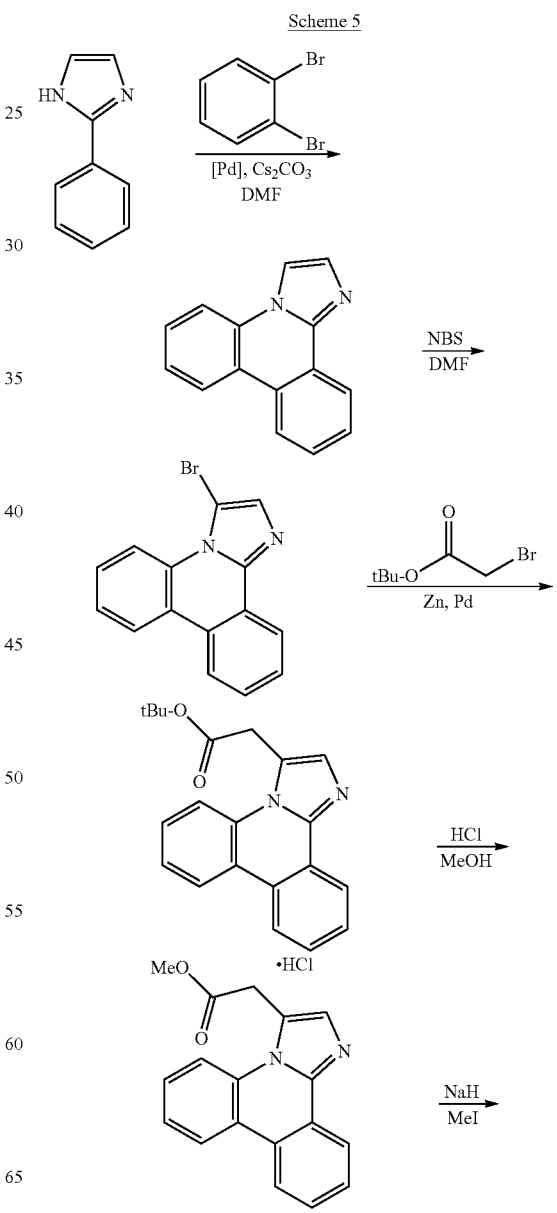

261
-continued

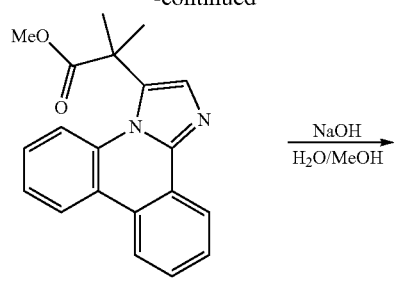
NaOH
H₂O/MeOH

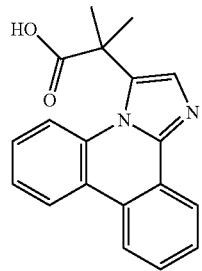
SOCl₂
DCM

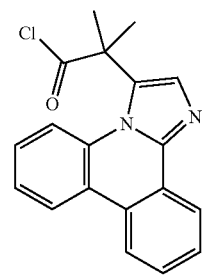
AlCl₃
DCM

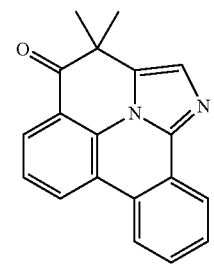
NaBH₄
EtOH

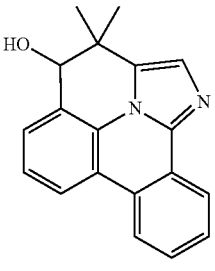
CS₂
NaH/MeI

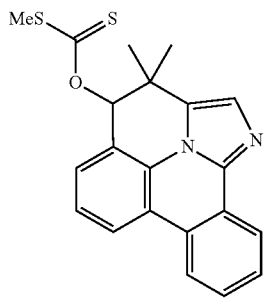
Bu₃SnH
AIBN, toluene

262
-continued

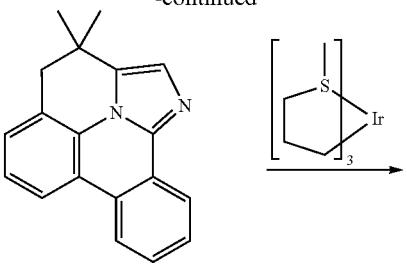

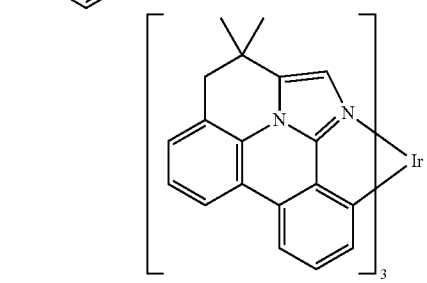

Compound 35

A. Synthesis of imidazo[1,2-f]phenanthridine

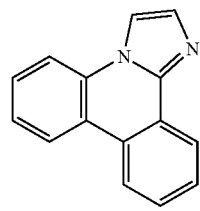 [SMILES: c1ccc2c(c1)c1ccccc1n1ccnc21]

A mixture of 2-phenyl-1H-imidazole (10.0 g, 69.3 mmol, 1 equiv), 1,2-dibromobenzene (19.63 g, 83.2 mmol, 1.2 equiv), cesium carbonate (67.79 g, 208.0 mmol, 3 equiv), Xantphos (4.01 g, 6.9 mmol, 0.1 equiv) and tetrakis(triphenylphosphine)palladium (8.01 g, 6.9 mmol, 0.1 equiv) in DMF (550 mL) was sparged with a stream of nitrogen for 15 minutes. The mixture was heated at 140° C. for 24 hours, then concentrated under reduced pressure. The residue was purified by column chromatography to imidazo[1,2-f]phenanthridine (10 g, 67% yield) as pale yellow solid.

B. Synthesis of 3-Bromoimidazo[1,2-f]phenanthridine

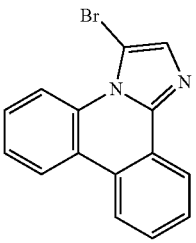 [SMILES: Brc1cnc2c3ccccc3c3ccccc3n12]

N-bromosuccinimide (1.62 g, 9.1 mmol, 1 equiv) was added to a solution of 15 (1.99 g, 9.1 mmol, 1 equiv) in DMF (32 mL) at 0° C. After stirring at room temperature for 18 hours, the reaction was diluted with water (300 mL) and sequentially extracted with 10% dichloromethane in methyl t-butyl ether (3×500 mL), ethyl acetate (2×300 mL) and dichloromethane (400 mL). The combined organic layers were dried over sodium sulfate, filtered and concentrated under reduced pressure. The residue was purified by column chromatography to yield 3-Bromoimidazo[1,2-f]phenanthridine (1.66 g, 65% yield) as an off-white solid.

C. Synthesis of tert-Butyl 2-(imidazo[1,2-f]phenanthridin-3-yl)acetate

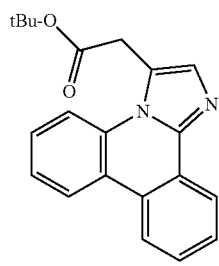

Di-µ-bromobis(tri-t-butylphosphino)dipalladium (I) (2.01 g, 2.5 mmol, 0.05 equiv) was added to a solution of 16 (15.4 g, 51.8 mmol, 1 equiv) in anhydrous tetrahydrofuran (220 mL) and the solution was sparged with a stream of nitrogen for 15 minutes. 0.5M 2-tert-butoxy-2-oxoethylzinc bromide in diethyl ether (155 mL, 77.7 mmol, 1.5 equiv) was added under nitrogen. The reaction was stirred at 60° C. for 16 hours. Additional 0.5M 2-tert-butoxy-2-oxoethylzinc chloride solution (155 mL, 77.7 mmol, 1.5 equiv) and di-µ-bromobis(tri-t-butylphosphino)-dipalladium (I) (2.01 g, 2.5 mmol, 0.05 equiv) were added and the reaction was stirred at 60° C. until LC/MS analysis indicated it was complete. The reaction mixture was concentrated under reduced pressure. The residue was dissolved in dichloromethane (1 L) and filtered through a Celite pad. The filtrate was concentrated under reduced pressure. The residue was purified by column chromatography to give tert-Butyl 2-(imidazo[1,2-f]phenanthridin-3-yl)acetate (5 g, 30% yield) as an orange solid.

D. Synthesis of Methyl 2-(imidazo[1,2-f]phenanthridin-3-yl)acetate hydrochloride

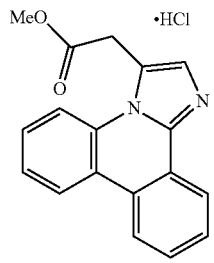 [SMILES: COC(=O)Cc1cnc2c3ccccc3c3ccccc3n12 ; Cl]

A solution of 17 (2.8 g, 8.4 mmol, 1 equiv) in 1.25M HCl (55 mL, 68.7 mmol, 6.5 equiv) in methanol was stirred at 60° C. for 16 hours. The reaction mixture was concentrated under reduced pressure. The residue was washed with diethyl ether and dried under vacuum for 16 hours at 40° C. to give methyl 2-(imidazo[1,2-f]phenanthridin-3-yl)acetate hydrochloride (2.5 g, 100% yield) as an off-white solid.

E. Synthesis of Methyl 2-(imidazo[1,2-f]phenanthridin-3-yl)-2-methylpropanoate

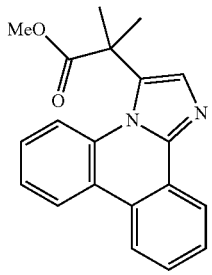 [SMILES: COC(=O)C(C)(C)c1cnc2c3ccccc3c3ccccc3n12]

A 60% dispersion of sodium hydride in mineral oil (2.45 g, 61.2 mmol, 5 equiv) and iodomethane (2 mL, 32.1 mmol, 2.6 equiv) were sequentially added to a solution of methyl 2-(imidazo[1,2-f]phenanthridin-3-yl)acetate hydrochloride (4.0 g, 12.24 mmol, 1 equiv) in anhydrous DMF (45 mL) at 5° C. The mixture was stirred in a cooling bath for 30 minutes, warmed to room temperature and stirred for 6 hours. Additional iodomethane (1.2 mL, 19.2 mmol, 1.6 equiv) was added. The reaction was stirred at room temperature over a weekend, quenched with methanol (32 mL) and concentrated under reduced pressure. The residual oil was diluted with dichloromethane (350 mL) and washed with water (100 mL). The aqueous layer was extracted with dichloromethane (2×100 mL). The combined organic layers were washed with saturated ammonium chloride (100 mL), dried over sodium sulfate, filtered and concentrated under reduced pressure. The residue was purified by column chromatography to give methyl 2-(imidazo[1,2-f]phenanthridin-3-yl)-2-methylpropanoate (1.6 g, 41% yield) as an off-white solid.

F. Synthesis of 2-(Imidazo[1,2-f]phenanthridin-3-yl)-2-methylpropanoic acid

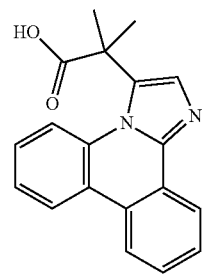

A solution of methyl 2-(imidazo[1,2-f]phenanthridin-3-yl)-2-methylpropanoate (1.6 g, 5.0 mmol, 1 equiv) in methanol (100 mL) was treated with aqueous 1N sodium hydroxide (30 mL, 30 mmol, 6 equiv) and further diluted with water (100 mL). After refluxing for 5 days, the reaction was concentrated under reduced pressure. The residue was dissolved in water (100 mL) and acidified with conc. HCl to pH 5-6. The resulting white suspension was extracted with 1 to 2 mixture of isopropanol and dichloro-methane (4×200 mL). The combined organic layers were dried over sodium sulfate, filtered, concentrated under reduced pressure. The residue was dried under high vacuum at 40° C. for 16 hours to give 2-(Imidazo[1,2-f]phenanthridin-3-yl)-2-methylpropanoic acid (1.3 g, 82% yield) as white solid.

G. Synthesis of 2-(Imidazo[1,2-f]phenanthridin-3-yl)-2-methylpropanoyl chloride

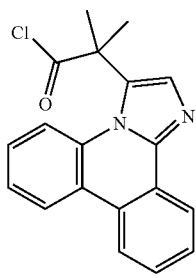 [SMILES: CC(C)(C(=O)Cl)c1cnc2c3ccccc3c3ccccc3n12]

Thionyl chloride (1 mL, 13.7 mmol, 2 equiv) and anhydrous DMF (0.05 mL, 0.6 mmol, 0.11 equiv) were added to a suspension of 2-(Imidazo[1,2-f]phenanthridin-3-yl)-2-methylpropanoic acid (1.3 g, 4.2 mmol, 1 equiv) in anhydrous dichloromethane (100 mL). After stirring at room temperature for 16 hours, the mixture was concentrated under reduced pressure to give the 2-(Imidazo[1,2-f]phenanthridin-3-yl)-2-methylpropanoyl chloride (1.37 g, 100% yield) as an off-white solid.

H. Synthesis of 3,3-Dimethyldibenzo[b,ij]imidazo[2,1,5-de]quinolizin-4(3H)-one

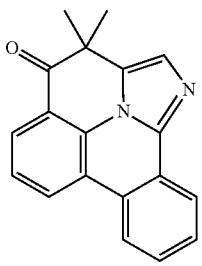 [SMILES: CC1(C)C(=O)c2cccc3c4ccccc4c4ncc1n4c23]

A mixture of 2-(Imidazo[1,2-f]phenanthridin-3-yl)-2-methylpropanoyl chloride (1.37 g, 4.2 mmol, 1 equiv) and anhydrous aluminum chloride (6.0 g, 44.9 mmol, 10 equiv) in anhydrous dichloromethane (60 mL) was stirred at room temperature for 6 hours. The reaction was cooled with an ice-water bath, quenched with ice, diluted with saturated sodium bicarbonate (300 mL) and extracted with dichloromethane (4×400 mL). The combined organic layers were dried over sodium sulfate, filtered and concentrated under reduced pressure. The residue was purified using column chromatography to give 3,3-dimethyldibenzo[b,ij]imidazo[2,1,5-de]quinolizin-4(3H)-one (1 g, 81% yield) as a white solid.

I. Synthesis of 3,3-Dimethyl-3,4-dihydrodibenzo[b,ij]imidazo[2,1,5-de]quinolizin-4-ol Sodium borohydride (0.24 g, 6.3 mmol, 2 equiv) was added in one portion to a solution of 3,3-dimethyldibenzo[b,ij]imidazo[2,1,5-de]quinolizin-4(3H)-one (0.9 g, 3.1 mmol, 1 equiv) in ethanol (70 mL) at 5° C. The reaction was stirred at room temperature for 1.5 hours and then quenched with acetone (2 mL). The reaction mixture was concentrated under reduced pressure. The residue was dissolved in methyl t-butyl ether (300 mL), washed with saturated sodium bicarbonate (2×60 mL) and saturated brine (60 mL). The organic layer was dried over sodium sulfate, filtered and concentrated under reduced pressure. The crude product was purified by column chromatography to give 3,3-Dimethyl-3,4-dihydrodibenzo[b,ij]imidazo[2,1,5-de]quinolizin-4-ol (0.9 g, 100% yield) as a white solid.

J. o-(3,3-Dimethyl-3,4-dihydrodibenzo[b,ij]imidazo[2,1,5-de]quinolizin-4-yl)S-methyl carbonodithioate A 60% dispersion of sodium hydride (0.48 g, 20.2 mmol, 5 equiv) in mineral oil was added to a solution of 3,3-Dimethyl-3,4-dihydrodibenzo[b,ij]imidazo[2,1,5-de]quinolizin-4-ol (0.71 g, 2.46 mmol, 1 equiv) in anhydrous THF (70 mL) at 0° C. After stirring for 30 minutes at 5° C., a solution of imidazole (0.0168 g, 0.24 mmol, 0.1 equiv) in anhydrous tetrahydrofuran (3.2 mL) was added, followed by the dropwise addition of carbon disulfide (0.89 mL, 14.8 mmol, 6 equiv). The reaction was allowed to slowly warm to 12° C. over 30 minutes. Iodomethane (0.92 mL, 14.7 mmol, 6 equiv) was added dropwise (exothermic) and the reaction was stirred at room temperature for 1 hour. The reaction mixture was cooled to 5° C., diluted with saturated brine (140 mL) and extracted with dichloromethane (5×100 mL). The combined organic layers were dried over sodium sulfate, filtered and concentrated under reduced pressure. The crude product was purified by column chromatography to give o-(3,3-Dimethyl-3,4-dihydrodibenzo[b,ij]imidazo[2,1,5-de]quinolizin-4-yl) S-methyl carbonodithioate (0.86 g, 93% yield) as a white solid.

K. Synthesis of 3,3-Dimethyl-3,4-dihydrodibenzo[b,ij]imidazo[2,1,5-de]quinolizine

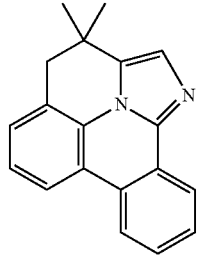 [SMILES: CC1(C)Cc2cccc3c4ccccc4c4ncc1n4c23]

A solution of o-(3,3-Dimethyl-3,4-dihydrodibenzo[b,ij]imidazo[2,1,5-de]quinolizin-4-yl)S-methyl carbonodithioate (0.98 g, 2.6 mmol, 1 equiv), 2,2'-azabis(2-methylpropionitrile) (0.098 g, 0.6 mmol, 0.2 equiv) and tributyltin hydride (1.81 mL, 6.7 mmol, 2.6 equiv) in anhydrous toluene (70 mL) was stirred at 80° C. for 3.5 hours. After cooling to room temperature, the reaction mixture was concentrated under reduced pressure at 35° C. and absorbed onto silica gel (10 g). The crude material was purified by column chromatography to give 3,3-Dimethyl-3,4-dihydrodibenzo[b,ij]imidazo[2,1,5-de]quinolizine (0.53 g, 72% yield) as a white solid.

L. Synthesis of (3-chloropropyl)(methyl)sulfane

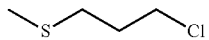

Sodium methanethiolate (6.14 g, 88 mmol) was dissolved in 150 mL of EtOH, cooled in an ice bath, then 1-bromo-3-chloropropane (8.6 ml, 87 mmol) was added. The solution was warmed to room temperature and stirred for 2 hours. The precipitated solids were filtered and the filtrates condensed under vacuum. The residue was distilled under vacuum to yield the product as a colorless oil, 36%.

M. Synthesis of tris-[(3-methylthio)propyl]iridium(III)

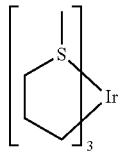

(3-chloropropyl)(methyl)sulfane was synthesized by stirring the Grignard made from (3-chloropropyl)(methyl)sulfane and magnesium turnings with IrCl₃(THT)₃ in THF, followed by column chromatography to yield a white solid, 32%.

N. Synthesis of Compound 35

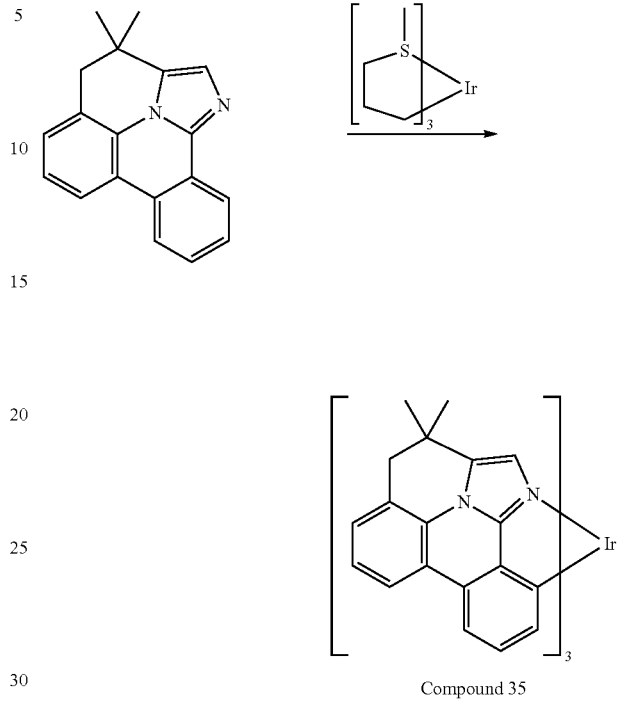

Compound 35 tris-[(3-methylthio)propyl]iridium(III) from Example 5M (0.020 g, 0.044 mmol) and 3,3-Dimethyl-3,4-dihydrodibenzo[b,ij]imidazo[2,1,5-de]quinolizine from Example 5K (0.036 g, 0.131 mmol) were combined in ethylene glycol (0.5 ml), degassed by vacuum/backfill cycles, and stirred at reflux, turning yellow then black. The cooled residue was partitioned between water and DCM, the organics were dried and coated on celite. Purification by column chromatography yielded 4 mg of Compound 35 as a beige solid (9%).

Example 6: Synthesis of Compound 48 was Carried Out as in Scheme 6

Scheme 6

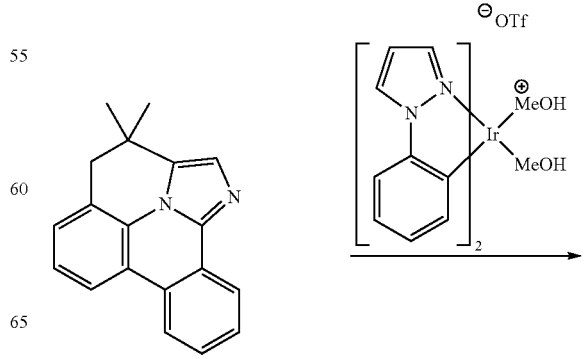

-continued

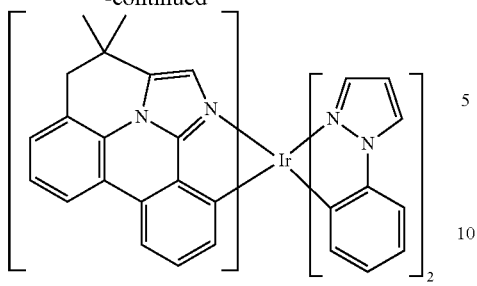

Compound 48

(3-phenyl-1H-pyrazole)$_2$Ir(MeOH)$_2$(OTf) from Example 4 (0.031 g, 0.045 mmol) and 3,3-Dimethyl-3,4-dihydrodibenzo[b, ij]imidazo[2,1,5-de]quinolizine from Example 5K (0.024 g, 0.090 mmol) were combined in 2-ethoxyethanol (0.5 ml), vacuum/backfill quickly three times, then heated at reflux under nitrogen for 2 hours. The reaction mixture was dissolved in DCM, coated on celite, and purified by column chromatography to yield Compound 35 as a nearly colorless residue, 6 mg (18%).

Example 7: Synthesis of Compound 49 was Carried Out According to Scheme 7 Below

Scheme 7

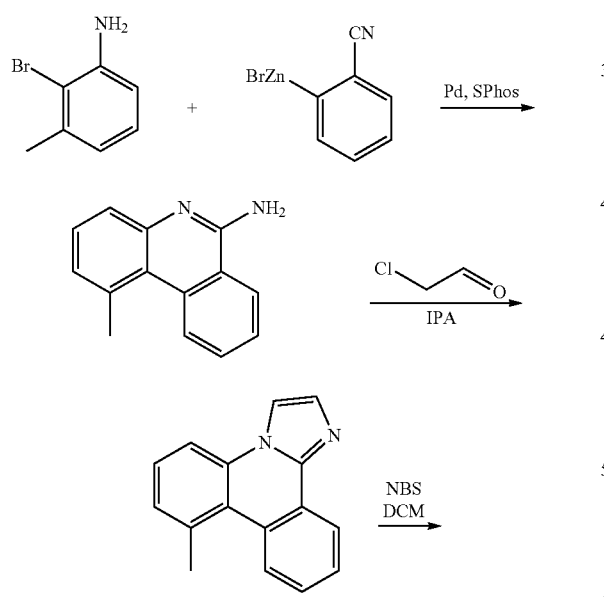

-continued

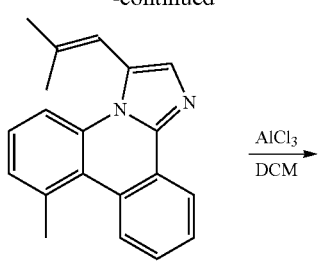
AlCl$_3$ / DCM

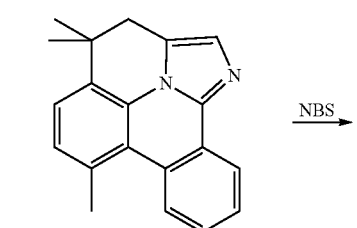
NBS

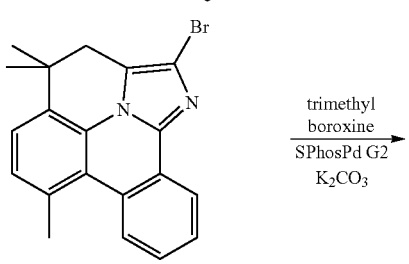
trimethyl boroxine
SPhosPd G2
K$_2$CO$_3$

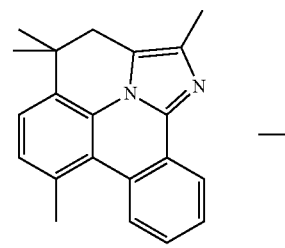

32

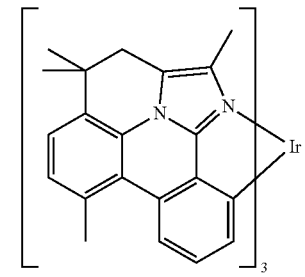

Comound 49

A. Synthesis of 1-Methylphenanthridin-6-amine

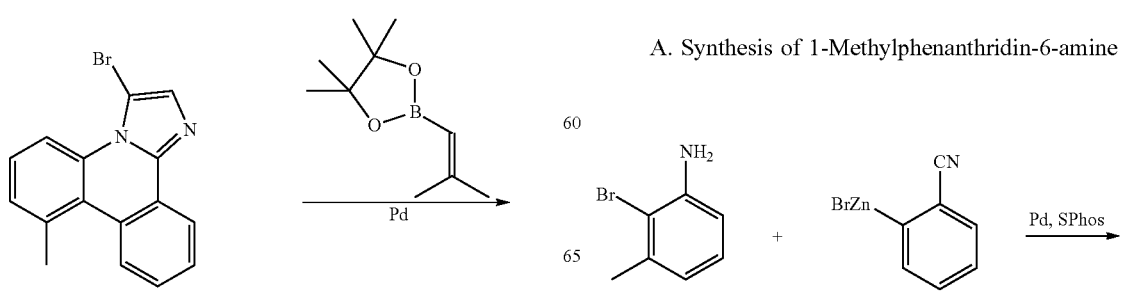
Pd, SPhos

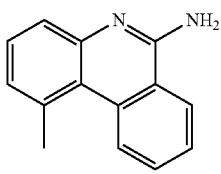

A mixture of 2-bromo-3-methylaniline (38.8 g, 208 mmol, 1 equiv), (chloro(2-dicyclohexylphosphino-2',6'-dimethoxy-1,1'-biphenyl)[2-(2'-amino-1,1'-biphenyl)]palladium(II) (2.99 g, 4.16 mmol, 0.02 equiv), 2-dicyclohexyl-phosphino-2',6'-dimethoxybiphenyl (1.71 g, 4.16 mmol, 0.02 equiv) in THF (832 mL) was sparged with nitrogen for 15 minutes. (2-Cyanophenyl)zinc bromide solution (500 mL, 0.5 M in THF, 250 mmol, 1.2 equiv) was added to the mixture and the reaction was refluxed for 16 hours. After cooling to room temperature, the reaction was diluted with saturated brine (10 mL) and concentrated under reduced pressure. The solids were dissolved in 10% methanol in dichloromethane (500 mL) and 24% wt. aqueous sodium hydroxide (500 mL). The layers were separated and the aqueous was extracted with dichloromethane (3×500 mL). The combined organic layers were dried over sodium sulfate, and concentrated under reduced pressure. The brown solid was sequentially triturated with 25% MTBE in heptanes (1.5 L) and dichloromethane (5×25 mL) to give 26 (10.7 g, 25% yield, >95% purity) as a pale yellow solid.

B. Synthesis of 8-Methylimidazo[1,2-f]phenanthridine

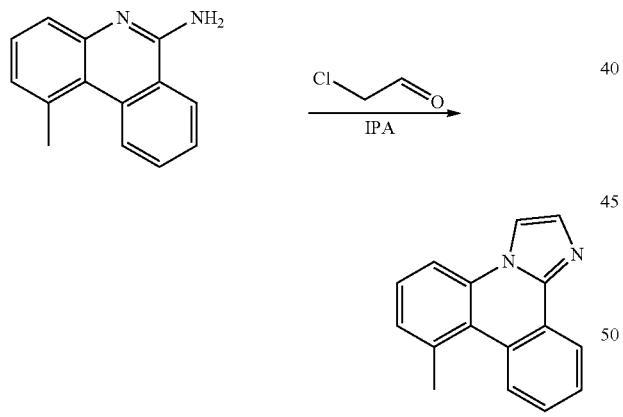

A mixture of 1-methylphenanthridin-6-amine (10.7 g, 51 mmol, 1 equiv), 50% wt chloroacetaldehyde in water (16 mL, 102 mmol, 2 equiv), sodium carbonate (13.5 g, 128 mmol, 2.5 equiv) in isopropanol (340 mL) was refluxed for 2 hours. The reaction was cooled to 4° C. and diluted with dichloromethane (250 mL) and saturated sodium bicarbonate (500 mL). The layers were separated and the aqueous layer was extracted with dichloromethane (3×250 mL). The combined organics layers were dried over sodium sulfate, and concentrated under reduced pressure to give crude 8-methylimidazo[1,2-f]phenanthridine (23.8 g) as a brown solid, which was used subsequently.

C. Synthesis of 3-Bromo-8-methylimidazo[1,2-f]phenanthridine

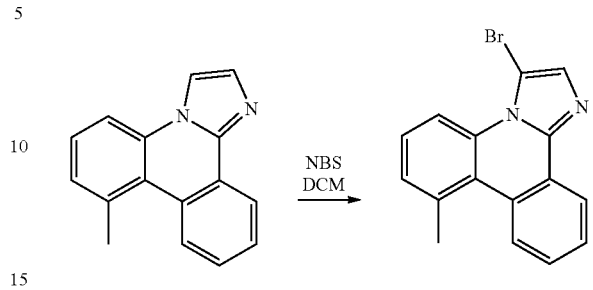

A mixture of crude 8-methylimidazo[1,2-f]phenanthridine (23.8 g), N-bromosuccinimide (9.1 g, 51 mmol, 1 equiv) in dichloromethane (306 mL) was stirred at room temperature for 2 hours. Water (500 mL) was added and the layers were separated. The aqueous was extracted with dichloromethane (3×500 mL). The combined organic layers were dried over sodium sulfate and concentrated under reduced pressure. The solids were pre-absorbed onto silica gel and purified by column chromatography to give 3-bromo-8-methylimidazo [1,2-f]phenanthridine (12 g, 98% purity) as a light brown solid.

D. Synthesis of 8-Methyl-3-(2-methylprop-1-en-1-yl)imidazo[1,2-f]phenanthridine

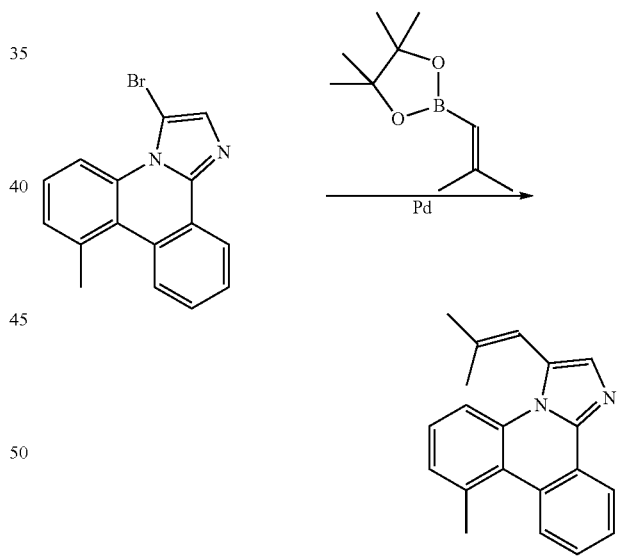

A mixture of 3-bromo-8-methylimidazo[1,2-f]phenanthridine (12 g, 38.5 mmol, 1 equiv), 4,4,5,5-tetramethyl-2-(2-methylprop-1-en-1-yl)-1,3,2-dioxaborolane (10.5 g, 58 mmol, 1.5 equiv), and potassium carbonate (16 g, 115.5 mmol, 3 equiv) in a 5 to 1 mixture of 1,4-dioxane and water (185 mL) was sparged with nitrogen for 15 minutes. (Chloro (2-dicyclohexylphosphino-2',6'-dimethoxy-1,1'-biphenyl) [2-(2'-amino-1,1'-biphenyl)]palladium(II) (4.16 g, 5.78 mmol, 0.15 equiv) and 2-dicyclohexylphosphino-2',6'-dimethoxybiphenyl (2.38 g, 5.78 mmol, 0.15 equiv) were added and the reaction was refluxed for 36 hours. After cooling to room temperature, the reaction was diluted with water (200 mL). The layers were separated and the aqueous was extracted with ethyl acetate (3×200 mL). The combined organics layers were dried over sodium sulfate and concentrated under reduced pressure. The crude solid was purified by column chromatography to give 8-methyl-3-(2-methyl-prop-1-en-1-yl)imidazo[1,2-f]phenanthridine (8.5 g, 70% yield, 90% purity) as a light brown solid.

E. Synthesis of 4,4,7-Trimethyl-3,4-dihydrodibenzo[b,ij]imidazo[2,1,5-de]quinolizine

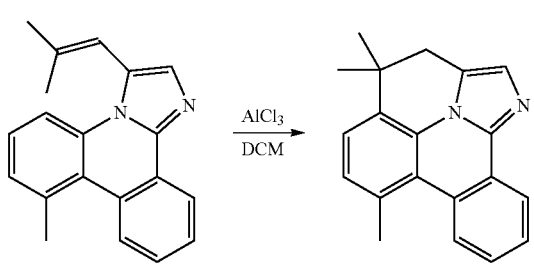

A mixture of 8-methyl-3-(2-methylprop-1-en-1-yl)imidazo[1,2-f]phenanthridine (1.6 g, 5.69 mmol, 1 equiv) and anhydrous aluminum chloride (3.8 g, 28.4 mmol, 5 equiv) in dichloromethane (57 mL) were stirred at room temperature for 16 hours. The reaction was cooled in an ice bath and water (10 mL) was added dropwise. The layers were separated and the aqueous layer was extracted with dichloromethane (3×50 mL). The combined organic layers were dried over sodium sulfate and concentrated under reduced pressure. The crude solids purified by column chromatography to give 4,4,7-Trimethyl-3,4-dihydrodibenzo[b,ij]imidazo[2,1,5-de]quinolizine (1.43 g, 88% yield, 98% purity) as a light yellow solid.

F. Synthesis of 2-Bromo-4,4,7-trimethyl-3,4-dihydrodibenzo[b,ij]imidazo[2,1,5-de]quinolizine

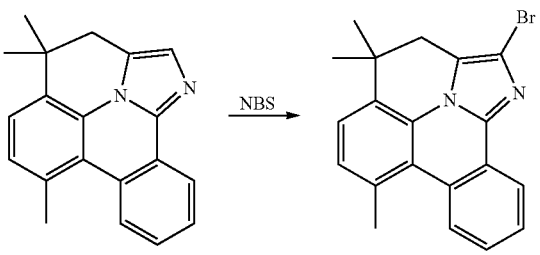

A mixture of 4,4,7-Trimethyl-3,4-dihydrodibenzo[b,ij]imidazo[2,1,5-de]quinolizine (500 mg, 1.75 mmol, 1 equiv) and N-bromosuccinimide (311 mg, 1.75 mmol, 1 equiv) in dichloromethane (11 mL) was stirred at room temperature for 2 hours. The reaction was diluted with water (20 m L) and dichloromethane (10 mL). The layers were separated and the aqueous were extracted with dichloromethane (3×20 mL). The combined organic layers were dried over sodium sulfate and concentrated under reduced pressure. The residue was purified by column chromatography to give 2-bromo-4,4,7-trimethyl-3,4-dihydrodibenzo[b,ij]imidazo[2,1,5-de]quinolizine (575 mg, 90% yield, 97% purity) as a light brown solid.

G. Synthesis of 2,4,4,7-Tetramethyl-3,4-dihydrodibenzo[b,ij]imidazo[2,1,5-de]quinolizine

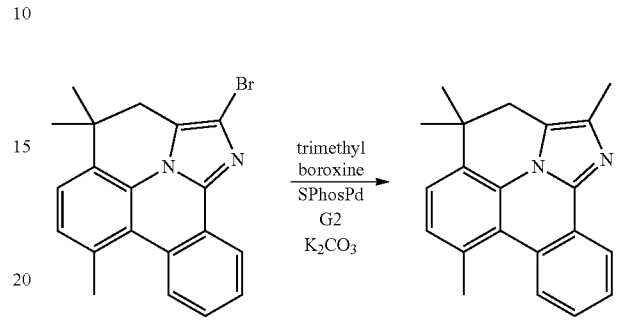

A mixture of 2-bromo-4,4,7-trimethyl-3,4-dihydrodibenzo[b,ij]imidazo[2,1,5-de]quinolizine (265 mg, 0.73 mmol, 1 equiv), trimethylboroxine (0.6 mL, 4.4 mmol, 6 equiv) and potassium carbonate (608 mg, 4.4 mmol, 6 equiv) in a 10 to 1 mixture of 1,4-dioxane and water (7 mL) was sparged with nitrogen for 15 minutes. (Chloro(2dicyclo-hexylphosphino-2',6'-dimethoxy-1,1'-biphenyl)[2-(2'-amino-1,1'-biphenyl)] palladium(II) (108 mg, 0.15 mmol, 0.2 equiv) and 2-dicyclohexylphosphino-2',6'-dimethoxybiphenyl (62 mg, 0.15 mmol, 0.2 equiv) were added and the reaction was refluxed for 16 hours. After cooling to room temperature, the reaction was diluted with water (10 mL) and ethyl acetate (10 mL). The layers were separated and the aqueous were extracted with ethyl acetate (3×20 mL). The combined organic layers were dried over sodium sulfate and concentrated under reduced pressure. The residue was purified by column chromatography to give 2,4,4,7-Tetramethyl-3,4-dihydrodibenzo[b,ij]imidazo[2,1,5-de]quinolizine (100 mg, 46% yield, 95% purity) as a pale yellow solid.

H. Synthesis of Compound 49

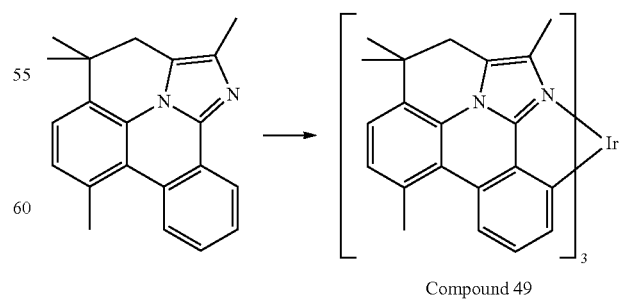

Compound 49

Compound 49 was synthesized in an analogous way to Compound 35, yielding 13 mg of yellow powder (15%).

Example 8: Synthesis of Compound 50 was Carried Out According to Scheme 8 Below

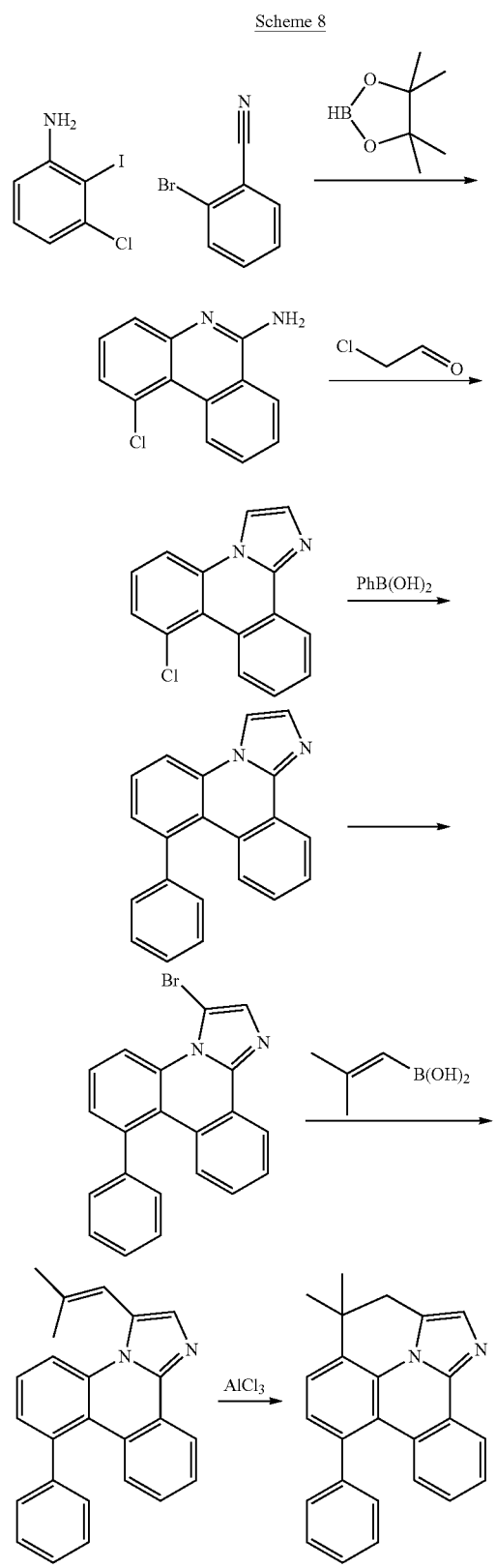

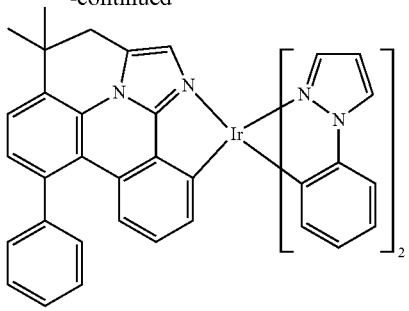

Compound 50

A. Synthesis of 1-chlorophenanthridin-6-amine

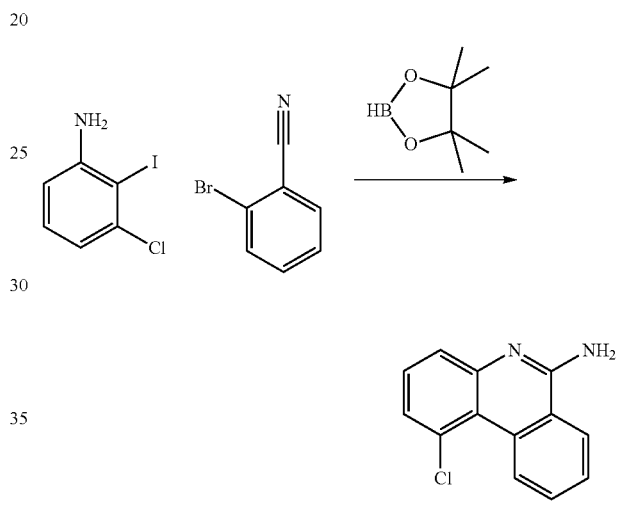

A mixture of 3-chloro-2-iodoaniline (8.77 g, 34.6 mmol), CyJohnPhos (0.462 g, 1.319 mmol), and Pd(CH$_3$CN)$_2$Cl$_2$ (0.171 g, 0.659 mmol) was dissolved in dioxane (80 ml). Triethylamine (13.78 ml, 99 mmol) and 4,4,5,5-tetramethyl-1,3,2-dioxaborolane (10.04 ml, 69.2 mmol) were added to the solution in sequence via syringe. The reaction was reflux for 4 h. The reaction was cooled to room temperature and a solid mixture of 2-bromobenzonitrile (6 g, 33.0 mmol), S-Phos Pd G2 (0.475 g, 0.659 mmol), S-Phos (0.271 g, 0.659 mmol), and potassium carbonate (9.11 g, 65.9 mmol) was added to the reaction mixture followed by dioxane (20 ml) and water (20 ml) and the reaction was heated to 85° C. for 16 hours. The crude product was extracted with DCM and vacuumed down to yield an orange oil. This was dissolved in THF (80 mL) and sodium hydride (1.978 g, 49.4 mmol) was added at 0° C. and stirred for 20 min. The reaction was quenched with brine and extracted with DCM. Evaporation of the reaction mixture followed by trituration with ether yielded 1-chlorophenanthridin-6-amine as an off-white solid (52% yield).

B. Synthesis of 8-chloroimidazo[1,2-f]phenanthridine

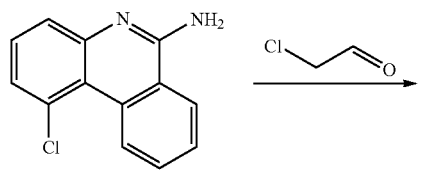

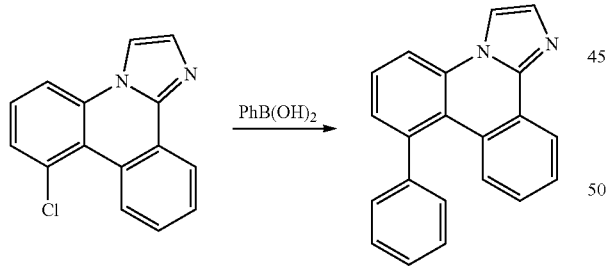

1-chlorophenanthridin-6-amine (864 mg, 3.78 mmol), 2-chloroacetaldehyde (50 wt % in water, 1.02 mL, 7.56 mmol), and sodium bicarbonate (635 mg, 7.56 mmol) were combined in iPrOH and refluxed for 1 h. The mixture was cooled to room temperature and poured into water and filtered (99% yield).

C. Synthesis of 8-phenylimidazo[1,2-f]phenanthridine

A mixture of 8-chloroimidazo[1,2-f]phenanthridine (955 mg, 3.78 mmol), phenylboronic acid (829 mg, 6.80 mmol), S-Phos Pd G2 (109 mg, 0.151 mmol), S-Phos (62.1 mg, 0.151 mmol), and potassium carbonate (522 mg, 3.78 mmol) was vacuumed and back-filled with nitrogen several times. Dioxane (20 ml) and water (4 ml) were added and refluxed for 1 h. The crude product was extracted with DCM and brine and purified by column chromatography to yield product (99% yield).

D. Synthesis of 3-bromo-8-phenylimidazo[1,2-f]phenanthridine

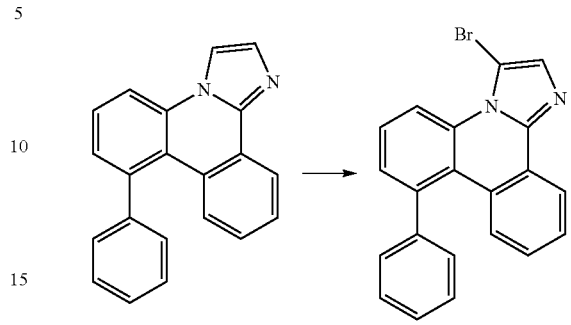

8-phenylimidazo[1,2-f]phenanthridine (1.15 mg, 3.91 mmol) and NBS (0.765 g, 4.30 mmol) were combined in DMF and stirred at room temperature for 30 minutes, followed by quenching with water. The resultant solid was filtered and dried in vacuum, yielding 3-bromo-8-phenylimidazo[1,2-f]phenanthridine in 75% yield.

E. Synthesis of 3-(2-methylprop-1-en-1-yl)-8-phenylimidazo[1,2-f]phenanthridine

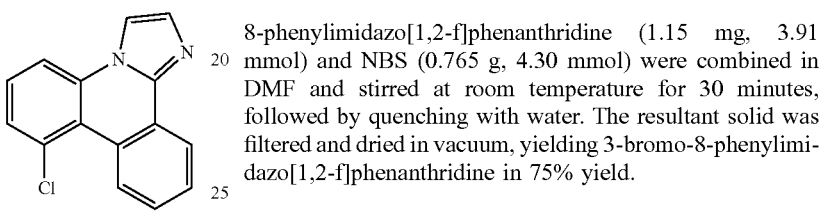

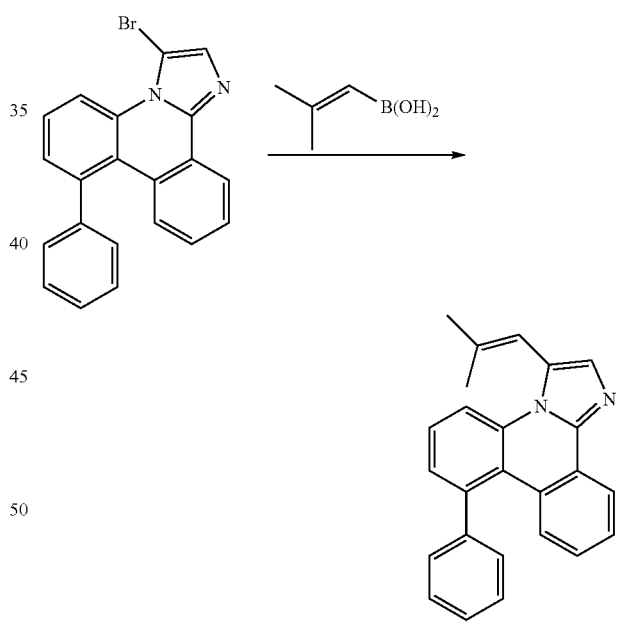

A mixture of 3-bromo-8-phenylimidazo[1,2-f]phenanthridine (980 mg, 2.63 mmol), SPhos Pd G2 (76 mg, 0.105 mmol), SPhos (43.1 mg, 0.105 mmol), and potassium carbonate (363 mg, 2.63 mmol) was vacuumed and back-filled with nitrogen several times. Toluene (15 ml), Water (3 ml), and 4,4,5,5-tetramethyl-2-(2-methylprop-1-en-1-yl)-1,3,2-dioxaborolane (1.077 ml, 5.25 mmol) were added and heated at reflux for 16 hours. The product was extracted with DCM and brine and purified by column chromatography to give 3-(2-methylprop-1-en-1-yl)-8-phenylimidazo[1,2-f]phenanthridine in 20% yield.

F. Synthesis of 4,4-dimethyl-7-phenyl-3,4-dihydrodibenzo[b,ij]imidazo[2,1,5-de]quinolizine

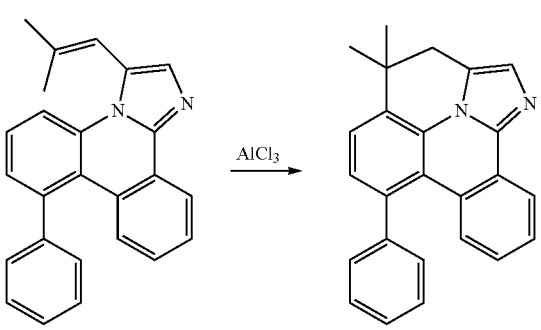

3-(2-methylprop-1-en-1-yl)-8-phenylimidazo[1,2-f]phenanthridine (160 mg, 0.459 mmol) was dissolved in DCM (10 ml) and aluminum trichloride (184 mg, 1.378 mmol) was added. The reaction was stirred for 40 min at room temperature. The mixture was quenched with KOH(aq)/brine and extracted several times with DCM. The product was purified by column chromatography to give 4,4-dimethyl-7-phenyl-3,4-dihydrodibenzo[b,ij]imidazo[2,1,5-de]quinolizine in 63% yield.

G. Synthesis of Compound 50

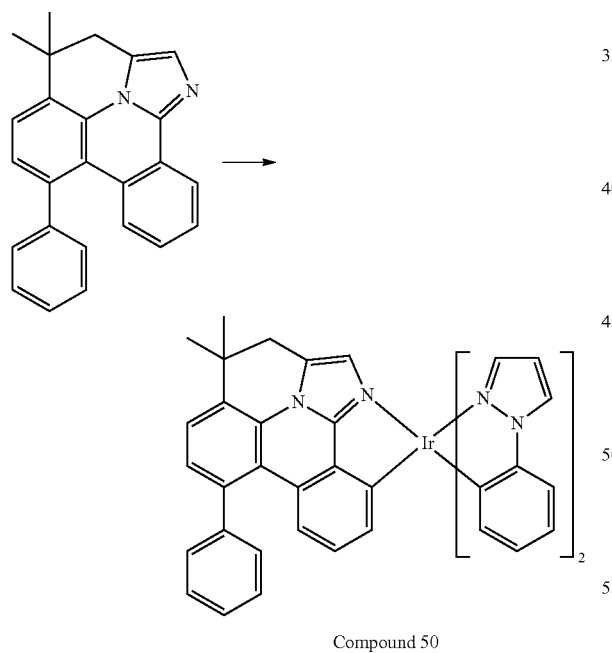

Compound 50

(3-phenyl-1H-pyrazole)$_2$Ir(MeOH)$_2$(OTf) from Example 4 (0.03 g, 0.043 mmol) and 4,4-dimethyl-7-phenyl-3,4-dihydrodibenzo[b,ij]imidazo[2,1,5-de]quinolizine (0.030 g, 0.087 mmol) were combined in 2-ethoxyethanol (0.5 ml), vacuum/backfilled quickly three times with nitrogen, then heated at reflux under nitrogen for 2 h. The product was purified by column chromatography to give Compound 50 in 56% yield.

Example 9: Synthesis of Compound 108 was Carried Out According to Scheme 8 Below Scheme 9

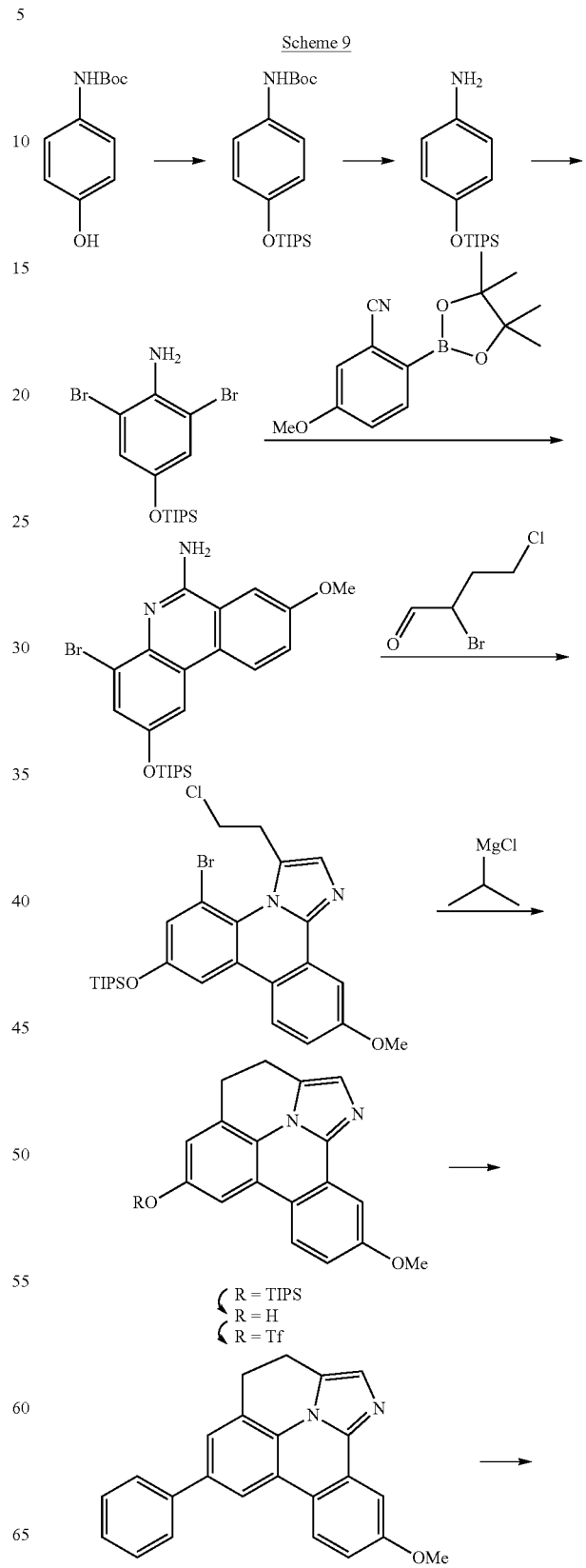

281
-continued

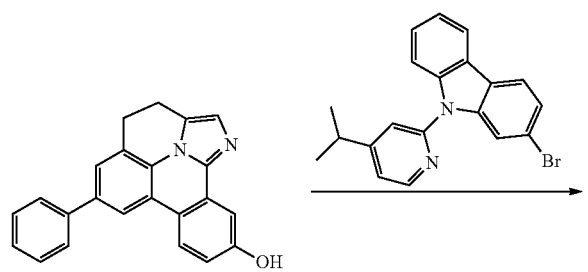

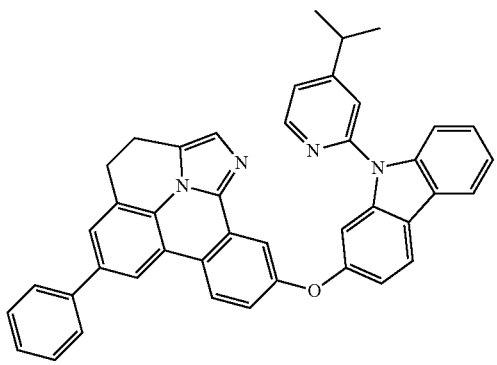

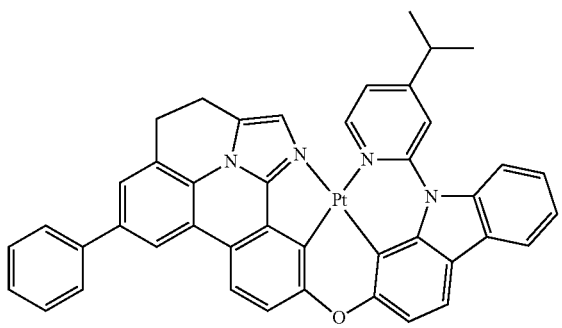

A. Synthesis of tert-Butyl (4-((triisopropylsilyl)oxy)phenyl)carbamate

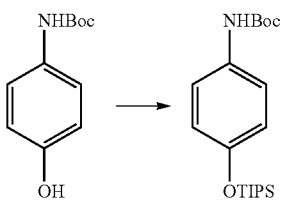

Triisopropylchlorosilane (32 mL, 0.15 mol, 1.2 equiv) and triethylamine (21 mL, 0.15 mol, 1.2 equiv) were sequentially added to a solution of tert-butyl(4-hydroxyphenyl)carbamate (26.1 g, 0.125 mol, 1 equiv) in THF (200 mL). The reaction mixture was stirred for 16 hours at room temperature. The reaction was filtered and the solids were washed with THF (2×30 mL). The combined filtrates were concentrated under reduced pressure. The crude product was purified by column chromatography to give tert-Butyl (4-((triisopropylsilyl)oxy)phenyl)carbamate (39.66 g, 87% yield) as yellow oil.

282
B. Synthesis of 4-((Triisopropylsilyl)oxy)aniline

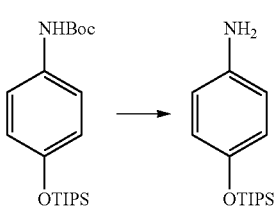

Trifluoroacetic acid (41.51 mL, 0.54 mol, 5 equiv) was added at room temperature to a solution of tert-Butyl (4-((triisopropylsilyl)oxy)phenyl)carbamate (39.66 g, 0.1085 mol, 1 equiv) in dichloromethane (400 mL). After stirring for 16 hours the solvent was removed under reduced pressure. The residue was azeotroped with toluene (3×50 mL). The crude product was purified over silica to give 4-((Triisopropylsilyl)oxy)aniline (25 g, 87% yield).

C. Synthesis of 2,6-Dibromo-4-((triisopropylsilyl)oxy)aniline

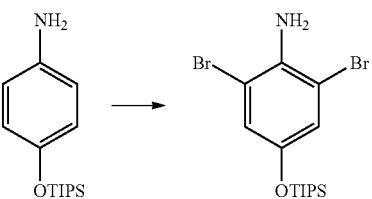

Bromine (8.2 mL, 0.16 mol, 2.5 equiv) was added dropwise at 0° C. to a solution of 4-((Triisopropylsilyl)oxy)aniline (17 g, 64.4 mmol, 1 equiv) in a 1:1 mixture of dichloromethane and methanol (60 mL). The reaction mixture was allowed to warm up to room temperature and stirred for 16 hours. The reaction mixture was diluted with dichloromethane (200 mL) and washed sequentially with 1M NaOH (2×100 mL) and saturated brine (2×100 mL). The organic layer was dried over sodium sulfate and concentrated under reduced pressure to give 2,6-Dibromo-4-((triisopropylsilyl)oxy)aniline (26.37 g, 97% yield) as a brown oil, which was used subsequently.

D. Synthesis of 4-Bromo-8-methoxy-2-((triisopropylsilyl)oxy)phenanthridin-6-amine

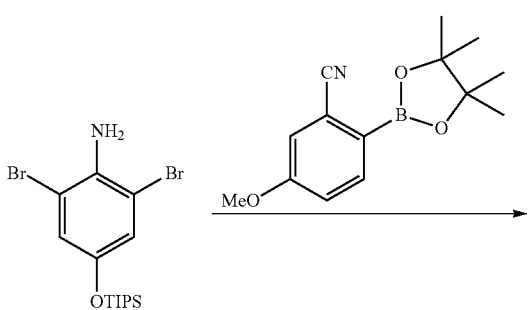

-continued

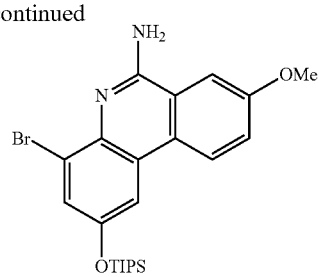

A mixture of 5-methoxy-2-(4,4,5,5-tetramethyl-1,3,2-dioxaborolan-2-yl)benzonitrile (16.14 g, 62.3 mmol, 1 equiv), 51 (26.37 g, 62.3 mmol, 1 equiv) and potassium phosphate (43.04 g, 0.187 mol, 3 equiv) in a 4 to 1 mixture of toluene and water (500 mL) was sparged with nitrogen for 1 hour. trans-Pd(PPh$_3$)$_2$Cl$_2$ (2.8 g, 3.11 mmol, 0.05 equiv) was added and the reaction mixture was refluxed for 20 hours. Additional 5-methoxy-2-(4,4,5,5-tetramethyl-1,3,2-dioxaborolan-2-yl)benzonitrile (2.2 g, 8.5 mmol, 0.14 equiv) and trans-Pd(PPh$_3$)$_2$Cl$_2$ (0.3 g, 0.43 mmol, 0.0069 equiv) were added and the reaction mixture was refluxed for an additional 4 hours. The layers were separated and the organic layer was washed with hot water (2×200 mL). The organic layer was dried over sodium sulfate and concentrated under reduced pressure. The residue was purified by column chromatography to yield 4-bromo-8-methoxy-2-((triisopropylsilyl)oxy)phenanthridin-6-amine in 20% yield.

E. Synthesis of 5-Bromo-3-(2-chloroethyl)-11-methoxy-7-((triisopropylsilyl)oxy)imidazo[1,2-f]phenanthridine

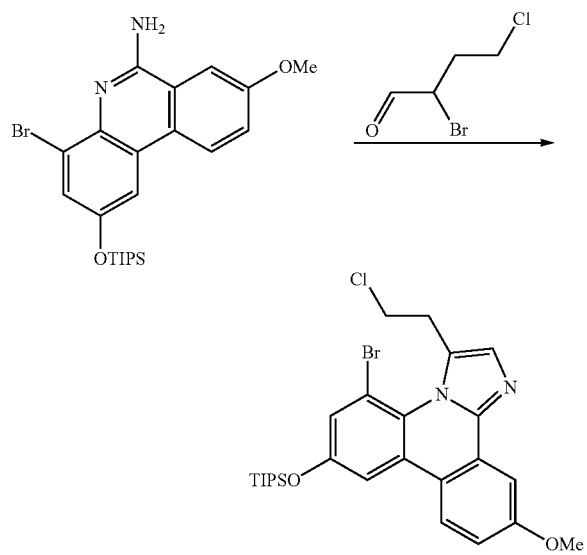

A suspension of 4-bromo-8-methoxy-2-((triisopropylsilyl)oxy)phenanthridin-6-amine (5.95 g, 12.53 mmol, 1 equiv), p-toluenesulfonic acid monohydrate (175 mg) and fresh prepared 2 (6.67 g, 62.63 mmol, 5 equiv) in i-propanol (500 mL) was stirred at the room temperature for 2 hours. Sodium carbonate (3.25 g, 37.6 mmol, 3 equiv) and deionized water (12 ml) were added and the reaction mixture was refluxed for 16 hours. After cooling to room temperature, the volume of reaction mixture was reduced to ~60 ml under reduced pressure. The mixture was diluted with ethyl acetate (300 mL) and washed with saturated brine (200 mL). The organic layer was dried over sodium sulfate and concentrated under reduced pressure. The crude product was purified by column chromatography to give 5-bromo-3-(2-chloroethyl)-11-methoxy-7-((triisopropylsilyl)oxy)imidazo[1,2-f]phenanthridine (5.53 g, 79% yield).

F. Synthesis of 10-Methoxy-6-((triisopropylsilyl)oxy)-3,4-dihydrodibenzo[b,ij]imidazo[2,1,5-de]quinolizine

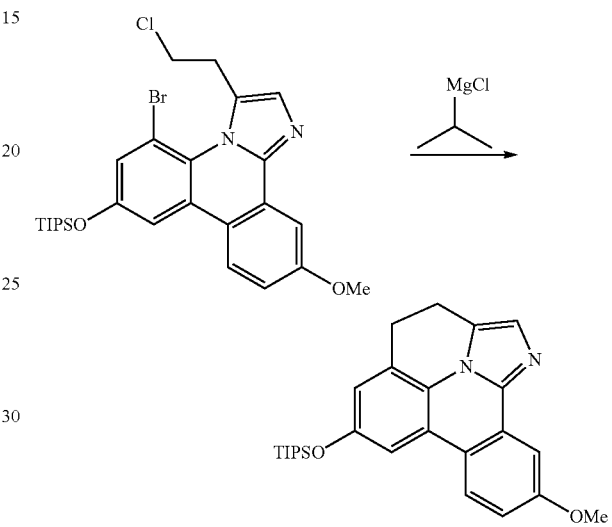

A solution of 5-bromo-3-(2-chloroethyl)-11-methoxy-7-((triisopropylsilyl)oxy)imidazo[1,2-f]phenanthridine (5.53 g, 9.84 mmol, 1.0 equiv) in dry THF (300 mL) was sparged with nitrogen for 30 minutes. After cooling to 0° C., 2M isopropylmagnesium chloride in THF (7.4 mL, 14.76 mmol, 1.5 equiv) was added dropwise via syringe. The reaction mixture was warmed to the room temperature and stirred for 16 hours. The reaction was quenched with water (10 mL) and the THF was removed under reduced pressure. The residue was extracted with dichloromethane (500 mL). The organic layer was washed with water (2×200 mL), dried over sodium sulfate and concentrated under reduced pressure. The crude product was purified by column chromatography to give 10-methoxy-6-((triisopropylsilyl)oxy)-3,4-dihydrodibenzo[b,ij]imidazo[2,1,5-de]quinolizine (3 g, 68% yield).

G. Synthesis of 10-Methoxy-3,4-dihydrodibenzo[b,ij]imidazo[2,1,5-de]quinolizin-6-ol

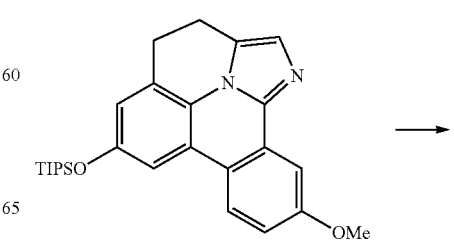

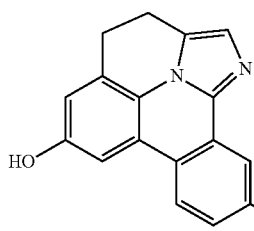

Tetrabutylammonium fluoride trihydrate in THF (30 mL) was added dropwise to a solution of 10-methoxy-6-((triisopropylsilyl)oxy)-3,4-dihydrodibenzo[b,ij]imidazo[2,1,5-de]quinolizine (3 g, 6.72 mmol, 1 equiv) in THF (100 mL). After stirring at room temperature for 16 hours, the solvent was removed under reduced pressure and the residue was extracted with dichloromethane. (80 mL). The organic layer was washed with saturated brine (2×100 mL). Upon washing with saturated brine, a large precipitate started to form in the organic layer. The precipitation was filtered and washed with heptanes (2×10 mL) to give pure 10-methoxy-3,4-dihydrodibenzo[b,ij]imidazo[2,1,5-de]quinolizin-6-ol (1.83 g, 94% yield).

H. Synthesis of 10-Methoxy-3,4-dihydrodibenzo[b,ij]imidazo[2,1,5-de]quinolizin-6-yl trifluoromethanesulfonate

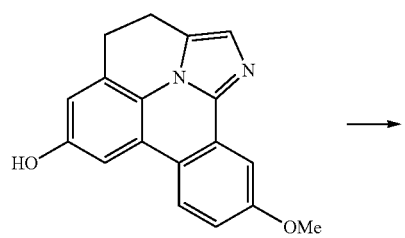

Trifluoroacetic anhydride (1.14 mL, 6.77 mmol, 1.1 equiv) and pyridine (0.744 mL, 9.24 mmol, 1.5 equiv) were sequentially added at 0° C. to a mixture of 10-methoxy-3,4-dihydrodibenzo[b,ij]imidazo[2,1,5-de]quinolizin-6-ol (1.79 g, 6.16 mmol, 1 equiv) in dichloromethane (100 mL). After stirring for 15 minutes, the reaction was warm to room temperature and stirred for 6 hours. The reaction mixture was diluted with dichloromethane (200 mL) and washed with water (3×100 mL). The organic layer was dried over sodium sulfate and solvent was removed under reduced pressure. The residue was triturated with a 10 to 1 mixture of heptanes and dichloromethane (10 mL) to give 10-methoxy-3,4-dihydrodibenzo[b,ij]imidazo[2,1,5-de]quinolizin-6-yl trifluoromethanesulfonate (2.17 g, 83% yield).

I. Synthesis of 10-Methoxy-6-phenyl-3,4-dihydrodibenzo[b,ij]imidazo[2,1,5-de]quinolizine

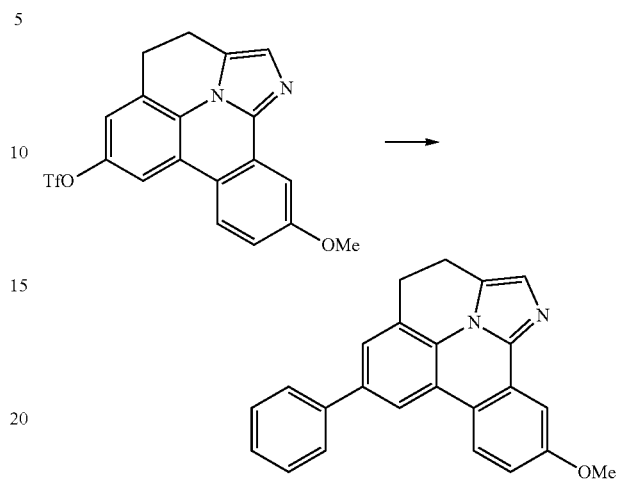

A mixture of 10-methoxy-3,4-dihydrodibenzo[b,j]imidazo[2,1,5-de]quinolizin-6-yl trifluoromethanesulfonate (0.65 g, 1.54 mmol, 1 equiv), phenylboronic acid (0.188 g, 1.54 mmol, 1 equiv) and potassium phosphate (1.06 g, 4.62 mmol, 3 equiv) in a 3:1:1 mixture of toluene: 1,4-dioxane: water (500 mL) was sparged with nitrogen for 1 hour. Trans-Pd(PPh$_3$)$_2$Cl$_2$ (54 mg, 0.077 mmol, 0.05 equiv) was added and the reaction mixture was refluxed for 16 hours. The reaction mixture was diluted with dichloromethane (200 mL). The organic layer was washed with warm water (2×100 mL), dried over sodium sulfate and concentrated under reduced pressure to give 10-methoxy-6-phenyl-3,4-dihydrodibenzo[b,ij]imidazo[2,1,5-de]quinolizine (0.527 g, 97% yield).

J. Synthesis of 6-Phenyl-3,4-dihydrodibenzo[b,ij]imidazo[2,1,5-de]quinolizin-10-ol

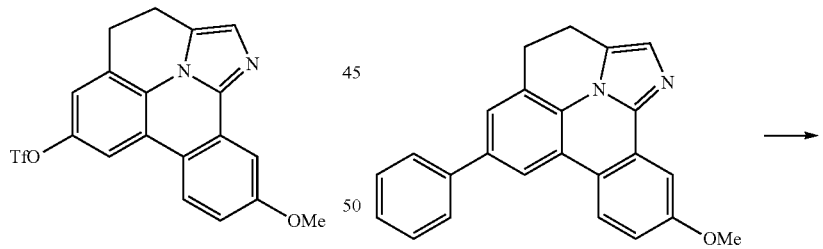

1M Boron tribromide in dichloromethane (7.5 mL, 7.5 mmol, 5 equiv) was added dropwise at −78° C. to a solution of 10-methoxy-6-phenyl-3,4-dihydrodibenzo[b,ij]imidazo[2,1,5-de]quinolizine (0.527 g, 1.5 mmol, 1 equiv) in dichloromethane (100 mL). The reaction warmed to the room temperature and stirred for 16 hours. The reaction mixture was carefully poured in ice water (150 mL) and the resulting solid was filtered and washed sequentially with water (30 ml) and heptanes (10 mL) to give 6-phenyl-3,4-dihydrodibenzo[b,ij]imidazo[2,1,5-de]quinolizin-10-ol (0.47 g, 93% yield).

K. Synthesis of 10-((9-(4-Isopropylpyridin-2-yl)-9H-carbazol-2-yl)oxy)-6-phenyl-3,4-dihydro-dibenzo[b, j]imidazo[2,1,5-de]quinolizine

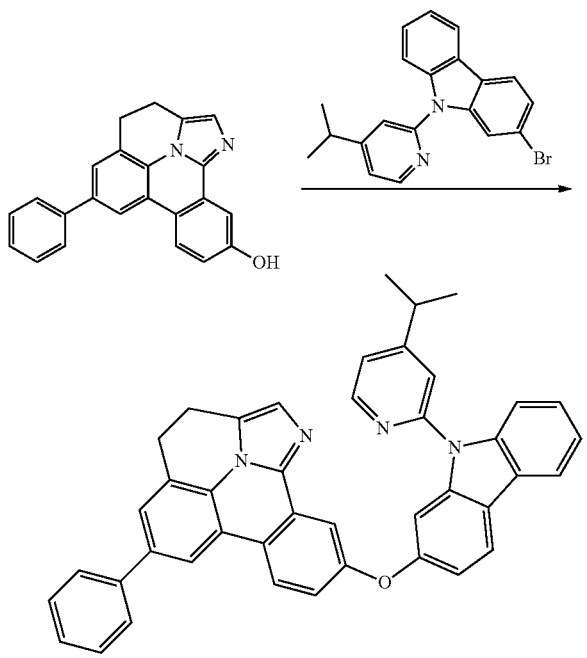

A mixture of 2-Bromo-9-(4-isopropylpyridin-2-yl)-9H-carbazole (0.528 g, 1.446 mmol, 1 equiv), 6-phenyl-3,4-dihydrodibenzo[b,ij]imidazo[2,1,5-de]quinolizin-10-ol (0.486 g, 1.446 mmol, 1 equiv), potassium phosphate (1.67 g, 7.23 mmol, 5 equiv), copper (I) iodide (0.138 g, 0.723 mmol, 0.5 equiv), and picolinic acid (0.445 g, 3.62 mmol, 2.5 equiv) in DMSO (50 mL) was heated at 150° C. for 4.5 hours. After cooling to room temperature, the reaction mixture was poured into water (300 mL) and extracted with ethyl acetate (4×100 mL). The combined organic layers were dried over sodium sulfate and concentrated under reduced pressure. The crude product was purified by column chromatography to give 10-((9-(4-isopropylpyridin-2-yl)-9H-carbazol-2-yl) oxy)-6-phenyl-3,4-dihydro-dibenzo[b, j]imidazo[2,1,5-de] quinolizine as a tan solid (0.55 g, 61% yield).

L. Synthesis of Compound 108

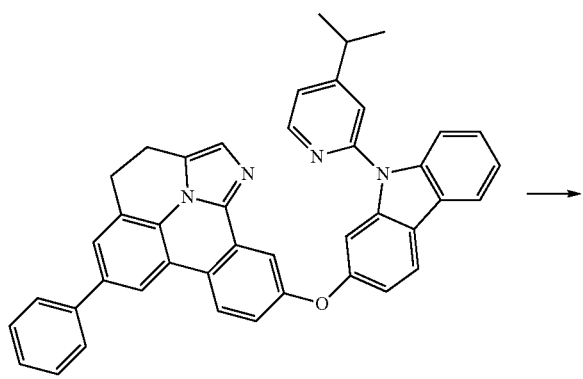

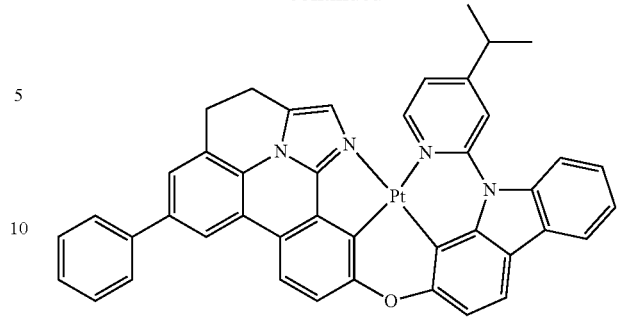

A solution of 10-((9-(4-isopropylpyridin-2-yl)-9H-carbazol-2-yl)oxy)-6-phenyl-3,4-dihydro-dibenzo[b,ij]imidazo[2,1, 5-de]quinolizine (350 mg, 0.564 mmol, 1 equiv) glacial acetic acid (60 mL) was sparged with argon for 40 minutes. $K_2PtCl_4$ (234 mg, 0.564 mmol, 1 equiv) was added and the reaction mixture was refluxed for 16 hours. After cooling to room temperature, the yellow-greenish precipitate was filtered and washed sequentially with water (4×15 mL) and heptanes (2×10 mL) and dried under vacuum at 20° C. for 18 hours. The crude product was dissolved in dichloromethane (500 mL) and passed through a plug of silica gel 10 g) to remove residual $K_2PtCl_4$. The solvent was removed under reduced pressure. The residue was triturated with a 1 to 1 mixture of dichloromethane and heptanes (20 mL), filtered and washed with dichloromethane (2×3 mL) to give Compound 108 (40 mg, yield 8.7% yield, 83.2%).

Discussion:

The general structure of one embodiment of the metal-coordinated imidazophenanthridine ligand is shown below. The bonds of interest in the computational study are the four carbon-nitrogen (C—N) single bonds. They are labeled as C—$N_1$, C—$N_2$, C—$N_{ph}$ for the nitrogen that has three single C—N bonds, and C—$N_m$ for the nitrogen that is coordinated to the metal.

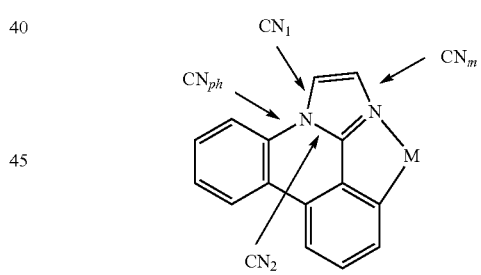

Geometry optimizations of all complexes and ligands were performed in the Gaussian 09 software package using the hybrid B3LYP functional with the CEP-31g effective core potential basis set. All results use this method unless otherwise stated in the results and discussion.

Bond strengths were calculated by breaking a bond to form a diradical species on the imidazophenanthridine ligand. The bond-broken diradical species was calculated as a triplet state as this is normally lower in energy than a diradical singlet and therefore the more likely product formed in a bond breaking event. Calculations were performed at the B3LYP/6-31g(d) level and thermodynamics reported for the ground state singlet→bond broken triplet and a lowest energy triplet (excited state)→bond broken triplet.

Calculated TD-DFT values for the lowest triplet excited state (TI) were also performed at the B3LYP/CEP-31g level of theory but included the CPCM continuum solvent field using THF as the solvent which has been shown to better match experimental results.

Bond strength calculations were performed on the following compounds:

Comparative compound 1

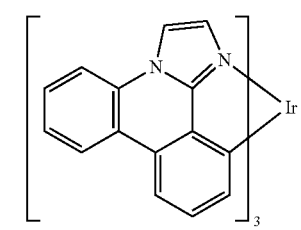

comparative compound 2

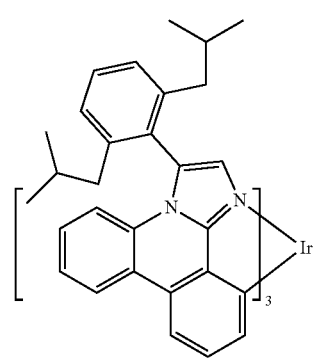

comparative compound 3

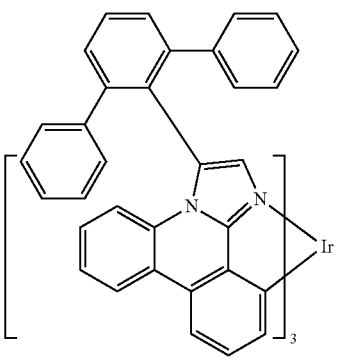

comparative compound 4

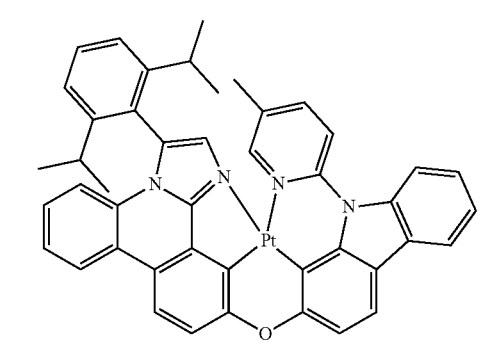

comparative compound 5

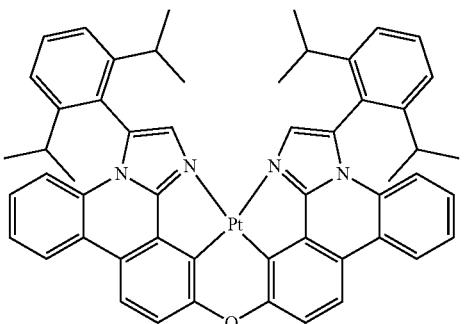

Comparative compound 6

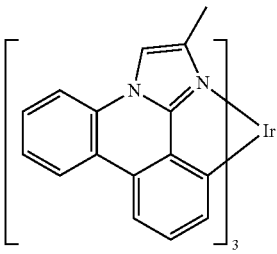

comparative compound 7

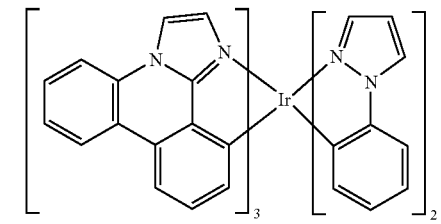

comparative compound 8

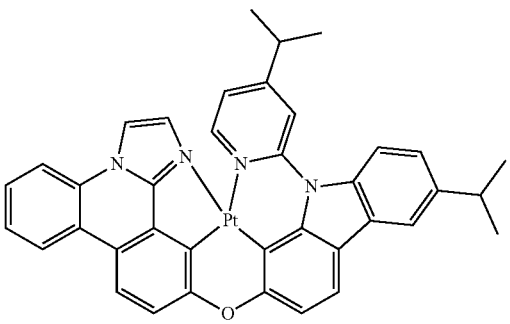

Comparative Ligand 1

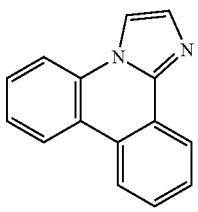

Calculated bond strengths are shown in Table 1.

TABLE 1

| | Structure | Calc T1 (nm) | C—N$_1$ bond strength (kcal/mol) | C—N$_{ph}$ bond strength (kcal/mol) | C—N$_2$ bond strength (kcal/mol) | C—N$_m$ bond strength (kcal/mol) | Weakest bond (kcal/mol) |
|---|---|---|---|---|---|---|---|
| Comparative compound 1 | 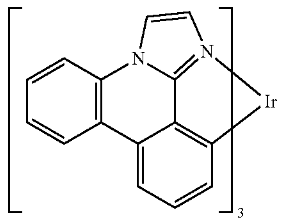 | 463 | 11.81<br>74.06 | 25.92<br>88.17 | n/a | 39.80<br>102.05 | 11.81 |
| Comparative compound 2 | 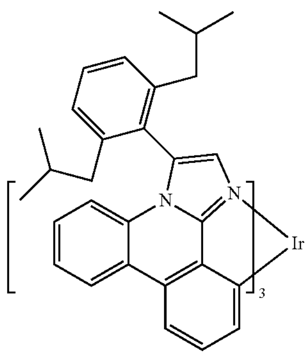 | 474 | −1.54<br>61.26 | 22.00<br>84.79 | n/a | 46.85<br>109.64 | −1.54 |
| Comparative compound 3 | 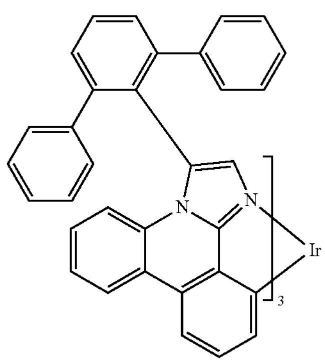 | 476 | −1.54<br>60.08 | 22.34<br>82.96 | n/a | 45.18<br>105.80 | −0.55 |
| Comparative compound 4 | 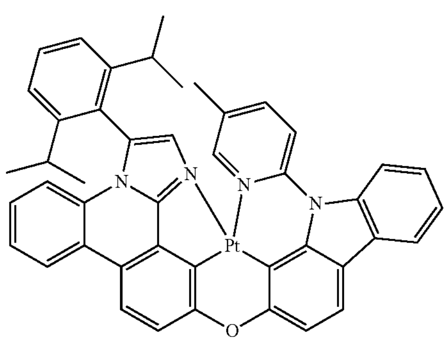 | | 5.31 | 28.66 | n/a | 45.57 | 5.31 |
| Compound 1 | 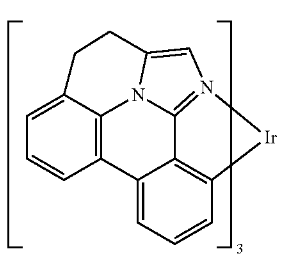 | 468 | 35.38 | 90.51 | n/a | 36.56 | 35.38 |

TABLE 1-continued

| Structure | | Calc T1 (nm) | C—N$_1$ bond strength (kcal/mol) | C—N$_{ph}$ bond strength (kcal/mol) | C—N$_2$ bond strength (kcal/mol) | C—N$_m$ bond strength (kcal/mol) | Weakest bond (kcal/mol) |
|---|---|---|---|---|---|---|---|
| Comparative ligand 1 | *structure* | 470 | 18.73 83.76 | 34.85 99.87 | n/a | 45.62 110.64 | 18.73 |
| Compound (1-3) | *structure* | 472 | 40.35 | | | | |

Table 1 shows calculated bond strengths for a series of comparative examples and invention Compound 1. Where two numbers are seen in the same cell, the top number represents the thermodynamic difference between the excited state triplet→bond broken triplet. The lower number represents the ground state singlet→bond broken triplet. If there is only one number in the cell, it represents the triplet→triplet bond strength (T→T). For all comparative compounds 1-4, the C—N$_1$ bond is shown to be the weakest bond. Bond strengths are found to be weaker in the excited triplet state compared to the ground state singlet. This is due to the complex having the energy of the excited state available as the starting point to the, generally, higher energy bond broken state. In some cases, as shown for comparative compound 2 and 3, the bond broken state is lower in energy than the starting triplet state. Therefore a bond breaking event may be considered thermodynamically favorable or exothermic. It is found that when aryl substitutions are added at the C—N$_1$ bond carbon atom, the bond strength decreases, as seen comparing comparative compound 1 to comparative compounds 2 and 3. This effect may be due to resonance stabilization of the radical species at the bond breaking site which is stabilized by the aryl substitution.

Stabilization of the weak C—N$_1$ bond can be achieved by a linking substitution that links the C—N$_1$ carbon to the carbon on the adjacent fused aryl ring as depicted by "A" in Formula (1a). This linking group is preferably comprised of elements that provide the proper structural geometry to form a bridge across the two carbons of the phenanthridine ring system, providing the necessary rigidity to stabilize the C—N$_1$ bond while not lowering the triplet energy of the resulting ligand and complex.

The effect of the stabilizing linker is shown in Table 1 for invention Compound 1. Here the triplet C—N$_1$ bond strength has greatly improved from 11.81 kcal/mol, for the analogous comparative Compound 1, to 35.38 kcal/mol for the invention compound, an increase in theromodynmic bond strength of >20 kcal/mol. The two carbon linking substituent prevents the ligand from being able to obtain the appropriate relaxed geometry of a CN$_1$ bond broken state.

Importantly, the triplet energy is not affected by this substitution as both invention Compound 1 and Comparative Compound 1 both have identical triplet energies of 468 nm by calculation.

Figure 3A:
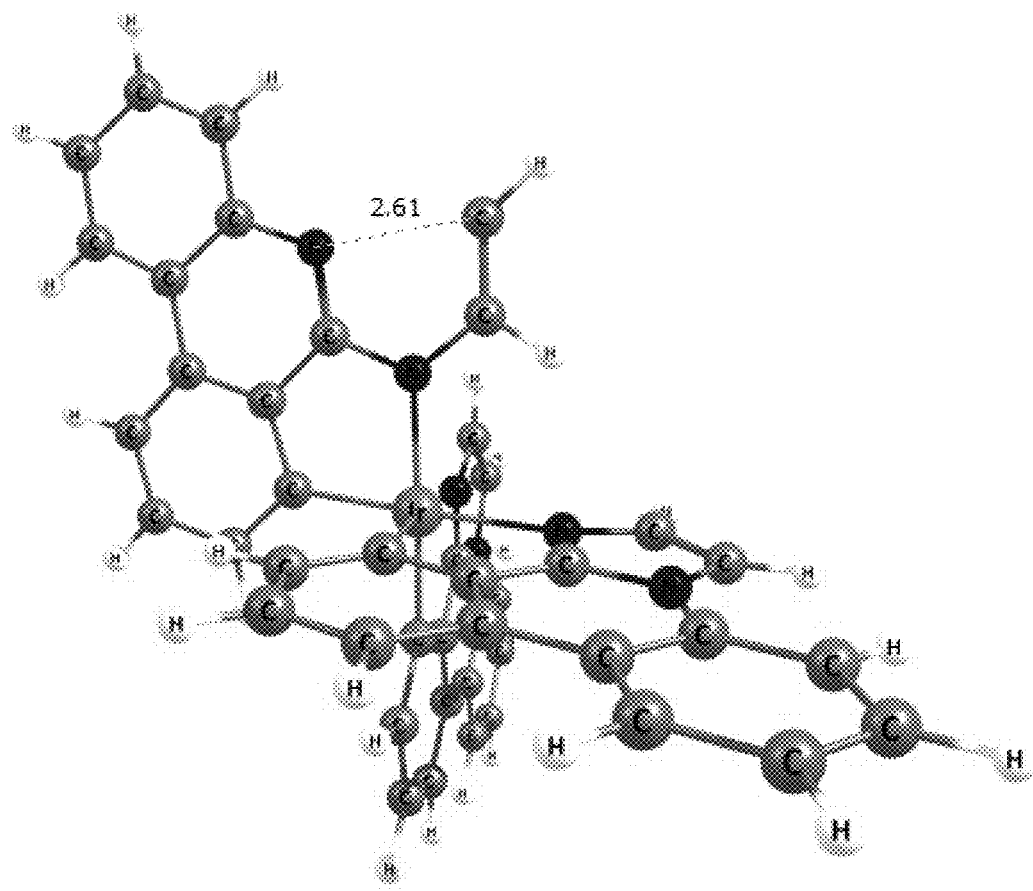
FIGS. 3a and 3b illustrate a computational model of minimized bond-broken geometry (top) and minimized nonbond broken geometry (bottom) for comparative example 1.
Figure 3B:
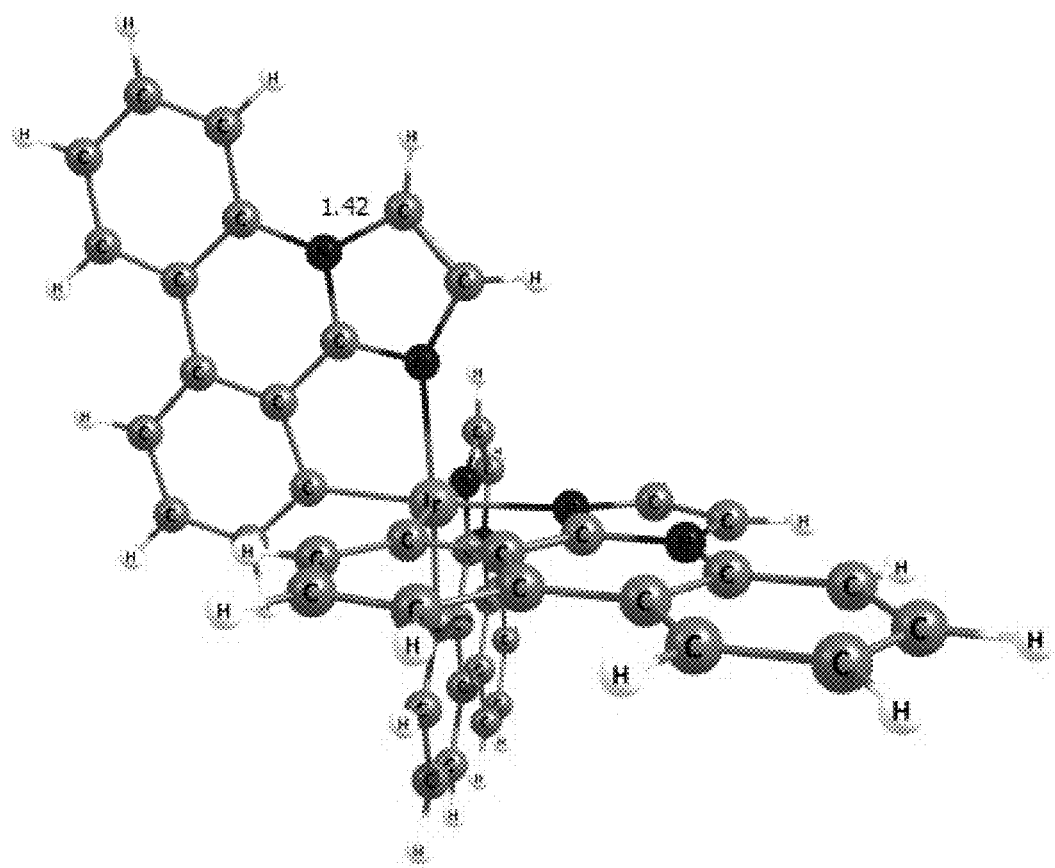

The minimized non bond-broken and bond-broken geometries of comparative example 1 are shown in FIGS. 3a and 3b. It can be seen that the bond broken geometry relaxes the ring strain of the fused ring system of the imidazophenanthridine ligand. The tethering substitution, as shown for invention Compound 1, inhibits the relaxed bond broken geometry, thereby increasing the thermodynamic bond strength of the C—N$_1$ bond.

Figure 4:
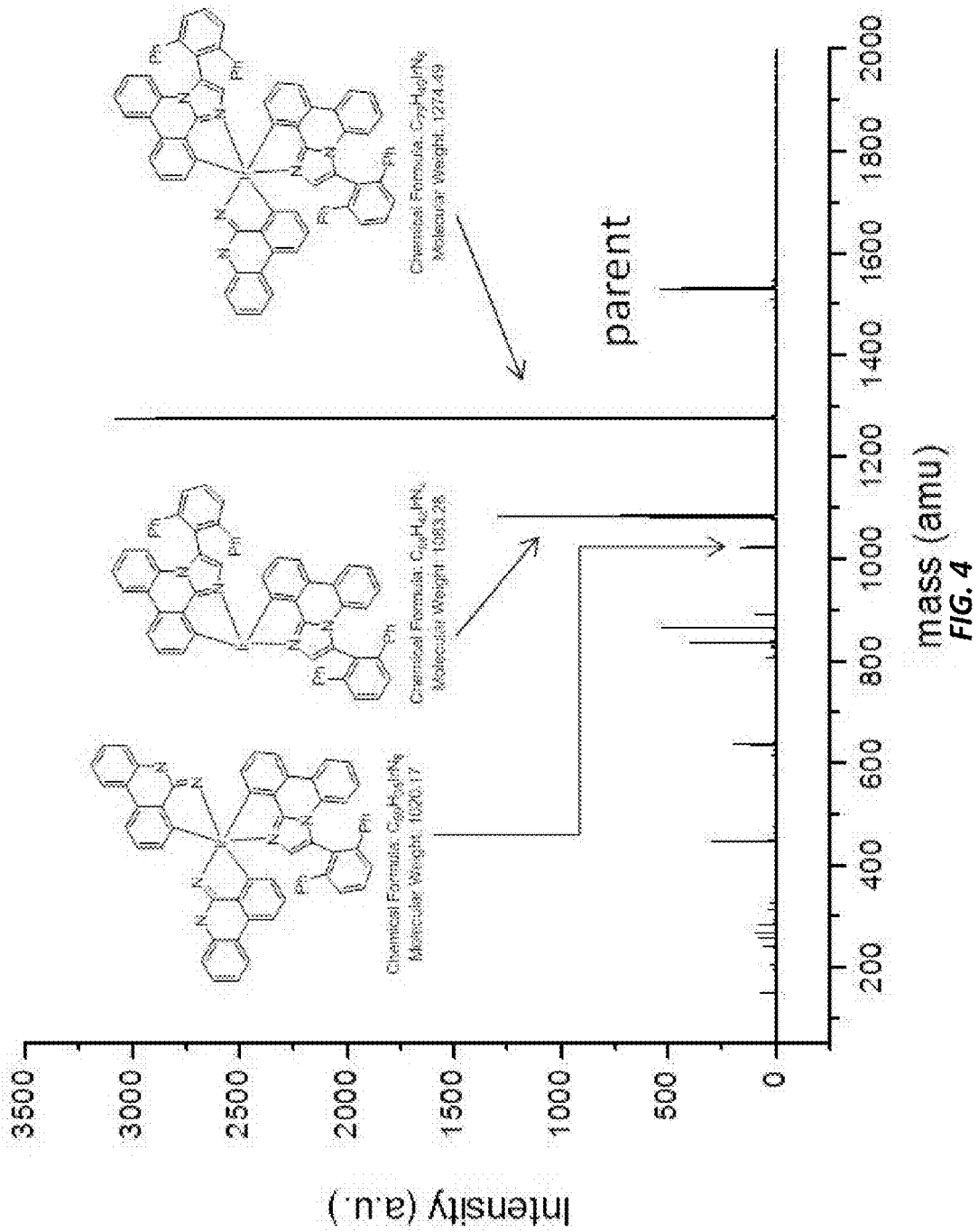
FIG. 4 illustrates a MALDI negative mode mass spectrum for comparative compound 4. The highest intensity peak corresponds to fragmentation of the imidazole ring.

Further experimental evidence of the weakness of the C—N$_1$ bond is shown by matrix assisted laser desorption ionization mass spectroscopy (MALDI-MS). MALDI-MS can be used to probe weaknesses in bonds in the excited states of molecules. It is believed that as a measure of photochemical stability, MALDI-MS can simulate some of the conditions found inside an OLED device, where both charged and excited states are present. FIG. 3 shows the MALDI-MS taken in the negative mode for comparative compound 3. The peak for the parent ion is identified at 1529 amu. However the highest intensity peak is found at 1275 amu. This mass corresponds to a fragment of comparative compound 3 where the imidazole ring has lost the mass of two carbons and the terphenyl substitution. The structure of proposed fragment is shown in FIG. 3. The isotopic pattern confirms this fragment contains iridium and is consistent with the chemical formula of the proposed fragment. Further fragments are identified for ligand loss at 1083 amu and imidazole ring decomposition for two ligands at 1020 amu, as shown in FIG. 4. The data suggests that the formation of the major fragment requires the rupture of the C—N$_1$ bond that is predicted to be a weak bond by calculation.

Photophysical Properties of the Compounds of the Invention

The measured photophysical properties of the invention compounds are reported in the Table 2 below. Complexes were measured at 77K and at room temperature in 2-methyl tetrahydrofuran solvent at highly dilute concentrations. Photoluminescent quantum yields (PLQY, $\Phi_{PL}$) were measured at 1 wt % in polymethylmethacrylate (PMMA) solid state matrix or 0.4 wt % polystyrene (PS) solid state matrix using a Hamamatsu C9920 system equipped with a xenon lamp, integrating sphere and a model C10027 photonic multi-channel analyzer. PL transient measurements ($\tau$) were carried out by time correlated single photon counting method using a Horiba Jobin Yvon Fluorolog-3 integrated with an IBH datastation hub using a 335 nm nanoLED as the excitation source.

TABLE 2

| Compound | $\lambda_{max}$ (nm) @ 77 K | $\tau$ (μs) @ 77 K | $\lambda_{max}$ (nm) @ 298 K | $\Phi_{PL}$ PMMA | $\Phi_{PL}$ PS |
|---|---|---|---|---|---|
| Compound 35 | 451 | 5.1 | 461 | 0.05 | — |
| Compound 48 | 440 | 9.5 | 448 | 0.04 | — |
| Compound 49 | 464 | 2.9 | 467 | 0.62 | — |
| Compound 50 | — | — | — | 0.09 | — |

TABLE 2-continued

| Compound | λ_max (nm) @ 77 K | τ (μs) @ 77 K | λ_max (nm) @ 298 K | Φ_PL PMMA | Φ_PL PS |
|---|---|---|---|---|---|
| Compound 105 | 444 | 7.5 | 448 | — | 0.85 |
| Compound 106 | 448 | 6.7 | 452 | — | — |
| Comparative compound 6 | — | — | — | 0.68 | — |
| Comparative Compound 7 | — | — | — | — | 0.87 |

TABLE 2-continued

| Compound | λ_max (nm) @ 77 K | τ (μs) @ 77 K | λ_max (nm) @ 298 K | Φ_PL PMMA | Φ_PL PS |
|---|---|---|---|---|---|
| 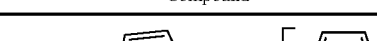  Comparative Compound 8 | 441 | 18 | 447 | 0.14 | — |

Compound 35 was measured to have deep blue emission, with a highest energy peak at 77 K of 451 nm, however, the PLQY for the complex is only 5%. Compound 49 demonstrates how modifications to the ligand can be used to improve PLQY. The methyl substitution on the imidazole ring has been found to improve the PLQY of non-ethyl bridged phenanthridine imidazole analogues. In addition, methyl substitution on the exterior phenyl ring is shown by calculation to affect the ligand bite angle due to the steric influence of the methyl substituent and the proton on the adjacent aryl ring. This steric effect pushes the phenanthridine imidazole polycyclic ring system geometry closer to the geometry of a non-bridged ligand where the coordinating sites can more closely connect to the metal. This subtle change in the geometry of the ligand allows for a stronger interaction between the metal and neutrally coordinated nitrogen, improving the metal-nitrogen bond strength. It is believed that a stronger metal-nitrogen bond strength can improve the emissivity of a complex by reducing metal-nitrogen bond breaking non-radiative decay. Therefore both methyl substitutions might be responsible for enhancing the PLQY of Compound 49 compared to Compound 35. Compound 49 was measured to have a PLQY of 62% in PMMA matrix, which is very close to the PLQY value of the non-bridged analog, Comparative Compound 6, which is measured to have a PLQY of 68%. In addition, Compound 49 is measured to have a much shorter excited state lifetime at 77 K of 2.9 microseconds, compared to an excited state lifetime of 5.1 microseconds for Compound 35. This further demonstrates that the methyl substituents improved the radiative properties of Compound 49.

Heteroleptic examples with phenylpyrazole ligands (ppz), Compound 48 and Compound 50, are measured to have deep blue emission, but low PLQY. However, the non-bridged reference compound, Comparative Compound 8, is also measured to have a low PLQY of 14%. It is believed that the low efficiency may be due to the weak metal-nitrogen bond of the pyrazole ligand. To further support this assumption, tris Ir(ppz)₃ has been shown in the literature to be non-emissive in room temperature solution, but highly emissive at 77 K. The non emissivity at room temperature is attributed to a weak metal nitrogen bond.

Platinum complexes with bridged phenanthridine imidazole ligands are also found to be highly emissive with deep blue color. Compound 105 and Comparative Compound 7 are both measured to have high PLQY values of 85% and 87%, respectively, in the optically inert polystyrene matrix. Platinum complexes may not require the ligand modifications for improving PLQY as described for the iridium analogue, Compound 49, due to a relatively stronger platinum-nitrogen bond strength compared to iridium.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that any methods of the present invention do not rely on the particular order of steps set forth herein, the particular order of the steps should not be construed as limitation on the claims. The claims directed to such methods should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

We claim:

1. A compound having a structure $(L_A)_n ML_m$ according to Formula 1:

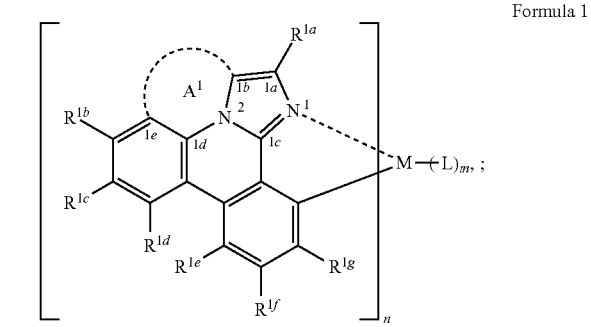

Formula 1 wherein M is a metal having an atomic weight greater than 40, n has a value of at least 1 and m+n is the maximum number of ligands that may be attached to the metal;

wherein A is a linking group selected from the group consisting of CR'R"CR'R"—, —CR'R'—CR"R"—, —CH$_2$—CH$_2$—, —CR'R'—CR'R'—CR'R'—, —CR'R"—NR'—, —CR'=CR'—CR'R'—, —O—SiR'R'—, —CR'R"—S—, —CR'R"—O—, and —CR'R"—SiR'R'—, wherein each R' is independently selected from the group consisting of H, D, alkyl, cycloalkyl, aryl, heteroaryl, and combinations thereof, wherein each R" is independently selected from the group consisting of alkyl, cycloalkyl, aryl, heteroaryl, and combinations thereof, wherein R's and R"s are optionally connected to form a saturated five membered ring or a saturated six membered ring, and combinations thereof, wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof, wherein any one of the ring atoms to which $R^{1b}$ to $R^{1g}$ are attached may be replaced with a nitrogen atom, wherein when the ring atom is replaced with a nitrogen atom the corresponding R group is not present;

wherein L is a substituted or unsubstituted cyclometallated ligand, wherein L can be joined to $R^{1g}$ through a linking group $L^2$;

wherein $L^2$ is selected from the group consisting of a single bond, BR, NR, PR, O, S, Se, C—O, S—O, SO$_2$, CR$^1$R$^2$, SiR'R$^2$, and GeR$^1$R$^2$, wherein $R^1$ and $R^2$ can be same or different, and are independently selected from the group consisting of hydrogen, deuterium, alkyl, cycloalkyl, aryl, heteroaryl, and combinations thereof;

wherein any adjacent $R^1$ and $R^2$ are optionally connected to form a saturated five membered ring or a saturated six membered ring.

2. The compound of claim 1, wherein the compound has a triplet excited state and wherein the linking group stabilizes the bond between $N^2$ and $C^{1b}$ from cleavage when the compound is in the triplet excited state.

3. The compound of claim 1, wherein the linking group is selected from the group consisting of:

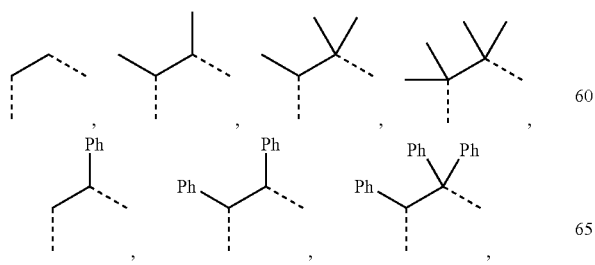

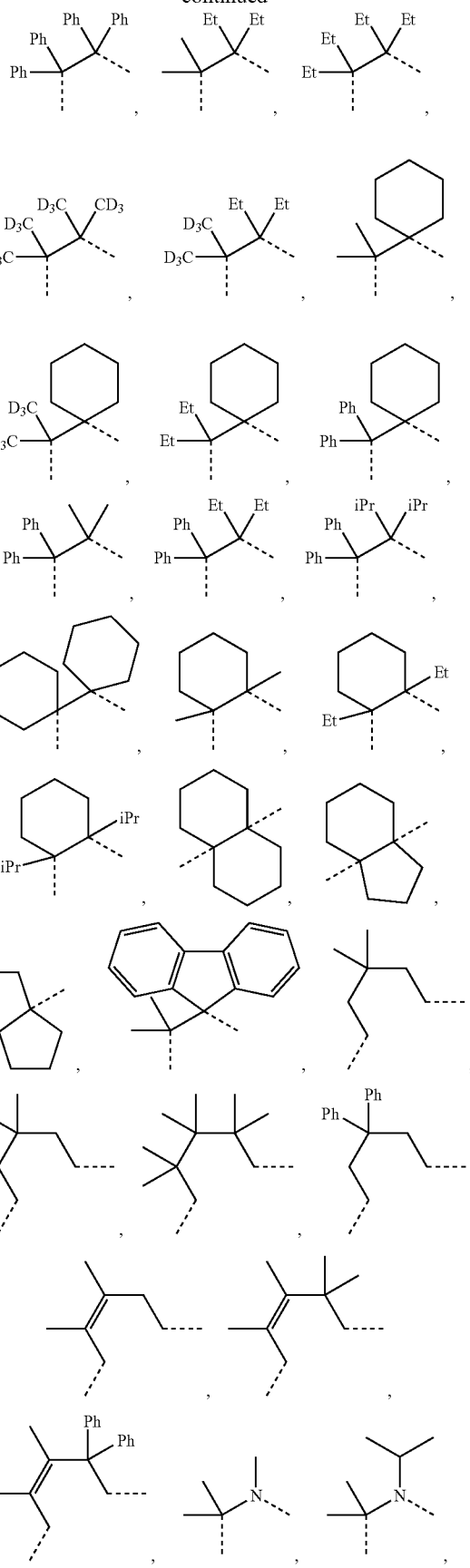

303
-continued

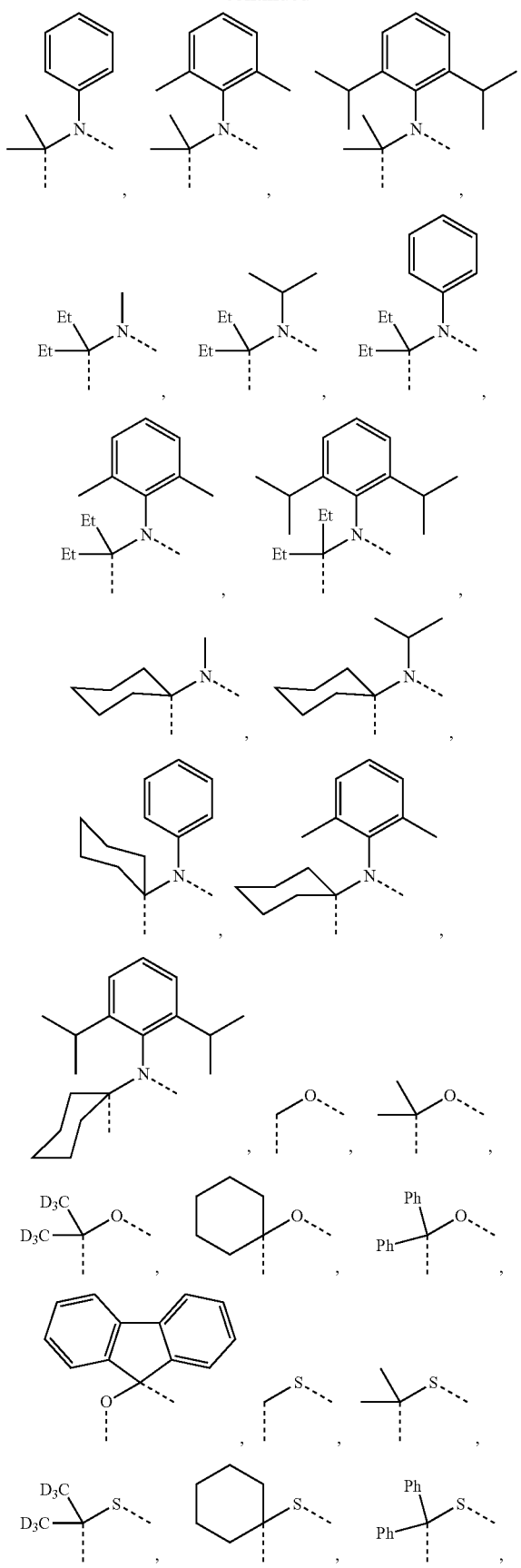

304
-continued

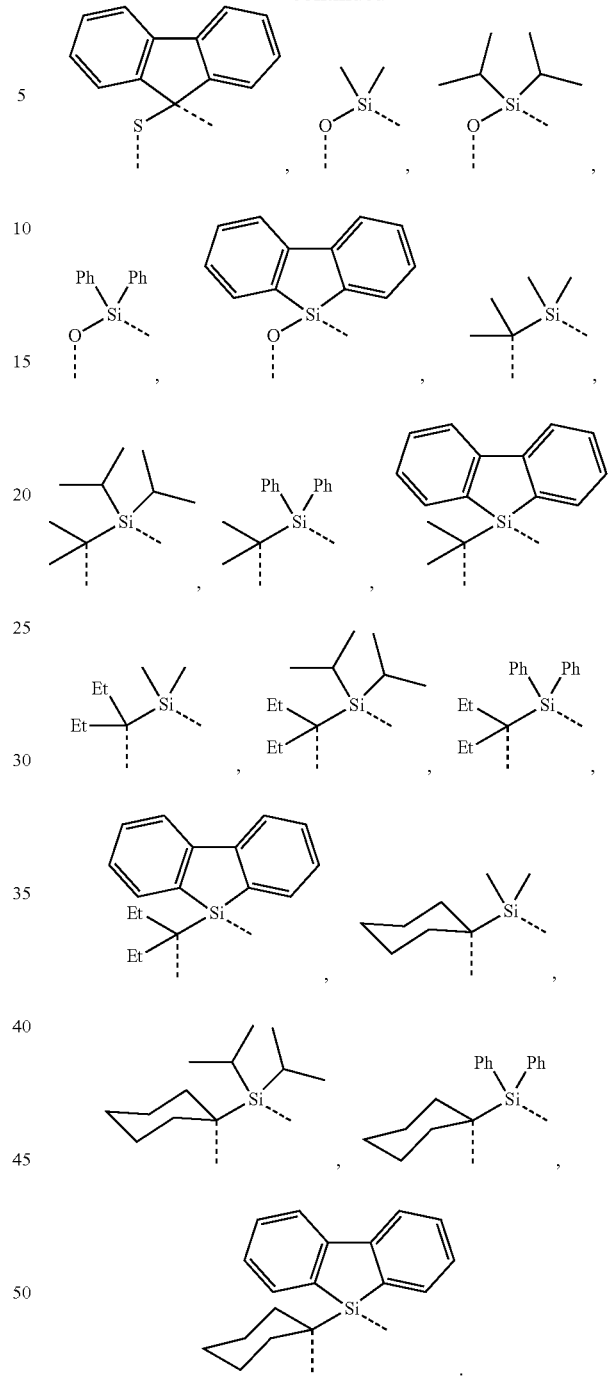

4. The compound of claim 1, wherein A is a saturated group.

5. The compound of claim 1, wherein at least one of $R^{1a}$ to $R^{1g}$ is selected from the group consisting of alkyl, cycloalkyl, aryl, heteroaryl, partially or fully deuterated variants thereof, and combinations thereof.

6. The compound of claim 1, wherein the metal is selected from the group consisting of Re, Ru, Os, Rh, Ir, Pd, Pt, and Au.

7. The compound of claim 1, wherein the ligand $L_A$ is selected from the group consisting of:

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A1$ | 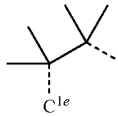 | H | H | H | H | H | H | H |
| $L_A2$ | | Me | H | H | H | H | H | H |
| $L_A3$ | | H | Me | H | H | H | H | H |
| $L_A4$ | | H | H | Me | H | H | H | H |
| $L_A5$ | | H | H | H | Me | H | H | H |
| $L_A6$ | | H | H | H | H | Me | H | H |
| $L_A7$ | | $CD_3$ | H | H | H | H | H | H |
| $L_A8$ | | H | $CD_3$ | H | H | H | H | H |
| $L_A9$ | | H | H | $CD_3$ | H | H | H | H |
| $L_A10$ | | H | H | H | $CD_3$ | H | H | H |
| $L_A11$ | | H | H | H | H | $CD_3$ | H | H |
| $L_A12$ | | $^i$Pr | H | H | H | H | H | H |
| $L_A13$ | | H | $^i$Pr | H | H | H | H | H |
| $L_A14$ | | H | H | $^i$Pr | H | H | H | H |
| $L_A15$ | | H | H | H | $^i$Pr | H | H | H |
| $L_A16$ | | H | H | H | H | $^i$Pr | H | H |
| $L_A17$ | | Ph | H | H | H | H | H | H |
| $L_A18$ | | H | Ph | H | H | H | H | H |
| $L_A19$ | | H | H | Ph | H | H | H | H |
| $L_A20$ | | H | H | H | Ph | H | H | H |
| $L_A21$ | | H | H | H | H | Ph | H | H |
| $L_A22$ | | Me | Me | H | H | H | H | H |
| $L_A23$ | | Me | H | Me | H | H | H | H |
| $L_A24$ | | Me | H | H | Me | H | H | H |
| $L_A25$ | | Me | H | H | H | Me | H | H |
| $L_A26$ | | Me | $CD_3$ | H | H | H | H | H |
| $L_A27$ | | Me | H | $CD_3$ | H | H | H | H |
| $L_A28$ | | Me | H | H | $CD_3$ | H | H | H |
| $L_A29$ | | Me | H | H | H | $CD_3$ | H | H |
| $L_A30$ | | Me | $^i$Pr | H | H | H | H | H |
| $L_A31$ | | Me | H | $^i$Pr | H | H | H | H |
| $L_A32$ | | Me | H | H | $^i$Pr | H | H | H |
| $L_A33$ | | Me | H | H | H | $^i$Pr | H | H |
| $L_A34$ | | Me | Ph | H | H | H | H | H |
| $L_A35$ | | Me | H | Ph | H | H | H | H |
| $L_A36$ | | Me | H | H | Ph | H | H | H |
| $L_A37$ | | Me | H | H | H | Ph | H | H |
| $L_A38$ | | $CD_3$ | Me | H | H | H | H | H |
| $L_A39$ | | $CD_3$ | H | Me | H | H | H | H |
| $L_A40$ | | $CD_3$ | H | H | Me | H | H | H |
| $L_A41$ | | $CD_3$ | H | H | H | Me | H | H |
| $L_A42$ | | $CD_3$ | $CD_3$ | H | H | H | H | H |
| $L_A43$ | | $CD_3$ | H | $CD_3$ | H | H | H | H |
| $L_A44$ | | $CD_3$ | H | H | $CD_3$ | H | H | H |
| $L_A45$ | | $CD_3$ | H | H | H | $CD_3$ | H | H |
| $L_A46$ | | $CD_3$ | $^i$Pr | H | H | H | H | H |
| $L_A47$ | | $CD_3$ | H | $^i$Pr | H | H | H | H |
| $L_A48$ | | $CD_3$ | H | H | $^i$Pr | H | H | H |
| $L_A49$ | | $CD_3$ | H | H | H | $^i$Pr | H | H |
| $L_A50$ | | $CD_3$ | Ph | H | H | H | H | H |
| $L_A51$ | | $CD_3$ | H | Ph | H | H | H | H |
| $L_A52$ | | $CD_3$ | H | H | Ph | H | H | H |
| $L_A53$ | 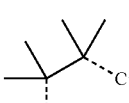 | $CD_3$ | H | H | H | Ph | H | H |
| $L_A54$ | | $^i$Pr | Me | H | H | H | H | H |
| $L_A55$ | | $^i$Pr | H | Me | H | H | H | H |
| $L_A56$ | | $^i$Pr | H | H | Me | H | H | H |
| $L_A57$ | | $^i$Pr | H | H | H | Me | H | H |
| $L_A58$ | | $^i$Pr | $CD_3$ | H | H | H | H | H |
| $L_A59$ | | $^i$Pr | H | $CD_3$ | H | H | H | H |
| $L_A60$ | | $^i$Pr | H | H | $CD_3$ | H | H | H |
| $L_A61$ | | $^i$Pr | H | H | H | $CD_3$ | H | H |
| $L_A62$ | | $^i$Pr | $^i$Pr | H | H | H | H | H |
| $L_A63$ | | $^i$Pr | H | $^i$Pr | H | H | H | H |
| $L_A64$ | | $^i$Pr | H | H | $^i$Pr | H | H | H |
| $L_A65$ | | $^i$Pr | H | H | H | $^i$Pr | H | H |
| $L_A66$ | | $^i$Pr | Ph | H | H | H | H | H |
| $L_A67$ | | $^i$Pr | H | Ph | H | H | H | H |
| $L_A68$ | | $^i$Pr | H | H | Ph | H | H | H |
| $L_A69$ | | $^i$Pr | H | H | H | Ph | H | H |
| $L_A70$ | | Ph | Me | H | H | H | H | H |
| $L_A71$ | | Ph | H | Me | H | H | H | H |
| $L_A72$ | | Ph | H | H | Me | H | H | H |
| $L_A73$ | | Ph | H | H | H | Me | H | H |
| $L_A74$ | | Ph | $CD_3$ | H | H | H | H | H |
| $L_A75$ | | Ph | H | $CD_3$ | H | H | H | H |
| $L_A76$ | | Ph | H | H | $CD_3$ | H | H | H |
| $L_A77$ | | Ph | H | H | H | $CD_3$ | H | H |
| $L_A78$ | | Ph | $^i$Pr | H | H | H | H | H |
| $L_A79$ | | Ph | H | $^i$Pr | H | H | H | H |
| $L_A80$ | | Ph | H | H | $^i$Pr | H | H | H |
| $L_A81$ | | Ph | H | H | H | $^i$Pr | H | H |
| $L_A82$ | | Ph | Ph | H | H | H | H | H |
| $L_A83$ | | Ph | H | Ph | H | H | H | H |
| $L_A84$ | | Ph | H | H | Ph | H | H | H |
| $L_A85$ | | Ph | H | H | H | Ph | H | H |
| $L_A86$ | | H | Me | Me | H | H | H | H |
| $L_A87$ | | H | Me | H | Me | H | H | H |
| $L_A88$ | | H | Me | H | H | Me | H | H |
| $L_A89$ | | H | Me | $CD_3$ | H | H | H | H |
| $L_A90$ | | H | Me | H | $CD_3$ | H | H | H |
| $L_A91$ | | H | Me | H | H | $CD_3$ | H | H |
| $L_A92$ | | H | Me | $^i$Pr | H | H | H | H |
| $L_A93$ | | H | Me | H | $^i$Pr | H | H | H |
| $L_A94$ | | H | Me | H | H | $^i$Pr | H | H |
| $L_A95$ | | H | Me | Ph | H | H | H | H |
| $L_A96$ | | H | Me | H | Ph | H | H | H |
| $L_A97$ | | H | Me | H | H | Ph | H | H |
| $L_A98$ | | H | $CD_3$ | Me | H | H | H | H |
| $L_A99$ | | H | $CD_3$ | H | Me | H | H | H |
| $L_A100$ | | H | $CD_3$ | H | H | Me | H | H |
| $L_A101$ | | H | $CD_3$ | $CD_3$ | H | H | H | H |
| $L_A102$ | | H | $CD_3$ | H | $CD_3$ | H | H | H |
| $L_A103$ | | H | $CD_3$ | H | H | $CD_3$ | H | H |
| $L_A104$ | | H | $CD_3$ | $^i$Pr | H | H | H | H |
| $L_A105$ | | H | $CD_3$ | H | $^i$Pr | H | H | H |
| $L_A106$ | | H | $CD_3$ | H | H | $^i$Pr | H | H |
| $L_A107$ | | H | $CD_3$ | Ph | H | H | H | H |
| $L_A108$ | | H | $CD_3$ | H | Ph | H | H | H |
| $L_A109$ | | H | $CD_3$ | H | H | Ph | H | H |
| $L_A110$ | | H | $^i$Pr | Me | H | H | H | H |
| $L_A111$ | | H | $^i$Pr | H | Me | H | H | H |
| $L_A112$ | | H | $^i$Pr | H | H | Me | H | H |
| $L_A113$ | | H | $^i$Pr | $CD_3$ | H | H | H | H |
| $L_A114$ | | H | $^i$Pr | H | $CD_3$ | H | H | H |
| $L_A115$ | | H | $^i$Pr | H | H | $CD_3$ | H | H |
| $L_A116$ | | H | $^i$Pr | $^i$Pr | H | H | H | H |
| $L_A117$ | | H | $^i$Pr | H | $^i$Pr | H | H | H |
| $L_A118$ | | H | $^i$Pr | H | H | $^i$Pr | H | H |
| $L_A119$ | | H | $^i$Pr | Ph | H | H | H | H |
| $L_A120$ | | H | $^i$Pr | H | Ph | H | H | H |
| $L_A121$ | | H | $^i$Pr | H | H | Ph | H | H |
| $L_A122$ | | H | Ph | Me | H | H | H | H |
| $L_A123$ | | H | Ph | H | Me | H | H | H |
| $L_A124$ | | H | Ph | H | H | Me | H | H |
| $L_A125$ | | H | Ph | $CD_3$ | H | H | H | H |
| $L_A126$ | | H | Ph | H | $CD_3$ | H | H | H |
| $L_A127$ | | H | Ph | H | H | $CD_3$ | H | H |
| $L_A128$ | | H | Ph | $^i$Pr | H | H | H | H |
| $L_A129$ | | H | Ph | H | $^i$Pr | H | H | H |
| $L_A130$ | | H | Ph | H | H | $^i$Pr | H | H |
| $L_A131$ | | H | Ph | Ph | H | H | H | H |
| $L_A132$ | | H | Ph | H | Ph | H | H | H |
| $L_A133$ | | H | Ph | H | H | Ph | H | H |
| $L_A134$ | | H | H | Me | Me | H | H | H |
| $L_A135$ | | H | H | $CD_3$ | Me | H | H | H |
| $L_A136$ | | H | H | $^i$Pr | Me | H | H | H |
| $L_A137$ | | H | H | Ph | Me | H | H | H |
| $L_A138$ | | H | H | Me | $CD_3$ | H | H | H |
| $L_A139$ | | H | H | $CD_3$ | $CD_3$ | H | H | H |
| $L_A140$ | | H | H | $^i$Pr | $CD_3$ | H | H | H |
| $L_A141$ | | H | H | Ph | $CD_3$ | H | H | H |
| $L_A142$ | | H | H | Me | $^i$Pr | H | H | H |
| $L_A143$ | | H | H | $CD_3$ | $^i$Pr | H | H | H |
| $L_A144$ | | H | H | $^i$Pr | $^i$Pr | H | H | H |
| $L_A145$ | | H | H | Ph | $^i$Pr | H | H | H |
| $L_A146$ | | H | H | Me | Ph | H | H | H |
| $L_A147$ | | H | H | $CD_3$ | Ph | H | H | H |
| $L_A148$ | | H | H | $^i$Pr | Ph | H | H | H |
| $L_A149$ | | H | H | Ph | Ph | H | H | H |
| $L_A150$ | | H | H | Me | H | Me | H | H |
| $L_A151$ | | H | H | $CD_3$ | H | Me | H | H |
| $L_A152$ | | H | H | $^i$Pr | H | Me | H | H |
| $L_A153$ | | H | H | Ph | H | Me | H | H |
| $L_A154$ | | H | H | Me | H | $CD_3$ | H | H |
| $L_A155$ | | H | H | $CD_3$ | H | $CD_3$ | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A156$ | | H | H | $^i$Pr | H | $CD_3$ | H | H |
| $L_A157$ | | H | H | Ph | H | $CD_3$ | H | H |
| $L_A158$ |  | H | H | Me | H | $^i$Pr | H | H |
| $L_A159$ | | H | H | $CD_3$ | H | $^i$Pr | H | H |
| $L_A150$ | | H | H | $^i$Pr | H | $^i$Pr | H | H |
| $L_A161$ | | H | H | Ph | H | $^i$Pr | H | H |
| $L_A162$ | | H | H | Me | H | Ph | H | H |
| $L_A163$ | | H | H | $CD_3$ | H | Ph | H | H |
| $L_A164$ | | H | H | $^i$Pr | H | Ph | H | H |
| $L_A165$ | | H | H | Ph | H | Ph | H | H |
| $L_A166$ | | Me | Me | H | Me | H | H | H |
| $L_A167$ | | H | Me | Me | Me | H | H | H |
| $L_A168$ | | $CD_3$ | Me | H | Me | H | H | H |
| $L_A169$ | | H | Me | $CD_3$ | Me | H | H | H |
| $L_A170$ | | $^i$Pr | Me | H | Me | H | H | H |
| $L_A171$ | | H | Me | $^i$Pr | Me | H | H | H |
| $L_A172$ | | Ph | Me | H | Me | H | H | H |
| $L_A173$ | | H | Me | Ph | Me | H | H | H |
| $L_A174$ | | Me | $CD_3$ | H | $CD_3$ | H | H | H |
| $L_A175$ | | H | $CD_3$ | Me | $CD_3$ | H | H | H |
| $L_A176$ | | $CD_3$ | $CD_3$ | H | $CD_3$ | H | H | H |
| $L_A177$ | | H | $CD_3$ | $CD_3$ | $CD_3$ | H | H | H |
| $L_A178$ | | $^i$Pr | $CD_3$ | H | $CD_3$ | H | H | H |
| $L_A179$ | | H | $CD_3$ | $^i$Pr | $CD_3$ | H | H | H |
| $L_A180$ | | Ph | $CD_3$ | H | $CD_3$ | H | H | H |
| $L_A181$ | | H | $CD_3$ | Ph | $CD_3$ | H | H | H |
| $L_A182$ | | Me | $^i$Pr | H | $^i$Pr | H | H | H |
| $L_A183$ | | H | $^i$Pr | Me | $^i$Pr | H | H | H |
| $L_A184$ | | $CD_3$ | $^i$Pr | H | $^i$Pr | H | H | H |
| $L_A185$ | | H | $^i$Pr | $CD_3$ | $^i$Pr | H | H | H |
| $L_A186$ | | $^i$Pr | $^i$Pr | H | $^i$Pr | H | H | H |
| $L_A187$ | | H | $^i$Pr | $^i$Pr | $^i$Pr | H | H | H |
| $L_A188$ | | Ph | $^i$Pr | H | $^i$Pr | H | H | H |
| $L_A189$ | | H | $^i$Pr | Ph | $^i$Pr | H | H | H |
| $L_A190$ | | Me | Ph | H | Ph | H | H | H |
| $L_A191$ | | H | Ph | Me | Ph | H | H | H |
| $L_A192$ | | $CD_3$ | Ph | H | Ph | H | H | H |
| $L_A193$ | | H | Ph | $CD_3$ | Ph | H | H | H |
| $L_A194$ | | $^i$Pr | Ph | H | Ph | H | H | H |
| $L_A195$ | | H | Ph | $^i$Pr | Ph | H | H | H |
| $L_A196$ | | Ph | Ph | H | Ph | H | H | H |
| $L_A197$ | | H | Ph | Ph | Ph | H | H | H |
| $L_A198$ |  | H | H | H | H | H | H | H |
| $L_A199$ | | Me | H | H | H | H | H | H |
| $L_A200$ | | H | Me | H | H | H | H | H |
| $L_A201$ | | H | H | Me | H | H | H | H |
| $L_A202$ | | H | H | H | Me | H | H | H |
| $L_A203$ | | H | H | H | H | Me | H | H |
| $L_A204$ | | $CD_3$ | H | H | H | H | H | H |
| $L_A205$ | | H | $CD_3$ | H | H | H | H | H |
| $L_A206$ | | H | H | $CD_3$ | H | H | H | H |
| $L_A207$ | | H | H | H | $CD_3$ | H | H | H |
| $L_A208$ | | H | H | H | H | $CD_3$ | H | H |
| $L_A209$ | | $^i$Pr | H | H | H | H | H | H |
| $L_A210$ | | H | $^i$Pr | H | H | H | H | H |
| $L_A211$ | | H | H | $^i$Pr | H | H | H | H |
| $L_A212$ | | H | H | H | $^i$Pr | H | H | H |
| $L_A213$ |  | H | H | H | H | $^i$Pr | H | H |
| $L_A214$ | | Ph | H | H | H | H | H | H |
| $L_A215$ | | H | Ph | H | H | H | H | H |
| $L_A216$ | | H | H | Ph | H | H | H | H |
| $L_A217$ | | H | H | H | Ph | H | H | H |
| $L_A218$ | | H | H | H | H | Ph | H | H |
| $L_A219$ | | Me | Me | H | H | H | H | H |
| $L_A220$ | | Me | H | Me | H | H | H | H |
| $L_A221$ | | Me | H | H | Me | H | H | H |
| $L_A222$ | | Me | H | H | H | Me | H | H |
| $L_A223$ | | Me | $CD_3$ | H | H | H | H | H |
| $L_A224$ | | Me | H | $CD_3$ | H | H | H | H |
| $L_A225$ | | Me | H | H | $CD_3$ | H | H | H |
| $L_A226$ | | Me | H | H | H | $CD_3$ | H | H |
| $L_A227$ | | Me | $^i$Pr | H | H | H | H | H |
| $L_A228$ | | Me | H | $^i$Pr | H | H | H | H |
| $L_A229$ | | Me | H | H | $^i$Pr | H | H | H |
| $L_A230$ | | Me | H | H | H | $^i$Pr | H | H |
| $L_A231$ | | Me | Ph | H | H | H | H | H |
| $L_A232$ | | Me | H | Ph | H | H | H | H |
| $L_A233$ | | Me | H | H | Ph | H | H | H |
| $L_A234$ | | Me | H | H | H | Ph | H | H |
| $L_A235$ | | $CD_3$ | Me | H | H | H | H | H |
| $L_A236$ | | $CD_3$ | H | Me | H | H | H | H |
| $L_A237$ | | $CD_3$ | H | H | Me | H | H | H |
| $L_A238$ | | $CD_3$ | H | H | H | Me | H | H |
| $L_A239$ | | $CD_3$ | $CD_3$ | H | H | H | H | H |
| $L_A240$ | | $CD_3$ | H | $CD_3$ | H | H | H | H |
| $L_A241$ | | $CD_3$ | H | H | $CD_3$ | H | H | H |
| $L_A242$ | | $CD_3$ | H | H | H | $CD_3$ | H | H |
| $L_A243$ | | $CD_3$ | $^i$Pr | H | H | H | H | H |
| $L_A244$ | | $CD_3$ | H | $^i$Pr | H | H | H | H |
| $L_A245$ | | $CD_3$ | H | H | $^i$Pr | H | H | H |
| $L_A246$ | | $CD_3$ | H | H | H | $^i$Pr | H | H |
| $L_A247$ | | $CD_3$ | Ph | H | H | H | H | H |
| $L_A248$ | | $CD_3$ | H | Ph | H | H | H | H |
| $L_A249$ | | $CD_3$ | H | H | Ph | H | H | H |
| $L_A250$ | | $CD_3$ | H | H | H | Ph | H | H |
| $L_A251$ | | $^i$Pr | Me | H | H | H | H | H |
| $L_A252$ | | $^i$Pr | H | Me | H | H | H | H |
| $L_A253$ | | $^i$Pr | H | H | Me | H | H | H |
| $L_A254$ | | $^i$Pr | H | H | H | Me | H | H |
| $L_A255$ | | $^i$Pr | $CD_3$ | H | H | H | H | H |
| $L_A256$ | | $^i$Pr | H | $CD_3$ | H | H | H | H |
| $L_A257$ | | $^i$Pr | H | H | $CD_3$ | H | H | H |
| $L_A258$ | | $^i$Pr | H | H | H | $CD_3$ | H | H |
| $L_A259$ | | $^i$Pr | $^i$Pr | H | H | H | H | H |
| $L_A260$ | | $^i$Pr | H | $^i$Pr | H | H | H | H |
| $L_A261$ | | $^i$Pr | H | H | $^i$Pr | H | H | H |
| $L_A262$ | | $^i$Pr | H | H | H | $^i$Pr | H | H |
| $L_A263$ | | $^i$Pr | Ph | H | H | H | H | H |
| $L_A264$ | | $^i$Pr | H | Ph | H | H | H | H |
| $L_A265$ | | $^i$Pr | H | H | Ph | H | H | H |
| $L_A266$ | | $^i$Pr | H | H | H | Ph | H | H |
| $L_A267$ | | Ph | Me | H | H | H | H | H |
| $L_A268$ | | Ph | H | Me | H | H | H | H |
| $L_A269$ | | Ph | H | H | Me | H | H | H |
| $L_A270$ | | Ph | H | H | H | Me | H | H |
| $L_A271$ | | Ph | $CD_3$ | H | H | H | H | H |
| $L_A272$ | | Ph | H | $CD_3$ | H | H | H | H |
| $L_A273$ | | Ph | H | H | $CD_3$ | H | H | H |
| $L_A274$ | | Ph | H | H | H | $CD_3$ | H | H |
| $L_A275$ | | Ph | $^i$Pr | H | H | H | H | H |
| $L_A276$ | | Ph | H | $^i$Pr | H | H | H | H |
| $L_A277$ | | Ph | H | H | $^i$Pr | H | H | H |
| $L_A278$ | | Ph | H | H | H | $^i$Pr | H | H |
| $L_A279$ | | Ph | Ph | H | H | H | H | H |
| $L_A280$ | | Ph | H | Ph | H | H | H | H |
| $L_A281$ | | Ph | H | H | Ph | H | H | H |
| $L_A282$ | | Ph | H | H | H | Ph | H | H |
| $L_A283$ | | H | Me | Me | H | H | H | H |
| $L_A284$ | | H | Me | H | Me | H | H | H |
| $L_A285$ | | H | Me | H | H | Me | H | H |
| $L_A286$ | | H | Me | $CD_3$ | H | H | H | H |
| $L_A287$ | | H | Me | H | $CD_3$ | H | H | H |
| $L_A288$ | | H | Me | H | H | $CD_3$ | H | H |
| $L_A289$ | | H | Me | $^i$Pr | H | H | H | H |
| $L_A290$ | | H | Me | H | $^i$Pr | H | H | H |
| $L_A291$ | | H | Me | H | H | $^i$Pr | H | H |
| $L_A292$ | | H | Me | Ph | H | H | H | H |
| $L_A293$ | | H | Me | H | Ph | H | H | H |
| $L_A294$ | | H | Me | H | H | Ph | H | H |
| $L_A295$ | | H | $CD_3$ | Me | H | H | H | H |
| $L_A296$ | | H | $CD_3$ | H | Me | H | H | H |
| $L_A297$ | | H | $CD_3$ | H | H | Me | H | H |
| $L_A298$ | | H | $CD_3$ | $CD_3$ | H | H | H | H |
| $L_A299$ | | H | $CD_3$ | H | $CD_3$ | H | H | H |
| $L_A300$ | | H | $CD_3$ | H | H | $CD_3$ | H | H |
| $L_A301$ | | H | $CD_3$ | $^i$Pr | H | H | H | H |
| $L_A302$ | | H | $CD_3$ | H | $^i$Pr | H | H | H |
| $L_A303$ | | H | $CD_3$ | H | H | $^i$Pr | H | H |
| $L_A304$ | | H | $CD_3$ | Ph | H | H | H | H |
| $L_A305$ | | H | $CD_3$ | H | Ph | H | H | H |
| $L_A306$ | | H | $CD_3$ | H | H | Ph | H | H |
| $L_A307$ | | H | $^i$Pr | Me | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_4 308$ | | H | $^i$Pr | H | Me | H | H | H |
| $L_4 309$ | | H | $^i$Pr | H | H | Me | H | H |
| $L_4 310$ | | H | $^i$Pr | CD$_3$ | H | H | H | H |
| $L_4 311$ | | H | $^i$Pr | H | CD$_3$ | H | H | H |
| $L_4 312$ | | H | $^i$Pr | H | H | CD$_3$ | H | H |
| $L_4 313$ | | H | $^i$Pr | $^i$Pr | H | H | H | H |
| $L_4 314$ | | H | $^i$Pr | H | $^i$Pr | H | H | H |
| $L_4 315$ | | H | $^i$Pr | H | H | $^i$Pr | H | H |
| $L_4 316$ | | H | $^i$Pr | Ph | H | H | H | H |
| $L_4 317$ | | H | $^i$Pr | H | Ph | H | H | H |
| $L_4 318$ | | H | $^i$Pr | H | H | Ph | H | H |
| $L_4 319$ | | H | Ph | Me | H | H | H | H |
| $L_4 320$ | | H | Ph | H | Me | H | H | H |
| $L_4 321$ | | H | Ph | H | H | Me | H | H |
| $L_4 322$ | | H | Ph | CD$_3$ | H | H | H | H |
| $L_4 323$ | Et, Et linker (C1b, C1e) | H | Ph | H | CD$_3$ | H | H | H |
| $L_4 324$ | | H | Ph | H | H | CD$_3$ | H | H |
| $L_4 325$ | | H | Ph | $^i$Pr | H | H | H | H |
| $L_4 326$ | | H | Ph | H | $^i$Pr | H | H | H |
| $L_4 327$ | | H | Ph | H | H | $^i$Pr | H | H |
| $L_4 328$ | | H | Ph | Ph | H | H | H | H |
| $L_4 329$ | | H | Ph | H | Ph | H | H | H |
| $L_4 330$ | | H | Ph | H | H | Ph | H | H |
| $L_4 331$ | | H | H | Me | Me | H | H | H |
| $L_4 332$ | | H | H | CD$_3$ | Me | H | H | H |
| $L_4 333$ | | H | H | $^i$Pr | Me | H | H | H |
| $L_4 334$ | | H | H | Ph | Me | H | H | H |
| $L_4 335$ | | H | H | Me | CD$_3$ | H | H | H |
| $L_4 336$ | | H | H | CD$_3$ | CD$_3$ | H | H | H |
| $L_4 337$ | | H | H | $^i$Pr | CD$_3$ | H | H | H |
| $L_4 338$ | | H | H | Ph | CD$_3$ | H | H | H |
| $L_4 339$ | | H | H | Me | $^i$Pr | H | H | H |
| $L_4 340$ | | H | H | CD$_3$ | $^i$Pr | H | H | H |
| $L_4 341$ | | H | H | $^i$Pr | $^i$Pr | H | H | H |
| $L_4 342$ | | H | H | Ph | $^i$Pr | H | H | H |
| $L_4 343$ | | H | H | Me | Ph | H | H | H |
| $L_4 344$ | | H | H | CD$_3$ | Ph | H | H | H |
| $L_4 345$ | | H | H | $^i$Pr | Ph | H | H | H |
| $L_4 346$ | | H | H | Ph | Ph | H | H | H |
| $L_4 347$ | | H | H | Me | H | Me | H | H |
| $L_4 348$ | | H | H | CD$_3$ | H | Me | H | H |
| $L_4 349$ | | H | H | $^i$Pr | H | Me | H | H |
| $L_4 350$ | | H | H | Ph | H | Me | H | H |
| $L_4 351$ | | H | H | Me | H | CD$_3$ | H | H |
| $L_4 352$ | | H | H | CD$_3$ | H | CD$_3$ | H | H |
| $L_4 353$ | | H | H | $^i$Pr | H | CD$_3$ | H | H |
| $L_4 354$ | | H | H | Ph | H | CD$_3$ | H | H |
| $L_4 355$ | | H | H | Me | H | $^i$Pr | H | H |
| $L_4 356$ | | H | H | CD$_3$ | H | $^i$Pr | H | H |
| $L_4 357$ | | H | H | $^i$Pr | H | $^i$Pr | H | H |
| $L_4 358$ | | H | H | Ph | H | $^i$Pr | H | H |
| $L_4 359$ | | H | H | Me | H | Ph | H | H |
| $L_4 360$ | | H | H | CD$_3$ | H | Ph | H | H |
| $L_4 361$ | | H | H | $^i$Pr | H | Ph | H | H |
| $L_4 362$ | | H | H | Ph | H | Ph | H | H |
| $L_4 363$ | | Me | Me | H | Me | H | H | H |
| $L_4 364$ | | H | Me | Me | Me | H | H | H |
| $L_4 365$ | | CD$_3$ | Me | H | Me | H | H | H |
| $L_4 366$ | | H | Me | CD$_3$ | Me | H | H | H |
| $L_4 367$ | | $^i$Pr | Me | H | Me | H | H | H |
| $L_4 368$ | | H | Me | $^i$Pr | Me | H | H | H |
| $L_4 369$ | | Ph | Me | H | Me | H | H | H |
| $L_4 370$ | | H | Me | Ph | Me | H | H | H |
| $L_4 371$ | | Me | CD$_3$ | H | CD$_3$ | H | H | H |
| $L_4 372$ | | H | CD$_3$ | Me | CD$_3$ | H | H | H |
| $L_4 373$ | | CD$_3$ | CD$_3$ | H | CD$_3$ | H | H | H |
| $L_4 374$ | | H | CD$_3$ | CD$_3$ | CD$_3$ | H | H | H |
| $L_4 375$ | | $^i$Pr | CD$_3$ | H | CD$_3$ | H | H | H |
| $L_4 376$ | | H | CD$_3$ | $^i$Pr | CD$_3$ | H | H | H |
| $L_4 377$ | | Ph | CD$_3$ | H | CD$_3$ | H | H | H |
| $L_4 378$ | Et, Et linker (C1b, C1e) | H | CD$_3$ | Ph | CD$_3$ | H | H | H |
| $L_4 379$ | | Me | $^i$Pr | H | H | H | H | H |
| $L_4 380$ | | H | $^i$Pr | Me | $^i$Pr | H | H | H |
| $L_4 381$ | | CD$_3$ | $^i$Pr | H | $^i$Pr | H | H | H |
| $L_4 382$ | | H | $^i$Pr | CD$_3$ | $^i$Pr | H | H | H |
| $L_4 383$ | | $^i$Pr | $^i$Pr | H | $^i$Pr | H | H | H |
| $L_4 384$ | | H | $^i$Pr | $^i$Pr | $^i$Pr | H | H | H |
| $L_4 385$ | | Ph | $^i$Pr | H | $^i$Pr | H | H | H |
| $L_4 386$ | | H | $^i$Pr | Ph | $^i$Pr | H | H | H |
| $L_4 387$ | | Me | Ph | H | Ph | H | H | H |
| $L_4 388$ | | H | Ph | Me | Ph | H | H | H |
| $L_4 389$ | | CD$_3$ | Ph | H | Ph | H | H | H |
| $L_4 390$ | | H | Ph | CD$_3$ | Ph | H | H | H |
| $L_4 391$ | | $^i$Pr | Ph | H | Ph | H | H | H |
| $L_4 392$ | | H | Ph | $^i$Pr | Ph | H | H | H |
| $L_4 393$ | | Ph | Ph | H | Ph | H | H | H |
| $L_4 394$ | | H | Ph | Ph | Ph | H | H | H |
| $L_4 395$ | | H | H | H | H | H | H | H |
| $L_4 396$ | | Me | H | H | H | H | H | H |
| $L_4 397$ | | H | Me | H | H | H | H | H |
| $L_4 398$ | | H | H | Me | H | H | H | H |
| $L_4 399$ | cyclohexyl linker (C1b) | H | H | H | Me | H | H | H |
| $L_4 400$ | | H | H | H | H | Me | H | H |
| $L_4 401$ | (C1e) | CD$_3$ | H | H | H | H | H | H |
| $L_4 402$ | | H | CD$_3$ | H | H | H | H | H |
| $L_4 403$ | | H | H | CD$_3$ | H | H | H | H |
| $L_4 404$ | | H | H | H | CD$_3$ | H | H | H |
| $L_4 405$ | | H | H | H | H | CD$_3$ | H | H |
| $L_4 406$ | | $^i$Pr | H | H | H | H | H | H |
| $L_4 407$ | | H | $^i$Pr | H | H | H | H | H |
| $L_4 408$ | | H | H | $^i$Pr | H | H | H | H |
| $L_4 409$ | | H | H | H | $^i$Pr | H | H | H |
| $L_4 410$ | | H | H | H | H | $^i$Pr | H | H |
| $L_4 411$ | | Ph | H | H | H | H | H | H |
| $L_4 412$ | | H | Ph | H | H | H | H | H |
| $L_4 413$ | | H | H | Ph | H | H | H | H |
| $L_4 414$ | | H | H | H | Ph | H | H | H |
| $L_4 415$ | | H | H | H | H | Ph | H | H |
| $L_4 416$ | | Me | Me | H | H | H | H | H |
| $L_4 417$ | | Me | H | Me | H | H | H | H |
| $L_4 418$ | | Me | H | H | Me | H | H | H |
| $L_4 419$ | | Me | H | H | H | Me | H | H |
| $L_4 420$ | | Me | CD$_3$ | H | H | H | H | H |
| $L_4 421$ | | Me | H | CD$_3$ | H | H | H | H |
| $L_4 422$ | | Me | H | H | CD$_3$ | H | H | H |
| $L_4 423$ | | Me | H | H | H | CD$_3$ | H | H |
| $L_4 424$ | | Me | $^i$Pr | H | H | H | H | H |
| $L_4 425$ | | Me | H | $^i$Pr | H | H | H | H |
| $L_4 426$ | | Me | H | H | $^i$Pr | H | H | H |
| $L_4 427$ | | Me | H | H | H | $^i$Pr | H | H |
| $L_4 428$ | | Me | Ph | H | H | H | H | H |
| $L_4 429$ | | Me | H | Ph | H | H | H | H |
| $L_4 430$ | | Me | H | H | Ph | H | H | H |
| $L_4 431$ | | Me | H | H | H | Ph | H | H |
| $L_4 432$ | | CD$_3$ | Me | H | H | H | H | H |
| $L_4 433$ | cyclohexyl linker (C1b) | CD$_3$ | H | Me | H | H | H | H |
| $L_4 434$ | | CD$_3$ | H | H | Me | H | H | H |
| $L_4 435$ | | CD$_3$ | H | H | H | Me | H | H |
| $L_4 436$ | | CD$_3$ | CD$_3$ | H | H | H | H | H |
| $L_4 437$ | | CD$_3$ | H | CD$_3$ | H | H | H | H |
| $L_4 438$ | (C1e) | CD$_3$ | H | H | CD$_3$ | H | H | H |
| $L_4 439$ | | CD$_3$ | H | H | H | CD$_3$ | H | H |
| $L_4 440$ | | CD$_3$ | $^i$Pr | H | H | H | H | H |
| $L_4 441$ | | CD$_3$ | H | $^i$Pr | H | H | H | H |
| $L_4 442$ | | CD$_3$ | H | H | $^i$Pr | H | H | H |
| $L_4 443$ | | CD$_3$ | H | H | H | $^i$Pr | H | H |
| $L_4 444$ | | CD$_3$ | Ph | H | H | H | H | H |
| $L_4 445$ | | CD$_3$ | H | Ph | H | H | H | H |
| $L_4 446$ | | CD$_3$ | H | H | Ph | H | H | H |
| $L_4 447$ | | CD$_3$ | H | H | H | Ph | H | H |
| $L_4 448$ | | $^i$Pr | Me | H | H | H | H | H |
| $L_4 449$ | | $^i$Pr | H | Me | H | H | H | H |
| $L_4 450$ | | $^i$Pr | H | H | Me | H | H | H |
| $L_4 451$ | | $^i$Pr | H | H | H | Me | H | H |
| $L_4 452$ | | $^i$Pr | CD$_3$ | H | H | H | H | H |
| $L_4 453$ | | $^i$Pr | H | CD$_3$ | H | H | H | H |
| $L_4 454$ | | $^i$Pr | H | H | CD$_3$ | H | H | H |
| $L_4 455$ | | $^i$Pr | H | H | H | CD$_3$ | H | H |
| $L_4 456$ | | $^i$Pr | $^i$Pr | H | H | H | H | H |
| $L_4 457$ | | $^i$Pr | H | $^i$Pr | H | H | H | H |
| $L_4 458$ | | $^i$Pr | H | H | $^i$Pr | H | H | H |
| $L_4 459$ | | $^i$Pr | H | H | H | $^i$Pr | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A460$ | | $^iPr$ | Ph | H | H | H | H | H |
| $L_A461$ | | $^iPr$ | H | Ph | H | H | H | H |
| $L_A462$ | | $^iPr$ | H | H | Ph | H | H | H |
| $L_A463$ | | $^iPr$ | H | H | H | Ph | H | H |
| $L_A464$ | | Ph | Me | H | H | H | H | H |
| $L_A465$ | | Ph | H | Me | H | H | H | H |
| $L_A466$ | | Ph | H | H | Me | H | H | H |
| $L_A467$ | | Ph | H | H | H | Me | H | H |
| $L_A468$ | | Ph | $CD_3$ | H | H | H | H | H |
| $L_A469$ | | Ph | H | $CD_3$ | H | H | H | H |
| $L_A470$ | | Ph | H | H | $CD_3$ | H | H | H |
| $L_A471$ | | Ph | H | H | H | $CD_3$ | H | H |
| $L_A472$ | | Ph | $^iPr$ | H | H | H | H | H |
| $L_A473$ | | Ph | H | $^iPr$ | H | H | H | H |
| $L_A474$ | | Ph | H | H | $^iPr$ | H | H | H |
| $L_A475$ | | Ph | H | H | H | $^iPr$ | H | H |
| $L_A476$ | | Ph | Ph | H | H | H | H | H |
| $L_A477$ | | Ph | H | Ph | H | H | H | H |
| $L_A478$ | | Ph | H | H | Ph | H | H | H |
| $L_A479$ | | Ph | H | H | H | Ph | H | H |
| $L_A480$ | | H | Me | Me | H | H | H | H |
| $L_A481$ | | H | Me | H | Me | H | H | H |
| $L_A482$ | | H | Me | H | H | Me | H | H |
| $L_A483$ | | H | Me | $CD_3$ | H | H | H | H |
| $L_A484$ | | H | Me | H | $CD_3$ | H | H | H |
| $L_A485$ | | H | Me | H | H | $CD_3$ | H | H |
| $L_A486$ | | H | Me | $^iPr$ | H | H | H | H |
| $L_A487$ | | H | Me | H | $^iPr$ | H | H | H |
| $L_A488$ | | H | Me | H | H | $^iPr$ | H | H |
| $L_A489$ | | H | Me | Ph | H | H | H | H |
| $L_A490$ | | H | Me | H | Ph | H | H | H |
| $L_A491$ | | H | Me | H | H | Ph | H | H |
| $L_A492$ | | H | $CD_3$ | Me | H | H | H | H |
| $L_A493$ | | H | $CD_3$ | H | Me | H | H | H |
| $L_A494$ | | H | $CD_3$ | H | H | Me | H | H |
| $L_A495$ | | H | $CD_3$ | $CD_3$ | H | H | H | H |
| $L_A496$ | | H | $CD_3$ | H | $CD_3$ | H | H | H |
| $L_A497$ | | H | $CD_3$ | H | H | $CD_3$ | H | H |
| $L_A498$ | | H | $CD_3$ | $^iPr$ | H | H | H | H |
| $L_A499$ | | H | $CD_3$ | H | $^iPr$ | H | H | H |
| $L_A500$ | | H | $CD_3$ | H | H | $^iPr$ | H | H |
| $L_A501$ | | H | $CD_3$ | Ph | H | H | H | H |
| $L_A502$ | | H | $CD_3$ | H | Ph | H | H | H |
| $L_A503$ | | H | $CD_3$ | H | H | Ph | H | H |
| $L_A504$ | | H | $^iPr$ | Me | H | H | H | H |
| $L_A505$ | | H | $^iPr$ | H | Me | H | H | H |
| $L_A506$ | | H | $^iPr$ | H | H | Me | H | H |
| $L_A507$ | | H | $^iPr$ | $CD_3$ | H | H | H | H |
| $L_A508$ | | H | $^iPr$ | H | $CD_3$ | H | H | H |
| $L_A509$ | | H | $^iPr$ | H | H | $CD_3$ | H | H |
| $L_A510$ | | H | $^iPr$ | $^iPr$ | H | H | H | H |
| $L_A511$ | | H | $^iPr$ | H | $^iPr$ | H | H | H |
| $L_A512$ | | H | $^iPr$ | H | H | $^iPr$ | H | H |
| $L_A513$ | | H | $^iPr$ | Ph | H | H | H | H |
| $L_A514$ | | H | $^iPr$ | H | Ph | H | H | H |
| $L_A515$ | | H | $^iPr$ | H | H | Ph | H | H |
| $L_A516$ | | H | Ph | Me | H | H | H | H |
| $L_A517$ | | H | Ph | H | Me | H | H | H |
| $L_A518$ | | H | Ph | H | H | Me | H | H |
| $L_A519$ | | H | Ph | $CD_3$ | H | H | H | H |
| $L_A520$ | | H | Ph | H | $CD_3$ | H | H | H |
| $L_A521$ | | H | Ph | H | H | $CD_3$ | H | H |
| $L_A522$ | | H | Ph | $^iPr$ | H | H | H | H |
| $L_A523$ | | H | Ph | H | $^iPr$ | H | H | H |
| $L_A524$ | | H | Ph | H | H | $^iPr$ | H | H |
| $L_A525$ | | H | Ph | Ph | H | H | H | H |
| $L_A526$ | | H | Ph | H | Ph | H | H | H |
| $L_A527$ | | H | Ph | H | H | Ph | H | H |
| $L_A528$ | | H | H | Me | Me | H | H | H |
| $L_A529$ | | H | H | $CD_3$ | Me | H | H | H |
| $L_A530$ | | H | H | $^iPr$ | Me | H | H | H |
| $L_A531$ | | H | H | Ph | Me | H | H | H |
| $L_A532$ | | H | H | Me | $CD_3$ | H | H | H |
| $L_A533$ | | H | H | $CD_3$ | $CD_3$ | H | H | H |
| $L_A534$ | | H | H | $^iPr$ | $CD_3$ | H | H | H |
| $L_A535$ | | H | H | Ph | $CD_3$ | H | H | H |
| $L_A536$ | | H | H | Me | $^iPr$ | H | H | H |
| $L_A537$ | | H | H | $CD_3$ | $^iPr$ | H | H | H |
| $L_A538$ | | H | H | $^iPr$ | $^iPr$ | H | H | H |
| $L_A539$ | | H | H | Ph | $^iPr$ | H | H | H |
| $L_A540$ | | H | H | Me | Ph | H | H | H |
| $L_A541$ | | H | H | $CD_3$ | Ph | H | H | H |
| $L_A542$ | | H | H | $^iPr$ | Ph | H | H | H |
| $L_A543$ | cyclohexyl ($C^{1b}$, $C^{1e}$) | H | H | Ph | Ph | H | H | H |
| $L_A544$ | | H | H | Me | H | Me | H | H |
| $L_A545$ | | H | H | $CD_3$ | H | Me | H | H |
| $L_A546$ | | H | H | $^iPr$ | H | Me | H | H |
| $L_A547$ | | H | H | Ph | H | Me | H | H |
| $L_A548$ | | H | H | Me | H | $CD_3$ | H | H |
| $L_A549$ | | H | H | $CD_3$ | H | $CD_3$ | H | H |
| $L_A550$ | | H | H | $^iPr$ | H | $CD_3$ | H | H |
| $L_A551$ | | H | H | Ph | H | $CD_3$ | H | H |
| $L_A552$ | | H | H | Me | H | $^iPr$ | H | H |
| $L_A553$ | | H | H | $CD_3$ | H | $^iPr$ | H | H |
| $L_A554$ | | H | H | $^iPr$ | H | $^iPr$ | H | H |
| $L_A555$ | | H | H | Ph | H | $^iPr$ | H | H |
| $L_A556$ | | H | H | Me | H | Ph | H | H |
| $L_A557$ | | H | H | $CD_3$ | H | Ph | H | H |
| $L_A558$ | | H | H | $^iPr$ | H | Ph | H | H |
| $L_A559$ | | H | H | Ph | H | Ph | H | H |
| $L_A560$ | | Me | Me | H | Me | H | H | H |
| $L_A561$ | | H | Me | Me | Me | H | H | H |
| $L_A562$ | | $CD_3$ | Me | H | Me | H | H | H |
| $L_A563$ | | H | Me | $CD_3$ | Me | H | H | H |
| $L_A564$ | | $^iPr$ | Me | H | Me | H | H | H |
| $L_A565$ | | H | Me | $^iPr$ | Me | H | H | H |
| $L_A566$ | | Ph | Me | H | Me | H | H | H |
| $L_A567$ | | H | Me | Ph | Me | H | H | H |
| $L_A568$ | | Me | $CD_3$ | H | $CD_3$ | H | H | H |
| $L_A569$ | | H | $CD_3$ | Me | $CD_3$ | H | H | H |
| $L_A570$ | | $CD_3$ | $CD_3$ | H | $CD_3$ | H | H | H |
| $L_A571$ | | H | $CD_3$ | $CD_3$ | $CD_3$ | H | H | H |
| $L_A572$ | | $^iPr$ | $CD_3$ | H | $CD_3$ | H | H | H |
| $L_A573$ | | H | $CD_3$ | $^iPr$ | $CD_3$ | H | H | H |
| $L_A574$ | | Ph | $CD_3$ | H | $CD_3$ | H | H | H |
| $L_A575$ | | H | $CD_3$ | Ph | $CD_3$ | H | H | H |
| $L_A576$ | | Me | $^iPr$ | H | $^iPr$ | H | H | H |
| $L_A577$ | | H | $^iPr$ | Me | $^iPr$ | H | H | H |
| $L_A578$ | | $CD_3$ | $^iPr$ | H | $^iPr$ | H | H | H |
| $L_A579$ | | H | $^iPr$ | $CD_3$ | $^iPr$ | H | H | H |
| $L_A580$ | | $^iPr$ | $^iPr$ | H | $^iPr$ | H | H | H |
| $L_A581$ | | H | $^iPr$ | $^iPr$ | $^iPr$ | H | H | H |
| $L_A582$ | | Ph | $^iPr$ | H | $^iPr$ | H | H | H |
| $L_A583$ | | H | $^iPr$ | Ph | $^iPr$ | H | H | H |
| $L_A584$ | | Me | Ph | H | Ph | H | H | H |
| $L_A585$ | | H | Ph | Me | Ph | H | H | H |
| $L_A586$ | | $CD_3$ | Ph | H | Ph | H | H | H |
| $L_A587$ | | H | Ph | $CD_3$ | Ph | H | H | H |
| $L_A588$ | | $^iPr$ | Ph | H | Ph | H | H | H |
| $L_A589$ | | H | Ph | $^iPr$ | Ph | H | H | H |
| $L_A590$ | | Ph | Ph | H | Ph | H | H | H |
| $L_A591$ | | H | Ph | Ph | Ph | H | H | H |
| $L_A592$ | Bn, Bn ($C^{1b}$, $C^{1e}$) | H | H | H | H | H | H | H |
| $L_A593$ | | Me | H | H | H | H | H | H |
| $L_A594$ | | H | Me | H | H | H | H | H |
| $L_A595$ | | H | H | Me | H | H | H | H |
| $L_A596$ | | H | H | H | Me | H | H | H |
| $L_A597$ | | H | H | H | H | Me | H | H |
| $L_A598$ | Bn, Bn ($C^{1b}$, $C^{1e}$) | $CD_3$ | H | H | H | H | H | H |
| $L_A599$ | | H | $CD_3$ | H | H | H | H | H |
| $L_A600$ | | H | H | $CD_3$ | H | H | H | H |
| $L_A601$ | | H | H | H | $CD_3$ | H | H | H |
| $L_A602$ | | H | H | H | H | $CD_3$ | H | H |
| $L_A603$ | | $^iPr$ | H | H | H | H | H | H |
| $L_A604$ | | H | $^iPr$ | H | H | H | H | H |
| $L_A605$ | | H | H | $^iPr$ | H | H | H | H |
| $L_A606$ | | H | H | H | $^iPr$ | H | H | H |
| $L_A607$ | | H | H | H | H | $^iPr$ | H | H |
| $L_A608$ | | Ph | H | H | H | H | H | H |
| $L_A609$ | | H | Ph | H | H | H | H | H |
| $L_A610$ | | H | H | Ph | H | H | H | H |
| $L_A611$ | | H | H | H | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_4$612 | | H | H | H | H | Ph | H | H |
| $L_4$613 | | Me | Me | H | H | H | H | H |
| $L_4$614 | | Me | H | Me | H | H | H | H |
| $L_4$615 | | Me | H | H | Me | H | H | H |
| $L_4$616 | | Me | H | H | H | Me | H | H |
| $L_4$617 | | Me | $CD_3$ | H | H | H | H | H |
| $L_4$618 | | Me | H | $CD_3$ | H | H | H | H |
| $L_4$619 | | Me | H | H | $CD_3$ | H | H | H |
| $L_4$620 | | Me | H | H | H | $CD_3$ | H | H |
| $L_4$621 | | Me | $^i$Pr | H | H | H | H | H |
| $L_4$622 | | Me | H | $^i$Pr | H | H | H | H |
| $L_4$623 | | Me | H | H | $^i$Pr | H | H | H |
| $L_4$624 | | Me | H | H | H | $^i$Pr | H | H |
| $L_4$625 | | Me | Ph | H | H | H | H | H |
| $L_4$626 | | Me | H | Ph | H | H | H | H |
| $L_4$627 | | Me | H | H | Ph | H | H | H |
| $L_4$628 | | Me | H | H | H | Ph | H | H |
| $L_4$629 | | $CD_3$ | Me | H | H | H | H | H |
| $L_4$630 | | $CD_3$ | H | Me | H | H | H | H |
| $L_4$631 | | $CD_3$ | H | H | Me | H | H | H |
| $L_4$632 | | $CD_3$ | H | H | H | Me | H | H |
| $L_4$633 | | $CD_3$ | $CD_3$ | H | H | H | H | H |
| $L_4$634 | | $CD_3$ | H | $CD_3$ | H | H | H | H |
| $L_4$635 | | $CD_3$ | H | H | $CD_3$ | H | H | H |
| $L_4$636 | | $CD_3$ | H | H | H | $CD_3$ | H | H |
| $L_4$637 | | $CD_3$ | $^i$Pr | H | H | H | H | H |
| $L_4$638 | | $CD_3$ | H | $^i$Pr | H | H | H | H |
| $L_4$639 | | $CD_3$ | H | H | $^i$Pr | H | H | H |
| $L_4$640 | | $CD_3$ | H | H | H | $^i$Pr | H | H |
| $L_4$641 | | $CD_3$ | Ph | H | H | H | H | H |
| $L_4$642 | | $CD_3$ | H | Ph | H | H | H | H |
| $L_4$643 | | $CD_3$ | H | H | Ph | H | H | H |
| $L_4$644 | | $CD_3$ | H | H | H | Ph | H | H |
| $L_4$645 | | $^i$Pr | Me | H | H | H | H | H |
| $L_4$646 | | $^i$Pr | H | Me | H | H | H | H |
| $L_4$647 | | $^i$Pr | H | H | Me | H | H | H |
| $L_4$648 | | $^i$Pr | H | H | H | Me | H | H |
| $L_4$649 | | $^i$Pr | $CD_3$ | H | H | H | H | H |
| $L_4$650 | | $^i$Pr | H | $CD_3$ | H | H | H | H |
| $L_4$651 | | $^i$Pr | H | H | $CD_3$ | H | H | H |
| $L_4$652 | | $^i$Pr | H | H | H | $CD_3$ | H | H |
| $L_4$653 | Bn–C(Bn)(–C$^{1b}$)–C$^{1e}$ | $^i$Pr | $^i$Pr | H | H | H | H | H |
| $L_4$654 | | $^i$Pr | H | $^i$Pr | H | H | H | H |
| $L_4$655 | | $^i$Pr | H | H | $^i$Pr | H | H | H |
| $L_4$656 | | $^i$Pr | H | H | H | $^i$Pr | H | H |
| $L_4$657 | | $^i$Pr | Ph | H | H | H | H | H |
| $L_4$658 | | $^i$Pr | H | Ph | H | H | H | H |
| $L_4$659 | | $^i$Pr | H | H | Ph | H | H | H |
| $L_4$660 | | $^i$Pr | H | H | H | Ph | H | H |
| $L_4$661 | | Ph | Me | H | H | H | H | H |
| $L_4$662 | | Ph | H | Me | H | H | H | H |
| $L_4$663 | | Ph | H | H | Me | H | H | H |
| $L_4$664 | | Ph | H | H | H | Me | H | H |
| $L_4$665 | | Ph | $CD_3$ | H | H | H | H | H |
| $L_4$666 | | Ph | H | $CD_3$ | H | H | H | H |
| $L_4$667 | | Ph | H | H | $CD_3$ | H | H | H |
| $L_4$668 | | Ph | H | H | H | $CD_3$ | H | H |
| $L_4$669 | | Ph | $^i$Pr | H | H | H | H | H |
| $L_4$670 | | Ph | H | $^i$Pr | H | H | H | H |
| $L_4$671 | | Ph | H | H | $^i$Pr | H | H | H |
| $L_4$672 | | Ph | H | H | H | $^i$Pr | H | H |
| $L_4$673 | | Ph | Ph | H | H | H | H | H |
| $L_4$674 | | Ph | H | Ph | H | H | H | H |
| $L_4$675 | | Ph | H | H | Ph | H | H | H |
| $L_4$676 | | Ph | H | H | H | Ph | H | H |
| $L_4$677 | | H | Me | Me | H | H | H | H |
| $L_4$678 | | H | Me | H | Me | H | H | H |
| $L_4$679 | | H | Me | H | H | Me | H | H |
| $L_4$680 | | H | Me | $CD_3$ | H | H | H | H |
| $L_4$681 | | H | Me | H | $CD_3$ | H | H | H |
| $L_4$682 | | H | Me | H | H | $CD_3$ | H | H |
| $L_4$683 | | H | Me | $^i$Pr | H | H | H | H |
| $L_4$684 | | H | Me | H | $^i$Pr | H | H | H |
| $L_4$685 | | H | Me | H | H | $^i$Pr | H | H |
| $L_4$686 | | H | Me | Ph | H | H | H | H |
| $L_4$687 | | H | Me | H | Ph | H | H | H |
| $L_4$688 | | H | Me | H | H | Ph | H | H |
| $L_4$689 | | H | $CD_3$ | Me | H | H | H | H |
| $L_4$690 | | H | $CD_3$ | H | Me | H | H | H |
| $L_4$691 | | H | $CD_3$ | H | H | Me | H | H |
| $L_4$692 | | H | $CD_3$ | $CD_3$ | H | H | H | H |
| $L_4$693 | | H | $CD_3$ | H | $CD_3$ | H | H | H |
| $L_4$694 | | H | $CD_3$ | H | H | $CD_3$ | H | H |
| $L_4$695 | | H | $CD_3$ | $^i$Pr | H | H | H | H |
| $L_4$696 | | H | $CD_3$ | H | $^i$Pr | H | H | H |
| $L_4$697 | | H | $CD_3$ | H | H | $^i$Pr | H | H |
| $L_4$698 | | H | $CD_3$ | Ph | H | H | H | H |
| $L_4$699 | | H | $CD_3$ | H | Ph | H | H | H |
| $L_4$700 | | H | $CD_3$ | H | H | Ph | H | H |
| $L_4$701 | | H | $^i$Pr | Me | H | H | H | H |
| $L_4$702 | | H | $^i$Pr | H | Me | H | H | H |
| $L_4$703 | | H | $^i$Pr | H | H | Me | H | H |
| $L_4$704 | | H | $^i$Pr | $CD_3$ | H | H | H | H |
| $L_4$705 | | H | $^i$Pr | H | $CD_3$ | H | H | H |
| $L_4$706 | | H | $^i$Pr | H | H | $CD_3$ | H | H |
| $L_4$707 | | H | $^i$Pr | $^i$Pr | H | H | H | H |
| $L_4$708 | Bn–C(Bn)(–C$^{1b}$)–C$^{1e}$ | H | $^i$Pr | H | $^i$Pr | H | H | H |
| $L_4$709 | | H | $^i$Pr | H | H | $^i$Pr | H | H |
| $L_4$710 | | H | $^i$Pr | Ph | H | H | H | H |
| $L_4$711 | | H | $^i$Pr | H | Ph | H | H | H |
| $L_4$712 | | H | $^i$Pr | H | H | Ph | H | H |
| $L_4$713 | | H | Ph | Me | H | H | H | H |
| $L_4$714 | | H | Ph | H | Me | H | H | H |
| $L_4$715 | | H | Ph | H | H | Me | H | H |
| $L_4$716 | | H | Ph | $CD_3$ | H | H | H | H |
| $L_4$717 | | H | Ph | H | $CD_3$ | H | H | H |
| $L_4$718 | | H | Ph | H | H | $CD_3$ | H | H |
| $L_4$719 | | H | Ph | $^i$Pr | H | H | H | H |
| $L_4$720 | | H | Ph | H | $^i$Pr | H | H | H |
| $L_4$721 | | H | Ph | H | H | $^i$Pr | H | H |
| $L_4$722 | | H | Ph | Ph | H | H | H | H |
| $L_4$723 | | H | Ph | H | Ph | H | H | H |
| $L_4$724 | | H | Ph | H | H | Ph | H | H |
| $L_4$725 | | H | H | Me | Me | H | H | H |
| $L_4$726 | | H | H | $CD_3$ | Me | H | H | H |
| $L_4$727 | | H | H | $^i$Pr | Me | H | H | H |
| $L_4$728 | | H | H | Ph | Me | H | H | H |
| $L_4$729 | | H | H | Me | $CD_3$ | H | H | H |
| $L_4$730 | | H | H | $CD_3$ | $CD_3$ | H | H | H |
| $L_4$731 | | H | H | $^i$Pr | $CD_3$ | H | H | H |
| $L_4$732 | | H | H | Ph | $CD_3$ | H | H | H |
| $L_4$733 | | H | H | Me | $^i$Pr | H | H | H |
| $L_4$734 | | H | H | $CD_3$ | $^i$Pr | H | H | H |
| $L_4$735 | | H | H | $^i$Pr | $^i$Pr | H | H | H |
| $L_4$736 | | H | H | Ph | $^i$Pr | H | H | H |
| $L_4$737 | | H | H | Me | Ph | H | H | H |
| $L_4$738 | | H | H | $CD_3$ | Ph | H | H | H |
| $L_4$739 | | H | H | $^i$Pr | Ph | H | H | H |
| $L_4$740 | | H | H | Ph | Ph | H | H | H |
| $L_4$741 | | H | H | Me | H | Me | H | H |
| $L_4$742 | | H | H | $CD_3$ | H | Me | H | H |
| $L_4$743 | | H | H | $^i$Pr | H | Me | H | H |
| $L_4$744 | | H | H | Ph | H | Me | H | H |
| $L_4$745 | | H | H | Me | H | $CD_3$ | H | H |
| $L_4$746 | | H | H | $CD_3$ | H | $CD_3$ | H | H |
| $L_4$747 | | H | H | $^i$Pr | H | $CD_3$ | H | H |
| $L_4$748 | | H | H | Ph | H | $CD_3$ | H | H |
| $L_4$749 | | H | H | Me | H | $^i$Pr | H | H |
| $L_4$750 | | H | H | $CD_3$ | H | $^i$Pr | H | H |
| $L_4$751 | | H | H | $^i$Pr | H | $^i$Pr | H | H |
| $L_4$752 | | H | H | Ph | H | $^i$Pr | H | H |
| $L_4$753 | | H | H | Me | H | Ph | H | H |
| $L_4$754 | | H | H | $CD_3$ | H | Ph | H | H |
| $L_4$755 | | H | H | $^i$Pr | H | Ph | H | H |
| $L_4$756 | | H | H | Ph | H | Ph | H | H |
| $L_4$757 | | Me | Me | Me | Me | H | H | H |
| $L_4$758 | | H | Me | Me | Me | H | H | H |
| $L_4$759 | | $CD_3$ | Me | H | Me | H | H | H |
| $L_4$760 | | H | Me | $CD_3$ | Me | H | H | H |
| $L_4$761 | | $^i$Pr | Me | H | Me | H | H | H |
| $L_4$762 | | H | Me | $^i$Pr | Me | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A763$ | Bn, Bn on C1b/C1e branch | Ph | Me | H | Me | H | H | H |
| $L_A764$ |  | H | Me | Ph | Me | H | H | H |
| $L_A765$ |  | Me | $CD_3$ | H | $CD_3$ | H | H | H |
| $L_A766$ |  | H | $CD_3$ | Me | $CD_3$ | H | H | H |
| $L_A767$ |  | $CD_3$ | $CD_3$ | H | $CD_3$ | H | H | H |
| $L_A768$ |  | H | $CD_3$ | $CD_3$ | $CD_3$ | H | H | H |
| $L_A769$ |  | $^iPr$ | $CD_3$ | H | $CD_3$ | H | H | H |
| $L_A770$ |  | H | $CD_3$ | $^iPr$ | $CD_3$ | H | H | H |
| $L_A771$ |  | Ph | $CD_3$ | H | $CD_3$ | H | H | H |
| $L_A772$ |  | H | $CD_3$ | Ph | $CD_3$ | H | H | H |
| $L_A773$ |  | Me | $^iPr$ | H | $^iPr$ | H | H | H |
| $L_A774$ |  | H | $^iPr$ | Me | $^iPr$ | H | H | H |
| $L_A775$ |  | $CD_3$ | $^iPr$ | H | $^iPr$ | H | H | H |
| $L_A776$ |  | H | $^iPr$ | $CD_3$ | $^iPr$ | H | H | H |
| $L_A777$ |  | $^iPr$ | $^iPr$ | H | $^iPr$ | H | H | H |
| $L_A778$ |  | H | $^iPr$ | $^iPr$ | $^iPr$ | H | H | H |
| $L_A779$ |  | Ph | $^iPr$ | H | $^iPr$ | H | H | H |
| $L_A780$ |  | H | $^iPr$ | Ph | $^iPr$ | H | H | H |
| $L_A781$ |  | Me | Ph | H | Ph | H | H | H |
| $L_A782$ |  | H | Ph | Me | Ph | H | H | H |
| $L_A783$ |  | $CD_3$ | Ph | H | Ph | H | H | H |
| $L_A784$ |  | H | Ph | $CD_3$ | Ph | H | H | H |
| $L_A785$ |  | $^iPr$ | Ph | H | Ph | H | H | H |
| $L_A786$ |  | H | Ph | $^iPr$ | Ph | H | H | H |
| $L_A787$ |  | Ph | Ph | H | Ph | H | H | H |
| $L_A788$ |  | H | Ph | Ph | Ph | H | H | H |
| $L_A789$ | Ph, Ph on C1b/C1e branch | H | H | H | H | H | H | H |
| $L_A790$ |  | Me | H | H | H | H | H | H |
| $L_A791$ |  | H | Me | H | H | H | H | H |
| $L_A792$ |  | H | H | Me | H | H | H | H |
| $L_A793$ |  | H | H | H | Me | H | H | H |
| $L_A794$ |  | H | H | H | H | Me | H | H |
| $L_A795$ |  | $CD_3$ | H | H | H | H | H | H |
| $L_A796$ |  | H | $CD_3$ | H | H | H | H | H |
| $L_A797$ |  | H | H | $CD_3$ | H | H | H | H |
| $L_A798$ |  | H | H | H | $CD_3$ | H | H | H |
| $L_A799$ |  | H | H | H | H | $CD_3$ | H | H |
| $L_A800$ |  | $^iPr$ | H | H | H | H | H | H |
| $L_A801$ |  | H | $^iPr$ | H | H | H | H | H |
| $L_A802$ |  | H | H | $^iPr$ | H | H | H | H |
| $L_A803$ |  | H | H | H | $^iPr$ | H | H | H |
| $L_A804$ |  | H | H | H | H | $^iPr$ | H | H |
| $L_A805$ |  | Ph | H | H | H | H | H | H |
| $L_A806$ |  | H | Ph | H | H | H | H | H |
| $L_A807$ |  | H | H | Ph | H | H | H | H |
| $L_A808$ |  | H | H | H | Ph | H | H | H |
| $L_A809$ |  | H | H | H | H | Ph | H | H |
| $L_A810$ |  | Me | Me | H | H | H | H | H |
| $L_A811$ |  | Me | H | Me | H | H | H | H |
| $L_A812$ |  | Me | H | H | Me | H | H | H |
| $L_A813$ |  | Me | H | H | H | Me | H | H |
| $L_A814$ |  | Me | $CD_3$ | H | H | H | H | H |
| $L_A815$ |  | Me | H | $CD_3$ | H | H | H | H |
| $L_A816$ |  | Me | H | H | $CD_3$ | H | H | H |
| $L_A817$ |  | Me | H | H | H | $CD_3$ | H | H |
| $L_A818$ | Ph, Ph on C1b/C1e branch | Me | $^iPr$ | H | H | H | H | H |
| $L_A819$ |  | Me | H | $^iPr$ | H | H | H | H |
| $L_A820$ |  | Me | H | H | $^iPr$ | H | H | H |
| $L_A821$ |  | Me | H | H | H | $^iPr$ | H | H |
| $L_A822$ |  | Me | Ph | H | H | H | H | H |
| $L_A823$ |  | Me | H | Ph | H | H | H | H |
| $L_A824$ |  | Me | H | H | Ph | H | H | H |
| $L_A825$ |  | Me | H | H | H | Ph | H | H |
| $L_A826$ |  | $CD_3$ | Me | H | H | H | H | H |
| $L_A827$ |  | $CD_3$ | H | Me | H | H | H | H |
| $L_A828$ |  | $CD_3$ | H | H | Me | H | H | H |
| $L_A829$ |  | $CD_3$ | H | H | H | Me | H | H |
| $L_A830$ |  | $CD_3$ | $CD_3$ | H | H | H | H | H |
| $L_A831$ |  | $CD_3$ | H | $CD_3$ | H | H | H | H |
| $L_A832$ |  | $CD_3$ | H | H | $CD_3$ | H | H | H |
| $L_A833$ |  | $CD_3$ | H | H | H | $CD_3$ | H | H |
| $L_A834$ |  | $CD_3$ | $^iPr$ | H | H | H | H | H |
| $L_A835$ |  | $CD_3$ | H | $^iPr$ | H | H | H | H |
| $L_A836$ |  | $CD_3$ | H | H | $^iPr$ | H | H | H |
| $L_A837$ |  | $CD_3$ | H | H | H | $^iPr$ | H | H |
| $L_A838$ |  | $CD_3$ | Ph | H | H | H | H | H |
| $L_A839$ |  | $CD_3$ | H | Ph | H | H | H | H |
| $L_A840$ |  | $CD_3$ | H | H | Ph | H | H | H |
| $L_A841$ |  | $CD_3$ | H | H | H | Ph | H | H |
| $L_A842$ |  | $^iPr$ | Me | H | H | H | H | H |
| $L_A843$ |  | $^iPr$ | H | Me | H | H | H | H |
| $L_A844$ |  | $^iPr$ | H | H | Me | H | H | H |
| $L_A845$ |  | $^iPr$ | H | H | H | Me | H | H |
| $L_A846$ |  | $^iPr$ | $CD_3$ | H | H | H | H | H |
| $L_A847$ |  | $^iPr$ | H | $CD_3$ | H | H | H | H |
| $L_A848$ |  | $^iPr$ | H | H | $CD_3$ | H | H | H |
| $L_A849$ |  | $^iPr$ | H | H | H | $CD_3$ | H | H |
| $L_A850$ |  | $^iPr$ | $^iPr$ | H | H | H | H | H |
| $L_A851$ |  | $^iPr$ | H | $^iPr$ | H | H | H | H |
| $L_A852$ |  | $^iPr$ | H | H | $^iPr$ | H | H | H |
| $L_A853$ |  | $^iPr$ | H | H | H | $^iPr$ | H | H |
| $L_A854$ |  | $^iPr$ | Ph | H | H | H | H | H |
| $L_A855$ |  | $^iPr$ | H | Ph | H | H | H | H |
| $L_A856$ |  | $^iPr$ | H | H | Ph | H | H | H |
| $L_A857$ |  | $^iPr$ | H | H | H | Ph | H | H |
| $L_A858$ |  | Ph | Me | H | H | H | H | H |
| $L_A859$ |  | Ph | H | Me | H | H | H | H |
| $L_A860$ |  | Ph | H | H | Me | H | H | H |
| $L_A861$ |  | Ph | H | H | H | Me | H | H |
| $L_A862$ |  | Ph | $CD_3$ | H | H | H | H | H |
| $L_A863$ |  | Ph | H | $CD_3$ | H | H | H | H |
| $L_A864$ |  | Ph | H | H | $CD_3$ | H | H | H |
| $L_A865$ |  | Ph | H | H | H | $CD_3$ | H | H |
| $L_A866$ |  | Ph | $^iPr$ | H | H | H | H | H |
| $L_A867$ |  | Ph | H | $^iPr$ | H | H | H | H |
| $L_A868$ |  | Ph | H | H | $^iPr$ | H | H | H |
| $L_A869$ |  | Ph | H | H | H | $^iPr$ | H | H |
| $L_A870$ |  | Ph | Ph | H | H | H | H | H |
| $L_A871$ |  | Ph | H | Ph | H | H | H | H |
| $L_A872$ |  | Ph | H | H | Ph | H | H | H |
| $L_A873$ | Ph, Ph on C1b/C1e branch | Ph | H | H | H | Ph | H | H |
| $L_A874$ |  | H | Me | Me | H | H | H | H |
| $L_A875$ |  | H | Me | H | Me | H | H | H |
| $L_A876$ |  | H | Me | H | H | Me | H | H |
| $L_A877$ |  | H | Me | $CD_3$ | H | H | H | H |
| $L_A878$ |  | H | Me | H | $CD_3$ | H | H | H |
| $L_A879$ |  | H | Me | H | H | $CD_3$ | H | H |
| $L_A880$ |  | H | Me | $^iPr$ | H | H | H | H |
| $L_A881$ |  | H | Me | H | $^iPr$ | H | H | H |
| $L_A882$ |  | H | Me | H | H | $^iPr$ | H | H |
| $L_A883$ |  | H | Me | Ph | H | H | H | H |
| $L_A884$ |  | H | Me | H | Ph | H | H | H |
| $L_A885$ |  | H | Me | H | H | Ph | H | H |
| $L_A886$ |  | H | $CD_3$ | Me | H | H | H | H |
| $L_A887$ |  | H | $CD_3$ | H | Me | H | H | H |
| $L_A888$ |  | H | $CD_3$ | H | H | Me | H | H |
| $L_A889$ |  | H | $CD_3$ | $CD_3$ | H | H | H | H |
| $L_A890$ |  | H | $CD_3$ | H | $CD_3$ | H | H | H |
| $L_A891$ |  | H | $CD_3$ | H | H | $CD_3$ | H | H |
| $L_A892$ |  | H | $CD_3$ | $^iPr$ | H | H | H | H |
| $L_A893$ |  | H | $CD_3$ | H | $^iPr$ | H | H | H |
| $L_A894$ |  | H | $CD_3$ | H | H | $^iPr$ | H | H |
| $L_A895$ |  | H | $CD_3$ | Ph | H | H | H | H |
| $L_A896$ |  | H | $CD_3$ | H | Ph | H | H | H |
| $L_A897$ |  | H | $CD_3$ | H | H | Ph | H | H |
| $L_A898$ |  | H | $^iPr$ | Me | H | H | H | H |
| $L_A899$ |  | H | $^iPr$ | H | Me | H | H | H |
| $L_A900$ |  | H | $^iPr$ | H | H | Me | H | H |
| $L_A901$ |  | H | $^iPr$ | $CD_3$ | H | H | H | H |
| $L_A902$ |  | H | $^iPr$ | H | $CD_3$ | H | H | H |
| $L_A903$ |  | H | $^iPr$ | H | H | $CD_3$ | H | H |
| $L_A904$ |  | H | $^iPr$ | $^iPr$ | H | H | H | H |
| $L_A905$ |  | H | $^iPr$ | H | $^iPr$ | H | H | H |
| $L_A906$ |  | H | $^iPr$ | H | H | $^iPr$ | H | H |
| $L_A907$ |  | H | $^iPr$ | Ph | H | H | H | H |
| $L_A908$ |  | H | $^iPr$ | H | Ph | H | H | H |
| $L_A909$ |  | H | $^iPr$ | H | H | Ph | H | H |
| $L_A910$ |  | H | Ph | Me | H | H | H | H |
| $L_A911$ |  | H | Ph | H | Me | H | H | H |
| $L_A912$ |  | H | Ph | H | H | Me | H | H |
| $L_A913$ |  | H | Ph | $CD_3$ | H | H | H | H |
| $L_A914$ |  | H | Ph | H | $CD_3$ | H | H | H |
| $L_A915$ |  | H | Ph | H | H | $CD_3$ | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A916$ | | H | Ph | $^iPr$ | H | H | H | H |
| $L_A917$ | | H | Ph | H | $^iPr$ | H | H | H |
| $L_A918$ | | H | Ph | H | H | $^iPr$ | H | H |
| $L_A919$ | | H | Ph | Ph | H | H | H | H |
| $L_A920$ | | H | Ph | H | Ph | H | H | H |
| $L_A921$ | | H | Ph | H | H | Ph | H | H |
| $L_A922$ | | H | H | Me | Me | H | H | H |
| $L_A923$ | | H | H | $CD_3$ | Me | H | H | H |
| $L_A924$ | | H | H | $^iPr$ | Me | H | H | H |
| $L_A925$ | | H | H | Ph | Me | H | H | H |
| $L_A926$ | | H | H | Me | $CD_3$ | H | H | H |
| $L_A927$ | | H | H | $CD_3$ | $CD_3$ | H | H | H |
| $L_A928$ | Ph-Ph / $C^{1b}$ / $C^{1e}$ | H | H | $^iPr$ | $CD_3$ | H | H | H |
| $L_A929$ | | H | H | Ph | $CD_3$ | H | H | H |
| $L_A930$ | | H | H | Me | $^iPr$ | H | H | H |
| $L_A931$ | | H | H | $CD_3$ | $^iPr$ | H | H | H |
| $L_A932$ | | H | H | $^iPr$ | $^iPr$ | H | H | H |
| $L_A933$ | | H | H | Ph | $^iPr$ | H | H | H |
| $L_A934$ | | H | H | Me | Ph | H | H | H |
| $L_A935$ | | H | H | $CD_3$ | Ph | H | H | H |
| $L_A936$ | | H | H | $^iPr$ | Ph | H | H | H |
| $L_A937$ | | H | H | Ph | Ph | H | H | H |
| $L_A938$ | | H | H | Me | H | Me | H | H |
| $L_A939$ | | H | H | $CD_3$ | H | Me | H | H |
| $L_A940$ | | H | H | $^iPr$ | H | Me | H | H |
| $L_A941$ | | H | H | Ph | H | Me | H | H |
| $L_A942$ | | H | H | Me | H | $CD_3$ | H | H |
| $L_A943$ | | H | H | $CD_3$ | H | $CD_3$ | H | H |
| $L_A944$ | | H | H | $^iPr$ | H | $CD_3$ | H | H |
| $L_A945$ | | H | H | Ph | H | $CD_3$ | H | H |
| $L_A946$ | | H | H | Me | H | $^iPr$ | H | H |
| $L_A947$ | | H | H | $CD_3$ | H | $^iPr$ | H | H |
| $L_A948$ | | H | H | $^iPr$ | H | $^iPr$ | H | H |
| $L_A949$ | | H | H | Ph | H | $^iPr$ | H | H |
| $L_A950$ | | H | H | Me | H | Ph | H | H |
| $L_A951$ | | H | H | $CD_3$ | H | Ph | H | H |
| $L_A952$ | | H | H | $^iPr$ | H | Ph | H | H |
| $L_A953$ | | H | H | Ph | H | Ph | H | H |
| $L_A954$ | | Me | Me | H | Me | H | H | H |
| $L_A955$ | | H | Me | Me | Me | H | H | H |
| $L_A956$ | | $CD_3$ | Me | H | Me | H | H | H |
| $L_A957$ | | H | Me | $CD_3$ | Me | H | H | H |
| $L_A958$ | | $^iPr$ | Me | H | Me | H | H | H |
| $L_A959$ | | H | Me | $^iPr$ | Me | H | H | H |
| $L_A960$ | | Ph | Me | H | Me | H | H | H |
| $L_A961$ | | H | Me | Ph | Me | H | H | H |
| $L_A962$ | | Me | $CD_3$ | H | $CD_3$ | H | H | H |
| $L_A963$ | | H | $CD_3$ | Me | $CD_3$ | H | H | H |
| $L_A964$ | | $CD_3$ | $CD_3$ | H | $CD_3$ | H | H | H |
| $L_A965$ | | H | $CD_3$ | $CD_3$ | $CD_3$ | H | H | H |
| $L_A966$ | | $^iPr$ | $CD_3$ | H | $CD_3$ | H | H | H |
| $L_A967$ | | H | $CD_3$ | $^iPr$ | $CD_3$ | H | H | H |
| $L_A968$ | | Ph | $CD_3$ | H | $CD_3$ | H | H | H |
| $L_A969$ | | H | $CD_3$ | Ph | $CD_3$ | H | H | H |
| $L_A970$ | | Me | $^iPr$ | H | $^iPr$ | H | H | H |
| $L_A971$ | | H | $^iPr$ | Me | $^iPr$ | H | H | H |
| $L_A972$ | | $CD_3$ | $^iPr$ | H | $^iPr$ | H | H | H |
| $L_A973$ | | H | $^iPr$ | $CD_3$ | $^iPr$ | H | H | H |
| $L_A974$ | | $^iPr$ | $^iPr$ | H | $^iPr$ | H | H | H |
| $L_A975$ | | H | $^iPr$ | $^iPr$ | $^iPr$ | H | H | H |
| $L_A976$ | | Ph | $^iPr$ | H | $^iPr$ | H | H | H |
| $L_A977$ | | H | $^iPr$ | Ph | $^iPr$ | H | H | H |
| $L_A978$ | | Me | Ph | H | Ph | H | H | H |
| $L_A979$ | | H | Ph | Me | Ph | H | H | H |
| $L_A980$ | | $CD_3$ | Ph | H | Ph | H | H | H |
| $L_A981$ | | H | Ph | $CD_3$ | Ph | H | H | H |
| $L_A982$ | | $^iPr$ | Ph | H | Ph | H | H | H |
| $L_A983$ | Ph-Ph / $C^{1b}$ / $C^{1e}$ | H | Ph | $^iPr$ | Ph | H | H | H |
| $L_A984$ | | Ph | Ph | H | Ph | H | H | H |
| $L_A985$ | | H | Ph | Ph | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A986$ | $D_3C$-$CD_3$ / $D_3C$ / $C^{1b}$ / $C^{1e}$ | H | H | H | H | H | H | H |
| $L_A987$ | | Me | H | H | H | H | H | H |
| $L_A988$ | | H | Me | H | H | H | H | H |
| $L_A989$ | | H | H | Me | H | H | H | H |
| $L_A990$ | | H | H | H | Me | H | H | H |
| $L_A991$ | | H | H | H | H | Me | H | H |
| $L_A992$ | | $CD_3$ | H | H | H | H | H | H |
| $L_A993$ | | H | $CD_3$ | H | H | H | H | H |
| $L_A994$ | | H | H | $CD_3$ | H | H | H | H |
| $L_A995$ | | H | H | H | $CD_3$ | H | H | H |
| $L_A996$ | | H | H | H | H | $CD_3$ | H | H |
| $L_A997$ | | $^iPr$ | H | H | H | H | H | H |
| $L_A998$ | | H | $^iPr$ | H | H | H | H | H |
| $L_A999$ | | H | H | $^iPr$ | H | H | H | H |
| $L_A1000$ | | H | H | H | $^iPr$ | H | H | H |
| $L_A1001$ | | H | H | H | H | $^iPr$ | H | H |
| $L_A1002$ | | Ph | H | H | H | H | H | H |
| $L_A1003$ | | H | Ph | H | H | H | H | H |
| $L_A1004$ | | H | H | Ph | H | H | H | H |
| $L_A1005$ | | H | H | H | Ph | H | H | H |
| $L_A1006$ | | H | H | H | H | Ph | H | H |
| $L_A1007$ | | Me | Me | H | H | H | H | H |
| $L_A1008$ | | Me | H | Me | H | H | H | H |
| $L_A1009$ | | Me | H | H | Me | H | H | H |
| $L_A1010$ | | Me | H | H | H | Me | H | H |
| $L_A1011$ | | Me | $CD_3$ | H | H | H | H | H |
| $L_A1012$ | | Me | H | $CD_3$ | H | H | H | H |
| $L_A1013$ | | Me | H | H | $CD_3$ | H | H | H |
| $L_A1014$ | | Me | H | H | H | $CD_3$ | H | H |
| $L_A1015$ | | Me | $^iPr$ | H | H | H | H | H |
| $L_A1016$ | | Me | H | $^iPr$ | H | H | H | H |
| $L_A1017$ | | Me | H | H | $^iPr$ | H | H | H |
| $L_A1018$ | | Me | H | H | H | $^iPr$ | H | H |
| $L_A1019$ | | Me | Ph | H | H | H | H | H |
| $L_A1020$ | | Me | H | Ph | H | H | H | H |
| $L_A1021$ | | Me | H | H | Ph | H | H | H |
| $L_A1022$ | | Me | H | H | H | Ph | H | H |
| $L_A1023$ | | $CD_3$ | Me | H | H | H | H | H |
| $L_A1024$ | | $CD_3$ | H | Me | H | H | H | H |
| $L_A1025$ | | $CD_3$ | H | H | Me | H | H | H |
| $L_A1026$ | | $CD_3$ | H | H | H | Me | H | H |
| $L_A1027$ | | $CD_3$ | $CD_3$ | H | H | H | H | H |
| $L_A1028$ | | $CD_3$ | H | $CD_3$ | H | H | H | H |
| $L_A1029$ | | $CD_3$ | H | H | $CD_3$ | H | H | H |
| $L_A1030$ | | $CD_3$ | H | H | H | $CD_3$ | H | H |
| $L_A1031$ | | $CD_3$ | $^iPr$ | H | H | H | H | H |
| $L_A1032$ | | $CD_3$ | H | $^iPr$ | H | H | H | H |
| $L_A1033$ | | $CD_3$ | H | H | $^iPr$ | H | H | H |
| $L_A1034$ | | $CD_3$ | H | H | H | $^iPr$ | H | H |
| $L_A1035$ | | $CD_3$ | Ph | H | H | H | H | H |
| $L_A1036$ | | $CD_3$ | H | Ph | H | H | H | H |
| $L_A1037$ | | $CD_3$ | H | H | Ph | H | H | H |
| $L_A1038$ | $D_3C$-$CD_3$ / $D_3C$ / $C^{1b}$ / $C^{1e}$ | $CD_3$ | H | H | H | Ph | H | H |
| $L_A1039$ | | $^iPr$ | Me | H | H | H | H | H |
| $L_A1040$ | | $^iPr$ | H | Me | H | H | H | H |
| $L_A1041$ | | $^iPr$ | H | H | Me | H | H | H |
| $L_A1042$ | | $^iPr$ | H | H | H | Me | H | H |
| $L_A1043$ | | $^iPr$ | $CD_3$ | H | H | H | H | H |
| $L_A1044$ | | $^iPr$ | H | $CD_3$ | H | H | H | H |
| $L_A1045$ | | $^iPr$ | H | H | $CD_3$ | H | H | H |
| $L_A1046$ | | $^iPr$ | H | H | H | $CD_3$ | H | H |
| $L_A1047$ | | $^iPr$ | $^iPr$ | H | H | H | H | H |
| $L_A1048$ | | $^iPr$ | H | $^iPr$ | H | H | H | H |
| $L_A1049$ | | $^iPr$ | H | H | $^iPr$ | H | H | H |
| $L_A1050$ | | $^iPr$ | H | H | H | $^iPr$ | H | H |
| $L_A1051$ | | $^iPr$ | Ph | H | H | H | H | H |
| $L_A1052$ | | $^iPr$ | H | Ph | H | H | H | H |
| $L_A1053$ | | $^iPr$ | H | H | Ph | H | H | H |
| $L_A1054$ | | $^iPr$ | H | H | H | Ph | H | H |
| $L_A1055$ | | Ph | Me | H | H | H | H | H |
| $L_A1056$ | | Ph | H | Me | H | H | H | H |
| $L_A1057$ | | Ph | H | H | Me | H | H | H |
| $L_A1058$ | | Ph | H | H | H | Me | H | H |
| $L_A1059$ | | Ph | $CD_3$ | H | H | H | H | H |
| $L_A1060$ | | Ph | H | $CD_3$ | H | H | H | H |
| $L_A1061$ | | Ph | H | H | $CD_3$ | H | H | H |
| $L_A1062$ | | Ph | H | H | H | $CD_3$ | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1063 | | Ph | $^i$Pr | H | H | H | H | H |
| $L_A$1064 | | Ph | H | $^i$Pr | H | H | H | H |
| $L_A$1065 | | Ph | H | H | $^i$Pr | H | H | H |
| $L_A$1066 | | Ph | H | H | H | $^i$Pr | H | H |
| $L_A$1067 | | Ph | Ph | H | H | H | H | H |
| $L_A$1068 | | Ph | H | Ph | H | H | H | H |
| $L_A$1069 | | Ph | H | H | Ph | H | H | H |
| $L_A$1070 | | Ph | H | H | H | Ph | H | H |
| $L_A$1071 | | H | Me | Me | H | H | H | H |
| $L_A$1072 | | H | Me | H | Me | H | H | H |
| $L_A$1073 | | H | Me | H | H | Me | H | H |
| $L_A$1074 | | H | Me | CD$_3$ | H | H | H | H |
| $L_A$1075 | | H | Me | H | CD$_3$ | H | H | H |
| $L_A$1076 | | H | Me | H | H | CD$_3$ | H | H |
| $L_A$1077 | | H | Me | $^i$Pr | H | H | H | H |
| $L_A$1078 | | H | Me | H | $^i$Pr | H | H | H |
| $L_A$1079 | | H | Me | H | H | $^i$Pr | H | H |
| $L_A$1080 | | H | Me | Ph | H | H | H | H |
| $L_A$1081 | | H | Me | H | Ph | H | H | H |
| $L_A$1082 | | H | Me | H | H | Ph | H | H |
| $L_A$1083 | | H | CD$_3$ | Me | H | H | H | H |
| $L_A$1084 | | H | CD$_3$ | H | Me | H | H | H |
| $L_A$1085 | | H | CD$_3$ | H | H | Me | H | H |
| $L_A$1086 | | H | CD$_3$ | CD$_3$ | H | H | H | H |
| $L_A$1087 | | H | CD$_3$ | H | CD$_3$ | H | H | H |
| $L_A$1088 | | H | CD$_3$ | H | H | CD$_3$ | H | H |
| $L_A$1089 | | H | CD$_3$ | $^i$Pr | H | H | H | H |
| $L_A$1090 | | H | CD$_3$ | H | $^i$Pr | H | H | H |
| $L_A$1091 | | H | CD$_3$ | H | H | $^i$Pr | H | H |
| $L_A$1092 | | H | CD$_3$ | Ph | H | H | H | H |
| $L_A$1093 | (D$_3$C)$_3$C–C$^{1b}$/C$^{1e}$ | H | CD$_3$ | H | Ph | H | H | H |
| $L_A$1094 | | H | CD$_3$ | H | H | Ph | H | H |
| $L_A$1095 | | H | $^i$Pr | Me | H | H | H | H |
| $L_A$1096 | | H | $^i$Pr | H | Me | H | H | H |
| $L_A$1097 | | H | $^i$Pr | H | H | Me | H | H |
| $L_A$1098 | | H | $^i$Pr | CD$_3$ | H | H | H | H |
| $L_A$1099 | | H | $^i$Pr | H | CD$_3$ | H | H | H |
| $L_A$1100 | | H | $^i$Pr | H | H | CD$_3$ | H | H |
| $L_A$1101 | | H | $^i$Pr | $^i$Pr | H | H | H | H |
| $L_A$1102 | | H | $^i$Pr | H | $^i$Pr | H | H | H |
| $L_A$1103 | | H | $^i$Pr | H | H | $^i$Pr | H | H |
| $L_A$1104 | | H | $^i$Pr | Ph | H | H | H | H |
| $L_A$1105 | | H | $^i$Pr | H | Ph | H | H | H |
| $L_A$1106 | | H | $^i$Pr | H | H | Ph | H | H |
| $L_A$1107 | | H | Ph | Me | H | H | H | H |
| $L_A$1108 | | H | Ph | H | Me | H | H | H |
| $L_A$1109 | | H | Ph | H | H | Me | H | H |
| $L_A$1110 | | H | Ph | CD$_3$ | H | H | H | H |
| $L_A$1111 | | H | Ph | H | CD$_3$ | H | H | H |
| $L_A$1112 | | H | Ph | H | H | CD$_3$ | H | H |
| $L_A$1113 | | H | Ph | $^i$Pr | H | H | H | H |
| $L_A$1114 | | H | Ph | H | $^i$Pr | H | H | H |
| $L_A$1115 | | H | Ph | H | H | $^i$Pr | H | H |
| $L_A$1116 | | H | Ph | Ph | H | H | H | H |
| $L_A$1117 | | H | Ph | H | Ph | H | H | H |
| $L_A$1118 | | H | Ph | H | H | Ph | H | H |
| $L_A$1119 | | H | H | Me | Me | H | H | H |
| $L_A$1120 | | H | H | CD$_3$ | Me | H | H | H |
| $L_A$1121 | | H | H | $^i$Pr | Me | H | H | H |
| $L_A$1122 | | H | H | Ph | Me | H | H | H |
| $L_A$1123 | | H | H | Me | CD$_3$ | H | H | H |
| $L_A$1124 | | H | H | CD$_3$ | CD$_3$ | H | H | H |
| $L_A$1125 | | H | H | $^i$Pr | CD$_3$ | H | H | H |
| $L_A$1126 | | H | H | Ph | CD$_3$ | H | H | H |
| $L_A$1127 | | H | H | Me | $^i$Pr | H | H | H |
| $L_A$1128 | | H | H | CD$_3$ | $^i$Pr | H | H | H |
| $L_A$1129 | | H | H | $^i$Pr | $^i$Pr | H | H | H |
| $L_A$1130 | | H | H | Ph | $^i$Pr | H | H | H |
| $L_A$1131 | | H | H | Me | Ph | H | H | H |
| $L_A$1132 | | H | H | CD$_3$ | Ph | H | H | H |
| $L_A$1133 | | H | H | $^i$Pr | Ph | H | H | H |
| $L_A$1134 | | H | H | Ph | Ph | H | H | H |
| $L_A$1135 | | H | H | Me | H | Me | H | H |
| $L_A$1136 | | H | H | CD$_3$ | H | Me | H | H |
| $L_A$1137 | | H | H | $^i$Pr | H | Me | H | H |
| $L_A$1138 | | H | H | Ph | H | Me | H | H |
| $L_A$1139 | | H | H | Me | H | CD$_3$ | H | H |
| $L_A$1140 | | H | H | CD$_3$ | H | CD$_3$ | H | H |
| $L_A$1141 | | H | H | $^i$Pr | H | CD$_3$ | H | H |
| $L_A$1142 | | H | H | Ph | H | CD$_3$ | H | H |
| $L_A$1143 | | H | H | Me | H | $^i$Pr | H | H |
| $L_A$1144 | | H | H | CD$_3$ | H | $^i$Pr | H | H |
| $L_A$1145 | | H | H | $^i$Pr | H | $^i$Pr | H | H |
| $L_A$1146 | | H | H | Ph | H | $^i$Pr | H | H |
| $L_A$1147 | | H | H | Me | H | Ph | H | H |
| $L_A$1148 | (D$_3$C)$_3$C–C$^{1b}$/C$^{1e}$ | H | H | CD$_3$ | H | Ph | H | H |
| $L_A$1149 | | H | H | $^i$Pr | H | Ph | H | H |
| $L_A$1150 | | H | H | Ph | H | Ph | H | H |
| $L_A$1151 | | Me | Me | H | Me | H | H | H |
| $L_A$1152 | | H | Me | Me | Me | H | H | H |
| $L_A$1153 | | CD$_3$ | Me | H | H | H | H | H |
| $L_A$1154 | | H | Me | CD$_3$ | Me | H | H | H |
| $L_A$1155 | | $^i$Pr | Me | H | Me | H | H | H |
| $L_A$1156 | | H | Me | $^i$Pr | Me | H | H | H |
| $L_A$1157 | | Ph | Me | H | Me | H | H | H |
| $L_A$1158 | | H | Me | Ph | Me | H | H | H |
| $L_A$1159 | | Me | CD$_3$ | H | CD$_3$ | H | H | H |
| $L_A$1160 | | H | CD$_3$ | Me | CD$_3$ | H | H | H |
| $L_A$1161 | | CD$_3$ | CD$_3$ | H | CD$_3$ | H | H | H |
| $L_A$1162 | | H | CD$_3$ | CD$_3$ | CD$_3$ | H | H | H |
| $L_A$1163 | | $^i$Pr | CD$_3$ | H | CD$_3$ | H | H | H |
| $L_A$1164 | | H | CD$_3$ | $^i$Pr | CD$_3$ | H | H | H |
| $L_A$1165 | | Ph | CD$_3$ | H | CD$_3$ | H | H | H |
| $L_A$1166 | | H | CD$_3$ | Ph | CD$_3$ | H | H | H |
| $L_A$1167 | | Me | $^i$Pr | H | $^i$Pr | H | H | H |
| $L_A$1168 | | H | $^i$Pr | Me | $^i$Pr | H | H | H |
| $L_A$1169 | | CD$_3$ | $^i$Pr | H | $^i$Pr | H | H | H |
| $L_A$1170 | | H | $^i$Pr | CD$_3$ | $^i$Pr | H | H | H |
| $L_A$1171 | | $^i$Pr | $^i$Pr | H | $^i$Pr | H | H | H |
| $L_A$1172 | | H | $^i$Pr | $^i$Pr | $^i$Pr | H | H | H |
| $L_A$1173 | | Ph | $^i$Pr | H | $^i$Pr | H | H | H |
| $L_A$1174 | | H | $^i$Pr | Ph | $^i$Pr | H | H | H |
| $L_A$1175 | | Me | Ph | H | Ph | H | H | H |
| $L_A$1176 | | H | Ph | Me | Ph | H | H | H |
| $L_A$1177 | | CD$_3$ | Ph | H | Ph | H | H | H |
| $L_A$1178 | | H | Ph | CD$_3$ | Ph | H | H | H |
| $L_A$1179 | | $^i$Pr | Ph | H | Ph | H | H | H |
| $L_A$1180 | | H | Ph | $^i$Pr | Ph | H | H | H |
| $L_A$1181 | | Ph | Ph | H | Ph | H | H | H |
| $L_A$1182 | | H | Ph | Ph | Ph | H | H | H |
| $L_A$1183 | (D$_3$C)(Et)$_2$C–C$^{1b}$/C$^{1e}$ | H | H | H | H | H | H | H |
| $L_A$1184 | | Me | H | H | H | H | H | H |
| $L_A$1185 | | H | Me | H | H | H | H | H |
| $L_A$1186 | | H | H | Me | H | H | H | H |
| $L_A$1187 | | H | H | H | Me | H | H | H |
| $L_A$1188 | | H | H | H | H | Me | H | H |
| $L_A$1189 | | CD$_3$ | H | H | H | H | H | H |
| $L_A$1190 | | H | CD$_3$ | H | H | H | H | H |
| $L_A$1191 | | H | H | CD$_3$ | H | H | H | H |
| $L_A$1192 | | H | H | H | CD$_3$ | H | H | H |
| $L_A$1193 | | H | H | H | H | CD$_3$ | H | H |
| $L_A$1194 | | $^i$Pr | H | H | H | H | H | H |
| $L_A$1195 | | H | $^i$Pr | H | H | H | H | H |
| $L_A$1196 | | H | H | $^i$Pr | H | H | H | H |
| $L_A$1197 | | H | H | H | $^i$Pr | H | H | H |
| $L_A$1198 | | H | H | H | H | $^i$Pr | H | H |
| $L_A$1199 | | Ph | H | H | H | H | H | H |
| $L_A$1200 | | H | Ph | H | H | H | H | H |
| $L_A$1201 | | H | H | Ph | H | H | H | H |
| $L_A$1202 | | H | H | H | Ph | H | H | H |
| $L_A$1203 | (D$_3$C)(Et)$_2$C–C$^{1b}$/C$^{1e}$ | H | H | H | H | Ph | H | H |
| $L_A$1204 | | Me | Me | H | H | H | H | H |
| $L_A$1205 | | Me | H | Me | H | H | H | H |
| $L_A$1206 | | Me | H | H | Me | H | H | H |
| $L_A$1207 | | Me | H | H | H | Me | H | H |
| $L_A$1208 | | Me | CD$_3$ | H | H | H | H | H |
| $L_A$1209 | | Me | H | CD$_3$ | H | H | H | H |
| $L_A$1210 | | Me | H | H | CD$_3$ | H | H | H |
| $L_A$1211 | | Me | H | H | H | CD$_3$ | H | H |
| $L_A$1212 | | Me | $^i$Pr | H | H | H | H | H |
| $L_A$1213 | | Me | H | $^i$Pr | H | H | H | H |
| $L_A$1214 | | Me | H | H | $^i$Pr | H | H | H |

-continued

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A1215$ | | Me | H | H | H | $^i$Pr | H | H |
| $L_A1216$ | | Me | Ph | H | H | H | H | H |
| $L_A1217$ | | Me | H | Ph | H | H | H | H |
| $L_A1218$ | | Me | H | H | Ph | H | H | H |
| $L_A1219$ | | Me | H | H | H | Ph | H | H |
| $L_A1220$ | | $CD_3$ | Me | H | H | H | H | H |
| $L_A1221$ | | $CD_3$ | H | Me | H | H | H | H |
| $L_A1222$ | | $CD_3$ | H | H | Me | H | H | H |
| $L_A1223$ | | $CD_3$ | H | H | H | Me | H | H |
| $L_A1224$ | | $CD_3$ | $CD_3$ | H | H | H | H | H |
| $L_A1225$ | | $CD_3$ | H | $CD_3$ | H | H | H | H |
| $L_A1226$ | | $CD_3$ | H | H | $CD_3$ | H | H | H |
| $L_A1227$ | | $CD_3$ | H | H | H | $CD_3$ | H | H |
| $L_A1228$ | | $CD_3$ | $^i$Pr | H | H | H | H | H |
| $L_A1229$ | | $CD_3$ | H | $^i$Pr | H | H | H | H |
| $L_A1230$ | | $CD_3$ | H | H | $^i$Pr | H | H | H |
| $L_A1231$ | | $CD_3$ | H | H | H | $^i$Pr | H | H |
| $L_A1232$ | | $CD_3$ | Ph | H | H | H | H | H |
| $L_A1233$ | | $CD_3$ | H | Ph | H | H | H | H |
| $L_A1234$ | | $CD_3$ | H | H | Ph | H | H | H |
| $L_A1235$ | | $CD_3$ | H | H | H | Ph | H | H |
| $L_A1236$ | | $^i$Pr | Me | H | H | H | H | H |
| $L_A1237$ | | $^i$Pr | H | Me | H | H | H | H |
| $L_A1238$ | | $^i$Pr | H | H | Me | H | H | H |
| $L_A1239$ | | $^i$Pr | H | H | H | Me | H | H |
| $L_A1240$ | | $^i$Pr | $CD_3$ | H | H | H | H | H |
| $L_A1241$ | | $^i$Pr | H | $CD_3$ | H | H | H | H |
| $L_A1242$ | | $^i$Pr | H | H | $CD_3$ | H | H | H |
| $L_A1243$ | | $^i$Pr | H | H | H | $CD_3$ | H | H |
| $L_A1244$ | | $^i$Pr | $^i$Pr | H | H | H | H | H |
| $L_A1245$ | | $^i$Pr | H | $^i$Pr | H | H | H | H |
| $L_A1246$ | | $^i$Pr | H | H | $^i$Pr | H | H | H |
| $L_A1247$ | | $^i$Pr | H | H | H | $^i$Pr | H | H |
| $L_A1248$ | | $^i$Pr | Ph | H | H | H | H | H |
| $L_A1249$ | | $^i$Pr | H | Ph | H | H | H | H |
| $L_A1250$ | | $^i$Pr | H | H | Ph | H | H | H |
| $L_A1251$ | | $^i$Pr | H | H | H | Ph | H | H |
| $L_A1252$ | | Ph | Me | H | H | H | H | H |
| $L_A1253$ | | Ph | H | Me | H | H | H | H |
| $L_A1254$ | | Ph | H | H | Me | H | H | H |
| $L_A1255$ | | Ph | H | H | H | Me | H | H |
| $L_A1256$ | | Ph | $CD_3$ | H | H | H | H | H |
| $L_A1257$ | | Ph | H | $CD_3$ | H | H | H | H |
| $L_A1258$ | $D_3C-C(Et)(Et)-C^{1b}$ with $C^{1e}$, $D_3C$ | Ph | H | H | $CD_3$ | H | H | H |
| $L_A1259$ | | Ph | H | H | H | $CD_3$ | H | H |
| $L_A1260$ | | Ph | $^i$Pr | H | H | H | H | H |
| $L_A1261$ | | Ph | H | $^i$Pr | H | H | H | H |
| $L_A1262$ | | Ph | H | H | $^i$Pr | H | H | H |
| $L_A1263$ | | Ph | H | H | H | $^i$Pr | H | H |
| $L_A1264$ | | Ph | Ph | H | H | H | H | H |
| $L_A1265$ | | Ph | H | Ph | H | H | H | H |
| $L_A1266$ | | Ph | H | H | Ph | H | H | H |
| $L_A1267$ | | Ph | H | H | H | Ph | H | H |
| $L_A1268$ | | H | Me | Me | H | H | H | H |
| $L_A1269$ | | H | Me | H | Me | H | H | H |
| $L_A1270$ | | H | Me | H | H | Me | H | H |
| $L_A1271$ | | H | Me | $CD_3$ | H | H | H | H |
| $L_A1272$ | | H | Me | H | $CD_3$ | H | H | H |
| $L_A1273$ | | H | Me | H | H | $CD_3$ | H | H |
| $L_A1274$ | | H | Me | $^i$Pr | H | H | H | H |
| $L_A1275$ | | H | Me | H | $^i$Pr | H | H | H |
| $L_A1276$ | | H | Me | H | H | $^i$Pr | H | H |
| $L_A1277$ | | H | Me | Ph | H | H | H | H |
| $L_A1278$ | | H | Me | H | Ph | H | H | H |
| $L_A1279$ | | H | Me | H | H | Ph | H | H |
| $L_A1280$ | | H | $CD_3$ | Me | H | H | H | H |
| $L_A1281$ | | H | $CD_3$ | H | Me | H | H | H |
| $L_A1282$ | | H | $CD_3$ | H | H | Me | H | H |
| $L_A1283$ | | H | $CD_3$ | $CD_3$ | H | H | H | H |
| $L_A1284$ | | H | $CD_3$ | H | $CD_3$ | H | H | H |
| $L_A1285$ | | H | $CD_3$ | H | H | $CD_3$ | H | H |
| $L_A1286$ | | H | $CD_3$ | $^i$Pr | H | H | H | H |
| $L_A1287$ | | H | $CD_3$ | H | $^i$Pr | H | H | H |
| $L_A1288$ | | H | $CD_3$ | H | H | $^i$Pr | H | H |
| $L_A1289$ | | H | $CD_3$ | Ph | H | H | H | H |
| $L_A1290$ | | H | $CD_3$ | H | Ph | H | H | H |
| $L_A1291$ | | H | $CD_3$ | H | H | Ph | H | H |
| $L_A1292$ | | H | $^i$Pr | Me | H | H | H | H |
| $L_A1293$ | | H | $^i$Pr | H | Me | H | H | H |
| $L_A1294$ | | H | $^i$Pr | H | H | Me | H | H |
| $L_A1295$ | | H | $^i$Pr | $CD_3$ | H | H | H | H |
| $L_A1296$ | | H | $^i$Pr | H | $CD_3$ | H | H | H |
| $L_A1297$ | | H | $^i$Pr | H | H | $CD_3$ | H | H |
| $L_A1298$ | | H | $^i$Pr | $^i$Pr | H | H | H | H |
| $L_A1299$ | | H | $^i$Pr | H | $^i$Pr | H | H | H |
| $L_A1300$ | | H | $^i$Pr | H | H | $^i$Pr | H | H |
| $L_A1301$ | | H | $^i$Pr | Ph | H | H | H | H |
| $L_A1302$ | | H | $^i$Pr | H | Ph | H | H | H |
| $L_A1303$ | | H | $^i$Pr | H | H | Ph | H | H |
| $L_A1304$ | | H | Ph | Me | H | H | H | H |
| $L_A1305$ | | H | Ph | H | Me | H | H | H |
| $L_A1306$ | | H | Ph | H | H | Me | H | H |
| $L_A1307$ | | H | Ph | $CD_3$ | H | H | H | H |
| $L_A1308$ | | H | Ph | H | $CD_3$ | H | H | H |
| $L_A1309$ | | H | Ph | H | H | $CD_3$ | H | H |
| $L_A1310$ | | H | Ph | $^i$Pr | H | H | H | H |
| $L_A1311$ | | H | Ph | H | $^i$Pr | H | H | H |
| $L_A1312$ | | H | Ph | H | H | $^i$Pr | H | H |
| $L_A1313$ | $D_3C-C(Et)(Et)-C^{1b}$ with $C^{1e}$, $D_3C$ | H | Ph | Ph | H | H | H | H |
| $L_A1314$ | | H | Ph | H | Ph | H | H | H |
| $L_A1315$ | | H | Ph | H | H | Ph | H | H |
| $L_A1316$ | | H | H | Me | Me | H | H | H |
| $L_A1317$ | | H | H | $CD_3$ | Me | H | H | H |
| $L_A1318$ | | H | H | $^i$Pr | Me | H | H | H |
| $L_A1319$ | | H | H | Ph | Me | H | H | H |
| $L_A1320$ | | H | H | Me | $CD_3$ | H | H | H |
| $L_A1321$ | | H | H | $CD_3$ | $CD_3$ | H | H | H |
| $L_A1322$ | | H | H | $^i$Pr | $CD_3$ | H | H | H |
| $L_A1323$ | | H | H | Ph | $CD_3$ | H | H | H |
| $L_A1324$ | | H | H | Me | $^i$Pr | H | H | H |
| $L_A1325$ | | H | H | $CD_3$ | $^i$Pr | H | H | H |
| $L_A1326$ | | H | H | $^i$Pr | $^i$Pr | H | H | H |
| $L_A1327$ | | H | H | Ph | $^i$Pr | H | H | H |
| $L_A1328$ | | H | H | Me | Ph | H | H | H |
| $L_A1329$ | | H | H | $CD_3$ | Ph | H | H | H |
| $L_A1330$ | | H | H | $^i$Pr | Ph | H | H | H |
| $L_A1331$ | | H | H | Ph | Ph | H | H | H |
| $L_A1332$ | | H | H | Me | H | Me | H | H |
| $L_A1333$ | | H | H | $CD_3$ | H | Me | H | H |
| $L_A1334$ | | H | H | $^i$Pr | H | Me | H | H |
| $L_A1335$ | | H | H | Ph | H | Me | H | H |
| $L_A1336$ | | H | H | Me | H | $CD_3$ | H | H |
| $L_A1337$ | | H | H | $CD_3$ | H | $CD_3$ | H | H |
| $L_A1338$ | | H | H | $^i$Pr | H | $CD_3$ | H | H |
| $L_A1339$ | | H | H | Ph | H | $CD_3$ | H | H |
| $L_A1340$ | | H | H | Me | H | $^i$Pr | H | H |
| $L_A1341$ | | H | H | $CD_3$ | H | $^i$Pr | H | H |
| $L_A1342$ | | H | H | $^i$Pr | H | $^i$Pr | H | H |
| $L_A1343$ | | H | H | Ph | H | $^i$Pr | H | H |
| $L_A1344$ | | H | H | Me | H | Ph | H | H |
| $L_A1345$ | | H | H | $CD_3$ | H | Ph | H | H |
| $L_A1346$ | | H | H | $^i$Pr | H | Ph | H | H |
| $L_A1347$ | | H | H | Ph | H | Ph | H | H |
| $L_A1348$ | | Me | Me | H | Me | H | H | H |
| $L_A1349$ | | H | Me | Me | Me | H | H | H |
| $L_A1350$ | | $CD_3$ | Me | H | Me | H | H | H |
| $L_A1351$ | | H | Me | $CD_3$ | Me | H | H | H |
| $L_A1352$ | | $^i$Pr | Me | H | Me | H | H | H |
| $L_A1353$ | | H | Me | $^i$Pr | Me | H | H | H |
| $L_A1354$ | | Ph | Me | H | Me | H | H | H |
| $L_A1355$ | | H | Me | Ph | Me | H | H | H |
| $L_A1356$ | | Me | $CD_3$ | H | $CD_3$ | H | H | H |
| $L_A1357$ | | H | $CD_3$ | Me | $CD_3$ | H | H | H |
| $L_A1358$ | | $CD_3$ | $CD_3$ | H | $CD_3$ | H | H | H |
| $L_A1359$ | | H | $CD_3$ | $CD_3$ | $CD_3$ | H | H | H |
| $L_A1360$ | | $^i$Pr | $CD_3$ | H | $CD_3$ | H | H | H |
| $L_A1361$ | | H | $CD_3$ | $^i$Pr | $CD_3$ | H | H | H |
| $L_A1362$ | | Ph | $CD_3$ | H | $CD_3$ | H | H | H |
| $L_A1363$ | | H | $CD_3$ | Ph | $CD_3$ | H | H | H |
| $L_A1364$ | | Me | $^i$Pr | H | $^i$Pr | H | H | H |
| $L_A1365$ | | H | $^i$Pr | Me | $^i$Pr | H | H | H |
| $L_A1366$ | | $CD_3$ | $^i$Pr | H | $^i$Pr | H | H | H |
| $L_A1367$ | | H | $^i$Pr | $CD_3$ | $^i$Pr | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1368 | 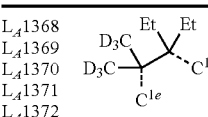 | $^i$Pr | $^i$Pr | H | $^i$Pr | H | H | H |
| $L_A$1369 | | H | $^i$Pr | $^i$Pr | $^i$Pr | H | H | H |
| $L_A$1370 | | Ph | $^i$Pr | H | $^i$Pr | H | H | H |
| $L_A$1371 | | H | $^i$Pr | Ph | $^i$Pr | H | H | H |
| $L_A$1372 | | Me | Ph | H | Ph | H | H | H |
| $L_A$1373 | | H | Ph | Me | Ph | H | H | H |
| $L_A$1374 | | CD$_3$ | Ph | H | Ph | H | H | H |
| $L_A$1375 | | H | Ph | CD$_3$ | Ph | H | H | H |
| $L_A$1376 | | $^i$Pr | Ph | H | Ph | H | H | H |
| $L_A$1377 | | H | Ph | $^i$Pr | Ph | H | H | H |
| $L_A$1378 | | Ph | Ph | H | Ph | H | H | H |
| $L_A$1379 | | H | Ph | Ph | Ph | H | H | H |
| $L_A$1380 | 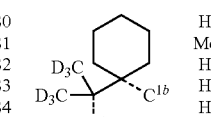 | H | H | H | H | H | H | H |
| $L_A$1381 | | Me | H | H | H | H | H | H |
| $L_A$1382 | | H | Me | H | H | H | H | H |
| $L_A$1383 | | H | H | Me | H | H | H | H |
| $L_A$1384 | | H | H | H | Me | H | H | H |
| $L_A$1385 | | H | H | H | H | Me | H | H |
| $L_A$1386 | | CD$_3$ | H | H | H | H | H | H |
| $L_A$1387 | | H | CD$_3$ | H | H | H | H | H |
| $L_A$1388 | | H | H | CD$_3$ | H | H | H | H |
| $L_A$1389 | | H | H | H | CD$_3$ | H | H | H |
| $L_A$1390 | | H | H | H | H | CD$_3$ | H | H |
| $L_A$1391 | | $^i$Pr | H | H | H | H | H | H |
| $L_A$1392 | | H | $^i$Pr | H | H | H | H | H |
| $L_A$1393 | | H | H | $^i$Pr | H | H | H | H |
| $L_A$1394 | | H | H | H | $^i$Pr | H | H | H |
| $L_A$1395 | | H | H | H | H | $^i$Pr | H | H |
| $L_A$1396 | | Ph | H | H | H | H | H | H |
| $L_A$1397 | | H | Ph | H | H | H | H | H |
| $L_A$1398 | | H | H | Ph | H | H | H | H |
| $L_A$1399 | | H | H | H | Ph | H | H | H |
| $L_A$1400 | | H | H | H | H | Ph | H | H |
| $L_A$1401 | | Me | Me | H | H | H | H | H |
| $L_A$1402 | | Me | H | Me | H | H | H | H |
| $L_A$1403 | | Me | H | H | Me | H | H | H |
| $L_A$1404 | | Me | H | H | H | Me | H | H |
| $L_A$1405 | | Me | CD$_3$ | H | H | H | H | H |
| $L_A$1406 | | Me | H | CD$_3$ | H | H | H | H |
| $L_A$1407 | | Me | H | H | CD$_3$ | H | H | H |
| $L_A$1408 | | Me | H | H | H | CD$_3$ | H | H |
| $L_A$1409 | | Me | $^i$Pr | H | H | H | H | H |
| $L_A$1410 | | Me | H | $^i$Pr | H | H | H | H |
| $L_A$1411 | | Me | H | H | $^i$Pr | H | H | H |
| $L_A$1412 | | Me | H | H | H | $^i$Pr | H | H |
| $L_A$1413 | | Me | Ph | H | H | H | H | H |
| $L_A$1414 | | Me | H | Ph | H | H | H | H |
| $L_A$1415 | | Me | H | H | Ph | H | H | H |
| $L_A$1416 | | Me | H | H | H | Ph | H | H |
| $L_A$1417 | | CD$_3$ | Me | H | H | H | H | H |
| $L_A$1418 | | CD$_3$ | H | Me | H | H | H | H |
| $L_A$1419 | | CD$_3$ | H | H | Me | H | H | H |
| $L_A$1420 | | CD$_3$ | H | H | H | Me | H | H |
| $L_A$1421 | | CD$_3$ | CD$_3$ | H | H | H | H | H |
| $L_A$1422 | | CD$_3$ | H | CD$_3$ | H | H | H | H |
| $L_A$1423 | 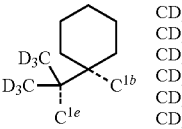 | CD$_3$ | H | H | CD$_3$ | H | H | H |
| $L_A$1424 | | CD$_3$ | H | H | H | CD$_3$ | H | H |
| $L_A$1425 | | CD$_3$ | $^i$Pr | H | H | H | H | H |
| $L_A$1426 | | CD$_3$ | H | $^i$Pr | H | H | H | H |
| $L_A$1427 | | CD$_3$ | H | H | $^i$Pr | H | H | H |
| $L_A$1428 | | CD$_3$ | H | H | H | $^i$Pr | H | H |
| $L_A$1429 | | CD$_3$ | Ph | H | H | H | H | H |
| $L_A$1430 | | CD$_3$ | H | Ph | H | H | H | H |
| $L_A$1431 | | CD$_3$ | H | H | Ph | H | H | H |
| $L_A$1432 | | CD$_3$ | H | H | H | Ph | H | H |
| $L_A$1433 | | $^i$Pr | Me | H | H | H | H | H |
| $L_A$1434 | | $^i$Pr | H | Me | H | H | H | H |
| $L_A$1435 | | $^i$Pr | H | H | Me | H | H | H |
| $L_A$1436 | | $^i$Pr | H | H | H | Me | H | H |
| $L_A$1437 | | $^i$Pr | CD$_3$ | H | H | H | H | H |
| $L_A$1438 | | $^i$Pr | H | CD$_3$ | H | H | H | H |
| $L_A$1439 | | $^i$Pr | H | H | CD$_3$ | H | H | H |
| $L_A$1440 | | $^i$Pr | H | H | H | CD$_3$ | H | H |
| $L_A$1441 | | $^i$Pr | $^i$Pr | H | H | H | H | H |
| $L_A$1442 | | $^i$Pr | H | $^i$Pr | H | H | H | H |
| $L_A$1443 | | $^i$Pr | H | H | $^i$Pr | H | H | H |
| $L_A$1444 | | $^i$Pr | H | H | H | $^i$Pr | H | H |
| $L_A$1445 | | $^i$Pr | Ph | H | H | H | H | H |
| $L_A$1446 | | $^i$Pr | H | Ph | H | H | H | H |
| $L_A$1447 | | $^i$Pr | H | H | Ph | H | H | H |
| $L_A$1448 | | $^i$Pr | H | H | H | Ph | H | H |
| $L_A$1449 | | Ph | Me | H | H | H | H | H |
| $L_A$1450 | | Ph | H | Me | H | H | H | H |
| $L_A$1451 | | Ph | H | H | Me | H | H | H |
| $L_A$1452 | | Ph | H | H | H | Me | H | H |
| $L_A$1453 | | Ph | CD$_3$ | H | H | H | H | H |
| $L_A$1454 | | Ph | H | CD$_3$ | H | H | H | H |
| $L_A$1455 | | Ph | H | H | CD$_3$ | H | H | H |
| $L_A$1456 | | Ph | H | H | H | CD$_3$ | H | H |
| $L_A$1457 | | Ph | $^i$Pr | H | H | H | H | H |
| $L_A$1458 | | Ph | H | $^i$Pr | H | H | H | H |
| $L_A$1459 | | Ph | H | H | $^i$Pr | H | H | H |
| $L_A$1460 | | Ph | H | H | H | $^i$Pr | H | H |
| $L_A$1461 | | Ph | Ph | H | H | H | H | H |
| $L_A$1462 | | Ph | H | Ph | H | H | H | H |
| $L_A$1463 | | Ph | H | H | Ph | H | H | H |
| $L_A$1464 | | Ph | H | H | H | Ph | H | H |
| $L_A$1465 | | H | Me | Me | H | H | H | H |
| $L_A$1466 | | H | Me | H | Me | H | H | H |
| $L_A$1467 | | H | Me | H | H | Me | H | H |
| $L_A$1468 | | H | Me | CD$_3$ | H | H | H | H |
| $L_A$1469 | | H | Me | H | CD$_3$ | H | H | H |
| $L_A$1470 | | H | Me | H | H | CD$_3$ | H | H |
| $L_A$1471 | | H | Me | $^i$Pr | H | H | H | H |
| $L_A$1472 | | H | Me | H | $^i$Pr | H | H | H |
| $L_A$1473 | | H | Me | H | H | $^i$Pr | H | H |
| $L_A$1474 | | H | Me | Ph | H | H | H | H |
| $L_A$1475 | | H | Me | H | Ph | H | H | H |
| $L_A$1476 | | H | Me | H | H | Ph | H | H |
| $L_A$1477 | | H | CD$_3$ | Me | H | H | H | H |
| $L_A$1478 | | H | CD$_3$ | H | Me | H | H | H |
| $L_A$1479 | | H | CD$_3$ | H | H | Me | H | H |
| $L_A$1480 | | H | CD$_3$ | CD$_3$ | H | H | H | H |
| $L_A$1481 | | H | CD$_3$ | H | CD$_3$ | H | H | H |
| $L_A$1482 | | H | CD$_3$ | H | H | CD$_3$ | H | H |
| $L_A$1483 | | H | CD$_3$ | $^i$Pr | H | H | H | H |
| $L_A$1484 | | H | CD$_3$ | H | $^i$Pr | H | H | H |
| $L_A$1485 | | H | CD$_3$ | H | H | $^i$Pr | H | H |
| $L_A$1486 | | H | CD$_3$ | Ph | H | H | H | H |
| $L_A$1487 | | H | CD$_3$ | H | Ph | H | H | H |
| $L_A$1488 | | H | CD$_3$ | H | H | Ph | H | H |
| $L_A$1489 | | H | $^i$Pr | Me | H | H | H | H |
| $L_A$1490 | | H | $^i$Pr | H | Me | H | H | H |
| $L_A$1491 | | H | $^i$Pr | H | H | Me | H | H |
| $L_A$1492 | | H | $^i$Pr | CD$_3$ | H | H | H | H |
| $L_A$1493 | | H | $^i$Pr | H | CD$_3$ | H | H | H |
| $L_A$1494 | | H | $^i$Pr | H | H | CD$_3$ | H | H |
| $L_A$1495 | | H | $^i$Pr | $^i$Pr | H | H | H | H |
| $L_A$1496 | | H | $^i$Pr | H | $^i$Pr | H | H | H |
| $L_A$1497 | | H | $^i$Pr | H | H | $^i$Pr | H | H |
| $L_A$1498 | | H | $^i$Pr | Ph | H | H | H | H |
| $L_A$1499 | | H | $^i$Pr | H | Ph | H | H | H |
| $L_A$1500 | | H | $^i$Pr | H | H | Ph | H | H |
| $L_A$1501 | | H | Ph | Me | H | H | H | H |
| $L_A$1502 | | H | Ph | H | Me | H | H | H |
| $L_A$1503 | | H | Ph | H | H | Me | H | H |
| $L_A$1504 | | H | Ph | CD$_3$ | H | H | H | H |
| $L_A$1505 | | H | Ph | H | CD$_3$ | H | H | H |
| $L_A$1506 | | H | Ph | H | H | CD$_3$ | H | H |
| $L_A$1507 | | H | Ph | $^i$Pr | H | H | H | H |
| $L_A$1508 | | H | Ph | H | $^i$Pr | H | H | H |
| $L_A$1509 | | H | Ph | H | H | $^i$Pr | H | H |
| $L_A$1510 | | H | Ph | Ph | H | H | H | H |
| $L_A$1511 | | H | Ph | H | Ph | H | H | H |
| $L_A$1512 | | H | Ph | H | H | Ph | H | H |
| $L_A$1513 | | H | H | Me | Me | H | H | H |
| $L_A$1514 | | H | H | CD$_3$ | Me | H | H | H |
| $L_A$1515 | | H | H | $^i$Pr | Me | H | H | H |
| $L_A$1516 | | H | H | Ph | Me | H | H | H |
| $L_A$1517 | | H | H | Me | CD$_3$ | H | H | H |
| $L_A$1518 | | H | H | CD$_3$ | CD$_3$ | H | H | H |
| $L_A$1519 | | H | H | $^i$Pr | CD$_3$ | H | H | H |
| $L_A$1520 | | H | H | Ph | CD$_3$ | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1521 | | H | H | Me | $^i$Pr | H | H | H |
| $L_A$1522 | | H | H | CD$_3$ | $^i$Pr | H | H | H |
| $L_A$1523 | | H | H | $^i$Pr | $^i$Pr | H | H | H |
| $L_A$1524 | | H | H | Ph | $^i$Pr | H | H | H |
| $L_A$1525 | | H | H | Me | Ph | H | H | H |
| $L_A$1526 | | H | H | CD$_3$ | Ph | H | H | H |
| $L_A$1527 | | H | H | $^i$Pr | Ph | H | H | H |
| $L_A$1528 | | H | H | Ph | Ph | H | H | H |
| $L_A$1529 | | H | H | Me | H | Me | H | H |
| $L_A$1530 | | H | H | CD$_3$ | H | Me | H | H |
| $L_A$1531 | | H | H | $^i$Pr | H | Me | H | H |
| $L_A$1532 | | H | H | Ph | H | Me | H | H |
| $L_A$1533 | cyclohexyl with D$_3$C, D$_3$C, C$^{1b}$, C$^{1e}$ | H | H | Me | H | CD$_3$ | H | H |
| $L_A$1534 | | H | H | CD$_3$ | H | CD$_3$ | H | H |
| $L_A$1535 | | H | H | $^i$Pr | H | CD$_3$ | H | H |
| $L_A$1536 | | H | H | Ph | H | CD$_3$ | H | H |
| $L_A$1537 | | H | H | Me | H | $^i$Pr | H | H |
| $L_A$1538 | | H | H | CD$_3$ | H | $^i$Pr | H | H |
| $L_A$1539 | | H | H | $^i$Pr | H | $^i$Pr | H | H |
| $L_A$1540 | | H | H | Ph | H | $^i$Pr | H | H |
| $L_A$1541 | | H | H | Me | H | Ph | H | H |
| $L_A$1542 | | H | H | CD$_3$ | H | Ph | H | H |
| $L_A$1543 | | H | H | $^i$Pr | H | Ph | H | H |
| $L_A$1544 | | H | H | Ph | H | Ph | H | H |
| $L_A$1545 | | Me | Me | H | Me | H | H | H |
| $L_A$1546 | | H | Me | Me | Me | H | H | H |
| $L_A$1547 | | CD$_3$ | Me | H | Me | H | H | H |
| $L_A$1548 | | H | Me | CD$_3$ | Me | H | H | H |
| $L_A$1549 | | $^i$Pr | Me | H | Me | H | H | H |
| $L_A$1550 | | H | Me | $^i$Pr | Me | H | H | H |
| $L_A$1551 | | Ph | Me | H | Me | H | H | H |
| $L_A$1552 | | H | Me | Ph | Me | H | H | H |
| $L_A$1553 | | Me | CD$_3$ | H | CD$_3$ | H | H | H |
| $L_A$1554 | | H | CD$_3$ | Me | CD$_3$ | H | H | H |
| $L_A$1555 | | CD$_3$ | CD$_3$ | H | CD$_3$ | H | H | H |
| $L_A$1556 | | H | CD$_3$ | CD$_3$ | CD$_3$ | H | H | H |
| $L_A$1557 | | $^i$Pr | CD$_3$ | H | CD$_3$ | H | H | H |
| $L_A$1558 | | H | CD$_3$ | $^i$Pr | CD$_3$ | H | H | H |
| $L_A$1559 | | Ph | CD$_3$ | H | CD$_3$ | H | H | H |
| $L_A$1560 | | H | CD$_3$ | Ph | CD$_3$ | H | H | H |
| $L_A$1561 | | Me | $^i$Pr | H | $^i$Pr | H | H | H |
| $L_A$1562 | | H | $^i$Pr | Me | $^i$Pr | H | H | H |
| $L_A$1563 | | CD$_3$ | $^i$Pr | H | $^i$Pr | H | H | H |
| $L_A$1564 | | H | $^i$Pr | CD$_3$ | $^i$Pr | H | H | H |
| $L_A$1565 | | $^i$Pr | $^i$Pr | H | $^i$Pr | H | H | H |
| $L_A$1566 | | H | $^i$Pr | $^i$Pr | $^i$Pr | H | H | H |
| $L_A$1567 | | Ph | $^i$Pr | H | $^i$Pr | H | H | H |
| $L_A$1568 | | H | $^i$Pr | Ph | $^i$Pr | H | H | H |
| $L_A$1569 | | Me | Ph | H | Ph | H | H | H |
| $L_A$1570 | | H | Ph | Me | Ph | H | H | H |
| $L_A$1571 | | CD$_3$ | Ph | H | Ph | H | H | H |
| $L_A$1572 | | H | Ph | CD$_3$ | Ph | H | H | H |
| $L_A$1573 | | $^i$Pr | Ph | H | Ph | H | H | H |
| $L_A$1574 | | H | Ph | $^i$Pr | Ph | H | H | H |
| $L_A$1575 | | Ph | Ph | H | Ph | H | H | H |
| $L_A$1576 | | H | Ph | Ph | Ph | H | H | H |
| $L_A$1577 | cyclohexyl with C$^{1b}$, C$^{1e}$ | H | H | H | H | H | H | H |
| $L_A$1578 | | Me | H | H | H | H | H | H |
| $L_A$1579 | | H | Me | H | H | H | H | H |
| $L_A$1580 | | H | H | Me | H | H | H | H |
| $L_A$1581 | | H | H | H | Me | H | H | H |
| $L_A$1582 | | H | H | H | H | Me | H | H |
| $L_A$1583 | | CD$_3$ | H | H | H | H | H | H |
| $L_A$1584 | | H | CD$_3$ | H | H | H | H | H |
| $L_A$1585 | | H | H | CD$_3$ | H | H | H | H |
| $L_A$1586 | | H | H | H | CD$_3$ | H | H | H |
| $L_A$1587 | | H | H | H | H | CD$_3$ | H | H |
| $L_A$1588 | cyclohexyl with C$^{1b}$, C$^{1e}$ | $^i$Pr | H | H | H | H | H | H |
| $L_A$1589 | | H | $^i$Pr | H | H | H | H | H |
| $L_A$1590 | | H | H | $^i$Pr | H | H | H | H |
| $L_A$1591 | | H | H | H | $^i$Pr | H | H | H |
| $L_A$1592 | | H | H | H | H | $^i$Pr | H | H |
| $L_A$1593 | | Ph | H | H | H | H | H | H |
| $L_A$1594 | | H | Ph | H | H | H | H | H |
| $L_A$1595 | | H | H | Ph | H | H | H | H |
| $L_A$1596 | | H | H | H | Ph | H | H | H |
| $L_A$1597 | | H | H | H | H | Ph | H | H |
| $L_A$1598 | | Me | Me | H | H | H | H | H |
| $L_A$1599 | | Me | H | Me | H | H | H | H |
| $L_A$1600 | | Me | H | H | Me | H | H | H |
| $L_A$1601 | | Me | H | H | H | Me | H | H |
| $L_A$1602 | | Me | CD$_3$ | H | H | H | H | H |
| $L_A$1603 | | Me | H | CD$_3$ | H | H | H | H |
| $L_A$1604 | | Me | H | H | CD$_3$ | H | H | H |
| $L_A$1605 | | Me | H | H | H | CD$_3$ | H | H |
| $L_A$1606 | | Me | $^i$Pr | H | H | H | H | H |
| $L_A$1607 | | Me | H | $^i$Pr | H | H | H | H |
| $L_A$1608 | | Me | H | H | $^i$Pr | H | H | H |
| $L_A$1609 | | Me | H | H | H | $^i$Pr | H | H |
| $L_A$1610 | | Me | Ph | H | H | H | H | H |
| $L_A$1611 | | Me | H | Ph | H | H | H | H |
| $L_A$1612 | | Me | H | H | Ph | H | H | H |
| $L_A$1613 | | Me | H | H | H | Ph | H | H |
| $L_A$1614 | | CD$_3$ | Me | H | H | H | H | H |
| $L_A$1615 | | CD$_3$ | H | Me | H | H | H | H |
| $L_A$1616 | | CD$_3$ | H | H | Me | H | H | H |
| $L_A$1617 | | CD$_3$ | H | H | H | Me | H | H |
| $L_A$1618 | | CD$_3$ | CD$_3$ | H | H | H | H | H |
| $L_A$1619 | | CD$_3$ | H | CD$_3$ | H | H | H | H |
| $L_A$1620 | | CD$_3$ | H | H | CD$_3$ | H | H | H |
| $L_A$1621 | | CD$_3$ | H | H | H | CD$_3$ | H | H |
| $L_A$1622 | | CD$_3$ | $^i$Pr | H | H | H | H | H |
| $L_A$1623 | | CD$_3$ | H | $^i$Pr | H | H | H | H |
| $L_A$1624 | | CD$_3$ | H | H | $^i$Pr | H | H | H |
| $L_A$1625 | | CD$_3$ | H | H | H | $^i$Pr | H | H |
| $L_A$1626 | | CD$_3$ | Ph | H | H | H | H | H |
| $L_A$1627 | | CD$_3$ | H | Ph | H | H | H | H |
| $L_A$1628 | | CD$_3$ | H | H | Ph | H | H | H |
| $L_A$1629 | | CD$_3$ | H | H | H | Ph | H | H |
| $L_A$1630 | | $^i$Pr | Me | H | H | H | H | H |
| $L_A$1631 | | $^i$Pr | H | Me | H | H | H | H |
| $L_A$1632 | | $^i$Pr | H | H | Me | H | H | H |
| $L_A$1633 | | $^i$Pr | H | H | H | Me | H | H |
| $L_A$1634 | | $^i$Pr | CD$_3$ | H | H | H | H | H |
| $L_A$1635 | | $^i$Pr | H | CD$_3$ | H | H | H | H |
| $L_A$1636 | | $^i$Pr | H | H | CD$_3$ | H | H | H |
| $L_A$1637 | | $^i$Pr | H | H | H | CD$_3$ | H | H |
| $L_A$1638 | | $^i$Pr | $^i$Pr | H | H | H | H | H |
| $L_A$1639 | | $^i$Pr | H | $^i$Pr | H | H | H | H |
| $L_A$1640 | | $^i$Pr | H | H | $^i$Pr | H | H | H |
| $L_A$1641 | | $^i$Pr | H | H | H | $^i$Pr | H | H |
| $L_A$1642 | | $^i$Pr | Ph | H | H | H | H | H |
| $L_A$1643 | cyclohexyl with C$^{1b}$, C$^{1e}$ | $^i$Pr | H | Ph | H | H | H | H |
| $L_A$1644 | | $^i$Pr | H | H | Ph | H | H | H |
| $L_A$1645 | | $^i$Pr | H | H | H | Ph | H | H |
| $L_A$1646 | | Ph | Me | H | H | H | H | H |
| $L_A$1647 | | Ph | H | Me | H | H | H | H |
| $L_A$1648 | | Ph | H | H | Me | H | H | H |
| $L_A$1649 | | Ph | H | H | H | Me | H | H |
| $L_A$1650 | | Ph | CD$_3$ | H | H | H | H | H |
| $L_A$1651 | | Ph | H | CD$_3$ | H | H | H | H |
| $L_A$1652 | | Ph | H | H | CD$_3$ | H | H | H |
| $L_A$1653 | | Ph | H | H | H | CD$_3$ | H | H |
| $L_A$1654 | | Ph | $^i$Pr | H | H | H | H | H |
| $L_A$1655 | | Ph | H | $^i$Pr | H | H | H | H |
| $L_A$1656 | | Ph | H | H | $^i$Pr | H | H | H |
| $L_A$1657 | | Ph | H | H | H | $^i$Pr | H | H |
| $L_A$1658 | | Ph | Ph | H | H | H | H | H |
| $L_A$1659 | | Ph | H | Ph | H | H | H | H |
| $L_A$1660 | | Ph | H | H | Ph | H | H | H |
| $L_A$1661 | | Ph | H | H | H | Ph | H | H |
| $L_A$1662 | | H | Me | Me | H | H | H | H |
| $L_A$1663 | | H | Me | H | Me | H | H | H |
| $L_A$1664 | | H | Me | H | H | Me | H | H |
| $L_A$1665 | | H | Me | CD$_3$ | H | H | H | H |
| $L_A$1666 | | H | Me | H | CD$_3$ | H | H | H |
| $L_A$1667 | | H | Me | H | H | CD$_3$ | H | H |
| $L_A$1668 | | H | Me | $^i$Pr | H | H | H | H |
| $L_A$1669 | | H | Me | H | $^i$Pr | H | H | H |
| $L_A$1670 | | H | Me | H | H | $^i$Pr | H | H |
| $L_A$1671 | | H | Me | Ph | H | H | H | H |
| $L_A$1672 | | H | Me | H | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1673 | | H | Me | H | H | Ph | H | H |
| $L_A$1674 | | H | CD$_3$ | Me | H | H | H | H |
| $L_A$1675 | | H | CD$_3$ | H | Me | H | H | H |
| $L_A$1676 | | H | CD$_3$ | H | H | Me | H | H |
| $L_A$1677 | | H | CD$_3$ | CD$_3$ | H | H | H | H |
| $L_A$1678 | | H | CD$_3$ | H | CD$_3$ | H | H | H |
| $L_A$1679 | | H | CD$_3$ | H | H | CD$_3$ | H | H |
| $L_A$1680 | | H | CD$_3$ | $^i$Pr | H | H | H | H |
| $L_A$1681 | | H | CD$_3$ | H | $^i$Pr | H | H | H |
| $L_A$1682 | | H | CD$_3$ | H | H | $^i$Pr | H | H |
| $L_A$1683 | | H | CD$_3$ | Ph | H | H | H | H |
| $L_A$1684 | | H | CD$_3$ | H | Ph | H | H | H |
| $L_A$1685 | | H | CD$_3$ | H | H | Ph | H | H |
| $L_A$1686 | | H | $^i$Pr | Me | H | H | H | H |
| $L_A$1687 | | H | $^i$Pr | H | Me | H | H | H |
| $L_A$1688 | | H | $^i$Pr | H | H | Me | H | H |
| $L_A$1689 | | H | $^i$Pr | CD$_3$ | H | H | H | H |
| $L_A$1690 | | H | $^i$Pr | H | CD$_3$ | H | H | H |
| $L_A$1691 | | H | $^i$Pr | H | H | CD$_3$ | H | H |
| $L_A$1692 | | H | $^i$Pr | $^i$Pr | H | H | H | H |
| $L_A$1693 | | H | $^i$Pr | H | $^i$Pr | H | H | H |
| $L_A$1694 | | H | $^i$Pr | H | H | $^i$Pr | H | H |
| $L_A$1695 | | H | $^i$Pr | Ph | H | H | H | H |
| $L_A$1696 | | H | $^i$Pr | H | Ph | H | H | H |
| $L_A$1697 | | H | $^i$Pr | H | H | Ph | H | H |
| $L_A$1698 | cyclohexyl (C$^{1b}$, C$^{1e}$) | H | Ph | Me | H | H | H | H |
| $L_A$1699 | | H | Ph | H | Me | H | H | H |
| $L_A$1700 | | H | Ph | H | H | Me | H | H |
| $L_A$1701 | | H | Ph | CD$_3$ | H | H | H | H |
| $L_A$1702 | | H | Ph | H | CD$_3$ | H | H | H |
| $L_A$1703 | | H | Ph | H | H | CD$_3$ | H | H |
| $L_A$1704 | | H | Ph | $^i$Pr | H | H | H | H |
| $L_A$1705 | | H | Ph | H | $^i$Pr | H | H | H |
| $L_A$1706 | | H | Ph | H | H | $^i$Pr | H | H |
| $L_A$1707 | | H | Ph | Ph | H | H | H | H |
| $L_A$1708 | | H | Ph | H | Ph | H | H | H |
| $L_A$1709 | | H | Ph | H | H | Ph | H | H |
| $L_A$1710 | | H | H | Me | Me | H | H | H |
| $L_A$1711 | | H | CD$_3$ | Me | H | H | H | H |
| $L_A$1712 | | H | H | $^i$Pr | Me | H | H | H |
| $L_A$1713 | | H | H | Ph | Me | H | H | H |
| $L_A$1714 | | H | H | Me | CD$_3$ | H | H | H |
| $L_A$1715 | | H | H | CD$_3$ | CD$_3$ | H | H | H |
| $L_A$1716 | | H | H | $^i$Pr | CD$_3$ | H | H | H |
| $L_A$1717 | | H | H | Ph | CD$_3$ | H | H | H |
| $L_A$1718 | | H | H | Me | $^i$Pr | H | H | H |
| $L_A$1719 | | H | H | CD$_3$ | $^i$Pr | H | H | H |
| $L_A$1720 | | H | H | $^i$Pr | $^i$Pr | H | H | H |
| $L_A$1721 | | H | H | Ph | $^i$Pr | H | H | H |
| $L_A$1722 | | H | H | Me | Ph | H | H | H |
| $L_A$1723 | | H | H | CD$_3$ | Ph | H | H | H |
| $L_A$1724 | | H | H | $^i$Pr | Ph | H | H | H |
| $L_A$1725 | | H | H | Ph | Ph | H | H | H |
| $L_A$1726 | | H | H | Me | H | Me | H | H |
| $L_A$1727 | | H | H | CD$_3$ | H | Me | H | H |
| $L_A$1728 | | H | H | $^i$Pr | H | Me | H | H |
| $L_A$1729 | | H | H | Ph | H | Me | H | H |
| $L_A$1730 | | H | H | Me | H | CD$_3$ | H | H |
| $L_A$1731 | | H | H | CD$_3$ | H | CD$_3$ | H | H |
| $L_A$1732 | | H | H | $^i$Pr | H | CD$_3$ | H | H |
| $L_A$1733 | | H | H | Ph | H | CD$_3$ | H | H |
| $L_A$1734 | | H | H | Me | H | $^i$Pr | H | H |
| $L_A$1735 | | H | H | CD$_3$ | H | $^i$Pr | H | H |
| $L_A$1736 | | H | H | $^i$Pr | H | $^i$Pr | H | H |
| $L_A$1737 | | H | H | Ph | H | $^i$Pr | H | H |
| $L_A$1738 | | H | H | Me | H | Ph | H | H |
| $L_A$1739 | | H | H | CD$_3$ | H | Ph | H | H |
| $L_A$1740 | | H | H | $^i$Pr | H | Ph | H | H |
| $L_A$1741 | | H | H | Ph | H | Ph | H | H |
| $L_A$1742 | | Me | Me | H | Me | H | H | H |
| $L_A$1743 | | H | Me | Me | Me | H | H | H |
| $L_A$1744 | | CD$_3$ | Me | H | Me | H | H | H |
| $L_A$1745 | | H | Me | CD$_3$ | Me | H | H | H |
| $L_A$1746 | | $^i$Pr | Me | H | Me | H | H | H |
| $L_A$1747 | | H | Me | $^i$Pr | Me | H | H | H |
| $L_A$1748 | | Ph | Me | H | Me | H | H | H |
| $L_A$1749 | | H | Me | Ph | Me | H | H | H |
| $L_A$1750 | | Me | CD$_3$ | H | CD$_3$ | H | H | H |
| $L_A$1751 | | H | CD$_3$ | Me | CD$_3$ | H | H | H |
| $L_A$1752 | | CD$_3$ | CD$_3$ | H | CD$_3$ | H | H | H |
| $L_A$1753 | cyclohexyl (C$^{1b}$, C$^{1e}$) | H | CD$_3$ | CD$_3$ | CD$_3$ | H | H | H |
| $L_A$1754 | | $^i$Pr | CD$_3$ | H | CD$_3$ | H | H | H |
| $L_A$1755 | | H | CD$_3$ | $^i$Pr | CD$_3$ | H | H | H |
| $L_A$1756 | | Ph | CD$_3$ | H | CD$_3$ | H | H | H |
| $L_A$1757 | | H | CD$_3$ | Ph | CD$_3$ | H | H | H |
| $L_A$1758 | | Me | $^i$Pr | H | $^i$Pr | H | H | H |
| $L_A$1759 | | H | $^i$Pr | Me | $^i$Pr | H | H | H |
| $L_A$1760 | | CD$_3$ | $^i$Pr | H | $^i$Pr | H | H | H |
| $L_A$1761 | | H | $^i$Pr | CD$_3$ | $^i$Pr | H | H | H |
| $L_A$1762 | | $^i$Pr | $^i$Pr | H | $^i$Pr | H | H | H |
| $L_A$1763 | | H | $^i$Pr | $^i$Pr | $^i$Pr | H | H | H |
| $L_A$1764 | | Ph | $^i$Pr | H | $^i$Pr | H | H | H |
| $L_A$1765 | | H | $^i$Pr | Ph | $^i$Pr | H | H | H |
| $L_A$1766 | | Me | Ph | H | Ph | H | H | H |
| $L_A$1767 | | H | Ph | Me | Ph | H | H | H |
| $L_A$1768 | | CD$_3$ | Ph | H | Ph | H | H | H |
| $L_A$1769 | | H | Ph | CD$_3$ | Ph | H | H | H |
| $L_A$1770 | | $^i$Pr | Ph | H | Ph | H | H | H |
| $L_A$1771 | | H | Ph | $^i$Pr | Ph | H | H | H |
| $L_A$1772 | | Ph | Ph | H | Ph | H | H | H |
| $L_A$1773 | | H | Ph | Ph | Ph | H | H | H |
| $L_A$1774 | cyclohexyl with Et (C$^{1b}$, C$^{1e}$) | H | H | H | H | H | H | H |
| $L_A$1775 | | Me | H | H | H | H | H | H |
| $L_A$1776 | | H | Me | H | H | H | H | H |
| $L_A$1777 | | H | H | Me | H | H | H | H |
| $L_A$1778 | | H | H | H | Me | H | H | H |
| $L_A$1779 | | H | H | H | H | Me | H | H |
| $L_A$1780 | | CD$_3$ | H | H | H | H | H | H |
| $L_A$1781 | | H | CD$_3$ | H | H | H | H | H |
| $L_A$1782 | | H | H | CD$_3$ | H | H | H | H |
| $L_A$1783 | | H | H | H | CD$_3$ | H | H | H |
| $L_A$1784 | | H | H | H | H | CD$_3$ | H | H |
| $L_A$1785 | | $^i$Pr | H | H | H | H | H | H |
| $L_A$1786 | | H | $^i$Pr | H | H | H | H | H |
| $L_A$1787 | | H | H | $^i$Pr | H | H | H | H |
| $L_A$1788 | | H | H | H | $^i$Pr | H | H | H |
| $L_A$1789 | | H | H | H | H | $^i$Pr | H | H |
| $L_A$1790 | | Ph | H | H | H | H | H | H |
| $L_A$1791 | | H | Ph | H | H | H | H | H |
| $L_A$1792 | | H | H | Ph | H | H | H | H |
| $L_A$1793 | | H | H | H | Ph | H | H | H |
| $L_A$1794 | | H | H | H | H | Ph | H | H |
| $L_A$1795 | | Me | Me | H | H | H | H | H |
| $L_A$1796 | | Me | H | Me | H | H | H | H |
| $L_A$1797 | | Me | H | H | Me | H | H | H |
| $L_A$1798 | | Me | H | H | H | Me | H | H |
| $L_A$1799 | | Me | CD$_3$ | H | H | H | H | H |
| $L_A$1800 | | Me | H | CD$_3$ | H | H | H | H |
| $L_A$1801 | | Me | H | H | CD$_3$ | H | H | H |
| $L_A$1802 | | Me | H | H | H | CD$_3$ | H | H |
| $L_A$1803 | | Me | $^i$Pr | H | H | H | H | H |
| $L_A$1804 | | Me | H | $^i$Pr | H | H | H | H |
| $L_A$1805 | | Me | H | H | $^i$Pr | H | H | H |
| $L_A$1806 | | Me | H | H | H | $^i$Pr | H | H |
| $L_A$1807 | | Me | Ph | H | H | H | H | H |
| $L_A$1808 | | Me | H | Ph | H | H | H | H |
| $L_A$1809 | cyclohexyl with Et (C$^{1b}$, C$^{1e}$) | Me | H | H | Ph | H | H | H |
| $L_A$1810 | | Me | H | H | H | Ph | H | H |
| $L_A$1811 | | CD$_3$ | Me | H | H | H | H | H |
| $L_A$1812 | | CD$_3$ | H | Me | H | H | H | H |
| $L_A$1813 | | CD$_3$ | H | H | Me | H | H | H |
| $L_A$1814 | | CD$_3$ | H | H | H | Me | H | H |
| $L_A$1815 | | CD$_3$ | CD$_3$ | H | H | H | H | H |
| $L_A$1816 | | CD$_3$ | H | CD$_3$ | H | H | H | H |
| $L_A$1817 | | CD$_3$ | H | H | CD$_3$ | H | H | H |
| $L_A$1818 | | CD$_3$ | H | H | H | CD$_3$ | H | H |
| $L_A$1819 | | CD$_3$ | $^i$Pr | H | H | H | H | H |
| $L_A$1820 | | CD$_3$ | H | $^i$Pr | H | H | H | H |
| $L_A$1821 | | CD$_3$ | H | H | $^i$Pr | H | H | H |
| $L_A$1822 | | CD$_3$ | H | H | H | $^i$Pr | H | H |
| $L_A$1823 | | CD$_3$ | Ph | H | H | H | H | H |
| $L_A$1824 | | CD$_3$ | H | Ph | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1825 | | $CD_3$ | H | H | Ph | H | H | H |
| $L_A$1826 | | $CD_3$ | H | H | H | Ph | H | H |
| $L_A$1827 | | $^i$Pr | Me | H | H | H | H | H |
| $L_A$1828 | | $^i$Pr | H | Me | H | H | H | H |
| $L_A$1829 | | $^i$Pr | H | H | Me | H | H | H |
| $L_A$1830 | | $^i$Pr | H | H | H | Me | H | H |
| $L_A$1831 | | $^i$Pr | $CD_3$ | H | H | H | H | H |
| $L_A$1832 | | $^i$Pr | H | $CD_3$ | H | H | H | H |
| $L_A$1833 | | $^i$Pr | H | H | $CD_3$ | H | H | H |
| $L_A$1834 | | $^i$Pr | H | H | H | $CD_3$ | H | H |
| $L_A$1835 | | $^i$Pr | $^i$Pr | H | H | H | H | H |
| $L_A$1836 | | $^i$Pr | H | $^i$Pr | H | H | H | H |
| $L_A$1837 | | $^i$Pr | H | H | $^i$Pr | H | H | H |
| $L_A$1838 | | $^i$Pr | H | H | H | $^i$Pr | H | H |
| $L_A$1839 | | $^i$Pr | Ph | H | H | H | H | H |
| $L_A$1840 | | $^i$Pr | H | Ph | H | H | H | H |
| $L_A$1841 | | $^i$Pr | H | H | Ph | H | H | H |
| $L_A$1842 | | $^i$Pr | H | H | H | Ph | H | H |
| $L_A$1843 | | Ph | Me | H | H | H | H | H |
| $L_A$1844 | | Ph | H | Me | H | H | H | H |
| $L_A$1845 | | Ph | H | H | Me | H | H | H |
| $L_A$1846 | | Ph | H | H | H | Me | H | H |
| $L_A$1847 | | Ph | $CD_3$ | H | H | H | H | H |
| $L_A$1848 | | Ph | H | $CD_3$ | H | H | H | H |
| $L_A$1849 | | Ph | H | H | $CD_3$ | H | H | H |
| $L_A$1850 | | Ph | H | H | H | $CD_3$ | H | H |
| $L_A$1851 | | Ph | $^i$Pr | H | H | H | H | H |
| $L_A$1852 | | Ph | H | $^i$Pr | H | H | H | H |
| $L_A$1853 | | Ph | H | H | $^i$Pr | H | H | H |
| $L_A$1854 | | Ph | H | H | H | $^i$Pr | H | H |
| $L_A$1855 | | Ph | Ph | H | H | H | H | H |
| $L_A$1856 | | Ph | H | Ph | H | H | H | H |
| $L_A$1857 | | Ph | H | H | Ph | H | H | H |
| $L_A$1858 | | Ph | H | H | H | Ph | H | H |
| $L_A$1859 | | H | Me | Me | H | H | H | H |
| $L_A$1860 | | H | Me | H | Me | H | H | H |
| $L_A$1861 | | H | Me | H | H | Me | H | H |
| $L_A$1862 | | H | Me | $CD_3$ | H | H | H | H |
| $L_A$1863 | cyclohexyl (Et, Et, $C^{1b}$, $C^{1e}$) | H | Me | H | $CD_3$ | H | H | H |
| $L_A$1864 | | H | Me | H | H | $CD_3$ | H | H |
| $L_A$1865 | | H | Me | $^i$Pr | H | H | H | H |
| $L_A$1866 | | H | Me | H | $^i$Pr | H | H | H |
| $L_A$1867 | | H | Me | H | H | $^i$Pr | H | H |
| $L_A$1868 | | H | Me | Ph | H | H | H | H |
| $L_A$1869 | | H | Me | H | Ph | H | H | H |
| $L_A$1870 | | H | Me | H | H | Ph | H | H |
| $L_A$1871 | | H | $CD_3$ | Me | H | H | H | H |
| $L_A$1872 | | H | $CD_3$ | H | Me | H | H | H |
| $L_A$1873 | | H | $CD_3$ | H | H | Me | H | H |
| $L_A$1874 | | H | $CD_3$ | $CD_3$ | H | H | H | H |
| $L_A$1875 | | H | $CD_3$ | H | $CD_3$ | H | H | H |
| $L_A$1876 | | H | $CD_3$ | H | H | $CD_3$ | H | H |
| $L_A$1877 | | H | $CD_3$ | $^i$Pr | H | H | H | H |
| $L_A$1878 | | H | $CD_3$ | H | $^i$Pr | H | H | H |
| $L_A$1879 | | H | $CD_3$ | H | H | $^i$Pr | H | H |
| $L_A$1880 | | H | $CD_3$ | Ph | H | H | H | H |
| $L_A$1881 | | H | $CD_3$ | H | Ph | H | H | H |
| $L_A$1882 | | H | $CD_3$ | H | H | Ph | H | H |
| $L_A$1883 | | H | $^i$Pr | Me | H | H | H | H |
| $L_A$1884 | | H | $^i$Pr | H | Me | H | H | H |
| $L_A$1885 | | H | $^i$Pr | H | H | Me | H | H |
| $L_A$1886 | | H | $^i$Pr | $CD_3$ | H | H | H | H |
| $L_A$1887 | | H | $^i$Pr | H | $CD_3$ | H | H | H |
| $L_A$1888 | | H | $^i$Pr | H | H | $CD_3$ | H | H |
| $L_A$1889 | | H | $^i$Pr | $^i$Pr | H | H | H | H |
| $L_A$1890 | | H | $^i$Pr | H | $^i$Pr | H | H | H |
| $L_A$1891 | | H | $^i$Pr | H | H | $^i$Pr | H | H |
| $L_A$1892 | | H | $^i$Pr | Ph | H | H | H | H |
| $L_A$1893 | | H | $^i$Pr | H | Ph | H | H | H |
| $L_A$1894 | | H | $^i$Pr | H | H | Ph | H | H |
| $L_A$1895 | | H | Ph | Me | H | H | H | H |
| $L_A$1896 | | H | Ph | H | Me | H | H | H |
| $L_A$1897 | | H | Ph | H | H | Me | H | H |
| $L_A$1898 | | H | Ph | $CD_3$ | H | H | H | H |
| $L_A$1899 | | H | Ph | H | $CD_3$ | H | H | H |
| $L_A$1900 | | H | Ph | H | H | $CD_3$ | H | H |
| $L_A$1901 | | H | Ph | $^i$Pr | H | H | H | H |
| $L_A$1902 | | H | Ph | H | $^i$Pr | H | H | H |
| $L_A$1903 | | H | Ph | H | H | $^i$Pr | H | H |
| $L_A$1904 | | H | Ph | Ph | H | H | H | H |
| $L_A$1905 | | H | Ph | H | Ph | H | H | H |
| $L_A$1906 | | H | Ph | H | H | Ph | H | H |
| $L_A$1907 | | H | H | Me | Me | H | H | H |
| $L_A$1908 | | H | H | $CD_3$ | Me | H | H | H |
| $L_A$1909 | | H | H | $^i$Pr | Me | H | H | H |
| $L_A$1910 | | H | H | Ph | Me | H | H | H |
| $L_A$1911 | | H | H | Me | $CD_3$ | H | H | H |
| $L_A$1912 | | H | H | $CD_3$ | $CD_3$ | H | H | H |
| $L_A$1913 | | H | H | $^i$Pr | $CD_3$ | H | H | H |
| $L_A$1914 | | H | H | Ph | $CD_3$ | H | H | H |
| $L_A$1915 | | H | H | Me | $^i$Pr | H | H | H |
| $L_A$1916 | | H | H | $CD_3$ | $^i$Pr | H | H | H |
| $L_A$1917 | | H | H | $^i$Pr | $^i$Pr | H | H | H |
| $L_A$1918 | | H | H | Ph | $^i$Pr | H | H | H |
| $L_A$1919 | cyclohexyl (Et, Et, $C^{1b}$, $C^{1e}$) | H | H | Me | Ph | H | H | H |
| $L_A$1920 | | H | H | $CD_3$ | Ph | H | H | H |
| $L_A$1921 | | H | H | $^i$Pr | Ph | H | H | H |
| $L_A$1922 | | H | H | Ph | Ph | H | H | H |
| $L_A$1923 | | H | H | Me | H | Me | H | H |
| $L_A$1924 | | H | H | $CD_3$ | H | Me | H | H |
| $L_A$1925 | | H | H | $^i$Pr | H | Me | H | H |
| $L_A$1926 | | H | H | Ph | H | Me | H | H |
| $L_A$1927 | | H | H | Me | H | $CD_3$ | H | H |
| $L_A$1928 | | H | H | $CD_3$ | H | $CD_3$ | H | H |
| $L_A$1929 | | H | H | $^i$Pr | H | $CD_3$ | H | H |
| $L_A$1930 | | H | H | Ph | H | $CD_3$ | H | H |
| $L_A$1931 | | H | H | Me | H | $^i$Pr | H | H |
| $L_A$1932 | | H | H | $CD_3$ | H | $^i$Pr | H | H |
| $L_A$1933 | | H | H | $^i$Pr | H | $^i$Pr | H | H |
| $L_A$1934 | | H | H | Ph | H | $^i$Pr | H | H |
| $L_A$1935 | | H | H | Me | H | Ph | H | H |
| $L_A$1936 | | H | H | $CD_3$ | H | Ph | H | H |
| $L_A$1937 | | H | H | $^i$Pr | H | Ph | H | H |
| $L_A$1938 | | H | H | Ph | H | Ph | H | H |
| $L_A$1939 | | Me | Me | H | Me | H | H | H |
| $L_A$1940 | | H | Me | Me | Me | H | H | H |
| $L_A$1941 | | $CD_3$ | Me | H | Me | H | H | H |
| $L_A$1942 | | H | Me | $CD_3$ | Me | H | H | H |
| $L_A$1943 | | $^i$Pr | Me | H | Me | H | H | H |
| $L_A$1944 | | H | Me | $^i$Pr | Me | H | H | H |
| $L_A$1945 | | Ph | Me | H | Me | H | H | H |
| $L_A$1946 | | H | Me | Ph | Me | H | H | H |
| $L_A$1947 | | Me | $CD_3$ | H | $CD_3$ | H | H | H |
| $L_A$1948 | | H | $CD_3$ | Me | $CD_3$ | H | H | H |
| $L_A$1949 | | $CD_3$ | $CD_3$ | H | $CD_3$ | H | H | H |
| $L_A$1950 | | H | $CD_3$ | $CD_3$ | $CD_3$ | H | H | H |
| $L_A$1951 | | $^i$Pr | $CD_3$ | H | $CD_3$ | H | H | H |
| $L_A$1952 | | H | $CD_3$ | $^i$Pr | $CD_3$ | H | H | H |
| $L_A$1953 | | Ph | $CD_3$ | H | $CD_3$ | H | H | H |
| $L_A$1954 | | H | $CD_3$ | Ph | $CD_3$ | H | H | H |
| $L_A$1955 | | Me | $^i$Pr | H | $^i$Pr | H | H | H |
| $L_A$1956 | | H | $^i$Pr | Me | $^i$Pr | H | H | H |
| $L_A$1957 | | $CD_3$ | $^i$Pr | H | $^i$Pr | H | H | H |
| $L_A$1958 | | H | $^i$Pr | $CD_3$ | $^i$Pr | H | H | H |
| $L_A$1959 | | $^i$Pr | $^i$Pr | H | $^i$Pr | H | H | H |
| $L_A$1960 | | H | $^i$Pr | $^i$Pr | $^i$Pr | H | H | H |
| $L_A$1961 | | Ph | $^i$Pr | H | $^i$Pr | H | H | H |
| $L_A$1962 | | H | $^i$Pr | Ph | $^i$Pr | H | H | H |
| $L_A$1963 | | Me | Ph | H | Ph | H | H | H |
| $L_A$1964 | | H | Ph | Me | Ph | H | H | H |
| $L_A$1965 | | $CD_3$ | Ph | H | Ph | H | H | H |
| $L_A$1966 | | H | Ph | $CD_3$ | Ph | H | H | H |
| $L_A$1967 | | $^i$Pr | Ph | H | Ph | H | H | H |
| $L_A$1968 | | H | Ph | $^i$Pr | Ph | H | H | H |
| $L_A$1969 | | Ph | Ph | H | Ph | H | H | H |
| $L_A$1970 | | H | Ph | Ph | Ph | H | H | H |
| $L_A$1971 | cyclohexyl ($^i$Pr, $^i$Pr, $C^{1b}$, $C^{1e}$) | H | H | H | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$1972 | cyclohexyl with iPr, C$^{1b}$, iPr, C$^{1e}$ | Me | H | H | H | H | H | H |
| $L_A$1973 | | H | Me | H | H | H | H | H |
| $L_A$1974 | | H | H | Me | H | H | H | H |
| $L_A$1975 | | H | H | H | Me | H | H | H |
| $L_A$1976 | | H | H | H | H | Me | H | H |
| $L_A$1977 | | CD$_3$ | H | H | H | H | H | H |
| $L_A$1978 | | H | CD$_3$ | H | H | H | H | H |
| $L_A$1979 | | H | H | CD$_3$ | H | H | H | H |
| $L_A$1980 | | H | H | H | CD$_3$ | H | H | H |
| $L_A$1981 | | H | H | H | H | CD$_3$ | H | H |
| $L_A$1982 | | $^i$Pr | H | H | H | H | H | H |
| $L_A$1983 | | H | $^i$Pr | H | H | H | H | H |
| $L_A$1984 | | H | H | $^i$Pr | H | H | H | H |
| $L_A$1985 | | H | H | H | $^i$Pr | H | H | H |
| $L_A$1986 | | H | H | H | H | $^i$Pr | H | H |
| $L_A$1987 | | Ph | H | H | H | H | H | H |
| $L_A$1988 | | H | Ph | H | H | H | H | H |
| $L_A$1989 | | H | H | Ph | H | H | H | H |
| $L_A$1990 | | H | H | H | Ph | H | H | H |
| $L_A$1991 | | H | H | H | H | Ph | H | H |
| $L_A$1992 | | Me | Me | H | H | H | H | H |
| $L_A$1993 | | Me | H | Me | H | H | H | H |
| $L_A$1994 | | Me | H | H | Me | H | H | H |
| $L_A$1995 | | Me | H | H | H | Me | H | H |
| $L_A$1996 | | Me | CD$_3$ | H | H | H | H | H |
| $L_A$1997 | | Me | H | CD$_3$ | H | H | H | H |
| $L_A$1998 | | Me | H | H | CD$_3$ | H | H | H |
| $L_A$1999 | | Me | H | H | H | CD$_3$ | H | H |
| $L_A$2000 | | Me | $^i$Pr | H | H | H | H | H |
| $L_A$2001 | | Me | H | $^i$Pr | H | H | H | H |
| $L_A$2002 | | Me | H | H | $^i$Pr | H | H | H |
| $L_A$2003 | | Me | H | H | H | $^i$Pr | H | H |
| $L_A$2004 | | Me | Ph | H | H | H | H | H |
| $L_A$2005 | | Me | H | Ph | H | H | H | H |
| $L_A$2006 | | Me | H | H | Ph | H | H | H |
| $L_A$2007 | | Me | H | H | H | Ph | H | H |
| $L_A$2008 | | CD$_3$ | Me | H | H | H | H | H |
| $L_A$2009 | | CD$_3$ | H | Me | H | H | H | H |
| $L_A$2010 | | CD$_3$ | H | H | Me | H | H | H |
| $L_A$2011 | | CD$_3$ | H | H | H | Me | H | H |
| $L_A$2012 | | CD$_3$ | CD$_3$ | H | H | H | H | H |
| $L_A$2013 | | CD$_3$ | H | CD$_3$ | H | H | H | H |
| $L_A$2014 | | CD$_3$ | H | H | CD$_3$ | H | H | H |
| $L_A$2015 | | CD$_3$ | H | H | H | CD$_3$ | H | H |
| $L_A$2016 | | CD$_3$ | $^i$Pr | H | H | H | H | H |
| $L_A$2017 | | CD$_3$ | H | $^i$Pr | H | H | H | H |
| $L_A$2018 | | CD$_3$ | H | H | $^i$Pr | H | H | H |
| $L_A$2019 | | CD$_3$ | H | H | H | $^i$Pr | H | H |
| $L_A$2020 | | CD$_3$ | Ph | H | H | H | H | H |
| $L_A$2021 | | CD$_3$ | H | Ph | H | H | H | H |
| $L_A$2022 | | CD$_3$ | H | H | Ph | H | H | H |
| $L_A$2023 | | CD$_3$ | H | H | H | Ph | H | H |
| $L_A$2024 | | $^i$Pr | Me | H | H | H | H | H |
| $L_A$2025 | | $^i$Pr | H | Me | H | H | H | H |
| $L_A$2026 | | $^i$Pr | H | H | Me | H | H | H |
| $L_A$2027 | cyclohexyl with iPr, C$^{1b}$, iPr, C$^{1e}$ | $^i$Pr | H | H | H | Me | H | H |
| $L_A$2028 | | $^i$Pr | CD$_3$ | H | H | H | H | H |
| $L_A$2029 | | $^i$Pr | H | CD$_3$ | H | H | H | H |
| $L_A$2030 | | $^i$Pr | H | H | CD$_3$ | H | H | H |
| $L_A$2031 | | $^i$Pr | H | H | H | CD$_3$ | H | H |
| $L_A$2032 | | $^i$Pr | $^i$Pr | H | H | H | H | H |
| $L_A$2033 | | $^i$Pr | H | $^i$Pr | H | H | H | H |
| $L_A$2034 | | $^i$Pr | H | H | $^i$Pr | H | H | H |
| $L_A$2035 | | $^i$Pr | H | H | H | $^i$Pr | H | H |
| $L_A$2036 | | $^i$Pr | Ph | H | H | H | H | H |
| $L_A$2037 | | $^i$Pr | H | Ph | H | H | H | H |
| $L_A$2038 | | $^i$Pr | H | H | Ph | H | H | H |
| $L_A$2039 | | $^i$Pr | H | H | H | Ph | H | H |
| $L_A$2040 | | Ph | Me | H | H | H | H | H |
| $L_A$2041 | | Ph | H | Me | H | H | H | H |
| $L_A$2042 | | Ph | H | H | Me | H | H | H |
| $L_A$2043 | | Ph | H | H | H | Me | H | H |
| $L_A$2044 | | Ph | CD$_3$ | H | H | H | H | H |
| $L_A$2045 | | Ph | H | CD$_3$ | H | H | H | H |
| $L_A$2046 | | Ph | H | H | CD$_3$ | H | H | H |
| $L_A$2047 | | Ph | H | H | H | CD$_3$ | H | H |
| $L_A$2048 | | Ph | $^i$Pr | H | H | H | H | H |
| $L_A$2049 | | Ph | H | $^i$Pr | H | H | H | H |
| $L_A$2050 | | Ph | H | H | $^i$Pr | H | H | H |
| $L_A$2051 | | Ph | H | H | H | $^i$Pr | H | H |
| $L_A$2052 | | Ph | Ph | H | H | H | H | H |
| $L_A$2053 | | Ph | H | Ph | H | H | H | H |
| $L_A$2054 | | Ph | H | H | Ph | H | H | H |
| $L_A$2055 | | Ph | H | H | H | Ph | H | H |
| $L_A$2056 | | H | Me | Me | H | H | H | H |
| $L_A$2057 | | H | Me | H | Me | H | H | H |
| $L_A$2058 | | H | Me | H | H | Me | H | H |
| $L_A$2059 | | H | Me | CD$_3$ | H | H | H | H |
| $L_A$2060 | | H | Me | H | CD$_3$ | H | H | H |
| $L_A$2061 | | H | Me | H | H | CD$_3$ | H | H |
| $L_A$2062 | | H | Me | $^i$Pr | H | H | H | H |
| $L_A$2063 | | H | Me | H | $^i$Pr | H | H | H |
| $L_A$2064 | | H | Me | H | H | $^i$Pr | H | H |
| $L_A$2065 | | H | Me | Ph | H | H | H | H |
| $L_A$2066 | | H | Me | H | Ph | H | H | H |
| $L_A$2067 | | H | Me | H | H | Ph | H | H |
| $L_A$2068 | | H | CD$_3$ | Me | H | H | H | H |
| $L_A$2069 | | H | CD$_3$ | H | Me | H | H | H |
| $L_A$2070 | | H | CD$_3$ | H | H | Me | H | H |
| $L_A$2071 | | H | CD$_3$ | CD$_3$ | H | H | H | H |
| $L_A$2072 | | H | CD$_3$ | H | CD$_3$ | H | H | H |
| $L_A$2073 | | H | CD$_3$ | H | H | CD$_3$ | H | H |
| $L_A$2074 | | H | CD$_3$ | $^i$Pr | H | H | H | H |
| $L_A$2075 | | H | CD$_3$ | H | $^i$Pr | H | H | H |
| $L_A$2076 | | H | CD$_3$ | H | H | $^i$Pr | H | H |
| $L_A$2077 | | H | CD$_3$ | Ph | H | H | H | H |
| $L_A$2078 | | H | CD$_3$ | H | Ph | H | H | H |
| $L_A$2079 | | H | CD$_3$ | H | H | Ph | H | H |
| $L_A$2080 | | H | $^i$Pr | Me | H | H | H | H |
| $L_A$2081 | | H | $^i$Pr | H | Me | H | H | H |
| $L_A$2082 | cyclohexyl with iPr, C$^{1b}$, iPr, C$^{1e}$ | H | $^i$Pr | H | H | Me | H | H |
| $L_A$2083 | | H | $^i$Pr | CD$_3$ | H | H | H | H |
| $L_A$2084 | | H | $^i$Pr | H | CD$_3$ | H | H | H |
| $L_A$2085 | | H | $^i$Pr | H | H | CD$_3$ | H | H |
| $L_A$2086 | | H | $^i$Pr | $^i$Pr | H | H | H | H |
| $L_A$2087 | | H | $^i$Pr | H | $^i$Pr | H | H | H |
| $L_A$2088 | | H | $^i$Pr | H | H | $^i$Pr | H | H |
| $L_A$2089 | | H | $^i$Pr | Ph | H | H | H | H |
| $L_A$2090 | | H | $^i$Pr | H | Ph | H | H | H |
| $L_A$2091 | | H | $^i$Pr | H | H | Ph | H | H |
| $L_A$2092 | | H | Ph | Me | H | H | H | H |
| $L_A$2093 | | H | Ph | H | Me | H | H | H |
| $L_A$2094 | | H | Ph | H | H | Me | H | H |
| $L_A$2095 | | H | Ph | CD$_3$ | H | H | H | H |
| $L_A$2096 | | H | Ph | H | CD$_3$ | H | H | H |
| $L_A$2097 | | H | Ph | H | H | CD$_3$ | H | H |
| $L_A$2098 | | H | Ph | $^i$Pr | H | H | H | H |
| $L_A$2099 | | H | Ph | H | $^i$Pr | H | H | H |
| $L_A$2100 | | H | Ph | H | H | $^i$Pr | H | H |
| $L_A$2101 | | H | Ph | Ph | H | H | H | H |
| $L_A$2102 | | H | Ph | H | Ph | H | H | H |
| $L_A$2103 | | H | Ph | H | H | Ph | H | H |
| $L_A$2104 | | H | H | Me | Me | H | H | H |
| $L_A$2105 | | H | H | CD$_3$ | Me | H | H | H |
| $L_A$2106 | | H | H | $^i$Pr | Me | H | H | H |
| $L_A$2107 | | H | H | Ph | Me | H | H | H |
| $L_A$2108 | | H | H | Me | CD$_3$ | H | H | H |
| $L_A$2109 | | H | H | CD$_3$ | CD$_3$ | H | H | H |
| $L_A$2110 | | H | H | $^i$Pr | CD$_3$ | H | H | H |
| $L_A$2111 | | H | H | Ph | CD$_3$ | H | H | H |
| $L_A$2112 | | H | H | Me | $^i$Pr | H | H | H |
| $L_A$2113 | | H | H | CD$_3$ | $^i$Pr | H | H | H |
| $L_A$2114 | | H | H | $^i$Pr | $^i$Pr | H | H | H |
| $L_A$2115 | | H | H | Ph | $^i$Pr | H | H | H |
| $L_A$2116 | | H | H | Me | Ph | H | H | H |
| $L_A$2117 | | H | H | CD$_3$ | Ph | H | H | H |
| $L_A$2118 | | H | H | $^i$Pr | Ph | H | H | H |
| $L_A$2119 | | H | H | Ph | Ph | H | H | H |
| $L_A$2120 | | H | H | Me | H | Me | H | H |
| $L_A$2121 | | H | H | CD$_3$ | H | Me | H | H |
| $L_A$2122 | | H | H | $^i$Pr | H | Me | H | H |
| $L_A$2123 | | H | H | Ph | H | Me | H | H |
| $L_A$2124 | | H | H | Me | H | CD$_3$ | H | H |
| $L_A$2125 | | H | H | CD$_3$ | H | CD$_3$ | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A2126$ | | H | H | $^i$Pr | H | CD$_3$ | H | H |
| $L_A2127$ | | H | H | Ph | H | CD$_3$ | H | H |
| $L_A2128$ | | H | H | Me | H | $^i$Pr | H | H |
| $L_A2129$ | | H | H | CD$_3$ | H | $^i$Pr | H | H |
| $L_A2130$ | | H | H | $^i$Pr | H | $^i$Pr | H | H |
| $L_A2131$ | | H | H | Ph | H | $^i$Pr | H | H |
| $L_A2132$ | | H | H | Me | H | Ph | H | H |
| $L_A2133$ | | H | H | CD$_3$ | H | Ph | H | H |
| $L_A2134$ | | H | H | $^i$Pr | H | Ph | H | H |
| $L_A2135$ | | H | H | Ph | H | Ph | H | H |
| $L_A2136$ | | Me | Me | H | Me | H | H | H |
| $L_A2137$ | (cyclohexane linker with iPr groups at C$^{1b}$/C$^{1e}$) | H | Me | Me | Me | H | H | H |
| $L_A2138$ | | CD$_3$ | Me | H | Me | H | H | H |
| $L_A2139$ | | H | Me | CD$_3$ | Me | H | H | H |
| $L_A2140$ | | $^i$Pr | Me | H | Me | H | H | H |
| $L_A2141$ | | H | Me | $^i$Pr | Me | H | H | H |
| $L_A2142$ | | Ph | Me | H | Me | H | H | H |
| $L_A2143$ | | H | Me | Ph | Me | H | H | H |
| $L_A2144$ | | Me | CD$_3$ | H | CD$_3$ | H | H | H |
| $L_A2145$ | | H | CD$_3$ | Me | CD$_3$ | H | H | H |
| $L_A2146$ | | CD$_3$ | CD$_3$ | H | CD$_3$ | H | H | H |
| $L_A2147$ | | H | CD$_3$ | CD$_3$ | CD$_3$ | H | H | H |
| $L_A2148$ | | $^i$Pr | CD$_3$ | H | CD$_3$ | H | H | H |
| $L_A2149$ | | H | CD$_3$ | $^i$Pr | CD$_3$ | H | H | H |
| $L_A2150$ | | Ph | CD$_3$ | H | CD$_3$ | H | H | H |
| $L_A2151$ | | H | CD$_3$ | Ph | CD$_3$ | H | H | H |
| $L_A2152$ | | Me | $^i$Pr | H | $^i$Pr | H | H | H |
| $L_A2153$ | | H | $^i$Pr | Me | $^i$Pr | H | H | H |
| $L_A2154$ | | CD$_3$ | $^i$Pr | H | $^i$Pr | H | H | H |
| $L_A2155$ | | H | $^i$Pr | CD$_3$ | $^i$Pr | H | H | H |
| $L_A2156$ | | $^i$Pr | $^i$Pr | H | $^i$Pr | H | H | H |
| $L_A2157$ | | H | $^i$Pr | $^i$Pr | $^i$Pr | H | H | H |
| $L_A2158$ | | Ph | $^i$Pr | H | $^i$Pr | H | H | H |
| $L_A2159$ | | H | $^i$Pr | Ph | $^i$Pr | H | H | H |
| $L_A2160$ | | Me | Ph | H | Ph | H | H | H |
| $L_A2161$ | | H | Ph | Me | Ph | H | H | H |
| $L_A2162$ | | CD$_3$ | Ph | H | Ph | H | H | H |
| $L_A2163$ | | H | Ph | CD$_3$ | Ph | H | H | H |
| $L_A2164$ | | $^i$Pr | Ph | H | Ph | H | H | H |
| $L_A2165$ | | H | Ph | $^i$Pr | Ph | H | H | H |
| $L_A2166$ | | Ph | Ph | H | Ph | H | H | H |
| $L_A2167$ | | H | Ph | Ph | Ph | H | H | H |
| $L_A2168$ | (decalin linker at C$^{1b}$/C$^{1e}$) | H | H | H | H | H | H | H |
| $L_A2169$ | | Me | H | H | H | H | H | H |
| $L_A2170$ | | H | Me | H | H | H | H | H |
| $L_A2171$ | | H | H | Me | H | H | H | H |
| $L_A2172$ | | H | H | H | Me | H | H | H |
| $L_A2173$ | | H | H | H | H | Me | H | H |
| $L_A2174$ | | CD$_3$ | H | H | H | H | H | H |
| $L_A2175$ | | H | CD$_3$ | H | H | H | H | H |
| $L_A2176$ | | H | H | CD$_3$ | H | H | H | H |
| $L_A2177$ | | H | H | H | CD$_3$ | H | H | H |
| $L_A2178$ | | H | H | H | H | CD$_3$ | H | H |
| $L_A2179$ | | $^i$Pr | H | H | H | H | H | H |
| $L_A2180$ | | H | $^i$Pr | H | H | H | H | H |
| $L_A2181$ | | H | H | $^i$Pr | H | H | H | H |
| $L_A2182$ | | H | H | H | $^i$Pr | H | H | H |
| $L_A2183$ | | H | H | H | H | $^i$Pr | H | H |
| $L_A2184$ | | Ph | H | H | H | H | H | H |
| $L_A2185$ | | H | Ph | H | H | H | H | H |
| $L_A2186$ | | H | H | Ph | H | H | H | H |
| $L_A2187$ | | H | H | H | Ph | H | H | H |
| $L_A2188$ | | H | H | H | H | Ph | H | H |
| $L_A2189$ | | Me | Me | H | H | H | H | H |
| $L_A2190$ | | Me | H | Me | H | H | H | H |
| $L_A2191$ | | Me | H | H | Me | H | H | H |
| $L_A2192$ | (decalin linker at C$^{1b}$/C$^{1e}$) | Me | H | H | H | Me | H | H |
| $L_A2193$ | | Me | CD$_3$ | H | H | H | H | H |
| $L_A2194$ | | Me | H | CD$_3$ | H | H | H | H |
| $L_A2195$ | | Me | H | H | CD$_3$ | H | H | H |
| $L_A2196$ | | Me | H | H | H | CD$_3$ | H | H |
| $L_A2197$ | | Me | $^i$Pr | H | H | H | H | H |
| $L_A2198$ | | Me | H | $^i$Pr | H | H | H | H |
| $L_A2199$ | | Me | H | H | $^i$Pr | H | H | H |
| $L_A2200$ | | Me | H | H | H | $^i$Pr | H | H |
| $L_A2201$ | | Me | Ph | H | H | H | H | H |
| $L_A2202$ | | Me | H | Ph | H | H | H | H |
| $L_A2203$ | | Me | H | H | Ph | H | H | H |
| $L_A2204$ | | Me | H | H | H | Ph | H | H |
| $L_A2205$ | | CD$_3$ | Me | H | H | H | H | H |
| $L_A2206$ | | CD$_3$ | H | Me | H | H | H | H |
| $L_A2207$ | | CD$_3$ | H | H | Me | H | H | H |
| $L_A2208$ | | CD$_3$ | H | H | H | Me | H | H |
| $L_A2209$ | | CD$_3$ | CD$_3$ | H | H | H | H | H |
| $L_A2210$ | | CD$_3$ | H | CD$_3$ | H | H | H | H |
| $L_A2211$ | | CD$_3$ | H | H | CD$_3$ | H | H | H |
| $L_A2212$ | | CD$_3$ | H | H | H | CD$_3$ | H | H |
| $L_A2213$ | | CD$_3$ | $^i$Pr | H | H | H | H | H |
| $L_A2214$ | | CD$_3$ | H | $^i$Pr | H | H | H | H |
| $L_A2215$ | | CD$_3$ | H | H | $^i$Pr | H | H | H |
| $L_A2216$ | | CD$_3$ | H | H | H | $^i$Pr | H | H |
| $L_A2217$ | | CD$_3$ | Ph | H | H | H | H | H |
| $L_A2218$ | | CD$_3$ | H | Ph | H | H | H | H |
| $L_A2219$ | | CD$_3$ | H | H | Ph | H | H | H |
| $L_A2220$ | | CD$_3$ | H | H | H | Ph | H | H |
| $L_A2221$ | | $^i$Pr | Me | H | H | H | H | H |
| $L_A2222$ | | $^i$Pr | H | Me | H | H | H | H |
| $L_A2223$ | | $^i$Pr | H | H | Me | H | H | H |
| $L_A2224$ | | $^i$Pr | H | H | H | Me | H | H |
| $L_A2225$ | | $^i$Pr | CD$_3$ | H | H | H | H | H |
| $L_A2226$ | | $^i$Pr | H | CD$_3$ | H | H | H | H |
| $L_A2227$ | | $^i$Pr | H | H | CD$_3$ | H | H | H |
| $L_A2228$ | | $^i$Pr | H | H | H | CD$_3$ | H | H |
| $L_A2229$ | | $^i$Pr | $^i$Pr | H | H | H | H | H |
| $L_A2230$ | | $^i$Pr | H | $^i$Pr | H | H | H | H |
| $L_A2231$ | | $^i$Pr | H | H | $^i$Pr | H | H | H |
| $L_A2232$ | | $^i$Pr | H | H | H | $^i$Pr | H | H |
| $L_A2233$ | | $^i$Pr | Ph | H | H | H | H | H |
| $L_A2234$ | | $^i$Pr | H | Ph | H | H | H | H |
| $L_A2235$ | | $^i$Pr | H | H | Ph | H | H | H |
| $L_A2236$ | | $^i$Pr | H | H | H | Ph | H | H |
| $L_A2237$ | | Ph | Me | H | H | H | H | H |
| $L_A2238$ | | Ph | H | Me | H | H | H | H |
| $L_A2239$ | | Ph | H | H | Me | H | H | H |
| $L_A2240$ | | Ph | H | H | H | Me | H | H |
| $L_A2241$ | | Ph | CD$_3$ | H | H | H | H | H |
| $L_A2242$ | | Ph | H | CD$_3$ | H | H | H | H |
| $L_A2243$ | | Ph | H | H | CD$_3$ | H | H | H |
| $L_A2244$ | | Ph | H | H | H | CD$_3$ | H | H |
| $L_A2245$ | | Ph | $^i$Pr | H | H | H | H | H |
| $L_A2246$ | | Ph | H | $^i$Pr | H | H | H | H |
| $L_A2247$ | | Ph | H | H | $^i$Pr | H | H | H |
| $L_A2248$ | | Ph | H | H | H | $^i$Pr | H | H |
| $L_A2249$ | (decalin linker at C$^{1b}$/C$^{1e}$) | Ph | Ph | H | H | H | H | H |
| $L_A2250$ | | Ph | H | Ph | H | H | H | H |
| $L_A2251$ | | Ph | H | H | Ph | H | H | H |
| $L_A2252$ | | Ph | H | H | H | Ph | H | H |
| $L_A2253$ | | H | Me | Me | H | H | H | H |
| $L_A2254$ | | H | Me | H | Me | H | H | H |
| $L_A2255$ | | H | Me | H | H | Me | H | H |
| $L_A2256$ | | H | Me | CD$_3$ | H | H | H | H |
| $L_A2257$ | | H | Me | H | CD$_3$ | H | H | H |
| $L_A2258$ | | H | Me | H | H | CD$_3$ | H | H |
| $L_A2259$ | | H | Me | $^i$Pr | H | H | H | H |
| $L_A2260$ | | H | Me | H | $^i$Pr | H | H | H |
| $L_A2261$ | | H | Me | H | H | $^i$Pr | H | H |
| $L_A2262$ | | H | Me | Ph | H | H | H | H |
| $L_A2263$ | | H | Me | H | Ph | H | H | H |
| $L_A2264$ | | H | Me | H | H | Ph | H | H |
| $L_A2265$ | | H | CD$_3$ | Me | H | H | H | H |
| $L_A2266$ | | H | CD$_3$ | H | Me | H | H | H |
| $L_A2267$ | | H | CD$_3$ | H | H | Me | H | H |
| $L_A2268$ | | H | CD$_3$ | CD$_3$ | H | H | H | H |
| $L_A2269$ | | H | CD$_3$ | H | CD$_3$ | H | H | H |
| $L_A2270$ | | H | CD$_3$ | H | H | CD$_3$ | H | H |
| $L_A2271$ | | H | CD$_3$ | $^i$Pr | H | H | H | H |
| $L_A2272$ | | H | CD$_3$ | H | $^i$Pr | H | H | H |
| $L_A2273$ | | H | CD$_3$ | H | H | $^i$Pr | H | H |
| $L_A2274$ | | H | CD$_3$ | Ph | H | H | H | H |
| $L_A2275$ | | H | CD$_3$ | H | Ph | H | H | H |
| $L_A2276$ | | H | CD$_3$ | H | H | Ph | H | H |
| $L_A2277$ | | H | $^i$Pr | Me | H | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A2278$ | | H | $^iPr$ | H | Me | H | H | H |
| $L_A2279$ | | H | $^iPr$ | H | H | Me | H | H |
| $L_A2280$ | | H | $^iPr$ | $CD_3$ | H | H | H | H |
| $L_A2281$ | | H | $^iPr$ | H | $CD_3$ | H | H | H |
| $L_A2282$ | | H | $^iPr$ | H | H | $CD_3$ | H | H |
| $L_A2283$ | | H | $^iPr$ | $^iPr$ | H | H | H | H |
| $L_A2284$ | | H | $^iPr$ | H | $^iPr$ | H | H | H |
| $L_A2285$ | | H | $^iPr$ | H | H | $^iPr$ | H | H |
| $L_A2286$ | | H | $^iPr$ | Ph | H | H | H | H |
| $L_A2287$ | | H | $^iPr$ | H | Ph | H | H | H |
| $L_A2288$ | | H | $^iPr$ | H | H | Ph | H | H |
| $L_A2289$ | | H | Ph | Me | H | H | H | H |
| $L_A2290$ | | H | Ph | H | Me | H | H | H |
| $L_A2291$ | | H | Ph | H | H | Me | H | H |
| $L_A2292$ | | H | Ph | $CD_3$ | H | H | H | H |
| $L_A2293$ | | H | Ph | H | $CD_3$ | H | H | H |
| $L_A2294$ | | H | Ph | H | H | $CD_3$ | H | H |
| $L_A2295$ | | H | Ph | $^iPr$ | H | H | H | H |
| $L_A2296$ | | H | Ph | H | $^iPr$ | H | H | H |
| $L_A2297$ | | H | Ph | H | H | $^iPr$ | H | H |
| $L_A2298$ | | H | Ph | Ph | H | H | H | H |
| $L_A2299$ | | H | Ph | H | Ph | H | H | H |
| $L_A2300$ | | H | Ph | H | H | Ph | H | H |
| $L_A2301$ | | H | H | Me | Me | H | H | H |
| $L_A2302$ | decahydronaphthalene ($C^{1b}$, $C^{1e}$) | H | H | $CD_3$ | Me | H | H | H |
| $L_A2303$ | | H | H | $^iPr$ | Me | H | H | H |
| $L_A2304$ | | H | H | Ph | Me | H | H | H |
| $L_A2305$ | | H | H | Me | $CD_3$ | H | H | H |
| $L_A2306$ | | H | H | $CD_3$ | $CD_3$ | H | H | H |
| $L_A2307$ | | H | H | $^iPr$ | $CD_3$ | H | H | H |
| $L_A2308$ | | H | H | Ph | $CD_3$ | H | H | H |
| $L_A2309$ | | H | H | Me | $^iPr$ | H | H | H |
| $L_A2310$ | | H | H | $CD_3$ | $^iPr$ | H | H | H |
| $L_A2311$ | | H | H | $^iPr$ | $^iPr$ | H | H | H |
| $L_A2312$ | | H | H | Ph | $^iPr$ | H | H | H |
| $L_A2313$ | | H | H | Me | Ph | H | H | H |
| $L_A2314$ | | H | H | $CD_3$ | Ph | H | H | H |
| $L_A2315$ | | H | H | $^iPr$ | Ph | H | H | H |
| $L_A2316$ | | H | H | Ph | Ph | H | H | H |
| $L_A2317$ | | H | H | Me | H | Me | H | H |
| $L_A2318$ | | H | H | $CD_3$ | H | Me | H | H |
| $L_A2319$ | | H | H | $^iPr$ | H | Me | H | H |
| $L_A2320$ | | H | H | Ph | H | Me | H | H |
| $L_A2321$ | | H | H | Me | H | $CD_3$ | H | H |
| $L_A2322$ | | H | H | $CD_3$ | $CD_3$ | H | H | H |
| $L_A2323$ | | H | H | $^iPr$ | H | $CD_3$ | H | H |
| $L_A2324$ | | H | H | Ph | H | $CD_3$ | H | H |
| $L_A2325$ | | H | H | Me | H | $^iPr$ | H | H |
| $L_A2326$ | | H | H | $CD_3$ | H | $^iPr$ | H | H |
| $L_A2327$ | | H | H | $^iPr$ | H | $^iPr$ | H | H |
| $L_A2328$ | | H | H | Ph | H | $^iPr$ | H | H |
| $L_A2329$ | | H | H | Me | H | Ph | H | H |
| $L_A2330$ | | H | H | $CD_3$ | H | Ph | H | H |
| $L_A2331$ | | H | H | $^iPr$ | H | Ph | H | H |
| $L_A2332$ | | H | H | Ph | H | Ph | H | H |
| $L_A2333$ | | Me | Me | H | Me | H | H | H |
| $L_A2334$ | | H | Me | Me | Me | H | H | H |
| $L_A2335$ | | $CD_3$ | Me | H | Me | H | H | H |
| $L_A2336$ | | H | Me | $CD_3$ | Me | H | H | H |
| $L_A2337$ | | $^iPr$ | Me | H | Me | H | H | H |
| $L_A2338$ | | H | Me | $^iPr$ | Me | H | H | H |
| $L_A2339$ | | Ph | Me | H | Me | H | H | H |
| $L_A2340$ | | H | Me | Ph | Me | H | H | H |
| $L_A2341$ | | Me | $CD_3$ | H | $CD_3$ | H | H | H |
| $L_A2342$ | | H | $CD_3$ | Me | $CD_3$ | H | H | H |
| $L_A2343$ | | $CD_3$ | $CD_3$ | H | $CD_3$ | H | H | H |
| $L_A2344$ | | H | $CD_3$ | $CD_3$ | $CD_3$ | H | H | H |
| $L_A2345$ | | $^iPr$ | $CD_3$ | H | $CD_3$ | H | H | H |
| $L_A2346$ | | H | $CD_3$ | $^iPr$ | $CD_3$ | H | H | H |
| $L_A2347$ | | Ph | $CD_3$ | H | $CD_3$ | H | H | H |
| $L_A2348$ | | H | $CD_3$ | Ph | $CD_3$ | H | H | H |
| $L_A2349$ | | Me | $^iPr$ | H | $^iPr$ | H | H | H |
| $L_A2350$ | | H | $^iPr$ | Me | $^iPr$ | H | H | H |
| $L_A2351$ | | $CD_3$ | $^iPr$ | H | $^iPr$ | H | H | H |
| $L_A2352$ | | H | $^iPr$ | $CD_3$ | $^iPr$ | H | H | H |
| $L_A2353$ | | $^iPr$ | $^iPr$ | H | $^iPr$ | H | H | H |
| $L_A2354$ | | H | $^iPr$ | $^iPr$ | $^iPr$ | H | H | H |
| $L_A2355$ | | Ph | $^iPr$ | H | $^iPr$ | H | H | H |
| $L_A2356$ | | H | $^iPr$ | Ph | $^iPr$ | H | H | H |
| $L_A2357$ | decahydronaphthalene ($C^{1b}$, $C^{1e}$) | Me | Ph | H | Ph | H | H | H |
| $L_A2358$ | | H | Ph | Me | Ph | H | H | H |
| $L_A2359$ | | $CD_3$ | Ph | H | Ph | H | H | H |
| $L_A2360$ | | H | Ph | $CD_3$ | Ph | H | H | H |
| $L_A2361$ | | $^iPr$ | Ph | H | Ph | H | H | H |
| $L_A2362$ | | H | Ph | $^iPr$ | Ph | H | H | H |
| $L_A2363$ | | Ph | Ph | H | Ph | H | H | H |
| $L_A2364$ | | H | Ph | Ph | Ph | H | H | H |
| $L_A2365$ | hexahydroindane ($C^{1b}$, $C^{1e}$) | H | H | H | H | H | H | H |
| $L_A2366$ | | Me | H | H | H | H | H | H |
| $L_A2367$ | | H | Me | H | H | H | H | H |
| $L_A2368$ | | H | H | Me | H | H | H | H |
| $L_A2369$ | | H | H | H | Me | H | H | H |
| $L_A2370$ | | H | H | H | H | Me | H | H |
| $L_A2371$ | | $CD_3$ | H | H | H | H | H | H |
| $L_A2372$ | | H | $CD_3$ | H | H | H | H | H |
| $L_A2373$ | | H | H | $CD_3$ | H | H | H | H |
| $L_A2374$ | | H | H | H | $CD_3$ | H | H | H |
| $L_A2375$ | | H | H | H | H | $CD_3$ | H | H |
| $L_A2376$ | | $^iPr$ | H | H | H | H | H | H |
| $L_A2377$ | | H | $^iPr$ | H | H | H | H | H |
| $L_A2378$ | | H | H | $^iPr$ | H | H | H | H |
| $L_A2379$ | | H | H | H | $^iPr$ | H | H | H |
| $L_A2380$ | | H | H | H | H | $^iPr$ | H | H |
| $L_A2381$ | | Ph | H | H | H | H | H | H |
| $L_A2382$ | | H | Ph | H | H | H | H | H |
| $L_A2383$ | | H | H | Ph | H | H | H | H |
| $L_A2384$ | | H | H | H | Ph | H | H | H |
| $L_A2385$ | | H | H | H | H | Ph | H | H |
| $L_A2386$ | | Me | Me | H | H | H | H | H |
| $L_A2387$ | | Me | H | Me | H | H | H | H |
| $L_A2388$ | | Me | H | H | Me | H | H | H |
| $L_A2389$ | | Me | H | H | H | Me | H | H |
| $L_A2390$ | | Me | $CD_3$ | H | H | H | H | H |
| $L_A2391$ | | Me | H | $CD_3$ | H | H | H | H |
| $L_A2392$ | | Me | H | H | $CD_3$ | H | H | H |
| $L_A2393$ | | Me | H | H | H | $CD_3$ | H | H |
| $L_A2394$ | | Me | $^iPr$ | H | H | H | H | H |
| $L_A2395$ | | Me | H | $^iPr$ | H | H | H | H |
| $L_A2396$ | | Me | H | H | $^iPr$ | H | H | H |
| $L_A2397$ | | Me | H | H | H | $^iPr$ | H | H |
| $L_A2398$ | | Me | Ph | H | H | H | H | H |
| $L_A2399$ | | Me | H | Ph | H | H | H | H |
| $L_A2400$ | | Me | H | H | Ph | H | H | H |
| $L_A2401$ | | Me | H | H | H | Ph | H | H |
| $L_A2402$ | | $CD_3$ | Me | H | H | H | H | H |
| $L_A2403$ | | $CD_3$ | H | Me | H | H | H | H |
| $L_A2404$ | | $CD_3$ | H | H | Me | H | H | H |
| $L_A2405$ | | $CD_3$ | H | H | H | Me | H | H |
| $L_A2406$ | | $CD_3$ | $CD_3$ | H | H | H | H | H |
| $L_A2407$ | | $CD_3$ | H | $CD_3$ | H | H | H | H |
| $L_A2408$ | | $CD_3$ | H | H | $CD_3$ | H | H | H |
| $L_A2409$ | | $CD_3$ | H | H | H | $CD_3$ | H | H |
| $L_A2410$ | | $CD_3$ | $^iPr$ | H | H | H | H | H |
| $L_A2411$ | hexahydroindane ($C^{1b}$, $C^{1e}$) | $CD_3$ | H | $^iPr$ | H | H | H | H |
| $L_A2412$ | | $CD_3$ | H | H | $^iPr$ | H | H | H |
| $L_A2413$ | | $CD_3$ | H | H | H | $^iPr$ | H | H |
| $L_A2414$ | | $CD_3$ | Ph | H | H | H | H | H |
| $L_A2415$ | | $CD_3$ | H | Ph | H | H | H | H |
| $L_A2416$ | | $CD_3$ | H | H | Ph | H | H | H |
| $L_A2417$ | | $CD_3$ | H | H | H | Ph | H | H |
| $L_A2418$ | | $^iPr$ | Me | H | H | H | H | H |
| $L_A2419$ | | $^iPr$ | H | Me | H | H | H | H |
| $L_A2420$ | | $^iPr$ | H | H | Me | H | H | H |
| $L_A2421$ | | $^iPr$ | H | H | H | Me | H | H |
| $L_A2422$ | | $^iPr$ | $CD_3$ | H | H | H | H | H |
| $L_A2423$ | | $^iPr$ | H | $CD_3$ | H | H | H | H |
| $L_A2424$ | | $^iPr$ | H | H | $CD_3$ | H | H | H |
| $L_A2425$ | | $^iPr$ | H | H | H | $CD_3$ | H | H |
| $L_A2426$ | | $^iPr$ | $^iPr$ | H | H | H | H | H |
| $L_A2427$ | | $^iPr$ | H | $^iPr$ | H | H | H | H |
| $L_A2428$ | | $^iPr$ | H | H | $^iPr$ | H | H | H |
| $L_A2429$ | | $^iPr$ | H | H | H | $^iPr$ | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$2430 | | $^i$Pr | Ph | H | H | H | H | H |
| $L_A$2431 | | $^i$Pr | H | Ph | H | H | H | H |
| $L_A$2432 | | $^i$Pr | H | H | Ph | H | H | H |
| $L_A$2433 | | $^i$Pr | H | H | H | Ph | H | H |
| $L_A$2434 | | Ph | Me | H | H | H | H | H |
| $L_A$2435 | | Ph | H | Me | H | H | H | H |
| $L_A$2436 | | Ph | H | H | Me | H | H | H |
| $L_A$2437 | | Ph | H | H | H | Me | H | H |
| $L_A$2438 | | Ph | $CD_3$ | H | H | H | H | H |
| $L_A$2439 | | Ph | H | $CD_3$ | H | H | H | H |
| $L_A$2440 | | Ph | H | H | $CD_3$ | H | H | H |
| $L_A$2441 | | Ph | H | H | H | $CD_3$ | H | H |
| $L_A$2442 | | Ph | $^i$Pr | H | H | H | H | H |
| $L_A$2443 | | Ph | H | $^i$Pr | H | H | H | H |
| $L_A$2444 | | Ph | H | H | $^i$Pr | H | H | H |
| $L_A$2445 | | Ph | H | H | H | $^i$Pr | H | H |
| $L_A$2446 | | Ph | Ph | H | H | H | H | H |
| $L_A$2447 | | Ph | H | Ph | H | H | H | H |
| $L_A$2448 | | Ph | H | H | Ph | H | H | H |
| $L_A$2449 | | Ph | H | H | H | Ph | H | H |
| $L_A$2450 | | H | Me | Me | H | H | H | H |
| $L_A$2451 | | H | Me | H | Me | H | H | H |
| $L_A$2452 | | H | Me | H | H | Me | H | H |
| $L_A$2453 | | H | Me | $CD_3$ | H | H | H | H |
| $L_A$2454 | | H | Me | H | $CD_3$ | H | H | H |
| $L_A$2455 | | H | Me | H | H | $CD_3$ | H | H |
| $L_A$2456 | | H | Me | $^i$Pr | H | H | H | H |
| $L_A$2457 | | H | Me | H | $^i$Pr | H | H | H |
| $L_A$2458 | | H | Me | H | H | $^i$Pr | H | H |
| $L_A$2459 | | H | Me | Ph | H | H | H | H |
| $L_A$2460 | | H | Me | H | Ph | H | H | H |
| $L_A$2461 | | H | Me | H | H | Ph | H | H |
| $L_A$2462 | | H | $CD_3$ | Me | H | H | H | H |
| $L_A$2463 | | H | $CD_3$ | H | Me | H | H | H |
| $L_A$2464 | | H | $CD_3$ | H | H | Me | H | H |
| $L_A$2465 | | H | $CD_3$ | $CD_3$ | H | H | H | H |
| $L_A$2466 | bicyclic (C$^{1b}$/C$^{1e}$) | H | $CD_3$ | H | $CD_3$ | H | H | H |
| $L_A$2467 | | H | $CD_3$ | H | H | $CD_3$ | H | H |
| $L_A$2468 | | H | $CD_3$ | $^i$Pr | H | H | H | H |
| $L_A$2469 | | H | $CD_3$ | H | $^i$Pr | H | H | H |
| $L_A$2470 | | H | $CD_3$ | H | H | $^i$Pr | H | H |
| $L_A$2471 | | H | $CD_3$ | Ph | H | H | H | H |
| $L_A$2472 | | H | $CD_3$ | H | Ph | H | H | H |
| $L_A$2473 | | H | $CD_3$ | H | H | Ph | H | H |
| $L_A$2474 | | H | $^i$Pr | Me | H | H | H | H |
| $L_A$2475 | | H | $^i$Pr | H | Me | H | H | H |
| $L_A$2476 | | H | $^i$Pr | H | H | Me | H | H |
| $L_A$2477 | | H | $^i$Pr | $CD_3$ | H | H | H | H |
| $L_A$2478 | | H | $^i$Pr | H | $CD_3$ | H | H | H |
| $L_A$2479 | | H | $^i$Pr | H | H | $CD_3$ | H | H |
| $L_A$2480 | | H | $^i$Pr | $^i$Pr | H | H | H | H |
| $L_A$2481 | | H | $^i$Pr | H | $^i$Pr | H | H | H |
| $L_A$2482 | | H | $^i$Pr | H | H | $^i$Pr | H | H |
| $L_A$2483 | | H | $^i$Pr | Ph | H | H | H | H |
| $L_A$2484 | | H | $^i$Pr | H | Ph | H | H | H |
| $L_A$2485 | | H | $^i$Pr | H | H | Ph | H | H |
| $L_A$2486 | | H | Ph | Me | H | H | H | H |
| $L_A$2487 | | H | Ph | H | Me | H | H | H |
| $L_A$2488 | | H | Ph | H | H | Me | H | H |
| $L_A$2489 | | H | Ph | $CD_3$ | H | H | H | H |
| $L_A$2490 | | H | Ph | H | $CD_3$ | H | H | H |
| $L_A$2491 | | H | Ph | H | H | $CD_3$ | H | H |
| $L_A$2492 | | H | Ph | $^i$Pr | H | H | H | H |
| $L_A$2493 | | H | Ph | H | $^i$Pr | H | H | H |
| $L_A$2494 | | H | Ph | H | H | $^i$Pr | H | H |
| $L_A$2495 | | H | Ph | Ph | H | H | H | H |
| $L_A$2496 | | H | Ph | H | Ph | H | H | H |
| $L_A$2497 | | H | Ph | H | H | Ph | H | H |
| $L_A$2498 | | H | H | Me | Me | H | H | H |
| $L_A$2499 | | H | H | $CD_3$ | Me | H | H | H |
| $L_A$2500 | | H | H | $^i$Pr | Me | H | H | H |
| $L_A$2501 | | H | H | Ph | Me | H | H | H |
| $L_A$2502 | | H | H | Me | $CD_3$ | H | H | H |
| $L_A$2503 | | H | H | $CD_3$ | $CD_3$ | H | H | H |
| $L_A$2504 | | H | H | $^i$Pr | $CD_3$ | H | H | H |
| $L_A$2505 | | H | H | Ph | $CD_3$ | H | H | H |
| $L_A$2506 | | H | H | Me | $^i$Pr | H | H | H |
| $L_A$2507 | | H | H | $CD_3$ | $^i$Pr | H | H | H |
| $L_A$2508 | | H | H | $^i$Pr | $^i$Pr | H | H | H |
| $L_A$2509 | | H | H | Ph | $^i$Pr | H | H | H |
| $L_A$2510 | | H | H | Me | Ph | H | H | H |
| $L_A$2511 | | H | H | $CD_3$ | Ph | H | H | H |
| $L_A$2512 | | H | H | $^i$Pr | Ph | H | H | H |
| $L_A$2513 | | H | H | Ph | Ph | H | H | H |
| $L_A$2514 | | H | H | Me | H | Me | H | H |
| $L_A$2515 | | H | H | $CD_3$ | H | Me | H | H |
| $L_A$2516 | | H | H | $^i$Pr | H | Me | H | H |
| $L_A$2517 | | H | H | Ph | H | Me | H | H |
| $L_A$2518 | | H | H | Me | H | $CD_3$ | H | H |
| $L_A$2519 | | H | H | $CD_3$ | H | $CD_3$ | H | H |
| $L_A$2520 | | H | H | $^i$Pr | H | $CD_3$ | H | H |
| $L_A$2521 | bicyclic (C$^{1b}$/C$^{1e}$) | H | H | Ph | H | $CD_3$ | H | H |
| $L_A$2522 | | H | H | Me | H | $^i$Pr | H | H |
| $L_A$2523 | | H | H | $CD_3$ | H | $^i$Pr | H | H |
| $L_A$2524 | | H | H | $^i$Pr | H | $^i$Pr | H | H |
| $L_A$2525 | | H | H | Ph | H | $^i$Pr | H | H |
| $L_A$2526 | | H | H | Me | H | Ph | H | H |
| $L_A$2527 | | H | H | $CD_3$ | H | Ph | H | H |
| $L_A$2528 | | H | H | $^i$Pr | H | Ph | H | H |
| $L_A$2529 | | H | H | Ph | H | Ph | H | H |
| $L_A$2530 | | Me | Me | H | Me | H | H | H |
| $L_A$2531 | | H | Me | Me | Me | H | H | H |
| $L_A$2532 | | $CD_3$ | Me | H | Me | H | H | H |
| $L_A$2533 | | H | Me | $CD_3$ | Me | H | H | H |
| $L_A$2534 | | $^i$Pr | Me | H | Me | H | H | H |
| $L_A$2535 | | H | Me | $^i$Pr | Me | H | H | H |
| $L_A$2536 | | Ph | Me | H | Me | H | H | H |
| $L_A$2537 | | H | Me | Ph | Me | H | H | H |
| $L_A$2538 | | Me | $CD_3$ | H | $CD_3$ | H | H | H |
| $L_A$2539 | | H | $CD_3$ | Me | $CD_3$ | H | H | H |
| $L_A$2540 | | $CD_3$ | $CD_3$ | H | $CD_3$ | H | H | H |
| $L_A$2541 | | H | $CD_3$ | $CD_3$ | $CD_3$ | H | H | H |
| $L_A$2542 | | $^i$Pr | $CD_3$ | H | $CD_3$ | H | H | H |
| $L_A$2543 | | H | $CD_3$ | $^i$Pr | $CD_3$ | H | H | H |
| $L_A$2544 | | Ph | $CD_3$ | H | $CD_3$ | H | H | H |
| $L_A$2545 | | H | $CD_3$ | Ph | $CD_3$ | H | H | H |
| $L_A$2546 | | Me | $^i$Pr | H | $^i$Pr | H | H | H |
| $L_A$2547 | | H | $^i$Pr | Me | $^i$Pr | H | H | H |
| $L_A$2548 | | $CD_3$ | $^i$Pr | H | $^i$Pr | H | H | H |
| $L_A$2549 | | H | $^i$Pr | $CD_3$ | $^i$Pr | H | H | H |
| $L_A$2550 | | $^i$Pr | $^i$Pr | H | $^i$Pr | H | H | H |
| $L_A$2551 | | H | $^i$Pr | $^i$Pr | $^i$Pr | H | H | H |
| $L_A$2552 | | Ph | $^i$Pr | H | $^i$Pr | H | H | H |
| $L_A$2553 | | H | $^i$Pr | Ph | $^i$Pr | H | H | H |
| $L_A$2554 | | Me | Ph | H | Ph | H | H | H |
| $L_A$2555 | | H | Ph | Me | Ph | H | H | H |
| $L_A$2556 | | $CD_3$ | Ph | H | Ph | H | H | H |
| $L_A$2557 | | H | Ph | $CD_3$ | Ph | H | H | H |
| $L_A$2558 | | $^i$Pr | Ph | H | Ph | H | H | H |
| $L_A$2559 | | H | Ph | $^i$Pr | Ph | H | H | H |
| $L_A$2560 | | Ph | Ph | H | Ph | H | H | H |
| $L_A$2561 | | H | Ph | Ph | Ph | H | H | H |
| $L_A$2562 | bicyclic (C$^{1b}$/C$^{1e}$) | H | H | H | H | H | H | H |
| $L_A$2563 | | Me | H | H | H | H | H | H |
| $L_A$2564 | | H | Me | H | H | H | H | H |
| $L_A$2565 | | H | H | Me | H | H | H | H |
| $L_A$2566 | | H | H | H | Me | H | H | H |
| $L_A$2567 | | H | H | H | H | Me | H | H |
| $L_A$2568 | | $CD_3$ | H | H | H | H | H | H |
| $L_A$2569 | | H | $CD_3$ | H | H | H | H | H |
| $L_A$2570 | | H | H | $CD_3$ | H | H | H | H |
| $L_A$2571 | | H | H | H | $CD_3$ | H | H | H |
| $L_A$2572 | | H | H | H | H | $CD_3$ | H | H |
| $L_A$2573 | | $^i$Pr | H | H | H | H | H | H |
| $L_A$2574 | | H | $^i$Pr | H | H | H | H | H |
| $L_A$2575 | | H | H | $^i$Pr | H | H | H | H |
| $L_A$2576 | bicyclic (C$^{1b}$/C$^{1e}$) | H | H | H | $^i$Pr | H | H | H |
| $L_A$2577 | | H | H | H | H | $^i$Pr | H | H |
| $L_A$2578 | | Ph | H | H | H | H | H | H |
| $L_A$2579 | | H | Ph | H | H | H | H | H |
| $L_A$2580 | | H | H | Ph | H | H | H | H |
| $L_A$2581 | | H | H | H | Ph | H | H | H |

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A2582$ | | H | H | H | H | Ph | H | H |
| $L_A2583$ | | Me | Me | H | H | H | H | H |
| $L_A2584$ | | Me | H | Me | H | H | H | H |
| $L_A2585$ | | Me | H | H | Me | H | H | H |
| $L_A2586$ | | Me | H | H | H | Me | H | H |
| $L_A2587$ | | Me | $CD_3$ | H | H | H | H | H |
| $L_A2588$ | | Me | H | $CD_3$ | H | H | H | H |
| $L_A2589$ | | Me | H | H | $CD_3$ | H | H | H |
| $L_A2590$ | | Me | H | H | H | $CD_3$ | H | H |
| $L_A2591$ | | Me | $^iPr$ | H | H | H | H | H |
| $L_A2592$ | | Me | H | $^iPr$ | H | H | H | H |
| $L_A2593$ | | Me | H | H | $^iPr$ | H | H | H |
| $L_A2594$ | | Me | H | H | H | $^iPr$ | H | H |
| $L_A2595$ | | Me | Ph | H | H | H | H | H |
| $L_A2596$ | | Me | H | Ph | H | H | H | H |
| $L_A2597$ | | Me | H | H | Ph | H | H | H |
| $L_A2598$ | | Me | H | H | H | Ph | H | H |
| $L_A2599$ | | $CD_3$ | Me | H | H | H | H | H |
| $L_A2600$ | | $CD_3$ | H | Me | H | H | H | H |
| $L_A2601$ | | $CD_3$ | H | H | Me | H | H | H |
| $L_A2602$ | | $CD_3$ | H | H | H | Me | H | H |
| $L_A2603$ | | $CD_3$ | $CD_3$ | H | H | H | H | H |
| $L_A2604$ | | $CD_3$ | H | $CD_3$ | H | H | H | H |
| $L_A2605$ | | $CD_3$ | H | H | $CD_3$ | H | H | H |
| $L_A2606$ | | $CD_3$ | H | H | H | $CD_3$ | H | H |
| $L_A2607$ | | $CD_3$ | $^iPr$ | H | H | H | H | H |
| $L_A2608$ | | $CD_3$ | H | $^iPr$ | H | H | H | H |
| $L_A2609$ | | $CD_3$ | H | H | $^iPr$ | H | H | H |
| $L_A2610$ | | $CD_3$ | H | H | H | $^iPr$ | H | H |
| $L_A2611$ | | $CD_3$ | Ph | H | H | H | H | H |
| $L_A2612$ | | $CD_3$ | H | Ph | H | H | H | H |
| $L_A2613$ | | $CD_3$ | H | H | Ph | H | H | H |
| $L_A2614$ | | $CD_3$ | H | H | H | Ph | H | H |
| $L_A2615$ | | $^iPr$ | Me | H | H | H | H | H |
| $L_A2616$ | | $^iPr$ | H | Me | H | H | H | H |
| $L_A2617$ | | $^iPr$ | H | H | Me | H | H | H |
| $L_A2618$ | | $^iPr$ | H | H | H | Me | H | H |
| $L_A2619$ | | $^iPr$ | $CD_3$ | H | H | H | H | H |
| $L_A2620$ | | $^iPr$ | H | $CD_3$ | H | H | H | H |
| $L_A2621$ | | $^iPr$ | H | H | $CD_3$ | H | H | H |
| $L_A2622$ | | $^iPr$ | H | H | H | $CD_3$ | H | H |
| $L_A2623$ | | $^iPr$ | $^iPr$ | H | H | H | H | H |
| $L_A2624$ | | $^iPr$ | H | $^iPr$ | H | H | H | H |
| $L_A2625$ | | $^iPr$ | H | H | $^iPr$ | H | H | H |
| $L_A2626$ | | $^iPr$ | H | H | H | $^iPr$ | H | H |
| $L_A2627$ | | $^iPr$ | Ph | H | H | H | H | H |
| $L_A2628$ | | $^iPr$ | H | Ph | H | H | H | H |
| $L_A2629$ | | $^iPr$ | H | H | Ph | H | H | H |
| $L_A2630$ | | $^iPr$ | H | H | H | Ph | H | H |
| $L_A2631$ | 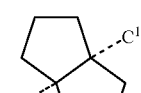 | Ph | Me | H | H | H | H | H |
| $L_A2632$ | | Ph | H | Me | H | H | H | H |
| $L_A2633$ | | Ph | H | H | Me | H | H | H |
| $L_A2634$ | | Ph | H | H | H | Me | H | H |
| $L_A2635$ | | Ph | $CD_3$ | H | H | H | H | H |
| $L_A2636$ | | Ph | H | $CD_3$ | H | H | H | H |
| $L_A2637$ | | Ph | H | H | $CD_3$ | H | H | H |
| $L_A2638$ | | Ph | H | H | H | $CD_3$ | H | H |
| $L_A2639$ | | Ph | $^iPr$ | H | H | H | H | H |
| $L_A2640$ | | Ph | H | $^iPr$ | H | H | H | H |
| $L_A2641$ | | Ph | H | H | $^iPr$ | H | H | H |
| $L_A2642$ | | Ph | H | H | H | $^iPr$ | H | H |
| $L_A2643$ | | Ph | Ph | H | H | H | H | H |
| $L_A2644$ | | Ph | H | Ph | H | H | H | H |
| $L_A2645$ | | Ph | H | H | Ph | H | H | H |
| $L_A2646$ | | Ph | H | H | H | Ph | H | H |
| $L_A2647$ | | H | Me | Me | H | H | H | H |
| $L_A2648$ | | H | Me | H | Me | H | H | H |
| $L_A2649$ | | H | Me | H | H | Me | H | H |
| $L_A2650$ | | H | Me | $CD_3$ | H | H | H | H |
| $L_A2651$ | | H | Me | H | $CD_3$ | H | H | H |
| $L_A2652$ | | H | Me | H | H | $CD_3$ | H | H |
| $L_A2653$ | | H | Me | $^iPr$ | H | H | H | H |
| $L_A2654$ | | H | Me | H | $^iPr$ | H | H | H |
| $L_A2655$ | | H | Me | H | H | $^iPr$ | H | H |
| $L_A2656$ | | H | Me | Ph | H | H | H | H |
| $L_A2657$ | | H | Me | H | Ph | H | H | H |
| $L_A2658$ | | H | Me | H | H | Ph | H | H |
| $L_A2659$ | | H | $CD_3$ | Me | H | H | H | H |
| $L_A2660$ | | H | $CD_3$ | H | Me | H | H | H |
| $L_A2661$ | | H | $CD_3$ | H | H | Me | H | H |
| $L_A2662$ | | H | $CD_3$ | $CD_3$ | H | H | H | H |
| $L_A2663$ | | H | $CD_3$ | H | $CD_3$ | H | H | H |
| $L_A2664$ | | H | $CD_3$ | H | H | $CD_3$ | H | H |
| $L_A2665$ | | H | $CD_3$ | $^iPr$ | H | H | H | H |
| $L_A2666$ | | H | $CD_3$ | H | $^iPr$ | H | H | H |
| $L_A2667$ | | H | $CD_3$ | H | H | $^iPr$ | H | H |
| $L_A2668$ | | H | $CD_3$ | Ph | H | H | H | H |
| $L_A2669$ | | H | $CD_3$ | H | Ph | H | H | H |
| $L_A2670$ | | H | $CD_3$ | H | H | Ph | H | H |
| $L_A2671$ | | H | $^iPr$ | Me | H | H | H | H |
| $L_A2672$ | | H | $^iPr$ | H | Me | H | H | H |
| $L_A2673$ | | H | $^iPr$ | H | H | Me | H | H |
| $L_A2674$ | | H | $^iPr$ | $CD_3$ | H | H | H | H |
| $L_A2675$ | | H | $^iPr$ | H | $CD_3$ | H | H | H |
| $L_A2676$ | | H | $^iPr$ | H | H | $CD_3$ | H | H |
| $L_A2677$ | | H | $^iPr$ | $^iPr$ | H | H | H | H |
| $L_A2678$ | | H | $^iPr$ | H | $^iPr$ | H | H | H |
| $L_A2679$ | | H | $^iPr$ | H | H | $^iPr$ | H | H |
| $L_A2680$ | | H | $^iPr$ | Ph | H | H | H | H |
| $L_A2681$ | | H | $^iPr$ | H | Ph | H | H | H |
| $L_A2682$ | | H | $^iPr$ | H | H | Ph | H | H |
| $L_A2683$ | | H | Ph | Me | H | H | H | H |
| $L_A2684$ | | H | Ph | H | Me | H | H | H |
| $L_A2685$ | | H | Ph | H | H | Me | H | H |
| $L_A2686$ | 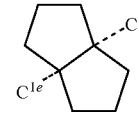 | H | Ph | $CD_3$ | H | H | H | H |
| $L_A2687$ | | H | Ph | H | $CD_3$ | H | H | H |
| $L_A2688$ | | H | Ph | H | H | $CD_3$ | H | H |
| $L_A2689$ | | H | Ph | $^iPr$ | H | H | H | H |
| $L_A2690$ | | H | Ph | H | $^iPr$ | H | H | H |
| $L_A2691$ | | H | Ph | H | H | $^iPr$ | H | H |
| $L_A2692$ | | H | Ph | Ph | H | H | H | H |
| $L_A2693$ | | H | Ph | H | Ph | H | H | H |
| $L_A2694$ | | H | Ph | H | H | Ph | H | H |
| $L_A2695$ | | H | H | Me | Me | H | H | H |
| $L_A2696$ | | H | H | $CD_3$ | Me | H | H | H |
| $L_A2697$ | | H | H | $^iPr$ | Me | H | H | H |
| $L_A2698$ | | H | H | Ph | Me | H | H | H |
| $L_A2699$ | | H | H | Me | $CD_3$ | H | H | H |
| $L_A2700$ | | H | H | $CD_3$ | $CD_3$ | H | H | H |
| $L_A2701$ | | H | H | $^iPr$ | $CD_3$ | H | H | H |
| $L_A2702$ | | H | H | Ph | $CD_3$ | H | H | H |
| $L_A2703$ | | H | H | Me | $^iPr$ | H | H | H |
| $L_32704$ | | H | H | $CD_3$ | $^iPr$ | H | H | H |
| $L_A2705$ | | H | H | $^iPr$ | $^iPr$ | H | H | H |
| $L_A2706$ | | H | H | Ph | $^iPr$ | H | H | H |
| $L_A2707$ | | H | H | Me | Ph | H | H | H |
| $L_A2708$ | | H | H | $CD_3$ | Ph | H | H | H |
| $L_A2709$ | | H | H | $^iPr$ | Ph | H | H | H |
| $L_A2710$ | | H | H | Ph | Ph | H | H | H |
| $L_A2711$ | | H | H | Me | H | Me | H | H |
| $L_A2712$ | | H | H | $CD_3$ | H | Me | H | H |
| $L_A2713$ | | H | H | $^iPr$ | H | Me | H | H |
| $L_A2714$ | | H | H | Ph | H | Me | H | H |
| $L_A2715$ | | H | H | Me | H | $CD_3$ | H | H |
| $L_A2716$ | | H | H | $CD_3$ | H | $CD_3$ | H | H |
| $L_A2717$ | | H | H | $^iPr$ | H | $CD_3$ | H | H |
| $L_A2718$ | | H | H | Ph | H | $CD_3$ | H | H |
| $L_A2719$ | | H | H | Me | H | $^iPr$ | H | H |
| $L_A2720$ | | H | H | $CD_3$ | H | $^iPr$ | H | H |
| $L_A2721$ | | H | H | $^iPr$ | H | $^iPr$ | H | H |
| $L_A2722$ | | H | H | Ph | H | $^iPr$ | H | H |
| $L_A2723$ | | H | H | Me | H | Ph | H | H |
| $L_A2724$ | | H | H | $CD_3$ | H | Ph | H | H |
| $L_A2725$ | | H | H | $^iPr$ | H | Ph | H | H |
| $L_A2726$ | | H | H | Ph | H | Ph | H | H |
| $L_A2727$ | | Me | Me | H | Me | H | H | H |
| $L_A2728$ | | H | Me | Me | Me | H | H | H |
| $L_A2729$ | | $CD_3$ | Me | H | Me | H | H | H |
| $L_A2730$ | | H | Me | $CD_3$ | Me | H | H | H |
| $L_A2731$ | | $^iPr$ | Me | H | Me | H | H | H |
| $L_A2732$ | | H | Me | $^iPr$ | Me | H | H | H |
| $L_A2733$ | | Ph | Me | H | Me | H | H | H |
| $L_A2734$ | | H | Me | Ph | Me | H | H | H |
| $L_A2735$ | | Me | $CD_3$ | H | $CD_3$ | H | H | H |

-continued

| $L_A$ | Linker A | $R^{1a}$ | $R^{1b}$ | $R^{1c}$ | $R^{1d}$ | $R^{1e}$ | $R^{1f}$ | $R^{1g}$ |
|---|---|---|---|---|---|---|---|---|
| $L_A$2736 | | H | $CD_3$ | Me | $CD_3$ | H | H | H |
| $L_A$2737 | | $CD_3$ | $CD_3$ | H | $CD_3$ | H | H | H |
| $L_A$2738 | | H | $CD_3$ | $CD_3$ | $CD_3$ | H | H | H |
| $L_A$2739 | | $^iPr$ | $CD_3$ | H | $CD_3$ | H | H | H |
| $L_A$2740 | | H | $CD_3$ | $^iPr$ | $CD_3$ | H | H | H |
| $L_A$2741 | | Ph | $CD_3$ | H | $CD_3$ | H | H | H |
| $L_A$2742 | | H | $CD_3$ | Ph | $CD_3$ | H | H | H |
| $L_A$2743 | | Me | $^iPr$ | H | $^iPr$ | H | H | H |
| $L_A$2744 | | H | $^iPr$ | Me | $^iPr$ | H | H | H |
| $L_A$2745 | | $CD_3$ | $^iPr$ | H | $^iPr$ | H | H | H |
| $L_A$2746 | | H | $^iPr$ | $CD_3$ | $^iPr$ | H | H | H |
| $L_A$2747 | | $^iPr$ | $^iPr$ | H | $^iPr$ | H | H | H |
| $L_A$2748 | | H | $^iPr$ | $^iPr$ | $^iPr$ | H | H | H |
| $L_A$2749 | | Ph | $^iPr$ | H | $^iPr$ | H | H | H |
| $L_A$2750 | | H | $^iPr$ | Ph | $^iPr$ | H | H | H |
| $L_A$2751 | | Me | Ph | H | Ph | H | H | H |
| $L_A$2752 | | H | Ph | Me | Ph | H | H | H |
| $L_A$2753 | | $CD_3$ | Ph | H | Ph | H | H | H |
| $L_A$2754 | | H | Ph | $CD_3$ | Ph | H | H | H |
| $L_A$2755 | | $^iPr$ | Ph | H | Ph | H | H | H |
| $L_A$2756 | | H | Ph | $^iPr$ | Ph | H | H | H |
| $L_A$2757 | | Ph | Ph | H | Ph | H | H | H |
| $L_A$2758 | | H | Ph | Ph | Ph | H | H | H. |

Linker A structures for $L_A$2741–2749: bicyclic pentalene with $C^{1b}$ and $C^{1e}$ labels.
Linker A structures for $L_A$2750–2758: bicyclic pentalene with $C^{1b}$ and $C^{1e}$ labels.

8. The compound of claim 1, wherein the ligand L is selected from the group consisting of:

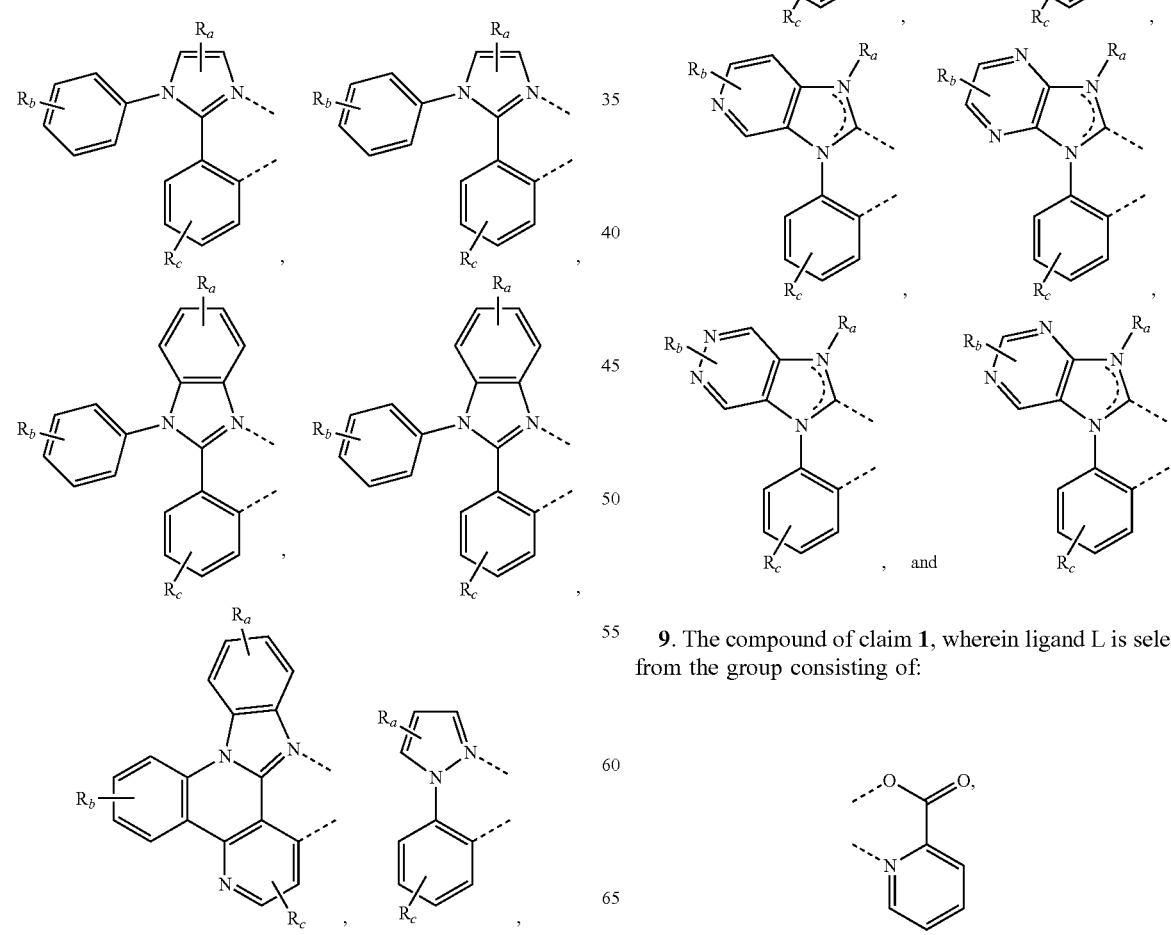

9. The compound of claim 1, wherein ligand L is selected from the group consisting of:

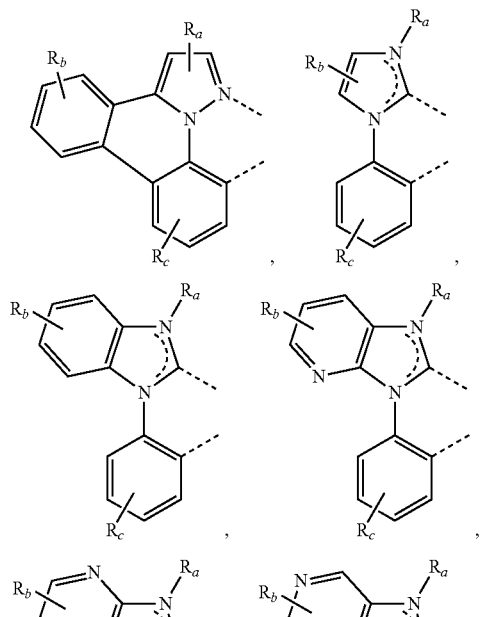

-continued
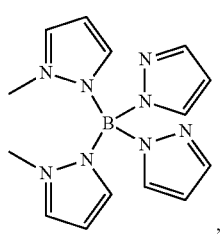, L₂
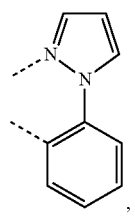, L₃
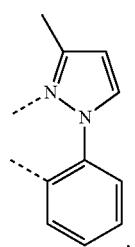, L₄
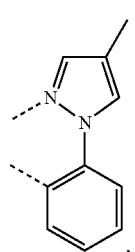, L₅
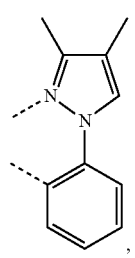, L₆
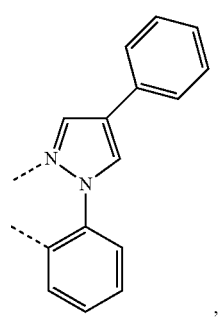, L₇
-continued
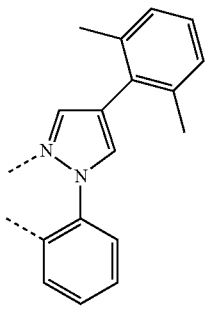, L₈
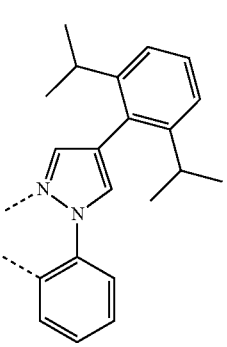, L₉
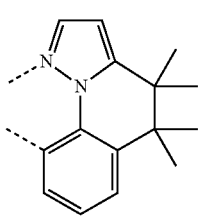, L₁₀
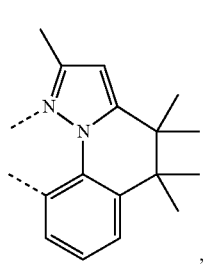, L₁₁
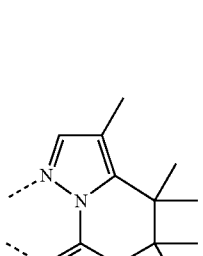, L₁₂
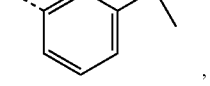, 345
-continued
L13 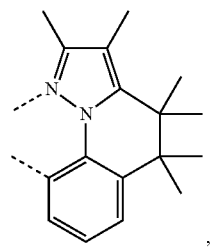,
L14 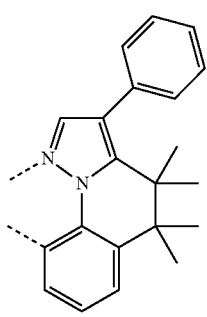,
L15 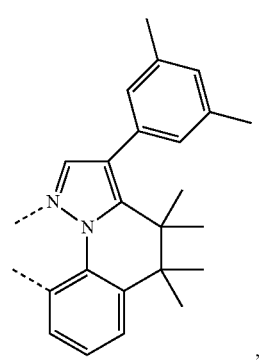,
L16 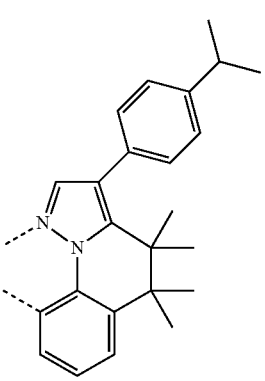,
L17 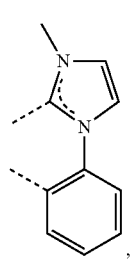,
346
-continued
L18 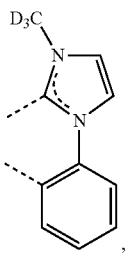,
L19 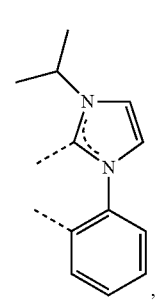,
L20 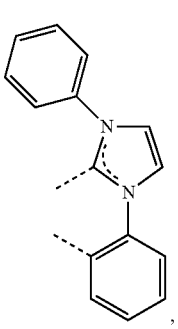,
L21 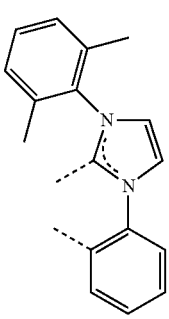,
L22 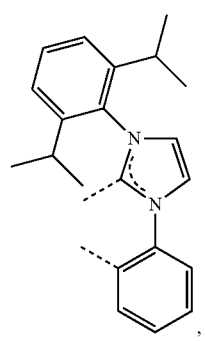, -continued
| | |
|---|---|
| 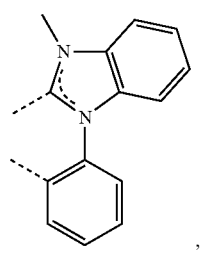 L23 | 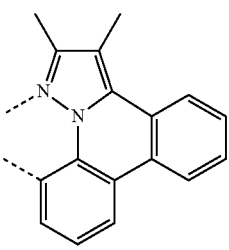 L29 |
| 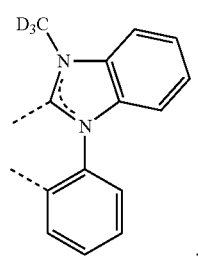 L24 | 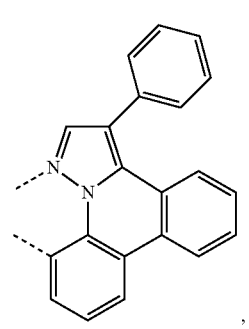 L30 |
| 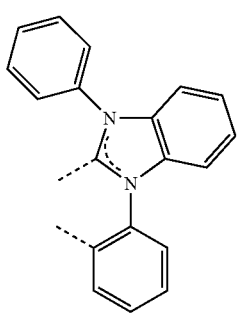 L25 | 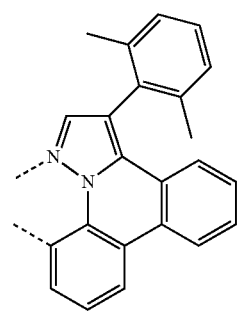 L31 |
| 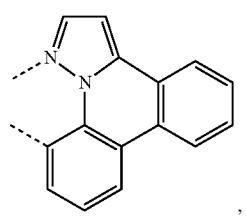 L26 | 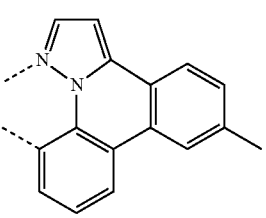 L32 |
| 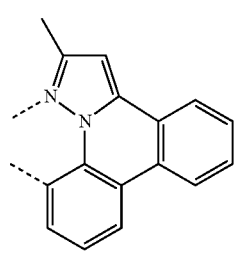 L27 | 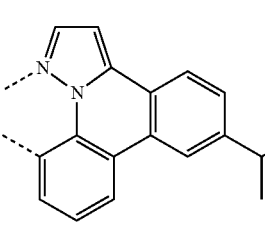 L33 |
| 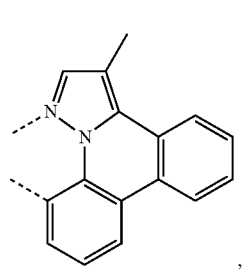 L28 | 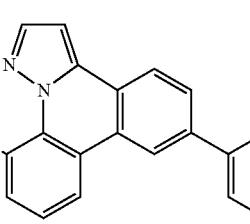 L34 |

L35 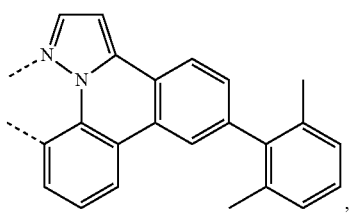,

L36 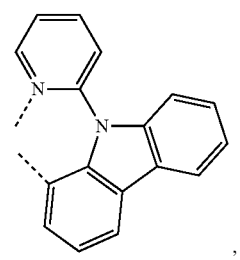,

L37 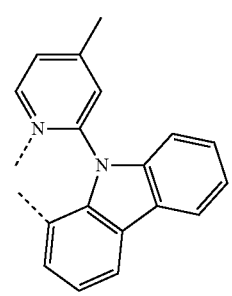,

L38 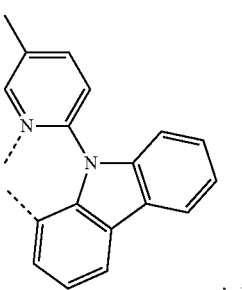, and

L39 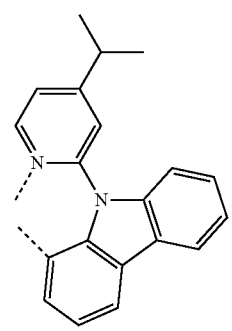

10. The compound of claim 7, wherein the compound is selected from the group consisting of Compound By having the formula $Ir(L_{Ai})(L_j)_2$ or selected from the group consisting of Compound Cz having the formula $Ir(L_{Ai})_2(L_j)$;

wherein y is an integer defined by y=39i+j-39, and z is an integer defined by z=39i+j-39, wherein i is an integer from 1 to 2758, and j is an integer from 1 to 39; and wherein Compound By denotes Compound $B_1$ to Compound $B_{107,562}$, Compound Cz denotes Compound $C_1$ to $C_{107,562}$, $L_{Ai}$ denotes $L_{A1}$ to $L_{A2758}$, and $L_j$ denotes $L_1$ to $L_{39}$ having the following structures:

$L_1$ 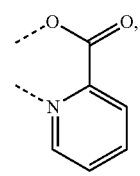

$L_2$ 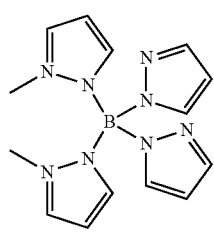

$L_3$ 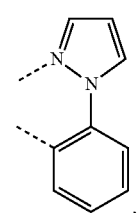

$L_4$ 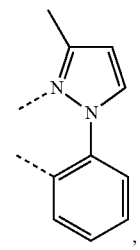

$L_5$ 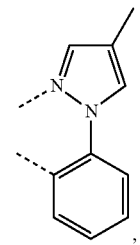

$L_6$ 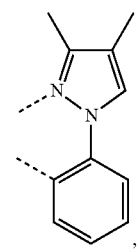

L7 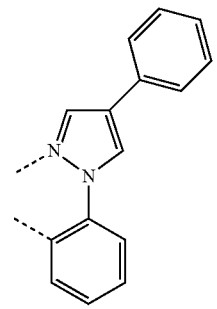
L8 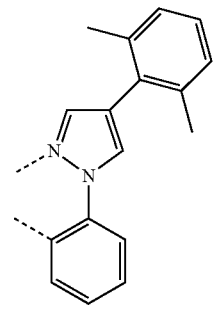
L9 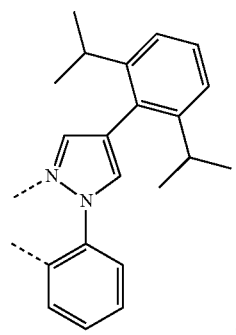
L10 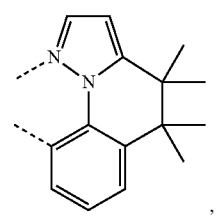
L11 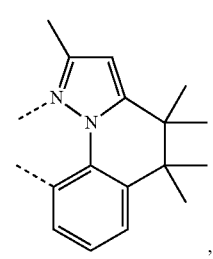
L12 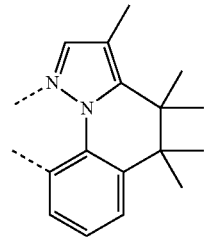
L13 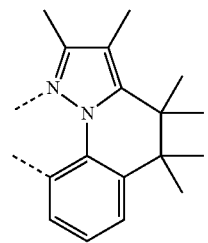
L14 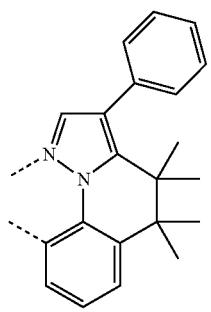
L15 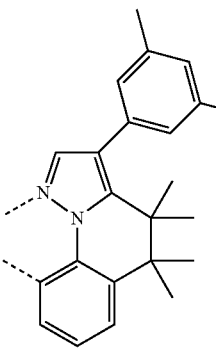
L16 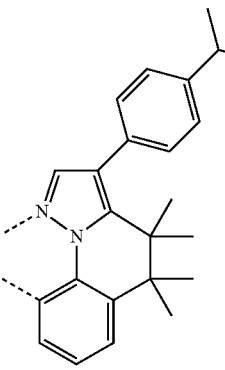

L17
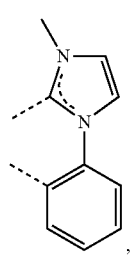
L18
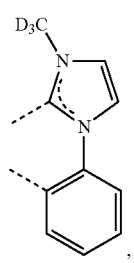
L19
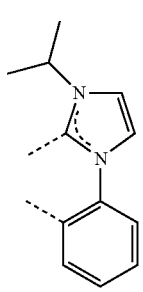
L20
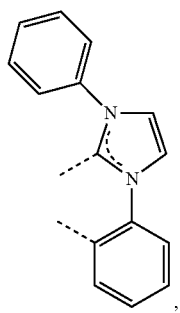
L21
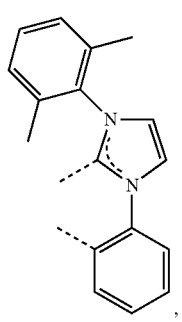
L22
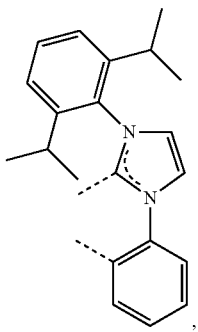
L23
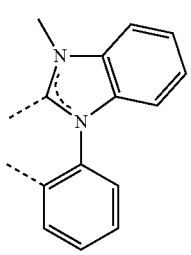
L24
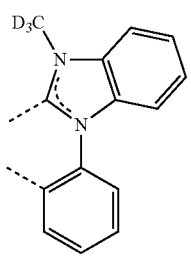
L25
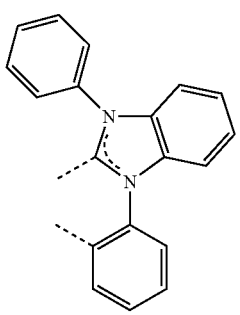
L26
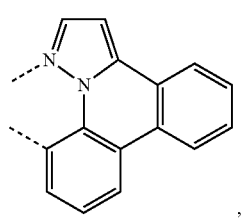

355
-continued
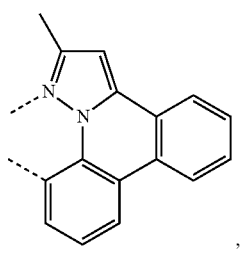 L27,
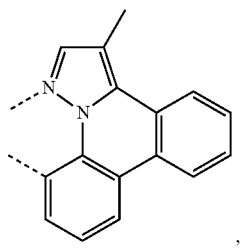 L28,
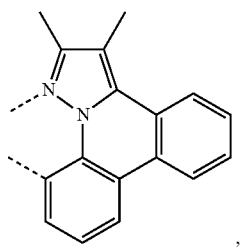 L29,
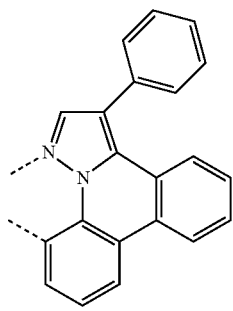 L30,
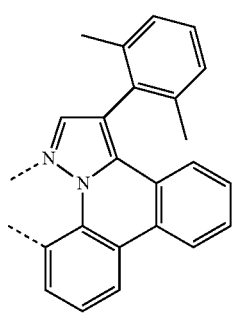 L31,
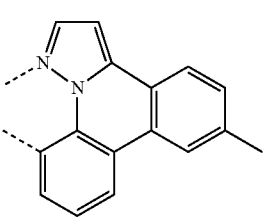 L32,
356
-continued
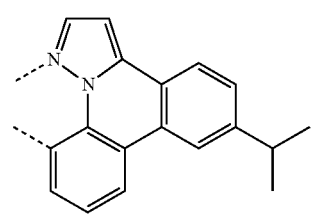 L33,
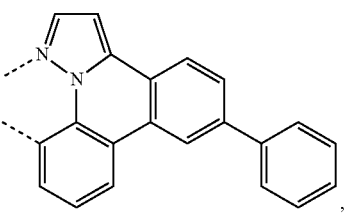 L34,
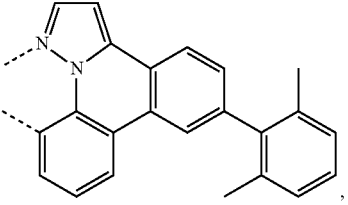 L35,
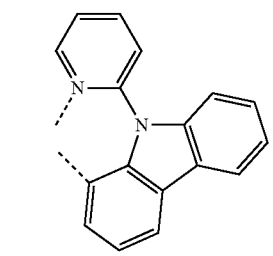 L36,
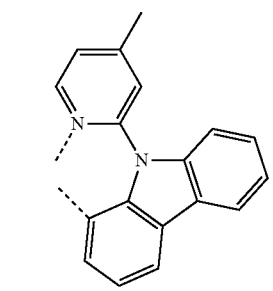 L37,
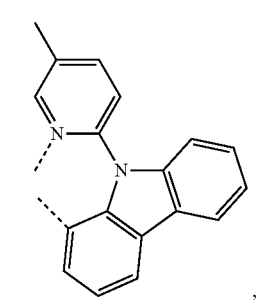 , and -continued

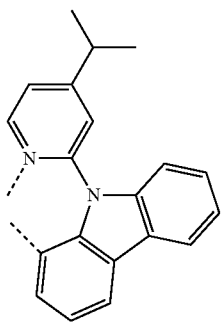

, and wherein $L_A1$ through $L_A2758$ are as defined above.

11. The compound of claim 1, wherein the compound has a structure of Formula 2:

Formula 2

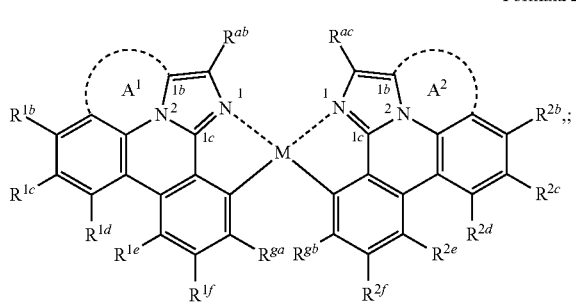

wherein M is Pt;
wherein $A^1$ and $A^2$ are each independently a first linking group selected from the group consisting of —CR'R"—CR'R"—, —CR'R'—CR"R"—, —CH$_2$—CH$_2$—, —CR'R'—CR'R'—CR'R'—, —CR'R"—NR'—, —CR'=CR'—CR'R'—, —O—SiR'R'—, —CR'R"—S—, —CR'R"—O—, and —CR'R"—SiR'R'—,
wherein each R' is independently selected from the group consisting of H, D, alkyl, cycloalkyl, aryl, heteroaryl, and combinations thereof,
wherein each R" is independently selected from the group consisting of alkyl, cycloalkyl, aryl, heteroaryl, and combinations thereof,
wherein R's and R"s are optionally connected to form a saturated five membered ring or a saturated six membered ring, and combinations thereof,
wherein $R^{1b}$ to $R^{1f}$ and $R^{2b}$ to $R^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;
wherein any one of the ring atoms to which $R^{1b}$ to $R^{1f}$ and $R^{2b}$ to $R^{2f}$ are attached may be replaced with a nitrogen atom, wherein when the ring atom is replaced with a nitrogen atom the corresponding R group is not present; and
wherein $R^{ab}$ and $R^{ac}$ and/or $R^{ga}$ and $R^{gb}$ may bond to form a second linking group having one to three linking atoms each independently selected from the group consisting of B, N, P, O, S, Se, C, Si, Ge or combinations thereof.

12. The compound of claim 1, wherein the compound has Formula 3:

Formula 3

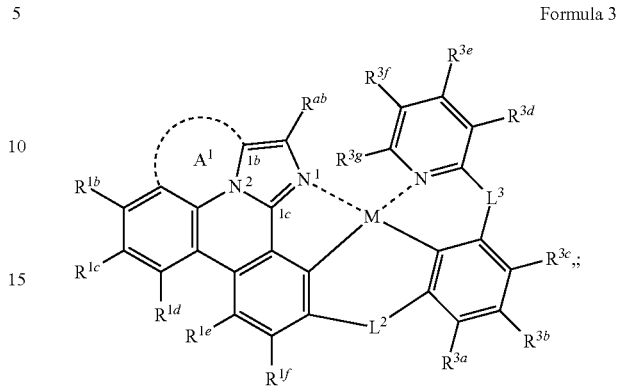

wherein M is Pt;
wherein $L^3$ is selected from the group consisting of a single bond, BR, NR, PR, O, S, Se, C=O, S=O, SO$_2$, CR$^1$R$^2$, SiR$^1$R$^2$, and GeR$^1$R$^2$;
wherein $R^{3a}$-$R^{3f}$, are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;
wherein any two adjacent $R^{1f}$, $R^{3a}$, $R^{3c}$, $R^{3d}$, $R^1$ and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings; and
wherein $L^3$ and $R^{3c}$, $L^3$ and $R^{3d}$, or $L^3$ and both $R^{3c}$ and $R^{3d}$ are optionally joined to form one or more rings.

13. A formulation comprising a compound according to claim 1.

14. The compound of claim 1, wherein the compound is selected from the group consisting of:

Compound 20

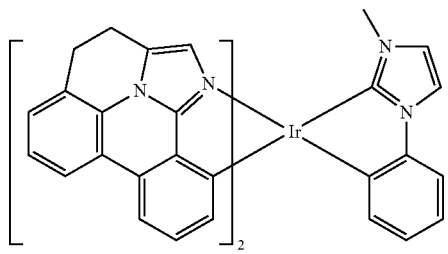

Compound 21

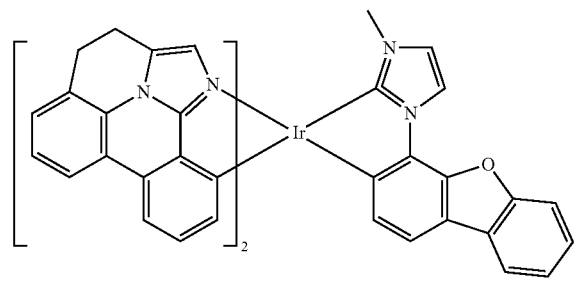

-continued
Compound 48
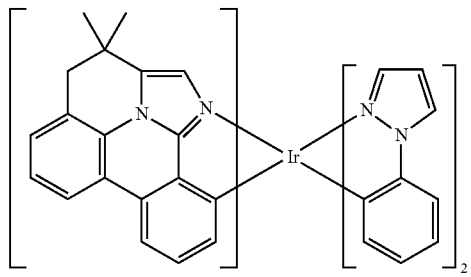
Compound 50
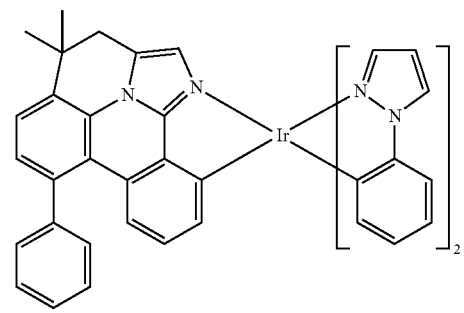
Compound 75
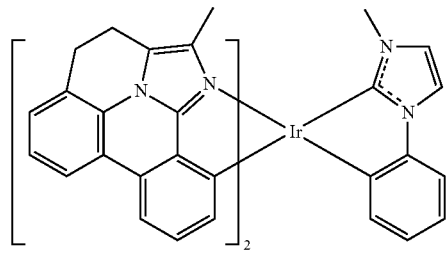
Compound 76
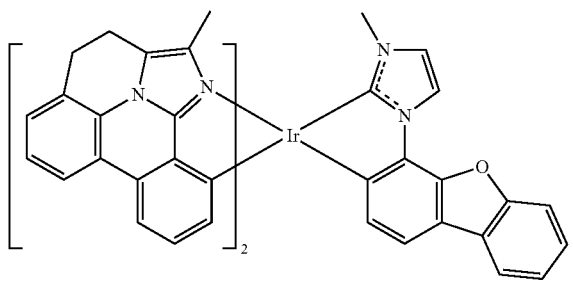
Compound 97
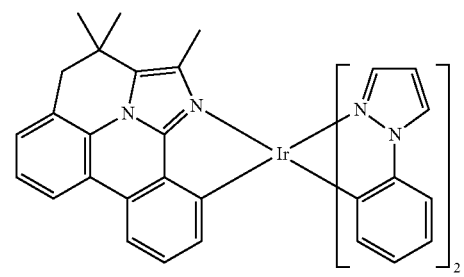
-continued
Compound 98
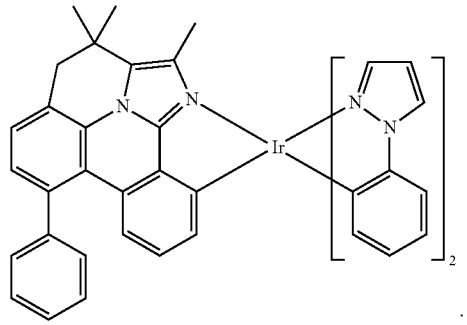
15. The compound of claim 1, wherein the linking group A is independently selected from the group consisting of —CR'R"—CR'R"—, —CR'R'—CR"R"—, and —CH$_2$—CH$_2$—.
16. The compound of claim 1, wherein the ligand L is selected from the group consisting of:
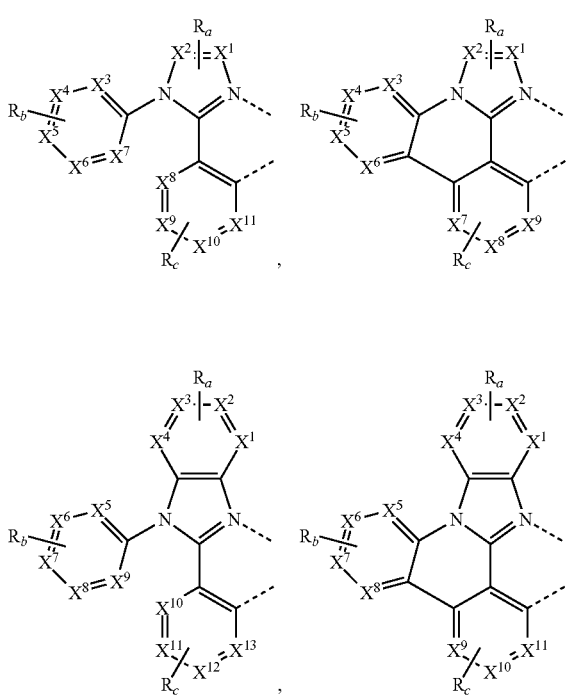
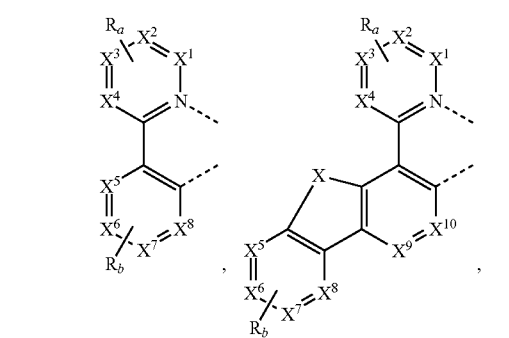

-continued

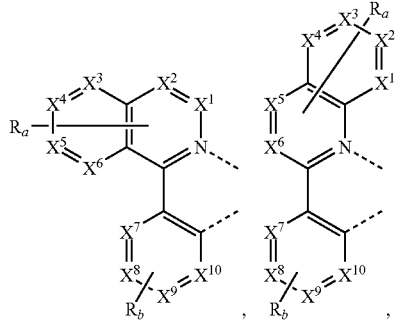

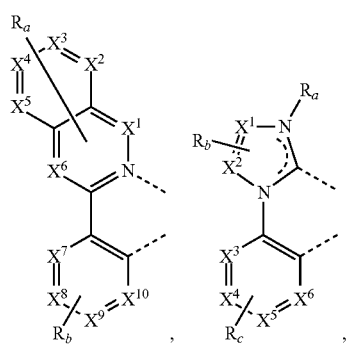

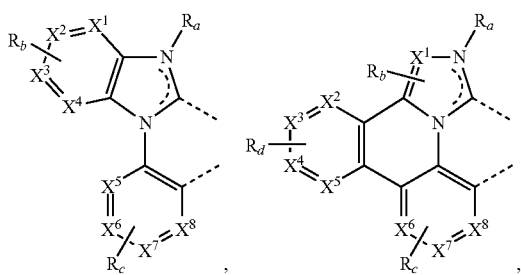

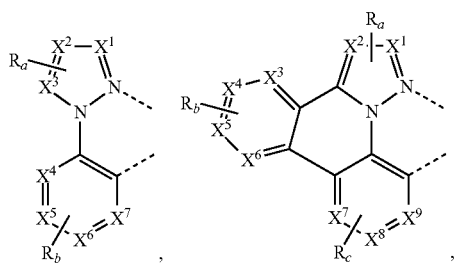

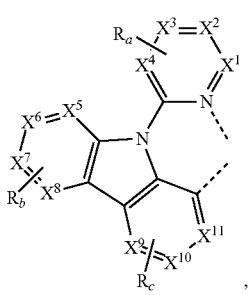

-continued

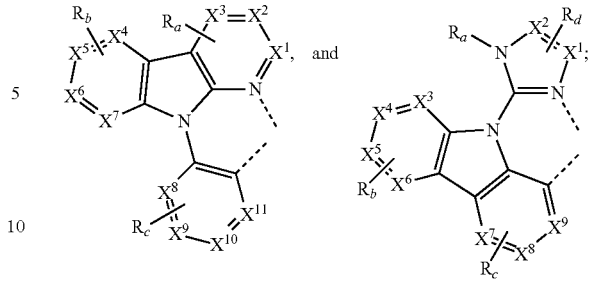

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

17. An organic light emitting device (OLED) comprising:
an anode;
a cathode;
an organic layer disposed between the anode and the cathode, wherein the organic layer comprising a compound having a structure $(L_A)_n ML_m$ according to Formula 1:

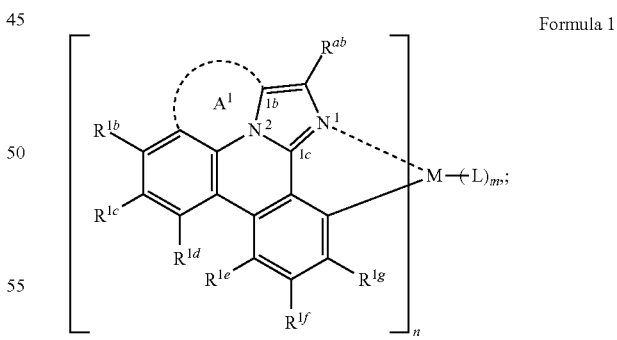

Formula 1 wherein M is a metal having an atomic weight greater than 40, n has a value of at least 1 and m+n is the maximum number of ligands that may be attached to the metal;

wherein A is a linking group selected from the group consisting of —CR'R"—CR'R"—, —CR'R'—CR"R"—, —$CH_2$—$CH_2$—, —CR'R'—CR'R'—, —CR'R"—NR'—, —CR'=CR'—CR'R'—, —O—SiR'R'—, —CR'R"—S—, —CR'R"—O—, and —CR'R"—SiR'R'—, wherein each R' is independently selected from the group consisting of H, D, alkyl, cycloalkyl, aryl, heteroaryl, and combinations thereof, wherein each R" is independently selected from the group consisting of alkyl, cycloalkyl, aryl, heteroaryl, and combinations thereof, wherein R's and R"s are optionally connected to form a saturated five membered ring or a saturated six membered ring, and combinations thereof, wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present;

wherein L is a substituted or unsubstituted cyclometallated ligand, wherein L can be joined to $R^{1g}$ through a linking group $L^2$;

wherein $L^2$ is selected from the group consisting of a single bond, BR, NR, PR, O, S, Se, C—O, S—O, $SO_2$, $CR^1R^2$, $SiR^1R^2$, and $GeR^1R^2$;

wherein $R^1$ and $R^2$ can be same or different, and are independently selected from the group consisting of hydrogen, deuterium, alkyl, cycloalkyl, aryl, heteroaryl, and combinations thereof; wherein any adjacent $R^1$ and $R^2$ are optionally connected to form a saturated five membered ring or a saturated six membered ring.

18. The OLED of claim 17, wherein the OLED is incorporated into a device selected from the group consisting of a consumer product, an electronic component module, and a lighting panel.

19. The OLED of claim 17, wherein the organic layer further comprises a host, wherein host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

* * * * *

UNITED STATES PATENT AND TRADEMARK OFFICE
CERTIFICATE OF CORRECTION

PATENT NO. : 10,256,419 B2  
APPLICATION NO. : 14/933684  
DATED : April 9, 2019  
INVENTOR(S) : Jason Brooks et al.

Page 1 of 3

It is certified that error appears in the above-identified patent and that said Letters Patent is hereby corrected as shown below:

In the Claims

In Claim 1, Column 300, Lines 54-67, please delete the compound

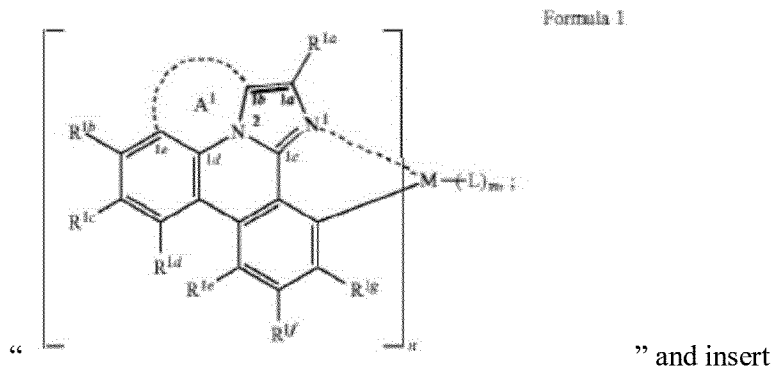

" and insert

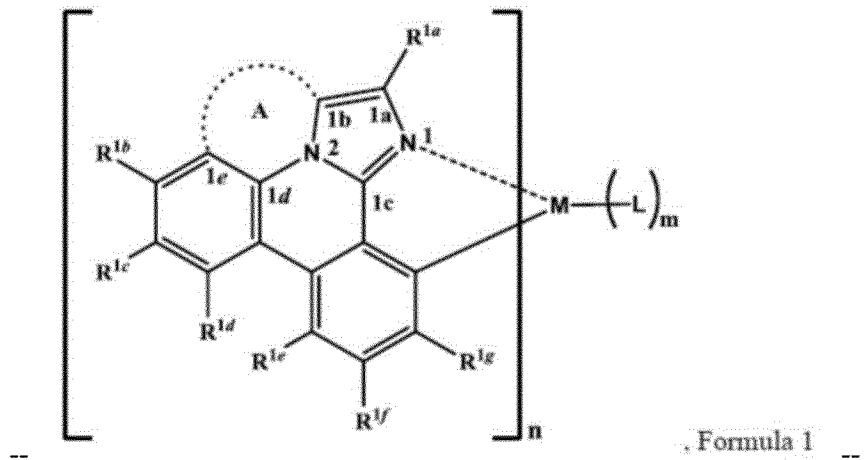

Signed and Sealed this  
Third Day of September, 2019

Andrei Iancu  
*Director of the United States Patent and Trademark Office*

CERTIFICATE OF CORRECTION (continued)

In Claim 3, Column 303, Lines 56-62, please delete compound " 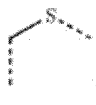 " in the middle of the row.

In Claim 12, Column 358, Lines 5-19, please delete

"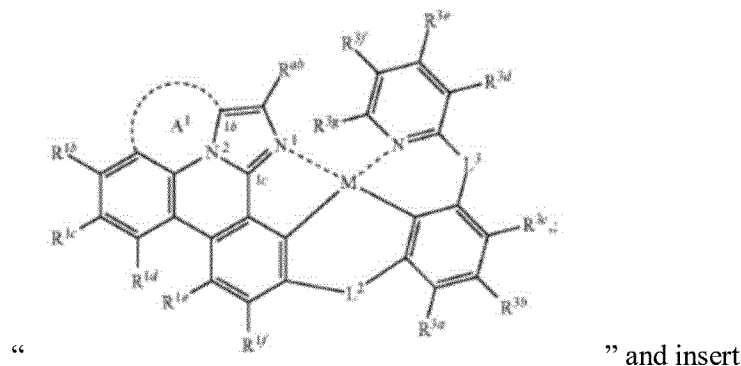" and insert

--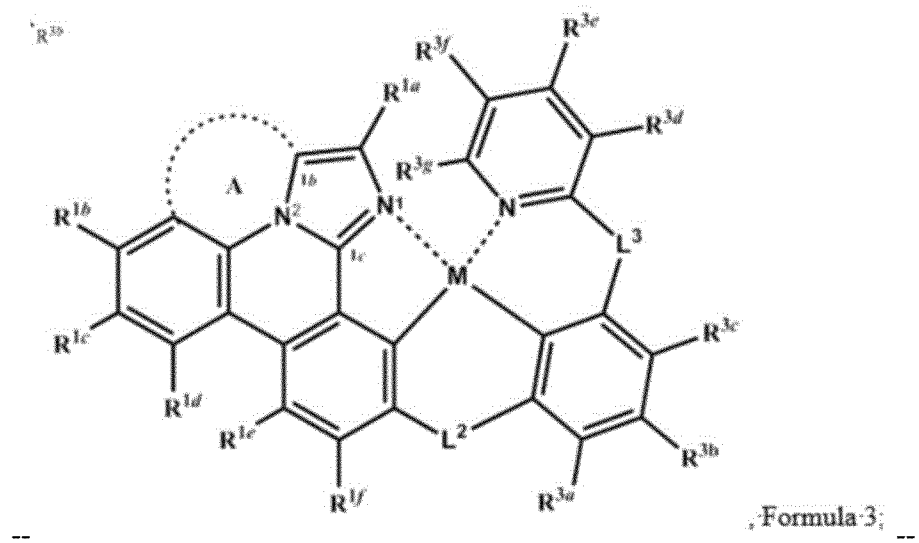, Formula 3; --

In Claim 17, Column 362, Lines 44-58, please delete

"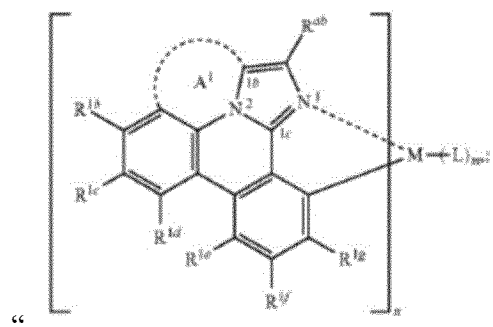" and insert

CERTIFICATE OF CORRECTION (continued)
U.S. Pat. No. 10,256,419 B2

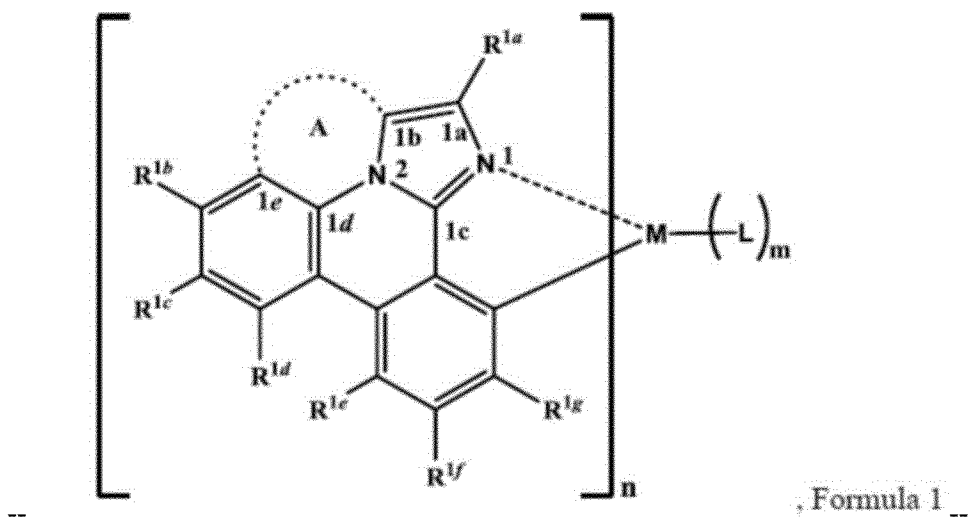

, Formula 1